United States Patent
Kuduk et al.

(10) Patent No.: US 10,975,077 B2
(45) Date of Patent: Apr. 13, 2021

(54) DIAZEPINONE DERIVATIVES AND THEIR USE IN THE TREATMENT OF HEPATITIS B INFECTIONS

(71) Applicant: Novira Therapeutics, Inc., Spring House, PA (US)

(72) Inventors: Scott Kuduk, Harleysville, PA (US); George D. Hartman, Lansdale, PA (US)

(73) Assignee: Novira Therapeutics, Inc., Spring House, PA (US)

(*) Notice: Subject to any disclaimer, the term of this patent is extended or adjusted under 35 U.S.C. 154(b) by 100 days.

(21) Appl. No.: 16/314,001

(22) PCT Filed: Jun. 29, 2017

(86) PCT No.: PCT/US2017/040132
§ 371 (c)(1),
(2) Date: Dec. 28, 2018

(87) PCT Pub. No.: WO2018/005883
PCT Pub. Date: Jan. 4, 2018

(65) Prior Publication Data
US 2020/0181144 A1 Jun. 11, 2020

Related U.S. Application Data

(60) Provisional application No. 62/511,573, filed on May 26, 2017, provisional application No. 62/356,489, filed on Jun. 29, 2016.

(51) Int. Cl.
| | |
|---|---|
| C07D 471/04 | (2006.01) |
| A61K 31/551 | (2006.01) |
| A61P 31/12 | (2006.01) |
| C07D 471/14 | (2006.01) |
| A61P 31/20 | (2006.01) |

(52) U.S. Cl.
CPC ............ *C07D 471/14* (2013.01); *A61P 31/20* (2018.01)

(58) Field of Classification Search
CPC ...... C07D 471/04; A61K 31/551; A61P 31/12
See application file for complete search history.

(56) References Cited

U.S. PATENT DOCUMENTS

| | | | |
|---|---|---|---|
| 4,500,525 A | 2/1985 | Winters et al. | |
| 7,531,531 B2 | 5/2009 | Fancelli et al. | |
| 8,288,425 B2 | 10/2012 | Edwards et al. | |
| 8,309,578 B2 | 11/2012 | Mantegani et al. | |
| 9,351,965 B2 | 5/2016 | Shipps, Jr. et al. | |
| 9,518,057 B2 | 12/2016 | Hartman et al. | |
| 9,527,845 B2 | 12/2016 | Hartman et al. | |
| 9,550,779 B2 | 1/2017 | Hartman et al. | |
| 9,890,161 B2 | 2/2018 | Hartman et al. | |
| 10,077,264 B2 | 9/2018 | Hartman et al. | |
| 10,093,669 B2 | 10/2018 | Hartman et al. | |
| 10,189,835 B2 | 1/2019 | Hartman et al. | |

(Continued)

FOREIGN PATENT DOCUMENTS

| | | |
|---|---|---|
| EP | 0086422 A | 8/1983 |
| WO | 2002014314 A1 | 2/2002 |

(Continued)

OTHER PUBLICATIONS

Haiyong et al. (2015) "Recent Advance of the hepatitis B virus inhibitors: a medicinal chemistry overview," Future Medicinal Chemistry, 7 (5): 587-607.

(Continued)

*Primary Examiner* — Bruck Kifle
(74) *Attorney, Agent, or Firm* — Brian C. Trinque; Lathrop GPM LLP

(57) ABSTRACT

Provided herein are compounds of formula (I) and (V) useful for the treatment of HBV infection in a subject in need thereof, pharmaceutical compositions thereof, and methods of inhibiting, suppressing, or preventing HBV infection in the subject.

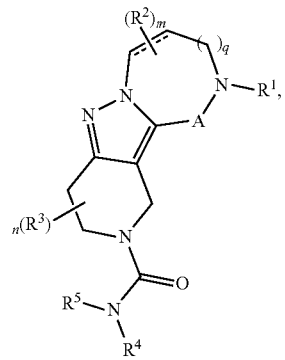

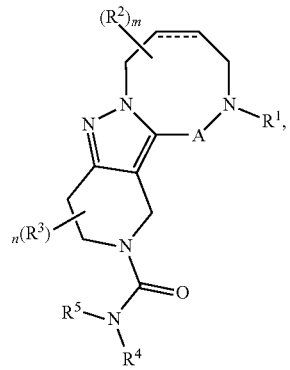

31 Claims, 1 Drawing Sheet

(56) References Cited

U.S. PATENT DOCUMENTS

| | | |
|---|---|---|
| 10,538,519 B2 | 1/2020 | Hartman et al. |
| 10,544,141 B2 | 1/2020 | Hartman et al. |
| 10,556,904 B2 | 2/2020 | Hartman et al. |
| 2015/0132258 A1 | 5/2015 | Hartman |
| 2020/0181142 A1 | 6/2020 | Hartman et al. |
| 2020/0197408 A1 | 6/2020 | Kuduk et al. |

FOREIGN PATENT DOCUMENTS

| | | |
|---|---|---|
| WO | 2003070236 A2 | 8/2003 |
| WO | 2004014374 A1 | 2/2004 |
| WO | 2008005511 A1 | 1/2008 |
| WO | 2012036997 A1 | 3/2012 |

OTHER PUBLICATIONS

Samala, G. et al. Eur. J. Med. Chem. 2013, 69, 356-364.

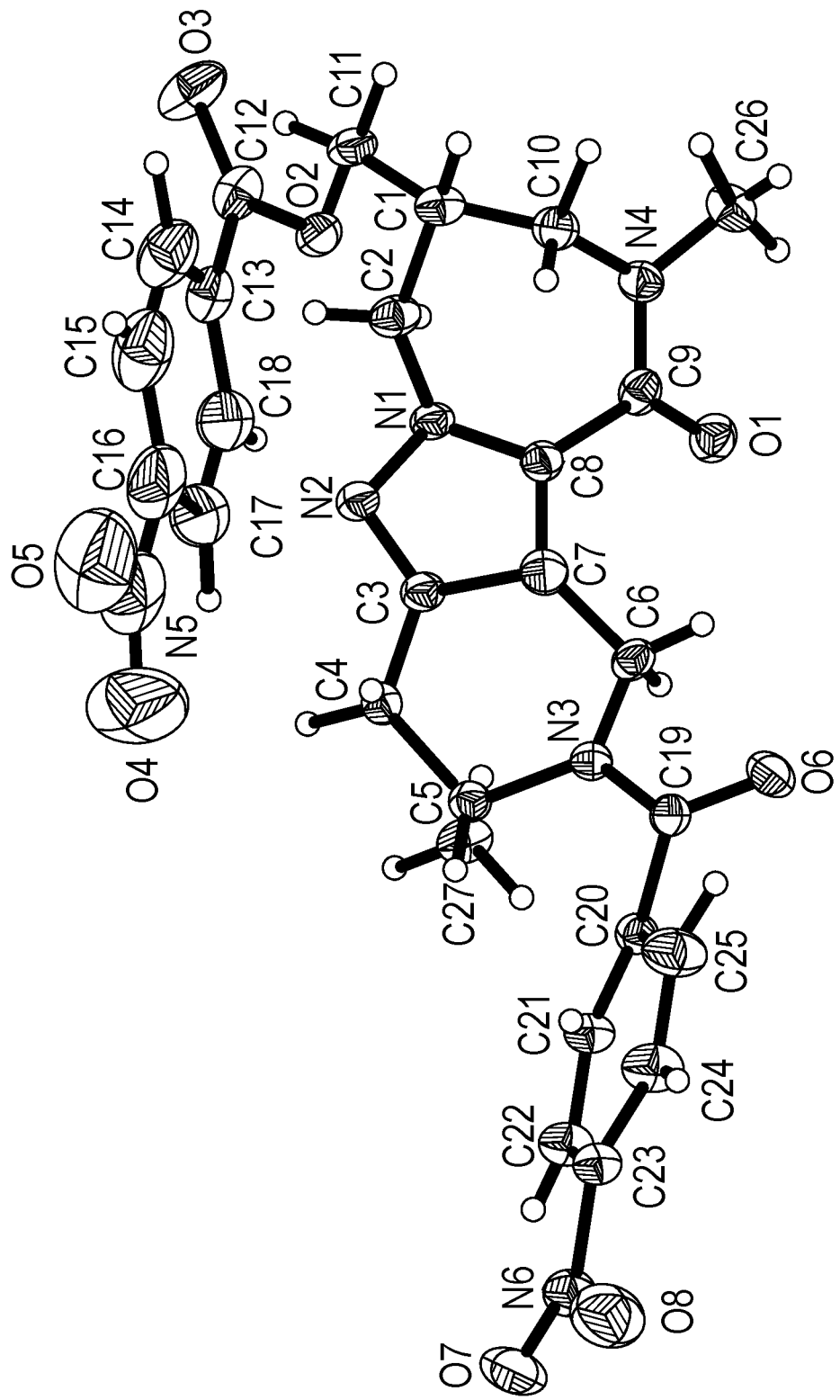

DIAZEPINONE DERIVATIVES AND THEIR USE IN THE TREATMENT OF HEPATITIS B INFECTIONS

RELATED APPLICATIONS

This application is a 35 U.S.C. § 371 filing of International Application No. PCT/US2017/040132, filed Jun. 29, 2017, which claims the benefit of U.S. provisional patent application No. 62/356,489, filed Jun. 29, 2016; and U.S. provisional patent application No. 62/511,573, filed May 26, 2017; the entire contents of each of which are incorporated herein by reference.

BACKGROUND

Chronic hepatitis B virus (HBV) infection is a significant global health problem, affecting over 5% of the world population (over 350 million people worldwide and 1.25 million individuals in the U.S.).

Despite the availability of a prophylactic HBV vaccine, the burden of chronic HBV infection continues to be a significant unmet worldwide medical problem, due to suboptimal treatment options and sustained rates of new infections in most parts of the developing world. Current treatments do not provide a cure and are limited to only two classes of agents (interferon alpha and nucleoside analogues/inhibitors of the viral polymerase); drug resistance, low efficacy, and tolerability issues limit their impact. The low cure rates of HBV are attributed at least in part to the fact that complete suppression of virus production is difficult to achieve with a single antiviral agent. However, persistent suppression of HBV DNA slows liver disease progression and helps to prevent hepatocellular carcinoma. Current therapy goals for HBV-infected patients are directed to reducing serum HBV DNA to low or undetectable levels, and to ultimately reducing or preventing the development of cirrhosis and hepatocellular carcinoma.

The HBV capsid protein plays essential functions during the viral life cycle. HBV capsid/core proteins form metastable viral particles or protein shells that protect the viral genome during intercellular passage, and also play a central role in viral replication processes, including genome encapsidation, genome replication, and virion morphogenesis and egress. Capsid structures also respond to environmental cues to allow un-coating after viral entry. Consistently, the appropriate timing of capsid assembly and disassembly, the appropriate capsid stability and the function of core protein have been found to be critical for viral infectivity.

There is a need in the art for therapeutic agents that can increase the suppression of virus production and that can treat, ameliorate, or prevent HBV infection. Administration of such therapeutic agents to an HBV infected patient, either as monotherapy or in combination with other HBV treatments or ancillary treatments, will lead to significantly reduced virus burden, improved prognosis, diminished progression of the disease and enhanced seroconversion rates.

SUMMARY

Provided herein are compounds useful for the treatment of HBV infection in a subject in need thereof.

Thus, in an aspect, provided herein is a compound of Formula I:

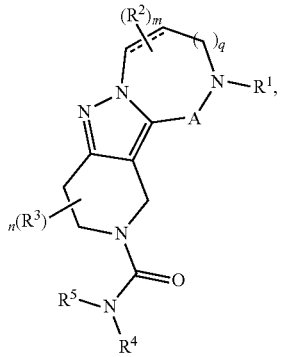

I or a pharmaceutically acceptable salt thereof, wherein

A is $CH_2$ or $C=O$;

$R^1$ is H, $C_1$-$C_6$-alkyl, $C_1$-$C_6$-alkenyl, $C_1$-$C_6$-alkyl-OH, or $C_1$-$C_6$-haloalkyl; $R^2$ is, at each occurrence, independently selected from —OH, halo, $C_1$-$C_6$-alkyl, $C_1$-$C_6$-alkylene, $C_0$-$C_6$-alkyl-$C_3$-$C_6$-cycloalkyl, $C_0$-$C_6$-alkyl-$C_2$-$C_6$-heterocycloalkyl, $C_0$-$C_6$-alkyl-$OR^6$, $C_0$-$C_6$-alkyl-$N(R^7)_2$, $C_0$-$C_6$-alkyl-$SR^8$, $C_0$-$C_6$-alkyl-$S(O)R^8$, $C_0$-$C_6$-alkyl-$S(O)_2R^8$, $C_0$-$C_6$-alkyl-$C(O)OR^9$, $C_0$-$C_6$-alkyl-$OC(O)R^9$, $C_0$-$C_6$-alkyl-$OC(O)OR^9$, $C_0$-$C_6$-alkyl-$OC(O)N(R^7)_2$, and $C_0$-$C_6$-alkyl-$C(O)N(R^7)_2$, wherein alkyl, alkylene, cycloalkyl, and heterocycloalkyl are optionally substituted with 1, 2, or 3 groups, each independently selected from —OH and halo; or two $R^2$ groups together form a $C_3$-$C_6$ spiro cycloalkyl, wherein the cyloalkyl is optionally substituted with 1, 2, or 3 groups, each individually selected from —OH and halo;

$R^3$ is, at each occurrence, independently selected from —OH, halo, $C_1$-$C_6$-alkyl, $C_1$-$C_6$-haloalkyl, —O—$C_1$-$C_6$-alkyl, and $C_1$-$C_6$-alkyl-OH;

$R^4$ is selected from $(CR^aR^b)_p$—$C_1$-$C_9$-heteroaryl, $(CR^aR^b)_p$—$C_6$-$C_{12}$-aryl, $(CR^aR^b)_p$—$C_3$-$C_7$-cycloalkyl, and $(CR^aR^b)_p$—$C_2$-$C_6$-heterocycloalkyl, wherein heteroaryl, aryl, cycloalkyl, and heterocycloalkyl are optionally substituted with 1, 2, 3, or 4 groups, each independently selected from —OH, halo, —CN, —$SF_5$, $C_1$-$C_6$-alkyl, $C_1$-$C_6$-haloalkyl, —O—$C_1$-$C_6$-alkyl, and $C_1$-$C_6$-alkyl-OH;

$R^5$ is selected from H, $C_1$-$C_6$-alkyl, and $C_1$-$C_6$-alkyl-OH;

$R^6$ is selected from H, $C_1$-$C_6$-alkyl, $C_1$-$C_6$-haloalkyl, $C_1$-$C_6$-alkenyl, and $C_0$-$C_6$-alkyl-$C_3$-$C_6$-cycloalkyl;

$R^7$ is, at each occurrence, independently selected from H, $C_1$-$C_6$-alkyl, $C_1$-$C_6$-haloalkyl, $C(O)$ $C_1$-$C_6$-alkyl and $C_1$-$C_6$-alkyl-OH;

$R^8$ is selected from H and $C_1$-$C_6$-alkyl;

$R^9$ is selected from H and $C_1$-$C_6$-alkyl;

$R^a$ is, at each occurrence, independently selected from H, —OH, halo, $C_1$-$C_6$-alkyl, $C_1$-$C_6$-haloalkyl, —O—$C_1$-$C_6$-alkyl, and $C_1$-$C_6$-alkyl-OH;

$R^b$ is, at each occurrence, independently selected from H and $C_1$-$C_6$-alkyl;

m is 0, 1, 2, 3, or 4;

n is 0, 1, 2, 3, or 4;

p is 0, 1, 2, 3, or 4;

q is 0 or 1; and a ---- line denotes an optionally double bond.

In an embodiment, provided herein is a compound of Formula I, or a pharmaceutically acceptable salt thereof, wherein A is $CH_2$ or $C=O$;

$R^1$ is H, $C_1$-$C_6$-alkyl, $C_1$-$C_6$-alkenyl, $C_1$-$C_6$-alkyl-OH, or $C_1$-$C_6$-haloalkyl;

$R^2$ is, at each occurrence, independently selected from —OH, halo, $C_1$-$C_6$-alkyl, $C_1$-$C_6$-alkylene, $C_0$-$C_6$-alkyl-$C_3$-$C_6$-cycloalkyl, $C_0$-$C_6$-alkyl-$C_2$-$C_6$-heterocycloalkyl, $C_0$-$C_6$-alkyl-$OR^6$, $C_0$-$C_6$-alkyl-$N(R^7)_2$, $C_0$-$C_6$-alkyl-$SR^8$, $C_0$-$C_6$-alkyl-$S(O)R^8$, $C_0$-$C_6$-alkyl-$S(O)_2R^8$, $C_0$-$C_6$-alkyl-$C(O)OR^9$, $C_0$-$C_6$-alkyl-$OC(O)R^9$, $C_0$-$C_6$-alkyl-$OC(O)OR^9$, $C_0$-$C_6$-alkyl-$OC(O)N(R^7)_2$, and $C_0$-$C_6$-alkyl-$C(O)N(R^7)_2$, wherein alkyl, cycloalkyl, and heterocycloalkyl are optionally substituted with 1, 2, or 3 groups, each independently selected from —OH and halo;

$R^3$ is, at each occurrence, independently selected from —OH, halo, $C_1$-$C_6$-alkyl, $C_1$-$C_6$-haloalkyl, —O—$C_1$-$C_6$-alkyl, and $C_1$-$C_6$-alkyl-OH;

$R^4$ is selected from $(CR^aR^b)_p$—$C_1$-$C_9$-heteroaryl, $(CR^aR^b)_p$—$C_6$-$C_{12}$-aryl, $(CR^aR^b)_p$—$C_3$-$C_7$-cycloalkyl, and $(CR^aR^b)_p$—$C_2$-$C_6$-heterocycloalkyl, wherein heteroaryl, aryl, cycloalkyl, and heterocycloalkyl are optionally substituted with 1, 2, 3, or 4 groups, each independently selected from —OH, halo, —CN, —$SF_5$, $C_1$-$C_6$-alkyl, $C_1$-$C_6$-haloalkyl, —O—$C_1$-$C_6$-alkyl, and $C_1$-$C_6$-alkyl-OH;

$R^5$ is selected from H, $C_1$-$C_6$-alkyl, and $C_1$-$C_6$-alkyl-OH;

$R^6$ is selected from H, $C_1$-$C_6$-alkyl, $C_1$-$C_6$-haloalkyl, $C_1$-$C_6$-alkenyl, and $C_0$-$C_6$-alkyl-$C_3$-$C_6$-cycloalkyl;

$R^7$ is, at each occurrence, independently selected from H, $C_1$-$C_6$-alkyl, and $C_1$-$C_6$-alkyl-OH;

$R^8$ is selected from H and $C_1$-$C_6$-alkyl;

$R^9$ is selected from H and $C_1$-$C_6$-alkyl;

$R^a$ is, at each occurrence, independently selected from H, —OH, halo, $C_1$-$C_6$-alkyl, $C_1$-$C_6$-haloalkyl, —O—$C_1$-$C_6$-alkyl, and $C_1$-$C_6$-alkyl-OH;

$R^b$ is, at each occurrence, independently selected from H and $C_1$-$C_6$-alkyl;

m is 0, 1, 2, 3, or 4;

n is 0, 1, 2, 3, or 4;

p is 0, 1, 2, 3, or 4;

q is 0 or 1; and a ---- line denotes an optionally double bond.

In an embodiment, the compound of Formula I has the structure of Formula II:

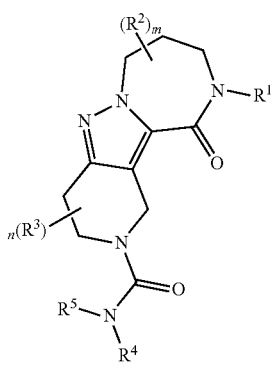

or a pharmaceutically acceptable salt thereof.

In another embodiment, the compound of Formula I or Formula II has the structure of Formula III:

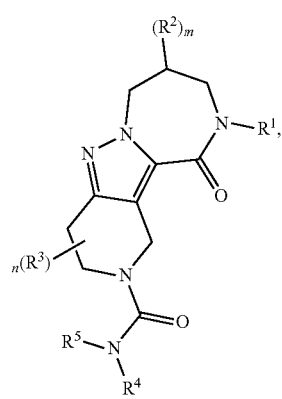

or a pharmaceutically acceptable salt thereof.

In another embodiment, provided herein is a compound of Formula V:

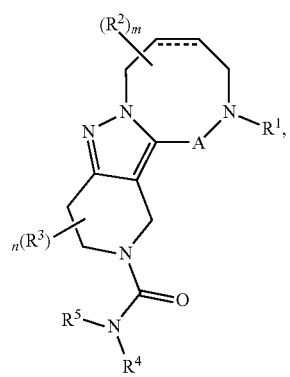

or a pharmaceutically acceptable salt thereof, wherein

A is $CH_2$ or $C=O$;

$R^1$ is H, $C_1$-$C_6$-alkyl, $C_1$-$C_6$-alkenyl, $C_1$-$C_6$-alkyl-OH, or $C_1$-$C_6$-haloalkyl;

$R^2$ is, at each occurrence, independently selected from —OH, halo, $C_1$-$C_6$-alkyl, $C_1$-$C_6$-alkylene, $C_0$-$C_6$-alkyl-$C_3$-$C_6$-cycloalkyl, $C_0$-$C_6$-alkyl-$C_2$-$C_6$-heterocycloalkyl, $C_0$-$C_6$-alkyl-$OR^6$, $C_0$-$C_6$-alkyl-$N(R^7)_2$, $C_0$-$C_6$-alkyl-$SR^8$, $C_0$-$C_6$-alkyl-$S(O)R^8$, $C_0$-$C_6$-alkyl-$S(O)_2R^8$, $C_0$-$C_6$-alkyl-$C(O)OR^9$, $C_0$-$C_6$-alkyl-$OC(O)R^9$, $C_0$-$C_6$-alkyl-$OC(O)OR^9$, $C_0$-$C_6$-alkyl-$OC(O)N(R^7)_2$, and $C_0$-$C_6$-alkyl-$C(O)N(R^7)_2$, wherein alkyl, alkylene, cycloalkyl, and heterocycloalkyl are optionally substituted with 1, 2, or 3 groups, each independently selected from —OH and halo; or two $R^2$ groups together form a $C_3$-$C_6$ spiro cycloalkyl, wherein the cyloalkyl is optionally substituted with 1, 2, or 3 groups, each individually selected from —OH and halo;

$R^3$ is, at each occurrence, independently selected from —OH, halo, $C_1$-$C_6$-alkyl, $C_1$-$C_6$-haloalkyl, —O—$C_1$-$C_6$-alkyl, and $C_1$-$C_6$-alkyl-OH;

$R^4$ is selected from $(CR^aR^b)_p$—$C_1$-$C_9$-heteroaryl, $(CR^aR^b)_p$—$C_6$-$C_{12}$-aryl, $(CR^aR^b)_p$—$C_3$-$C_7$-cycloalkyl, and $(CR^aR^b)_p$—$C_2$-$C_6$-heterocycloalkyl, wherein heteroaryl, aryl, cycloalkyl, and heterocycloalkyl are optionally substituted with 1, 2, 3, or 4 groups, each independently selected from —OH, halo, —CN, —SF$_5$, C$_1$-C$_6$-alkyl, C$_1$-C$_6$-haloalkyl, —O—C$_1$-C$_6$-alkyl, and C$_1$-C$_6$-alkyl-OH;

R$^5$ is selected from H, C$_1$-C$_6$-alkyl, and C$_1$-C$_6$-alkyl-OH;

R$^6$ is selected from H, C$_1$-C$_6$-alkyl, C$_1$-C$_6$-haloalkyl, C$_1$-C$_6$-alkenyl, and C$_0$-C$_6$-alkyl-C$_3$-C$_6$-cycloalkyl;

R$^7$ is, at each occurrence, independently selected from H, C$_1$-C$_6$-alkyl, C$_1$-C$_6$-haloalkyl, C(O) C$_1$-C$_6$-alkyl and C$_1$-C$_6$-alkyl-OH;

R$^8$ is selected from H and C$_1$-C$_6$-alkyl;

R$^9$ is selected from H and C$_1$-C$_6$-alkyl;

R$^a$ is, at each occurrence, independently selected from H, —OH, halo, C$_1$-C$_6$-alkyl, C$_1$-C$_6$-haloalkyl, —O—C$_1$-C$_6$-alkyl, and C$_1$-C$_6$-alkyl-OH;

R$^b$ is, at each occurrence, independently selected from H and C$_1$-C$_6$-alkyl;

m is 0, 1, 2, 3, or 4;

n is 0, 1, 2, 3, or 4;

p is 0, 1, 2, 3, or 4; and a ==== line denotes an optionally double bond.

In another aspect, provided herein is a pharmaceutical composition comprising a compound of Formula I, II, III, IV, or V, or a pharmaceutically acceptable salt thereof, together with a pharmaceutically acceptable carrier.

In another aspect, provided herein is a pharmaceutical composition comprising a disclosed compound and a pharmaceutically acceptable carrier.

In another aspect, provided herein is a method of treating an HBV infection in an individual in need thereof, comprising administering to the individual a therapeutically effective amount of a compound of Formula I, II, III, IV, or V, or a pharmaceutically acceptable salt thereof.

In another aspect, provided herein is a method of inhibiting or reducing the formation or presence of HBV DNA-containing particles or HBV RNA-containing particles in an individual in need thereof, comprising administering to the individual a therapeutically effective amount of a compound of Formula, I, II, III, IV, or V, or a pharmaceutically acceptable salt thereof.

In an embodiment, any of the methods provided herein can further comprising administering to the individual at least one additional therapeutic agent selected from the group consisting of an HBV polymerase inhibitor, immunomodulatory agents, interferon, viral entry inhibitor, viral maturation inhibitor, capsid assembly modulator, reverse transcriptase inhibitor, a cyclophilin/TNF inhibitor, a TLR-agonist, an HBV vaccine, and any combination thereof.

BRIEF DESCRIPTION OF THE DRAWING

FIG. 1 shows the X-ray crystal structure of the di p-nitrobenzoic acid analogue of Intermediate 16, also referred to as compound 151.

DETAILED DESCRIPTION

Provided herein are compounds, e.g., the compounds of Formulas I, II, III, IV, or V, or pharmaceutically acceptable salts thereof, that are useful in the treatment and prevention of HBV infection in subject.

Without being bound to any particular mechanism of action, these compounds are believed to modulate or disrupt HBV assembly and other HBV core protein functions necessary for HBV replication or the generation of infectious particles. In addition, or alternatively, the compounds may disrupt HBV capsid assembly to induce production of defective viral particles with greatly reduced infectivity or replication capacity. In other words, the compounds provided herein may act as capsid assembly modulators by modulating (e.g., accelerating, delaying, inhibiting, disrupting or reducing) normal viral capsid assembly or disassembly, binding capsids, and/or altering metabolism of cellular polyproteins and precursors. The modulation may occur when the capsid protein is mature, or during viral infectivity. The disclosed compounds can be used in methods of modulating the activity or properties of HBV cccDNA, or the generation or release of HBV RNA particles from within an infected cell.

In one embodiment, the compounds described herein are suitable for monotherapy and are effective against natural or native HBV strains and against HBV strains resistant to currently known drugs. In another embodiment, the compounds described herein are suitable for use in combination therapy.

Definitions

Listed below are definitions of various terms used to describe this invention. These definitions apply to the terms as they are used throughout this specification and claims, unless otherwise limited in specific instances, either individually or as part of a larger group.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and peptide chemistry are those well-known and commonly employed in the art.

As used herein, the articles "a" and "an" refer to one or to more than one (i.e. to at least one) of the grammatical object of the article. By way of example, "an element" means one element or more than one element. Furthermore, use of the term "including" as well as other forms, such as "include", "includes," and "included," is not limiting.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±20% or ±10%, including ±5%, ±1%, and ±0.1% from the specified value, as such variations are appropriate to perform the disclosed methods.

As used herein, the term "capsid assembly modulator" refers to a compound that disrupts or accelerates or inhibits or hinders or delays or reduces or modifies normal capsid assembly (e.g., during maturation) or normal capsid disassembly (e.g., during infectivity) or perturbs capsid stability, thereby inducing aberrant capsid morphology and function. In one embodiment, a capsid assembly modulator accelerates capsid assembly or disassembly, thereby inducing aberrant capsid morphology. In another embodiment, a capsid assembly modulator interacts (e.g. binds at an active site, binds at an allosteric site, modifies or hinders folding and the like) with the major capsid assembly protein (CA), thereby disrupting capsid assembly or disassembly. In yet another embodiment, a capsid assembly modulator causes a perturbation in structure or function of CA (e.g., ability of CA to assemble, disassemble, bind to a substrate, fold into a suitable conformation, or the like), which attenuates viral infectivity or is lethal to the virus.

As used herein, the term "treatment" or "treating" is defined as the application or administration of a therapeutic agent, i.e., a disclosed compound (alone or in combination with another pharmaceutical agent), to a patient, or application or administration of a therapeutic agent to an isolated tissue or cell line from a patient (e.g., for diagnosis or ex vivo applications), who has an HBV infection, a symptom of HBV infection or the potential to develop an HBV infection, with the purpose to cure, heal, alleviate, relieve, alter, remedy, ameliorate, improve or affect the HBV infection, the symptoms of HBV infection, or the potential to develop an HBV infection. Such treatments may be specifically tailored or modified, based on knowledge obtained from the field of pharmacogenomics.

As used herein, the term "prevent" or "prevention" means no disorder or disease development if none had occurred, or no further disorder or disease development if there had already been development of the disorder or disease. Also considered is the ability of one to prevent some or all of the symptoms associated with the disorder or disease.

As used herein, the term "patient," "individual" or "subject" refers to a human or a non-human mammal. Non-human mammals include, for example, livestock and pets, such as ovine, bovine, porcine, canine, feline and murine mammals. Preferably, the patient, subject, or individual is human.

As used herein, the terms "effective amount," "pharmaceutically effective amount," and "therapeutically effective amount" refer to a nontoxic but sufficient amount of an agent to provide the desired biological result. That result may be reduction or alleviation of the signs, symptoms, or causes of a disease, or any other desired alteration of a biological system. An appropriate therapeutic amount in any individual case may be determined by one of ordinary skill in the art using routine experimentation.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable salt" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

As used herein, the term "composition" or "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary, and topical administration.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations.

As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

As used herein, the term "alkyl," by itself or as part of another substituent means, unless otherwise stated, a straight or branched chain hydrocarbon having the number of carbon atoms designated (i.e., $C_0$-$C_6$-alkyl means null or an alkyl having one to six carbon atoms) and includes straight and branched chains. Examples include methyl, ethyl, propyl, isopropyl, butyl, isobutyl, tert-butyl, pentyl, neopentyl, and hexyl. Other examples of $C_1$-$C_6$-alkyl include ethyl, methyl, isopropyl, isobutyl, n-pentyl, and n-hexyl.

As used herein, the term "alkenyl," denotes a monovalent group derived from a hydrocarbon moiety containing at least two carbon atoms and at least one carbon-carbon double bond. The double bond may or may not be the point of attachment to another group. Alkenyl groups (e.g., $C_2$-$C_8$-alkenyl) include, but are not limited to, for example, ethenyl, propenyl, prop-1-en-2-yl, butenyl, 1-methyl-2-buten-1-yl, heptenyl, octenyl and the like.

As used herein, the term "halo" or "halogen" alone or as part of another substituent means, unless otherwise stated, a fluorine, chlorine, bromine, or iodine atom, preferably, fluorine, chlorine, or bromine, more preferably, fluorine or chlorine.

As used herein, the term "haloalkyl" refers to alkl radicals wherein any one or more of the alkyl carbon atoms is substituted with halo as defined above. Haloalkyl embraces monohaloalkyl, dihaloalkyl, and polyhaloalkyl radicals. The term "haloalkyl" includes, but is not limited to, fluoromethyl, difluoromethyl, trifluoromethyl, chloromethyl, dichloromethyl, trichloromethyl, and pentafluoroethyl.

As used herein, the term "cycloalkyl" refers to a mono cyclic or polycyclic non-aromatic radical, wherein each of the atoms forming the ring (i.e., skeletal atoms) is a carbon atom. In one embodiment, the cycloalkyl group is saturated or partially unsaturated. In another embodiment, the cycloalkyl group is fused with an aromatic ring. Cycloalkyl groups include groups having 3 to 10 ring atoms ($C_3$-$C_{10}$-cycloalkyl), groups having 3 to 8 ring atoms ($C_3$-$C_8$-cycloalkyl), groups having 3 to 7 ring atoms ($C_3$-$C_7$-cycloalkyl), and groups having 3 to 6 ring atoms ($C_3$-$C_6$-cycloalkyl). Monocyclic cycloalkyls include, but are not limited to, cyclopropyl, cyclobutyl, cyclopentyl, cyclohexyl, cycloheptyl, and cyclooctyl. Dicyclic cycloalkyls include, but are not limited to, tetrahydronaphthyl, indanyl, and tetrahydropentalene. Polycyclic cycloalkyls include adamantine and norbornane. The term cycloalkyl includes unsaturated nonaromatic cyclic groups, which contain at least one carbon carbon double bond or one carbon carbon triple bond.

As used herein, the term "heterocycloalkyl" or "heterocyclyl" refers to a heteroalicyclic group containing one to four ring heteroatoms each selected from O, S, and N. In one embodiment, each heterocyclyl group has from 3 to 10 atoms in its ring system, with the proviso that the ring of said group does not contain two adjacent O or S atoms. Heterocyclyl substituents may be alternatively defined by the number of carbon atoms, e.g., $C_2$-$C_8$-heterocyclyl indicates the number of carbon atoms contained in the heterocyclic group without including the number of heteroatoms. For example, a $C_2$-$C_8$-heterocyclyl will include an additional one to four heteroatoms. Preferably, the heterocyclyl group has less than three heteroatoms. More preferably, the heterocyclyl group has one to two heteroatoms. In another embodiment, the heterocycloalkyl group is fused with an aromatic ring. In one embodiment, the nitrogen and sulfur heteroatoms may be optionally oxidized, and the nitrogen atom may be optionally quaternized. The heterocyclic system may be attached, unless otherwise stated, at any heteroatom or carbon atom that affords a stable structure.

An example of a 3-membered heterocyclyl group includes, and is not limited to, aziridine. Examples of 4-membered heterocycloalkyl groups include, and are not limited to, azetidine and a beta lactam. Examples of 5-membered heterocyclyl groups include, and are not limited to, pyrrolidine, oxazolidine and thiazolidinedione. Examples of 6-membered heterocycloalkyl groups include, and are not limited to, piperidine, morpholine, and piperazine.

Other non-limiting examples of heterocyclyl groups include monocyclic groups such as aziridine, oxirane, thiirane, azetidine, oxetane, thietane, pyrrolidine, pyrroline, pyrazolidine, imidazoline, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin, and hexamethyleneoxide.

As used herein, the term "aromatic" refers to a carbocycle or heterocycle with one or more polyunsaturated rings and having aromatic character, i.e., having (4n+2) delocalized π (pi) electrons, where n is an integer.

As used herein, the term "aryl," employed alone or in combination with other terms, means, unless otherwise stated, a carbocyclic aromatic system containing one or more rings (typically one, two, or three rings), wherein such rings may be attached together in a pendent manner, such as a biphenyl, or may be fused, such as naphthalene. Examples of aryl groups include phenyl, anthracyl, and naphthyl. Preferred examples are phenyl (e.g., $C_6$-aryl) and biphenyl (e.g., $C_{12}$-aryl). In some embodiments, aryl groups have from six to sixteen carbon atoms. In some embodiments, aryl groups have from six to twelve carbon atoms (e.g., $C_6$-$C_{12}$-aryl). In some embodiments, aryl groups have six carbon atoms (e.g., $C_6$-aryl).

As used herein, the term "heteroaryl" or "heteroaromatic" refers to a heterocycle having aromatic character. Heteroaryl substituents may be defined by the number of carbon atoms, e.g., $C_1$-$C_9$-heteroaryl indicates the number of carbon atoms contained in the heteroaryl group without including the number of heteroatoms. For example, a $C_1$-$C_9$-heteroaryl will include an additional one to four heteroatoms. Preferably, the heteroaryl group has less than three heteroatoms. More preferably, the heteroaryl group has one to two heteroatoms. A polycyclic heteroaryl may include one or more rings that are partially saturated. Non-limiting examples of heteroaryls include pyridyl, pyrazinyl, pyrimidinyl (including, e.g., 2- and 4-pyrimidinyl), pyridazinyl, thienyl, furyl, pyrrolyl (including, e.g., 2-pyrrolyl), imidazolyl, thiazolyl, oxazolyl, pyrazolyl (including, e.g., 3- and 5-pyrazolyl), isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Non-limiting examples of polycyclic heterocycles and heteroaryls include indolyl (including, e.g., 3-, 4-, 5-, 6- and 7-indolyl), indolinyl, quinolyl, tetrahydroquinolyl, isoquinolyl (including, e.g., 1- and 5-isoquinolyl), 1,2,3,4-tetrahydroisoquinolyl, cinnolinyl, quinoxalinyl (including, e.g., 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (including, e.g., 3-, 4-, 5-, 6- and 7-benzofuryl), 2,3-dihydrobenzofuryl, 1,2-benzisoxazolyl, benzothienyl (including, e.g., 3-, 4-, 5-, 6-, and 7-benzothienyl), benzoxazolyl, benzothiazolyl (including, e.g., 2-benzothiazolyl and 5-benzothiazolyl), purinyl, benzimidazolyl (including, e.g., 2-benzimidazolyl), benzotriazolyl, thioxanthinyl, carbazolyl, carbolinyl, acridinyl, pyrrolizidinyl, and quinolizidinyl.

As used herein, the term "substituted" means that an atom or group of atoms has replaced hydrogen as the substituent attached to another group.

As used herein, the terminology "selected from . . ." (e.g., "$R^4$ is selected from A, B and C") is understood to be equivalent to the terminology "selected from the group consisting of . . . " (e.g., "$R^4$ is selected from the group consisting of A, B and C").

Compounds

Provided herein are compounds having the structure of Formula I:

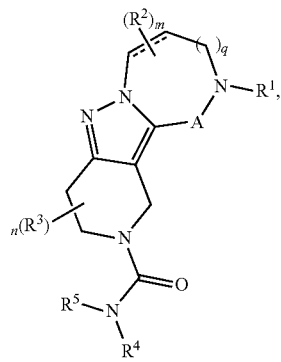

I or a pharmaceutically acceptable salt thereof.

In embodiments, A is $CH_2$ or $C=O$. In embodiments, A is $CH_2$. In other embodiments, A is $C=O$.

$R^1$ may be H, $C_1$-$C_6$-alkyl, $C_1$-$C_6$-alkenyl, $C_1$-$C_6$-alkyl-OH, or $C_1$-$C_6$-haloalkyl. In embodiments, $R^1$ is H. In embodiments, $R^1$ is $C_1$-$C_6$-alkyl. In particular embodiments, $R^1$ is $-CH_3$. In embodiments, $R^1$ is $C_1$-$C_6$-alkenyl. In embodiments, $R^1$ is $C_1$-$C_6$-alkyl-OH. In embodiments, $R^1$ is $C_1$-$C_6$-haloalkyl.

In embodiments, there may be 0, 1, 2, 3, or 4 $R^2$ substituents: m is 0, 1, 2, 3, or 4. Each $R^2$ may be independently selected from $-OH$, halo, $C_1$-$C_6$-alkyl, $C_1$-$C_6$-alkylene, $C_0$-$C_6$-alkyl-$C_3$-$C_6$-cycloalkyl, $C_0$-$C_6$-alkyl-$C_2$-$C_6$-heterocycloalkyl, $C_0$-$C_6$-alkyl-$OR^6$, $C_0$-$C_6$-alkyl-$N(R^7)_2$, $C_0$-$C_6$-alkyl-$SR^8$, $C_0$-$C_6$-alkyl-$S(O)R^8$, $C_0$-$C_6$-alkyl-$S(O)_2R^8$, $C_0$-$C_6$-alkyl-$C(O)OR^9$, $C_0$-$C_6$-alkyl-$OC(O)R^9$, $C_0$-$C_6$-alkyl-$OC(O)OR^9$, $C_0$-$C_6$-alkyl-$OC(O)N(R^7)_2$, and $C_0$-$C_6$-alkyl-$C(O)N(R^7)_2$, wherein alkyl, alkylene, cycloalkyl, and heterocycloalkyl are optionally substituted with 1, 2, or 3 groups, each independently selected from $-OH$ and halo; or two $R^2$ groups together form a $C_3$-$C_6$ spiro cycloalkyl, wherein the cyloalkyl is optionally substituted with 1, 2, or 3 groups, each individually selected from $-OH$ and halo.

In certain embodiments, m is 0 and there is no $R^2$ substitution. In certain embodiments, m is 1 and there is one $R^2$ substitution. In certain embodiments, m is 2 and there are two $R^2$ substitutions. In certain embodiments, m is 3 and there are three $R^2$ substitutions. In certain embodiments, m is 4 and there are four $R^2$ substitutions.

In certain embodiments, at least one $R^2$ is $-OH$. In certain embodiments, at least one $R^2$ is halo. In certain embodiments, at least one $R^2$ is $C_1$-$C_6$-alkyl. In certain embodiments, at least one $R^2$ is $C_1$-$C_6$-alkylene. In certain embodiments, at least one $R^2$ is $C_0$-$C_6$-alkyl-$C_3$-$C_6$-cycloalkyl. In certain embodiments, at least one $R^2$ is $C_0$-$C_6$-alkyl-$C_2$-$C_6$-heterocycloalkyl. In certain embodiments, at least one $R^2$ is $C_0$-$C_6$-alkyl-$OR^6$. In certain embodiments, at least one $R^2$ is $C_0$-$C_6$-alkyl-$N(R^7)_2$. In certain embodiments, at least one $R^2$ is $C_0$-$C_6$-alkyl-$SR^8$. In certain embodiments, at least one $R^2$ is $C_0$-$C_6$-alkyl-$S(O)R^8$. In certain embodiments, at least one $R^2$ is $C_0$-$C_6$-alkyl-$S(O)_2R^8$. In certain embodiments, at least one $R^2$ is $C_0$-$C_6$-alkyl-$C(O)OR^9$. In certain embodiments, at least one $R^2$ is $C_0$-$C_6$-alkyl-$OC(O)R^9$. In certain embodiments, at least one $R^2$ is $C_0$-$C_6$-alkyl-$OC(O)OR^9$. In certain embodiments, at least one $R^2$ is $C_0$-$C_6$-alkyl-$OC(O)N(R^7)_2$. In certain embodiments, at least one $R^2$ is $C_0$-$C_6$-alkyl-$C(O)N(R^7)_2$. In certain embodiments, two $R^2$ groups together form a $C_3$-$C_6$ spiro cycloalkyl, wherein the cyloalkyl is optionally substituted with 1, 2, or 3 groups, each individually selected from $-OH$ and halo.

In certain embodiments, $R^2$ is substituted with 1, 2 or 3 groups. Each occurrence of $R^2$ as alkyl, alkylene, cycloalkyl or heterocycloalkyl optionally may be substituted with $-OH$ or halo. For example, $R^2$ may be alkyl, and the alkyl is substituted with $-OH$; or $R^2$ may be alkyl, and the alkyl is substituted with at least one fluorine atom. In a particular embodiment, $R^2$ may be $CH_2OH$. $R^2$ may be alkylene, and the alkylene group is substituted with $-OH$; or $R^2$ may be alkylene, and the alkylene group is substituted with at least one fluorine atom. $R^2$ may be cycloalkyl, and the cycloalkyl is substituted with $-OH$; or $R^2$ may be cycloalkyl, and the cycloalkyl is substituted with at least one fluorine atom. $R^2$ may be heterocycloalkyl, and the heterocycloalkyl is substituted with $-OH$; or $R^2$ may be heterocycloalkyl, and the heterocycloalkyl is substituted with at least one fluorine atom. In certain embodiments, two $R^2$ groups together form a $C_3$-$C_6$ spiro cycloalkyl, wherein the cyloalkyl is substituted with at least 1 $-OH$. In certain embodiments, two $R^2$ groups together form a $C_3$-$C_6$ spiro cycloalkyl, wherein the cyloalkyl is substituted with at least 1 halogen.

In certain embodiments, $R^2$ may be $C_1$-$C_6$-alkyl optionally substituted with 1, 2, or 3 halo groups. In certain embodiments, $R^2$ may be $C_0$-$C_6$-alkyl-$OR^6$, wherein $R^6$ is $C_1$-$C_6$-haloalkyl. In certain embodiments, $R^2$ may be $(CH_2)_{1-2}-O-C_1$-$C_3$-alkyl, wherein $C_1$-$C_3$-alkyl is optionally substituted with 1, 2, or 3 halo groups. In certain embodiments, m is 1 or 2.

In embodiments, there may be 0, 1, 2, 3, or 4 $R^3$ substituents: n is 0, 1, 2, 3, or 4. In certain embodiments, n is 0 and there is no $R^3$ substitution. In certain embodiments, n is 1 and there is one $R^3$ substitution. In certain embodiments, n is 2 and there are two $R^3$ substitutions. In certain embodiments, n is 3 and there are three $R^3$ substitutions. In certain embodiments, n is 4 and there are four $R^3$ substitutions.

Each $R^3$ may be independently selected from $-OH$, halo, $C_1$-$C_6$-alkyl, $C_1$-$C_6$-haloalkyl, $-O-C_1$-$C_6$-alkyl, and $C_1$-$C_6$-alkyl-OH. In certain embodiments, at least one $R^3$ is $-OH$. In certain embodiments, at least one $R^3$ is halo. In certain embodiments, at least one $R^3$ is $C_1$-$C_6$-alkyl. In certain embodiments, at least one $R^3$ is $C_1$-$C_6$-haloalkyl. In certain embodiments, at least one $R^3$ is $-O-C_1$-$C_6$-alkyl. In certain embodiments, at least one $R^3$ is $C_1$-$C_6$-alkyl-OH.

$R^4$ is selected from $(CR^aR^b)_p-C_1$-$C_9$-heteroaryl, $(CR^aR^b)_p-C_6$-$C_{12}$-aryl, $(CR^aR^b)_p-C_3$-$C_7$-cycloalkyl, and $(CR^aR^b)_p-C_2$-$C_6$-heterocycloalkyl, wherein heteroaryl, aryl, cycloalkyl, and heterocycloalkyl are optionally substituted with 1, 2, 3, or 4 groups, each independently selected from $-OH$, halo, $-CN$, $-SF_5$, $C_1$-$C_6$-alkyl, $C_1$-$C_6$-haloalkyl, $-O-C_1$-$C_6$-alkyl, and $C_1$-$C_6$-alkyl-OH. In certain embodiments, $R^4$ is $(CR^aR^b)_p-C_1$-$C_9$-heteroaryl optionally substituted with 1, 2, 3, or 4 groups, each independently selected from $-OH$, halo, $-CN$, $-SF_5$, $C_1$-$C_6$-alkyl, $C_1$-$C_6$-haloalkyl, $-O-C_1$-$C_6$-alkyl, and $C_1$-$C_6$-alkyl-OH. In certain embodiments, $R^4$ is $(CR^aR^b)_p-C_6$-$C_{12}$-aryl optionally substituted with 1, 2, 3, or 4 groups, each independently selected from $-OH$, halo, $-CN$, $-SF_5$, $C_1$-$C_6$-alkyl, $C_1$-$C_6$-haloalkyl, $-O-C_1$-$C_6$-alkyl, and $C_1$-$C_6$-alkyl-OH. In certain embodiments, $R^4$ is $(CR^aR^b)_p-C_3$-$C_7$-cycloalkyl optionally substituted with 1, 2, 3, or 4 groups, each independently selected from $-OH$, halo, $-CN$, $-SF_5$, $C_1$-$C_6$-alkyl, $C_1$-$C_6$-haloalkyl, $-O-C_1$-$C_6$-alkyl, and $C_1$-$C_6$-alkyl-OH. In certain embodiments, $R^4$ is $(CR^aR^b)_p$—$C_2$-$C_6$-heterocycloalkyl optionally substituted with 1, 2, 3, or 4 groups, each independently selected from —OH, halo, —CN, —SF$_5$, $C_1$-$C_6$-alkyl, $C_1$-$C_6$-haloalkyl, —O—$C_1$-$C_6$-alkyl, and $C_1$-$C_6$-alkyl-OH. In certain embodiments, $R^4$ is phenyl or pyridyl, wherein said phenyl or pyridyl is optionally substituted with 1, 2, 3, or 4 groups, each independently selected from halo, —CN, $C_1$-$C_6$-alkyl and $C_1$-$C_6$-haloalkyl. In a particular embodiment, $R^4$ is phenyl, wherein the phenyl is substituted with 1, 2, 3, or 4 groups, each independently selected from halo, —CN, $C_1$-$C_6$-alkyl and $C_1$-$C_6$-haloalkyl. In another particular embodiment, $R^4$ is pyridyl, wherein the pyridyl is substituted with 1, 2, 3, or 4 groups, each independently selected from halo, —CN, $C_1$-$C_6$-alkyl and $C_1$-$C_6$-haloalkyl.

$R^5$ may be selected from H, $C_1$-$C_6$-alkyl, and $C_1$-$C_6$-alkyl-OH. In a particular embodiment, $R^5$ is H.

$R^6$ may be selected from H, $C_1$-$C_6$-alkyl, $C_1$-$C_6$-haloalkyl, $C_1$-$C_6$-alkenyl, and $C_0$-$C_6$-alkyl-$C_3$-$C_6$-cycloalkyl. In a particular embodiment, $R^6$ is selected from H, $C_1$-$C_6$-alkyl, and $C_1$-$C_6$-haloalkyl.

$R^7$ may be independently selected from H, $C_1$-$C_6$-alkyl, $C_1$-$C_6$-haloalkyl, C(O) $C_1$-$C_6$-alkyl and $C_1$-$C_6$-alkyl-OH. In a particular embodiment, $R^7$ is, at each occurrence, independently selected from H, and $C_1$-$C_6$-alkyl. In another embodiment, $R^7$ is, at each occurrence, independently selected from $C_1$-$C_6$-haloalkyl, and C(O) $C_1$-$C_6$-alkyl.

$R^8$ may be selected from H and $C_1$-$C_6$-alkyl.

$R^9$ may be selected from H and $C_1$-$C_6$-alkyl.

$R^a$ may be independently selected from H, —OH, halo, $C_1$-$C_6$-alkyl, $C_1$-$C_6$-haloalkyl, —O—$C_1$-$C_6$-alkyl, and $C_1$-$C_6$-alkyl-OH.

$R^b$ may be independently selected from H and $C_1$-$C_6$-alkyl.

m may be 0, 1, 2, 3, or 4.

n may be 0, 1, 2, 3, or 4.

p may be 0, 1, 2, 3, or 4.

q may be 0 or 1.

a ==== line denotes an optionally double bond.

In embodiments, A is $CH_2$ or C=O. In embodiments, A is $CH_2$. In other embodiments, A is C=O.

$R^1$ may be H, $C_1$-$C_6$-alkyl, $C_1$-$C_6$-alkenyl, $C_1$-$C_6$-alkyl-OH, or $C_1$-$C_6$-haloalkyl. In embodiments, $R^1$ is H. In embodiments, $R^1$ is $C_1$-$C_6$-alkyl. In embodiments, $R^1$ is $C_1$-$C_6$-alkenyl. In embodiments, $R^1$ is $C_1$-$C_6$-alkyl-OH. In embodiments, $R^1$ is $C_1$-$C_6$-haloalkyl.

In embodiments, there may be 0, 1, 2, 3, or 4 $R^2$ substituents: m is 0, 1, 2, 3, or 4.

Each $R^2$ may be independently selected from —OH, halo, $C_1$-$C_6$-alkyl, $C_1$-$C_6$-alkylene, $C_0$-$C_6$-alkyl-$C_3$-$C_6$-cycloalkyl, $C_0$-$C_6$-alkyl-$C_2$-$C_6$-heterocycloalkyl, $C_0$-$C_6$-alkyl-OR$^6$, $C_0$-$C_6$-alkyl-N(R$^7$)$_2$, $C_0$-$C_6$-alkyl-SR$^8$, $C_0$-$C_6$-alkyl-S(O)R$^8$, $C_0$-$C_6$-alkyl-S(O)$_2$R$^8$, $C_0$-$C_6$-alkyl-C(O)OR$^9$, $C_0$-$C_6$-alkyl-OC(O)R$^9$, $C_0$-$C_6$-alkyl-OC(O)OR$^9$, $C_0$-$C_6$-alkyl-OC(O)N(R$^7$)$_2$, or $C_0$-$C_6$-alkyl-C(O)N(R$^7$)$_2$. In certain embodiments, m is 0 and there is no $R^2$ substitution. In certain embodiments, m is 1 and there is one $R^2$ substitution. In certain embodiments, m is 2 and there are two $R^2$ substitutions. In certain embodiments, m is 3 and there are three $R^2$ substitutions. In certain embodiments, m is 4 and there are four $R^2$ substitutions.

In certain embodiments, at least one $R^2$ is —OH. In certain embodiments, at least one $R^2$ is halo. In certain embodiments, at least one $R^2$ is $C_1$-$C_6$-alkyl. In certain embodiments, at least one $R^2$ is $C_1$-$C_6$-alkylene. In certain embodiments, at least one $R^2$ is $C_0$-$C_6$-alkyl-$C_3$-$C_6$-cycloalkyl. In certain embodiments, at least one $R^2$ is $C_0$-$C_6$-alkyl-$C_2$-$C_6$-heterocycloalkyl. In certain embodiments, at least one $R^2$ is $C_0$-$C_6$-alkyl-OR$^6$. In certain embodiments, at least one $R^2$ is $C_0$-$C_6$-alkyl-N(R$^7$)$_2$. In certain embodiments, at least one $R^2$ is $C_0$-$C_6$-alkyl-SR$^8$. In certain embodiments, at least one $R^2$ is $C_0$-$C_6$-alkyl-S(O)R$^8$. In certain embodiments, at least one $R^2$ is $C_0$-$C_6$-alkyl-S(O)$_2$R$^8$. In certain embodiments, at least one $R^2$ is $C_0$-$C_6$-alkyl-C(O)OR$^9$. In certain embodiments, at least one $R^2$ is $C_0$-$C_6$-alkyl-OC(O)R$^9$. In certain embodiments, at least one $R^2$ is $C_0$-$C_6$-alkyl-OC(O)OR$^9$. In certain embodiments, at least one $R^2$ is $C_0$-$C_6$-alkyl-OC(O)N(R$^7$)$_2$. In certain embodiments, at least one $R^2$ is $C_0$-$C_6$-alkyl-C(O)N(R$^7$)$_2$.

In certain embodiments, $R^2$ is substituted with 1, 2 or 3 groups. Each occurrence of $R^2$ as alkyl, cycloalkyl or heterocycloalkyl optionally may be substituted with —OH or halo. For example, $R^2$ may be alkyl, and the alkyl is substituted with —OH; or $R^2$ may be alkyl, and the alkyl is substituted with at least one fluorine atom. $R^2$ may be cycloalkyl, and the cycloalkyl is substituted with —OH; or $R^2$ may be cycloalkyl, and the cycloalkyl is substituted with at least one fluorine atom. $R^2$ may be heterocycloalkyl, and the heterocycloalkyl is substituted with —OH; or $R^2$ may be heterocycloalkyl, and the heterocycloalkyl is substituted with at least one fluorine atom.

In embodiments, there may be 0, 1, 2, 3, or 4 $R^3$ substituents: n is 0, 1, 2, 3, or 4. In certain embodiments, n is 0 and there is no $R^3$ substitution. In certain embodiments, n is 1 and there is one $R^3$ substitution. In certain embodiments, n is 2 and there are two $R^3$ substitutions. In certain embodiments, n is 3 and there are three $R^3$ substitutions. In certain embodiments, n is 4 and there are four $R^3$ substitutions.

Each $R^3$ may be independently selected from —OH, halo, $C_1$-$C_6$-alkyl, $C_1$-$C_6$-haloalkyl, —O—$C_1$-$C_6$-alkyl, and $C_1$-$C_6$-alkyl-OH. In certain embodiments, at least one $R^3$ is —OH. In certain embodiments, at least one $R^3$ is halo. In certain embodiments, at least one $R^3$ is $C_1$-$C_6$-alkyl. In certain embodiments, at least one $R^3$ is $C_1$-$C_6$-haloalkyl. In certain embodiments, at least one $R^3$ is —O—$C_1$-$C_6$-alkyl. In certain embodiments, at least one $R^3$ is $C_1$-$C_6$-alkyl-OH.

$R^4$ is selected from $(CR^aR^b)_p$—$C_1$-$C_9$-heteroaryl, $(CR^aR^b)_p$—$C_6$-$C_{12}$-aryl, $(CR^aR^b)_p$—$C_3$-$C_7$-cycloalkyl, and $(CR^aR^b)_p$—$C_2$-$C_6$-heterocycloalkyl, wherein heteroaryl, aryl, cycloalkyl, and heterocycloalkyl are optionally substituted with 1, 2, 3, or 4 groups, each independently selected from —OH, halo, —CN, —SF$_5$, $C_1$-$C_6$-alkyl, $C_1$-$C_6$-haloalkyl, —O—$C_1$-$C_6$-alkyl, and $C_1$-$C_6$-alkyl-OH. In certain embodiments, $R^4$ is $(CR^aR^b)_p$—$C_1$-$C_9$-heteroaryl optionally substituted with 1, 2, 3, or 4 groups, each independently selected from —OH, halo, —CN, —SF$_5$, $C_1$-$C_6$-alkyl, $C_1$-$C_6$-haloalkyl, —O—$C_1$-$C_6$-alkyl, and $C_1$-$C_6$-alkyl-OH. In certain embodiments, $R^4$ is $(CR^aR^b)_p$—$C_6$-$C_{12}$-aryl optionally substituted with 1, 2, 3, or 4 groups, each independently selected from —OH, halo, —CN, —SF$_5$, $C_1$-$C_6$-alkyl, $C_1$-$C_6$-haloalkyl, —O—$C_1$-$C_6$-alkyl, and $C_1$-$C_6$-alkyl-OH. In certain embodiments, $R^4$ is $(CR^aR^b)_p$—$C_3$-$C_7$-cycloalkyl optionally substituted with 1, 2, 3, or 4 groups, each independently selected from —OH, halo, —CN, —SF$_5$, $C_1$-$C_6$-alkyl, $C_1$-$C_6$-haloalkyl, —O—$C_1$-$C_6$-alkyl, and $C_1$-$C_6$-alkyl-OH. In certain embodiments, $R^4$ is $(CR^aR^b)_p$—$C_2$-$C_6$-heterocycloalkyl optionally substituted with 1, 2, 3, or 4 groups, each independently selected from —OH, halo, —CN, —SF$_5$, $C_1$-$C_6$-alkyl, $C_1$-$C_6$-haloalkyl, —O—$C_1$-$C_6$-alkyl, and $C_1$-$C_6$-alkyl-OH. In certain embodiments, $R^4$ is phenyl or pyridyl, wherein said phenyl or pyridyl is optionally substituted with 1, 2, 3, or 4 groups, each independently selected from halo, —CN, $C_1$-$C_6$-alkyl and $C_1$-$C_6$-haloalkyl. In a particular embodiment, $R^4$ is phenyl, wherein the phenyl is substituted with 1, 2, 3, or 4 groups, each independently selected from halo, —CN, $C_1$-$C_6$-alkyl and $C_1$-$C_6$-haloalkyl. In another particular embodiment, $R^4$ is pyridyl, wherein the pyridyl is substituted with 1, 2, 3, or 4 groups, each independently selected from halo, —CN, $C_1$-$C_6$-alkyl and $C_1$-$C_6$-haloalkyl.

$R^5$ may be selected from H, $C_1$-$C_6$-alkyl, and $C_1$-$C_6$-alkyl-OH. In a particular embodiment, $R^5$ is H.

$R^6$ may be selected from H, $C_1$-$C_6$-alkyl, $C_1$-$C_6$-haloalkyl, $C_1$-$C_6$-alkenyl, and $C_0$-$C_6$-alkyl-$C_3$-$C_6$-cycloalkyl. In a particular embodiment, $R^6$ is selected from H, $C_1$-$C_6$-alkyl, and $C_1$-$C_6$-haloalkyl.

$R^7$ may be independently selected from H, $C_1$-$C_6$-alkyl, and $C_1$-$C_6$-alkyl-OH. In a particular embodiment, $R^7$ is, at each occurrence, independently selected from H, and $C_1$-$C_6$-alkyl.

$R^8$ may be selected from H and $C_1$-$C_6$-alkyl.

$R^9$ may be selected from H and $C_1$-$C_6$-alkyl.

$R^a$ may be independently selected from H, —OH, halo, $C_1$-$C_6$-alkyl, $C_1$-$C_6$-haloalkyl, —O—$C_1$-$C_6$-alkyl, and $C_1$-$C_6$-alkyl-OH.

$R^b$ may be independently selected from H and $C_1$-$C_6$-alkyl.

m may be 0, 1, 2, 3, or 4.
n may be 0, 1, 2, 3, or 4.
p may be 0, 1, 2, 3, or 4.
q may be 0 or 1.

A ---- line denotes an optionally double bond.

In an embodiment of the compound of Formula I, A is C=O.

In another embodiment of the compound of Formula I, A is $CH_2$. In an embodiment of the compound of Formula I, q is 1.

In another embodiment of the compound of Formula I, $R^1$ is H, $C_1$-$C_6$-alkyl, or $C_1$-$C_6$-haloalkyl. In a particular embodiment, $R^1$ is $C_1$-$C_6$-alkyl. In another particular embodiment, $R^1$ is —$CH_3$ or —$CH_2CHF_2$. In a more particular embodiment, $R^1$ is —$CH_3$.

In another embodiment of the compound of Formula I, $R^4$ is phenyl or pyridyl, wherein said phenyl or pyridyl is optionally substituted with 1, 2, 3, or 4 groups, each independently selected from halo, —CN, $C_1$-$C_6$-alkyl and $C_1$-$C_6$-haloalkyl, and $R^5$ is H.

In another particular embodiment of Formula I, $R^1$ is $C_1$-$C_6$-alkyl; $R^2$ is $C_1$-$C_6$-alkyl or $C_0$-$C_6$-alkyl-$OR^6$, wherein alkyl is substituted with halo, and $R^6$ is H or $C_1$-$C_6$-haloalkyl; $R^3$ is $C_1$-$C_6$-alkyl; $R^4$ is phenyl substituted with 1 or 2 groups, each independently selected from halo and —CN; $R^5$ is H; m is 1; and n is 1.

In another particular embodiment of Formula I, $R^1$ is methyl; $R^2$ is —$CH_2F$ or $CH_2$—O—$CH_2CHF_2$; $R^3$ is methyl; $R^4$ is phenyl substituted with 1 or 2 groups, each independently selected from F and —CN; $R^5$ is H; m is 1; and n is 1.

In another particular embodiment of Formula I, $R^1$ is $C_1$-$C_6$-alkyl, $R^2$ is —$CH_2F$, $R^4$ is phenyl or pyridyl, wherein the phenyl or pyridyl is substituted with 1-3 groups independently selected from halo, —CN, —$SF_5$, $C_1$-$C_6$-alkyl, and $C_1$-$C_6$-haloalkyl, $R^5$ is H, and n is 0.

In another particular embodiment of Formula I, $R^1$ is $C_1$-$C_6$-alkyl, $R^2$ is —$CH_2OCH_2CHF_2$, $R^4$ is phenyl or pyridyl, wherein the phenyl or pyridyl is substituted with 1-3 groups independently selected from halo, —CN, —$SF_5$, $C_1$-$C_6$-alkyl, and $C_1$-$C_6$-haloalkyl, $R^5$ is H, n is 1, and $R^3$ is $C_1$-$C_6$-alkyl.

In another embodiment, the compound of Formula I has the structure of Formula II:

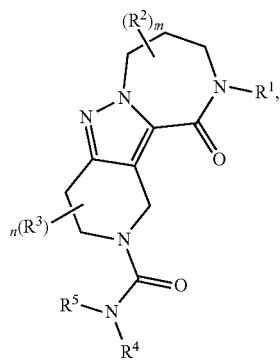

II or a pharmaceutically acceptable salt thereof.

In one embodiment of the compound of Formula II, $R^1$ is H, $C_1$-$C_6$-alkyl, or $C_1$-$C_6$-haloalkyl. In a particular embodiment, $R^1$ is $C_1$-$C_6$-alkyl. In another particular embodiment, $R^1$ is —$CH_3$ or —$CH_2CHF_2$. In a more particular embodiment, $R^1$ is —$CH_3$.

In another embodiment of the compound of Formula II, $R^4$ is phenyl or pyridyl, wherein said phenyl or pyridyl is optionally substituted with 1, 2, 3, or 4 groups, each independently selected from halo, —CN, $C_1$-$C_6$-alkyl and $C_1$-$C_6$-haloalkyl, and $R^5$ is H.

In another embodiment, the compound of Formula I or Formula II has the structure of Formula III:

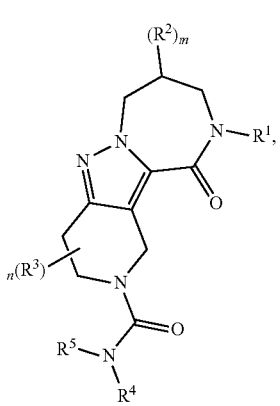

III or a pharmaceutically acceptable salt thereof, wherein m is 0, 1, or 2.

In one embodiment of the compound of Formula III, $R^1$ is H, $C_1$-$C_6$-alkyl, or $C_1$-$C_6$-haloalkyl. In a particular embodiment, $R^1$ is $C_1$-$C_6$-alkyl. In another particular embodiment, $R^1$ is —$CH_3$ or —$CH_2CHF_2$. In a more particular embodiment, $R^1$ is —$CH_3$ In another embodiment of the compound of Formula III, $R^4$ is phenyl or pyridyl, wherein said phenyl or pyridyl is optionally substituted with 1, 2, 3, or 4 groups, each independently selected from halo, —CN, $C_1$-$C_6$-alkyl and $C_1$-$C_6$-haloalkyl, and $R^5$ is H.

In another embodiment, provided herein are compounds having the structure of Formula V:

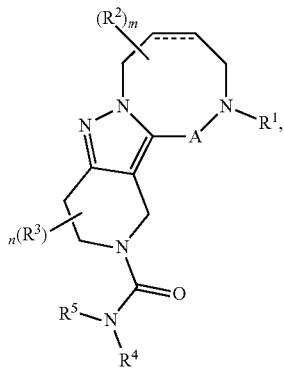

or a pharmaceutically acceptable salt thereof, wherein
A is $CH_2$ or $C=O$;
$R^1$ is H, $C_1$-$C_6$-alkyl, $C_1$-$C_6$-alkenyl, $C_1$-$C_6$-alkyl-OH, or $C_1$-$C_6$-haloalkyl;
$R^2$ is, at each occurrence, independently selected from —OH, halo, $C_1$-$C_6$-alkyl, $C_1$-$C_6$-alkylene, $C_0$-$C_6$-alkyl-$C_3$-$C_6$-cycloalkyl, $C_0$-$C_6$-alkyl-$C_2$-$C_6$-heterocycloalkyl, $C_0$-$C_6$-alkyl-$OR^6$, $C_0$-$C_6$-alkyl-$N(R^7)_2$, $C_0$-$C_6$-alkyl-$SR^8$, $C_0$-$C_6$-alkyl-$S(O)R^8$, $C_0$-$C_6$-alkyl-$S(O)_2R^8$, $C_0$-$C_6$-alkyl-$C(O)OR^9$, $C_0$-$C_6$-alkyl-$OC(O)R^9$, $C_0$-$C_6$-alkyl-$OC(O)OR^9$, $C_0$-$C_6$-alkyl-$OC(O)N(R^7)_2$, and $C_0$-$C_6$-alkyl-$C(O)N(R^7)_2$, wherein alkyl, alkylene, cycloalkyl, and heterocycloalkyl are optionally substituted with 1, 2, or 3 groups, each independently selected from —OH and halo; or
two $R^2$ groups together form a $C_3$-$C_6$ spiro cycloalkyl, wherein the cyloalkyl is optionally substituted with 1, 2, or 3 groups, each individually selected from —OH and halo;
$R^3$ is, at each occurrence, independently selected from —OH, halo, $C_1$-$C_6$-alkyl, $C_1$-$C_6$-haloalkyl, —O—$C_1$-$C_6$-alkyl, and $C_1$-$C_6$-alkyl-OH;
$R^4$ is selected from $(CR^aR^b)_p$—$C_1$-$C_9$-heteroaryl, $(CR^aR^b)_p$—$C_6$-$C_{12}$-aryl, $(CR^aR^b)_p$—$C_3$-$C_7$-cycloalkyl, and $(CR^aR^b)_p$—$C_2$-$C_6$-heterocycloalkyl, wherein heteroaryl, aryl, cycloalkyl, and heterocycloalkyl are optionally substituted with 1, 2, 3, or 4 groups, each independently selected from —OH, halo, —CN, —$SF_5$, $C_1$-$C_6$-alkyl, $C_1$-$C_6$-haloalkyl, —O—$C_1$-$C_6$-alkyl, and $C_1$-$C_6$-alkyl-OH;
$R^5$ is selected from H, $C_1$-$C_6$-alkyl, and $C_1$-$C_6$-alkyl-OH;
$R^6$ is selected from H, $C_1$-$C_6$-alkyl, $C_1$-$C_6$-haloalkyl, $C_1$-$C_6$-alkenyl, and $C_0$-$C_6$-alkyl-$C_3$-$C_6$-cycloalkyl;
$R^7$ is, at each occurrence, independently selected from H, $C_1$-$C_6$-alkyl, $C_1$-$C_6$-haloalkyl, C(O) $C_1$-$C_6$-alkyl and $C_1$-$C_6$-alkyl-OH;
$R^8$ is selected from H and $C_1$-$C_6$-alkyl;
$R^9$ is selected from H and $C_1$-$C_6$-alkyl;
$R^a$ is, at each occurrence, independently selected from H, —OH, halo, $C_1$-$C_6$-alkyl, $C_1$-$C_6$-haloalkyl, —O—$C_1$-$C_6$-alkyl, and $C_1$-$C_6$-alkyl-OH;
$R^b$ is, at each occurrence, independently selected from H and $C_1$-$C_6$-alkyl;
m is 0, 1, 2, 3, or 4;
n is 0, 1, 2, 3, or 4;
p is 0, 1, 2, 3, or 4; and
a ==== line denotes an optionally double bond.

In one embodiment of the compound of Formula V, A is $C=O$. In another embodiment, $R^1$ is H or $C_1$-$C_6$-alkyl. In another embodiment, $R^1$ is —$CH_3$. In a further embodiment, m is 0.

In another embodiment of the compound of Formula V, $R^4$ is $(CR^aR^b)_p$—$C_1$-$C_5$-heteroaryl or $(CR^aR^b)_p$—$C_6$-aryl, wherein heteroaryl and aryl are optionally substituted with 1, 2, 3, or 4 groups, each independently selected from —OH, halo, —CN, —$SF_5$, $C_1$-$C_6$-alkyl, $C_1$-$C_6$-haloalkyl, —O—$C_1$-$C_6$-alkyl, and $C_1$-$C_6$-alkyl-OH;
$R^a$ is H or $C_1$-$C_6$-alkyl;
$R^b$ is H or $C_1$-$C_6$-alkyl; and
p is 0 or 1.

In a further embodiment of the compound of Formula V, A is $C=O$;
$R^1$ is —$CH_3$;
$R^4$ is $(CR^aR^b)_p$—$C_6$-$C_{12}$-aryl, wherein aryl is optionally substituted with 1, 2, 3, or 4 groups, each independently selected from halo, —CN, and $C_1$-$C_6$-alkyl;
$R^5$ is H;
m is 0;
n is 0; and
p is 0.

In an embodiment of the compound of any one of Formulas I, II, III, or V, m is 0, 1, or 2; and
$R^2$ is, at each occurrence, independently selected from —OH, halo, $C_1$-$C_6$-alkyl, $C_1$-$C_6$-alkenyl, $C_0$-$C_6$-alkyl-$OR^6$, $C_0$-$C_6$-alkyl-$N(R^7)_2$, $C_0$-$C_6$-alkyl-$C_3$-$C_6$-cycloalkyl, $C_0$-$C_6$-alkyl-$C_2$-$C_6$-heterocycloalkyl, $C_0$-$C_6$-alkyl-$SR^8$, $C_0$-$C_6$-alkyl-$S(O)R^8$, $C_0$-$C_6$-alkyl-$S(O)_2R^8$, $C_0$-$C_6$-alkyl-$C(O)OR^9$, and $C_0$-$C_6$-alkyl-$C(O)N(R^7)_2$, wherein alkyl, alkylene, cycloalkyl, and heterocycloalkyl are optionally substituted with 1 or 2 groups, each independently selected from —OH and halo; or
two $R^2$ groups together form a $C_3$-$C_6$ spiro cycloalkyl, wherein the cyloalkyl is optionally substituted with 1, 2, or 3 groups, each individually selected from —OH and halo.

In an embodiment of the compound of any one of Formulas I, II, III, or V, m is 1 or 2; and
$R^2$ is, at each occurrence, independently selected from —$CH_2N(H)(C(O)$—$CH_3)$, —$CH_2N(H)CH_2CHF_2$, $CH_2N(H)CH_2CF_3$, or $CH(OH)CH=CH_2$; or two $R^2$ groups together form a spiro-cyclobutyl, which is substituted with —OH.

In an embodiment of the compound of any one of Formulas I, II, III, or V, m is 0, 1, or 2; and
$R^2$ is, at each occurrence, independently selected from —OH, halo, $C_1$-$C_6$-alkyl, $C_1$-$C_6$-alkenyl, $C_0$-$C_6$-alkyl-$OR^6$, $C_0$-$C_6$-alkyl-$N(R^7)_2$, $C_0$-$C_6$-alkyl-$C_3$-$C_6$-cycloalkyl, $C_0$-$C_6$-alkyl-$C_2$-$C_6$-heterocycloalkyl, $C_0$-$C_6$-alkyl-$SR^8$, $C_0$-$C_6$-alkyl-$S(O)R^8$, $C_0$-$C_6$-alkyl-$S(O)_2R^8$, $C_0$-$C_6$-alkyl-$C(O)OR^9$, and $C_0$-$C_6$-alkyl-$C(O)N(R^7)_2$, wherein alkyl, cycloalkyl, and heterocycloalkyl are optionally substituted with 1 or 2 groups, each independently selected from —OH and halo.

In an embodiment of the compound of any one of Formulas I, II, III, or V, m is 1 or 2; and $R^2$ is, at each occurrence, independently selected from =$CH_2$, —$CH_2OH$, —OH, —F, —$CH_3$, —$CHF_2$, —$OCH_3$, —$OCH_2CH_3$, —$OCH_2CHF_2$, —$NH_2$, —$N(CH_3)_2$, morpholinyl, azetidinyl, pyrrolidinyl, —$SCH_3$, —$S(O)CH_3$, —$S(O)_2CH_3$, —$CH_2C(O)OCH_3$, —$CH_2CH_2OH$, —$C(O)OH$, —$C(O)OCH_3$, —$C(O)OCH_2CH_3$, —$C(O)NHCH_3$, —$C(O)N(CH_3)_2$, —$C(OH)(CH_3)_2$, —$CH(OH)CH_3$, —$CH(OH)CH_2CH_3$, and —$CH(OH)$-cyclopropyl, wherein morpholinyl, azetidinyl, and pyrrolidinyl are optionally substituted with 1 or 2 groups, each independently selected from —OH and halo. In an embodiment of the compound of any one of Formulas I, II, or III, m is 0, 1, or 2; and
$R^2$ is, at each occurrence, independently selected from —OH, halo, $C_1$-$C_6$-alkyl, $C_1$-$C_6$-alkenyl, $C_0$-$C_6$-alkyl-$OR^6$, $C_0$-$C_6$-alkyl-$N(R^7)_2$, $C_0$-$C_6$-alkyl-$C_3$-$C_6$-cycloalkyl, $C_0$-$C_6$- alkyl-$C_2$-$C_6$-heterocycloalkyl, $C_0$-$C_6$-alkyl-$SR^8$, $C_0$-$C_6$-alkyl-$S(O)R^8$, $C_0$-$C_6$-alkyl-$S(O)_2R^8$, $C_0$-$C_6$-alkyl-$C(O)OR^9$, and $C_0$-$C_6$-alkyl-$C(O)N(R^7)_2$, wherein alkyl, cycloalkyl, and heterocycloalkyl are optionally substituted with 1 or 2 groups, each independently selected from —OH and halo.

In an embodiment of the compound of any one of Formulas I, II, or III, m is 1 or 2; and $R^2$ is, at each occurrence, independently selected from =$CH_2$, —$CH_2OH$, —OH, —F, —$CH_3$, —$CHF_2$, —$OCH_3$, —$OCH_2CH_3$, —$OCH_2CHF_2$, —$NH_2$, —$N(CH_3)_2$, morpholinyl, azetidinyl, pyrrolidinyl, —$SCH_3$, —$S(O)CH_3$, —$S(O)_2CH_3$, —$CH_2C(O)OCH_3$, —$CH_2CH_2OH$, —$C(O)OH$, —$C(O)OCH_3$, —$C(O)OCH_2CH_3$, —$C(O)NHCH_3$, —$C(O)N(CH_3)_2$, —$C(OH)(CH_3)_2$, —$CH(OH)CH_3$, —$CH(OH)CH_2CH_3$, and —$CH(OH)$-cyclopropyl, wherein morpholinyl, azetidinyl, and pyrrolidinyl are optionally substituted with 1 or 2 groups, each independently selected from —OH and halo.

In an embodiment of the compound of any one of Formulas I, II, or III, n is 0, 1, or 2; and $R^3$ is, at each occurrence, selected from —OH, halo, and $C_1$-$C_6$-alkyl.

In an embodiment of the compound of any one of Formula V, n is 0, 1, or 2; and $R^3$ is, at each occurrence, selected from —OH, halo, and $C_1$-$C_6$-alkyl.

In an embodiment of the compound of any one of Formulas I, II, III, or V, $R^4$ is $(CR^aR^b)_p$—$C_1$-$C_5$-heteroaryl or $(CR^aR^b)_p$—$C_6$-aryl, wherein heteroaryl and aryl are optionally substituted with 1, 2, or 3 groups, each independently selected from —OH, halo, —CN, —$SF_5$, $C_1$-$C_6$-alkyl, $C_1$-$C_6$-haloalkyl, —O—$C_1$-$C_6$-alkyl, and $C_1$-$C_6$-alkyl-OH;

$R^a$ is H or $C_1$-$C_6$-alkyl;

$R^b$ is H or $C_1$-$C_6$-alkyl; and p is 0 or 1.

In an embodiment of the compound of any one of Formulas I, II, III, or V, $R^4$ is $C_1$-$C_5$-heteroaryl or $C_6$-aryl, any of which is optionally substituted with 1, 2, or 3 groups, each independently selected from halo, —CN, $C_1$-$C_6$-alkyl, and $C_1$-$C_6$-haloalkyl.

In a further embodiment of the compound of any one of Formulas I, II, III, or V, $R^4$ is phenyl or pyridinyl, any of which is optionally substituted with 1, 2, or 3 groups, each independently selected from halo, —CN, $C_1$-$C_6$-alkyl, and $C_1$-$C_6$-haloalkyl.

In an embodiment of the compound of any one of Formulas I, II, III, or V, $R^4$ is selected from the group consisting of:

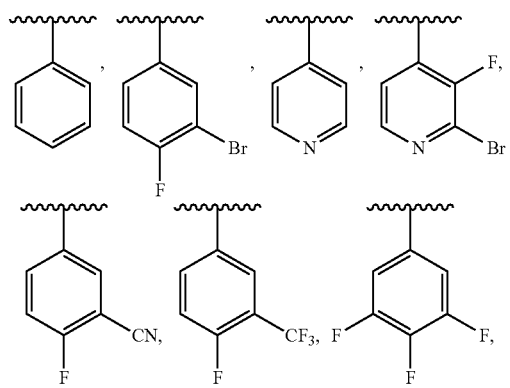

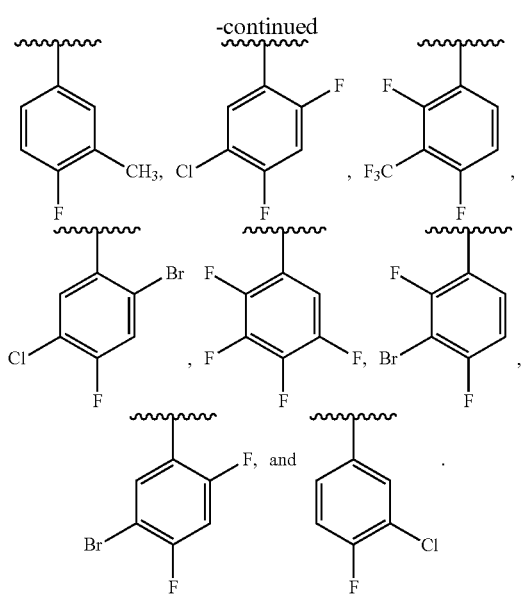

In another embodiment of the compound of any one of Formulas I, II, III, or V, $R^4$ is selected from the group consisting of:

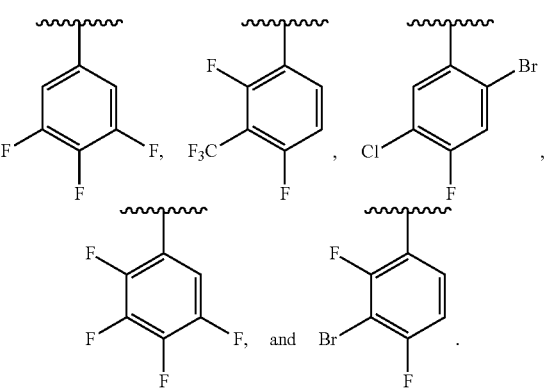

In another embodiment of the compound of any one of Formulas I, II, III, or V, $R^4$ is

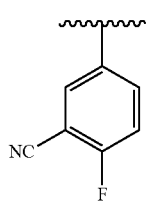

In an embodiment of the compound of any one of Formulas I, II, or III, $R^4$ is $(CR^aR^b)_p$—$C_1$-$C_5$-heteroaryl or $(CR^aR^b)_p$—$C_6$-aryl, wherein heteroaryl and aryl are optionally substituted with 1, 2, or 3 groups, each independently selected from —OH, halo, —CN, —$SF_5$, $C_1$-$C_6$-alkyl, $C_1$-$C_6$-haloalkyl, —O—$C_1$-$C_6$-alkyl, and $C_1$-$C_6$-alkyl-OH;

$R^a$ is H or $C_1$-$C_6$-alkyl;

$R^b$ is H or $C_1$-$C_6$-alkyl; and p is 0 or 1.

In an embodiment of the compound of any one of Formulas I, II, or III, $R^4$ is $C_1$-$C_5$-heteroaryl or $C_6$-aryl, any of which is optionally substituted with 1, 2, or 3 groups, each independently selected from halo, —CN, $C_1$-$C_6$-alkyl, and $C_1$-$C_6$-haloalkyl.

In a further embodiment of the compound of any one of Formulas I, II, or III, $R^4$ is phenyl or pyridinyl, any of which is optionally substituted with 1, 2, or 3 groups, each independently selected from halo, —CN, $C_1$-$C_6$-alkyl, and $C_1$-$C_6$-haloalkyl.

In an embodiment of the compound of any one of Formulas I, II, or III, $R^4$ is selected from the group consisting of:

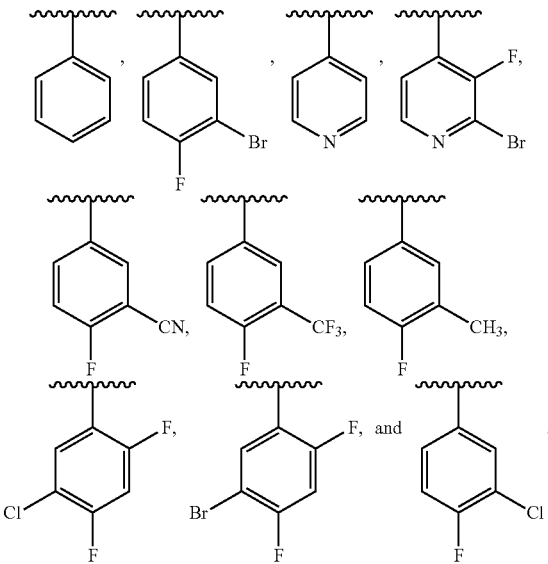

In another embodiment of the compound of any one of Formulas I, II, or III, $R^4$ is selected from the group consisting of:

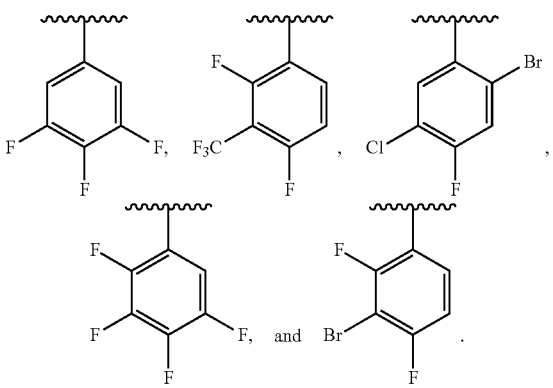

In an embodiment of the compound of any one of Formulas I, II, or III, $R^5$ is H or $C_1$-$C_6$-alkyl.

In an embodiment of the compound of any one of Formulas I, II, or III, $R^5$ is H.

In an embodiment of the compound of any one of Formula V, $R^5$ is H or $C_1$-$C_6$-alkyl.

In an embodiment of the compound of any one of Formula V, $R^5$ is H. In an embodiment of the compound of any one of Formulas I, II, or III, A is C=O;
$R^1$ is $C_1$-$C_6$-alkyl;

$R^2$ is, at each occurrence, independently selected from —OH, halo, $C_1$-$C_6$-alkyl, $C_1$-$C_6$-alkylene, $C_0$-$C_6$-alkyl-$C_3$-$C_6$-cycloalkyl, $C_0$-$C_6$-alkyl-$C_2$-$C_6$-heterocycloalkyl, $C_0$-$C_6$-alkyl-$OR^6$, $C_0$-$C_6$-alkyl-$N(R^7)_2$, $C_0$-$C_6$-alkyl-SR, $C_0$-$C_6$-alkyl-S(O)R, $C_0$-$C_6$-alkyl-S(O)$_2R^8$, $C_0$-$C_6$-alkyl-C(O)$OR^9$, $C_0$-$C_6$-alkyl-OC(O)$R^9$, $C_0$-$C_6$-alkyl-OC(O)$OR^9$, $C_0$-$C_6$-alkyl-OC(O)N($R^7$)$_2$, and $C_0$-$C_6$-alkyl-C(O)N($R^7$)$_2$, wherein alkyl, alkylene, cycloalkyl, and heterocycloalkyl are optionally substituted with 1, 2, or 3 groups, each independently selected from —OH and halo; or two $R^2$ groups together form a $C_3$-$C_6$ spiro cycloalkyl, wherein the cyloalkyl is optionally substituted with 1, 2, or 3 groups, each individually selected from —OH and halo;

$R^4$ is $(CR^aR^b)_p$—$C_6$-$C_{12}$-aryl, wherein aryl is optionally substituted with 1, 2, 3, or 4 groups, each independently selected from halo, —CN, and $C_1$-$C_6$-alkyl;

$R^5$ is H;
$R^6$ is selected from H, $C_1$-$C_6$-alkyl, $C_1$-$C_6$-haloalkyl, $C_1$-$C_6$-alkenyl, and $C_0$-$C_6$-alkyl-$C_3$-$C_6$-cycloalkyl;
$R^7$ is, at each occurrence, independently selected from H, $C_1$-$C_6$-alkyl, $C_1$-$C_6$-haloalkyl, C(O) $C_1$-$C_6$-alkyl and $C_1$-$C_6$-alkyl-OH;
$R^8$ is selected from H and $C_1$-$C_6$-alkyl;
$R^9$ is selected from H and $C_1$-$C_6$-alkyl;
m is 0, 1 or 2;
n is 0;
p is 0; and
q is 1.

In another embodiment of the compound of any one of Formulas I, II, or III,

A is C=O;
$R^1$ is $C_1$-$C_6$-alkyl;
$R^2$ is, at each occurrence, independently selected from —OH, halo, $C_1$-$C_6$-alkyl, $C_1$-$C_6$-alkylene, $C_0$-$C_6$-alkyl-$C_3$-$C_6$-cycloalkyl, $C_0$-$C_6$-alkyl-$C_2$-$C_6$-heterocycloalkyl, $C_0$-$C_6$-alkyl-$OR^6$, $C_0$-$C_6$-alkyl-$N(R^7)_2$, $C_0$-$C_6$-alkyl-$SR^8$, $C_0$-$C_6$-alkyl-S(O)$R^8$, $C_0$-$C_6$-alkyl-S(O)$_2R^8$, $C_0$-$C_6$-alkyl-C(O)$OR^9$, and $C_0$-$C_6$-alkyl-C(O)N($R^7$)$_2$, wherein alkyl, alkylene, cycloalkyl, and heterocycloalkyl are optionally substituted with 1, 2, or 3 groups, each independently selected from —OH and halo; or two $R^2$ groups together form a $C_3$-$C_6$ spiro cycloalkyl, wherein the cyloalkyl is optionally substituted with 1, 2, or 3 groups, each individually selected from —OH and halo;

$R^4$ is $(CR^aR^b)_p$—$C_6$-$C_{12}$-aryl, wherein aryl is optionally substituted with 1, 2, 3, or 4 groups, each independently selected from halo, —CN, and $C_1$-$C_6$-alkyl;

$R^5$ is H;
$R^6$ is selected from H, $C_1$-$C_6$-alkyl, and $C_1$-$C_6$-haloalkyl;
$R^7$ is, at each occurrence, independently selected from H, $C_1$-$C_6$-alkyl, $C_1$-$C_6$-haloalkyl, C(O) $C_1$-$C_6$-alkyl and $C_1$-$C_6$-alkyl-OH;
$R^8$ is $C_1$-$C_6$-alkyl;
$R^9$ is selected from H and $C_1$-$C_6$-alkyl;
m is 0, 1 or 2;
n is 0;
p is 0; and
q is 1.

In an embodiment of the compound of any one of Formulas I, II, or III,

A is C=O;
$R^1$ is $C_1$-$C_6$-alkyl;
$R^2$ is, at each occurrence, independently selected from —OH, halo, $C_1$-$C_6$-alkyl, $C_1$-$C_6$-alkylene, $C_0$-$C_6$-alkyl-$C_3$-$C_6$-cycloalkyl, $C_0$-$C_6$-alkyl-$C_2$-$C_6$-heterocycloalkyl, $C_0$-$C_6$-alkyl-$OR^6$, $C_0$-$C_6$-alkyl-$N(R^7)_2$, $C_0$-$C_6$-alkyl-$SR^8$, $C_0$-$C_6$-alkyl-S(O)$R^8$, $C_0$-$C_6$-alkyl-S(O)$_2R^8$, $C_0$-$C_6$-alkyl-C(O)$OR^9$, $C_0$-$C_6$-alkyl-OC(O)$R^9$, $C_0$-$C_6$-alkyl-OC(O)O$R^9$, $C_0$-$C_6$-alkyl-OC(O)N($R^7$)$_2$, and $C_0$-$C_6$-alkyl-C(O)N($R^7$)$_2$, wherein alkyl, cycloalkyl, and heterocycloalkyl are optionally substituted with 1, 2, or 3 groups, each independently selected from —OH and halo;

$R^4$ is $(CR^aR^b)_p$—$C_6$-$C_{12}$-aryl, wherein aryl is optionally substituted with 1, 2, 3, or 4 groups, each independently selected from halo, —CN, and $C_1$-$C_6$-alkyl;

$R^5$ is H;

$R^6$ is selected from H, $C_1$-$C_6$-alkyl, $C_1$-$C_6$-haloalkyl, $C_1$-$C_6$-alkenyl, and $C_0$-$C_6$-alkyl-$C_3$-$C_6$-cycloalkyl;

$R^7$ is, at each occurrence, independently selected from H, $C_1$-$C_6$-alkyl, and $C_1$-$C_6$-alkyl-OH;

$R^8$ is selected from H and $C_1$-$C_6$-alkyl;

$R^9$ is selected from H and $C_1$-$C_6$-alkyl;

m is 0, 1 or 2;

n is 0;

p is 0; and q is 1.

In another embodiment of the compound of any one of Formulas I, II, or III,

A is C=O;

$R^1$ is $C_1$-$C_6$-alkyl;

$R^2$ is, at each occurrence, independently selected from —OH, halo, $C_1$-$C_6$-alkyl, $C_1$-$C_6$-alkylene, $C_0$-$C_6$-alkyl-$C_3$-$C_6$-cycloalkyl, $C_0$-$C_6$-alkyl-$C_2$-$C_6$-heterocycloalkyl, $C_0$-$C_6$-alkyl-O$R^6$, $C_0$-$C_6$-alkyl-N($R^7$)$_2$, $C_0$-$C_6$-alkyl-S$R^8$, $C_0$-$C_6$-alkyl-S(O)$R^8$, $C_0$-$C_6$-alkyl-S(O)$_2$$R^8$, $C_0$-$C_6$-alkyl-C(O)O$R^9$, and $C_0$-$C_6$-alkyl-C(O)N($R^7$)$_2$, wherein alkyl, cycloalkyl, and heterocycloalkyl are optionally substituted with 1, 2, or 3 groups, each independently selected from —OH and halo;

$R^4$ is $(CR^aR^b)_p$—$C_6$-$C_{12}$-aryl, wherein aryl is optionally substituted with 1, 2, 3, or 4 groups, each independently selected from halo, —CN, and $C_1$-$C_6$-alkyl;

$R^5$ is H;

$R^6$ is selected from H, $C_1$-$C_6$-alkyl, and $C_1$-$C_6$-haloalkyl;

$R^7$ is, at each occurrence, independently selected from H, and $C_1$-$C_6$-alkyl;

$R^8$ is $C_1$-$C_6$-alkyl;

$R^9$ is selected from H and $C_1$-$C_6$-alkyl;

m is 0, 1 or 2;

n is 0;

p is 0; and q is 1.

In an embodiment of the compound of any one of Formulas I, II, or III,

A is C=O;

$R^1$ is $C_1$-$C_6$-alkyl;

$R^2$ is, at each occurrence, independently selected from —OH, halo, $C_1$-$C_6$-alkyl, $C_1$-$C_6$-alkylene, $C_0$-$C_6$-alkyl-$C_3$-$C_6$-cycloalkyl, $C_0$-$C_6$-alkyl-$C_2$-$C_6$-heterocycloalkyl, $C_0$-$C_6$-alkyl-O$R^6$, $C_0$-$C_6$-alkyl-N($R^7$)$_2$, $C_0$-$C_6$-alkyl-S$R^8$, $C_0$-$C_6$-alkyl-S(O)$R^8$, $C_0$-$C_6$-alkyl-S(O)$_2$$R^8$, $C_0$-$C_6$-alkyl-C(O)O$R^9$, $C_0$-$C_6$-alkyl-OC(O)$R^9$, $C_0$-$C_6$-alkyl-OC(O)O$R^9$, $C_0$-$C_6$-alkyl-OC(O)N($R^7$)$_2$, and $C_0$-$C_6$-alkyl-C(O)N($R^7$)$_2$, wherein alkyl, cycloalkyl, and heterocycloalkyl are optionally substituted with 1, 2, or 3 groups, each independently selected from —OH and halo;

$R^4$ is $(CR^aR^b)_p$—$C_6$-$C_{12}$-aryl, wherein aryl is optionally substituted with 1, 2, 3, or 4 groups, each independently selected from halo, —CN, and $C_1$-$C_6$-alkyl;

$R^5$ is H;

$R^6$ is selected from H, $C_1$-$C_6$-alkyl, $C_1$-$C_6$-haloalkyl, $C_1$-$C_6$-alkenyl, and $C_0$-$C_6$-alkyl-$C_3$-$C_6$-cycloalkyl;

$R^7$ is, at each occurrence, independently selected from H, $C_1$-$C_6$-alkyl, and $C_1$-$C_6$-alkyl-OH;

$R^8$ is selected from H and $C_1$-$C_6$-alkyl;

$R^9$ is selected from H and $C_1$-$C_6$-alkyl;

m is 0, 1 or 2;

n is 0;

p is 0; and q is 1.

In another embodiment of the compound of any one of Formulas I, II, or III,

A is C=O;

$R^1$ is $C_1$-$C_6$-alkyl;

$R^2$ is, at each occurrence, independently selected from —OH, halo, $C_1$-$C_6$-alkyl, $C_1$-$C_6$-alkylene, $C_0$-$C_6$-alkyl-$C_3$-$C_6$-cycloalkyl, $C_0$-$C_6$-alkyl-$C_2$-$C_6$-heterocycloalkyl, $C_0$-$C_6$-alkyl-O$R^6$, $C_0$-$C_6$-alkyl-N($R^7$)$_2$, $C_0$-$C_6$-alkyl-S$R^8$, $C_0$-$C_6$-alkyl-S(O)$R^8$, $C_0$-$C_6$-alkyl-S(O)$_2$$R^8$, $C_0$-$C_6$-alkyl-C(O)O$R^9$, and $C_0$-$C_6$-alkyl-C(O)N($R^7$)$_2$, wherein alkyl, cycloalkyl, and heterocycloalkyl are optionally substituted with 1, 2, or 3 groups, each independently selected from —OH and halo;

$R^4$ is $(CR^aR^b)_p$—$C_6$-$C_{12}$-aryl, wherein aryl is optionally substituted with 1, 2, 3, or 4 groups, each independently selected from halo, —CN, and $C_1$-$C_6$-alkyl;

$R^5$ is H;

$R^6$ is selected from H, $C_1$-$C_6$-alkyl, and $C_1$-$C_6$-haloalkyl;

$R^7$ is, at each occurrence, independently selected from H, and $C_1$-$C_6$-alkyl;

$R^8$ is $C_1$-$C_6$-alkyl;

$R^9$ is selected from H and $C_1$-$C_6$-alkyl;

m is 0, 1 or 2;

n is 0;

p is 0; and q is 1.

In another embodiment, the compound of Formula III has the structure of Formula IV wherein m is 1 or 2; and $R^2$ is, at each occurrence, independently selected from —CH$_2$N(H)C(O)—CH$_3$), —CH$_2$N(H)CH$_2$CHF$_2$, —CH$_2$N(H)CH$_2$CF$_3$, and —CH(OH)CH=CH$_2$; or two $R^2$ groups together form a spiro-cyclobutyl, which is substituted with —OH. In another embodiment, $R^2$ is, at each occurrence, independently selected from =CH$_2$, —CH$_2$OH, —OH, —F, —CH$_3$, —CHF$_2$, —OCH$_3$, —OCH$_2$CH$_3$, —OCH$_2$CHF$_2$, —NH$_2$, —N(CH$_3$)$_2$, morpholinyl, azetidinyl, pyrrolidinyl, —SCH$_3$, —S(O)CH$_3$, —S(O)$_2$CH$_3$, —CH$_2$C(O)OCH$_3$, —CH$_2$CH$_2$OH, —C(O)OH, —C(O)OCH$_3$, —C(O)OCH$_2$CH$_3$, —C(O)NHCH$_3$, —C(O)N(CH$_3$)$_2$, —C(OH)(CH$_3$)$_2$, —CH(OH)CH$_3$, —CH(OH)CH$_2$CH$_3$, and —CH(OH)-cyclopropyl, wherein morpholinyl, azetidinyl, and pyrrolidinyl are optionally substituted with 1 or 2 groups, each independently selected from —OH and halo.

In another embodiment of Formula IV,
m is 1 or 2; and
$R^2$ is, at each occurrence, independently selected from =$CH_2$, —$CH_2OH$, —OH, —F, —$CH_3$, —$CHF_2$, —$OCH_3$, —$OCH_2CH_3$, —$OCH_2CHF_2$, —$NH_2$, —$N(CH_3)_2$, morpholinyl, azetidinyl, pyrrolidinyl, —$SCH_3$, —$S(O)CH_3$, —$S(O)_2CH_3$, —$CH_2C(O)OCH_3$, —$CH_2CH_2OH$, —C(O)OH, —$C(O)OCH_3$, —$C(O)OCH_2CH_3$, —$C(O)NHCH_3$, —$C(O)N(CH_3)_2$, —$C(O)(CH_3)_2$, —$CH(OH)CH_3$, —CH(OH)$CH_2CH_3$, and —CH(OH)-cyclopropyl, wherein morpholinyl, azetidinyl, and pyrrolidinyl are optionally substituted with 1 or 2 groups, each independently selected from —OH and halo.

Provided herein are compounds according to the following embodiments:

In one embodiment of Formula I, A is C=O; $R^1$ is $C_1$-$C_6$-alkyl; $R^4$ is $(CR^aR^b)_p$—$C_6$-$C_{12}$-aryl substituted with at least one halo; $R^5$ is H; n is 0; p is 0; m is 1 or 2; and each $R^2$ is independently selected from —OH, halo, $C_1$-$C_6$-alkyl, $C_1$-$C_6$-alkylene, $C_0$-$C_6$-alkyl-$C_3$-$C_6$-cycloalkyl, $C_0$-$C_6$-alkyl-$C_2$-$C_6$-heterocycloalkyl, $C_0$-$C_6$-alkyl-$OR^6$, $C_0$-$C_6$-alkyl-$N(R^7)_2$, $C_0$-$C_6$-alkyl-$SR^8$, $C_0$-$C_6$-alkyl-$S(O)R^8$, $C_0$-$C_6$-alkyl-$S(O)_2R^8$, $C_0$-$C_6$-alkyl-$C(O)OR^9$, $C_0$-$C_6$-alkyl-OC(O)$R^9$, $C_0$-$C_6$-alkyl-OC(O)$OR^9$, $C_0$-$C_6$-alkyl-OC(O)$N(R^7)_2$, or $C_0$-$C_6$-alkyl-$C(O)N(R^7)_2$. In such an embodiment, if $R^2$ is alkyl, alkylene, cycloalkyl or heterocycloalkyl, $R^2$ may be substituted with —OH or halo.

In an embodiment of Formula III, $R^1$ is $C_1$-$C_6$-alkyl, $R^2$ is —$CH_2N(H)(C(O)CH_3)$, $R^4$ is phenyl substituted with 1-2 halogen atoms independently selected from fluorine and chlorine, $R^5$ is H, m is 1, and n is 0.

In an embodiment of Formula III, $R^1$ is $C_1$-$C_6$-alkyl, $R^2$ is —$CH_2N(H)(CH_2CHF_2)$, $R^4$ is phenyl substituted with 1-2 groups independently selected from fluorine and CN, $R^5$ is H, m is 1, and n is 0.

In an embodiment of Formula III, $R^1$ is $C_1$-$C_6$-alkyl, $R^2$ is —$CH_2N(H)(CH_2CHF_2)$, $R^4$ is phenyl substituted with 1-2 groups independently selected from fluorine and $CF_3$, $R^5$ is H, m is 1, and n is 0.

In an embodiment of Formula III, $R^1$ is $C_1$-$C_6$-alkyl, $R^2$ is —$CH_2N(H)(CH_2CF_3)$, $R^4$ is phenyl substituted with 1-2 groups independently selected from fluorine and CN, $R^5$ is H, m is 1, and n is 0.

In an embodiment of Formula III, $R^1$ is $C_1$-$C_6$-alkyl, $R^2$ is —$CH_2N(H)(CH_2CF_3)$, $R^4$ is phenyl substituted with 1-2 groups independently selected from fluorine and $CF_3$, $R^5$ is H, m is 1, and n is 0.

In an embodiment of Formula III, $R^1$ is $C_1$-$C_6$-alkyl, $R^2$ is —CH(OH)CH=$CH_2$, $R^3$ is $C_1$-$C_6$-alkyl, $R^4$ is phenyl substituted with 1-2 groups independently selected from fluorine and $CF_3$, $R^5$ is H, m is 1, and n is 1. In a more particular embodiment, $R^3$ is (R)-methyl.

In an embodiment of Formula III, $R^1$ is $C_1$-$C_6$-alkyl, $R^2$ is —CH(OH)CH=$CH_2$, $R^3$ is $C_1$-$C_6$-alkyl, $R^4$ is phenyl substituted with 1-2 groups independently selected from fluorine and CN, $R^5$ is H, m is 1, and n is 1. In a more particular embodiment, $R^3$ is (R)-methyl.

In an embodiment of Formula III, $R^1$ is $C_1$-$C_6$-alkyl, $R^2$ is —CH(OH)CH=$CH_2$, $R^3$ is $C_1$-$C_6$-alkyl, $R^4$ is phenyl substituted with 1-2 halogen atoms independently selected from fluorine and bromine, $R^5$ is H, m is 1, and n is 1. In a more particular embodiment, $R^3$ is (R)-methyl.

In an embodiment of Formula III, $R^1$ is $C_1$-$C_6$-alkyl, $R^2$ is —$CH_2N(H)(CH_2CHF_2)$, $R^4$ is phenyl substituted with 1-3 groups independently selected from fluorine and CN, $R^5$ is H, m is 1, and n is 0.

In an embodiment of Formula III, $R^1$ is $C_1$-$C_6$-alkyl, $R^2$ is —$CH_2N(H)(CH_2CHF_2)$, $R^4$ is phenyl substituted with 1-3 groups independently selected from fluorine and $CF_3$, $R^5$ is H, m is 1, and n is 0.

In an embodiment of Formula III, $R^1$ is $C_1$-$C_6$-alkyl, $R^2$ is —$CH_2N(H)(CH_2CHF_2)$, $R^4$ is phenyl substituted with 1-3 halogen atoms independently selected from fluorine and chlorine, $R^5$ is H, m is 1, and n is 0.

In an embodiment of Formula III, $R^1$ is $C_1$-$C_6$-alkyl, $R^2$ is —$CH_2N(H)(CH_2CHF_2)$, $R^4$ is phenyl substituted with 1-3 halogen atoms independently selected from fluorine and bromine, $R^5$ is H, m is 1, and n is 0.

In an embodiment of Formula III, $R^1$ is $C_1$-$C_6$-alkyl, $R^2$ is —$CH_2N(H)(CH_2CHF_2)$, $R^4$ is phenyl substituted with 1-2 halogen atoms independently selected from fluorine and bromine, $R^5$ is H, m is 1, and n is 0.

In an embodiment of Formula III, $R^1$ is $C_1$-$C_6$-alkyl, two $R^2$ groups together form a spiro-cyclobutyl, which is substituted with —OH, $R^4$ is phenyl substituted with 1-2 halogen atoms independently selected from fluorine and chlorine, $R^5$ is H, m is 2, and n is 0.

In one embodiment of Formula I, A is C=O; $R^1$ is $C_1$-$C_6$-alkyl; $R^4$ is $(CR^aR^b)_p$—$C_6$-$C_{12}$-aryl substituted with at least one halo; $R^5$ is H; n is 0; p is 0; m is 1 or 2; and each $R^2$ is independently selected from —OH, halo, $C_1$-$C_6$-alkyl, $C_1$-$C_6$-alkylene, $C_0$-$C_6$-alkyl-$C_3$-$C_6$-cycloalkyl, $C_0$-$C_6$-alkyl-$C_2$-$C_6$-heterocycloalkyl, $C_0$-$C_6$-alkyl-$OR^6$, $C_0$-$C_6$-alkyl-$N(R^7)_2$, $C_0$-$C_6$-alkyl-$SR^8$, $C_0$-$C_6$-alkyl-$S(O)R^8$, $C_0$-$C_6$-alkyl-$S(O)_2R^8$, $C_0$-$C_6$-alkyl-$C(O)OR^9$, $C_0$-$C_6$-alkyl-OC(O)$R^9$, $C_0$-$C_6$-alkyl-OC(O)$OR^9$, $C_0$-$C_6$-alkyl-OC(O)$N(R^7)_2$, or $C_0$-$C_6$-alkyl-$C(O)N(R^7)_2$. In such an embodiment, if $R^2$ is alkyl, cycloalkyl or heterocycloalkyl, $R^2$ may be substituted with —OH or halo.

In a particular embodiment of Formula III, $R^1$ is $C_1$-$C_6$-alkyl, $R^2$ is —CH(OH)$CH_2$-cyclopropyl, $R^4$ is phenyl substituted with 1-2 halogen atoms independently selected from fluorine and chlorine, $R^5$ is H, m is 1, and n is 0.

In another embodiment of Formula III, $R^1$ is $C_1$-$C_6$-haloalkyl, $R^2$ is —$CH_2OH$, $R^4$ is phenyl substituted with 1-2 halogen atoms independently selected from fluorine and chlorine, $R^5$ is H, m is 1, and n is 0.

In a further embodiment of Formula III, $R^1$ is $C_1$-$C_6$-alkyl, $R^2$ is —N(H)($C_1$-$C_6$-alkyl), $R^4$ is phenyl substituted with 1-2 halogen atoms independently selected from fluorine and chlorine, $R^5$ is H, m is 1, and n is 0.

In yet another embodiment of Formula III, $R^1$ is $C_1$-$C_6$-alkyl, one instance of $R^2$ is $C_1$-$C_6$-alkyl and the other instance of $R^2$ is —$C(O)OCH_2CH_3$, $R^4$ is phenyl substituted with 1-2 halogen atoms independently selected from fluorine and chlorine, $R^5$ is H, m is 2, and n is 0.

In yet another embodiment of Formula III, $R^1$ is $C_1$-$C_6$-alkyl, one instance of $R^2$ is $C_1$-$C_6$-alkyl and the other instance of $R^2$ is —$CH_2OH$, $R^4$ is phenyl substituted with 1-2 halogen atoms independently selected from fluorine and chlorine, $R^5$ is H, m is 2, and n is 0.

In a further embodiment of Formula III, $R^1$ is $C_1$-$C_6$-alkyl, $R^2$ is $C_2$-$C_6$-heterocycloalkyl which is substituted with two fluorine groups, $R^4$ is phenyl substituted with 1-2 halogen atoms independently selected from fluorine and chlorine, $R^5$ is H, m is 1, and n is 0.

In a another embodiment of Formula III, $R^1$ is $C_1$-$C_6$-alkyl, $R^2$ is $C_2$-$C_6$-heterocycloalkyl, $R^4$ is phenyl substituted with 1-2 halogen atoms independently selected from fluorine and chlorine, $R^5$ is H, m is 1, and n is 0.

In a another embodiment of Formula III, $R^1$ is $C_1$-$C_6$-alkyl, $R^2$ is —$CH_2$—$C_2$-$C_6$-heterocycloalkyl, $R^4$ is phenyl substituted with 1-2 halogen atoms independently selected from fluorine and chlorine, $R^5$ is H, m is 1, and n is 0.

In a another embodiment of Formula III, $R^1$ is $C_1$-$C_6$-alkyl, $R^2$ is —$CH_2$—$C_2$-$C_6$-heterocycloalkyl which is substituted with two fluorine groups, $R^4$ is phenyl substituted with 1-2 halogen atoms independently selected from fluorine and chlorine, $R^5$ is H, m is 1, and n is 0.

In a further embodiment of Formula III, $R^1$ is $C_1$-$C_6$-alkyl, $R^2$ is —$CH_2N(C_1$-$C_6$-alkyl)($C_1$-$C_6$-alkyl), $R^4$ is phenyl substituted with 1-2 halogen atoms independently selected from fluorine and chlorine, $R^5$ is H, m is 1, and n is 0.

In another embodiment of Formula III, $R^1$ is $C_1$-$C_6$-alkyl, $R^2$ is —$CH_2NH_2$, $R^4$ is phenyl substituted with 1-2 halogen atoms independently selected from fluorine and chlorine, $R^5$ is H, m is 1, and n is 0.

In yet another embodiment of Formula III, $R^1$ is $C_1$-$C_6$-alkyl, one instance of $R^2$ is —$CH_2CHF_2$ and the other instance of $R^2$ is —$CH_2OH$, $R^4$ is phenyl substituted with 1-2 halogen atoms independently selected from fluorine and chlorine, $R^5$ is H, m is 2, and n is 0.

In another embodiment of Formula III, $R^1$ is $C_1$-$C_6$-alkyl, $R^2$ is —$CH(OH)CH_2CH_2CH_3$, $R^4$ is phenyl substituted with 1-2 halogen atoms independently selected from fluorine and chlorine, $R^5$ is H, m is 1, and n is 0.

In a further embodiment of Formula III, $R^1$ is $C_1$-$C_6$-alkyl, $R^2$ is —$CH(OH)CH_2CH_2F$, $R^4$ is phenyl substituted with 1-2 halogen atoms independently selected from fluorine and chlorine, $R^5$ is H, m is 1, and n is 0.

In another embodiment of Formula III, $R^1$ is $C_1$-$C_6$-alkyl, $R^2$ is —$CH(OH)CH_2CHF_2$, $R^4$ is phenyl substituted with 1-2 halogen atoms independently selected from fluorine and chlorine, $R^5$ is H, m is 1, and n is 0.

In another embodiment of Formula II, $R^1$ is $C_1$-$C_6$-alkyl, $R^2$ is —$C(O)OCH_3$, $R^4$ is phenyl substituted with 1-2 halogen atoms independently selected from fluorine and chlorine, $R^5$ is H, m is 1, and n is 0.

In a further embodiment of Formula II, $R^1$ is $C_1$-$C_6$-alkyl, $R^2$ is —$C(O)N(C_1$-$C_6$-alkyl)($C_1$-$C_6$-alkyl), $R^4$ is phenyl substituted with 1-2 halogen atoms independently selected from fluorine and chlorine, $R^5$ is H, m is 1, and n is 0.

In yet another embodiment of Formula II, $R^1$ is $C_1$-$C_6$-alkyl, $R^2$ is $CH_2OH$, $R^4$ is phenyl substituted with 1-2 halogen atoms independently selected from fluorine and chlorine, $R^5$ is H, m is 1, and n is 0.

In another embodiment of Formula II, $R^1$ is $C_1$-$C_6$-alkyl, one instance of $R^2$ is $C_1$-$C_6$-alkyl and the other instance of $R^2$ is —$CH_2OH$, $R^4$ is phenyl substituted with 1-2 halogen atoms independently selected from fluorine and chlorine, $R^5$ is H, m is 2, and n is 0.

In another embodiment of Formula II, $R^1$ is $C_1$-$C_6$-alkyl, one instance of $R^2$ is $C_1$-$C_6$-alkyl and the other instance of $R^2$ is —$C(O)OH$, $R^4$ is phenyl substituted with 1-2 halogen atoms independently selected from fluorine and chlorine, $R^5$ is H, m is 2, and n is 0.

In a further embodiment of Formula II, $R^1$ is $C_1$-$C_6$-alkyl, $R^2$ is —$C(O)OH$, $R^4$ is phenyl substituted with 1-2 halogen atoms independently selected from fluorine and chlorine, $R^5$ is H, m is 1, and n is 0.

In another particular embodiment of Formula II, $R^1$ is $C_1$-$C_6$-alkyl; $R^2$ is $C_1$-$C_6$-alkyl or $C_0$-$C_6$-alkyl-$OR^6$, wherein alkyl is substituted with halo, and $R^6$ is H or $C_1$-$C_6$-haloalkyl; $R^3$ is $C_1$-$C_6$-alkyl; $R^4$ is phenyl substituted with 1 or 2 groups, each independently selected from halo and —CN; $R^5$ is H; m is 1; and n is 1.

In another particular embodiment of Formula II, $R^1$ is methyl; $R^2$ is —$CH_2F$ or $CH_2$—O—$CH_2CHF_2$; $R^3$ is methyl; $R^4$ is phenyl substituted with 1 or 2 groups, each independently selected from F and —CN; $R^5$ is H; m is 1; and n is 1.

In another particular embodiment of Formula II, $R^1$ is $C_1$-$C_6$-alkyl, $R^2$ is —$CH_2F$, $R^4$ is phenyl or pyridyl, wherein the phenyl or pyridyl is substituted with 1-3 groups independently selected from halo, —CN, —$SF_5$, $C_1$-$C_6$-alkyl, and $C_1$-$C_6$-haloalkyl, $R^5$ is H, and n is 0.

In another particular embodiment of Formula II, $R^1$ is $C_1$-$C_6$-alkyl, $R^2$ is —$CH_2OCH_2CHF_2$, $R^4$ is phenyl or pyridyl, wherein the phenyl or pyridyl is substituted with 1-3 groups independently selected from halo, —CN, —$SF_5$, $C_1$-$C_6$-alkyl, and $C_1$-$C_6$-haloalkyl, $R^5$ is H, n is 1, and $R^3$ is $C_1$-$C_6$-alkyl.

In a another embodiment of Formula III, $R^1$ is $C_1$-$C_6$-alkyl, $R^2$ is —$CH_2$—$C_2$-$C_6$-heterocycloalkyl which is substituted with two fluorine groups, $R^4$ is phenyl substituted with 1-2 groups independently selected from fluorine and $CF_3$, $R^5$ is H, m is 1, and n is 0.

In another embodiment of Formula III, $R^1$ is $C_1$-$C_6$-alkyl, $R^2$ is —$CH_2NH_2$, $R^4$ is phenyl substituted with 1-2 groups independently selected from fluorine and $CF_3$, $R^5$ is H, m is 1, and n is 0.

In a further embodiment of Formula III, $R^1$ is $C_1$-$C_6$-alkyl, $R^2$ is —N(H)($C_1$-$C_6$-alkyl), $R^4$ is phenyl substituted with 1-2 groups independently selected from fluorine and $CF_3$, $R^5$ is H, m is 1, and n is 0.

In a further embodiment of Formula III, $R^1$ is $C_1$-$C_6$-alkyl, $R^2$ is —$CH(OH)CH_2CH_3$, $R^4$ is phenyl substituted with 1-2 groups independently selected from fluorine and $CF_3$, $R^5$ is H, m is 1, and n is 0.

In a another embodiment of Formula III, $R^1$ is $C_1$-$C_6$-alkyl, $R^2$ is —$CH_2$—$C_2$-$C_6$-heterocycloalkyl which is substituted with two fluorine groups, $R^4$ is phenyl substituted with 1-2 groups independently selected from fluorine and CN, $R^5$ is H, m is 1, and n is 0.

In another embodiment of Formula III, $R^1$ is $C_1$-$C_6$-alkyl, $R^2$ is —$CH_2NH_2$, $R^4$ is phenyl substituted with 1-2 groups independently selected from fluorine and CN, $R^5$ is H, m is 1, and n is 0.

In a further embodiment of Formula III, $R^1$ is $C_1$-$C_6$-alkyl, $R^2$ is —$CH(OH)CH_2CH_3$, $R^4$ is phenyl substituted with 1-2 groups independently selected from fluorine and CN, $R^5$ is H, m is 1, and n is 0.

In a further embodiment of Formula III, $R^1$ is $C_1$-$C_6$-alkyl, $R^2$ is —$CH(OH)CH_2CHF_2$, $R^4$ is phenyl substituted with 1-2 groups independently selected from fluorine and CN, $R^5$ is H, m is 1, and n is 0.

In a further embodiment of Formula III, $R^1$ is $C_1$-$C_6$-alkyl, $R^2$ is —$CH(OH)CH_2CH_3$, $R^4$ is phenyl substituted with 1-3 halogen atoms independently selected from fluorine and chlorine, $R^5$ is H, m is 1, and n is 0.

In a further embodiment of Formula III, $R^1$ is $C_1$-$C_6$-alkyl, $R^2$ is —$CH(OH)CH_2CH_3$, $R^4$ is phenyl substituted with 1-3 groups independently selected from fluorine and CN, $R^5$ is H, m is 1, and n is 0.

In another embodiment of Formula III, $R^1$ is $C_1$-$C_6$-alkyl, $R^2$ is —$CH(OH)CH_2CH_3$, $R^4$ is phenyl substituted with 1-3 halogen atoms independently selected from fluorine and bromine, $R^5$ is H, m is 1, and n is 0.

In another embodiment of Formula III, $R^1$ is $C_1$-$C_6$-alkyl, $R^2$ is —$CH(OH)CH_2CH_3$, $R^4$ is phenyl substituted with 1-2 halogen atoms independently selected from fluorine and bromine, $R^5$ is H, m is 1, and n is 0.

In another embodiment of Formula III, $R^1$ is $C_1$-$C_6$-alkyl, $R^2$ is —CH(OH)CH$_2$CH$_3$, $R^4$ is phenyl substituted with 1-3 groups independently selected from fluorine and CF$_3$, $R^5$ is H, m is 1, and n is 0.

In another embodiment of Formula III, $R^1$ is $C_1$-$C_6$-alkyl, $R^2$ is —CH(OH)CH$_2$CH$_3$, $R^4$ is phenyl substituted with 1-3 fluorine groups, $R^5$ is H, m is 1, and n is 0.

In another embodiment of Formula III, $R^1$ is $C_1$-$C_6$-alkyl, $R^2$ is —CH(OH)CH$_2$CH$_3$, $R^4$ is phenyl substituted with 1-4 fluorine groups, $R^5$ is H, m is 1, and n is 0.

In an embodiment of Formula III, $R^1$ is $C_1$-$C_6$-alkyl-OH, $R^3$ is $C_1$-$C_6$-alkyl, $R^4$ is phenyl substituted with 1-2 halogen atoms independently selected from fluorine and chlorine, $R^5$ is H, m is 0, and n is 1. In a more particular embodiment, $R^3$ is (R)-methyl.

In another embodiment of Formula III, $R^1$ is $C_1$-$C_6$-haloalkyl, $R^3$ is $C_1$-$C_6$-alkyl, $R^4$ is phenyl substituted with 1-3 halogen atoms independently selected from fluorine, bromine, and chlorine, $R^5$ is H, m is 0, and n is 1. In a more particular embodiment, $R^3$ is (R)-methyl.

In an embodiment of Formula III, $R^1$ is $C_1$-$C_6$-haloalkyl, $R^3$ is $C_1$-$C_6$-alkyl, $R^4$ is phenyl substituted with 1-2 halogen atoms independently selected from fluorine and chlorine, $R^5$ is H, m is 0, and n is 1. In a more particular embodiment, $R^3$ is (R)-methyl.

In an embodiment of Formula III, $R^1$ is $C_1$-$C_6$-haloalkyl, $R^3$ is $C_1$-$C_6$-alkyl, $R^4$ is phenyl substituted with 1-2 groups independently selected from fluorine and CF$_3$, $R^5$ is H, m is 0, and n is 1. In a more particular embodiment, $R^3$ is (R)-methyl.

In an embodiment of Formula III, $R^1$ is $C_1$-$C_6$-haloalkyl, $R^3$ is $C_1$-$C_6$-alkyl, $R^4$ is phenyl substituted with 1-2 halogen atoms independently selected from fluorine and bromine, $R^5$ is H, m is 0, and n is 1. In a more particular embodiment, $R^3$ is (R)-methyl.

In an embodiment of Formula III, $R^1$ is $C_1$-$C_6$-haloalkyl, $R^3$ is $C_1$-$C_6$-alkyl, $R^4$ is pyridine substituted with 1-2 halogen atoms independently selected from fluorine and bromine, $R^5$ is H, m is 0, and n is 1. In a more particular embodiment, $R^3$ is (R)-methyl.

In an embodiment of Formula III, $R^1$ is $C_1$-$C_6$-haloalkyl, $R^3$ is $C_1$-$C_6$-alkyl, $R^4$ is phenyl substituted with 1-2 groups independently selected from fluorine and CN, $R^5$ is H, m is 0, and n is 1. In a more particular embodiment, $R^3$ is (R)-methyl.

In an embodiment of Formula III, $R^1$ is $C_1$-$C_6$-haloalkyl, $R^3$ is $C_1$-$C_6$-alkyl, $R^4$ is phenyl substituted with 1-2 groups independently selected from fluorine and Me, $R^5$ is H, m is 0, and n is 1. In a more particular embodiment, $R^3$ is (R)-methyl.

In an embodiment of Formula III, $R^1$ is $C_1$-$C_6$-haloalkyl, $R^3$ is $C_1$-$C_6$-alkyl, $R^4$ is phenyl substituted with 1-3 halogen atoms independently selected from fluorine and chlorine, $R^5$ is H, m is 0, and n is 1. In a more particular embodiment, $R^3$ is (R)-methyl.

In an embodiment of Formula III, $R^1$ is $C_1$-$C_6$-alkyl, one instance of $R^2$ is methyl and the other instance of $R^2$ is fluorine, $R^3$ is $C_1$-$C_6$-alkyl, $R^4$ is phenyl substituted with 1-2 halogen atoms independently selected from fluorine and chlorine, $R^5$ is H, m is 2, and n is 1. In a more particular embodiment, $R^3$ is (R)-methyl.

In an embodiment of Formula III, $R^1$ is $C_1$-$C_6$-alkyl, $R^2$ is methyl, $R^3$ is $C_1$-$C_6$-alkyl, $R^4$ is phenyl substituted with 1-2 halogen atoms independently selected from fluorine and chlorine, $R^5$ is H, m is 1, and n is 1. In a more particular embodiment, $R^3$ is (R)-methyl.

In an embodiment of Formula III, $R^1$ is $C_1$-$C_6$-alkyl, $R^2$ is CH$_2$OH, $R^3$ is $C_1$-$C_6$-alkyl, $R^4$ is phenyl substituted with 1-2 groups independently selected from fluorine and CF$_3$, $R^5$ is H, m is 1, and n is 1. In a more particular embodiment, $R^3$ is (R)-methyl.

In an embodiment of Formula III, $R^1$ is $C_1$-$C_6$-alkyl, $R^2$ is CH$_2$OH, $R^3$ is $C_1$-$C_6$-alkyl, $R^4$ is phenyl substituted with 1-3 groups independently selected from fluorine and CF$_3$, $R^5$ is H, m is 1, and n is 1. In a more particular embodiment, $R^3$ is (R)-methyl.

In an embodiment of Formula III, $R^1$ is $C_1$-$C_6$-alkyl, $R^2$ is CH$_2$OH, $R^3$ is $C_1$-$C_6$-alkyl, $R^4$ is phenyl substituted with 1-3 halogen atoms independently selected from fluorine and bromine, $R^5$ is H, m is 1, and n is 1. In a more particular embodiment, $R^3$ is (R)-methyl.

In an embodiment of Formula III, $R^1$ is $C_1$-$C_6$-alkyl, $R^2$ is CH$_2$OH, $R^3$ is $C_1$-$C_6$-alkyl, $R^4$ is phenyl substituted with 1-2 halogen atoms independently selected from fluorine and bromine, $R^5$ is H, m is 1, and n is 1. In a more particular embodiment, $R^3$ is (R)-methyl.

In an embodiment of Formula III, $R^1$ is $C_1$-$C_6$-alkyl, $R^2$ is CH$_2$OH, $R^3$ is $C_1$-$C_6$-alkyl, $R^4$ is phenyl substituted with 1-2 groups independently selected from fluorine and CN, $R^5$ is H, m is 1, and n is 1. In a more particular embodiment, $R^3$ is (R)-methyl.

In an embodiment of Formula III, $R^1$ is $C_1$-$C_6$-alkyl, $R^2$ is CH$_2$OH, $R^3$ is $C_1$-$C_6$-alkyl, $R^4$ is phenyl substituted with 1-3 groups independently selected from fluorine and CN, $R^5$ is H, m is 1, and n is 1. In a more particular embodiment, $R^3$ is (R)-methyl.

In an embodiment of Formula III, $R^1$ is $C_1$-$C_6$-alkyl, $R^2$ is CH$_2$OH, $R^3$ is $C_1$-$C_6$-alkyl, $R^4$ is phenyl substituted with 1-3 halogen atoms independently selected from fluorine and chlorine, $R^5$ is H, m is 1, and n is 1. In a more particular embodiment, $R^3$ is (R)-methyl.

In an embodiment of Formula III, $R^1$ is $C_1$-$C_6$-haloalkyl, $R^2$ is CH$_2$OH, $R^3$ is $C_1$-$C_6$-alkyl, $R^4$ is phenyl substituted with 1-2 halogen atoms independently selected from fluorine and chlorine, $R^5$ is H, m is 1, and n is 1. In a more particular embodiment, $R^3$ is (R)-methyl.

In an embodiment of Formula III, $R^1$ is $C_1$-$C_6$-alkyl, $R^2$ is CH(OH)CH$_2$CH$_3$, $R^3$ is $C_1$-$C_6$-alkyl, $R^4$ is phenyl substituted with 1-2 groups independently selected from fluorine and CF$_3$, $R^5$ is H, m is 1, and n is 1. In a more particular embodiment, $R^3$ is (R)-methyl.

In an embodiment of Formula III, $R^1$ is $C_1$-$C_6$-alkyl, $R^2$ is CH(OH)CH$_2$CH$_3$, $R^3$ is $C_1$-$C_6$-alkyl, $R^4$ is phenyl substituted with 1-2 groups independently selected from fluorine and CN, $R^5$ is H, m is 1, and n is 1. In a more particular embodiment, $R^3$ is (R)-methyl.

In an embodiment of Formula III, $R^1$ is $C_1$-$C_6$-alkyl, $R^2$ is CH(OH)CH$_2$CH$_3$, $R^3$ is $C_1$-$C_6$-alkyl, $R^4$ is phenyl substituted with 1-2 halogen atoms independently selected from fluorine and bromine, $R^5$ is H, m is 1, and n is 1. In a more particular embodiment, $R^3$ is (R)-methyl In one embodiment of Formula III, $R^1$ is $C_1$-$C_6$-alkyl, $R^4$ is phenyl substituted with 1-2 halogen atoms independently selected from fluorine and chlorine, $R^5$ is H, m is 1, and n is 0.

In another embodiment of Formula III, $R^1$ is $C_1$-$C_6$-alkyl, $R^2$ is fluorine, $R^5$ is H, m is 1, and n is 0.

In a particular embodiment of Formula III, $R^1$ is $C_1$-$C_6$-alkyl, $R^2$ is =CH$_2$, $R^4$ is phenyl substituted with 1-2 halogen atoms independently selected from fluorine and chlorine, $R^5$ is H, m is 1, and n is 0.

In another particular embodiment of Formula III, $R^1$ is $C_1$-$C_6$-alkyl, $R^2$ is —CH$_2$OH, $R^4$ is phenyl substituted with 1-2 halogen atoms independently selected from fluorine and chlorine, $R^5$ is H, m is 1, and n is 0.

In another particular embodiment of Formula III, $R^1$ is $C_1$-$C_6$-alkyl, one instance of $R^2$ is —OH and the other instance of $R^2$ is —CH$_2$OH, $R^4$ is phenyl substituted with 1-2 halogen atoms independently selected from fluorine and chlorine, $R^5$ is H, m is 2, and n is 0.

In another particular embodiment of Formula III, $R^1$ is $C_1$-$C_6$-alkyl, $R^2$ is —OH, $R^4$ is phenyl substituted with 1-2 halogen atoms independently selected from fluorine and chlorine, $R^5$ is H, m is 1, and n is 0.

In another particular embodiment of Formula III, $R^1$ is $C_1$-$C_6$-alkyl, both instances of $R^2$ are fluorine, $R^4$ is phenyl substituted with 1-2 halogen atoms independently selected from fluorine and chlorine, $R^5$ is H, m is 2, and n is 0.

In a particular embodiment of Formula III, $R^1$ is $C_1$-$C_6$-alkyl, $R^2$ is fluorine, $R^4$ is phenyl substituted with 1-2 halogen atoms independently selected from fluorine and chlorine, $R^5$ is H, m is 1, and n is 0.

In another particular embodiment of Formula III, $R^1$ is $C_1$-$C_6$-alkyl, $R^2$ is fluorine, $R^4$ is phenyl substituted with 1-2 halogen atoms independently selected from fluorine and bromine, $R^5$ is H, m is 1, and n is 0.

In another particular embodiment of Formula III, $R^1$ is $C_1$-$C_6$-alkyl, $R^2$ is fluorine, $R^4$ is pyridyl substituted with 1-2 halogen atoms independently selected from fluorine and bromine, $R^5$ is H, m is 1, and n is 0.

In another particular embodiment of Formula III, $R^1$ is $C_1$-$C_6$-alkyl, $R^2$ is fluorine, $R^4$ is phenyl substituted with 1-2 substituents independently selected from fluorine and —CN, $R^5$ is H, m is 1, and n is 0.

In another particular embodiment of Formula III, $R^1$ is $C_1$-$C_6$-alkyl, $R^2$ is fluorine, $R^4$ is phenyl substituted with 1-2 substituents independently selected from fluorine and —CH$_3$, $R^5$ is H, m is 1, and n is 0.

In another particular embodiment of Formula III, $R^1$ is $C_1$-$C_6$-alkyl, $R^2$ is fluorine, $R^4$ is phenyl substituted with 1-2 substituents independently selected from fluorine and —CF$_3$, $R^5$ is H, m is 1, and n is 0.

In another particular embodiment of Formula III, $R^1$ is $C_1$-$C_6$-alkyl, $R^2$ is fluorine, $R^4$ is pyridyl substituted with 1-3 halogen atoms independently selected from fluorine and chlorine, $R^5$ is H, m is 1, and n is 0.

In another particular embodiment of Formula III, $R^1$ is $C_1$-$C_6$-alkyl, $R^2$ is fluorine, $R^4$ is pyridyl substituted with 1-3 halogen atoms independently selected from fluorine and bromine, $R^5$ is H, m is 1, and n is 0.

In a particular embodiment of Formula III, $R^1$ is $C_1$-$C_6$-alkyl, $R^2$ is —CH$_3$, $R^4$ is phenyl substituted with 1-2 halogen atoms independently selected from fluorine and chlorine, $R^5$ is H, m is 1, and n is 0.

In a particular embodiment of Formula III, $R^1$ is $C_1$-$C_6$-alkyl, $R^4$ is phenyl substituted with 1-2 halogen atoms independently selected from fluorine and chlorine, $R^5$ is H, m is 0, and n is 0.

In a particular embodiment of Formula III, $R^1$ is $C_1$-$C_6$-alkyl, $R^2$ is —OCH$_3$, $R^4$ is phenyl substituted with 1-2 halogen atoms independently selected from fluorine and chlorine, $R^5$ is H, m is 1, and n is 0.

In a particular embodiment of Formula III, $R^1$ is $C_1$-$C_6$-alkyl, $R^2$ is —OCH$_2$CH$_3$, $R^4$ is phenyl substituted with 1-2 halogen atoms independently selected from fluorine and chlorine, $R^5$ is H, m is 1, and n is 0.

In a particular embodiment of Formula III, $R^1$ is $C_1$-$C_6$-alkyl, $R^2$ is —OCH$_2$CHF$_2$, $R^4$ is phenyl substituted with 1-2 halogen atoms independently selected from fluorine and chlorine, $R^5$ is H, m is 1, and n is 0.

In a particular embodiment of Formula III, $R^1$ is $C_1$-$C_6$-alkyl, $R^2$ is —NH$_2$, $R^4$ is phenyl substituted with 1-2 halogen atoms independently selected from fluorine and chlorine, $R^5$ is H, m is 1, and n is 0.

In a particular embodiment of Formula III, $R^1$ is $C_1$-$C_6$-alkyl, $R^2$ is —N(CH$_3$)$_2$, $R^4$ is phenyl substituted with 1-2 halogen atoms independently selected from fluorine and chlorine, $R^5$ is H, m is 1, and n is 0.

In a particular embodiment of Formula III, $R^1$ is $C_1$-$C_6$-alkyl, $R^2$ is morpholin-1-yl, $R^4$ is phenyl substituted with 1-2 halogen atoms independently selected from fluorine and chlorine, $R^5$ is H, m is 1, and n is 0.

In a particular embodiment of Formula III, $R^1$ is $C_1$-$C_6$-alkyl, $R^2$ is 3,3-difluoroazetidin-1-yl, $R^4$ is phenyl substituted with 1-2 halogen atoms independently selected from fluorine and chlorine, $R^5$ is H, m is 1, and n is 0.

In a particular embodiment of Formula III, $R^1$ is $C_1$-$C_6$-alkyl, $R^2$ is azetidin-1-yl, $R^4$ is phenyl substituted with 1-2 halogen atoms independently selected from fluorine and chlorine, $R^5$ is H, m is 1, and n is 0.

In a particular embodiment of Formula III, $R^1$ is $C_1$-$C_6$-alkyl, $R^2$ is pyrrolidin-1-yl, $R^4$ is phenyl substituted with 1-2 halogen atoms independently selected from fluorine and chlorine, $R^5$ is H, m is 1, and n is 0.

In a particular embodiment of Formula III, $R^1$ is $C_1$-$C_6$-alkyl, $R^2$ is —SCH$_3$, $R^4$ is phenyl substituted with 1-2 halogen atoms independently selected from fluorine and chlorine, $R^5$ is H, m is 1, and n is 0.

In a particular embodiment of Formula III, $R^1$ is $C_1$-$C_6$-alkyl, $R^2$ is —S(O)CH$_3$, $R^4$ is phenyl substituted with 1-2 halogen atoms independently selected from fluorine and chlorine, $R^5$ is H, m is 1, and n is 0.

In a particular embodiment of Formula III, $R^1$ is $C_1$-$C_6$-alkyl, $R^2$ is —S(O)$_2$CH$_3$, $R^4$ is phenyl substituted with 1-2 halogen atoms independently selected from fluorine and chlorine, $R^5$ is H, m is 1, and n is 0.

In a particular embodiment of Formula III, $R^1$ is $C_1$-$C_6$-alkyl, $R^2$ is —CH$_2$C(O)OCH$_3$, $R^4$ is phenyl substituted with 1-2 halogen atoms independently selected from fluorine and chlorine, $R^5$ is H, m is 1, and n is 0.

In a particular embodiment of Formula III, $R^1$ is $C_1$-$C_6$-alkyl, $R^2$ is —CH$_2$CH$_2$OH, $R^4$ is phenyl substituted with 1-2 halogen atoms independently selected from fluorine and chlorine, $R^5$ is H, m is 1, and n is 0.

In a particular embodiment of Formula III, $R^1$ is $C_1$-$C_6$-alkyl, $R^2$ is —C(O)OCH$_3$, $R^4$ is phenyl substituted with 1-2 halogen atoms independently selected from fluorine and chlorine, $R^5$ is H, m is 1, and n is 0.

In a particular embodiment of Formula III, $R^1$ is $C_1$-$C_6$-alkyl, $R^2$ is —C(OH)(CH$_3$)$_2$, $R^4$ is phenyl substituted with 1-2 halogen atoms independently selected from fluorine and chlorine, $R^5$ is H, m is 1, and n is 0.

In a particular embodiment of Formula III, $R^1$ is $C_1$-$C_6$-alkyl, $R^2$ is —C(O)NHCH$_3$, $R^4$ is phenyl substituted with 1-2 halogen atoms independently selected from fluorine and chlorine, $R^5$ is H, m is 1, and n is 0.

In a particular embodiment of Formula III, $R^1$ is $C_1$-$C_6$-alkyl, $R^2$ is —C(O)N(CH$_3$)$_2$, $R^4$ is phenyl substituted with 1-2 halogen atoms independently selected from fluorine and chlorine, $R^5$ is H, m is 1, and n is 0.

In a particular embodiment of Formula III, $R^1$ is $C_1$-$C_6$-alkyl, $R^2$ is —CH(OH)— cyclopropyl, $R^4$ is phenyl substituted with 1-2 halogen atoms independently selected from fluorine and chlorine, $R^5$ is H, m is 1, and n is 0.

In a particular embodiment of Formula III, $R^1$ is $C_1$-$C_6$-alkyl, $R^2$ is —CHF$_2$, $R^4$ is phenyl substituted with 1-2 halogen atoms independently selected from fluorine and chlorine, R⁵ is H, m is 1, and n is 0.

In a particular embodiment of Formula III, R¹ is $C_1$-$C_6$-alkyl, R² is —CHF₂, R⁴ is phenyl substituted with 1-2 halogen atoms independently selected from fluorine and chlorine, R⁵ is H, m is 1, and n is 0.

In another embodiment of Formula III, R¹ is $C_1$-$C_6$-haloalkyl, R⁴ is phenyl substituted with 1-2 halogen atoms independently selected from fluorine and chlorine, R⁵ is H, m is 0, and n is 0.

In an embodiment of Formula I, R¹ is $C_1$-$C_6$-alkyl, R⁴ is phenyl substituted with 1-2 halogen atoms independently selected from fluorine and chlorine, R⁵ is H, m is 0, n is 0, and q is 0.

In an embodiment of Formula II, R¹ is $C_1$-$C_6$-alkyl, R² is —CH₃, R⁴ is phenyl substituted with 1-2 halogen atoms independently selected from fluorine and chlorine, R⁵ is H, m is 1, and n is 0.

In another particular embodiment of Formula III, R¹ is $C_1$-$C_6$-alkyl; R² is $C_1$-$C_6$-alkyl or $C_0$-$C_6$-alkyl-OR⁶, wherein alkyl is substituted with halo, and R⁶ is H or $C_1$-$C_6$-haloalkyl; R³ is $C_1$-$C_6$-alkyl; R⁴ is phenyl substituted with 1 or 2 groups, each independently selected from halo and —CN; R⁵ is H; m is 1; and n is 1.

In another particular embodiment of Formula III, R¹ is methyl; R² is —CH₂F or CH₂—O—CH₂CHF₂; R³ is methyl; R⁴ is phenyl substituted with 1 or 2 groups, each independently selected from F and —CN; R⁵ is H; m is 1; and n is 1.

In another particular embodiment of Formula III, R¹ is $C_1$-$C_6$-alkyl, R² is —CH₂F, R⁴ is phenyl or pyridyl, wherein the phenyl or pyridyl is substituted with 1-3 groups independently selected from halo, —CN, —SF₅, $C_1$-$C_6$-alkyl, and $C_1$-$C_6$-haloalkyl, R⁵ is H, and n is 0.

In another particular embodiment of Formula III, R¹ is $C_1$-$C_6$-alkyl, R² is —CH₂OCH₂CHF₂, R⁴ is phenyl or pyridyl, wherein the phenyl or pyridyl is substituted with 1-3 groups independently selected from halo, —CN, —SF₅, $C_1$-$C_6$-alkyl, and $C_1$-$C_6$-haloalkyl, R⁵ is H, n is 1 and R³ is $C_1$-$C_6$-alkyl.

In an embodiment of Formula V, R¹ is $C_1$-$C_6$-alkyl, R⁴ is phenyl substituted with 1-2 halogen atoms independently selected from fluorine and chlorine, R⁵ is H, m is 0, and n is 0.

In an embodiment of Formula V, R¹ is $C_1$-$C_6$-alkyl, R⁴ is phenyl substituted with 1-2 halogen atoms independently selected from fluorine and chlorine, R⁵ is H, m is 0, n is 0, and ═══ is a double bond.

In another particular embodiment of Formula V, R¹ is $C_1$-$C_6$-alkyl; R² is $C_1$-$C_6$-alkyl or $C_0$-$C_6$-alkyl-OR⁶, wherein alkyl is substituted with halo, and R⁶ is H or $C_1$-$C_6$-haloalkyl; R³ is $C_1$-$C_6$-alkyl; R⁴ is phenyl substituted with 1 or 2 groups, each independently selected from halo and —CN; R⁵ is H; m is 1; and n is 1.

In another particular embodiment of Formula V, R¹ is methyl; R² is —CH₂F or CH₂—O—CH₂CHF₂; R³ is methyl; R⁴ is phenyl substituted with 1 or 2 groups, each independently selected from F and —CN; R⁵ is H; m is 1; and n is 1.

In another particular embodiment of Formula V, R¹ is $C_1$-$C_6$-alkyl, R² is —CH₂F, R⁴ is phenyl or pyridyl, wherein the phenyl or pyridyl is substituted with 1-3 groups independently selected from halo, —CN, —SF₅, $C_1$-$C_6$-alkyl, and $C_1$-$C_6$-haloalkyl, R⁵ is H, and n is 0.

In another particular embodiment of Formula V, R¹ is $C_1$-$C_6$-alkyl, R² is —CH₂OCH₂CHF₂, R⁴ is phenyl or pyridyl, wherein the phenyl or pyridyl is substituted with 1-3 groups independently selected from halo, —CN, —SF₅, $C_1$-$C_6$-alkyl, and $C_1$-$C_6$-haloalkyl, R⁵ is H, n is 1, and R³ is $C_1$-$C_6$-alkyl.

Certain embodiments of Formulas I, II, III and IV are shown below in Table 1. disclosed compounds.

TABLE 1

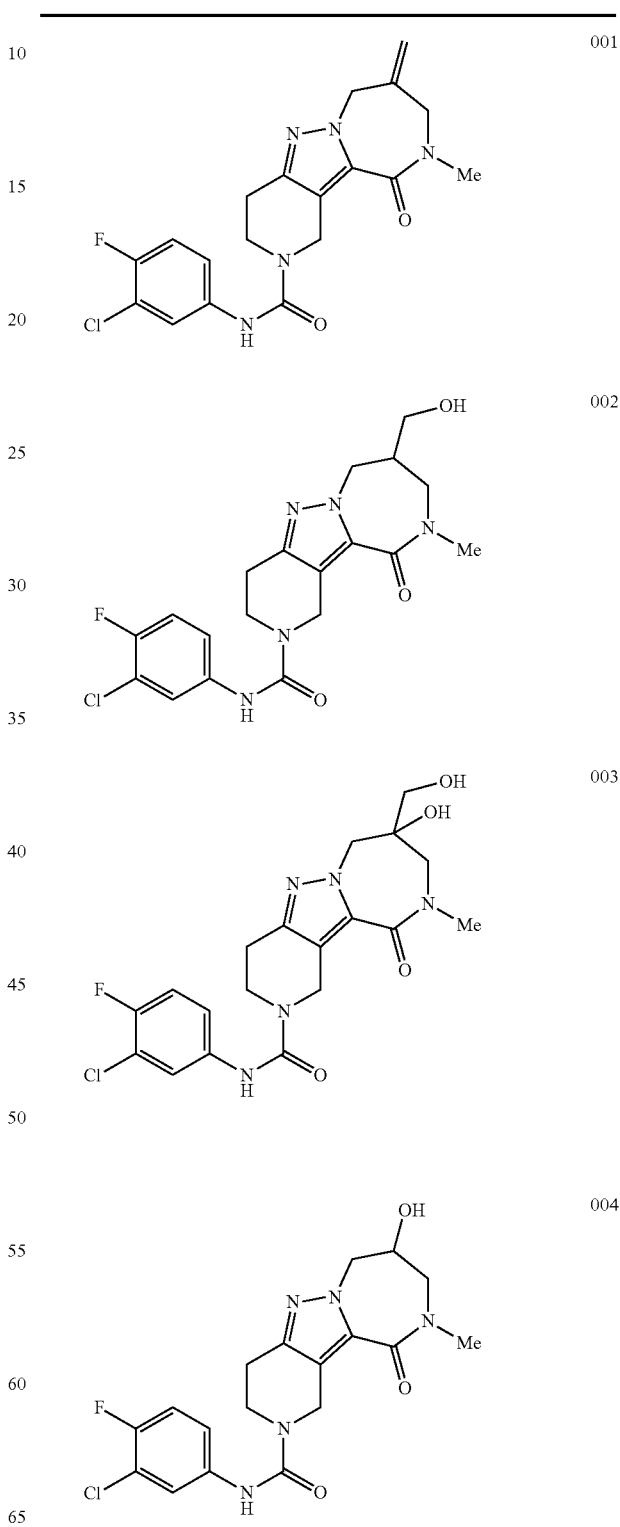

TABLE 1-continued
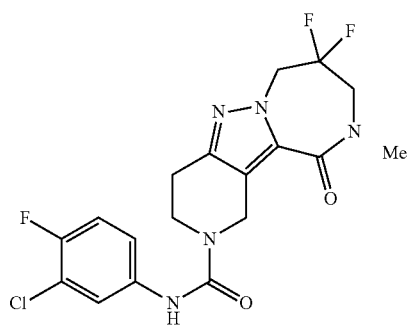 [SMILES: O=C1NCC(F)(F)Cn2nc3c(c21)CN(C(=O)Nc1ccc(F)c(Cl)c1)CC3 ; "Me"]
005
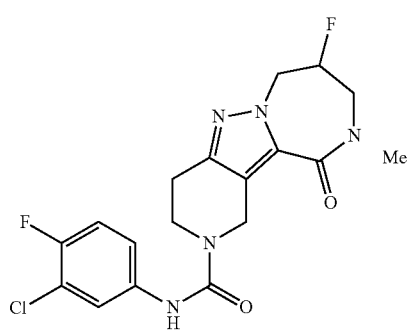 [SMILES: O=C1NCC(F)Cn2nc3c(c21)CN(C(=O)Nc1ccc(F)c(Cl)c1)CC3 ; "Me"]
006
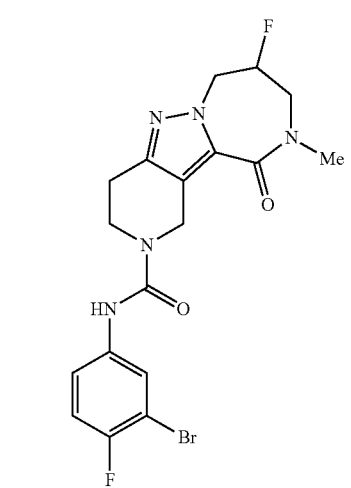 [SMILES: CN1CC(F)Cn2nc3c(c2C1=O)CN(C(=O)Nc1ccc(F)c(Br)c1)CC3]
007
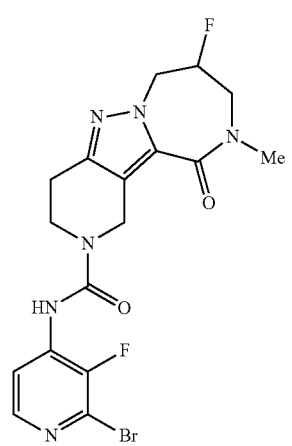 [SMILES: CN1CC(F)Cn2nc3c(c2C1=O)CN(C(=O)Nc1ccnc(Br)c1F)CC3]
008
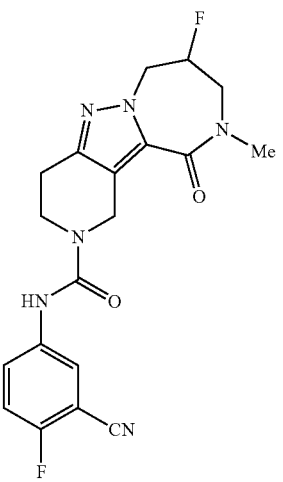 [SMILES: CN1CC(F)Cn2nc3c(c2C1=O)CN(C(=O)Nc1ccc(F)c(C#N)c1)CC3]
009
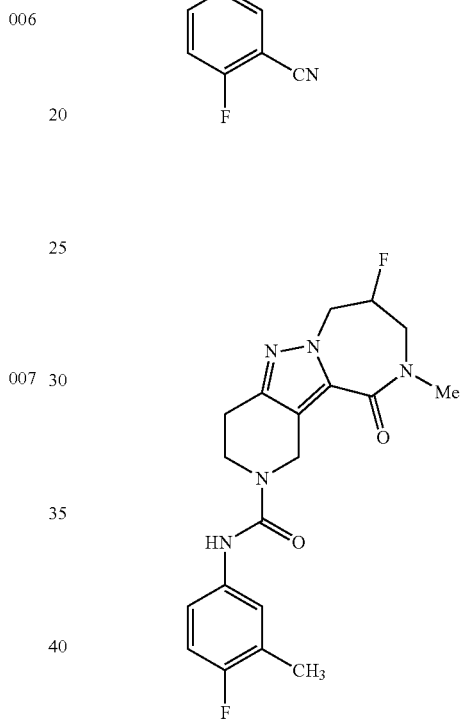
010
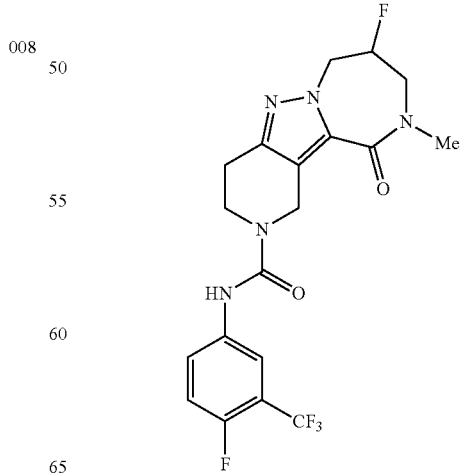
011

TABLE 1-continued
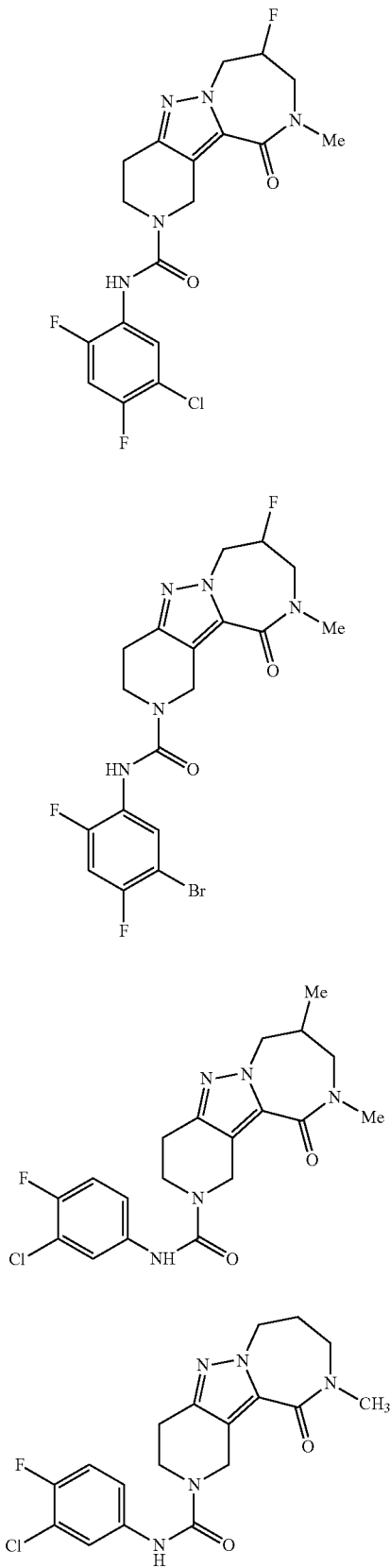
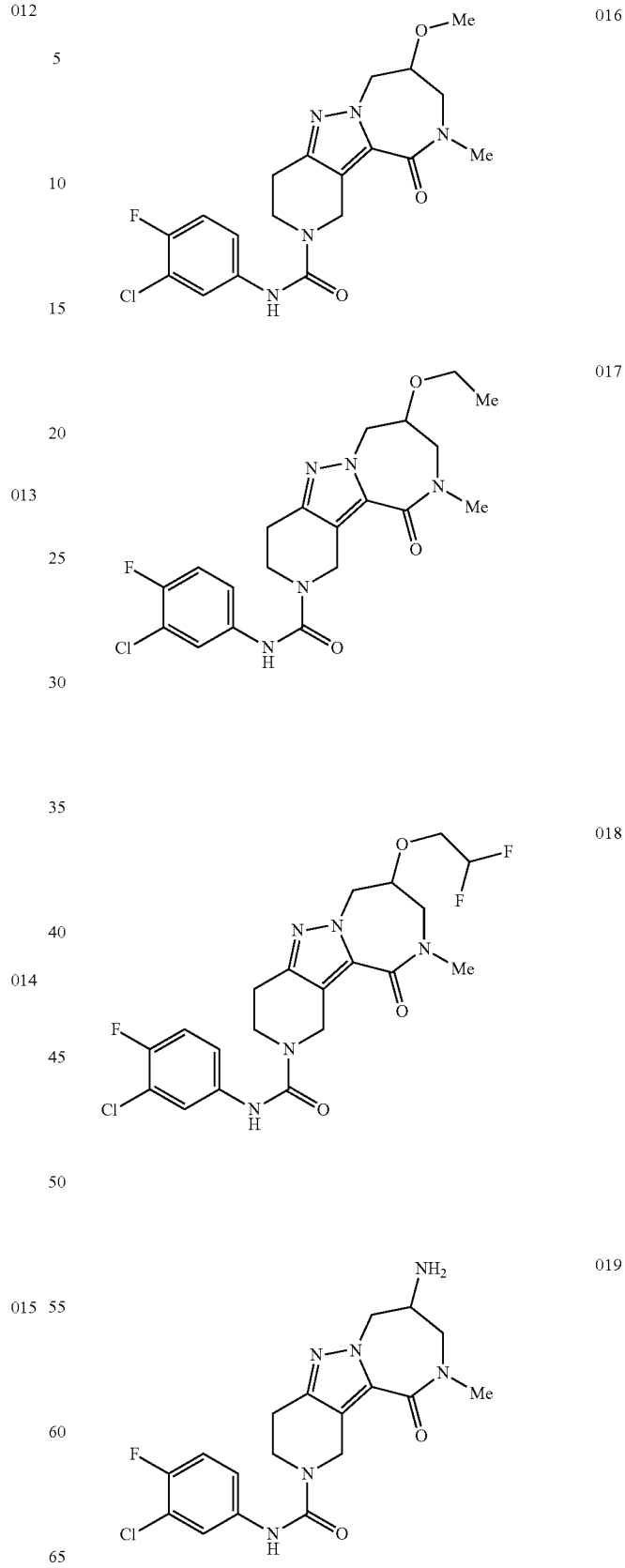

TABLE 1-continued
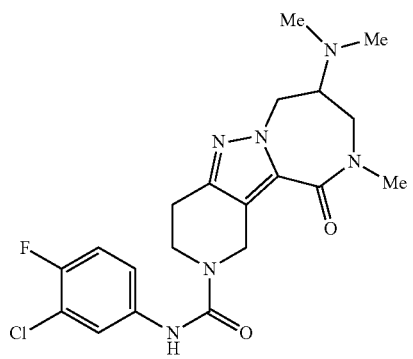 [SMILES: CN1CC(N(C)C)Cn2nc3c(c2C1=O)CN(C(=O)Nc1ccc(F)c(Cl)c1)CC3]
020
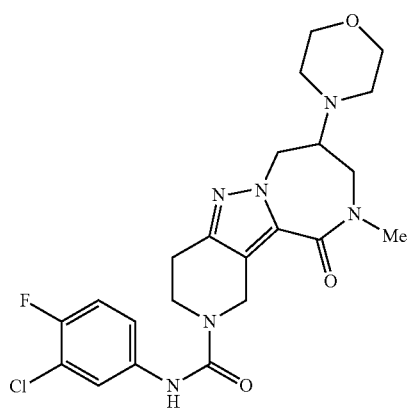 [SMILES: CN1CC(N2CCOCC2)Cn2nc3c(c2C1=O)CN(C(=O)Nc1ccc(F)c(Cl)c1)CC3]
021
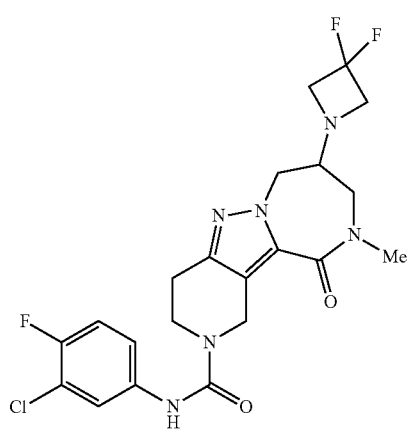 [SMILES: CN1CC(N2CC(F)(F)C2)Cn2nc3c(c2C1=O)CN(C(=O)Nc1ccc(F)c(Cl)c1)CC3]
022
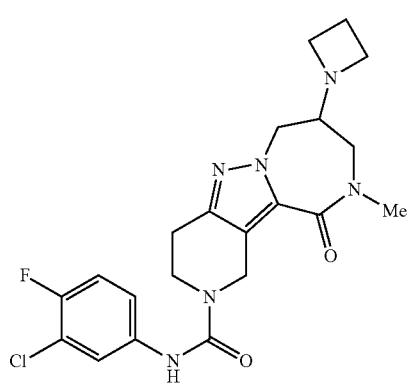 [SMILES: CN1CC(N2CCC2)Cn2nc3c(c2C1=O)CN(C(=O)Nc1ccc(F)c(Cl)c1)CC3]
023
TABLE 1-continued
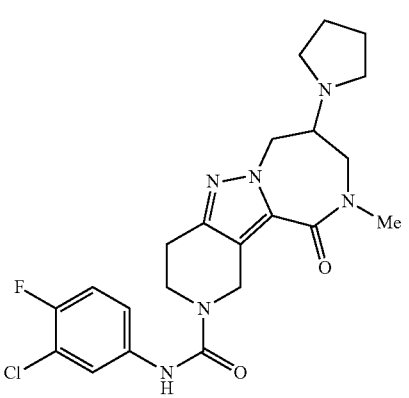 [SMILES: CN1CC(N2CCCC2)Cn2nc3c(c2C1=O)CN(C(=O)Nc1ccc(F)c(Cl)c1)CC3]
024
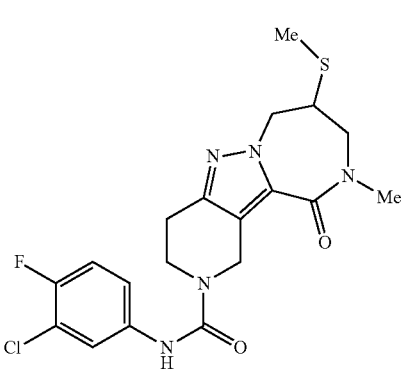 [SMILES: CSC1CN(C)C(=O)c2c3c(nn2C1)CCN(C(=O)Nc1ccc(F)c(Cl)c1)C3]
025
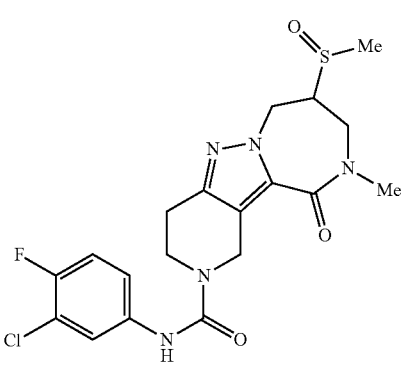 [SMILES: CN1CC(S(C)=O)Cn2nc3c(c2C1=O)CN(C(=O)Nc1ccc(F)c(Cl)c1)CC3]
026
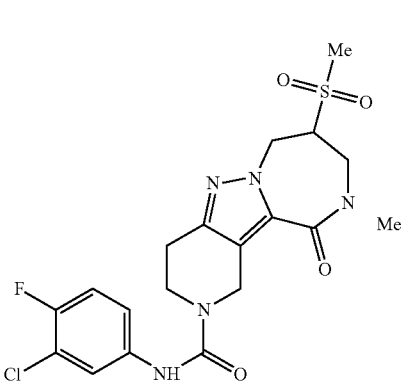 [SMILES: CS(=O)(=O)C1CNC(=O)c2c3c(nn2C1)CCN(C(=O)Nc1ccc(F)c(Cl)c1)C3 ; "Me"]
027

TABLE 1-continued
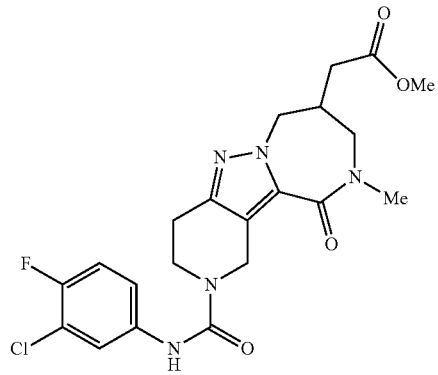 [SMILES: COC(=O)CC1CN(C)C(=O)c2c3c(nn2C1)CCN(C(=O)Nc1ccc(F)c(Cl)c1)C3]
028
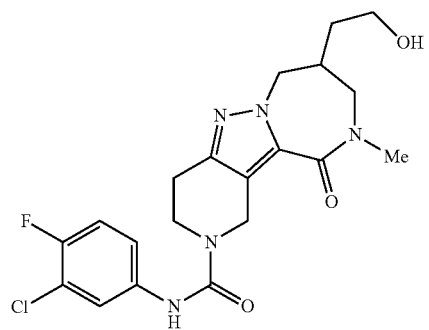 [SMILES: CN1CC(CCO)Cn2nc3c(c2C1=O)CN(C(=O)Nc1ccc(F)c(Cl)c1)CC3]
029
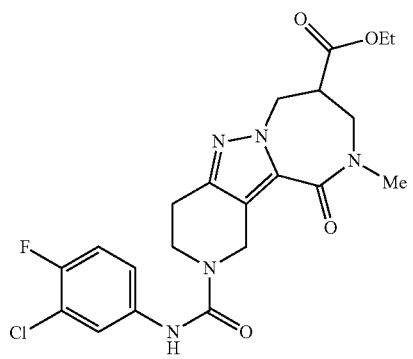 [SMILES: CCOC(=O)C1CN(C)C(=O)c2c3c(nn2C1)CCN(C(=O)Nc1ccc(F)c(Cl)c1)C3]
030
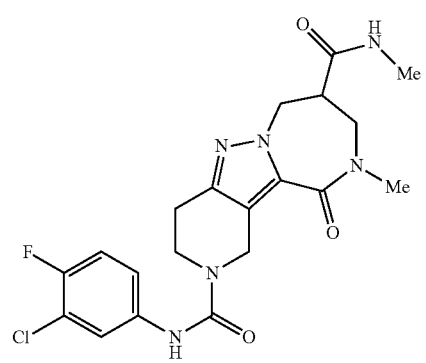 [SMILES: CNC(=O)C1CN(C)C(=O)c2c3c(nn2C1)CCN(C(=O)Nc1ccc(F)c(Cl)c1)C3]
031
TABLE 1-continued
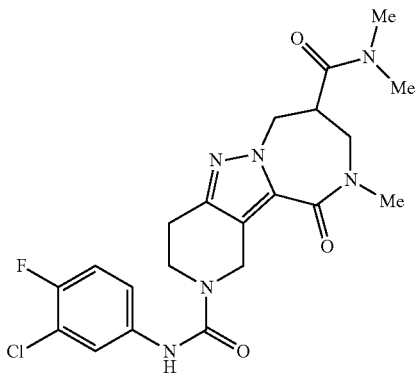 [SMILES: CN(C)C(=O)C1CN(C)C(=O)c2c3c(nn2C1)CCN(C(=O)Nc1ccc(F)c(Cl)c1)C3]
032
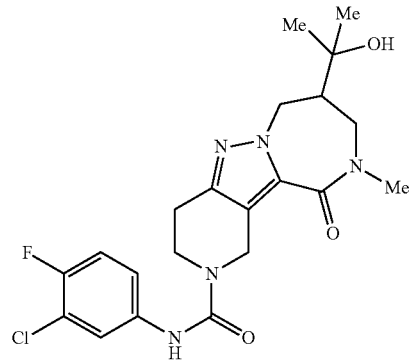 [SMILES: CN1CC(C(C)(C)O)Cn2nc3c(c2C1=O)CN(C(=O)Nc1ccc(F)c(Cl)c1)CC3]
033
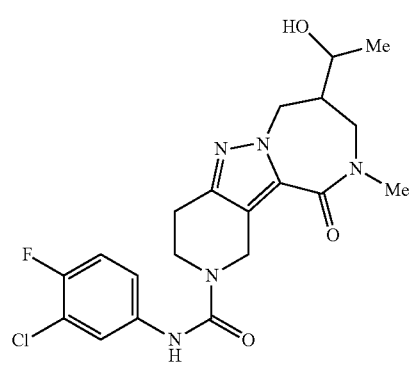 [SMILES: CC(O)C1CN(C)C(=O)c2c3c(nn2C1)CCN(C(=O)Nc1ccc(F)c(Cl)c1)C3]
034
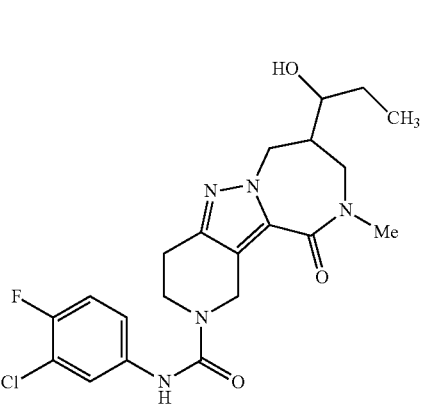 [SMILES: CCC(O)C1CN(C)C(=O)c2c3c(nn2C1)CCN(C(=O)Nc1ccc(F)c(Cl)c1)C3]
035

TABLE 1-continued
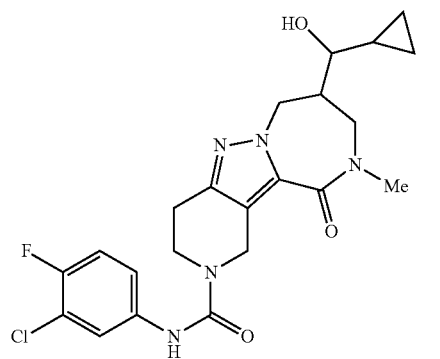 [SMILES: CN1CC(C(O)C2CC2)Cn2nc3c(c2C1=O)CN(C(=O)Nc1ccc(F)c(Cl)c1)CC3] 036
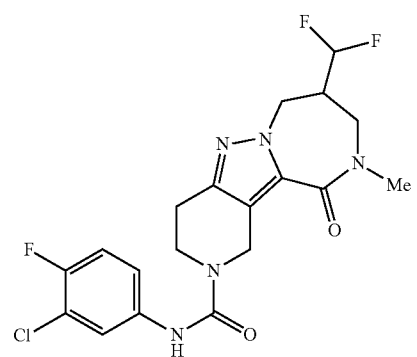 [SMILES: CN1CC(C(F)F)Cn2nc3c(c2C1=O)CN(C(=O)Nc1ccc(F)c(Cl)c1)CC3] 037
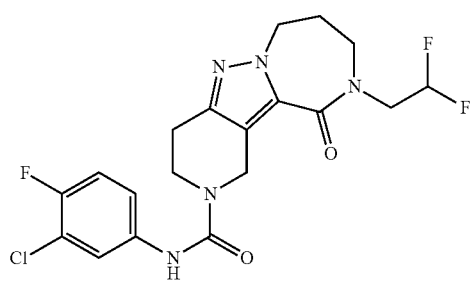 [SMILES: O=C(Nc1ccc(F)c(Cl)c1)N1CCc2nn3c(c2C1)C(=O)N(CC(F)F)CCC3] 038
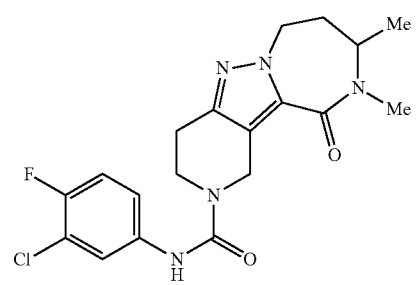 [SMILES: CC1CCn2nc3c(c2C(=O)N1C)CN(C(=O)Nc1ccc(F)c(Cl)c1)CC3] 039
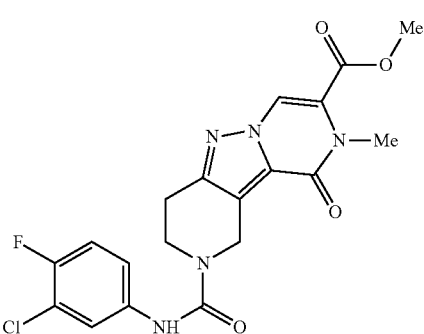 [SMILES: COC(=O)c1cn2nc3c(c2c(=O)n1C)CN(C(=O)Nc1ccc(F)c(Cl)c1)CC3] 040
TABLE 1-continued
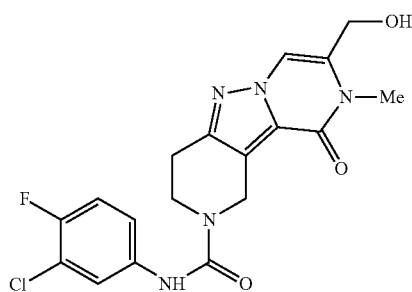 [SMILES: Cn1c(CO)cn2nc3c(c2c1=O)CN(C(=O)Nc1ccc(F)c(Cl)c1)CC3] 041
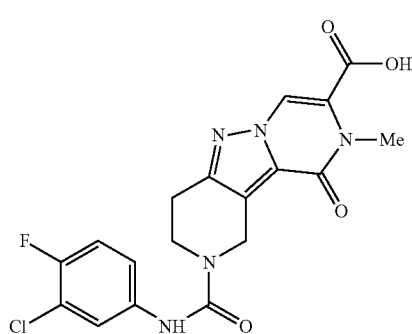 [SMILES: Cn1c(C(=O)O)cn2nc3c(c2c1=O)CN(C(=O)Nc1ccc(F)c(Cl)c1)CC3] 042
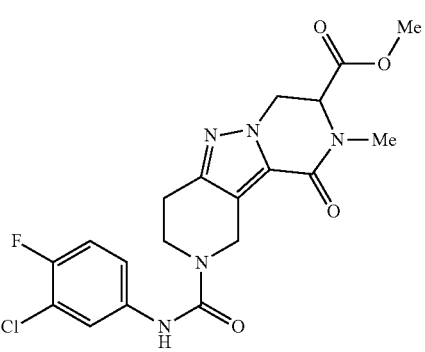 [SMILES: COC(=O)C1Cn2nc3c(c2C(=O)N1C)CN(C(=O)Nc1ccc(F)c(Cl)c1)CC3] 043
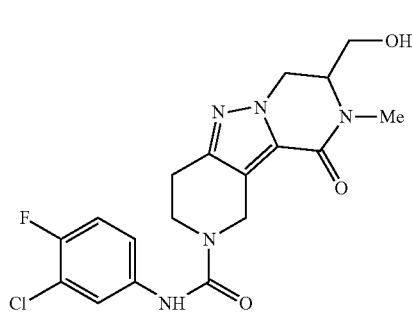 [SMILES: CN1C(=O)c2c3c(nn2CC1CO)CCN(C(=O)Nc1ccc(F)c(Cl)c1)C3] 044
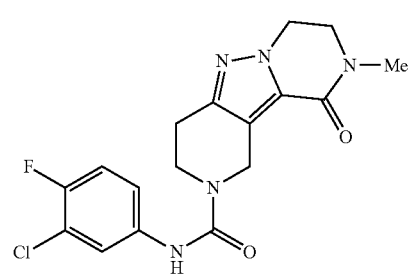 [SMILES: CN1CCn2nc3c(c2C1=O)CN(C(=O)Nc1ccc(F)c(Cl)c1)CC3] 045

TABLE 1-continued

046

In an embodiment, compounds of Formulas I, II, III and IV are selected from:

| Compound ID | Compound Name |
|---|---|
| 001 | N-(3-chloro-4-fluorophenyl)-10-methyl-8-methylene-11-oxo-1,3,4,7,8,9,10,11-octahydro-2H-pyrido[4',3':3,4]pyrazolo[1,5-a][1,4]diazepine-2-carboxamide |
| 002 | N-(3-chloro-4-fluorophenyl)-8-(hydroxymethyl)-10-methyl-11-oxo-1,3,4,7,8,9,10,11-octahydro-2H-pyrido[4',3':3,4]pyrazolo[1,5-a][1,4]diazepine-2-carboxamide |
| 003 | N-(3-chloro-4-fluorophenyl)-8-hydroxy-8-(hydroxymethyl)-10-methyl-11-oxo-1,3,4,7,8,9,10,11-octahydro-2H-pyrido[4',3':3,4]pyrazolo[1,5-a][1,4]diazepine-2-carboxamide |
| 004 | N-(3-chloro-4-fluorophenyl)-8-hydroxy-10-methyl-11-oxo-1,3,4,7,8,9,10,11-octahydro-2H-pyrido[4',3':3,4]pyrazolo[1,5-a][1,4]diazepine-2-carboxamide |
| 005 | N-(3-chloro-4-fluorophenyl)-8,8-difluoro-10-methyl-11-oxo-1,3,4,7,8,9,10,11-octahydro-2H-pyrido[4',3':3,4]pyrazolo[1,5-a][1,4]diazepine-2-carboxamide |
| 006 | N-(3-chloro-4-fluorophenyl)-8-fluoro-10-methyl-11-oxo-1,3,4,7,8,9,10,11-octahydro-2H-pyrido[4',3':3,4]pyrazolo[1,5-a][1,4]diazepine-2-carboxamide |
| 007 | N-(3-bromo-4-fluorophenyl)-8-fluoro-10-methyl-11-oxo-1,3,4,7,8,9,10,11-octahydro-2H-pyrido[4',3':3,4]pyrazolo[1,5-a][1,4]diazepine-2-carboxamide |
| 008 | N-(2-bromo-3-fluoropyridin-4-yl)-8-fluoro-10-methyl-11-oxo-1,3,4,7,8,9,10,11-octahydro-2H-pyrido[4',3':3,4]pyrazolo[1,5-a][1,4]diazepine-2-carboxamide |
| 009 | N-(3-cyano-4-fluorophenyl)-8-fluoro-10-methyl-11-oxo-1,3,4,7,8,9,10,11-octahydro-2H-pyrido[4',3':3,4]pyrazolo[1,5-a][1,4]diazepine-2-carboxamide |
| 010 | 8-fluoro-N-(4-fluoro-3-methylphenyl)-10-methyl-11-oxo-1,3,4,7,8,9,10,11-octahydro-2H-pyrido[4',3':3,4]pyrazolo[1,5-a][1,4]diazepine-2-carboxamide |
| 011 | 8-fluoro-N-(4-fluoro-3-(trifluoromethyl)phenyl)-10-methyl-11-oxo-1,3,4,7,8,9,10,11-octahydro-2H-pyrido[4',3':3,4]pyrazolo[1,5-a][1,4]diazepine-2-carboxamide |
| 012 | N-(5-chloro-2,4-difluorophenyl)-8-fluoro-10-methyl-11-oxo-1,3,4,7,8,9,10,11-octahydro-2H-pyrido[4',3':3,4]pyrazolo[1,5-a][1,4]diazepine-2-carboxamide |
| 013 | N-(5-bromo-2,4-difluorophenyl)-8-fluoro-10-methyl-11-oxo-1,3,4,7,8,9,10,11-octahydro-2H-pyrido[4',3':3,4]pyrazolo[1,5-a][1,4]diazepine-2-carboxamide |
| 014 | N-(3-chloro-4-fluoro-phenyl)-8,10-dimethyl-11-oxo-1,3,4,7,8,9-hexahydropyrido[2,3]pyrazolo[2,4-b][1,4]diazepine-2-carboxamide |
| 015 | N-(3-chloro-4-fluoro-phenyl)-10-methyl-11-oxo-1,3,4,7,8,9-hexahydropyrido [2,3]pyrazolo[2,4-b][1,4]diazepine-2-carboxamide |
| 016A | (S*)-N-(3-chloro-4-fluorophenyl)-8-methoxy-10-methyl-11-oxo-3,4,8,9,10,11-hexahydro-1H-pyrido[4',3':3,4]pyrazolo[1,5-a][1,4]diazepine-2(7H)-carboxamide |
| 016B | (R*)-N-(3-chloro-4-fluorophenyl)-8-methoxy-10-methyl-11-oxo-3,4,8,9,10,11-hexahydro-1H-pyrido[4',3':3,4]pyrazolo[1,5-a][1,4]diazepine-2(7H)-carboxamide |
| 017 | N-(3-chloro-4-fluorophenyl)-8-ethoxy-10-methyl-11-oxo-1,3,4,7,8,9,10,11-octahydro-2H-pyrido[4',3':3,4]pyrazolo[1,5-a][1,4]diazepine-2-carboxamide |
| 018 | N-(3-chloro-4-fluorophenyl)-8-(2,2-difluoroethoxy)-10-methyl-11-oxo-1,3,4,7,8,9,10,11-octahydro-2H-pyrido[4',3':3,4]pyrazolo[1,5-a][1,4]diazepine-2-carboxamide |
| 019 | 8-amino-N-(3-chloro-4-fluorophenyl)-10-methyl-11-oxo-1,3,4,7,8,9,10,11-octahydro-2H-pyrido[4',3':3,4]pyrazolo[1,5-a][1,4]diazepine-2-carboxamide |

-continued

| Compound ID | Compound Name |
|---|---|
| 020 | N-(3-chloro-4-fluorophenyl)-8-(dimethylamino)-10-methyl-11-oxo-1,3,4,7,8,9,10,11-octahydro-2H-pyrido[4',3':3,4]pyrazolo[1,5-a][1,4]diazepine-2-carboxamide |
| 021 | N-(3-chloro-4-fluorophenyl)-10-methyl-8-morpholino-11-oxo-1,3,4,7,8,9,10,11-octahydro-2H-pyrido[4',3':3,4]pyrazolo[1,5-a][1,4]diazepine-2-carboxamide |
| 022 | N-(3-chloro-4-fluorophenyl)-8-(3,3-difluoroazetidin-1-yl)-10-methyl-11-oxo-1,3,4,7,8,9,10,11-octahydro-2H-pyrido[4',3':3,4]pyrazolo[1,5-a][1,4]diazepine-2-carboxamide |
| 023 | 8-(azetidin-1-yl)-N-(3-chloro-4-fluorophenyl)-10-methyl-11-oxo-1,3,4,7,8,9,10,11-octahydro-2H-pyrido[4',3':3,4]pyrazolo[1,5-a][1,4]diazepine-2-carboxamide |
| 024 | N-(3-chloro-4-fluorophenyl)-10-methyl-11-oxo-8-(pyrrolidin-1-yl)-1,3,4,7,8,9,10,11-octahydro-2H-pyrido[4',3':3,4]pyrazolo[1,5-a][1,4]diazepine-2-carboxamide |
| 025 | N-(3-chloro-4-fluorophenyl)-10-methyl-8-(methylthio)-11-oxo-1,3,4,7,8,9,10,11-octahydro-2H-pyrido[4',3':3,4]pyrazolo[1,5-a][1,4]diazepine-2-carboxamide |
| 026A | N-(3-chloro-4-fluorophenyl)-10-methyl-8-(methylsulfinyl)-11-oxo-1,3,4,7,8,9,10,11-octahydro-2H-pyrido[4',3':3,4]pyrazolo[1,5-a][1,4]diazepine-2-carboxamide |
| 026B | N-(3-chloro-4-fluorophenyl)-10-methyl-8-(methylsulfinyl)-11-oxo-1,3,4,7,8,9,10,11-octahydro-2H-pyrido[4',3':3,4]pyrazolo[1,5-a][1,4]diazepine-2-carboxamide |
| 027 | N-(3-chloro-4-fluoro-phenyl)-10-methyl-8-methylsulfonyl-11-oxo-1,3,4,7,8,9-hexahydropyrido[2,3]pyrazolo[2,4-b][1,4]diazepine-2-carboxamide |
| 028 | methyl 2-(2-((3-chloro-4-fluorophenyl)carbamoyl)-10-methyl-11-oxo-1,3,4,7,8,9,10,11-octahydro-2H-pyrido[4',3':3,4]pyrazolo[1,5-a][1,4]diazepin-8-yl)acetate |
| 029 | N-(3-chloro-4-fluorophenyl)-8-(2-hydroxyethyl)-10-methyl-11-oxo-1,3,4,7,8,9,10,11-octahydro-2H-pyrido[4',3':3,4]pyrazolo[1,5-a][1,4]diazepine-2-carboxamide |
| 030 | ethyl 2-((3-chloro-4-fluorophenyl)carbamoyl)-10-methyl-11-oxo-2,3,4,7,8,9,10,11-octahydro-1H-pyrido[4',3':3,4]pyrazolo[1,5-a][1,4]diazepine-8-carboxylate |
| 031 | N2-(3-chloro-4-fluorophenyl)-N8,10-dimethyl-11-oxo-1,3,4,7,8,9,10,11-octahydro-2H-pyrido[4',3':3,4]pyrazolo[1,5-a][1,4]diazepine-2,8-dicarboxamide |
| 032 | N2-(3-chloro-4-fluorophenyl)-N8,N8,10-trimethyl-11-oxo-1,3,4,7,8,9,10,11-octahydro-2H-pyrido[4',3':3,4]pyrazolo[1,5-a][1,4]diazepine-2,8-dicarboxamide |
| 033 | N-(3-chloro-4-fluorophenyl)-8-(2-hydroxypropan-2-yl)-10-methyl-11-oxo-3,4,8,9,10,11-hexahydro-1H-pyrido[4',3':3,4]pyrazolo[1,5-a][1,4]diazepine-2(7H)-carboxamide |
| 034 | N-(3-chloro-4-fluorophenyl)-8-(1-hydroxyethyl)-10-methyl-11-oxo-1,3,4,7,8,9,10,11-octahydro-2H-pyrido[4',3':3,4]pyrazolo[1,5-a][1,4]diazepine-2-carboxamide |
| 035 | N-(3-chloro-4-fluorophenyl)-8-(1-hydroxypropyl)-10-methyl-11-oxo-1,3,4,7,8,9,10,11-octahydro-2H-pyrido[4',3':3,4]pyrazolo[1,5-a][1,4]diazepine-2-carboxamide |
| 036 | N-(3-chloro-4-fluorophenyl)-8-(cyclopropyl(hydroxy)methyl)-10-methyl-11-oxo-1,3,4,7,8,9,10,11-octahydro-2H-pyrido[4',3':3,4]pyrazolo[1,5-a][1,4]diazepine-2-carboxamide |
| 037 | N-(3-chloro-4-fluorophenyl)-8-(difluoromethyl)-10-methyl-11-oxo-1,3,4,7,8,9,10,11-octahydro-2H-pyrido[4',3':3,4]pyrazolo[1,5-a][1,4]diazepine-2-carboxamide |
| 038 | N-(3-chloro-4-fluorophenyl)-10-(2,2-difluoroethyl)-11-oxo-1,3,4,7,8,9,10,11-octahydro-2H-pyrido[4',3':3,4]pyrazolo[1,5-a][1,4]diazepine-2-carboxamide |
| 039 | N-(3-chloro-4-fluorophenyl)-9,10-dimethyl-11-oxo-1,3,4,7,8,9,10,11-octahydro-2H-pyrido[4',3':3,4]pyrazolo[1,5-a][1,4]diazepine-2-carboxamide |
| 040 | methyl 2-((3-chloro-4-fluorophenyl)carbamoyl)-9-methyl-10-oxo-1,2,3,4,9,10-hexahydropyrido[4',3':3,4]pyrazolo[1,5-a]pyrazine-8-carboxylate |
| 041 | N-(3-chloro-4-fluorophenyl)-8-(hydroxymethyl)-9-methyl-10-oxo-3,4,9,10-tetrahydropyrido[4',3':3,4]pyrazolo[1,5-a]pyrazine-2(1H)-carboxamide |
| 042 | 2-((3-chloro-4-fluorophenyl)carbamoyl)-9-methyl-10-oxo-1,2,3,4,9,10-hexahydropyrido[4',3':3,4]pyrazolo[1,5-a]pyrazine-8-carboxylic acid |
| 043 | methyl 2-((3-chloro-4-fluorophenyl)carbamoyl)-9-methyl-10-oxo-1,2,3,4,7,8,9,10-octahydropyrido[4',3':3,4]pyrazolo[1,5-a]pyrazine-8-carboxylate |
| 044 | N-(3-chloro-4-fluorophenyl)-8-(hydroxymethyl)-9-methyl-10-oxo-3,4,7,8,9,10-hexahydropyrido[4',3':3,4]pyrazolo[1,5-a]pyrazine-2(1H)-carboxamide |

| Compound ID | Compound Name |
|---|---|
| 045 | N-(3-chloro-4-fluorophenyl)-9-methyl-10-oxo-3,4,7,8,9,10-hexahydropyrido[4',3':3,4]pyrazolo[1,5-a]pyrazine-2(1H)-carboxamide |
| 046 | N-(3-chloro-4-fluorophenyl)-10-methyl-1,3,4,7,8,9,10,11-octahydro-2H-pyrido[4',3':3,4]pyrazolo[1,5-a][1,4]diazepine-2-carboxamide |

*Pure but unknown enantiomer or diastereomer. and pharmaceutically acceptable salts thereof.

Certain embodiments of Formulas I, II, III and IV are shown below in Table 2. disclosed compounds.

TABLE 2

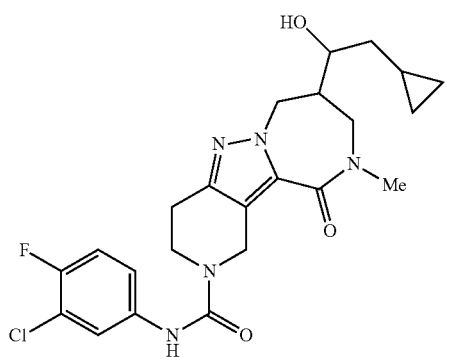 [SMILES: CN1CC(C(O)CC2CC2)Cn2nc3c(c2C1=O)CN(C(=O)Nc1ccc(F)c(Cl)c1)CC3]

047

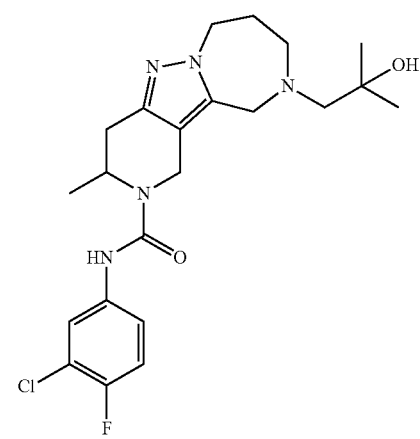 [SMILES: CC1Cc2nn3c(c2CN1C(=O)Nc1ccc(F)c(Cl)c1)CN(CC(C)(C)O)CCC3]

048

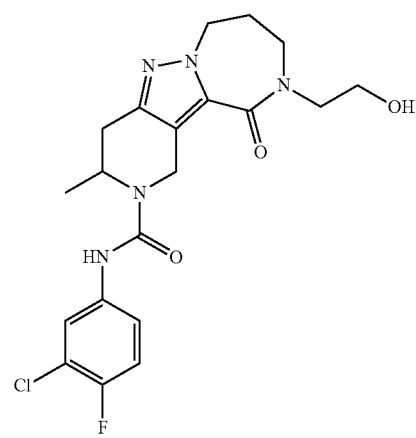 [SMILES: CC1Cc2nn3c(c2CN1C(=O)Nc1ccc(F)c(Cl)c1)C(=O)N(CCO)CCC3]

049

TABLE 2-continued

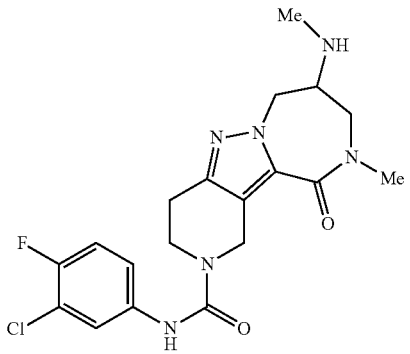 [SMILES: CNC1CN(C)C(=O)c2c3c(nn2C1)CCN(C(=O)Nc1ccc(F)c(Cl)c1)C3]

050

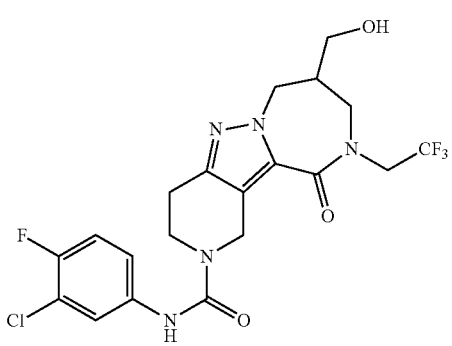 [SMILES: O=C(Nc1ccc(F)c(Cl)c1)N1CCc2nn3c(c2C1)C(=O)N(CC(F)(F)F)CC(CO)C3]

051

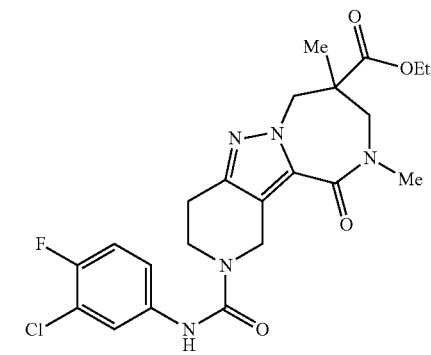 [SMILES: CCOC(=O)C1(C)CN(C)C(=O)c2c3c(nn2C1)CCN(C(=O)Nc1ccc(F)c(Cl)c1)C3]

052

TABLE 2-continued
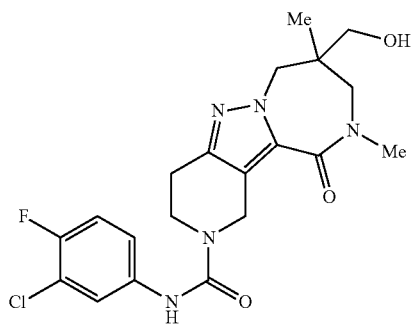 [SMILES: CN1CC(C)(CO)Cn2nc3c(c2C1=O)CN(C(=O)Nc1ccc(F)c(Cl)c1)CC3]
053
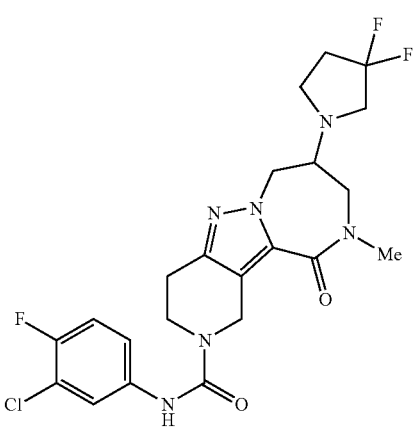 [SMILES: CN1CC(N2CCC(F)(F)C2)Cn2nc3c(c2C1=O)CN(C(=O)Nc1ccc(F)c(Cl)c1)CC3]
054
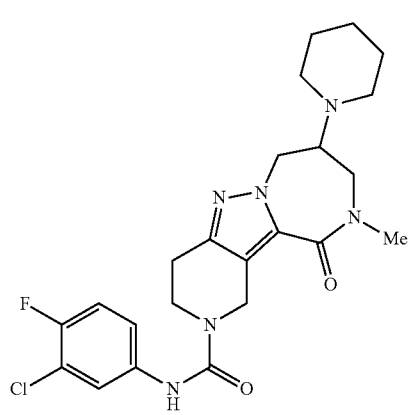 [SMILES: CN1CC(N2CCCCC2)Cn2nc3c(c2C1=O)CN(C(=O)Nc1ccc(F)c(Cl)c1)CC3]
055
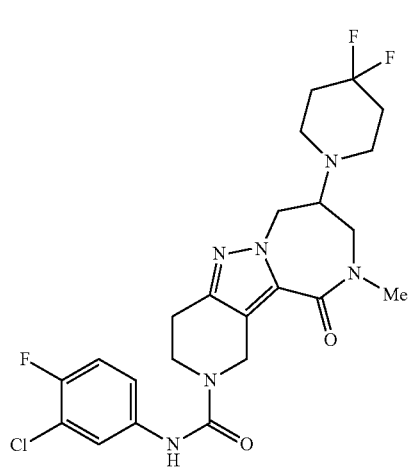 [SMILES: CN1CC(N2CCC(F)(F)CC2)Cn2nc3c(c2C1=O)CN(C(=O)Nc1ccc(F)c(Cl)c1)CC3]
056
TABLE 2-continued
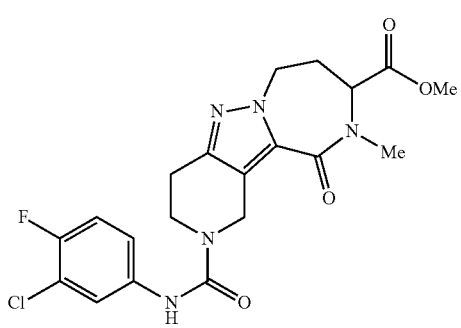 [SMILES: COC(=O)C1CCn2nc3c(c2C(=O)N1C)CN(C(=O)Nc1ccc(F)c(Cl)c1)CC3]
057
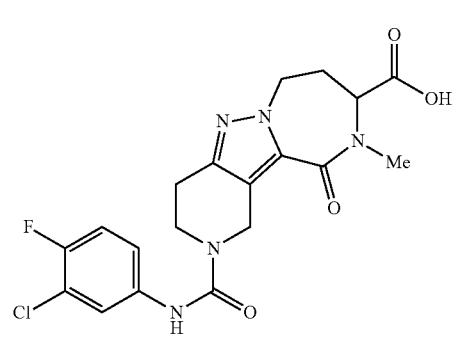 [SMILES: CN1C(=O)c2c3c(nn2CCC1C(=O)O)CCN(C(=O)Nc1ccc(F)c(Cl)c1)C3]
058
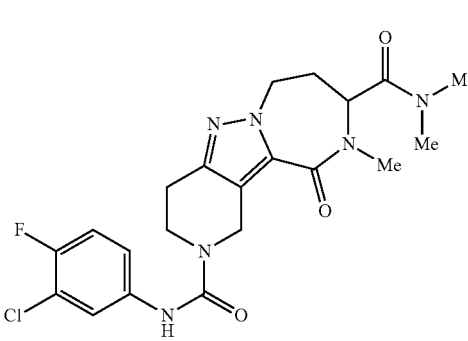
059
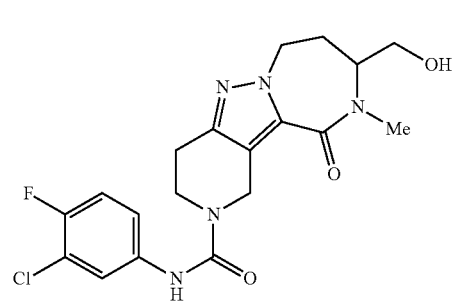 [SMILES: CN1C(=O)c2c3c(nn2CCC1CO)CCN(C(=O)Nc1ccc(F)c(Cl)c1)C3]
060
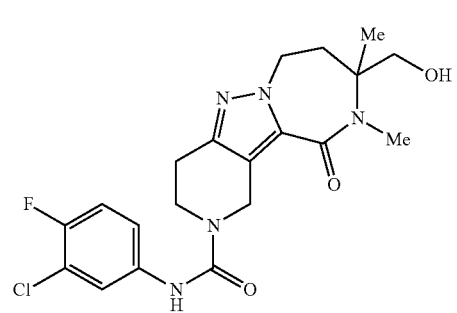 [SMILES: CN1C(=O)c2c3c(nn2CCC1(C)CO)CCN(C(=O)Nc1ccc(F)c(Cl)c1)C3]
061

TABLE 2-continued
062 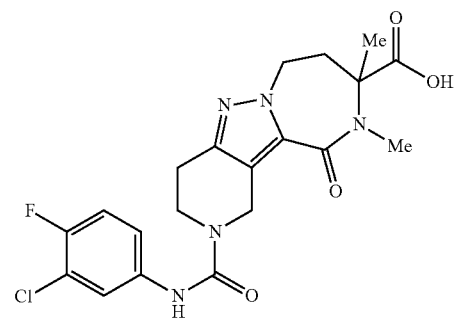 [SMILES: CN1C(=O)c2c3c(nn2CCC1(C)C(=O)O)CCN(C(=O)Nc1ccc(F)c(Cl)c1)C3]
063 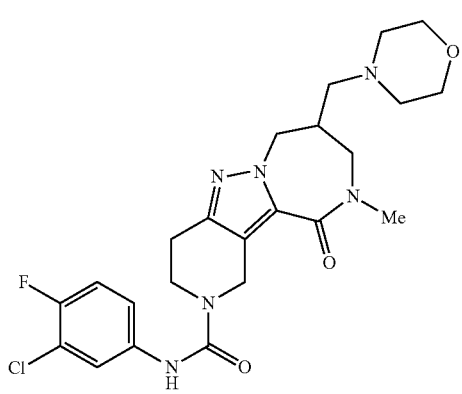 [SMILES: CN1CC(CN2CCOCC2)Cn2nc3c(c2C1=O)CN(C(=O)Nc1ccc(F)c(Cl)c1)CC3]
064 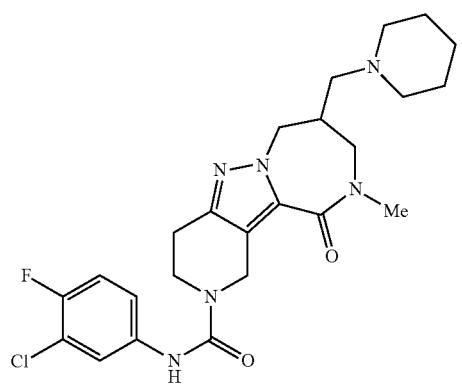 [SMILES: CN1CC(CN2CCCCC2)Cn2nc3c(c2C1=O)CN(C(=O)Nc1ccc(F)c(Cl)c1)CC3]
065 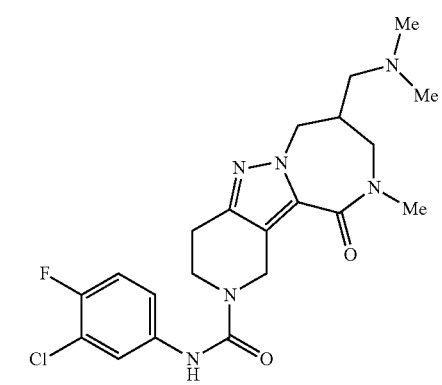 [SMILES: CN(C)CC1CN(C)C(=O)c2c3c(nn2C1)CCN(C(=O)Nc1ccc(F)c(Cl)c1)C3]
TABLE 2-continued
066 
067 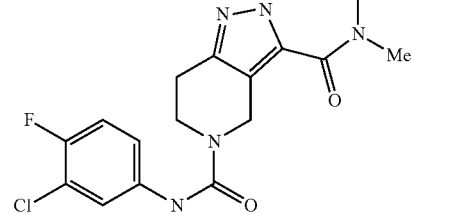
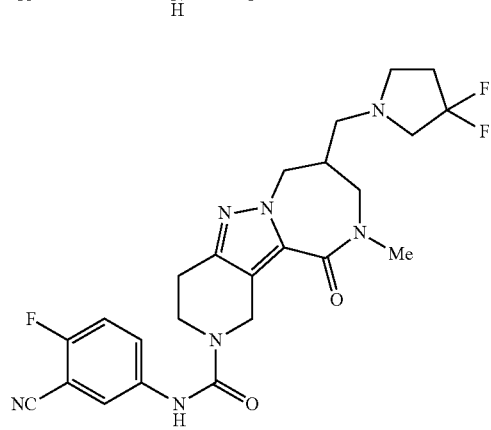
068 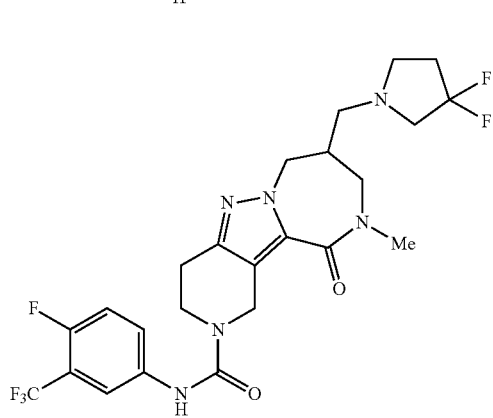
069 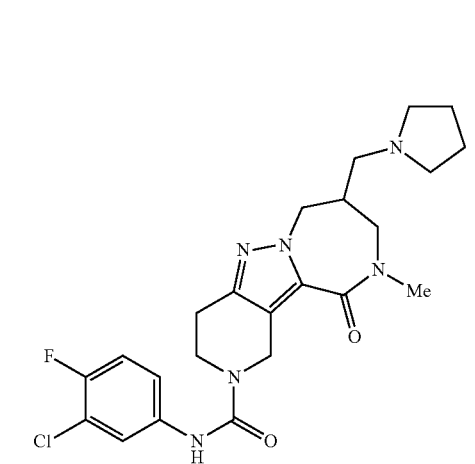 [SMILES: CN1CC(CN2CCCC2)Cn2nc3c(c2C1=O)CN(C(=O)Nc1ccc(F)c(Cl)c1)CC3]

TABLE 2-continued
070
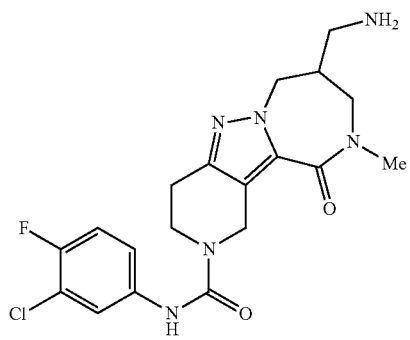
071
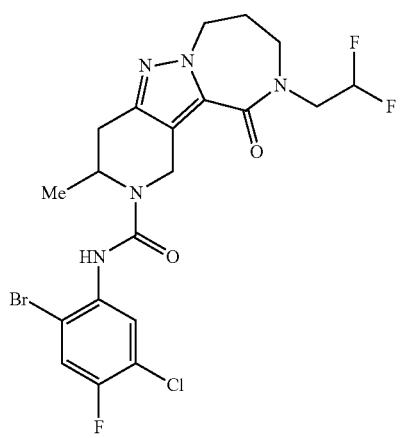 [SMILES: CC1Cc2nn3c(c2CN1C(=O)Nc1cc(Cl)c(F)cc1Br)C(=O)N(CC(F)F)CCC3]
072
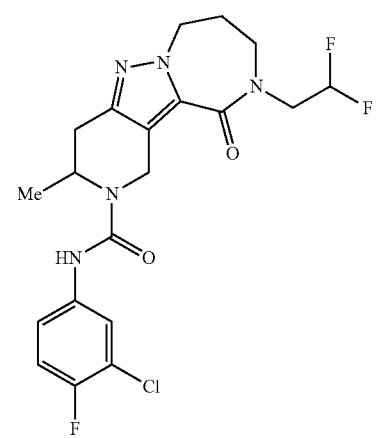 [SMILES: CC1Cc2nn3c(c2CN1C(=O)Nc1ccc(F)c(Cl)c1)C(=O)N(CC(F)F)CCC3]
TABLE 2-continued
073
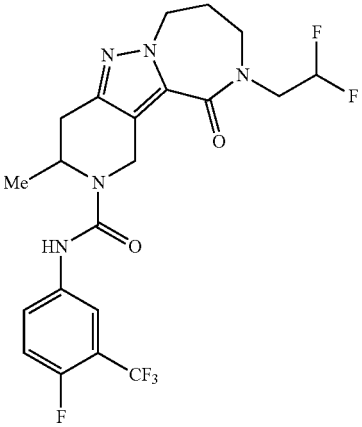
074
075
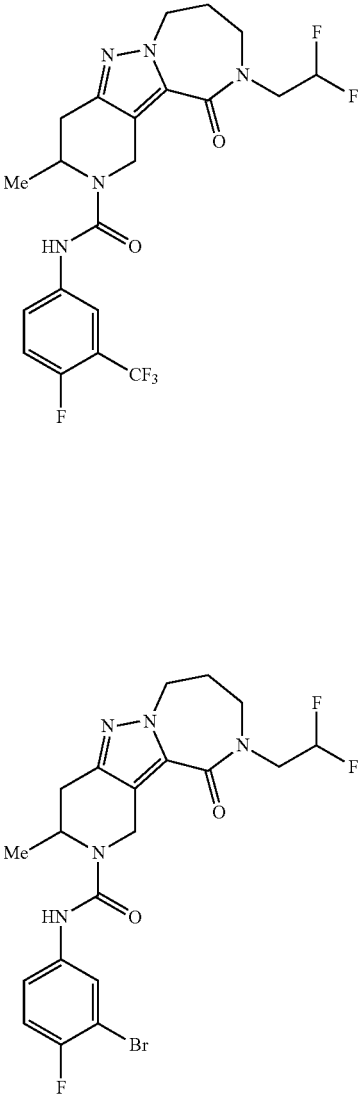
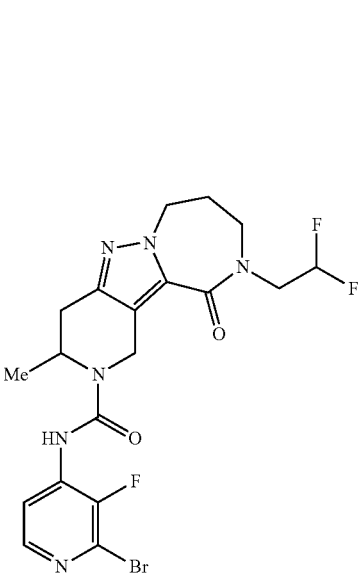 [SMILES: CC1Cc2nn3c(c2CN1C(=O)Nc1ccnc(Br)c1F)C(=O)N(CC(F)F)CCC3]

TABLE 2-continued
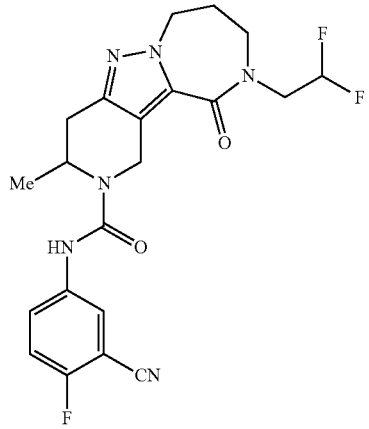
076
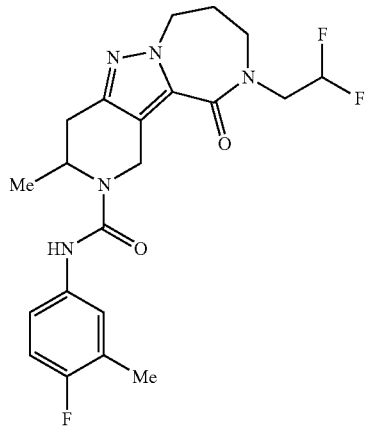 [SMILES: Cc1cc(NC(=O)N2Cc3c(nn4c3C(=O)N(CC(F)F)CCC4)CC2C)ccc1F]
077
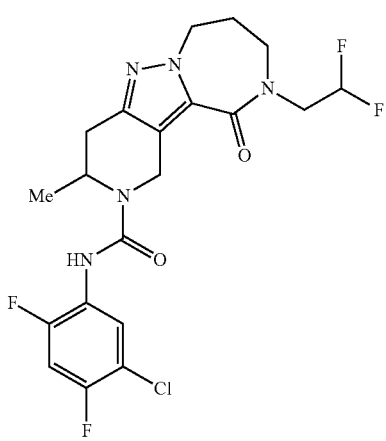 [SMILES: CC1Cc2nn3c(c2CN1C(=O)Nc1cc(Cl)c(F)cc1F)C(=O)N(CC(F)F)CCC3]
078
TABLE 2-continued
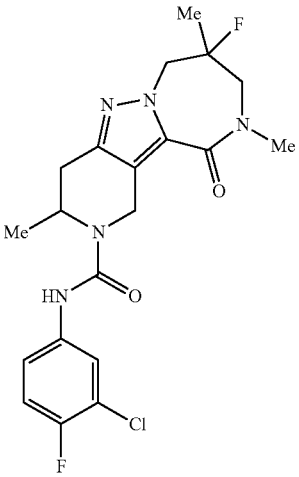 [SMILES: CC1Cc2nn3c(c2CN1C(=O)Nc1ccc(F)c(Cl)c1)C(=O)N(C)CC(C)(F)C3]
079
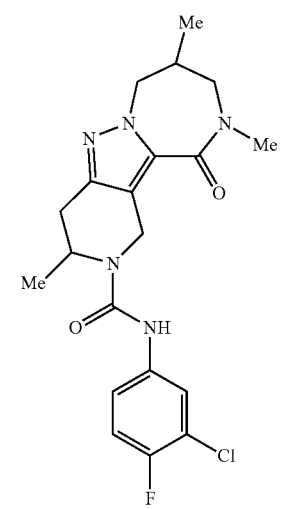 [SMILES: CC1CN(C)C(=O)c2c3c(nn2C1)CC(C)N(C(=O)Nc1ccc(F)c(Cl)c1)C3]
080
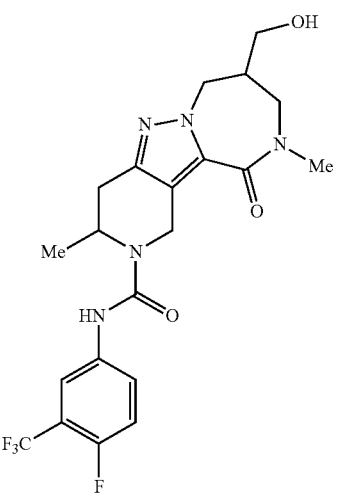 [SMILES: CC1Cc2nn3c(c2CN1C(=O)Nc1ccc(F)c(C(F)(F)F)c1)C(=O)N(C)CC(CO)C3]
081

TABLE 2-continued
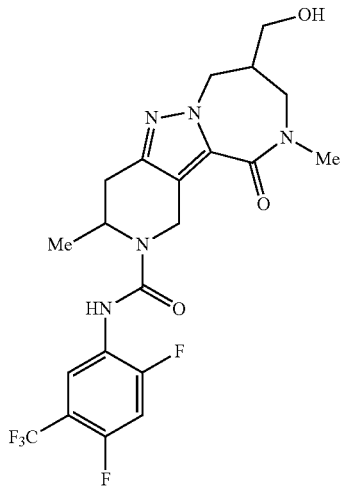
082
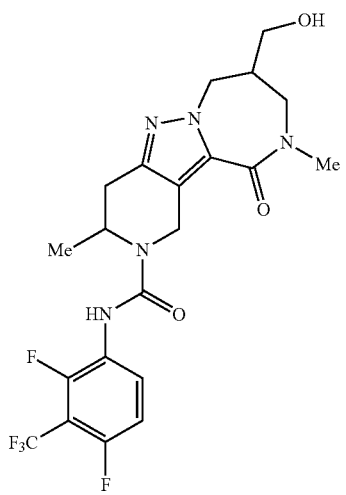
083
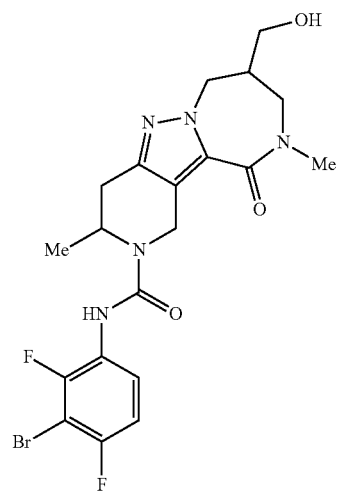
084
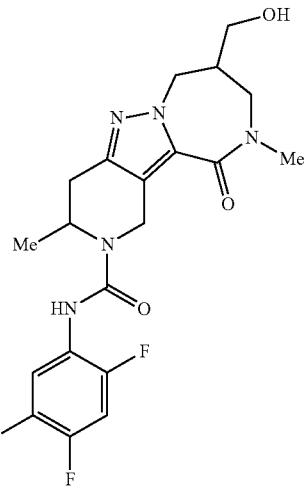
085
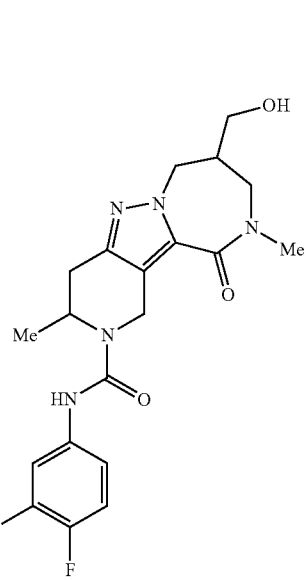
086
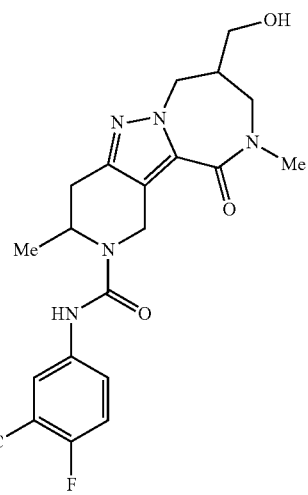
087

TABLE 2-continued
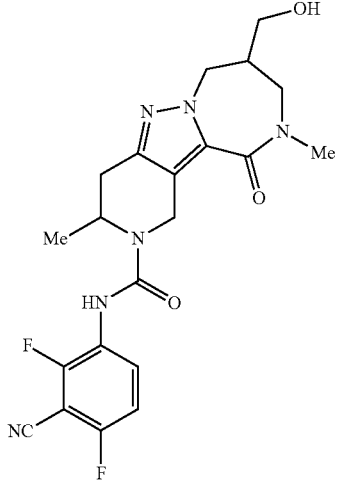 [SMILES: CC1Cc2nn3c(c2CN1C(=O)Nc1ccc(F)c(C#N)c1F)C(=O)N(C)CC(CO)C3]
088
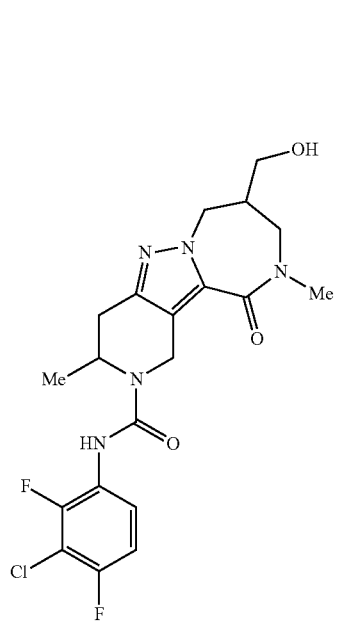 [SMILES: CC1Cc2nn3c(c2CN1C(=O)Nc1ccc(F)c(Cl)c1F)C(=O)N(C)CC(CO)C3]
089
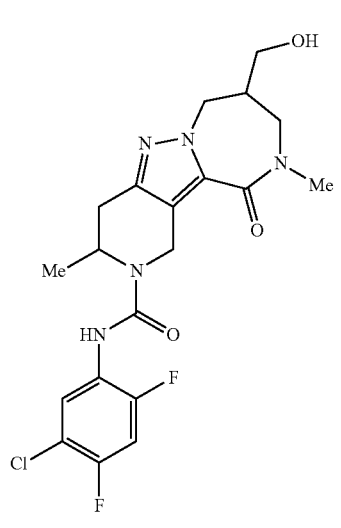 [SMILES: CC1Cc2nn3c(c2CN1C(=O)Nc1cc(Cl)c(F)cc1F)C(=O)N(C)CC(CO)C3]
090
TABLE 2-continued
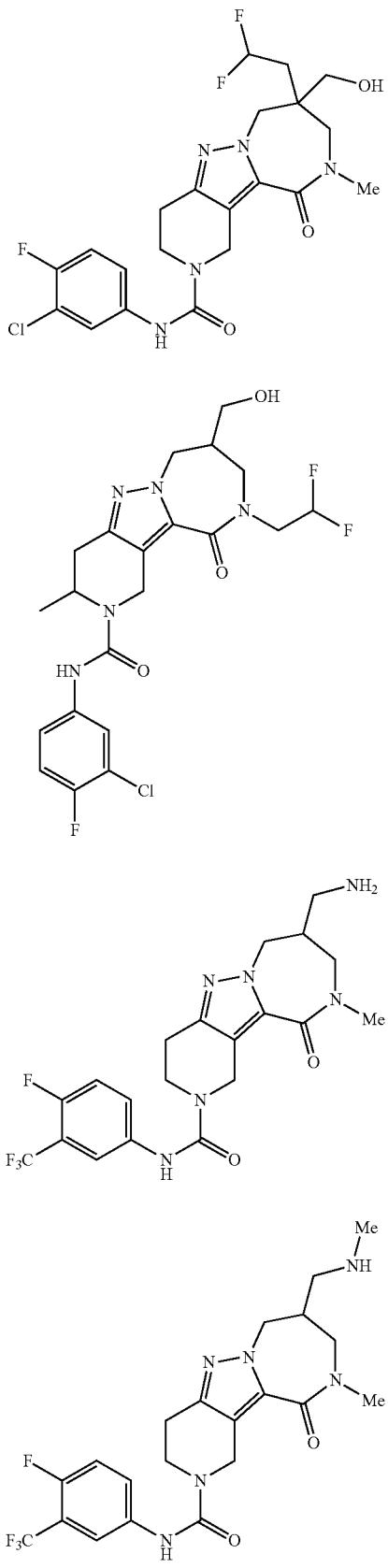
091
092
093
094

TABLE 2-continued
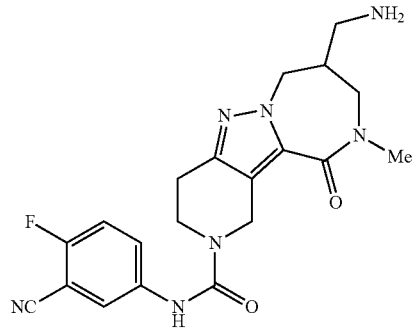 [SMILES: CN1CC(CN)Cn2nc3c(c2C1=O)CN(C(=O)Nc1ccc(F)c(C#N)c1)CC3]
095
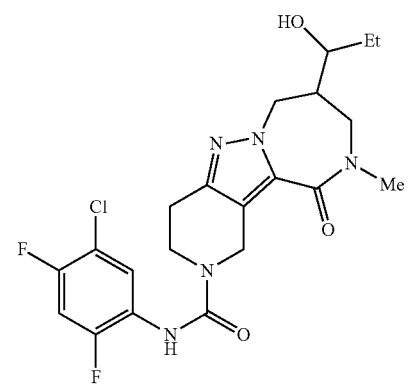 [SMILES: CCC(O)C1CN(C)C(=O)c2c3c(nn2C1)CCN(C(=O)Nc1cc(Cl)c(F)cc1F)C3]
096
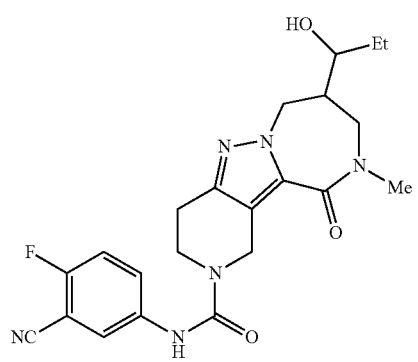 [SMILES: CCC(O)C1CN(C)C(=O)c2c3c(nn2C1)CCN(C(=O)Nc1ccc(F)c(C#N)c1)C3]
097
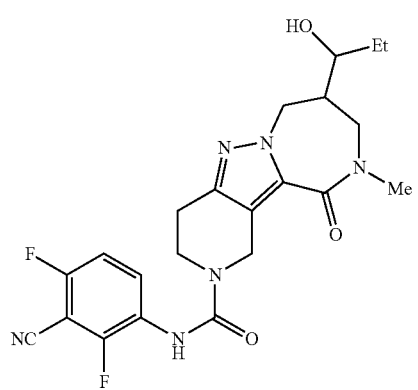 [SMILES: CCC(O)C1CN(C)C(=O)c2c3c(nn2C1)CCN(C(=O)Nc1ccc(F)c(C#N)c1F)C3]
098
TABLE 2-continued
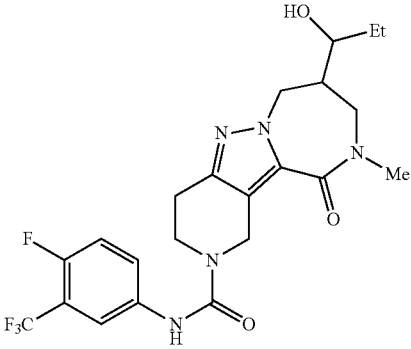 [SMILES: CCC(O)C1CN(C)C(=O)c2c3c(nn2C1)CCN(C(=O)Nc1ccc(F)c(C(F)(F)F)c1)C3]
099
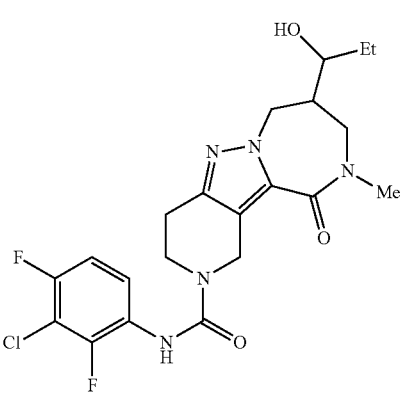 [SMILES: CCC(O)C1CN(C)C(=O)c2c3c(nn2C1)CCN(C(=O)Nc1ccc(F)c(Cl)c1F)C3]
100
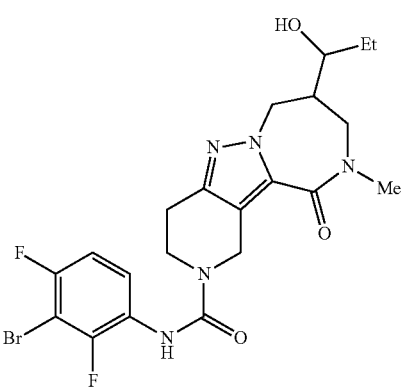 [SMILES: CCC(O)C1CN(C)C(=O)c2c3c(nn2C1)CCN(C(=O)Nc1ccc(F)c(Br)c1F)C3]
101
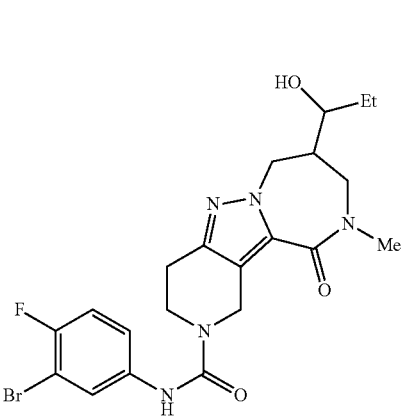 [SMILES: CCC(O)C1CN(C)C(=O)c2c3c(nn2C1)CCN(C(=O)Nc1ccc(F)c(Br)c1)C3]
102

TABLE 2-continued
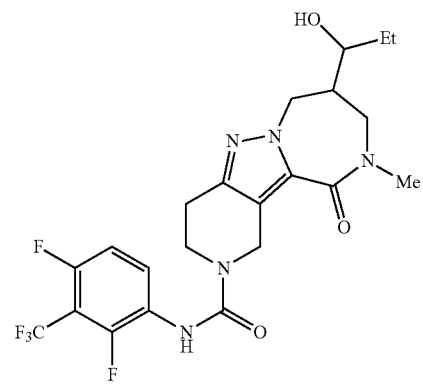 [SMILES: CCC(O)C1CN(C)C(=O)c2c3c(nn2C1)CCN(C(=O)Nc1ccc(F)c(C(F)(F)F)c1F)C3]
103
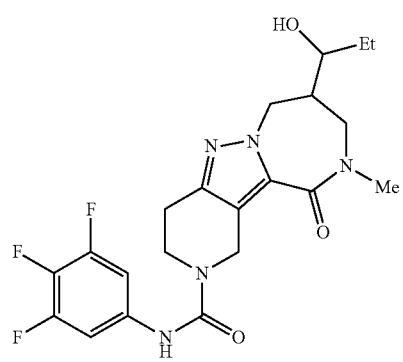 [SMILES: CCC(O)C1CN(C)C(=O)c2c3c(nn2C1)CCN(C(=O)Nc1cc(F)c(F)c(F)c1)C3]
104
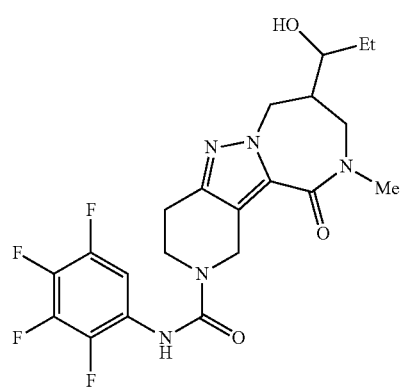 [SMILES: CCC(O)C1CN(C)C(=O)c2c3c(nn2C1)CCN(C(=O)Nc1cc(F)c(F)c(F)c1F)C3]
105
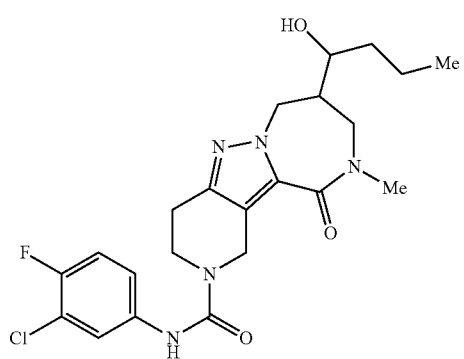 [SMILES: CCCC(O)C1CN(C)C(=O)c2c3c(nn2C1)CCN(C(=O)Nc1ccc(F)c(Cl)c1)C3]
106
TABLE 2-continued
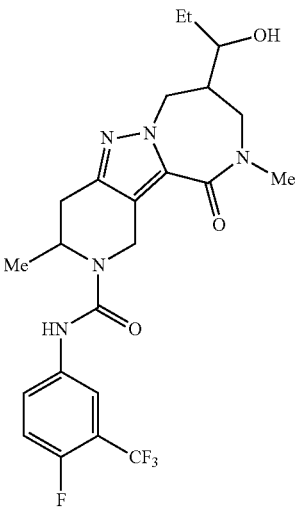 [SMILES: CCC(O)C1CN(C)C(=O)c2c3c(nn2C1)CC(C)N(C(=O)Nc1ccc(F)c(C#N)c1)C3]
107
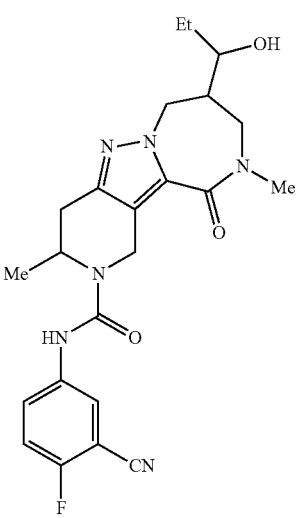
108
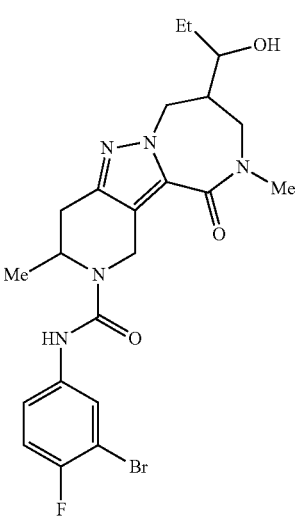 [SMILES: CCC(O)C1CN(C)C(=O)c2c3c(nn2C1)CC(C)N(C(=O)Nc1ccc(F)c(Br)c1)C3]
109

TABLE 2-continued

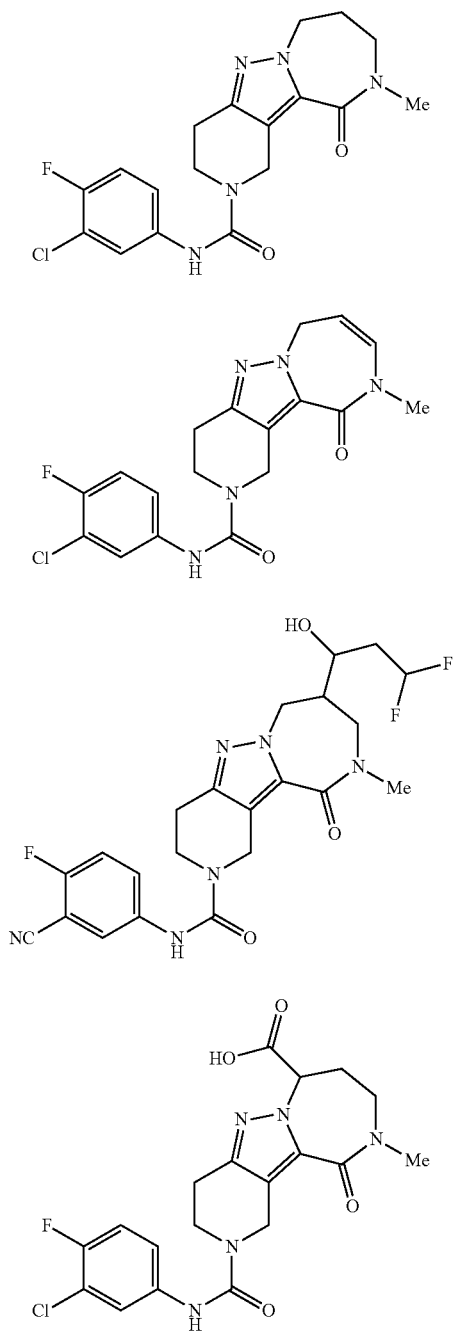
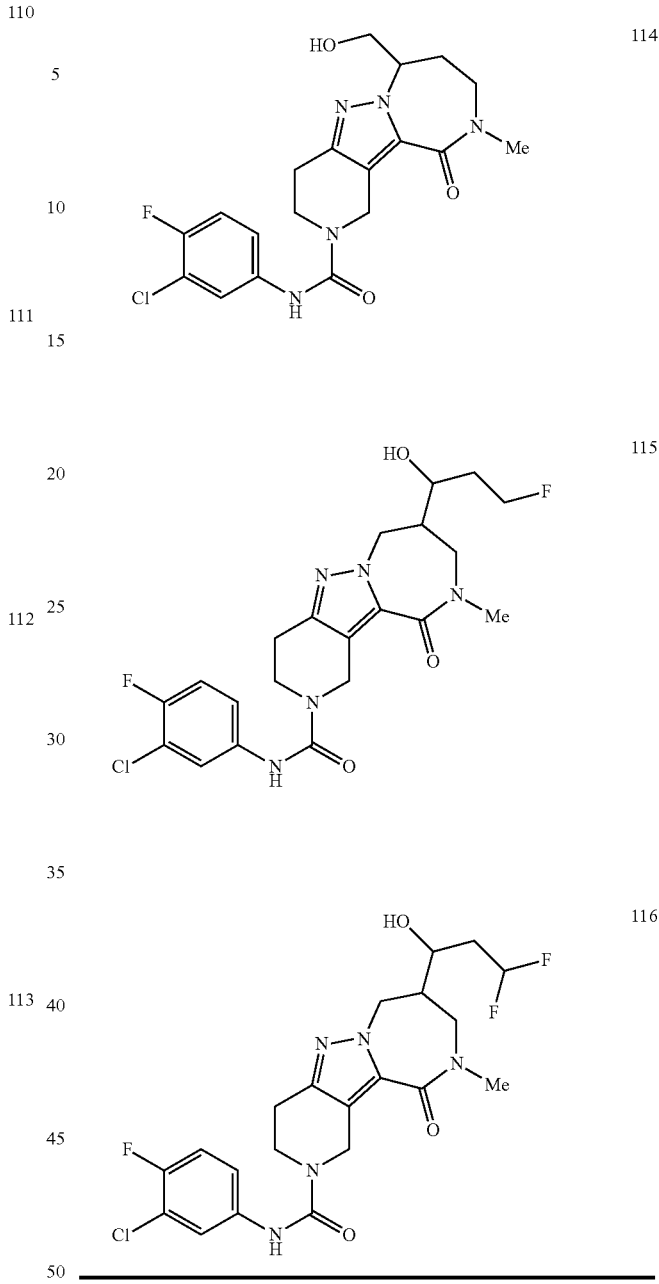

In an embodiment, compounds of Formulas I, II, III and IV are selected from:

| Compound ID | Compound Name |
|---|---|
| 047 | N-(3-chloro-4-fluorophenyl)-8-(2-cyclopropyl-1-hydroxyethyl)-10-methyl-11-oxo-1,3,4,7,8,9,10,11-octahydro-2H-pyrido[4',3':3,4]pyrazolo[1,5-a][1,4]diazepine-2-carboxamide |
| 048 | (3R)-N-(3-chloro-4-fluorophenyl)-10-(2-hydroxy-2-methylpropyl)-3-methyl-1,3,4,7,8,9,10,11-octahydro-2H-pyrido[4',3':3,4]pyrazolo[1,5-a][1,4]diazepine-2-carboxamide |
| 049 | (3R)-N-(3-chloro-4-fluorophenyl)-10-(2-hydroxyethyl)-3-methyl-11-oxo-1,3,4,7,8,9,10,11-octahydro-2H-pyrido[4',3':3,4]pyrazolo[1,5-a][1,4]diazepine-2-carboxamide |
| 050 | N-(3-chloro-4-fluorophenyl)-10-methyl-8-(methylamino)-11-oxo-1,3,4,7,8,9,10,11-octahydro-2H-pyrido[4',3':3,4]pyrazolo[1,5-a][1,4]diazepine-2-carboxamide |

-continued

| Compound ID | Compound Name |
|---|---|
| 051 | N-(3-chloro-4-fluorophenyl)-8-(hydroxymethyl)-11-oxo-10-(2,2,2-trifluoroethyl)-1,3,4,7,8,9,10,11-octahydro-2H-pyrido[4',3':3,4]pyrazolo[1,5-a][1,4]diazepine-2-carboxamide |
| 052 | ethyl 2-((3-chloro-4-fluorophenyl)carbamoyl)-8,10-dimethyl-11-oxo-1,3,4,7,8,9,10,11-octahydro-2H-pyrido[4',3':3,4]pyrazolo[1,5-a][1,4]diazepine-8-carboxylate |
| 053 | N-(3-chloro-4-fluorophenyl)-8-(hydroxymethyl)-8,10-dimethyl-11-oxo-1,3,4,7,8,9,10,11-octahydro-2H-pyrido[4',3':3,4]pyrazolo[1,5-a][1,4]diazepine-2-carboxamide |
| 054 | N-(3-chloro-4-fluorophenyl)-8-(3,3-difluoropyrrolidin-1-yl)-10-methyl-11-oxo-1,3,4,7,8,9,10,11-octahydro-2H-pyrido[4',3':3,4]pyrazolo[1,5-a][1,4]diazepine-2-carboxamide |
| 055 | N-(3-chloro-4-fluorophenyl)-10-methyl-11-oxo-8-(piperidin-1-yl)-1,3,4,7,8,9,10,11-octahydro-2H-pyrido[4',3':3,4]pyrazolo[1,5-a][1,4]diazepine-2-carboxamide |
| 056 | N-(3-chloro-4-fluorophenyl)-8-(4,4-difluoropiperidin-1-yl)-10-methyl-11-oxo-1,3,4,7,8,9,10,11-octahydro-2H-pyrido[4',3':3,4]pyrazolo[1,5-a][1,4]diazepine-2-carboxamide |
| 057 | methyl 2-((3-chloro-4-fluorophenyl)carbamoyl)-10-methyl-11-oxo-1,3,4,7,8,9,10,11-octahydro-2H-pyrido[4',3':3,4]pyrazolo[1,5-a][1,4]diazepine-9-carboxylate |
| 058 | 2-((3-chloro-4-fluorophenyl)carbamoyl)-10-methyl-11-oxo-1,3,4,7,8,9,10,11-octahydro-2H-pyrido[4',3':3,4]pyrazolo[1,5-a][1,4]diazepine-9-carboxylic acid |
| 059 | N2-(3-chloro-4-fluorophenyl)-N9,N9,10-trimethyl-11-oxo-1,3,4,7,8,9,10,11-octahydro-2H-pyrido[4',3':3,4]pyrazolo[1,5-a][1,4]diazepine-2,9-dicarboxamide |
| 060 | N-(3-chloro-4-fluorophenyl)-9-(hydroxymethyl)-10-methyl-11-oxo-1,3,4,7,8,9,10,11-octahydro-2H-pyrido[4',3':3,4]pyrazolo[1,5-a][1,4]diazepine-2-carboxamide |
| 061 | N-(3-chloro-4-fluorophenyl)-9-(hydroxymethyl)-9,10-dimethyl-11-oxo-1,3,4,7,8,9,10,11-octahydro-2H-pyrido[4',3':3,4]pyrazolo[1,5-a][1,4]diazepine-2-carboxamide |
| 062 | 2-((3-chloro-4-fluorophenyl)carbamoyl)-9,10-dimethyl-11-oxo-1,3,4,7,8,9,10,11-octahydro-2H-pyrido[4',3':3,4]pyrazolo[1,5-a][1,4]diazepine-9-carboxylic acid |
| 063 | N-(3-chloro-4-fluorophenyl)-10-methyl-8-(morpholinomethyl)-11-oxo-1,3,4,7,8,9,10,11-octahydro-2H-pyrido[4',3':3,4]pyrazolo[1,5-a][1,4]diazepine-2-carboxamide |
| 064 | N-(3-chloro-4-fluorophenyl)-10-methyl-11-oxo-8-(piperidin-1-ylmethyl)-1,3,4,7,8,9,10,11-octahydro-2H-pyrido[4',3':3,4]pyrazolo[1,5-a][1,4]diazepine-2-carboxamide |
| 065 | N-(3-chloro-4-fluorophenyl)-8-((dimethylamino)methyl)-10-methyl-11-oxo-1,3,4,7,8,9,10,11-octahydro-2H-pyrido[4',3':3,4]pyrazolo[1,5-a][1,4]diazepine-2-carboxamide |
| 066 | N-(3-chloro-4-fluorophenyl)-8-((3,3-difluoropyrrolidin-1-yl)methyl)-10-methyl-11-oxo-1,3,4,7,8,9,10,11-octahydro-2H-pyrido[4',3':3,4]pyrazolo[1,5-a][1,4]diazepine-2-carboxamide |
| 067 | N-(3-cyano-4-fluorophenyl)-8-((3,3-difluoropyrrolidin-1-yl)methyl)-10-methyl-11-oxo-1,3,4,7,8,9,10,11-octahydro-2H-pyrido[4',3':3,4]pyrazolo[1,5-a][1,4]diazepine-2-carboxamide |
| 068 | 8-((3,3-difluoropyrrolidin-1-yl)methyl)-N-(4-fluoro-3-(trifluoromethyl)phenyl)-10-methyl-11-oxo-1,3,4,7,8,9,10,11-octahydro-2H-pyrido[4',3':3,4]pyrazolo[1,5-a][1,4]diazepine-2-carboxamide |
| 069 | N-(3-chloro-4-fluorophenyl)-10-methyl-11-oxo-8-(pyrrolidin-1-ylmethyl)-1,3,4,7,8,9,10,11-octahydro-2H-pyrido[4',3':3,4]pyrazolo[1,5-a][1,4]diazepine-2-carboxamide |
| 070 | 8-(aminomethyl)-N-(3-chloro-4-fluorophenyl)-10-methyl-11-oxo-1,3,4,7,8,9,10,11-octahydro-2H-pyrido[4',3':3,4]pyrazolo[1,5-a][1,4]diazepine-2-carboxamide |
| 071 | (R)-N-(2-bromo-5-chloro-4-fluorophenyl)-10-(2,2-difluoroethyl)-3-methyl-11-oxo-3,4,8,9,10,11-hexahydro-1H-pyrido[4',3':3,4]pyrazolo[1,5-a][1,4]diazepine-2(7H)-carboxamide |
| 072 | (3R)-N-(3-chloro-4-fluorophenyl)-10-(2,2-difluoroethyl)-3-methyl-11-oxo-1,3,4,7,8,9,10,11-octahydro-2H-pyrido[4',3':3,4]pyrazolo[1,5-a][1,4]diazepine-2-carboxamide |
| 073 | (R)-10-(2,2-difluoroethyl)-N-(4-fluoro-3-(trifluoromethyl)phenyl)-3-methyl-11-oxo-3,4,8,9,10,11-hexahydro-1H-pyrido[4',3':3,4]pyrazolo[1,5-a][1,4]diazepine-2(7H)-carboxamide |
| 074 | (R)-N-(3-bromo-4-fluorophenyl)-10-(2,2-difluoroethyl)-3-methyl-11-oxo-3,4,8,9,10,11-hexahydro-1H-pyrido[4',3':3,4]pyrazolo[1,5-a][1,4]diazepine-2(7H)-carboxamide |
| 075 | (R)-N-(2-bromo-3-fluoropyridin-4-yl)-10-(2,2-difluoroethyl)-3-methyl-11-oxo-3,4,8,9,10,11-hexahydro-1H-pyrido[4',3':3,4]pyrazolo[1,5-a][1,4]diazepine-2(7H)-carboxamide |

-continued

| Compound ID | Compound Name |
|---|---|
| 076 | (R)-N-(3-cyano-4-fluorophenyl)-10-(2,2-difluoroethyl)-3-methyl-11-oxo-3,4,8,9,10,11-hexahydro-1H-pyrido[4',3':3,4]pyrazolo[1,5-a][1,4]diazepine-2(7H)-carboxamide |
| 077 | (R)-10-(2,2-difluoroethyl)-N-(4-fluoro-3-methylphenyl)-3-methyl-11-oxo-3,4,8,9,10,11-hexahydro-1H-pyrido[4',3':3,4]pyrazolo[1,5-a][1,4]diazepine-2(7H)-carboxamide |
| 078 | (R)-N-(5-chloro-2,4-difluorophenyl)-10-(2,2-difluoroethyl)-3-methyl-11-oxo-3,4,8,9,10,11-hexahydro-1H-pyrido[4',3':3,4]pyrazolo[1,5-a][1,4]diazepine-2(7H)-carboxamide |
| 079_D1 | (3R,8R*)-N-(3-chloro-4-fluorophenyl)-8-fluoro-3,8,10-trimethyl-11-oxo-3,4,8,9,10,11-hexahydro-1H-pyrido[4',3':3,4]pyrazolo[1,5-a][1,4]diazepine-2(7H)-carboxamide |
| 079_D2 | (3R,8S*)-N-(3-chloro-4-fluorophenyl)-8-fluoro-3,8,10-trimethyl-11-oxo-3,4,8,9,10,11-hexahydro-1H-pyrido[4',3':3,4]pyrazolo[1,5-a][1,4]diazepine-2(7H)-carboxamide |
| 080_D1 | (3R,8S*)-N-(3-chloro-4-fluorophenyl)-3,8,10-trimethyl-11-oxo-3,4,8,9,10,11-hexahydro-1H-pyrido[4',3':3,4]pyrazolo[1,5-a][1,4]diazepine-2(7H)-carboxamide |
| 080_D2 | (3R,8R*)-N-(3-chloro-4-fluorophenyl)-3,8,10-trimethyl-11-oxo-3,4,8,9,10,11-hexahydro-1H-pyrido[4',3':3,4]pyrazolo[1,5-a][1,4]diazepine-2(7H)-carboxamide |
| 081_D1 | (3R,8S*)-N-(4-fluoro-3-(trifluoromethyl)phenyl)-8-(hydroxymethyl)-3,10-dimethyl-11-oxo-3,4,8,9,10,11-hexahydro-1H-pyrido[4',3':3,4]pyrazolo[1,5-a][1,4]diazepine-2(7H)-carboxamide |
| 081_D2 | (3R,8R*)-N-(4-fluoro-3-(trifluoromethyl)phenyl)-8-(hydroxymethyl)-3,10-dimethyl-11-oxo-3,4,8,9,10,11-hexahydro-1H-pyrido[4',3':3,4]pyrazolo[1,5-a][1,4]diazepine-2(7H)-carboxamide |
| 082_D1 | (3R,8S*)-N-(2,4-difluoro-5-(trifluoromethyl)phenyl)-8-(hydroxymethyl)-3,10-dimethyl-11-oxo-3,4,8,9,10,11-hexahydro-1H-pyrido[4',3':3,4]pyrazolo[1,5-a][1,4]diazepine-2(7H)-carboxamide |
| 082_D2 | (3R,8R*)-N-(2,4-difluoro-5-(trifluoromethyl)phenyl)-8-(hydroxymethyl)-3,10-dimethyl-11-oxo-3,4,8,9,10,11-hexahydro-1H-pyrido[4',3':3,4]pyrazolo[1,5-a][1,4]diazepine-2(7H)-carboxamide |
| 083_D1 | (3R,8S*)-N-(2,4-difluoro-3-(trifluoromethyl)phenyl)-8-(hydroxymethyl)-3,10-dimethyl-11-oxo-3,4,8,9,10,11-hexahydro-1H-pyrido[4',3':3,4]pyrazolo[1,5-a][1,4]diazepine-2(7H)-carboxamide |
| 083_D2 | (3R,8R*)-N-(2,4-difluoro-3-(trifluoromethyl)phenyl)-8-(hydroxymethyl)-3,10-dimethyl-11-oxo-3,4,8,9,10,11-hexahydro-1H-pyrido[4',3':3,4]pyrazolo[1,5-a][1,4]diazepine-2(7H)-carboxamide |
| 084_D1 | (3R,8S*)-N-(3-bromo-2,4-difluorophenyl)-8-(hydroxymethyl)-3,10-dimethyl-11-oxo-3,4,8,9,10,11-hexahydro-1H-pyrido[4',3':3,4]pyrazolo[1,5-a][1,4]diazepine-2(7H)-carboxamide |
| 084_D2 | (3R,8R*)-N-(3-bromo-2,4-difluorophenyl)-8-(hydroxymethyl)-3,10-dimethyl-11-oxo-3,4,8,9,10,11-hexahydro-1H-pyrido[4',3':3,4]pyrazolo[1,5-a][1,4]diazepine-2(7H)-carboxamide |
| 085_D1 | (3R,8S*)-N-(5-bromo-2,4-difluorophenyl)-8-(hydroxymethyl)-3,10-dimethyl-11-oxo-3,4,8,9,10,11-hexahydro-1H-pyrido[4',3':3,4]pyrazolo[1,5-a][1,4]diazepine-2(7H)-carboxamide |
| 085_D2 | (3R,8R*)-N-(5-bromo-2,4-difluorophenyl)-8-(hydroxymethyl)-3,10-dimethyl-11-oxo-3,4,8,9,10,11-hexahydro-1H-pyrido[4',3':3,4]pyrazolo[1,5-a][1,4]diazepine-2(7H)-carboxamide |
| 086_D1 | (3R,8S*)-N-(3-bromo-4-fluorophenyl)-8-(hydroxymethyl)-3,10-dimethyl-11-oxo-3,4,8,9,10,11-hexahydro-1H-pyrido[4',3':3,4]pyrazolo[1,5-a][1,4]diazepine-2(7H)-carboxamide |
| 086_D2 | (3R,8R*)-N-(3-bromo-4-fluorophenyl)-8-(hydroxymethyl)-3,10-dimethyl-11-oxo-3,4,8,9,10,11-hexahydro-1H-pyrido[4',3':3,4]pyrazolo[1,5-a][1,4]diazepine-2(7H)-carboxamide |
| 087_D1 | (3R,8S*)-N-(3-cyano-4-fluorophenyl)-8-(hydroxymethyl)-3,10-dimethyl-11-oxo-3,4,8,9,10,11-hexahydro-1H-pyrido[4',3':3,4]pyrazolo[1,5-a][1,4]diazepine-2(7H)-carboxamide |
| 087_D2 | (3R,8R*)-N-(3-cyano-4-fluorophenyl)-8-(hydroxymethyl)-3,10-dimethyl-11-oxo-3,4,8,9,10,11-hexahydro-1H-pyrido[4',3':3,4]pyrazolo[1,5-a][1,4]diazepine-2(7H)-carboxamide |
| 088_D1 | (3R,8S*)-N-(3-cyano-2,4-difluorophenyl)-8-(hydroxymethyl)-3,10-dimethyl-11-oxo-3,4,8,9,10,11-hexahydro-1H-pyrido[4',3':3,4]pyrazolo[1,5-a][1,4]diazepine-2(7H)-carboxamide |
| 088_D2 | (3R,8R*)-N-(3-cyano-2,4-difluorophenyl)-8-(hydroxymethyl)-3,10-dimethyl-11-oxo-3,4,8,9,10,11-hexahydro-1H-pyrido[4',3':3,4]pyrazolo[1,5-a][1,4]diazepine-2(7H)-carboxamide |
| 089_D1 | (3R,8S*)-N-(3-chloro-2,4-difluorophenyl)-8-(hydroxymethyl)-3,10-dimethyl-11-oxo-3,4,8,9,10,11-hexahydro-1H-pyrido[4',3':3,4]pyrazolo[1,5-a][1,4]diazepine-2(7H)-carboxamide |
| 089_D2 | (3R,8R*)-N-(3-chloro-2,4-difluorophenyl)-8-(hydroxymethyl)-3,10-dimethyl-11-oxo-3,4,8,9,10,11-hexahydro-1H-pyrido[4',3':3,4]pyrazolo[1,5-a][1,4]diazepine-2(7H)-carboxamide |

-continued

| Compound ID | Compound Name |
| --- | --- |
| 090_D1 | (3R,8S*)-N-(5-chloro-2,4-difluorophenyl)-8-(hydroxymethyl)-3,10-dimethyl-11-oxo-3,4,8,9,10,11-hexahydro-1H-pyrido[4',3':3,4]pyrazolo[1,5-a][1,4]diazepine-2(7H)-carboxamide |
| 090_D2 | (3R,8R*)-N-(5-chloro-2,4-difluorophenyl)-8-(hydroxymethyl)-3,10-dimethyl-11-oxo-3,4,8,9,10,11-hexahydro-1H-pyrido[4',3':3,4]pyrazolo[1,5-a][1,4]diazepine-2(7H)-carboxamide |
| 091 | N-(3-chloro-4-fluorophenyl)-8-(2,2-difluoroethyl)-8-(hydroxymethyl)-10-methyl-11-oxo-1,3,4,7,8,9,10,11-octahydro-2H-pyrido[4',3':3,4]pyrazolo[1,5-a][1,4]diazepine-2-carboxamide |
| 092_D1 | (3R,8R*)-N-(3-chloro-4-fluorophenyl)-10-(2,2-difluoroethyl)-8-(hydroxymethyl)-3-methyl-11-oxo-3,4,8,9,10,11-hexahydro-1H-pyrido[4',3':3,4]pyrazolo[1,5-a][1,4]diazepine-2(7H)-carboxamide |
| 092_D2 | (3R,8S*)-N-(3-chloro-4-fluorophenyl)-10-(2,2-difluoroethyl)-8-(hydroxymethyl)-3-methyl-11-oxo-3,4,8,9,10,11-hexahydro-1H-pyrido[4',3':3,4]pyrazolo[1,5-a][1,4]diazepine-2(7H)-carboxamide |
| 093 | 8-(aminomethyl)-N-(4-fluoro-3-(trifluoromethyl)phenyl)-10-methyl-11-oxo-1,3,4,7,8,9,10,11-octahydro-2H-pyrido[4',3':3,4]pyrazolo[1,5-a][1,4]diazepine-2-carboxamide |
| 094 | N-(4-fluoro-3-(trifluoromethyl)phenyl)-10-methyl-8-((methylamino)methyl)-11-oxo-1,3,4,7,8,9,10,11-octahydro-2H-pyrido[4',3':3,4]pyrazolo[1,5-a][1,4]diazepine-2-carboxamide |
| 095 | 8-(aminomethyl)-N-(3-cyano-4-fluorophenyl)-10-methyl-11-oxo-1,3,4,7,8,9,10,11-octahydro-2H-pyrido[4',3':3,4]pyrazolo[1,5-a][1,4]diazepine-2-carboxamide |
| 096_E1 | (R*)-N-(5-chloro-2,4-difluorophenyl)-8-((S*)-1-hydroxypropyl)-10-methyl-11-oxo-3,4,8,9,10,11-hexahydro-1H-pyrido[4',3':3,4]pyrazolo[1,5-a][1,4]diazepine-2(7H)-carboxamide |
| 096_E2 | (S*)-N-(5-chloro-2,4-difluorophenyl)-8-((R*)-1-hydroxypropyl)-10-methyl-11-oxo-3,4,8,9,10,11-hexahydro-1H-pyrido[4',3':3,4]pyrazolo[1,5-a][1,4]diazepine-2(7H)-carboxamide |
| 096_E3 | (S*)-N-(5-chloro-2,4-difluorophenyl)-8-((S*)-1-hydroxypropyl)-10-methyl-11-oxo-3,4,8,9,10,11-hexahydro-1H-pyrido[4',3':3,4]pyrazolo[1,5-a][1,4]diazepine-2(7H)-carboxamide |
| 096_E4 | (R*)-N-(5-chloro-2,4-difluorophenyl)-8-((R*)-1-hydroxypropyl)-10-methyl-11-oxo-3,4,8,9,10,11-hexahydro-1H-pyrido[4',3':3,4]pyrazolo[1,5-a][1,4]diazepine-2(7H)-carboxamide |
| 097_E1 | (R*)-N-(3-cyano-4-fluorophenyl)-8-((S*)-1-hydroxypropyl)-10-methyl-11-oxo-1,3,4,7,8,9,10,11-octahydro-2H-pyrido[4',3':3,4]pyrazolo[1,5-a][1,4]diazepine-2-carboxamide |
| 097_E2 | (S*)-N-(3-cyano-4-fluorophenyl)-8-((R*)-1-hydroxypropyl)-10-methyl-11-oxo-1,3,4,7,8,9,10,11-octahydro-2H-pyrido[4',3':3,4]pyrazolo[1,5-a][1,4]diazepine-2-carboxamide |
| 097_E3 | (S*)-N-(3-cyano-4-fluorophenyl)-8-((S*)-1-hydroxypropyl)-10-methyl-11-oxo-1,3,4,7,8,9,10,11-octahydro-2H-pyrido[4',3':3,4]pyrazolo[1,5-a][1,4]diazepine-2-carboxamide |
| 097_E4 | (R*)-N-(3-cyano-4-fluorophenyl)-8-((R*)-1-hydroxypropyl)-10-methyl-11-oxo-1,3,4,7,8,9,10,11-octahydro-2H-pyrido[4',3':3,4]pyrazolo[1,5-a][1,4]diazepine-2-carboxamide |
| 098_E1 | (R*)-N-(3-cyano-2,4-difluorophenyl)-8-((S*)-1-hydroxypropyl)-10-methyl-11-oxo-1,3,4,7,8,9,10,11-octahydro-2H-pyrido[4',3':3,4]pyrazolo[1,5-a][1,4]diazepine-2-carboxamide |
| 098_E2 | (S*)-N-(3-cyano-2,4-difluorophenyl)-8-((R*)-1-hydroxypropyl)-10-methyl-11-oxo-1,3,4,7,8,9,10,11-octahydro-2H-pyrido[4',3':3,4]pyrazolo[1,5-a][1,4]diazepine-2-carboxamide |
| 098_E3 | (S*)-N-(3-cyano-2,4-difluorophenyl)-8-((S*)-1-hydroxypropyl)-10-methyl-11-oxo-1,3,4,7,8,9,10,11-octahydro-2H-pyrido[4',3':3,4]pyrazolo[1,5-a][1,4]diazepine-2-carboxamide |
| 098_E4 | (R*)-N-(3-cyano-2,4-difluorophenyl)-8-((R*)-1-hydroxypropyl)-10-methyl-11-oxo-1,3,4,7,8,9,10,11-octahydro-2H-pyrido[4',3':3,4]pyrazolo[1,5-a][1,4]diazepine-2-carboxamide |
| 099_E1 | (R*)-N-(4-fluoro-3-(trifluoromethyl)phenyl)-8-((S*)-1-hydroxypropyl)-10-methyl-11-oxo-1,3,4,7,8,9,10,11-octahydro-2H-pyrido[4',3':3,4]pyrazolo[1,5-a][1,4]diazepine-2-carboxamide |
| 099_E2 | (S*)-N-(4-fluoro-3-(trifluoromethyl)phenyl)-8-((R*)-1-hydroxypropyl)-10-methyl-11-oxo-1,3,4,7,8,9,10,11-octahydro-2H-pyrido[4',3':3,4]pyrazolo[1,5-a][1,4]diazepine-2-carboxamide |
| 099_E3 | (S*)-N-(4-fluoro-3-(trifluoromethyl)phenyl)-8-((S*)-1-hydroxypropyl)-10-methyl-11-oxo-1,3,4,7,8,9,10,11-octahydro-2H-pyrido[4',3':3,4]pyrazolo[1,5-a][1,4]diazepine-2-carboxamide |
| 099_E4 | (R*)-N-(4-fluoro-3-(trifluoromethyl)phenyl)-8-((R*)-1-hydroxypropyl)-10-methyl-11-oxo-1,3,4,7,8,9,10,11-octahydro-2H-pyrido[4',3':3,4]pyrazolo[1,5-a][1,4]diazepine-2-carboxamide |
| 100_E1 | N-(3-chloro-2,4-difluorophenyl)-8-(1-hydroxypropyl)-10-methyl-11-oxo-1,3,4,7,8,9,10,11-octahydro-2H-pyrido[4',3':3,4]pyrazolo[1,5-a][1,4]diazepine-2-carboxamide |

| Compound ID | Compound Name |
|---|---|
| 101_E1 | N-(3-bromo-2,4-difluorophenyl)-8-(1-hydroxypropyl)-10-methyl-11-oxo-1,3,4,7,8,9,10,11-octahydro-2H-pyrido[4',3':3,4]pyrazolo[1,5-a][1,4]diazepine-2-carboxamide |
| 102_E1 | N-(3-bromo-4-fluorophenyl)-8-(1-hydroxypropyl)-10-methyl-11-oxo-1,3,4,7,8,9,10,11-octahydro-2H-pyrido[4',3':3,4]pyrazolo[1,5-a][1,4]diazepine-2-carboxamide |
| 103_E1 | N-(2,4-difluoro-3-(trifluoromethyl)phenyl)-8-(1-hydroxypropyl)-10-methyl-11-oxo-1,3,4,7,8,9,10,11-octahydro-2H-pyrido[4',3':3,4]pyrazolo[1,5-a][1,4]diazepine-2-carboxamide |
| 104_E1 | 8-(1-hydroxypropyl)-10-methyl-11-oxo-N-(3,4,5-trifluorophenyl)-1,3,4,7,8,9,10,11-octahydro-2H-pyrido[4',3':3,4]pyrazolo[1,5-a][1,4]diazepine-2-carboxamide |
| 105_E1 | 8-(1-hydroxypropyl)-10-methyl-11-oxo-N-(2,3,4,5-tetrafluorophenyl)-1,3,4,7,8,9,10,11-octahydro-2H-pyrido[4',3':3,4]pyrazolo[1,5-a][1,4]diazepine-2-carboxamide |
| 106 | N-(3-chloro-4-fluorophenyl)-8-(1-hydroxybutyl)-10-methyl-11-oxo-1,3,4,7,8,9,10,11-octahydro-2H-pyrido[4',3':3,4]pyrazolo[1,5-a][1,4]diazepine-2-carboxamide |
| 107_D1 | (3R,8S*)-N-(4-fluoro-3-(trifluoromethyl)phenyl)-8-((R)-1-hydroxypropyl)-3,10-dimethyl-11-oxo-3,4,8,9,10,11-hexahydro-1H-pyrido[4',3':3,4]pyrazolo[1,5-a][1,4]diazepine-2(7H)-carboxamide |
| 107_D2 | (3R,8R*)-N-(4-fluoro-3-(trifluoromethyl)phenyl)-8-((R)-1-hydroxypropyl)-3,10-dimethyl-11-oxo-3,4,8,9,10,11-hexahydro-1H-pyrido[4',3':3,4]pyrazolo[1,5-a][1,4]diazepine-2(7H)-carboxamide |
| 108_D1 | (3R,8S*)-N-(3-cyano-4-fluorophenyl)-8-((R)-1-hydroxypropyl)-3,10-dimethyl-11-oxo-3,4,8,9,10,11-hexahydro-1H-pyrido[4',3':3,4]pyrazolo[1,5-a][1,4]diazepine-2(7H)-carboxamide |
| 108_D2 | (3R,8R*)-N-(3-cyano-4-fluorophenyl)-8-((R)-1-hydroxypropyl)-3,10-dimethyl-11-oxo-3,4,8,9,10,11-hexahydro-1H-pyrido[4',3':3,4]pyrazolo[1,5-a][1,4]diazepine-2(7H)-carboxamide |
| 109_D1 | (3R,8S*)-N-(3-bromo-4-fluorophenyl)-8-((R)-1-hydroxypropyl)-3,10-dimethyl-11-oxo-3,4,8,9,10,11-hexahydro-1H-pyrido[4',3':3,4]pyrazolo[1,5-a][1,4]diazepine-2(7H)-carboxamide |
| 109_D2 | (3R,8R*)-N-(3-bromo-4-fluorophenyl)-8-((R)-1-hydroxypropyl)-3,10-dimethyl-11-oxo-3,4,8,9,10,11-hexahydro-1H-pyrido[4',3':3,4]pyrazolo[1,5-a][1,4]diazepine-2(7H)-carboxamide |
| 110 | N-(3-chloro-4-fluorophenyl)-11-methyl-12-oxo-3,4,7,8,9,10,11,12-octahydropyrido[4',3':3,4]pyrazolo[1,5-a][1,4]diazocine-2(1H)-carboxamide |
| 111 | (Z)-N-(3-chloro-4-fluorophenyl)-11-methyl-12-oxo-3,4,7,10,11,12-hexahydropyrido[4',3':3,4]pyrazolo[1,5-a][1,4]diazocine-2(1H)-carboxamide |
| 112 | N-(3-cyano-4-fluorophenyl)-8-(3,3-difluoro-1-hydroxypropyl)-10-methyl-11-oxo-1,3,4,7,8,9,10,11-octahydro-2H-pyrido[4',3':3,4]pyrazolo[1,5-a][1,4]diazepine-2-carboxamide |
| 113 | 2-((3-chloro-4-fluorophenyl)carbamoyl)-10-methyl-11-oxo-1,3,4,7,8,9,10,11-octahydro-2H-pyrido[4',3':3,4]pyrazolo[1,5-a][1,4]diazepine-7-carboxylic acid |
| 114 | N-(3-chloro-4-fluorophenyl)-7-(hydroxymethyl)-10-methyl-11-oxo-1,3,4,7,8,9,10,11-octahydro-2H-pyrido[4',3':3,4]pyrazolo[1,5-a][1,4]diazepine-2-carboxamide |
| 115 | N-(3-chloro-4-fluorophenyl)-8-(3-fluoro-1-hydroxypropyl)-10-methyl-11-oxo-1,3,4,7,8,9,10,11-octahydro-2H-pyrido[4',3':3,4]pyrazolo[1,5-a][1,4]diazepine-2-carboxamide |
| 116 | N-(3-chloro-4-fluorophenyl)-8-(3,3-difluoro-1-hydroxypropyl)-10-methyl-11-oxo-1,3,4,7,8,9,10,11-octahydro-2H-pyrido[4',3':3,4]pyrazolo[1,5-a][1,4]diazepine-2-carboxamide |

*Pure but unknown enantiomer or diastereomer.

and pharmaceutically acceptable salts thereof.

Certain embodiments of Formulas I, II, III, and IV are shown below in Table 3. disclosed compounds.

TABLE 3
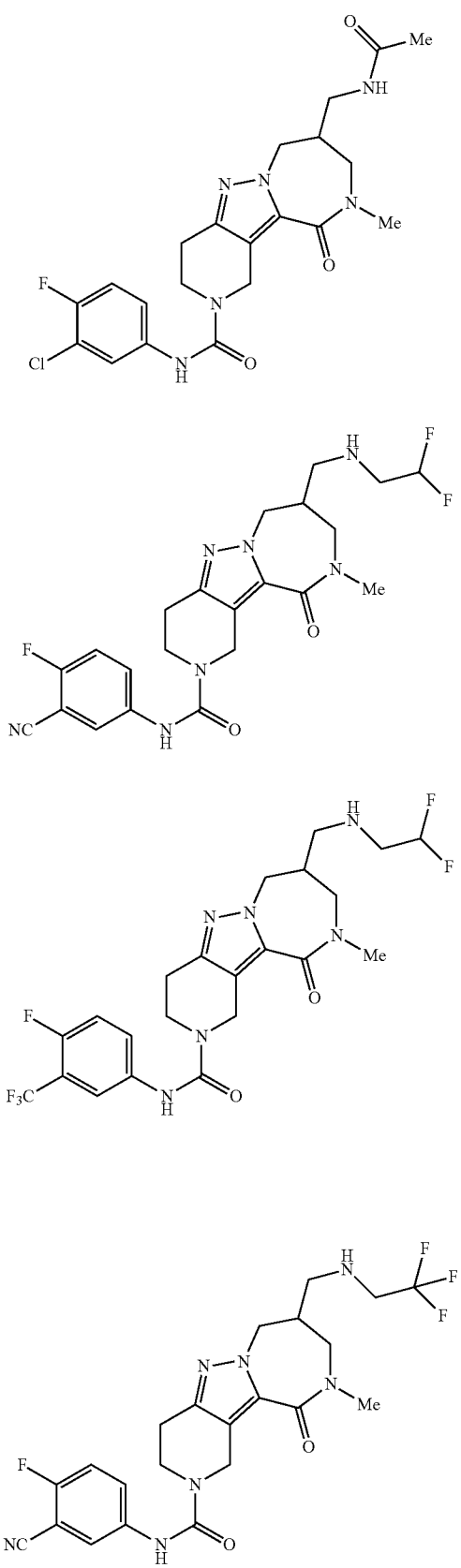
TABLE 3-continued
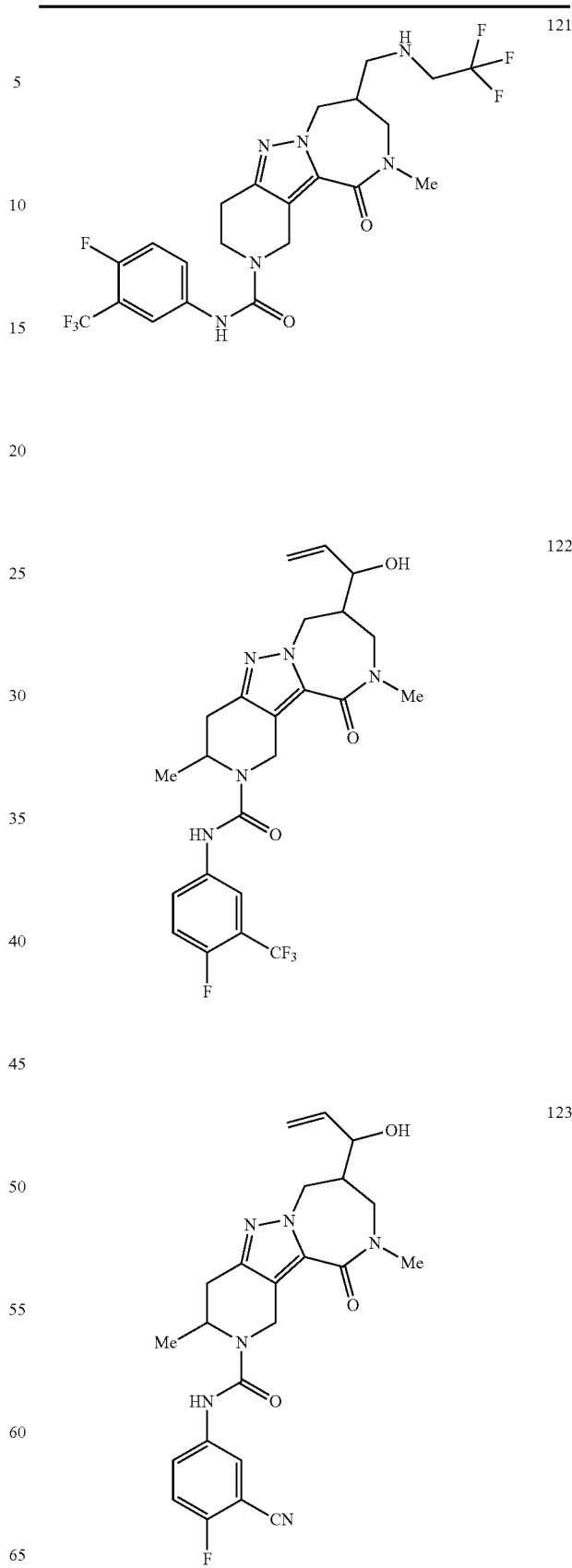

TABLE 3-continued
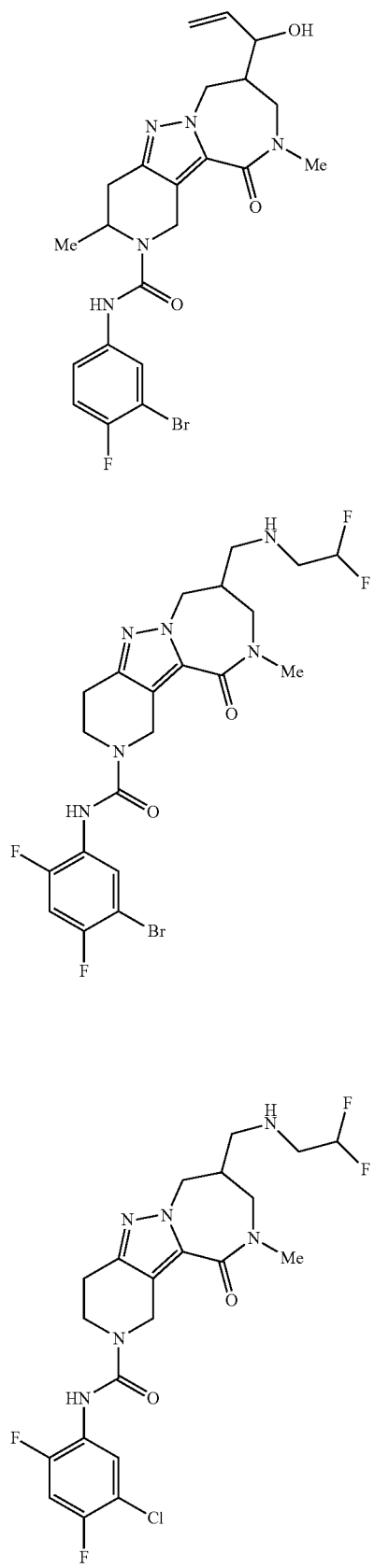
124
125
126
TABLE 3-continued
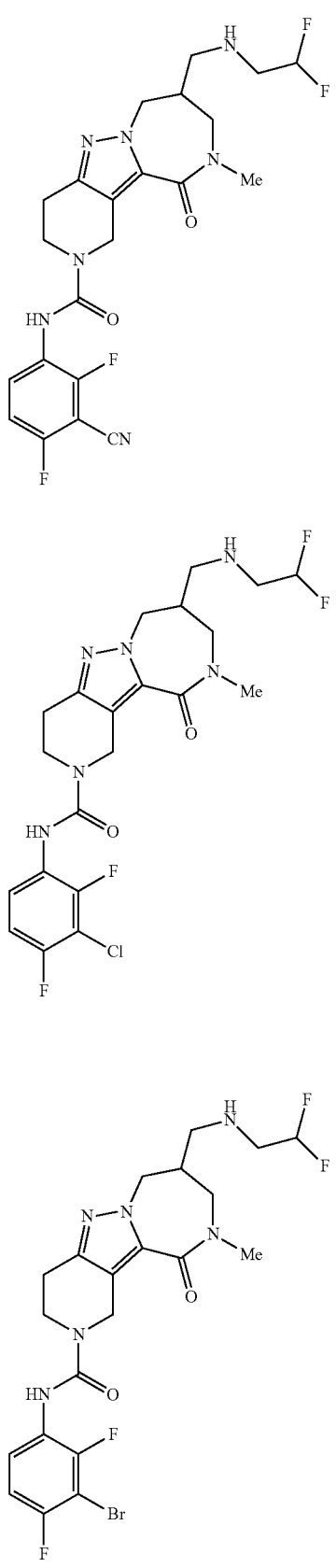
127
128
129

TABLE 3-continued

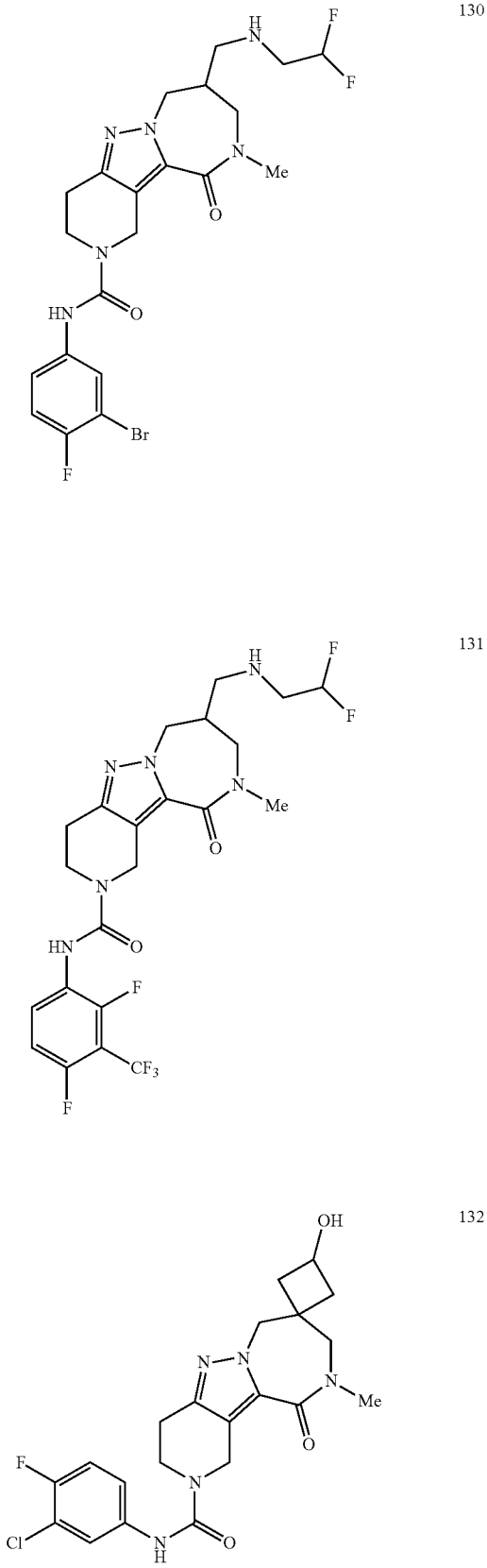

In an embodiment, compounds of Formulas I, II, III, and IV are selected from:

| Compound ID | Compound Name |
|---|---|
| 117 | 8-(acetamidomethyl)-N-(3-chloro-4-fluorophenyl)-10-methyl-11-oxo-1,3,4,7,8,9,10,11-octahydro-2H-pyrido[4',3':3,4]pyrazolo[1,5-a][1,4]diazepine-2-carboxamide |
| 118 | N-(3-cyano-4-fluorophenyl)-8-(((2,2-difluoroethyl)amino)methyl)-10-methyl-11-oxo-1,3,4,7,8,9,10,11-octahydro-2H-pyrido[4',3':3,4]pyrazolo[1,5-a][1,4]diazepine-2-carboxamide |
| 118_E1 | (R*)-N-(3-cyano-4-fluorophenyl)-8-(((2,2-difluoroethyl)amino)methyl)-10-methyl-11-oxo-3,4,8,9,10,11-hexahydro-1H-pyrido[4',3':3,4]pyrazolo[1,5-a][1,4]diazepine-2(7H)-carboxamide |
| 118_E2 | (S*)-N-(3-cyano-4-fluorophenyl)-8-(((2,2-difluoroethyl)amino)methyl)-10-methyl-11-oxo-3,4,8,9,10,11-hexahydro-1H-pyrido[4',3':3,4]pyrazolo[1,5-a][1,4]diazepine-2(7H)-carboxamide |
| 119 | 8-(((2,2-difluoroethyl)amino)methyl)-N-(4-fluoro-3-(trifluoromethyl)phenyl)-10-methyl-11-oxo-1,3,4,7,8,9,10,11-octahydro-2H-pyrido[4',3':3,4]pyrazolo[1,5-a][1,4]diazepine-2-carboxamide |
| 119_E1 | (R*)-8-(((2,2-difluoroethyl)amino)methyl)-N-(4-fluoro-3-(trifluoromethyl)phenyl)-10-methyl-11-oxo-3,4,8,9,10,11-hexahydro-1H-pyrido[4',3':3,4]pyrazolo[1,5-a][1,4]diazepine-2(7H)-carboxamide |
| 119_E2 | (S*)-8-(((2,2-difluoroethyl)amino)methyl)-N-(4-fluoro-3-(trifluoromethyl)phenyl)-10-methyl-11-oxo-3,4,8,9,10,11-hexahydro-1H-pyrido[4',3':3,4]pyrazolo[1,5-a][1,4]diazepine-2(7H)-carboxamide |
| 120 | N-(3-cyano-4-fluorophenyl)-10-methyl-11-oxo-8-(((2,2,2-trifluoroethyl)amino)methyl)-1,3,4,7,8,9,10,11-octahydro-2H-pyrido[4',3':3,4]pyrazolo[1,5-a][1,4]diazepine-2-carboxamide |
| 121 | N-(4-fluoro-3-(trifluoromethyl)phenyl)-10-methyl-11-oxo-8-(((2,2,2-trifluoroethyl)amino)methyl)-1,3,4,7,8,9,10,11-octahydro-2H-pyrido[4',3':3,4]pyrazolo[1,5-a][1,4]diazepine-2-carboxamide |
| 122_D1 | (3R,8S*)-N-(4-fluoro-3-(trifluoromethyl)phenyl)-8-((R)-1-hydroxyallyl)-3,10-dimethyl-11-oxo-3,4,8,9,10,11-hexahydro-1H-pyrido[4',3':3,4]pyrazolo[1,5-a][1,4]diazepine-2(7H)-carboxamide |
| 122_D2 | (3R,8R*)-N-(4-fluoro-3-(trifluoromethyl)phenyl)-8-((R)-1-hydroxyallyl)-3,10-dimethyl-11-oxo-3,4,8,9,10,11-hexahydro-1H-pyrido[4',3':3,4]pyrazolo[1,5-a][1,4]diazepine-2(7H)-carboxamide |
| 123_D1 | (3R,8S*)-N-(3-cyano-4-fluorophenyl)-8-((R)-1-hydroxyallyl)-3,10-dimethyl-11-oxo-3,4,8,9,10,11-hexahydro-1H-pyrido[4',3':3,4]pyrazolo[1,5-a][1,4]diazepine-2(7H)-carboxamide |
| 123_D2 | (3R,8R*)-N-(3-cyano-4-fluorophenyl)-8-((R)-1-hydroxyallyl)-3,10-dimethyl-11-oxo-3,4,8,9,10,11-hexahydro-1H-pyrido[4',3':3,4]pyrazolo[1,5-a][1,4]diazepine-2(7H)-carboxamide |
| 124_D1 | (3R,8S*)-N-(3-bromo-4-fluorophenyl)-8-((R)-1-hydroxyallyl)-3,10-dimethyl-11-oxo-3,4,8,9,10,11-hexahydro-1H-pyrido[4',3':3,4]pyrazolo[1,5-a][1,4]diazepine-2(7H)-carboxamide |
| 124_D2 | (3R,8R*)-N-(3-bromo-4-fluorophenyl)-8-((R)-1-hydroxyallyl)-3,10-dimethyl-11-oxo-3,4,8,9,10,11-hexahydro-1H-pyrido[4',3':3,4]pyrazolo[1,5-a][1,4]diazepine-2(7H)-carboxamide |
| 125_E1 | (R*)-N-(5-bromo-2,4-difluorophenyl)-8-(((2,2-difluoroethyl)amino)methyl)-10-methyl-11-oxo-3,4,8,9,10,11-hexahydro-1H-pyrido[4',3':3,4]pyrazolo[1,5-a][1,4]diazepine-2(7H)-carboxamide |
| 125_E2 | (S*)-N-(5-bromo-2,4-difluorophenyl)-8-(((2,2-difluoroethyl)amino)methyl)-10-methyl-11-oxo-3,4,8,9,10,11-hexahydro-1H-pyrido[4',3':3,4]pyrazolo[1,5-a][1,4]diazepine-2(7H)-carboxamide |
| 126_E1 | (R*)-N-(5-chloro-2,4-difluorophenyl)-8-(((2,2-difluoroethyl)amino)methyl)-10-methyl-11-oxo-3,4,8,9,10,11-hexahydro-1H-pyrido[4',3':3,4]pyrazolo[1,5-a][1,4]diazepine-2(7H)-carboxamide |
| 126_E2 | (S*)-N-(5-chloro-2,4-difluorophenyl)-8-(((2,2-difluoroethyl)amino)methyl)-10-methyl-11-oxo-3,4,8,9,10,11-hexahydro-1H-pyrido[4',3':3,4]pyrazolo[1,5-a][1,4]diazepine-2(7H)-carboxamide |

-continued

| Compound ID | Compound Name |
|---|---|
| 127_E1 | (R*)-N-(3-cyano-2,4-difluorophenyl)-8-(((2,2-difluoroethyl)amino)methyl)-10-methyl-11-oxo-3,4,8,9,10,11-hexahydro-1H-pyrido[4',3':3,4]pyrazolo[1,5-a][1,4]diazepine-2(7H)-carboxamide |
| 127_E2 | (S*)-N-(3-cyano-2,4-difluorophenyl)-8-(((2,2-difluoroethyl)amino)methyl)-10-methyl-11-oxo-3,4,8,9,10,11-hexahydro-1H-pyrido[4',3':3,4]pyrazolo[1,5-a][1,4]diazepine-2(7H)-carboxamide |
| 128_E1 | (R*)-N-(3-chloro-2,4-difluorophenyl)-8-(((2,2-difluoroethyl)amino)methyl)-10-methyl-11-oxo-3,4,8,9,10,11-hexahydro-1H-pyrido[4',3':3,4]pyrazolo[1,5-a][1,4]diazepine-2(7H)-carboxamide |
| 128_E2 | (S*)-N-(3-chloro-2,4-difluorophenyl)-8-(((2,2-difluoroethyl)amino)methyl)-10-methyl-11-oxo-3,4,8,9,10,11-hexahydro-1H-pyrido[4',3':3,4]pyrazolo[1,5-a][1,4]diazepine-2(7H)-carboxamide |
| 129_E1 | (R*)-N-(3-bromo-2,4-difluorophenyl)-8-(((2,2-difluoroethyl)amino)methyl)-10-methyl-11-oxo-3,4,8,9,10,11-hexahydro-1H-pyrido[4',3':3,4]pyrazolo[1,5-a][1,4]diazepine-2(7H)-carboxamide |
| 129_E2 | (S*)-N-(3-bromo-2,4-difluorophenyl)-8-(((2,2-difluoroethyl)amino)methyl)-10-methyl-11-oxo-3,4,8,9,10,11-hexahydro-1H-pyrido[4',3':3,4]pyrazolo[1,5-a][1,4]diazepine-2(7H)-carboxamide |
| 130_E1 | (R*)-N-(3-bromo-4-fluorophenyl)-8-(((2,2-difluoroethyl)amino)methyl)-10-methyl-11-oxo-3,4,8,9,10,11-hexahydro-1H-pyrido[4',3':3,4]pyrazolo[1,5-a][1,4]diazepine-2(7H)-carboxamide |
| 130_E2 | (S*)-N-(3-bromo-4-fluorophenyl)-8-(((2,2-difluoroethyl)amino)methyl)-10-methyl-11-oxo-3,4,8,9,10,11-hexahydro-1H-pyrido[4',3':3,4]pyrazolo[1,5-a][1,4]diazepine-2(7H)-carboxamide |
| 131_E1 | (R*)-N-(2,4-difluoro-3-(trifluoromethyl)phenyl)-8-(((2,2-difluoroethyl)amino)methyl)-10-methyl-11-oxo-3,4,8,9,10,11-hexahydro-1H-pyrido[4',3':3,4]pyrazolo[1,5-a][1,4]diazepine-2(7H)-carboxamide |
| 131_E2 | (S*)-N-(2,4-difluoro-3-(trifluoromethyl)phenyl)-8-(((2,2-difluoroethyl)amino)methyl)-10-methyl-11-oxo-3,4,8,9,10,11-hexahydro-1H-pyrido[4',3':3,4]pyrazolo[1,5-a][1,4]diazepine-2(7H)-carboxamide |
| 132 | N-(3-chloro-4-fluorophenyl)-3-hydroxy-10'-methyl-11'-oxo-1',3',4',9',10',11'-hexahydro-2'H,7'H-spiro[cyclobutane-1,8'-pyrido[4',3':3,4]pyrazolo[1,5-a][1,4]diazepine]-2'-carboxamide |

*Pure but unknown enantiomer or diastereomer. and pharmaceutically acceptable salts thereof.

Certain embodiments of Formulas I, II, III, and IV are shown below in Table 4. disclosed compounds.

TABLE 4

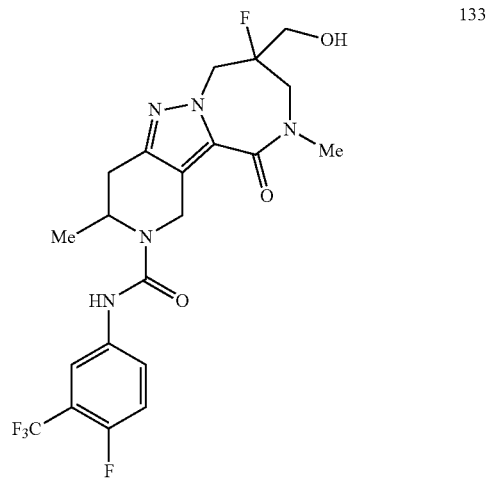

133

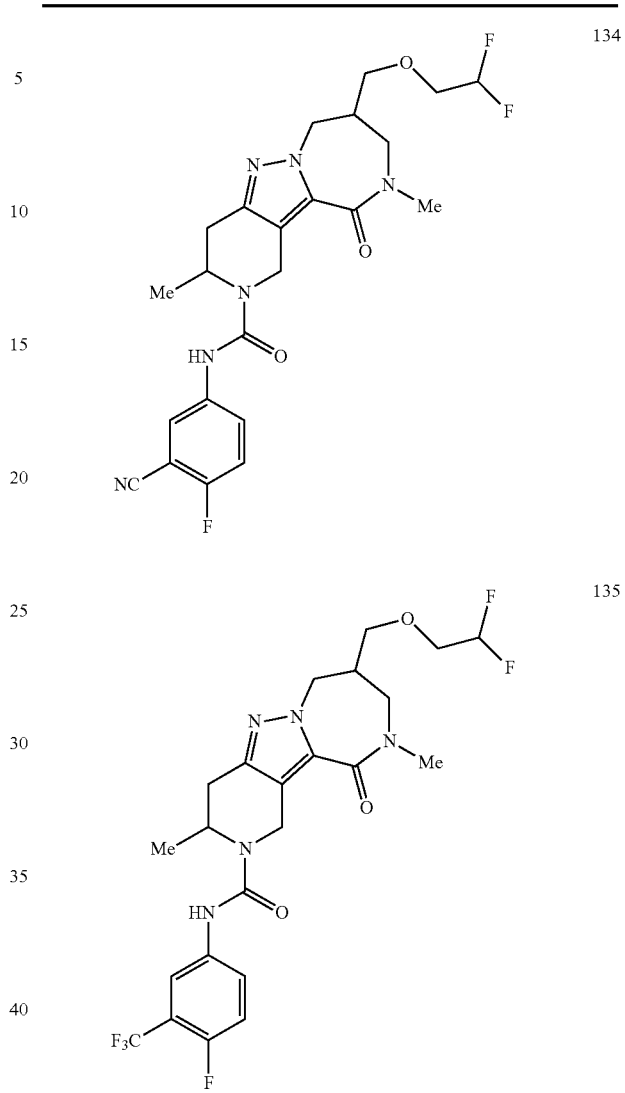

134

135

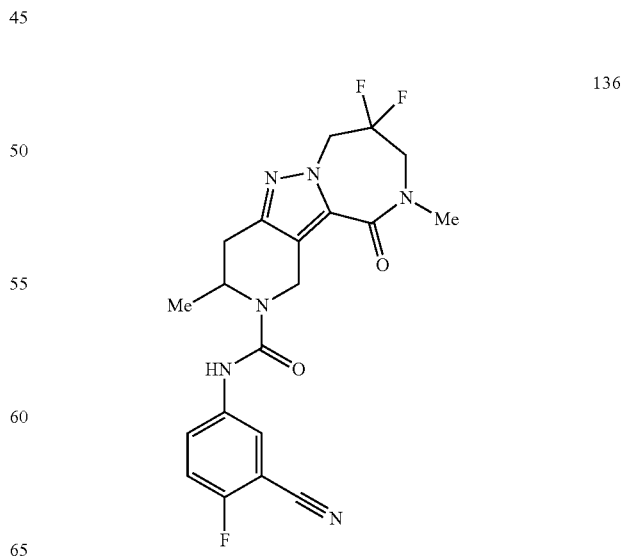

136

TABLE 4-continued
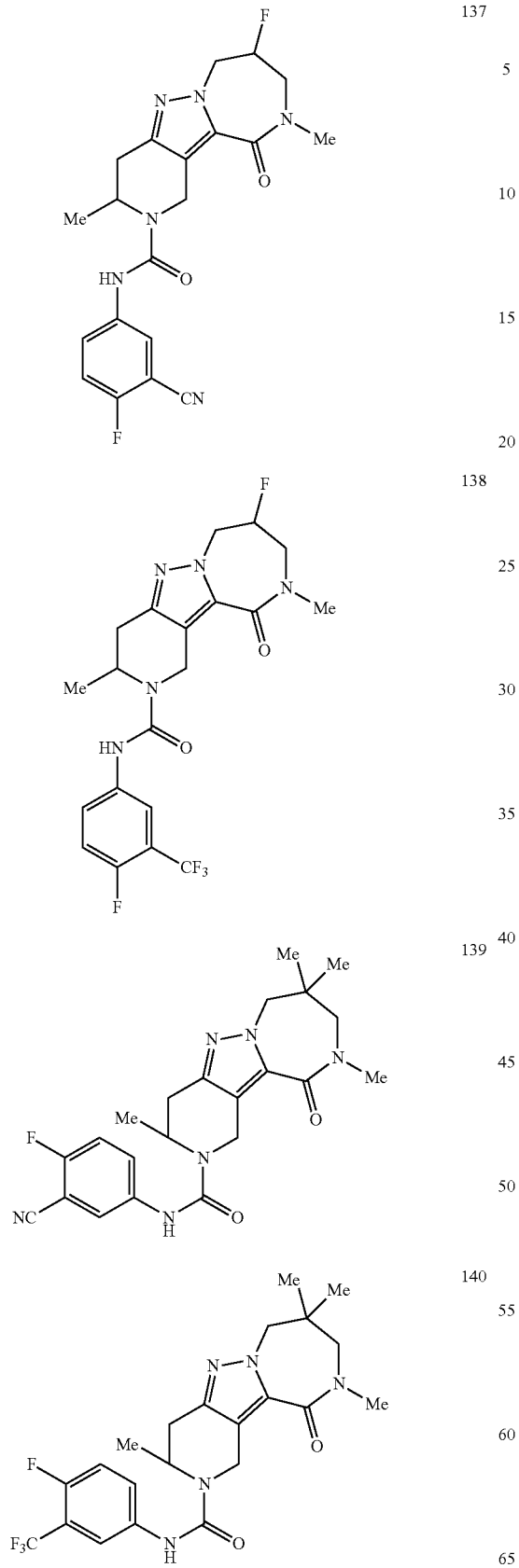
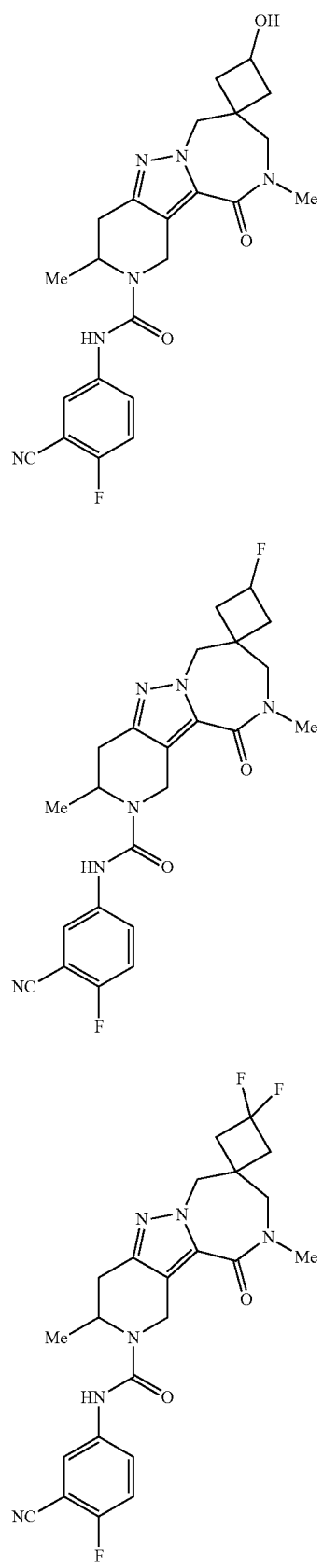

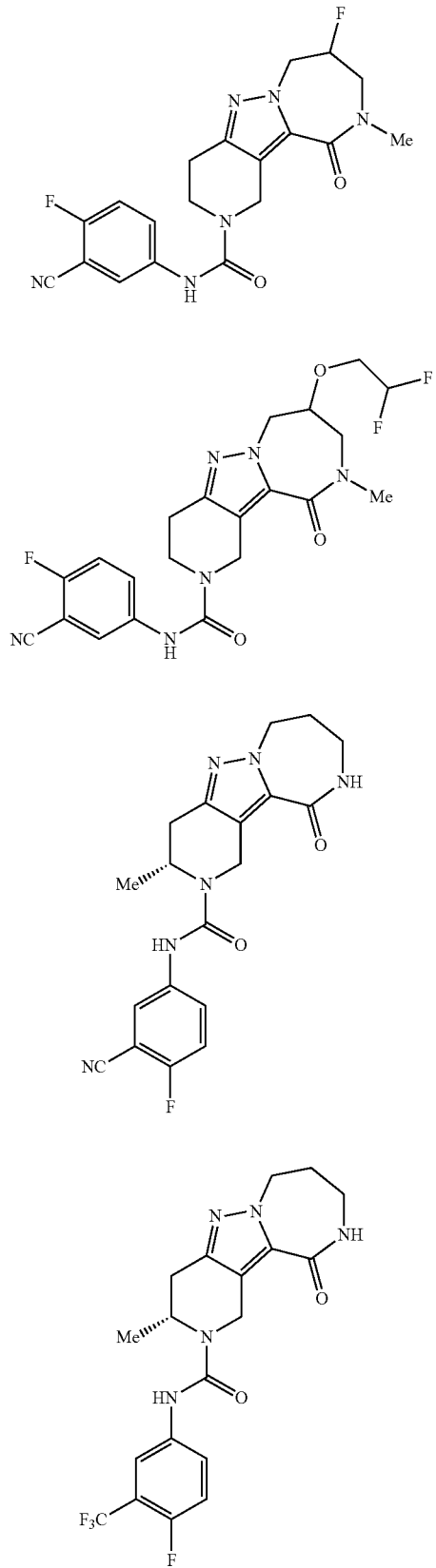

In an embodiment, compounds of Formulas I, II, III, and IV are selected from:

| Compound ID | Compound Name |
|---|---|
| 133_D1 | (3R,8R*)-8-fluoro-N-(4-fluoro-3-(trifluoromethyl)phenyl)-8-(hydroxymethyl)-3,10-dimethyl-11-oxo-1,3,4,7,8,9,10,11-octahydro-2H-pyrido[4',3':3,4]pyrazolo[1,5-a][1,4]diazepine-2-carboxamide |
| 133_D2 | (3R,8S*)-8-fluoro-N-(4-fluoro-3-(trifluoromethyl)phenyl)-8-(hydroxymethyl)-3,10-dimethyl-11-oxo-1,3,4,7,8,9,10,11-octahydro-2H-pyrido[4',3':3,4]pyrazolo[1,5-a][1,4]diazepine-2-carboxamide |
| 134_D1 | (3R,8R)-N-(3-Cyano-4-fluorophenyl)-8-((2,2-difluoroethoxy)methyl)-3,10-dimethyl-11-oxo-1,3,4,7,8,9,10,11-octahydro-2H-pyrido[4',3':3,4]pyrazolo[1,5-a][1,4]diazepine-2-carboxamide |
| 135_D1 | (3R,8R)-8-((2,2-difluoroethoxy)methyl)-N-(4-fluoro-3-(trifluoromethyl)phenyl)-3,10-dimethyl-11-oxo-1,3,4,7,8,9,10,11-octahydro-2H-pyrido[4',3':3,4]pyrazolo[1,5-a][1,4]diazepine-2-carboxamide |
| 134_D2 | (3R,8S)-N-(3-cyano-4-fluorophenyl)-8-((2,2-difluoroethoxy)methyl)-3,10-dimethyl-11-oxo-1,3,4,7,8,9,10,11-octahydro-2H-pyrido[4',3':3,4]pyrazolo[1,5-a][1,4]diazepine-2-carboxamide |
| 135_D2 | (3R,8S)-8-((2,2-difluoroethoxy)methyl)-N-(4-fluoro-3-(trifluoromethyl)phenyl)-3,10-dimethyl-11-oxo-1,3,4,7,8,9,10,11-octahydro-2H-pyrido[4',3':3,4]pyrazolo[1,5-a][1,4]diazepine-2-carboxamide |
| 136 | (R)-N-(3-cyano-4-fluorophenyl)-8,8-difluoro-3,10-dimethyl-11-oxo-1,3,4,7,8,9,10,11-octahydro-2H-pyrido[4',3':3,4]pyrazolo[1,5-a][1,4]diazepine-2-carboxamide. |
| 137_D1 | (3R,8R*)-N-(3-cyano-4-fluorophenyl)-8-fluoro-3,10-dimethyl-11-oxo-1,3,4,7,8,9,10,11-octahydro-2H-pyrido[4',3':3,4]pyrazolo[1,5-a][1,4]diazepine-2-carboxamide |
| 137_D2 | (3R,8S*)-N-(3-Cyano-4-fluorophenyl)-8-fluoro-3,10-dimethyl-11-oxo-1,3,4,7,8,9,10,11-octahydro-2H-pyrido[4',3':3,4]pyrazolo[1,5-a][1,4]diazepine-2-carboxamide |
| 138 | (3R,8R*)-8-fluoro-N-(4-fluoro-3-(trifluoromethyl)phenyl)-3,10-dimethyl-11-oxo-1,3,4,7,8,9,10,11-octahydro-2H-pyrido[4',3':3,4]pyrazolo[1,5-a][1,4]diazepine-2-carboxamide |
| 139 | (R)-N-(3-cyano-4-fluorophenyl)-3,8,8,10-tetramethyl-11-oxo-1,3,4,7,8,9,10,11-octahydro-2H-pyrido[4',3':3,4]pyrazolo[1,5-a][1,4]diazepine-2-carboxamide |
| 140 | (R)-N-(4-Fluoro-3-(trifluoromethyl)phenyl)-3,8,8,10-tetramethyl-11-oxo-1,3,4,7,8,9,10,11-octahydro-2H-pyrido[4',3':3,4]pyrazolo[1,5-a][1,4]diazepine-2-carboxamide |
| 141 | (R)-N-(3-Cyano-4-fluorophenyl)-3-hydroxy-3',10'-dimethyl-11'-oxo-1',3',4',9',10',11'-hexahydro-2'H,7'H-spiro[cyclobutane-1,8'-pyrido[4',3':3,4]pyrazolo[1,5-a][1,4]diazepine]-2'-carboxamide |
| 142 | (R)-N-(3-Cyano-4-fluorophenyl)-3-fluoro-3',10'-dimethyl-11'-oxo-1',3',4',9',10',11'-hexahydro-2'H,7'H-spiro[cyclobutane-1,8'-pyrido[4',3':3,4]pyrazolo[1,5-a][1,4]diazepine]-2'-carboxamide |
| 143 | (R)-N-(3-Cyano-4-fluorophenyl)-3,3-difluoro-3',10'-dimethyl-11'-oxo-1',3',4',9',10',11'-hexahydro-2'H,7'H-spiro[cyclobutane-1,8'-pyrido[4',3':3,4]pyrazolo[1,5-a][1,4]diazepine]-2'-carboxamide |
| 144_E1 | (S)-N-(3-Cyano-4-fluorophenyl)-8-fluoro-10-methyl-11-oxo-1,3,4,7,8,9,10,11-octahydro-2H-pyrido[4',3':3,4]pyrazolo[1,5-a][1,4]diazepine-2-carboxamide |
| 144_E2 | (R)-N-(3-Cyano-4-fluorophenyl)-8-fluoro-10-methyl-11-oxo-1,3,4,7,8,9,10,11-octahydro-2H-pyrido[4',3':3,4]pyrazolo[1,5-a][1,4]diazepine-2-carboxamide |
| 145_D1 | (R)-N-(3-Cyano-4-fluorophenyl)-8-(2,2-difluoroethoxy)-10-methyl-11-oxo-1,3,4,7,8,9,10,11-octahydro-2H-pyrido[4',3':3,4]pyrazolo[1,5-a][1,4]diazepine-2-carboxamide |
| 145_D2 | (S)-N-(3-Cyano-4-fluorophenyl)-8-(2,2-difluoroethoxy)-10-methyl-11-oxo-1,3,4,7,8,9,10,11-octahydro-2H-pyrido[4',3':3,4]pyrazolo[1,5-a][1,4]diazepine-2-carboxamide |
| 146 | (R)-N-(3-Cyano-4-fluorophenyl)-3-methyl-11-oxo-1,3,4,7,8,9,10,11-octahydro-2H-pyrido[4',3':3,4]pyrazolo[1,5-a][1,4]diazepine-2-carboxamide |
| 147 | (R)-N-(4-Fluoro-3-(trifluoromethyl)phenyl)-3-methyl-11-oxo-1,3,4,7,8,9,10,11-octahydro-2H-pyrido[4',3':3,4]pyrazolo[1,5-a][1,4]diazepine-2-carboxamide |
| 148 | (3R,8S)-N-(3-Cyano-4-fluorophenyl)-8-(hydroxymethyl)-3,9-dimethyl-10-oxo-3,4,7,8,9,10-hexahydropyrido[4',3':3,4]pyrazolo[1,5-a]pyrazine-2(1H)-carboxamide |
| 149 | (3R,8S)-N-(3-cyano-4-fluorophenyl)-8-(fluoromethyl)-3,9-dimethyl-10-oxo-3,4,7,8,9,10-hexahydropyrido[4',3':3,4]pyrazolo[1,5-a]pyrazine-2(1H)-carboxamide |
| 150 | (3R,8S)-N-(3-cyano-4-fluorophenyl)-8-((2,2-difluoroethoxy)methyl)-3,9-dimethyl-10-oxo-3,4,7,8,9,10-hexahydropyrido[4',3':3,4]pyrazolo[1,5-a]pyrazine-2(1H)-carboxamide |

*Pure but unknown enantiomer or diastereomer. and pharmaceutically acceptable salts thereof.

The disclosed compounds may possess one or more stereocenters, and each stereocenter may exist independently in either the R or S configuration. In one embodiment, compounds described herein are present in optically active or racemic forms. It is to be understood that the compounds described herein encompass racemic, optically-active, regioisomeric and stereoisomeric forms, or combinations thereof that possess the therapeutically useful properties described herein.

Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In one embodiment, a mixture of one or more isomer is utilized as the disclosed compound described herein. In another embodiment, compounds described herein contain one or more chiral centers. These compounds are prepared by any means, including stereoselective synthesis, enantioselective synthesis or separation of a mixture of enantiomers or diastereomers. Resolution of compounds and isomers thereof is achieved by any means including, by way of non-limiting example, chemical processes, enzymatic processes, fractional crystallization, distillation, and chromatography.

It is also to be understood that compounds that have the same molecular formula but differ in the nature or sequence of bonding of their atoms or the arrangement of their atoms in space are termed "isomers." Isomers that differ in the arrangement of their atoms in space are termed "stereoisomers," for example, diastereomers, enantiomers, and atropisomers.

Stereoisomers that are not mirror images of one another are termed "diastereomers" and those that are non-superimposable mirror images of each other are termed "enantiomers." When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture."

Unless indicated otherwise, the description or naming of a particular compound in the specification and claims is intended to include both individual enantiomers and mixtures, racemic or otherwise, thereof. Within the present disclosure, any open valency appearing on a carbon, oxygen, or nitrogen atom in any structure described herein indicates the presence of a hydrogen atom. Where a chiral center exists in a structure, but no specific stereochemistry is shown for that center, both enantiomers, separately or as a mixture, are encompassed by that structure. The methods for the determination of stereochemistry and the separation of stereoisomers are well-known in the art.

In embodiments, the disclosed compounds may exist as tautomers. All tautomers are included within the scope of the compounds presented herein.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^2H$, $^3H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$, and $^{35}S$. In one embodiment, isotopically-labeled compounds are useful in drug or substrate tissue distribution studies. In another embodiment, substitution with heavier isotopes such as deuterium affords greater metabolic stability (for example, increased in vivo half-life or reduced dosage requirements).

In yet another embodiment, substitution with positron emitting isotopes, such as $^{11}C$, $^{18}F$, $^{15}O$ and $^{13}N$, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

In one embodiment, the compounds described herein are labeled by other means, including, but not limited to, the use of chromophores or fluorescent moieties, bioluminescent labels, or chemiluminescent labels.

The compounds described herein, and other related compounds having different substituents are synthesized using techniques and materials described herein and as described, for example, in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry $4^{th}$ Ed., (Wiley 1992); Carey and Sundberg, Advanced Organic Chemistry 4th Ed., Vols. A and B (Plenum 2000, 2001), and Green and Wuts, Protective Groups in Organic Synthesis 3rd Ed., (Wiley 1999) (all of which are incorporated by reference for such disclosure). General methods for the preparation of compound as described herein are modified by the use of appropriate reagents and conditions, for the introduction of the various moieties found in the formula as provided herein.

Compounds described herein are synthesized using any suitable procedures starting from compounds that are available from commercial sources, or are prepared using procedures described herein.

Methods of Use

Provided herein is a method of treating an HBV infection in an individual in need thereof, comprising administering to the individual a therapeutically effective amount of a disclosed compound.

Also provided herein is a method of eradicating an HBV infection in an individual in need thereof, comprising administering to the individual a therapeutically effective amount of a disclosed compound.

Provided herein is a method of reducing HBV viral load associated with an HBV infection in an individual in need thereof, comprising administering to the individual a therapeutically effective amount of a disclosed compound.

Further, provided herein is a method of reducing reoccurrence of an HBV infection in an individual in need thereof, comprising administering to the individual a therapeutically effective amount of a disclosed compound.

Provided herein is a method of inhibiting or reducing the formation or presence of HBV DNA-containing particles or HBV RNA-containing particles in an individual in need thereof, comprising administering to the individual a therapeutically effective amount of a disclosed compound.

In certain aspects, the methods and/or compositions described herein are effective for inhibiting or reducing the formation or presence of HBV-associated particles in vitro or in vivo (e.g., in a cell, in a tissue, in an organ (e.g., in the liver), in an organism or the like). HBV-associated particles may contain HBV DNA (i.e., linear and/or covalently closed circular DNA (cccDNA)) and/or HBV RNA (i.e., pre-genomic RNA and/or sub-genomic RNA). Accordingly, HBV-associated particles include HBV DNA-containing particles or HBV RNA-containing particles.

As used herein, "HBV-associated particles" refer to both infectious HBV virions (i.e., Dane particles) and non-infectious HBV subviral particles (i.e., HBV filaments and/or HBV spheres). HBV virions comprise an outer envelope including surface proteins, a nucleocapsid comprising core proteins, at least one polymerase protein, and an HBV genome. HBV filaments and HBV spheres comprise HBV surface proteins, but lack core proteins, polymerase and an HBV genome. HBV filaments and HBV spheres are also known collectively as surface antigen (HBsAg) particles. HBV spheres comprise middle and small HBV surface proteins. HBV filaments also include middle, small and large HBV surface proteins. HBV subviral particles can include the nonparticulate or secretory HBeAg, which serves as a marker for active replication of HBV.

Provided herein is a method of reducing an adverse physiological impact of an HBV infection in an individual in need thereof, comprising administering to the individual a therapeutically effective amount of a disclosed compound.

Also provided herein is a method of reducing, slowing, or inhibiting an HBV infection in an individual in need thereof, comprising administering to the individual a therapeutically effective amount of a disclosed compound.

Provided herein is a method of inducing reversal of hepatic injury from an HBV infection in an individual in need thereof, comprising administering to the individual a therapeutically effective amount of a disclosed compound.

Provided herein is a method of reducing the physiological impact of long-term antiviral therapy for HBV infection in an individual in need thereof, comprising administering to the individual a therapeutically effective amount of a disclosed compound.

Provided herein is a method of prophylactically treating an HBV infection in an individual in need thereof, wherein the individual is afflicted with a latent HBV infection, comprising administering to the individual a therapeutically effective amount of a disclosed compound.

In one embodiment, the individual is refractory to other therapeutic classes of HBV drugs (e.g, HBV polymerase inhibitors, interferons, viral entry inhibitors, viral maturation inhibitors, literature-described capsid assembly modulators, antiviral compounds of distinct or unknown mechanism, and the like, or combinations thereof). In another embodiment, the disclosed method reduces viral load in an individual suffering from an HBV infection to a greater extent or at a faster rate compared to the extent that other therapeutic classes of HBV drugs reduce viral load in the individual.

In one embodiment, the administering of a disclosed compound, or a pharmaceutically acceptable salt thereof, allows for administering of the at least one additional therapeutic agent at a lower dose or frequency as compared to the administering of the at least one additional therapeutic agent alone that is required to achieve similar results in prophylactically treating an HBV infection in an individual in need thereof.

In one embodiment, the administering of a disclosed compound, or a pharmaceutically acceptable salt thereof, reduces the viral load in the individual to a greater extent or at a faster rate compared to the administering of a compound selected from the group consisting of an HBV polymerase inhibitor, interferon, viral entry inhibitor, viral maturation inhibitor, distinct capsid assembly modulator, antiviral compounds of distinct or unknown mechanism, and any combination thereof.

In one embodiment, the disclosed method reduces HBV viral load in an individual suffering from an HBV infection, thus allowing lower doses or varying regimens of combination therapies to be used.

In one embodiment, the disclosed method causes a lower incidence of HBV viral mutation or HBV viral resistance compared to other classes of HBV drugs, thereby allowing for long term therapy and minimizing the need for changes in treatment regimens.

In one embodiment, the administering of a compound the invention, or a pharmaceutically acceptable salt thereof, causes a lower incidence of viral mutation or viral resistance than the administering of a compound selected from the group consisting of an HBV polymerase inhibitor, interferon, viral entry inhibitor, viral maturation inhibitor, distinct capsid assembly modulator, antiviral compounds of distinct or unknown mechanism, and combination thereof.

In one embodiment, the disclosed method increases the seroconversion rate from HBV infected to non-HBV infected or from detectable HBV viral load to non-detectable HBV viral load beyond that of current treatment regimens. As used herein, "seroconversion" refers to the period of time during which HBV antibodies develop and become detectable.

In one embodiment, the disclosed method increases or normalizes or restores normal health, elicits full recovery of normal health, restores life expectancy, or resolves the viral infection in the individual in need thereof.

In one embodiment, the disclosed method eliminates or decreases the number of HBV RNA particles that are released from HBV infected cells thus enhancing, prolonging, or increasing the therapeutic benefit of the disclosed compounds.

In one embodiment, the disclosed method eradicates HBV from an individual infected with HBV, thereby obviating the need for long term or life-long treatment, or shortening the duration of treatment, or allowing for reduction in dosing of other antiviral agents.

In another embodiment, the disclosed method further comprises monitoring or detecting the HBV viral load of the subject, and wherein the method is carried out for a period of time In one embodiment, provided herein is a method of treating an HBV infection in an individual in need thereof, comprising administering to the individual a therapeutically effective amount of a compound of Formula I, or a pharmaceutically acceptable salt thereof.

In another embodiment, provided herein is a method of treating an HBV infection in an individual in need thereof, comprising administering to the individual a therapeutically effective amount of a compound of Formula II, or a pharmaceutically acceptable salt thereof.

In another embodiment, provided herein is a method of treating an HBV infection in an individual in need thereof, comprising administering to the individual a therapeutically effective amount of a compound of Formula III, or a pharmaceutically acceptable salt thereof.

In another embodiment, provided herein is a method of treating an HBV infection in an individual in need thereof, comprising administering to the individual a therapeutically effective amount of a compound of Formula IV, or a pharmaceutically acceptable salt thereof.

In another embodiment, provided herein is a method of treating an HBV infection in an individual in need thereof, comprising administering to the individual a therapeutically effective amount of a compound of Formula V, or a pharmaceutically acceptable salt thereof.

In another embodiment, provided herein is a method of treating an HBV infection in an individual in need thereof, comprising administering to the individual a therapeutically effective amount of a compound of Table 1, or a pharmaceutically acceptable salt thereof.

In another embodiment, provided herein is a method of treating an HBV infection in an individual in need thereof, comprising administering to the individual a therapeutically effective amount of a compound of Table 2, or a pharmaceutically acceptable salt thereof.

In another embodiment, provided herein is a method of treating an HBV infection in an individual in need thereof, comprising administering to the individual a therapeutically effective amount of a compound of Table 3, or a pharmaceutically acceptable salt thereof.

In another embodiment, provided herein is a method of treating an HBV infection in an individual in need thereof, comprising administering to the individual a therapeutically effective amount of a compound of Table 4, or a pharmaceutically acceptable salt thereof.

Any of the methods provided herein can further comprise monitoring or detecting the HBV viral load of the subject, wherein the method is carried out for a period of time including until such time that the HBV virus is undetectable.

Combination Therapies

The disclosed compounds may be useful in combination with one or more additional compounds useful for treating HBV infection. These additional compounds may comprise other disclosed compounds and/or compounds known to treat, prevent, or reduce the symptoms or effects of HBV infection. Such compounds include, but are not limited to, HBV polymerase inhibitors, interferons, viral entry inhibitors, viral maturation inhibitors, literature-described capsid assembly modulators, reverse transcriptase inhibitors, immunomodulatory agents, TLR-agonists, and other agents with distinct or unknown mechanisms that affect the HBV life cycle or affect the consequences of HBV infection.

In non-limiting examples, the disclosed compounds may be used in combination with one or more drugs (or a salt thereof) selected from the group comprising: HBV reverse transcriptase inhibitors, and DNA and RNA polymerase inhibitors including, but not limited to, lamivudine (3TC, Zeffix, Heptovir, Epivir, and Epivir-HBV), entecavir (Baraclude, Entavir), adefovir dipivoxil (Hepsara, Preveon, bis-POM PMEA), tenofovir disoproxil fumarate (Viread, TDF or PMPA);

interferons including, but not limited to, interferon alpha (IFN-α), interferon beta (IFN-β), interferon lambda (IFN-λ), and interferon gamma (IFN-γ);

viral entry inhibitors;

viral maturation inhibitors;

literature-described capsid assembly modulators, such as, but not limited to, BAY 41-4109;

reverse transcriptase inhibitors;

immunomodulatory agents such as TLR-agonists; and agents of distinct or unknown mechanisms, such as but not limited to AT-61 ((E)-N-(1-chloro-3-oxo-1-phenyl-3-(piperidin-1-yl)prop-1-en-2-yl)benzamide), AT-130 ((E)-N-(1-bromo-1-(2-methoxyphenyl)-3-oxo-3-(piperidin-1-yl)prop-1-en-2-yl)-4-nitrobenzamide), and similar analogs.

In one embodiment, the additional therapeutic agent is an interferon. The term "interferon" or "IFN" refers to any member of the family of highly homologous species-specific proteins that inhibit viral replication and cellular proliferation and modulate immune response.

Human interferons are grouped into three classes: Type I, which includes interferon-alpha (IFN-α), interferon-beta (IFN-β), and interferon-omega (IFN-ω), Type II, which includes interferon-gamma (IFN-γ), and Type III, which includes interferon-lambda (IFN-λ). Recombinant forms of interferons that have been developed and are commercially available are encompassed by the term "interferon" as used herein. Subtypes of interferons, such as chemically modified or mutated interferons, are also encompassed by the term "interferon" as used herein. Chemically modified interferons may include pegylated interferons and glycosylated interferons. Examples of interferons also include, but are not limited to, interferon-alpha-2a, interferon-alpha-2b, interferon-alpha-n1, interferon-beta-1a, interferon-beta-1b, interferon-lamda-1, interferon-lamda-2, and interferon-lamda-3. Examples of pegylated interferons include pegylated interferon-alpha-2a and pegylated interferon alpha-2b.

Accordingly, in one embodiment, the compounds of Formula I, II, III, IV or V can be administered in combination with an interferon selected from the group consisting of interferon alpha (IFN-α), interferon beta (IFN-β), interferon lambda (IFN-λ), and interferon gamma (IFN-γ). In one specific embodiment, the interferon is interferon-alpha-2a, interferon-alpha-2b, or interferon-alpha-n1. In another specific embodiment, the interferon-alpha-2a or interferon-alpha-2b is pegylated. In a preferred embodiment, the interferon-alpha-2a is pegylated interferon-alpha-2a (PEGASYS). In another embodiment, the additional therapeutic agent is selected from immune modulator or immune stimulator therapies, which includes biological agents belonging to the interferon class.

Further, the additional therapeutic agent may be an agent of distinct or unknown mechanism including agents that disrupt the function of other essential viral protein(s) or host proteins required for HBV replication or persistence.

In another embodiment, the additional therapeutic agent is an antiviral agent that blocks viral entry or maturation or targets the HBV polymerase such as nucleoside or nucleotide or non-nucleos(t)ide polymerase inhibitors. In a further embodiment of the combination therapy, the reverse transcriptase inhibitor or DNA or RNA polymerase inhibitor is Zidovudine, Didanosine, Zalcitabine, ddA, Stavudine, Lamivudine, Abacavir, Emtricitabine, Entecavir, Apricitabine, Atevirapine, ribavirin, acyclovir, famciclovir, valacyclovir, ganciclovir, valganciclovir, Tenofovir, Adefovir, PMPA, cidofovir, Efavirenz, Nevirapine, Delavirdine, or Etravirine.

In an embodiment, the additional therapeutic agent is an immunomodulatory agent that induces a natural, limited immune response leading to induction of immune responses against unrelated viruses. In other words, the immunomodulatory agent can effect maturation of antigen presenting cells, proliferation of T-cells and cytokine release (e.g., IL-12, IL-18, IFN-alpha, -beta, and -gamma and TNF-alpha among others), In a further embodiment, the additional therapeutic agent is a TLR modulator or a TLR agonist, such as a TLR-7 agonist or TLR-9 agonist. In further embodiment of the combination therapy, the TLR-7 agonist is selected from the group consisting of SM360320 (9-benzyl-8-hydroxy-2-(2-methoxy-ethoxy)adenine) and AZD 8848 (methyl [3-({[3-(6-amino-2-butoxy-8-oxo-7,8-dihydro-9H-purin-9-yl)propyl][3-(4-morpholinyl)propyl]amino}methyl)phenyl] acetate).

In any of the methods provided herein, the method may further comprise administering to the individual at least one HBV vaccine, a nucleoside HBV inhibitor, an interferon or any combination thereof. In an embodiment, the HBV vaccine is at least one of RECOMBIVAX HB, ENGERIX-B, ELOVAC B, GENEVAC-B, or SHANVAC B.

In one embodiment, the methods described herein further comprise administering at least one additional therapeutic agent selected from the group consisting of nucleotide/nucleoside analogs, entry inhibitors, fusion inhibitors, and any combination of these or other antiviral mechanisms.

In another aspect, provided herein is method of treating an HBV infection in an individual in need thereof, comprising reducing the HBV viral load by administering to the individual a therapeutically effective amount of a disclosed compound alone or in combination with a reverse transcriptase inhibitor; and further administering to the individual a therapeutically effective amount of HBV vaccine. The reverse transcriptase inhibitor may be at least one of Zidovudine, Didanosine, Zalcitabine, ddA, Stavudine, Lamivudine, Abacavir, Emtricitabine, Entecavir, Apricitabine, Atevirapine, ribavirin, acyclovir, famciclovir, valacyclovir, ganciclovir, valganciclovir, Tenofovir, Adefovir, PMPA, cidofovir, Efavirenz, Nevirapine, Delavirdine, or Etravirine.

In another aspect, provided herein is a method of treating an HBV infection in an individual in need thereof, comprising reducing the HBV viral load by administering to the individual a therapeutically effective amount of a disclosed compound alone or in combination with a antisense oligonucleotide or RNA interference agent that targets HBV nucleic acids; and further administering to the individual a therapeutically effective amount of HBV vaccine. The antisense oligonucleotide or RNA interference agent possesses sufficient complementarity to the the target HBV nucleic acids to inhibit replication of the viral genome, transcription of viral RNAs, or translation of viral proteins.

In another embodiment, the disclosed compound and the at least one additional therapeutic agent are co-formulated. In yet another embodiment, the disclosed compound and the at least one additional therapeutic agent are co-administered. For any combination therapy described herein, synergistic effect may be calculated, for example, using suitable methods such as the Sigmoid-$E_{max}$ equation (Holford & Scheiner, 19981, Clin. Pharmacokinet. 6: 429-453), the equation of Loewe additivity (Loewe & Muischnek, 1926, Arch. Exp. Pathol Pharmacol. 114: 313-326) and the median-effect equation (Chou & Talalay, 1984, Adv. Enzyme Regul. 22: 27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

In an embodiment of any of the methods of administering combination therapies provided herein, the method can further comprise monitoring or detecting the HBV viral load of the subject, wherein the method is carried out for a period of time including until such time that the HBV virus is undetectable.

Administration/Dosage/Formulations

In another aspect, provided herein is a pharmaceutical composition comprising a at least one disclosed compound, or a pharmaceutically acceptable salt thereof, together with a pharmaceutically acceptable carrier.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

In particular, the selected dosage level will depend upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could begin administration of the pharmaceutical composition to dose the disclosed compound at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of the disclosed compound calculated to produce the desired therapeutic effect in association with the required pharmaceutical vehicle. The dosage unit forms of the invention are dictated by and directly dependent on (a) the unique characteristics of the disclosed compound and the particular therapeutic effect to be achieved, and (b) the limitations inherent in the art of compounding/formulating such a disclosed compound for the treatment of HBV infection in a patient.

In one embodiment, the compositions of the invention are formulated using one or more pharmaceutically acceptable excipients or carriers. In one embodiment, the pharmaceutical compositions of the invention comprise a therapeutically effective amount of a disclosed compound and a pharmaceutically acceptable carrier.

In some embodiments, the dose of a disclosed compound is from about 1 mg to about 2,500 mg. In some embodiments, a dose of a disclosed compound used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound (i.e., another drug for HBV treatment) as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In one embodiment, the present invention is directed to a packaged pharmaceutical composition comprising a container holding a therapeutically effective amount of a disclosed compound, alone or in combination with a second pharmaceutical agent; and instructions for using the compound to treat, prevent, or reduce one or more symptoms of HBV infection in a patient.

Routes of administration of any of the compositions of the invention include oral, nasal, rectal, intravaginal, parenteral, buccal, sublingual or topical. The compounds for use in the invention may be formulated for administration by any suitable route, such as for oral or parenteral, for example, transdermal, transmucosal (e.g., sublingual, lingual, (trans) buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

For parenteral administration, the disclosed compounds may be formulated for injection or infusion, for example, intravenous, intramuscular or subcutaneous injection or infusion, or for administration in a bolus dose or continuous infusion. Suspensions, solutions or emulsions in an oily or aqueous vehicle, optionally containing other formulatory agents such as suspending, stabilizing or dispersing agents may be used.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

Exemplary compounds useful in methods of the invention will now be described by reference to the illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Unless otherwise specified, the variables are as defined above in reference to Formula (I). Reactions may be performed between the melting point and the reflux temperature of the solvent, and preferably between 0° C. and the reflux temperature of the solvent. Reactions may be heated employing conventional heating or microwave heating. Reactions may also be conducted in sealed pressure vessels above the normal reflux temperature of the solvent.

Abbreviations and acronyms used herein include the following:

TABLE 5

| Term | Acronym |
|---|---|
| Acetonitrile | ACN or MeCN |
| Aqueous | aq |
| Atmosphere | atm |
| tert-Butylcarbamoyl | Boc |
| Boron-dipyrromethene | BODIPY |
| Benzyl | Bn |
| Broad | br |
| Capside assembly | CA |
| Carboxybenzyl | CBz |
| Diatomaceous Earth | Celite ® |
| 1,1'-Carbonyldiimidazole | CDI |
| Doublet of doublets | dd |
| Diethylaminosulfur trifluoride | DAST |
| Di-tert-butyl azodicarboxylate | DBAD |
| 1,8-Diazabicyclo[5.4.0]undec-7-ene | DBU |
| Dichloroethane | DCE |
| Dichloromethane | DCM |
| Bis(2-methoxyethyl)aminosulfur trifluoride | Deoxo-Fluor ® |

TABLE 5-continued

| Term | Acronym |
|---|---|
| Diethyl azodicarboxylate | DEAD |
| Diisopropyl azodicarboxylate | DIAD |
| Diisopropylethylamine | DIPEA, DIEA, or Hunig's base |
| 4-Dimethylaminopyridine | DMAP |
| 1,2-Dimethoxyethane | DME |
| N,N-Dimethylformamide | DMF |
| Dimethyl sulfide | DMS |
| Dimethylsulfoxide | DMSO |
| Deoxyribonucleic Acid | DNA |
| 1-Ethyl-3-(3-dimethylaminopropyl)carbodiimide | EDCI, EDAC, or EDC |
| Diethyl ether | Ether, $Et_2O$ |
| Ethyl Acetate | EtOAc, or EA |
| Ethanol | EtOH |
| Electrospray ionization | ESI |
| Normal-phase silica gel chromatography | FCC |
| Grams | g |
| Hours | h or hr |
| (1-[Bis(dimethylamino)methylene]-1H-1,2,3-triazolo[4,5-b]pyridinium 3-oxid hexafluorophosphate) | HATU |
| Hepatitis B Virus | HBV |
| Acetic acid | HOAc |
| 1-Hydroxy-7-azabenzotriazole | HOAt |
| Hydroxybenzotriazole | HOBt |
| High-pressure liquid chromatography | HPLC |
| Hertz | Hz |
| Isopropyl alcohol | iPrOH, IPA |
| Potassium tert-butoxide | KOtBu |
| Lithium aluminum hydride | LAH |
| Liquid chromatography and mass spectrometry | LCMS |
| Lithium diisopropylamide | LDA |
| Lithium bis(trimethylsilyl)amide | LHMDS |
| Molar | M |
| multiplet | m |
| Mass to charge ratio | m/z |
| meta-Chloroperoxybenzoic acid | mCPBA |
| Methyl Iodide | MeI |
| Methanol | MeOH |
| Milligrams | mg |
| Megahertz | MHz |
| Minute | min |
| Milliliter | mL |
| Microliter | μL |
| Millimole | mmol |
| Micromole | μmol |
| Mass spectrometry | MS |
| Mesityl chloride | MsCl |
| Normal | N |
| Sodium acetate | NaOAc |
| Sodium tert-butoxide | NaOt-Bu |
| N-Methylmorpholine N-oxide | NMO |
| Nuclear magnetic resonance | NMR |
| $CF_3SO_3$— or triflate | OTf |
| Polymerase chain reaction | PCR |
| Petroleum ether | PE |
| Palladium (II) acetate | $Pd(OAc)_2$ |
| Palladium(II)bis(triphenylphosphine) dichloride | $Pd(PPh_3)_2Cl_2$ |
| Tetrakis(triphenylphosphine)palladium(0) | $Pd(PPh_3)_4$ |
| [1,1'-Bis(di-tert-butylphosphino)ferrocene]dichloropalladium(II) | $PdCl_2(dtbpf)$ or $Pd(dtbpf)_2Cl_2$ |
| [1,1'-Bis(diphenylphosphino)ferrocene]dichloropalladium(II) | $PdCl_2(dppf)$ or $Pd(dppf)_2Cl_2$ |
| 9-(2-Phosphonyl-methoxypropyly)adenine | PMPA |
| Parts per million | ppm |
| Precipitate | ppt |
| Polytetrafluoroethylene | PTFE |
| Pyridine | Py |
| Benzotriazol-1-yl-oxytripyrrolidinophosphonium hexafluorophosphate | PyBOP |
| Retention time | $R_t$ |
| Ribonucleic Acid | RNA |
| Room temperature | rt |
| singlet | s |
| Saturated | sat |
| 1-Chloromethyl-4-fluoro-1,4-diazoniabicyclo[2.2.2]octane bis(tetrafluoroborate) | Selectfluor ® |
| [2-(Trimethylsilyl)ethoxy]methyl acetal | SEM |

TABLE 5-continued

| Term | Acronym |
|---|---|
| Supercritical Fluid Chromatography | SFC |
| Temperature | T |
| triplet | t |
| Propylphosphonic anhydride | $T_3P$ |
| Tert-Butyl alcohol | tBuOH, t-BuOH |
| Tetra-n-butylammonium fluoride | TBAF |
| Tetra-n-butylammonium iodide | TBAI |
| Tert-butyldiphenylsilyl chloride | TBDPSCl |
| Triethylamine | TEA |
| Trifluoroacetic acid | TFA |
| Tetrahydrofuran | THF |
| Thin layer chromatography | TLC |
| Toll-like receptor | TLR |
| Tumor necrosis factor | TNF |
| Volume in milliliters of solvent per gram of substrate | V, or volumes |
| (Diethylamino)difluorosulfonium tetrafluoroborate | XtalFluor ® |

PREPARATIVE EXAMPLES

Exemplary compounds useful in methods of the invention will now be described by reference to the illustrative synthetic schemes for their general preparation below and the specific examples to follow.

SCHEME 1

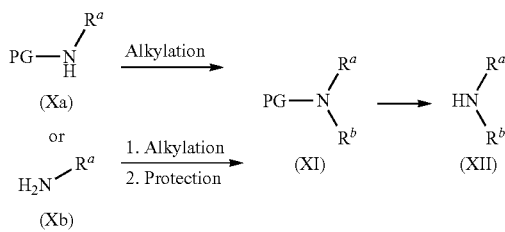

According to SCHEME 1, a commercially available or synthetically accessible compound of formula (Xa), where $R^a$ is $C_{1-6}$alkyl or $C_{1-6}$haloalkyl, and PG is a suitable nitrogen protecting group such as BOC, Bn, and the like, is alkylated with an alkylating agent such as ethyl prop-2-enoate, ethyl 2-(bromomethyl)prop-2-enoate, and the like, to provide a compound of formula (XI), where $R^b$ is $C_{2-6}$alkylene optionally substituted with $CO_2Et$. A compound of formula (Xa), where $R^a$ is $CH_3$ or $CH_2CHF_2$, and PG is BOC, is alkylated under conditions known to one skilled in the art, for example, reaction with or without a base such as NaH, $Cs_2CO_3$, $K_2CO_3$, and the like, in a suitable solvent such as THF, DMF and the like, with an alkylating agent such as ethyl 2-(bromomethyl)prop-2-enoate and the like, at temperatures ranging from 0° C. to 80° C., for a period of 12-24 h, to provide a compound of formula (XI), where $R^b$ is $CH_2(C=CH_2)CO_2Et$. In an alternate method, a compound of formula (Xb), is first alkylated under conditions previously described, then protected with a suitable nitrogen protecting group, to provide a compound of formula (XI). For example, a compound of formula (Xb), where $R^a$ is $C_{1-6}$alkyl, is alkylated with an alkylating agent such as 5-methylene-1,3,2-dioxathiane 2-oxide, in a solvent such as THF, and the like, at a temperature of about 50-80° C., subsequent protection with di-tert-butyl dicarbonate, provides a compound of formula (XI), where $R^b$ is $CH_2(C=CH_2)CH_2OH$, and PG is BOC.

Deprotection of the nitrogen protecting group, employing conditions known to one skilled in the art provides a compound of formula (XII). For example the BOC protecting group is removed with acid such as TFA, HCl, and the like, in a suitable solvent such as DCM, and the like.

SCHEME 2

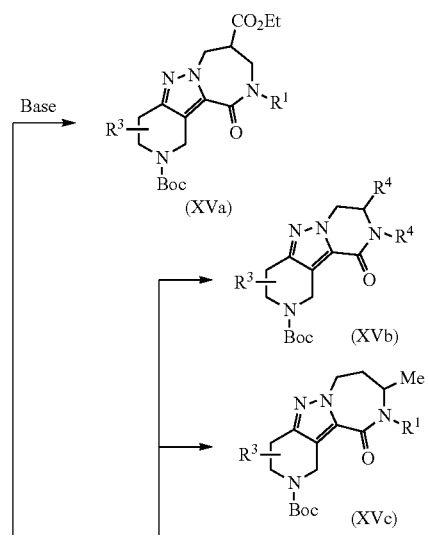

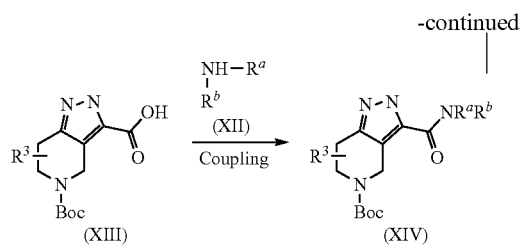

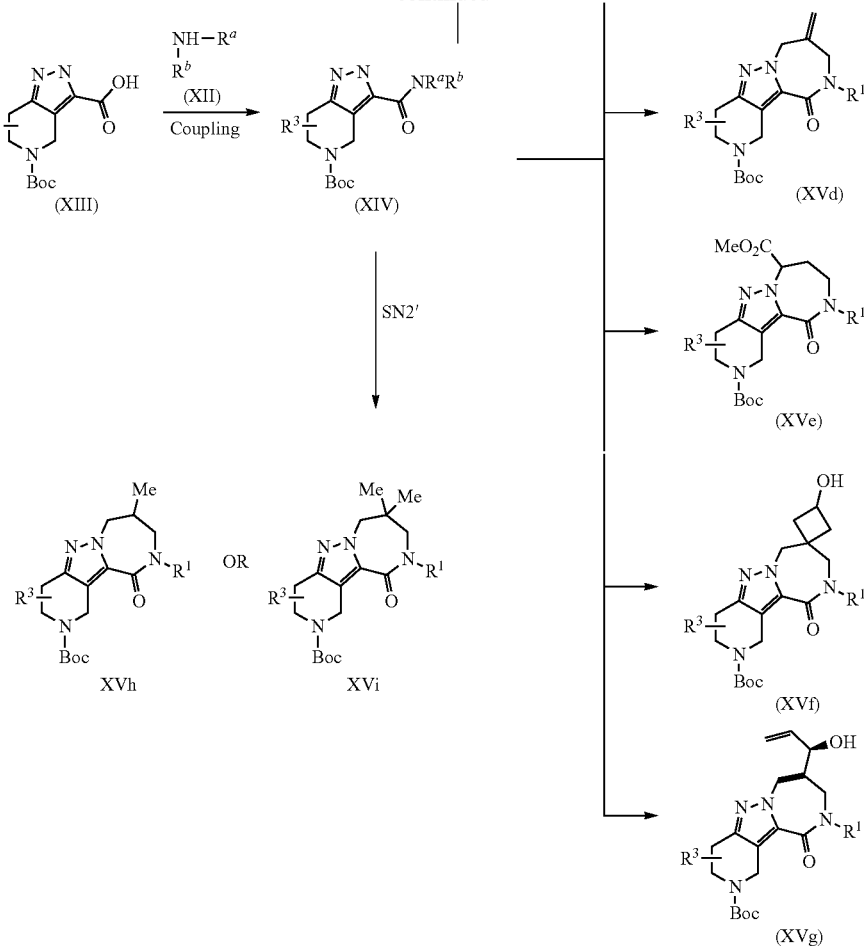

According to SCHEME 2, a commercially available or synthetically accessible compound of formula (XIII), where $R^3$ is H or $C_{1-6}$alkyl, is coupled with a compound of formula (XII), where $R^a$ is $C_{1-6}$alkyl or $C_{1-6}$haloalkyl, and $R^b$ is $CH_2CH_2OH$, $CH(CH_3)CH_2CH_2OH$, $CH(C=CH_2)CO_2Et$, $CH_2CH(C=CH_2)CH_2OH$, $CH_2CH_2CH(OPG)CO_2Me$, $CH_2CH(CH_2OH)CH(OTBDPS)CH=CH_2$, $CH_2C(CH_2OH)(CH_2CH(OBn)CH_2)$, $CH_2CH_2CH(OH)CO_2Me$, $CH_2C(Me)_2CH_2OH$, $CH(CH_2OTBS)(CH_2OCH_2CH=CH_2)$, and the like, under amide bond coupling conditions to provide a compound of formula (XIV). For example, an acid compound of formula (XIII) is reacted with an amine of formula (XII), in the presence of a dehydrating agent such as HOBt/EDAC, CDI, PyBOP, HATU, HOAT, propylphosphonic anhydride ($T_3P$), a suitably selected base such as DIPEA, TEA, and the like, in a solvent such as toluene, MeCN, EtOAc, DMF, THF, DCM, or a mixture thereof, to afford a compound of formula (XIV).

A compound of formula (XIV), where $R^3$ is H or $C_{1-6}$alkyl, $R^a$ is $C_{1-6}$alkyl or $C_{1-6}$haloalkyl, and $R^b$ is $CH(C=CH_2)CO_2Et$, is reacted with a base such as DBU (1,8-diazabicyclo[5.4.0]undec-7-ene), in a solvent such as ACN, at a temperature of about 40-60° C. for a period of 1-3 h provides a compound of formula (XVa).

A compound of formula (XIV) is cyclized under Mitsonobu conditions, to provide a compound of formulas (XVb) where $R^4$ is H, (XVc), and (XVd). For example, a compound of formula (XIV), where $R^3$ is H or $C_{1-6}$alkyl, $R^a$ is $C_{1-6}$alkyl or $C_{1-6}$haloalkyl, and $R^b$ is $CH_2CH_2OH$ is reacted with a trisubstituted phosphane such as triphenylphosphane, tributylphosphane, and the like, and an azodicarboxylate such as diethyl azodicarboxylate (DEAD), diisopropyl azodicarboxylate (DIAD), and the like, in a suitable solvent such as THF, and the like, at temperatures ranging from 70-100° C., for a period of 10-16 hours, to provide a compound of formula (XVb), where $R^1$ and $R^3$ are $C_{1-6}$alkyl or $C_{1-6}$haloalkyl.

A compound of formula (XIV), where $R^3$ is H or $C_{1-6}$alkyl, $R^a$ is $C_{1-6}$alkyl or $C_{1-6}$haloalkyl, and $R^b$ is $CH_2CH_2CH(OH)CO_2Me$, is reacted with a base such as TEA, and a sulfonyl such as MsCl, in a solvent such as DCM, at a temperature of about 0° C. for a period of 1-3 h. This is followed by a base such as NaH in a solvent such as THF to provide a compound of formula (XVe).

A compound of formula (XIV), where $R^3$ is H or $C_{1-6}$alkyl, $R^a$ is $C_{1-6}$alkyl or $C_{1-6}$haloalkyl, and $R^b$ is $CH_2C(CH_2OH)(CH_2CH(OBn)CH_2)$, is reacted with a base such as TEA, and a sulfonyl such as MsCl, in a solvent such as DCM, at a temperature of about 0° C. for a period of 1-3 h. This is followed by a base such as NaH in a solvent such as THF to provide a compound of formula (XVf).

A compound of formula (XIV), where $R^3$ is H or $C_{1-6}$alkyl, $R^a$ is $C_{1-6}$alkyl or $C_{1-6}$haloalkyl, and $R^b$ is $CH_2CH(CH_2OH)CH(OTBDPS)CH=CH_2$, is reacted with a base such as TEA, and a sulfonyl such as MsCl, in a solvent such as DCM, at a temperature of about 0° C. for a period of 1-3 h. This is followed by a base such as NaH in a solvent such as THF to provide a compound of formula (XVg).

A compound of formula (XIV), where $R^3$ is H or $C_{1-6}$alkyl, $R^a$ is $C_{1-6}$alkyl or $C_{1-6}$haloalkyl, and $R^b$ is $CH_2CH(C=CH_2)CH_2OH$, is reacted with a base such as TEA, and a sulfonyl such as MsCl, in a solvent such as DCM, at a temperature of about 0° C. for a period of 1-3 h. This is followed by a base such as potassium tert-butoxide in a solvent such as DMF. Followed by a reducing agent such palladium on carbon in the presence of hydrogen gas in a solvent such as methanol, at a temperature of about 30° C., for about 15-45 minutes provides a compound of formula (XVh).

A compound of formula (XIV), where $R^3$ is H or $C_{1-6}$alkyl, $R^a$ is $C_{1-6}$alkyl or $C_{1-6}$haloalkyl, and $R^b$ is $CH_2C(Me)_2CH_2OH$, is reacted with a base such as TEA, and a sulfonyl such as MsCl, in a solvent such as DCM, at a temperature of about 0° C. for a period of 1-3 h. This is followed by a base such as sodium hydride in a solvent such as THF to provide a compound of formula (XVi).

A compound of formula (XVb), where $R^3$ is H or $C_{1-6}$alkyl, $R^1$ is $C_{1-6}$alkyl or $C_{1-6}$haloalkyl, and $R^4$ is $CH_2OH$, is prepared in three steps. First, a compound of formula (XIV) where $R^b$ is $CH(CH_2OTBS)(CH_2OCH_2CH=CH_2)$ is deprotected using a suitable reagent such as TBAF, in a solvent such as THF, to provide a compound of formula (XIV) where $R^b$ is $CH(CH_2OH)(CH_2OCH_2CH=CH_2)$. Second, cyclized under the Mitsonobu conditions described above. Third, removal of the allyl group using suitable reagents such as osmium oxide, with sodium periodate, and with NMO, in a solvent such as THF, to provide a compound of formula (XVb), where $R^3$ is H or $C_{1-6}$alkyl, $R^1$ is $C_{1-6}$alkyl or $C_{1-6}$haloalkyl, and $R^4$ is $CH_2OH$.

A compound of formula (XVb), where $R^3$ is H or $C_{1-6}$alkyl, $R^1$ is $C_{1-6}$alkyl or $C_{1-6}$haloalkyl, and $R^4$ is $CH_2OH$, is reacted with a fluorinating reagent such as DAST, in a solvent such as DCM, to provide a compound of formula (XVb), where $R^3$ is H or $C_{1-6}$alkyl, $R^1$ is $C_{1-6}$alkyl or $C_{1-6}$haloalkyl, and $R^4$ is $CH_2F$.

A compound of formula (XVb), where $R^3$ is H or $C_{1-6}$alkyl, $R^1$ is $C_{1-6}$alkyl or $C_{1-6}$haloalkyl, and $R^4$ is $CH_2OH$, is reacted with a alkylating reagent such as $CF_2HCH_2OTf$, using a base such as sodium hydride, in a solvent such as THF, to provide a compound of formula (XVb), where $R^3$ is H or $C_{1-6}$alkyl, $R^1$ is $C_{1-6}$alkyl or $C_{1-6}$haloalkyl, and $R^4$ is $CH_2OCH_2CHF_2$.

SCHEME 3

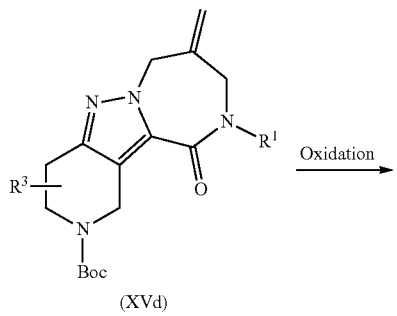

(XVd)

Oxidation

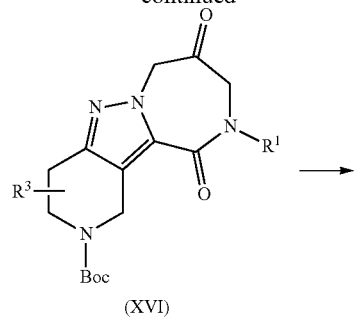

(XVI)

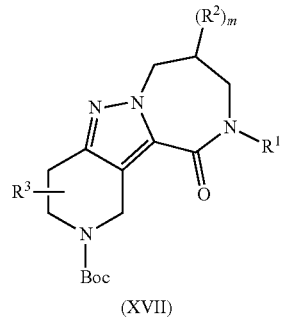

(XVII)

According to SCHEME 3, a compound of formula (XVd) is oxidized, employing oxidation conditions known to one skilled in the art, for example $OsO_4$ and $NaIO_4$.

A compound of formula (XVI), where $R^1$ is $C_{1-6}$alkyl or $C_{1-6}$haloalkyl and $R^3$ is H or $C_{1-6}$alkyl, is reduced with a reducing agent such as $NaBH_4$, and the like, in a suitable solvent such as MeOH, THF, and the like, to provide a compound of formula (XVII), where $R^2$ is OH, and m is 1.

A compound of formula (XVII), where $R^2$ is OH, and m is 1, is alkylated with an alkylating agent such as a $C_{1-6}$alkylhalide or $C_{1-6}$haloalkyl halide, and the like, a base such as NaH, and the like, in a suitable solvent such as such as THF, DMF, and the like, to provide a compound of formula (XVII), where $R^2$ is $OC_{1-6}$alkyl or $O-C_{1-6}$haloalkyl, and m is 1.

A compound of formula (XVII), where $R^2$ is OH, and m is 1, is fluorinated with a fluorinating agent such as, DAST, XtalFluor®, Deoxo-Fluor®, and the like, in a suitable solvent such as DCM, and the like, at temperatures ranging from −78° C. to 50° C., for a period of 2-16 h, to provide a compound of formula (XVII), where $R^2$ is F, and m is 1.

A compound of formula (XVII), where $R^2$ is $S-C_{1-6}$alkyl, and m is 1, is prepared in three steps from a compound of formula (XVII) where $R^2$ is OH, and m is 1. In a first step, mesylation of a compound of formula (XVII) where $R^2$ is OH, with mesyl chloride, a base such as TEA, in a solvent such as DCM, to provide a compound of formula (XVII), where $R^2$ is $O-SO_2CH_3$. Subsequent reaction of the mesylated compound of formula (XVII) with sodium methanethiolate, in a solvent such as DMF, at temperatures ranging from 0° C. to 20° C., provides a compound of formula (XVII), where $R^2$ is $S(C=O)CH_3$. Reaction of a compound of formula (XVII), where $R^2$ is $S(C=O)CH_3$ with a base such as $K_2CO_3$, and the like, and an $C_{1-6}$alkylhalide such as MeI, provides a compound of formula (XVII), where $R^2$ is $S-C_{1-6}$alkyl.

A carbonyl compound of formula (XVI), where $R^1$ is $C_{1-6}$alkyl or $C_{1-6}$haloalkyl and $R^3$ is H or $C_{1-6}$alkyl, is fluorinated with a fluorinating agent such as, DAST, XtalFluor®, Deoxo-Fluor®, and the like, in a suitable solvent such as DCM, and the like, at temperatures ranging from −78° C. to 50° C., for a period of 2-16 h, to provide a compound of formula (XVII), where $R^2$ is F, and m is 2.

A carbonyl compound of formula (XVI), where $R^1$ is $C_{1-6}$alkyl or $C_{1-6}$haloalkyl and $R^3$ is H or $C_{1-6}$alkyl, is reacted with an alkyl amine of formula $N(C_{1-6}alkyl)_{1-2}$ such as $NH(CH_3)_2$, or an optionally substituted $C_2$-$C_6$-heterocycloalkyl such as morpholine, azetidine, difluoroazetidine, pyrrolidine, and the like, under reductive amination conditions, to provide a compound of formula (XVII), where $R^2$ is an optionally substituted $C_2$-$C_6$-heterocycloalkyl, or $N(C_{1-6}alkyl)_2$. For example, a carbonyl compound of formula (XVI), where $R^1$ is $C_{1-6}$alkyl or $C_{1-6}$haloalkyl and $R^3$ is H or $C_{1-6}$alkyl, is reacted with $NH(CH_3)_2$, a reducing agent such as $NaCNBH_3$, $NaBH_3$, sodium triacetxyborohydride, and the like, with or without a dehydrating agent such as molecular sieves, with or without HOAc, or NaOAc, in a suitable solvent such as DCM, THF, DCE, and the like, provides a compound of formula (XVI) where $R^2$ is $N(CH_3)_2$.

A compound of formula (XVII), where $R^2$ is $CH_2CO_2C_{1-6}$alkyl, is prepared in two steps from a carbonyl compound of formula (XVI), where $R^1$ is $C_{1-6}$alkyl or $C_{1-6}$haloalkyl and $R^3$ is H or $C_{1-6}$alkyl. In a first step, carbonyl compound of formula (XVI) is reacted with methyl 2-dimethoxyphosphorylacetate, a base such as potassium 2-methylpropan-2-olate, in a solvent such as THF, and the like, at temperatures ranging from 0° C. to 20° C. In a second step, reduction of the alkene under hydrogenation conditions, for example, Pd/C and $H_2$, in a solvent such as EtOH, MeOH, and the like, provides a compound of formula (XVII), where $R^2$ is $CH_2CO_2CH_3$.

A compound of formula (XVII), where $R^2$ is $CH_2N(C_{1-6}alkyl)_{1-2}$ such as $NH(CH_3)_2$, $CH_2N(C_{1-6}haloalkyl)_{1-2}$, or an optionally substituted $CH_2C_2$-$C_6$-heterocycloalkyl such as morpholine, azetidine, difluoroazetidine, pyrrolidine, and the like, is prepared in three steps from a carbonyl compound of formula (XVI), where $R^1$ is $C_{1-6}$alkyl or $C_{1-6}$haloalkyl and $R^3$ is H or $C_{1-6}$alkyl. In a first step, carbonyl compound of formula (XVI) is reacted with a hydroboranation reagent such as wilkinson's catalyst and catecholborane, a base such as sodium hydroxide, in a solvent such as hydrogen peroxide, at temperatures ranging from −30° C. to 20° C. In a second step, mesylation of a compound of formula (XVII) where $R^2$ is $CH_2OH$, with mesyl chloride, a base such as TEA, in a solvent such as DCM, to provide a compound of formula (XVII), where $R^2$ is $CH_2O$—$SO_2CH_3$. Subsequent reaction of the mesylated compound of formula (XVII) with a $C_2$-$C_6$-heterocycloalkyl, in a solvent such as DMSO, at temperatures ranging from 80° C. to 90° C., provides a compound of formula (XVII), where $R^2$ is $CH_2N(C_{1-6}alkyl)_{1-2}$ such as $NH(CH_3)_2$, $CH_2N(C_{1-6}haloalkyl)_{1-2}$, or an optionally substituted $CH_2C_2$-$C_6$-heterocycloalkyl such as morpholine, azetidine, difluoroazetidine, pyrrolidine, and the like.

A compound of formula (XVII), where $R^2$ is F and $C_{1-6}$alkyl, and m is 2, is prepared from a compound of formula (XVII) where $R^2$ is OH and $C_{1-6}$alkyl, and m is 2 with a fluorinating agent such as, DAST, XtalFluor®, Deoxo-Fluor®, and the like, in a suitable solvent such as DCM, and the like, at temperatures ranging from −78° C. to 50° C., for a period of 2-16 h, to provide a compound of formula (XVII), where $R^2$ is F and $C_{1-6}$alkyl, and m is 2.

A compound of formula (XVII), where $R^2$ is $CH_2N(C_{1-6}haloalkyl)(COC_{1-6}haloalky)$, and m is 1, is prepared from a compound of formula (XVII), where $R^2$ is $CH_2N(C_{1-6}haloalkyl)H$ by reacting with an acylating reagent such as trifluoroacetic anhydride, a base such as trietyl amine, in a solvent such as DCM, at a temperature between the range of 0° C. to 20° C., for a period of 2-4 hours, to provide a compound of formula (XVII), where $R^2$ is $CH_2N(C_{1-6}haloalkyl)(COC_{1-6}haloalky)$, and m is 1.

SCHEME 4

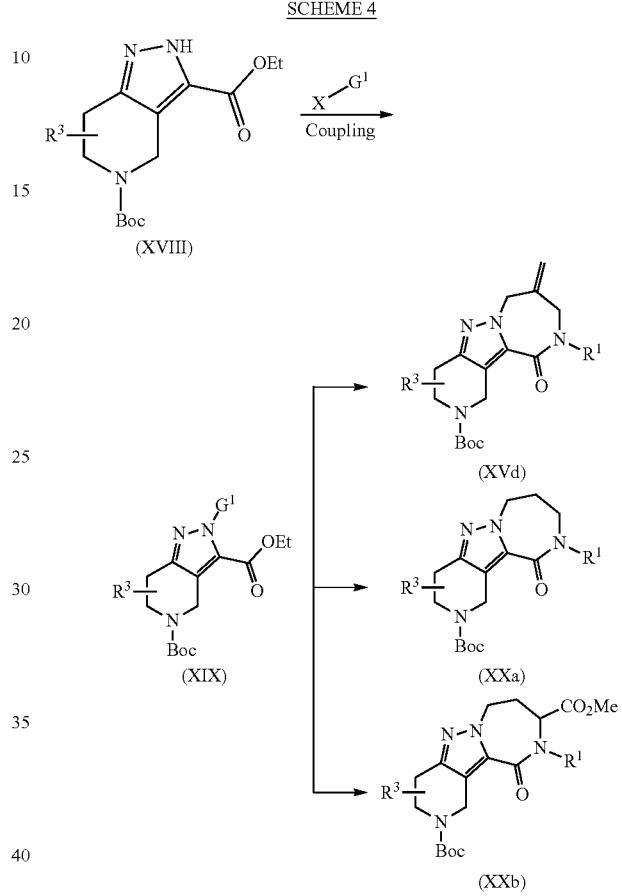

According to SCHEME 4, a commercially available or synthetically accessible alkyl halide, where X is a halide and $G^1$ is $CH_2C(CH_2C_1)$=$CH_2$, $CH_2CH_2CH_2N(H)(Boc)$, and $CH_2CH_2CH(NHCbz)CO_2Me$ and the like, is coupled with a compound of formula (XVIII), where $R^3$ is H or $C_{1-6}$alkyl, under coupling conditions to provide a compound of formula (XIX). For example, a compound of formula (XVIII) is reacted with an alkyl halide, a suitably selected base such as potassium carbonate and the like, in a solvent such as DMF or THF, to afford a compound of formula (XIX).

A compound of formula (XIX), where $R^3$ is H or $C_{1-6}$alkyl, is reacted with a primary a $C_{1-6}$alkyl or $C_{1-6}$haloalkyl amine such as methyl amine, in a solvent such as EtOH, at a temperature of about 80° C. for a period of 16 h provides a compound of formula (XVd) where $R^1$ is $C_{1-6}$alkyl or $C_{1-6}$haloalkyl.

A compound of formula (XXa), where $R^3$ is H or $C_{1-6}$alkyl, and $R^1$ is $C_{1-6}$alkyl or $C_{1-6}$haloalkyl, is made in three steps. The first being global deprotection of BOC protecting groups of a compound of Formula (XIX) where $G^1$ is $CH_2CH_2CH_2N(H)(Boc)$, using suitable conditions such as TFA in DCM. Second, cyclizing by forming an amide bond using a suitable base such as potassium carbonate, in a solvent such as EtOH, and reprotecting with boc anhydride to form a compound of Formula (XXa) where $R^1$ is H. Third, reacting a $C_{1-6}$alkyl or $C_{1-6}$haloalkyl halide, using a base such as NaH, in a solvent such as THF, to provide a compound of Formula (XXa) where $R^1$ is $C_{1-6}$alkyl or $C_{1-6}$haloalkyl.

A compound of formula (XXb), where $R^3$ is H or $C_{1-6}$alkyl, and $R^1$ is $C_{1-6}$alkyl or $C_{1-6}$haloalkyl, is made in four steps. The first being deprotection of the Cbz protecting group of a compound of Formula (XIX) where $G^1$ is $CH_2CH_2CH(NHCbz)CO_2Me$, using suitable deprotection conditions such as Pd/C in the presense of $H_2$, in a solvent such as MeOH. Second, cyclizing by forming an amide bond and subsequent hydrolysis, using a base such as sodium methoxide, and a solvent such as methanol. Third, esterification of the carboxylic acid, using a base such as NaH, alkyl halid such as methyl iodide, and a solvent such as DMF. Fourth, reacting a $C_{1-6}$alkyl or $C_{1-6}$haloalkyl halide, using a base such as NaH, in a solvent such as THF, to provide a compound of Formula (XXb) where $R^1$ is $C_{1-6}$alkyl or $C_{1-6}$haloalkyl.

SCHEME 5

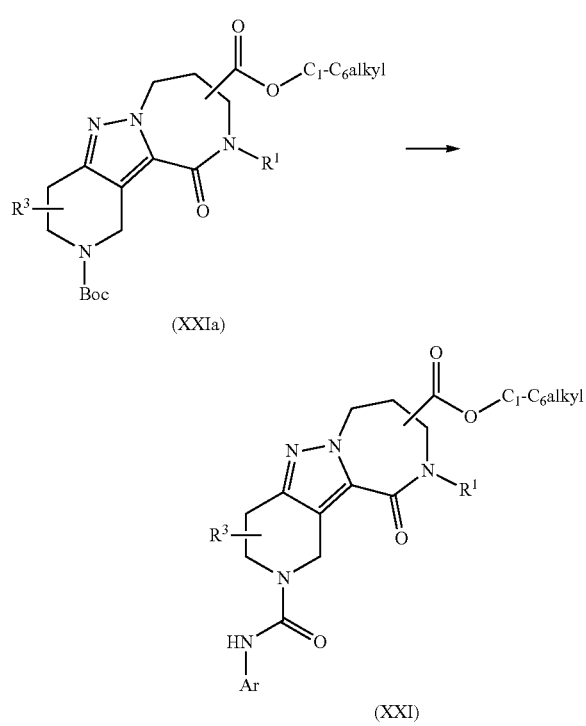

According to SCHEME 5, a compound of Formula (XXI) where $R^3$ is H or $C_{1-6}$alkyl, $R^1$ is $C_{1-6}$alkyl or $C_{1-6}$haloalkyl, and Ar is an optionally substituted aryl ring can be prepared in two steps. For example, the Boc protecting group can be removed from a compound of Formula (XXIa) using suitable conditions such as trifluoroacetic acid in DCM. The resulting product can then be reacted with an aryl carbamate such as N-Aryl-phenylcarbamate, a base such as TEA, and a solvent such as DCM to provide a compound of Formula (XXI) where $R^3$ is H or $C_{1-6}$alkyl, $R^1$ is $C_{1-6}$alkyl or $C_{1-6}$haloalkyl, and Ar is an optionally substituted aryl ring. Wherein, a compound of Formula (XXIa) is a compound of Formula (XXb), Formula (XVa), or Formula (XVe).

SCHEME 6

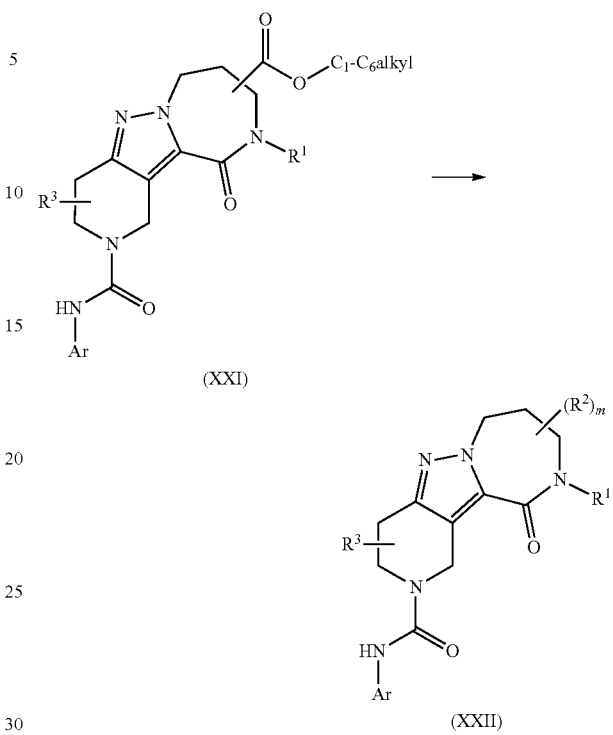

According to SCHEME 6, a compound of Formula (XXI) where $R^3$ is H or $C_{1-6}$alkyl, $R^1$ is $C_{1-6}$alkyl or $C_{1-6}$haloalkyl, and Ar is 4-fluoro-2-chloro-benzene, is reacted with a Grignard reagent such as methyl magnesium bromide, in a solvent such as THF to provide a compound of Formula (XXII) where $R^2$ is an optionally substituted $C_{1-6}$alkyl, and m is 1.

A compound of Formula (XXI) where $R^3$ is H or $C_{1-6}$alkyl, $R^1$ is $C_{1-6}$alkyl or $C_{1-6}$haloalkyl, and Ar is 4-fluoro-2-chloro-benzene, is reacted with an alkyl amine of formula $N(C_{1-6}alkyl)_{1-2}$ such as $NH(CH_3)_2$, in a solvent such as DMF, with a base such as DIPEA, and a coupling agent such as HATU to provide a compound of Formula (XXII) where $R^2$ is CO $N(C_{1-6}alkyl)_{1-2}$, and m is 1.

A compound of Formula (XXII) where $R^3$ is H or $C_{1-6}$alkyl, $R^1$ is $C_{1-6}$alkyl or $C_{1-6}$haloalkyl, and Ar is 4-fluoro-2-chloro-benzene, $R^2$ is $CH(OH)C_{1-6}$alkyl or $CH(OH)C_{3-6}$cycloalkyl, and m is 1, was prepared from a compound of Formula (XXI) in 4 steps. First, a compound of Formula (XXI) was hydrolyzed, using a base such as sodium hydroxide, in a solvent such as water, MeOH or a mix of both to provide a compound of Formula (XXII) where $R^2$ is COOH. Second, reacting with an alkyl alkoxy amide such MeN-HOMe, a coupling reagent such as HATU, a base such as DIPEA, and a solvent such as DMF to provide a compound of Formula (XXII) where $R^2$ is a Weinreb amide. Third, reacting with a Grignard such as methyl magnesium bromide, ethyl magnesium bromide or cyclopropyl magnesium bromide, and a solvent such as THF to provide a compound of Formula (XXII) where $R^2$ is C=OMe. Fourth, reacting with a reducing reagent such as $NaBH_4$, and a solvent such as EtOH to provide a compound of Formula (XXII) where $R^2$ is $CH(OH)C_{1-6}$alkyl or $CH(OH)C_{3-6}$cycloalkyl, and m is 1.

A compound of Formula (XXII) where $R^3$ is H or $C_{1-6}$alkyl, $R^1$ is $C_{1-6}$alkyl or $C_{1-6}$haloalkyl, and Ar is 4-fluoro-2-chloro-benzene, $R^2$ is $CHF_2$, and m is 1, was prepared from a compound of Formula (XXI) in 3 steps. First, a compound of Formula (XXI) was reduced, using a reducing reagent such as $LiAlH_4$, in a solvent such as THF to provide a compound of Formula (XXII) where $R^2$ is $CH_2OH$. Second, reacting with an oxidant such DMP, in a solvent such as DCM to provide a compound of Formula (XXII) where $R^2$ is CHO. Third, reacting with a fluorinating agent such as DAST, in a solvent such as DCM to provide a compound of Formula (XXII) where $R^2$ is $CHF_2$, and m is 1.

SCHEME 7

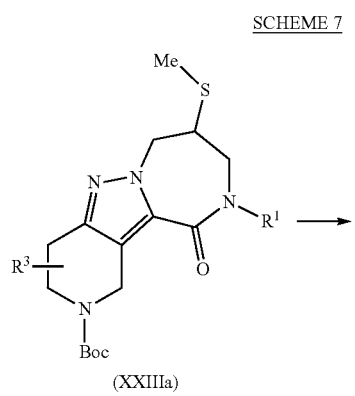

(XXIIIa)

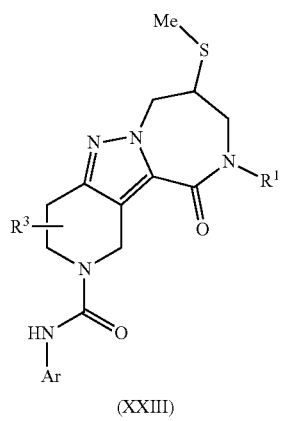

(XXIII)

According to SCHEME 7, a compound of Formula (XXIII) where $R^3$ is H or $C_{1-6}$alkyl, $R^1$ is $C_{1-6}$alkyl or $C_{1-6}$haloalkyl, and Ar is an optionally substituted aryl ring can be prepared in two steps. For example, the Boc protecting group can be removed from a compound of Formula (XXIIIa) using suitable conditions such as trifluoroacetic acid in DCM. The resulting product can then be reacted with an aryl carbamate such as N-Aryl-phenylcarbamate, a base such as TEA, and a solvent such as DCM to provide a compound of Formula (XXIII) where $R^3$ is H or $C_{1-6}$alkyl, $R^1$ is $C_{1-6}$alkyl or $C_{1-6}$haloalkyl, and Ar is an optionally substituted aryl ring. Wherein, a compound of Formula (XXIIIa) is prepared as described in SCHEME 3.

SCHEME 8

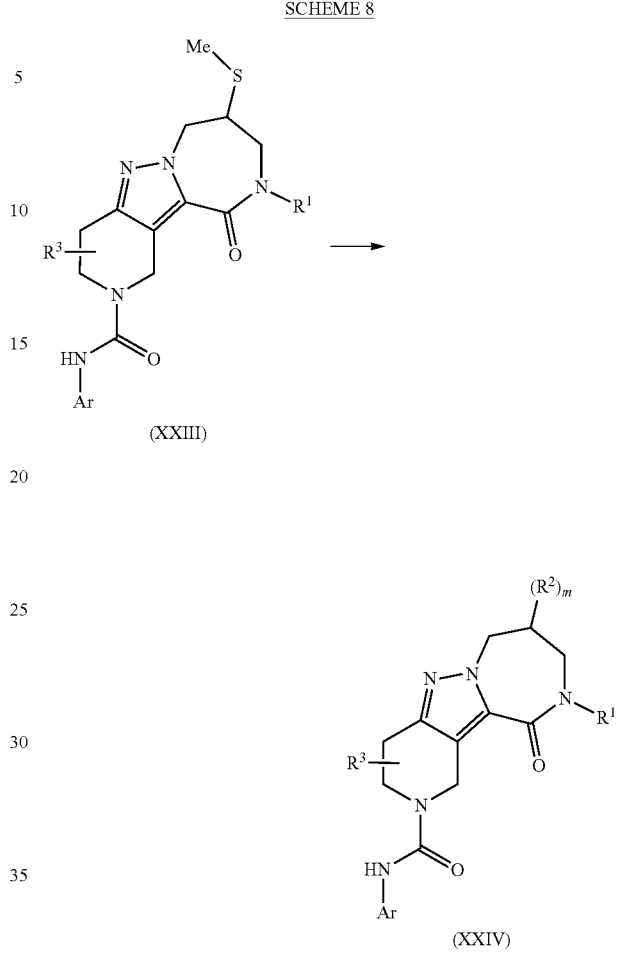

(XXIII)

(XXIV)

According to SCHEME 8, a compound of Formula (XXIII) where $R^3$ is H or $C_{1-6}$alkyl, $R^1$ is $C_{1-6}$alkyl or $C_{1-6}$haloalkyl, and Ar is 4-fluoro-2-chloro-benzene, is reacted with an oxidant such as $(Bu_3Sn)_2O$ and Bromide or m-CPBA, in a solvent such as DCM to provide a compound of Formula (XXIV) where $R^2$ is a sulfonate or sulfoxide, and m is 1.

SCHEME 9

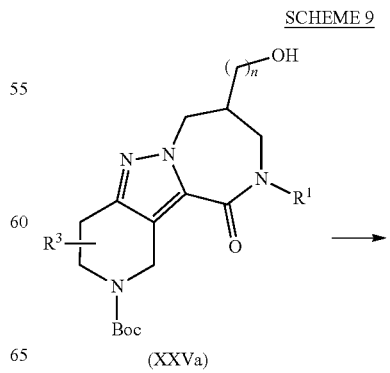

(XXVa)

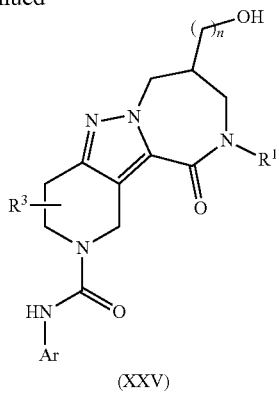

(XXV)

According to SCHEME 9, a compound of Formula (XXV) where $R^3$ is H or $C_{1-6}$alkyl, $R^1$ is $C_{1-6}$alkyl or $C_{1-6}$haloalkyl, and Ar is an optionally substituted aryl ring can be prepared in two steps. For example, the Boc protecting group can be removed from a compound of Formula (XXVa) using suitable conditions such as trifluoroacetic acid in DCM. The resulting product can then be reacted with an aryl carbamate such as N-Aryl-phenylcarbamate, a base such as TEA, and a solvent such as DCM to provide a compound of Formula (XXV) where $R^3$ is H or $C_{1-6}$alkyl, $R^1$ is $C_{1-6}$alkyl or $C_{1-6}$haloalkyl, and Ar is an optionally substituted aryl ring. Wherein, a compound of Formula (XXVa) is prepared as described in SCHEME 3.

SCHEME 10

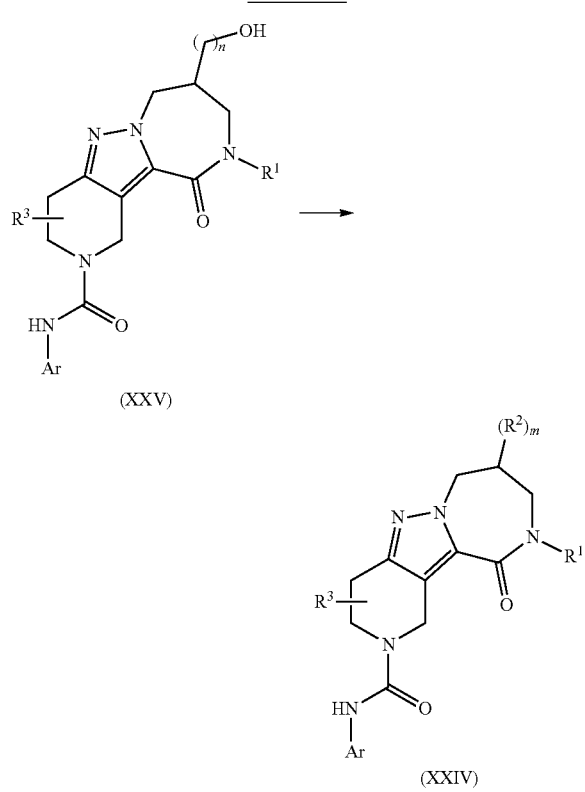

According to SCHEME 10, a compound of Formula (XXIV) where $R^3$ is H or $C_{1-6}$alkyl, $R^1$ is $C_{1-6}$alkyl or $C_{1-6}$haloalkyl, and Ar is 4-fluoro-2-chloro-benzene, $R^2$ is $N(C_{1-6}alkyl)_{0-2}$, and m is 1, was prepared from a compound of Formula (XXV) in 3 steps. First, a compound of Formula (XXV) where n is 0 was reacted with, sulfonating reagent such as MSCl, using a base such as TEA, in a solvent such as DCM to provide a compound of Formula (XXIV) where $R^2$ is OMs. Second, reacting with a nucleophilic azide such as sodium azide, in a solvent such as DMF to provide a compound of Formula (XXIV) where $R^2$ is $N_3$. Third, reacting with a reducing agent such as zinc/ammoniumchloride or Pd/C and hydrogen, in a solvent such as MeOH, EtOH, water, or a mixture of any to provide a compound of Formula (XXII) where $R^2$ is $N(C_{1-6}alkyl)_{0-2}$, and m is 1.

A compound of Formula (XXIV) where $R^3$ is H or $C_{1-6}$alkyl, $R^1$ is $C_{1-6}$alkyl or $C_{1-6}$haloalkyl, and Ar is 4-fluoro-2-chloro-benzene, $R^2$ is $N(C_{1-6}alkyl)_{0-2}$, and m is 1, was prepared from a compound of Formula (XXV) in 3 steps. First, a compound of Formula (XXV) where n is 1 was reacted with, sulfonating reagent such as MSCl, using a base such as TEA, in a solvent such as DCM to provide a compound of Formula (XXIV) where $R^2$ is $CH_2OMs$. Second, reacting with a nucleophilic azide such as sodium azide, in a solvent such as DMF to provide a compound of Formula (XXIV) where $R^2$ is $CH_2N_3$. Third, reacting with a reducing agent such as zinc/ammoniumchloride or Pd/C and hydrogen, in a solvent such as MeOH, EtOH, water, or a mixture of any to provide a compound of Formula (XXIV) where $R^2$ is $CH_2N(C_{1-6}alkyl)_{0-2}$, and m is 1.

SCHEME 11

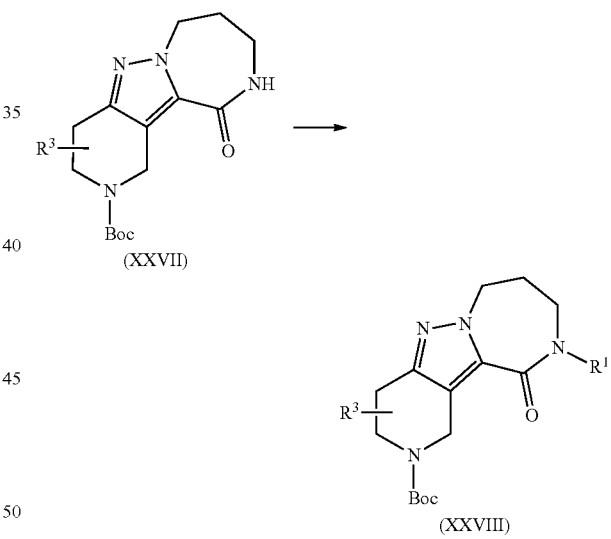

According to SCHEME 11, a compound of Formula (XXVIII) where $R^3$ is H or $C_{1-6}$alkyl, $R^1$ is $C_{1-6}$alkyl-OH was prepared from a compound of Formula (XXVII) in 2 steps. First, a compound of Formula (XXVII) where was reacted with, alkylating reagent with a terminal ester such as $BrCH_2COOMe$, using a base such as NaH, in a solvent such as THF to provide a compound of Formula (XXVI) where $R^1$ is a $C_1$-$C_6$alkyl ester. Second, reacting with a Grignard such as methyl magnesium bromide, in a solvent such as THF to provide a compound of Formula (XXVI) where $R^2$ is $C_1$-$C_6$ alkyl-OH.

A compound of Formula (XXVIII) where $R^3$ is H or $C_{1-6}$alkyl, $R^1$ is $C_{1-6}$alkyl-OH was prepared from a compound of Formula (XXVII) in 2 steps. First, a compound of Formula (XXVII) where was reacted with, alkylating reagent with a terminal ester such as BrCH$_2$COOMe, using a base such as NaH, in a solvent such as THF to provide a compound of Formula (XXVI) where R$^1$ is a C$_1$-C$_6$alkyl ester. Second, reacting with a reducing reagent such as LiAlH$_4$, in a solvent such as THF to provide a compound of Formula (XXVI) where R$^2$ is C$_1$-C$_6$ alkyl-OH.

SCHEME 12

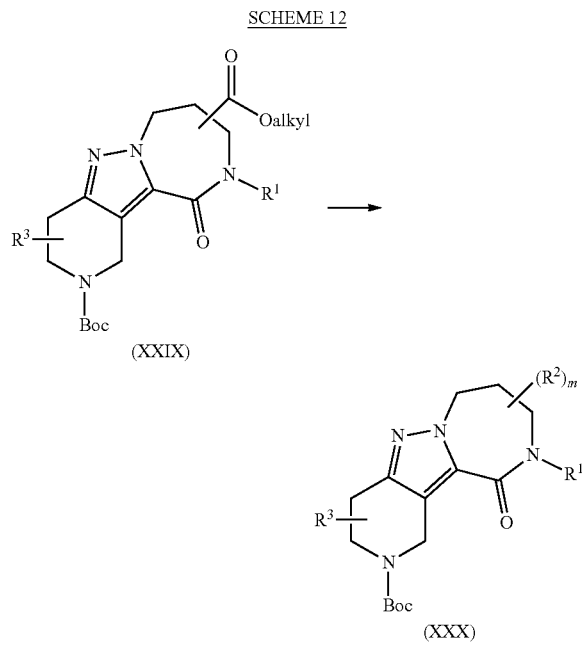

According to SCHEME 12, a compound of Formula (XXIX) where R$^3$ is H or C$_{1-6}$alkyl, and R$^1$ is C$_{1-6}$alkyl or C$_{1-6}$haloalkyl, is reacted with a strong base such as LDA, an alkylating agent such as MeI or CHF$_2$CH$_2$OTf, in a solvent such as THF to provide a compound of Formula (XXX) where R$^2$ is C$_{1-6}$alkyl or C$_{1-6}$haloalkyl and COOalkyl, and m is 2.

A compound of Formula (XXX) where R$^3$ is H or C$_{1-6}$alkyl, R$^1$ is C$_{1-6}$alkyl or C$_{1-6}$haloalkyl, R$^2$ is CH(OH)Et, and m is 1 was prepared from a compound of Formula (XXIX) in 5 steps. First, a compound of Formula (XXIX) where was hydrolyzed using suitable conditions such as NaOH in MeOH/water to provide a compound of Formula (XXX) where R$^2$ is COOH. Second, reacting with an alkyl alkoxy amide such MeNHOMe, a coupling reagent such as HATU, a base such as DIPEA, and a solvent such as DMF to provide a compound of Formula (XXX) where R$^2$ is a Weinreb amide. Third, reacting with a grignard such as vinyl magnesium bromide, in a solvent such as THF to provide a compound of Formula (XXX) where R$^2$ is C(O)CH=CH$_2$. Fourth, reacting with a reducing reagent such as NaBH$_4$/CeCl$_3$, in a solvent such as MeOH to provide a compound of Formula (XXX) where R$^2$ is CH(OH)CH=CH$_2$. Fifth, reacting with a reducing reagent such as Pd/C, in a solvent such as MeOH to provide a compound of Formula (XXX) where R$^2$ is CH(OH)CH$_2$CH$_3$, and m is 1.

A compound of Formula (XXX) where R$^3$ is H or C$_{1-6}$alkyl, R$^1$ is C$_{1-6}$alkyl or C$_{1-6}$haloalkyl, R$^2$ is CH(OH) C$_{1-6}$alkyl, and m is 1 was prepared from a compound of Formula (XXX) where R$^2$ is a Weinreb amide in 2 steps. First, reacting with a C$_{1-6}$alkyl Grignard such as n-propyl magnesium bromide, in a solvent such as THF to provide a compound of Formula (XXX) where R$^2$ is C(O)C$_{1-6}$alkyl. Second, reacting with a reducing reagent such as NaBH$_4$, in a solvent such as MeOH to provide a compound of Formula (XXX) where R$^2$ is CH(OH) C$_{1-6}$alkyl.

A compound of Formula (XXX) where R$^3$ is H or C$_{1-6}$alkyl, R$^1$ is C$_{1-6}$alkyl or C$_{1-6}$haloalkyl, R$^2$ is CH(OH)CH$_2$-cyclopropyl, and m is 1 was prepared from a compound of Formula (XXX) where R$^2$ is a Weinreb amide in 3 steps. First, reacting with a grignard such as allyl magnesium bromide, in a solvent such as THF to provide a compound of Formula (XXX) where R$^2$ is C(O)CH$_2$CH=CH$_2$. Second, reacting with a reducing reagent such as NaBH$_4$, in a solvent such as MeOH to provide a compound of Formula (XXX) where R$^2$ is CH(OH) CH$_2$CH=CH$_2$. Third, reacting with an alkyl halide such as ICH$_2$Cl, a zincate such as diethyl zinc, in a solvent such as DCM to provide a compound of Formula (XXX) where R$^2$ is CH(OH)CH$_2$-cyclopropyl.

A compound of Formula (XXX) where R$^3$ is H or C$_{1-6}$alkyl, R$^1$ is C$_{1-6}$alkyl or C$_{1-6}$haloalkyl, R$^2$ is CH$_2$OH and F, and m is 2 was prepared from a compound of Formula (XXIX) in 2 steps. First, reacting with a fluorinating reagent such as NFSI with LDA, in a solvent such as THF to provide a compound of Formula (XXX) where R$^2$ is C(O)C$_{1-6}$alkyl and F. and m is 2. Second, reacting with a reducing reagent such as LiBH$_4$, in a solvent such as THF to provide a compound of Formula (XXX) where R$^2$ is CH$_2$OH and F, and m is 2.

A compound of Formula (XXX) where R$^3$ is H or C$_{1-6}$alkyl, R$^1$ is C$_{1-6}$alkyl or C$_{1-6}$haloalkyl, R$^2$ is CH$_2$OC$_{1-6}$haloalkyl, and m is 1 was prepared from a compound of Formula (XXX) where R$^2$ is a Weinreb amide in 2 steps. First, reacting with a reducing agent such as NaBH$_4$, in a solvent such as THF to provide a compound of Formula (XXX) where R$^2$ is CH$_2$OH. Second, reacting with an alkylating reagent such as CHF$_2$CH$_2$OTf, using a suitable base such as NaH, in a solvent such as THF to provide a compound of Formula (XXX) where R$^2$ is CH$_2$OC$_{1-6}$haloalkyl.

SCHEME 13

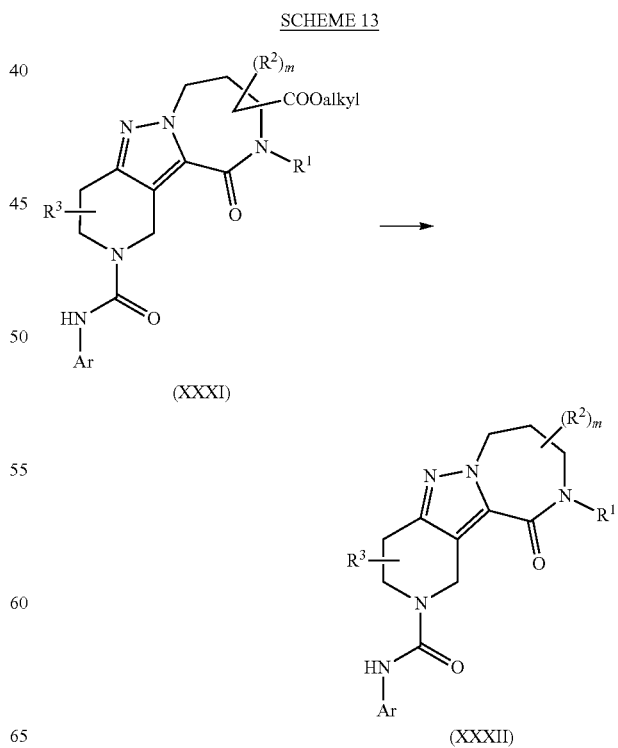

According to SCHEME 13, a compound of Formula (XXXI) where $R^3$ is H or $C_{1-6}$alkyl, $R^1$ is $C_{1-6}$alkyl or $C_{1-6}$haloalkyl, and $R^2$ is $C_{1-6}$alkyl or $C_{1-6}$haloalkyl, is reacted with a reducing agent such as $LiBH_4$, in a solvent such as THF to provide a compound of Formula (XXXII) where $R^2$ is $C_{1-6}$alkyl or $C_{1-6}$haloalkyl and $CH_2OH$, and m is 2.

A compound of Formula (XXXI) where $R^3$ is H or $C_{1-6}$alkyl, $R^1$ is $C_{1-6}$alkyl or $C_{1-6}$haloalkyl, and $R^2$ is $C_{1-6}$alkyl or $C_{1-6}$haloalkyl, is hydrolyzed using suitable conditions such as NaOH in MeOH/water to provide a compound of Formula (XXXII) where $R^2$ is $C_{1-6}$alkyl or $C_{1-6}$haloalkyl and COOH, and m is 2.

SCHEME 14

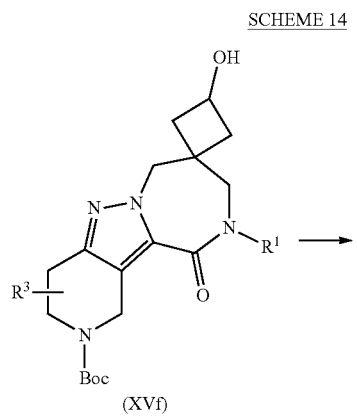

(XVf)

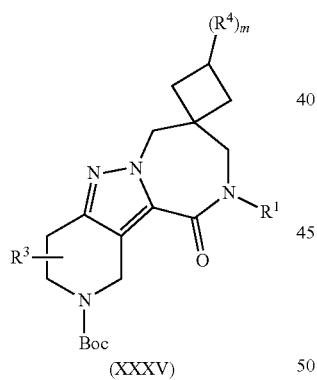

(XXXV)

According to SCHEME 13, a compound of Formula (XVf) where $R^3$ is H or $C_{1-6}$alkyl, and $R^1$ is $C_{1-6}$alkyl or $C_{1-6}$haloalkyl, is reacted with a flurorinating agent such as DAST, in a solvent such as DCM to provide a compound of Formula (XXXV) where $R^4$ is F, and m is 1.

A compound of Formula (XXXV) where $R^3$ is H or $C_{1-6}$alkyl, and $R^1$ is $C_{1-6}$alkyl or $C_{1-6}$haloalkyl, and $R^4$ is F and F, and m is 2, is prepared in two steps. First, a compound of Formula (XVf) is oxidized using a suitable reagent such as DMP, in a solvent such as DCM, to provide a compound of Formula (XXXV) where $R^4$ is =O. Second, reacting with a flurorinating agent such as DAST, in a solvent such as DCM to provide a compound of Formula (XXXV) where $R^4$ is F and F, and m is 2.

SCHEME 15

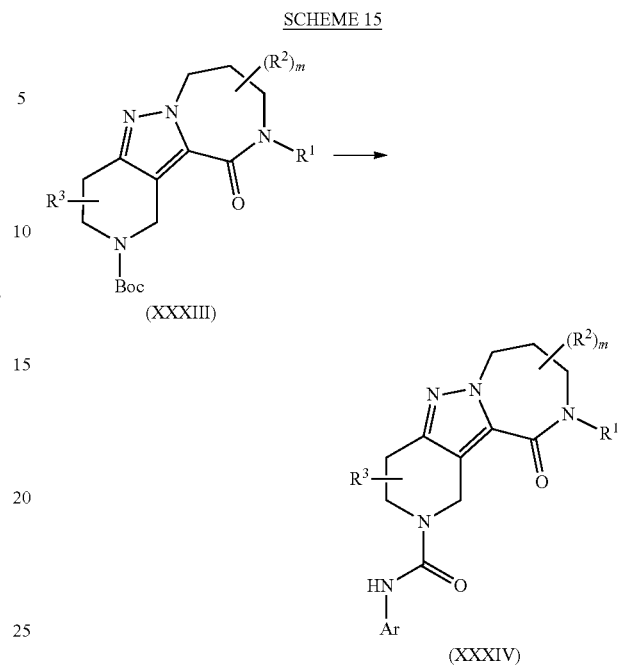

(XXXIII)

(XXXIV)

According to SCHEME 15, a compound of Formula (XXXIV) where $R^3$ is H or $C_{1-6}$alkyl, $R^1$ is as described by the schemes above, $R^2$ is described as the schemes above, Ar is an optionally substituted aryl ring, and m is 0, 1, or 2 is prepared in two steps. First, removal of the Boc protecting group from a compound of Formula (XXXIII) using suitable conditions such as trifluoroacetic acid in DCM. Second, reaction with a aryl carbamate such as N-Aryl-phenylcarbamate, a base such as TEA, and a solvent such as DCM to provide a compound of Formula (XXXIV) where $R^3$ is H or $C_{1-6}$alkyl, $R^1$ is as described by the schemes above, $R^2$ is described as the schemes above, Ar is an optionally substituted aryl ring, and m is 0, 1, or 2.

Intermediate 1. tert-butyl 10-methyl-8-methylene-11-oxo-1,3,4,7,8,9,10,11-octahydro-2H-pyrido[4',3': 3,4]pyrazolo[1,5-a][1,4]diazepine-2-carboxylate

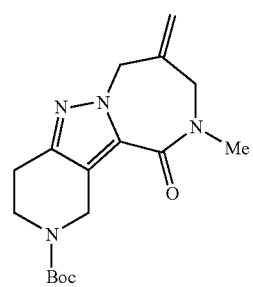 [SMILES: C=C1CN(C)C(=O)c2c3c(nn2C1)CCN(C(=O)OC(C)(C)C)C3]

Method A

Step 1. 5-methylene-1,3,2-dioxathiane 2-oxide

To a solution of 2-methylenepropane-1,3-diol (5.00 g, 56.75 mmol, 4.63 mL, 1.00 eq) in $CCl_4$ (50.00 mL) was added a solution of $SOCl_2$ (10.13 g, 85.13 mmol, 6.18 mL, 1.50 eq) in CCl$_4$ (10.00 mL) at 0° C. under N$_2$, and the mixture was stirred at 0° C. for 45 mins. The mixture was concentrated under reduced pressure to afford 5-methylene-1,3,2-dioxathiane 2-oxide (6.90 g, 51.43 mmol, 90.63% yield) as yellow oil, which was used directly for the next step. $^1$H NMR (400 MHz, CDCl$_3$) δ 5.36-5.39 (m, 2H), 5.16 (s, 2H), 4.22-4.28 (m, 2H).

Step 2. 2-((methylamino)methyl)prop-2-en-1-ol

A solution of 5-methylene-1,3,2-dioxathiane 2-oxide (1.00 g, 7.45 mmol, 1.00 eq) and methanamine (2 M, 11.18 mL, 3.00 eq) in THF (2.00 mL) was heated to 70° C. for 16 h. TLC (DCM/MeOH=20/1) showed the starting material was consumed completely and one major new spot with larger polarity was detected. The mixture was filtered and the filtrate was concentrated in vacuo to afford the title compound (750.00 mg, 7.41 mmol, 99.46% yield) as yellow oil, which was used directly for the next step.

Step 3. tert-butyl (2-(hydroxymethyl)allyl)(methyl)carbamate

To a solution of 2-(methylaminomethyl)prop-2-en-1-ol (750.00 mg, 7.41 mmol, 1.00 eq) in dioxane (5.00 mL)/H$_2$O (5.00 mL) was added Boc$_2$O (1.94 g, 8.89 mmol, 2.04 mL, 1.20 eq) and NaHCO$_3$ (622.40 mg, 7.41 mmol, 1.00 eq). The mixture was stirred at 30° C. for 16 h. The mixture with was diluted with EA (50 mL) and washed with brine (50 mL). The organic phase was dried over Na$_2$SO$_4$, filtered and concentrated to give yellow oil, which was purified by silica gel column to afford the title compound (710.00 mg, 3.53 mmol, 47.61% yield) as yellow oil. $^1$H NMR (400 MHz, CD$_3$OD) δ 5.10 (s, 1H), 4.97 (s, 1H), 3.91-4.10 (m, 4H), 2.81 (s, 3H), 1.50 (s, 9H).

Step 4. 2-((methylamino)methyl)prop-2-en-1-ol hydrochloride

To a solution of tert-butyl N-[2-(hydroxymethyl)allyl]-N-methyl-carbamate (710.00 mg, 3.53 mmol, 1.00 eq) in dioxane (3.00 mL) was added HCl/dioxane (4 M, 5.00 mL, 5.67 eq) and the mixture was stirred at 15° C. for 1 h. TLC (PE/EtOAc=2/1) showed the starting material was consumed completely and one major new spot with larger polarity was detected. The mixture was concentrated in vacuo to afford the title compound (480.00 mg, 3.49 mmol, 98.81% yield, HCl) as yellow oil, which was used directly for the next step. $^1$H NMR (400 MHz, CD$_3$OD) δ 5.46 (s, 1H), 5.32 (s, 1H), 4.20 (s, 2H), 3.71 (s, 2H), 2.73 (s, 3H).

Step 5. tert-butyl 3-((2-(hydroxymethyl)allyl) (methyl)carbamoyl)-6,7-dihydro-2H-pyrazolo[4,3-c] pyridine-5 (4H)-carboxylate A mixture of 5-tert-butoxycarbonyl-1,4,6,7-tetrahydropyrazolo [4,3-c]pyridine-3-carboxylic acid (550.00 mg, 2.06 mmol, 1.00 eq), DIPEA (798.70 mg, 6.18 mmol, 1.08 mL, 3.00 eq), HATU (939.93 mg, 2.47 mmol, 1.20 eq) and 2-(methylaminomethyl)prop-2-en-1-ol (425.21 mg, 3.09 mmol, 1.50 eq, HCl) in DMF (6.00 mL) was heated to 80° C. for 16 h. The mixture was diluted with EtOAc (80 mL) and washed with brine (80 mL*3). The organic phase was dried over Na$_2$SO$_4$, filtered and concentrated under reduced pressure to give yellow oil. The yellow oil was purified by silica gel column to afford the title compound (390.00 mg, 1.11 mmol, 54.03% yield) as yellow solid. LCMS: 351 [M+1].

Step 6. tert-butyl 10-methyl-8-methylene-11-oxo-3, 4,8,9,10,11-hexahydro-1H-pyrido[4',3':3,4]pyrazolo [1,5-a][1,4]diazepine-2 (7H)-carboxylate To a solution of tert-butyl 3-[2-(hydroxymethyl)allyl-methyl-carbamoyl]-2,4,6,7-tetrahydropyrazolo[4,3-c]pyridine-5-carboxylate (200.00 mg, 570.76 μmol, 1.00 eq) and triphenylphosphane (194.62 mg, 741.99 μmol, 1.30 eq) in THF (3.00 mL) was added DIAD (150.04 mg, 741.99 μmol, 144.27 μL, 1.30 eq) and the mixture was stirred at 30° C. for 4 h. The mixture was diluted with EtOAc (50 mL) and washed with HCl (1 M, 50 mL). The organic phase was dried over Na$_2$SO$_4$, filtered and concentrated in vacuo to give oil. The oil was purified by silica gel column to afford the title compound as impure product (320.00 mg, crude, containing Ph$_3$PO) as yellow oil. LCMS: 355 [M+23].

Method B

Step 1. 5-tert-butyl 3-ethyl 2-(2-(chloromethyl)allyl)-6,7-dihydro-2H-pyrazolo[4,3-c]pyridine-3,5 (4H)-dicarboxylate To a solution of 3-chloro-2-(chloromethyl)prop-1-ene (7.62 g, 60.95 mmol, 7.05 mL, 3.00 eq) in DMF (100.00 mL) was added 5-tert-butyl 3-ethyl 2,4,6,7-tetrahydropyrazolo[4,3-c]pyridine-3,5-dicarboxylate (6.00 g, 20.32 mmol, 1.00 eq) and K$_2$CO$_3$ (3.65 g, 26.41 mmol, 1.30 eq). The mixture was stirred at 25° C. for 6 h and then heated to 75° C. for 16 h. TLC showed the starting material was consumed completely. The mixture was diluted with EtOAc (80 mL), washed with HCl (1M, 80 mL) and brine (80 mL*2). The organic phase was dried over Na$_2$SO$_4$, filtered and concentrated in vacuo to give yellow oil. The oil was purified by silica gel column to afford the title compound (2.90 g, 7.55 mmol, 37.18% yield) as colorless oil.

Step 2. tert-butyl 10-methyl-8-methylene-11-oxo-3, 4,8,9,10,11-hexahydro-1H-pyrido[4',3':3,4]pyrazolo [1,5-a][1,4]diazepine-2 (7H)-carboxylate A solution of 5-tert-butyl 3-ethyl 2-(2-(chloromethyl) allyl)-6,7-dihydro-2H-pyrazolo[4,3-c]pyridine-3,5 (4H)-dicarboxylate (1.00 g, 2.61 mmol, 1.00 eq) and methanamine (7.5 M, 40.00 mL, 33% purity, 114.94 eq) in EtOH (30.00 mL) was heated to 80° C. in sealed tube for 16 h. The mixture was concentrated in vacuo to give yellow oil. The yellow oil was purified by silica gel column to afford the title compound (560.00 mg, 1.68 mmol, 64.37% yield) as yellow oil. LCMS: 333 [M+1].

121

Intermediate 2. tert-butyl 10-methyl-8,11-dioxo-3,4, 8,9,10,11-hexahydro-1H-pyrido[4',3':3,4]pyrazolo[1, 5-a][1,4]diazepine-2 (7H)-carboxylate

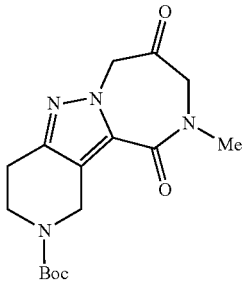 [SMILES: CN1CC(=O)Cn2nc3c(c2C1=O)CN(C(=O)OC(C)(C)C)CC3]

To a solution of tert-butyl 10-methyl-8-methylene-11-oxo-3,4,7,9-tetrahydro-1H-pyrido[2,3]pyrazolo[2,4-b][1,4] diazepine-2-carboxylate (150.00 mg, 451.26 μmol, 1.00 eq) in THF (3.00 mL) and H$_2$O (1.50 mL) was added OsO$_4$ (5.74 mg, 22.56 μmol, 1.17 μL, 0.05 eq) and NaIO$_4$ (386.08 mg, 1.81 mmol, 100.02 μL, 4.00 eq) at 0° C. The mixture was stirred at 15° C. for 16 hr. The mixture was diluted with EtOAc (40 mL) and washed with brine (40 mL). The organic phase was dried over Na$_2$SO$_4$, filtered and concentrated in vacuo to give yellow oil. The yellow oil was purified by silica gel column to afford the title compound (102.00 mg, 305.05 μmol, 67.60% yield) as yellow solid. $^1$H NMR (400 MHz, CDCl$_3$) δ 5.01 (s, 2H), 4.67 (s, 2H), 4.05 (s, 2H), 3.73 (s, 2H), 3.20 (s, 3H), 2.76 (s, 2H), 1.49 (s, 9H).

Intermediate 3: tert-butyl 8-hydroxy-10-methyl-11l-oxo-3,4,8,9,10,11-hexahydro-1H-pyrido[4',3':3,4] pyrazolo[1,5-a][1,4]diazepine-2 (7H)-carboxylate

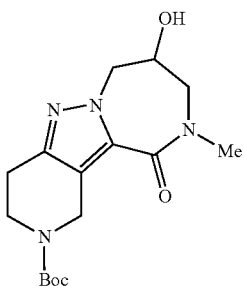 [SMILES: CN1CC(O)Cn2nc3c(c2C1=O)CN(C(=O)OC(C)(C)C)CC3]

To a solution of tert-butyl 10-methyl-8,11-dioxo-3,4,7,9-tetrahydro-1H-pyrido[2,3]pyrazolo[2,4-b][1,4]diazepine-2-carboxylate (60.00 mg, 179.44 μmol, 1.00 eq) (60.00 mg, 179.44 μmol, 1.00 eq) in MeOH (4.00 mL) was added NaBH$_4$ (13.58 mg, 358.88 μmol, 2.00 eq). The mixture was stirred at 15° C. for 1 h. The mixture was diluted with brine (30 mL), extracted with EtOAc (30 mL*2) and DCM (30 mL). The organic phase was dried over Na$_2$SO$_4$, filtered and concentrated in vacuo to afford the title compound (51.00 mg, 136.45 μmol, 76.04% yield, 90% purity) as yellow solid, which was used directly for the next step. LCMS: 337 [M+1].

122

Intermediate 4: tert-butyl 10-methyl-11-oxo-1,3,4,7, 8,9-hexahydropyrido[2,3]pyrazolo[2,4-b][1,4]diazepine-2-carboxylate

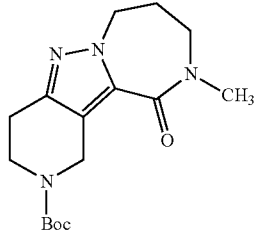 [SMILES: CN1CCCn2nc3c(c2C1=O)CN(C(=O)OC(C)(C)C)CC3]

Step 1. 5-tert-butyl 3-ethyl 2-(3-((tert-butoxycarbonyl)amino)propyl)-6,7-dihydro-2H-pyrazolo[4,3-c] pyridine-3,5 (4H)-dicarboxylate To a solution of 05-tert-butyl 03-ethyl 2,4,6,7-tetrahydropyrazolo[4,3-c]pyridine-3,5-dicarboxylate (500.00 mg, 1.69 mmol, 1.00 eq) in THF (5.00 mL) was added tert-butyl N-(3-bromopropyl)carbamate (482.91 mg, 2.03 mmol, 1.20 eq) followed by DBU (385.93 mg, 2.54 mmol, 382.11 μμL, 1.50 eq). The mixture was heated to 50° C. for 16 hr. TLC (PE:EA=1:1) showed the starting material consumed and two main spots appeared. The mixture was extracted with EtOAc (100 mL*2) and H$_2$O (50 mL). The combined organic layer was dried with Na$_2$SO$_4$, filtrated. The filtrate was concentrated in vacuum. The residue was purified by flash chromatography (PE:EA=20%~50%) to afford the title compound (400.00 mg, 875.06 μmol, 51.78% yield, 99% purity) as colorless oil. $^1$H NMR (400 MHz, CDCl$_3$) δ=4.97 (brs, 1H), 4.49-4.65 (m, 4H), 4.34 (q, J=7.0 Hz, 2H), 3.69 (brs, 2H), 3.08 (d, J=5.9 Hz, 2H), 2.74 (brs, 2H), 1.99 (quin, J=6.3 Hz, 2H), 1.49 (s, 9H), 1.44 (s, 9H), 1.39 (t, J=7.2 Hz, 4H).

Step 2. ethyl 2-(3-aminopropyl)-4,5,6,7-tetrahydro-2H-pyrazolo[4,3-c]pyridine-3-carboxylate To a solution of 05-tert-butyl 03-ethyl 2-[3-(tert-butoxycarbonylamino)propyl]-6,7-dihydro-4H-pyrazolo[4,3-c] pyridine-3,5-dicarboxylate (400.00 mg, 883.90 μmol, 1.00 eq) in DCM (2.00 mL) was added TFA (6.16 g, 54.02 mmol, 4.00 mL, 61.12 eq). The mixture was stirred at 10° C. for 1 hr. The mixture was concentrated in vacuum to afford the title compound (430.00 mg, crude, as brown oil.

Step 3. tert-butyl 11-oxo-3,4,7,8,9,10-hexahydro-1H-pyrido[2,3]pyrazolo[2,4-b][1,4]diazepine-2-carboxylate To a solution of ethyl 2-(3-aminopropyl)-4,5,6,7-tetrahydropyrazolo[4,3-c]pyridine-3-carboxylate (400.00 mg, 832.71 μmol, 1.00 eq, in EtOH (50.00 mL) was added K$_2$CO$_3$ (460.35 mg, 3.33 mmol, 4.00 eq). The mixture was stirred at 70-80° C. for 32 hr. The mixture was cooled to 10° C. and Boc$_2$O (363.48 mg, 1.67 mmol, 382.61 μμL, 2.00 eq) was added. The mixture was stirred at 10° C. for 1 hr. TLC (DCM:MeOH=10:1) showed one main spot appeared. The mixture was concentrated in vacuum. The residue was extracted with EtOAc (50 mL*2) and H$_2$O (20 mL). The combined organic layer was dried over Na$_2$SO$_4$, filtrated. The filtrate was concentrated in vacuum. The residue was purified by flash chromatography (DCM:MeOH:0%~7%) to afford the title compound (155.00 mg, 505.94 µmol, 60.76% yield) as white solid.

Step 4. tert-butyl 10-methyl-11-oxo-1,3,4,7,8,9-hexahydropyrido[2,3]pyrazolo[2,4-b][1,4]diazepine-2-carboxylate To a solution of tert-butyl 11-oxo-3,4,7,8,9,10-hexahydro-1H-pyrido[2,3]pyrazolo [2,4-b][1,4]diazepine-2-carboxylate (100.00 mg, 326.41 µmol, 1.00 eq) in THF (2.00 mL) was added NaH (19.58 mg, 489.61 µmol, 60% purity, 1.50 eq). The mixture was stirred at 0° C. for 30 min. CH$_3$I (69.50 mg, 489.61 µmol, 30.48 µL, 1.50 eq) was added. The mixture was stirred at 10° C. for 1 hr. LCMS showed one main peak with desired Ms detected. The mixture was poured into H$_2$O (10 mL) and extracted with EtOAc (10 mL*2). The combined organic layer was dried with Na$_2$SO$_4$, filtrated. The filtrates was concentrated in vacuum to afford the title compound (90.00 mg, crude) as colorless oil.

Intermediate 5: tert-butyl 11-oxo-3,4,7,8,9,10-hexahydro-1H-pyrido[2,3]pyrazolo[2,4-b][1,4]diazepine-2-carboxylate

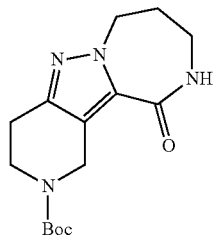 [SMILES: CC(C)(C)OC(=O)N1CCc2nn3c(c2C1)C(=O)NCCC3]

Step 1. 5-tert-butyl 3-ethyl 2-[3-(tert-butoxycarbonylamino)propyl]-6,7-dihydro-4H-pyrazolo[4,3-c]pyridine-3,5-dicarboxylate To a solution of 05-tert-butyl 03-ethyl 2,4,6,7-tetrahydropyrazolo[4,3-c]pyridine-3,5-dicarboxylate (2.00 g, 6.77 mmol, 1.00 eq) in THF (20.00 mL) was added tert-butyl N-(3-bromopropyl)carbamate (1.93 g, 8.12 mmol, 1.20 eq), followed by DBU (1.55 g, 10.16 mmol, 1.53 mL, 1.50 eq), the reaction mixture was stirred at 50° C. for 16 hours. Several new peaks were shown on LCMS and about 30% of desired product was detected. The reaction mixture was diluted with EtOAc (150 mL) and washed with water (50 mL*2), dried with anhydrous Na$_2$SO$_4$, filtered and concentrated in vacuum. The residue was purified by silica gel chromatography to afford the title compound (1.70 g, 3.76 mmol, 55.49% yield) as white solid. $^1$H NMR (400 MHz, CDCl$_3$) δ=4.94 (brs, 1H) 4.54-4.85 (m, 4H) 4.30-4.35 (m, 2H) 3.67 (br s, 2H) 3.06-3.08 (br d, J=5.90 Hz, 2H) 2.72 (br s, 2H) 1.94-2.01 (m, J=6.43 Hz, 2H) 1.47 (s, 9H) 1.42 (s, 9H) 1.36-1.39 (t, J=7.15 Hz, 3H). LCMS: 453 [M+].

Step 2. ethyl 2-(3-aminopropyl)-4,5,6,7-tetrahydropyrazolo[4,3-c]pyridine-3-carboxylate To a solution of 05-tert-butyl 03-ethyl 2-[3-(tert-butoxycarbonylamino)propyl]-6,7-dihydro-4H-pyrazolo[4,3-c]pyridine-3,5-dicarboxylate (1.70 g, 3.76 mmol, 1.00 eq) in dioxane (10.00 mL) was added HCl/dioxane (4 M, 20.00 mL, 21.28 eq). The reaction mixture was stirred at 20° C. for 2 hours. TLC indicated compound 3 was consumed completely, and one major new spot with larger polarity was detected. The solvent was removed on a rotary evaporator to afford the title compound (1.10 g, crude, as white solid. $^1$H NMR (400 MHz, METHANOL-d$_4$) δ=4.65-4.68 (t, J=6.65 Hz, 2H) 4.38-4.44 (m, 4H) 3.53-3.56 (t, J=6.27 Hz, 2H) 3.03-3.07 (t, J=6.21 Hz, 2H) 2.94-2.98 (br t, J=7.65 Hz, 2H) 2.17-2.24 (m, 2H) 1.39-1.42 (t, J=7.09 Hz, 3H)

Step 3. tert-butyl 11-oxo-3,4,7,8,9,10-hexahydro-1H-pyrido[2,3]pyrazolo[2,4-b][1,4]diazepine-2-carboxylate To a solution of ethyl 2-(3-aminopropyl)-4,5,6,7-tetrahydropyrazolo[4,3-c]pyridine-3-carboxylate (900.00 mg, 2.77 mmol, 1.00 eq) in EtOH (10.00 mL) was added NaOMe (597.95 mg, 11.07 mmol, 4.00 eq) under N$_2$. The reaction mixture was stirred at 20° C. for 3 hours. LCMS showed compound 4 was consumed completely. The solvent was removed on a rotary evaporator. To the residue, was added THF (10.00 mL), followed by a solution of NaHCO$_3$ (697.44 mg, 8.30 mmol, 322.89 µL, 3.00 eq) in H$_2$O (2.00 mL) and (Boc)$_2$O (905.94 mg, 4.15 mmol, 953.62 µL, 1.50 eq). The reaction mixture was stirred at 20° C. for one hour. LCMS showed one main peak with desired MS was detected. The reaction mixture was diluted with EtOAc (50 mL) and washed with water (30 mL*2), the organic phase was dried with anhydrous Na$_2$SO$_4$, filtered and concentrated in vacuum. The residue was purified by silica gel chromatography to afford the title compound (600.00 mg, 1.96 mmol, 70.70% yield) was obtained as white solid. LCMS: 329 [M+23].

Intermediate 6: tert-butyl 9-methyl-10-oxo-3,4,7,8-tetrahydro-1H-pyrido[2,3]pyrazolo[2,4-b]pyrazine-2-carboxylate

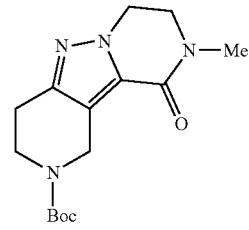 [SMILES: CN1CCn2nc3c(c2C1=O)CN(C(=O)OC(C)(C)C)CC3]

Step 1. tert-butyl 3-[2-hydroxyethyl(methyl) carbamoyl]-1,4,6,7-tetrahydropyrazolo[4,3-c]pyridine-5-carboxylate To a mixture of 5-tert-butoxycarbonyl-1,4,6,7-tetrahydropyrazolo[4,3-c]pyridine-3-carboxylic acid (1.00 g, 3.74 mmol, 1.00 eq) and 2-(methylamino)ethanol (1.41 g, 18.71 mmol, 1.49 mL, 5.00 eq) in DMF (5.00 mL) was added HATU (2.13 g, 5.61 mmol, 1.50 eq) and DIPEA (7.25 g, 56.12 mmol, 9.80 mL, 15.00 eq) in one portion under N$_2$. The mixture was stirred at 80° C. for 10 hours. LCMS and TLC (Dichloromethane:Methanol=10:1)showed the reaction was completed. The residue was poured into water (50 mL). The aqueous phase was extracted with ethyl acetate (50 mL*2). The combined organic phase was washed with brine (50 mL*2), dried with anhydrous Na$_2$SO$_4$, filtered and concentrated in vacuum. The residue was purified by silica gel chromatography (Petroleum ether/Ethyl acetate=1/1, Dichloromethane:Methanol=20:1) to afford the title compound (750.00 mg, 2.31 mmol, 61.82% yield, 100% purity) as white solid. LCMS: 325 [M+1].

Step 2. tert-butyl 9-methyl-10-oxo-3,4,7,8-tetrahydro-1H-pyrido[2,3]pyrazolo[2,4-b]pyrazine-2-carboxylate To a mixture of tert-butyl 3-[2-hydroxyethyl(methyl)carbamoyl]-1,4,6,7-tetrahydropyrazolo[4,3-c]pyridine-5-carboxylate (100.00 mg, 308.29 µmol, 1.00 eq) in THF (3.00 mL) was added tributylphosphane (81.09 mg, 400.78 µmol, 98.88 µL, 1.30 eq) and DIAD (81.04 mg, 400.78 µmol, 77.92 µL, 1.30 eq) under $N_2$. The mixture was stirred at 80° C. for 4 hours. TLC (Dichloromethane:Methanol=10:1) showed the reaction was completed. The mixture was poured into water (10 mL) and stirred for 2 min. The aqueous phase was extracted with ethyl acetate (10 mL*2). The combined organic phase was washed with brine (10 mL*2), dried with anhydrous $Na_2SO_4$, filtered and concentrated in vacuum. The residue was purified by prep-TLC (Dichloromethane:Methanol=10:1) to afford the title compound (70.00 mg, 228.49 mol, 74.12% yield) as yellow solid. LCMS: 307 [M+1].

Intermediate 7: 3-(methylamino)butan-1-ol

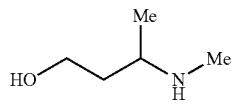

Step 1. N-(3-hydroxy-1-methyl-propyl)formamide

To a mixture of 3-aminobutan-1-ol (5.00 g, 56.09 mmol, 1.00 eq) and ethyl acetate (9.88 g, 112.18 mmol, 10.98 mL, 2.00 eq) in EtOH (30.00 mL) was added ethyl formate (9.88 g, 112.18 mmol, 10.98 mL, 2.00 eq) in one portion under $N_2$. The mixture was stirred at 80° C. for 12 hours. TLC (dichloromethane:methanol=10:1) showed the reaction was completed. The mixture was concentrated in vacuum to afford the title compound (6.00 g, 51.22 mmol, 91.31% yield) as yellow oil. $^1H$ NMR (400 MHz, $CDCl_3$) δ 8.17 (s, 1H), 5.75-5.97 (m, 1H), 4.13-4.43 (m, 1H), 3.53-3.68 (m, 2H), 3.27 (br s, 1H), 1.74-1.97 (m, 1H), 1.34-1.52 (m, 1H), 1.15-1.31 (m, 3H).

Step 2. 3-(methylamino)butan-1-ol

To a mixture of N-(3-hydroxy-1-methyl-propyl)formamide (2.00 g, 17.07 mmol, 1.00 eq) in THF (10.00 mL) was added $LiAlH_4$ (1.30 g, 34.14 mmol, 2.00 eq) in one portion at −10° C. under $N_2$. The mixture was stirred at −10° C. for 30 min, then heated to 20° C. and stirred for 12 hours, then heated to 80° C. and stirred for 3 hours. TLC (dichloromethane:methanol=10:1) showed the reaction was completed. The mixture was quenched with 1.3 mL of $H_2O$, followed by 1.3 mL of NaOH (15%) and 3.9 mL of $H_2O$. The mixture was dried with anhydrous $MgSO_4$, filtered and concentrated in vacuum to afford the title compound (1.20 g, 11.63 mmol, 68.15% yield) as yellow oil. $^1H$ NMR (400 MHz, $CDCl_3$) δ 3.71-3.93 (m, 2H), 2.83 (ddd, J=3.30, 6.39, 8.28 Hz, 1H), 2.43 (s, 3H), 1.66-1.74 (m, 1H), 1.53 (s, 1H), 1.15 (d, J=6.36 Hz, 3H).

Intermediate 8: tert-butyl 9,10-dimethyl-11-oxo-1,3,4,7,8,9-hexahydropyrido[2,3]pyrazolo [2,4-c][1,4]diazepine-2-carboxylate

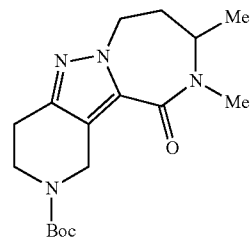 [SMILES: CC1CCn2nc3c(c2C(=O)N1C)CN(C(=O)OC(C)(C)C)CC3]

Step 1. tert-butyl 3-[(3-hydroxy-1-methyl-propyl)-methyl-carbamoyl]-1,4,6,7-tetrahydropyrazolo[4,3-c]pyridine-5-carboxylate To a mixture of 5-tert-butoxycarbonyl-1,4,6,7-tetrahydropyrazolo[4,3-c]pyridine-3-carboxylic acid (500.00 mg, 1.87 mmol, 1.00 eq) and 3-(methylamino)butan-1-ol (Intermediate 7, 771.92 mg, 7.48 mmol, 4.00 eq) in DMF (5.00 mL) was added HATU (1.07 g, 2.81 mmol, 1.50 eq) and DIPEA (3.63 g, 28.06 mmol, 4.90 mL, 15.00 eq) in one portion under $N_2$. The mixture was stirred at 80° C. for 10 hours. LCMS and TLC (dichloromethane:methanol=10:1) showed Desired product was detected. The residue was poured into water (10 mL). The aqueous phase was extracted with ethyl acetate (10 mL*2). The combined organic phase was washed with brine (10 mL*2), dried with anhydrous $Na_2SO_4$, filtered and concentrated in vacuum. The residue was purified by silica gel chromatography (petroleum ether/ethyl acetate=1/1, dichloromethane:methanol=20:1) to afford the title compound (300.00 mg, 510.74 µmol, 27.31% yield, 60% purity) as yellow solid. LCMS: 353 [M+1].

Step 2. tert-butyl 9,10-dimethyl-11-oxo-1,3,4,7,8,9-hexahydropyrido[2,3]pyrazolo [2,4-c][1,4] diazepine-2-carboxylate To a mixture of tert-butyl 3-[(3-hydroxy-1-methyl-propyl)-methyl-carbamoyl]-1,4,6,7-tetrahydropyrazolo[4,3-c]pyridine-5-carboxylate (300.00 mg, 851.23 mol, 1.00 eq) in THF (10.00 mL) was added tributylphosphane (223.89 mg, 1.11 mmol, 273.03 µL, 1.30 eq) and DIAD (223.77 mg, 1.11 mmol, 215.16 µL, 1.30 eq) in one portion under $N_2$. The mixture was stirred at 80° C. for 12 hours. LCMS and TLC (Dichloromethane:Methanol=10:1) showed the desired product was detected. The mixture was poured into water (10 mL) and stirred for 2 min. The aqueous phase was extracted with ethyl acetate (10 mL*2). The combined organic phase was washed with brine (10 mL*2), dried with anhydrous $Na_2SO_4$, filtered and concentrated in vacuum. The residue was purified by prep-HPLC(FA) to afford the title compound (66.00 mg, 197.36 µmol, 23.19% yield) as yellow solid. LCMS: 335 [M+1].

Intermediate 9: 2-tert-butyl8-methyl8-methoxy-9-methyl-10-oxo-1,3,4,7-tetrahydro pyrido[2,3]pyrazolo[2,4-c]pyrazine-2,8-dicarboxylate

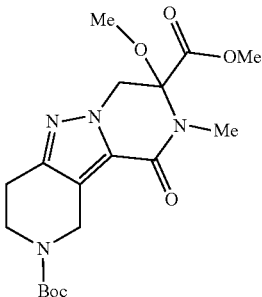 [SMILES: COC(=O)C1(OC)Cn2nc3c(c2C(=O)N1C)CN(C(=O)OC(C)(C)C)CC3]

Step 1. tert-butyl 3-[hydroxy(methyl)carbamoyl]-1,4,6,7-tetrahydropyrazolo[4,3-c]pyridine-5-carboxylate Na (7.78 g, 338.60 mmol, 8.02 mL, 10.00 eq) was added to MeOH (100.00 mL) portionwise at 0° C., and the mixture was stirred at 15° C. for 0.5 hr under $N_2$. Then N-methylhydroxylamine (8.48 g, 101.58 mmol, 3.00 eq, HCl) was added to the mixture and the mixture was stirred at 15° C. for 0.5 hr under $N_2$. Then 5-tert-butyl 3-ethyl 1,4,6,7-tetrahydropyrazolo[4,3-c]pyridine-3,5-dicarboxylate (Intermediate 30, 10.00 g, 33.86 mmol, 1.00 eq) was added, the mixture was stirred at 70° C. for 16 hr under $N_2$ atmosphere. TLC (PE/EA=1/1) showed the starting material was consumed completely and a new spot was detected mainly. The mixture was poured into ice-water (300 mL) and stirred for 5 min. Then the mixture was concentrated to remove MeOH. The aqueous phase was adjusted to pH=6 with HCl (1 N, aq) and then extracted with ethyl acetate (100 mL×3). The combined organic phase was washed with brine (300 mL), dried with anhydrous $Na_2SO_4$, filtered and concentrated in vacuum to afford the title compound (8.00 g, 27.00 mmol, 79.73% yield) as a yellow solid. LCMS: 297 [M+1]. $^1$H NMR (400 MHz, METHANOL-$d_4$) δ=4.62 (brs, 2H) 3.70 (t, J=5.52 Hz, 2H) 3.31-3.58 (m, 3H) 2.74 (s, 2H) 1.48 (s, 9H).

Step 2. tert-butyl 4-(hydroxymethyl)-2-methyl-1-oxo-5,8,9,11-tetrahydro-4H-pyrido[2,3]pyrazolo[2,4-d][1,2,5]oxadiazepine-10-carboxylate A mixture of tert-butyl 3-[hydroxy(methyl)carbamoyl]-1,4,6,7-tetrahydropyrazolo [4,3-c]pyridine-5-carboxylate (8.00 g, 27.00 mmol, 1.00 eq), 3-bromooxetane (4.07 g, 29.70 mmol, 1.10 eq), TBAI (997.22 mg, 2.70 mmol, 0.10 eq) and $Cs_2CO_3$ (13.19 g, 40.50 mmol, 1.50 eq) in DMF (80.00 mL) was degassed and purged with $N_2$ for 3 times, and then the mixture was stirred at 70° C. for 3 hr under $N_2$ atmosphere. TLC (DCM/MeOH=10/1) showed the starting material was consumed completely and the title compound was major. The mixture was poured into water (200 mL) and stirred for 5 min. The aqueous phase was extracted with ethyl acetate (100 mL×3). The combined organic phase was washed with brine (300 mL×2), dried with anhydrous $Na_2SO_4$, filtered and concentrated in vacuum. The residue was purified by column chromatography ($SiO_2$, PE/EA=100/1 to 1/2) to afford the title compound (4.50 g, 12.39 mmol, 45.88% yield, 97% purity) as a yellow solid.

LCMS: 353 [M+1]. $^1$H NMR (400 MHz, $CDCl_3CDCl_3$) δ=4.62 (brs, 2H) 4.53 (brs, 2H) 4.32-4.42 (m, 1H) 3.57-3.88 (m, 4H) 3.29 (br. s., 3H) 2.68-2.79 (m, 2H) 1.41-1.53 (m, 9H).

Step 3. 10-tert-butoxycarbonyl-2-methyl-1-oxo-5,8,9,11-tetrahydro-4H-pyrido[2,3]pyrazolo[2,4-d][1,2,5]oxadiazepine-4-carboxylic acid To a mixture of tert-butyl 4-(hydroxymethyl)-2-methyl-1-oxo-5,8,9,11-tetrahydro-4H-pyrido[2,3]pyrazolo[2,4-d][1,2,5]oxadiazepine-10-carboxylate (1.00 g, 2.84 mmol, 1.00 eq) and NMO (2.50 g, 21.30 mmol, 2.25 mL, 7.50 eq) in MeCN (30.00 mL) was added TPAP (199.61 mg, 568.00 μmol, 0.20 eq) in one portion at 0° C. under $N_2$. The mixture was stirred at 0° C. for 2 hr. LCMS showed the reaction was completed. The mixture was concentrated in vacuum to afford the title compound (1.04 g, crude) as black brown solid. LCMS: 367 [M+1].

Step 4. 2-tert-butyl 8-methyl 8-methoxy-9-methyl-10-oxo-1,3,4,7-tetrahydropyrido[2,3]pyrazolo[2,4-c]pyrazine-2,8-dicarboxylate To a mixture of 10-tert-butoxycarbonyl-2-methyl-1-oxo-5,8,9,11-tetrahydro-4H-pyrido[2,3]pyrazolo[2,4-d][1,2,5]oxadiazepine-4-carboxylic acid (1.04 g crude, 2.84 mmol, 1.00 eq) and $K_2CO_3$ (1.18 g, 8.52 mmol, 3.00 eq) in MeCN (20.00 mL) was added MeI (1.21 g, 8.52 mmol, 530.70 μL, 3.00 eq) in one portion at 25° C. under $N_2$. The mixture was stirred at 25° C. 12 hours. LCMS showed the reaction didn't react. The starting material was recovered: the reaction mixture was neutralized with HCl (1 N, aq) to pH=3, then extracted with ethyl acetate (20 mL×2). The combined organic layer was dried over $Na_2SO_4$, filtered and concentrated to dryness. The reaction was performed again. To the recovered starting material and $K_2CO_3$ (1.18 g, 8.52 mmol, 3.00 eq) in MeCN (20.00 mL) was added MeI (1.21 g, 8.52 mmol, 530.70 μL, 3.00 eq) in one portion at 25° C. under $N_2$. The mixture was stirred at 25° C. for 12 hours. LCMS and TLC (EA/PE=2/1) showed the reaction was completed, 50% of the title compound was detected. The residue was poured into water (20 mL) and stirred for 2 min. The aqueous phase was extracted with ethyl acetate (20 mL×2). The combined organic phase was washed with brine (20 mL×2), dried with anhydrous $Na_2SO_4$, filtered and concentrated in vacuum. The residue was purified by silica gel chromatography (PE/EA=10/1, 2/1) to the title compound (200.00 mg, 507.07 μmol, 17.85% yield, 100% purity) as yellow oil. LCMS: 395 [M+1]. $^1$H NMR (400 MHz, $CDCl_3$) 4.64-4.80 (m, 3H), 4.51-4.62 (m, 1H), 3.88 (s, 3H), 3.60-3.79 (m, 2H), 3.38 (s, 3H), 3.05 (s, 3H), 2.78 (br. s., 2H), 1.49 (s, 9H).

Intermediate 10: methyl 9-methyl-10-oxo-1,2,3,4-tetrahydropyrido[2,3]pyrazolo[2,4-b]pyrazine-8-carboxylate

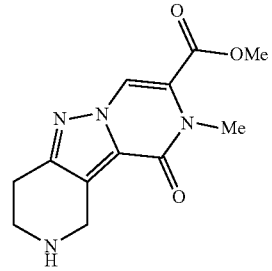 [SMILES: COC(=O)c1cn2nc3c(c2c(=O)n1C)CNCC3]

A mixture of 2-tert-butyl8-methyl8-methoxy-9-methyl-10-oxo-1,3,4,7-tetrahydro pyrido[2,3]pyrazolo[2,4-c]pyrazine-2,8-dicarboxylate (20.00 mg, 50.71 μmol, 1.00 eq) in HCl/dioxane (4 M, 20.00 mL, 1577.60 eq) was stirred at 20° C. for 2 hours. LCMS showed the reaction was completed. The residue was concentrated in vacuum to afford the title compound as the HCl salt (15.15 mg, 50.71 μmol, 100.00% yield) as yellow solid. LCMS: 263 [M+1].

Intermediate 11: tert-butyl 8-[methoxy(methyl)carbamoyl]-10-methyl-11-oxo-1,3,4,7,8,9-hexahydro-pyrido[2,3]pyrazolo[2,4-b][1,4]diazepine-2-carboxylate

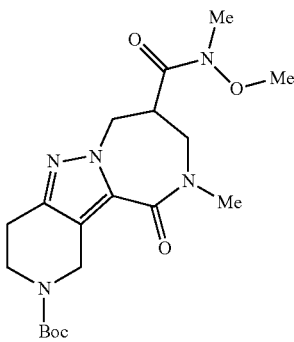 [SMILES: CON(C)C(=O)C1CN(C)C(=O)c2c3c(nn2C1)CCN(C(=O)OC(C)(C)C)C3]

To a mixture of 2-tert-butoxycarbonyl-10-methyl-11-oxo-1,3,4,7,8,9-hexahydropyrido[2,3]pyrazolo[2,4-b][1,4]diazepine-8-carboxylic acid (500.00 mg, 1.37 mmol, 1.00 eq) and N-methoxymethanamine hydrochloride (534.52 mg, 5.48 mmol, 4.00 eq) in THF (10.00 mL) was added T₃P (1.74 g, 2.74 mmol, 1.63 mL, 50% purity, 2.00 eq) and TEA (2.08 g, 20.55 mmol, 2.85 mL, 15.00 eq) in one portion under N₂. The mixture was stirred at 30° C. for 12 hours. LCMS and TLC (Dichloromethane:Methanol=10:1) showed the reaction was completed. The mixture was poured into water (15 mL) and stirred for 2 min. The aqueous phase was extracted with ethyl acetate (20 mL*2). The combined organic phase was washed with brine (10 mL*2), dried with anhydrous Na₂SO₄, filtered and concentrated in vacuum. The residue was purified by silica gel chromatography (Dichloromethane:Methanol=50:1-20:1) to afford the title compound (510.00 mg, 1.24 mmol, 90.45% yield, 99% purity) as white solid. LCMS[M+1]: 408.

Intermediate 12: tert-butyl (3R)-3-methyl-11-oxo-3,4,7,8,9,10-hexahydro-1H-pyrido [2,3]pyrazolo[2,4-b][1,4]diazepine-2-carboxylate Step 1. 5-tert-butyl 3-ethyl (6R)-2-[3-(tert-butoxycarbonylamino)propyl]-6-methyl-6,7-dihydro-4H-pyrazolo[4,3-c]pyridine-3,5-dicarboxylate To a solution of 5-tert-butyl 3-ethyl (6R)-6-methyl-2,4,6,7-tetrahydropyrazolo[4,3-c]pyridine-3,5-dicarboxylate (4.50 g, 14.55 mmol, 1.00 eq) in THF (50.00 mL) was added tert-butyl N-(3-bromopropyl)carbamate (4.16 g, 17.46 mmol, 1.20 eq) followed by DBU (3.32 g, 21.83 mmol, 3.29 mL, 1.50 eq). The mixture was heated to 60° C. for 16 hr. TLC (PE:EtOAc=1:1) showed the starting material consumed and two new main spots appeared. The mixture was extracted with EtOAc (200 mL*2) and H₂O (50 mL). The combined organic layer was dried with Na₂SO₄, filtrated. The filtrate was concentrated in vacuum. The residue was purified by flash chromatography (PE:EtOAc=20%~50%) to afford the title compound (4.50 g, 9.64 mmol, 66.29% yield) as colorless oil.

Step 2. ethyl (6R)-2-(3-aminopropyl)-6-methyl-4,5,6,7-tetrahydropyrazolo[4,3-c]pyridine-3-carboxylate 5-tert-butyl 3-ethyl (6R)-2-[3-(tert-butoxycarbonylamino)propyl]-6-methyl-6,7-dihydro-4H-pyrazolo[4,3-c]pyridine-3,5-dicarboxylate (4.50 g, 9.64 mmol, 1.00 eq) was dissolved in HCl/dioxane (4 M, 50.00 mL, 20.75 eq). The mixture was stirred at 20° C. for 2 hr. LCMS showed one main peak with desired Ms detected. The mixture was concentrated in vacuum to afford the title compound as the HCl salt (3.30 g, crude) as white solid.

Step 3. tert-butyl (3R)-3-methyl-11-oxo-3,4,7,8,9,10-hexahydro-1H-pyrido[2,3]pyrazolo[2,4-b][1,4]diazepine-2-carboxylate To a solution of ethyl (6R)-2-(3-aminopropyl)-6-methyl-4,5,6,7-tetrahydro pyrazolo[4,3-c]pyridine-3-carboxylate (3.27 g, 9.64 mmol, 1.00 eq) in MeOH (4.00 mL) was added CH₃ONa (2.08 g, 38.55 mmol, 4.00 eq). The mixture was stirred at 20° C. for 2 hr. LCMS showed one main peak with desired Ms detected. The mixture was concentrated in vacuum. The residue was dissolved in THF (8.00 mL) and H₂O (4.00 mL). NaHCO₃ (1.62 g, 19.28 mmol, 749.76 μL, 2.00 eq) and Boc₂O (2.52 g, 11.57 mmol, 2.66 mL, 1.20 eq) was added. The mixture was stirred at 20° C. for 16 hr. TLC (PE:EtOAc=0:1) showed one main spot appeared. The mixture was diluted with saturated NH₄Cl (100 mL) and extracted with EtOAc (200 mL*2). The combined organic layer was dried over Na₂SO₄, filtrated. The filtrate was concentrated in vacuum. The residue was purified by column chromatography (PE:EtOAc=50%~100%) to afford the title compound (2.40 g, 7.49 mmol, 77.71% yield) as white solid.

Intermediate 13: 2-(tert-butyl) 9-methyl 11-oxo-1,3,4,7,8,9,10,11-octahydro-2H-pyrido[4',3':3,4]pyrazolo[1,5-a][1,4]diazepine-2,9-dicarboxylate

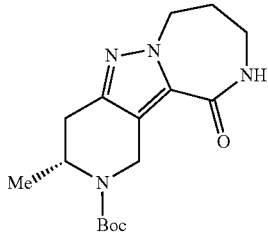 [SMILES: C[C@@H]1Cc2nn3c(c2CN1C(=O)OC(C)(C)C)C(=O)NCCC3]

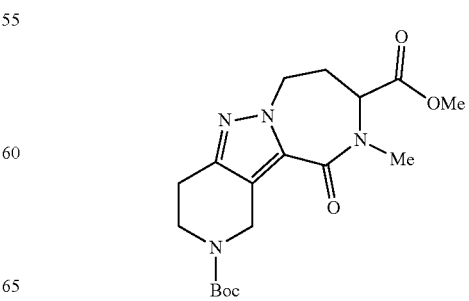

Step 1. 3-aminotetrahydrofuran-2-one

To a solution of 2-amino-4-hydroxy-butanoic acid (5.50 g, 46.17 mmol, 1.00 eq) in $H_2O$ (50.00 mL) was added HCl (12 M, 50.02 mL, 13.00 eq), the mixture was stirred at 120° C. for 3 hr. TLC (Dichloromethane:Methanol=10:1) showed the reactant consumed. The mixture was concentrated to give the residue, most of the solvent was removed azeotropically with ethanol. Following crystal formation the solution was cooled on ice. The resulting solid was filtered and rinsed three times with cold ethanol (20 mL). The filtrate was concentrated and cooled, producing additional homoserine lactone. The process was repeated 2 more times to afford the title compound as the HCl salt (4.20 g, 30.53 mmol, 66.13% yield) as white solid. H NMR (400 MHz, $d_6$-DMSO) δ 4.52-4.63 (m, 1H), 4.32-4.49 (m, 2H), 2.68-2.84 (m, 1H), 2.31-2.46 (m, 1H).

Step 2. 2-amino-4-bromo-butanoic acid

A mixture of 3-aminotetrahydrofuran-2-one (4.00 g, 29.08 mmol, 1.00 eq) in HBr (103.67 g, 615.00 mmol, 69.57 mL, 48% purity, 21.15 eq) was stirred at 100° C. for 6 hr. TLC (Dichloromethane:Methanol=10:1) showed the reaction was completed. The mixture was filtered to give the solid which was washed with methyl tertiary-butyl ether(50 mL) to afford the title compound (6.30 g, 23.96 mmol, 82.40% yield, HBr) as red solid

Step 3. methyl 2-amino-4-bromo-butanoate

To a solution of 2-amino-4-bromo-butanoic acid (6.30 g, 23.96 mmol, 1.00 eq, HBr) in MeOH (50.00 mL) was added $SOCl_2$ (5.70 g, 47.92 mmol, 3.48 mL, 2.00 eq) at 0° C., the mixture was stirred at 20° C. for 12 hr. TLC (Petroleum ether: Ethyl acetate=1:1) showed the reaction was completed. The mixture was concentrated in vacuum to afford the title compound (6.30 g, 22.75 mmol, 94.94% yield, HBr) as the red solid $^1H$ NMR (400 MHz, DEUTERIUM OXIDE) δ 4.34 (t, J=6.65 Hz, 1H), 3.84 (s, 3H), 3.54-3.68 (m, 2H), 2.58 (qd, J=6.53, 15.29 Hz, 1H), 2.29-2.47 (m, 1H).

Step 4. methyl 2-(benzyloxycarbonylamino)-4-bromo-butanoate

To a solution of methyl 2-amino-4-bromo-butanoate (6.30 g, 22.75 mmol, 1.00 eq, HBr) in $H_2O$ (50.00 mL) was added $NaHCO_3$ (4.78 g, 56.87 mmol, 2.21 mL, 2.50 eq) and CbzCl (4.66 g, 27.30 mmol, 3.88 mL, 1.20 eq) at 0° C., the mixture was stirred at 20° C. for 16 hr. TLC (Petroleum ether: Ethyl acetate=1:1) showed the reaction was completed. The mixture was extracted with ethyl acetate(200 mL*2), the organic layer was washed with brine (50 mL), dried over anhydrous $Na_2SO_4$, and concentrated in vacuum. The crude was triturated with Petroleum ether (30 mL) to afford the title compound (3.60 g, 10.79 mmol, 47.45% yield, 99% purity) as white solid.

Step 5. 5-tert-butyl 3-ethyl 2-[3-(benzyloxycarbonylamino)-4-methoxy-4-oxo-butyl]-6,7-dihydro-4H-pyrazolo[4,3-c]pyridine-3,5-dicarboxylate To a solution of 5-tert-butyl 3-ethyl 2,4,6,7-tetrahydropyrazolo[4,3-c]pyridine-3,5-dicarboxylate (3.60 g, 12.19 mmol, 1.00 eq) and methyl 2-(benzyloxycarbonylamino)-4-bromo-butanoate (4.31 g, 13.04 mmol, 1.07 eq) in THF (50.00 mL) was added DBU (5.57 g, 36.57 mmol, 5.51 mL, 3.00 eq), the mixture was stirred at 20° C. for 16 hr. TLC (Petroleum ether: Ethyl acetate=1:1) showed the reaction was complete. The mixture was poured into water (20 mL), extracted with Ethyl acetate (20 mL*2), the organic layer was washed with brine (20 mL), dried over anhydrous $Na_2SO_4$ and concentrated in vacuum. The crude was purified by prep.TLC (Petroleum ether: Ethyl acetate=1:1) to afford the title compound (3.60 g, 6.28 mmol, 51.52% yield, 95% purity) as colorless oil.

Step 6. 5-tert-butyl 3-ethyl 2-(3-amino-4-methoxy-4-oxo-butyl)-6,7-dihydro-4H-pyrazolo [4,3-c]pyridine-3,5-dicarboxylate To a solution of 5-tert-butyl 3-ethyl 2-[3-(benzyloxycarbonylamino)-4-methoxy-4-oxo-butyl]-6,7-dihydro-4H-pyrazolo[4,3-c]pyridine-3,5-dicarboxylate (3.60 g, 6.61 mmol, 1.00 eq) in MeOH (40.00 mL) was added Pd/C (700.00 mg, 6.61 mmol, 10% purity, 1.00 eq). The mixture was stirred under $H_2$ (15 Psi) at 20° C. for 2 hr. LCMS showed the reaction completed. The mixture was filtered and concentrated in vacuo to afford the title compound (2.60 g, 6.33 mmol, 95.83% yield) as colorless oil.

Step 7. 2-tert-butoxycarbonyl-11-oxo-3,4,7,8,9,10-hexahydro-1H-pyrido[2,3]pyrazolo[2,4-c][1,4]diazepine-9-carboxylic acid To a solution of 5-tert-butyl 3-ethyl 2-(3-amino-4-methoxy-4-oxo-butyl)-6,7-dihydro-4H-pyrazolo[4,3-c]pyridine-3,5-dicarboxylate (2.60 g, 6.33 mmol, 1.00 eq) in MeOH (3.00 mL) was added NaOMe (631.72 mg, 11.69 mmol, 3.00 eq). The mixture was stirred at 20° C. for 16 hr. LCMS showed the reaction complete. The solvent was evaporated to give the residue which was poured into aqueous HCl (0.5 M, 50 mL), extracted with DCM (30 mL*4), the organic layer was washed with brine (20 mL), dried over anhydrous $Na_2SO_4$ and concentrated in vacuum to afford the title compound (1.10 g, 3.14 mmol, 80.50% yield) as yellow solid.

Step 8. 2-tert-butyl 9-methyl 11-oxo-3,4,7,8,9,10-hexahydro-1H-pyrido[2,3]pyrazolo [2,4-c][1,4]diazepine-2,9-dicarboxylate To a solution of 2-tert-butoxycarbonyl-11-oxo-3,4,7,8,9,10-hexahydro-1H-pyrido[2,3]pyrazolo[2,4-c][1,4]diazepine-9-carboxylic acid (1.10 g, 3.14 mmol, 1.00 eq) in DMF (20.00 mL) was added $K_2CO_3$ (650.87 mg, 4.71 mmol, 1.50 eq) and MeI (1.34 g, 9.42 mmol, 586.44 µL, 3.00 eq). The mixture was stirred at 20° C. for 16 hr. LCMS showed the reaction was complete. The mixture was poured into water (100 mL), extracted with ethyl acetate (50 mL*2), the combined organic layer was washed with brine (30 mL*2), dried over anhydrous $Na_2SO_4$ and concentrated in vacuum to afford the title compound (1.10 g, 3.02 mmol, 96.18% yield) as colorless oil.

133

Intermediate 14: 2-tert-butyl 8-ethyl 10-methyl-11l-oxo-1,3,4,7,8,9-hexahydropyrido[2,3]pyrazolo[2,4-b][1,4]diazepine-2,8-dicarboxylate

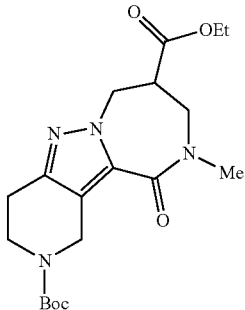 [SMILES: CCOC(=O)C1CN(C)C(=O)c2c3c(nn2C1)CCN(C(=O)OC(C)(C)C)C3]

Step 1. ethyl 2-[[tert-butoxycarbonyl(methyl)amino]methyl]prop-2-enoate

A mixture of tert-butyl N-methylcarbamate (200.00 mg, 1.52 mmol, 1.00 eq) in THF (5.00 mL) was added NaH (91.20 mg, 2.28 mmol, 60% purity, 1.50 eq) at 0° C. for 0.5 hr under $N_2$, then ethyl 2-(bromomethyl)prop-2-enoate (352.10 mg, 1.82 mmol, 1.20 eq) was added to the mixture dropwise at 0° C., and the mixture was stirred at 15° C. for 2 hr under $N_2$ atmosphere. TLC (PE/EA=10/1) the starting material was consumed completely and two new spots appeared. The mixture was poured into ice-water (10 mL) and stirred for 5 min. The aqueous phase was extracted with ethyl acetate (5 mL×3). The combined organic phase was washed with brine (10 mL), dried with anhydrous $Na_2SO_4$, filtered and concentrated in vacuum. The residue was purified by column chromatography ($SiO_2$, Petroleum ether/Ethyl acetate=100/1 to 5/1) to afford the title compound (112.00 mg, 460.34 μmol, 30.29% yield) as colorless oil. $^1$H NMR (400 MHz, $CDCl_3$) δ 6.28 (s, 1H), 5.55 (s, 1H), 4.23 (q, J=7.1 Hz, 2H), 4.07 (br s, 2H), 2.88 (br s, 3H), 1.45 (br s, 9H), 1.31 (br s, 3H).

Step 2. ethyl2-(methylaminomethyl)prop-2-enoate

A mixture of ethyl 2-[[tert-butoxycarbonyl(methyl)amino]methyl]prop-2-enoate (112.00 mg, 460.34 μmol, 1.00 eq) in dioxane (1.00 mL) was added HCl/dioxane (4 M, 5.00 mL, 43.45 eq), and then the mixture was stirred at 15° C. for 0.5 hour. TLC (PE/EA=10/1) showed the starting material was consumed completely, a new spot was major. The mixture was concentrated in vacuum to afford the title compound (82.50 mg, 459.25 μmol, 99.76% yield, HCl) as a white solid, which was used directly for the next step.

Step 3. tert-butyl 3-[2-ethoxycarbonylallyl (methyl)carbamoyl]-2,4,6,7-tetrahydropyrazolo[4,3-c]pyridine-5-carboxylate A mixture of 5-tert-butoxycarbonyl-2,4,6,7-tetrahydropyrazolo[4,3-c]pyridine-3-carboxylic acid (80.00 mg, 299.31 μmol, 1.00 eq), ethyl 2-(methylaminomethyl) prop-2-enoate (59.14 mg, 329.24 μmol, 1.10 eq, HCl), $T_3P$ (285.70 mg, 897.93 μmol, 267.01 μL, 3.00 eq) and TEA (151.44 mg, 1.50 mmol, 207.45 μL, 5.00 eq) in THF (3.00 mL) was degassed and purged with $N_2$ for 3 times, and then the mixture was stirred at 15° C. for 16 hours under $N_2$ atmosphere. TLC (DCM/MeOH=10/1) the starting material was consumed completely and a new spot appeared. The mixture was poured into water (10 mL) and stirred for 5 min. The aqueous phase was extracted with ethyl acetate (5 mL×3). The combined organic phase was washed with brine (10 mL), dried with anhydrous $Na_2SO_4$, filtered and concentrated in vacuum. The residue was purified by prep-TLC (DCM/MeOH=10/1) to afford the title compound (46.00 mg, 105.49 μmol, 35.24% yield, 90% purity) as a white solid. LCMS: 393 [M+1]. $^1$H NMR (400 MHz, $CDCl_3$) δ 6.35 (s, 1H), 5.67 (br s, 1H), 4.63 (s, 4H), 4.18-4.30 (m, 2H), 3.71 (br s, 2H), 2.91-3.47 (m, 3H), 2.74 (br t, J=5.4 Hz, 2H), 1.48 (s, 9H), 1.31 (t, J=7.2 Hz, 3H).

Step 4. tert-butyl 8-ethyl10-methyl-11-oxo-1,3,4,7,8,9-hexahydropyrido[2,3] pyrazolo[2,4-b][1,4]diazepine-2,8-dicarboxylate A mixture of tert-butyl 3-[2-ethoxycarbonylallyl(methyl)carbamoyl]-2,4,6,7-tetrahydropyrazolo[4,3-c]pyridine-5-carboxylate (36.00 mg, 91.73 μmol, 1.00 eq), DBU (6.98 mg, 45.87 μmol, 6.91 μL, 0.50 eq) in MeCN (1.00 mL) was degassed and purged with $N_2$ for 3 times, and then the mixture was stirred at 50° C. for 2 hour under $N_2$ atmosphere. TLC (DCM/MeOH=20/1) showed starting material was consumed completely and the title compound was major. The mixture were poured into water (5 mL) and stirred for 5 min. The aqueous phase was extracted with ethyl acetate (3 mL×3). The combined organic phase was washed with brine (5 mL), dried with anhydrous $Na_2SO_4$, filtered and concentrated in vacuum. The residue was purified by prep-TLC (DCM/MeOH=20/1) to afford the title compound (20.00 mg, 50.96 μmol, 55.56% yield) as a white solid. LCMS: 393 [M+1]

Intermediate 15: tert-butyl (3R)-3,10-dimethyl-8-methylene-11-oxo-3,4,7,9-tetrahydro-1H-pyrido[2,3]pyrazolo[2,4-b][1,4]diazepine-2-carboxylate

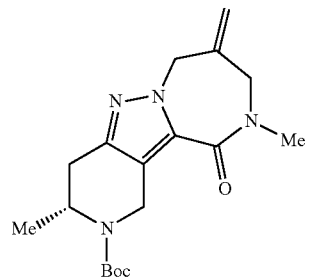 [SMILES: C=C1CN(C)C(=O)c2c3c(nn2C1)C[C@@H](C)N(C(=O)OC(C)(C)C)C3]

Step 1. 5-tert-butyl 3-ethyl (6R)-2-[2-(chloromethyl)allyl]-6-methyl-6,7-dihydro-4H-pyrazolo[4,3-c]pyridine-3,5-dicarboxylate To a solution of 5-tert-butyl 3-ethyl (6R)-6-methyl-1,4,6,7-tetrahydropyrazolo [4,3-c]pyridine-3,5-dicarboxylate (15.00 g, 48.49 mmol, 1.00 eq) in DMF (4.00 mL) was added $Cs_2CO_3$ (23.70 g, 72.73 mmol, 1.50 eq), followed by 3-chloro-2-(chloromethyl)prop-1-ene (12.12 g, 96.97 mmol, 11.22 mL, 2.00 eq). The mixture was heated to 50° C. for 16 hr. TLC (PE:EtOAc=4:1) showed four spots appeared. The mixture was diluted with $H_2O$ (300 mL) and extracted with EtOAc(500 mL*2). The combined organic layer was washed with H₂O (300 mL*3), dried over Na₂SO₄ and filtrated. The filtrate was concentrated in vacuum. The reisue was purified by flash chromatography (PE:EtOAc=0%~30%) to afford the title compound (7.00 g, 17.59 mmol, 36.28% yield) as colorless oil.

Step 2. tert-butyl (3R)-3,10-dimethyl-8-methylene-11-oxo-3,4,7,9-tetrahydro-1H-pyrido[2,3]pyrazolo[2,4-b][1,4]diazepine-2-carboxylate and by-product tert-butyl (6R)-6-methyl-2-[2-(methylaminomethyl)allyl]-3-(methylcarbamoyl)-6,7-dihydro-4H-pyrazolo[4,3-c]pyridine-5-carboxylate To a solution of 5-tert-butyl 3-ethyl (6R)-2-[2-(chloromethyl)allyl]-6-methyl-6,7-dihydro-4H-pyrazolo[4,3-c]pyridine-3,5-dicarboxylate (7.00 g, 17.59 mmol, 1.00 eq) in EtOH (28.00 mL) was added methanamine (54.63 g, 527.70 mmol, 120.00 mL, 30.00 eq, 30% EtOH solution). The mixture was heated to 80° C. for 16 hr in sealed tube. TLC (PE:EtOAc=1:1) showed that starting material consumed completely and two new spots formed mainly. The mixture was concerned and purified by column chromatography (SiO₂, Petroleum ether/Ethyl acetate=10/1 to 1/1) to afford the title compound (3.00 g, 6.36 mmol, 36.15% yield, 80% purity) as yellow gum.

Intermediate 16: tert-butyl (3R)-8-(hydroxymethyl)-3,10-dimethyl-11-oxo-1,3,4,7,8,9-hexahydropyrido[2,3]pyrazolo[2,4-b][1,4]diazepine-2-carboxylate

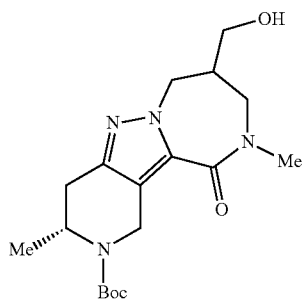

Step 1. tert-butyl (3R)-8-(hydroxymethyl)-3,10-dimethyl-11-oxo-1,3,4,7,8,9-hexahydropyrido[2,3]pyrazolo[2,4-b][1,4]diazepine-2-carboxylate, tert-butyl(3R)-8-hydroxy-3,8,10-trimethyl-11-oxo-3,4,7,9-tetrahydro-1H-pyrido[2,3]pyrazolo[2,4-b][1,4]diazepine-2-carboxylate (Intermediate 17), and tert-butyl (3R)-3,8,10-trimethyl-11-oxo-1,3,4,7,8,9-hexahydropyrido[2,3]pyrazolo[2,4-b][1,4]diazepine-2-carboxylate (Intermediate 18)

To a solution of tert-butyl (3R)-3,10-dimethyl-8-methylene-11-oxo-3,4,7,9-tetrahydro-1H-pyrido[2,3]pyrazolo[2,4-b][1,4]diazepine-2-carboxylate (Intermediate 15, 3.20 g, 9.24 mmol, 1.00 eq) in THF (50.00 mL) was added BH₃.DMS (10 M, 3.70 mL, 4.00 eq) at 0° C. under N₂. The mixture was stirred at 20° C. for 2 h. TLC (PE:EtOAc=1:2, showed that starting material consumed. A solution of NaOH (2.59 g, 64.68 mmol, 7.00 eq) in H₂O (10.00 mL) was added at −30° C. dropwise, then H₂O₂ (6.28 g, 55.44 mmol, 5.32 mL, 30% purity, 6.00 eq) was added slowly. The mixture was stirred at 20° C. for 16 h. LC-MS indicated that 8% of tert-butyl (3R)-3,10-dimethyl-8-methylene-11-oxo-3,4,7,9-tetrahydro-1H-pyrido[2,3]pyrazolo[2,4-b][1,4]diazepine-2-carboxylate was still remained and ~54% of tert-butyl (3R)-8-(hydroxymethyl)-3,10-dimethyl-11-oxo-1,3,4,7,8,9-hexahydropyrido[2,3]pyrazolo[2,4-b][1,4]diazepine-2-carboxylate and ~17% of tert-butyl (3R)-3,8,10-trimethyl-11-oxo-1,3,4,7,8,9-hexahydropyrido[2,3]pyrazolo[2,4-b][1,4]diazepine-2-carboxylate were detected. The mixture was extracted with ethyl acetate (30 mL*3) and H₂O (20 mL). The combined organic layer was washed with brine (20 mL*1), dried over Na₂SO₄, filtered and concentrated in vacuum. The residue was purified by column chromatography (SiO₂, Petroleum ether/Ethyl acetate=50/1 to 1/5, Plate 1), followed by prep-TLC to afford tert-butyl (3R)-8-(hydroxymethyl)-3,10-dimethyl-11-oxo-1,3,4,7,8,9-hexahydropyrido[2,3]pyrazolo[2,4,4-b][1,4]diazepine-2-carboxylate (2.00 g, 5.48 mmol, 59.27% yield, 99.8% purity) as off-white gum, tert-butyl(3R)-8-hydroxy-3,8,10-trimethyl-11-oxo-3,4,7,9-tetrahydro-1H-pyrido[2,3]pyrazolo[2,4-b][1,4]diazepine-2-carboxylate (150.00 mg, 382.78 μmol, 4.14% yield, 93% purity) as off-white gum and tert-butyl (3R)-3,8,10-trimethyl-11-oxo-1,3,4,7,8,9-hexahydropyrido[2,3]pyrazolo[2,4-b][1,4]diazepine-2-carboxylate (250.00 mg, 645.74 μmol, 6.99% yield, 90% purity) as off-white gum.

Intermediate 17: tert-butyl(3R)-8-hydroxy-3,8,10-trimethyl-11-oxo-3,4,7,9-tetrahydro-1H-pyrido[2,3]pyrazolo[2,4-b][1,4]diazepine-2-carboxylate

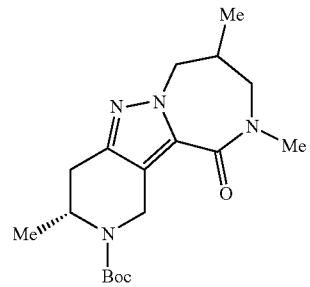 [SMILES: CC1CN(C)C(=O)c2c3c(nn2C1)C[C@@H](C)N(C(=O)OC(C)(C)C)C3]

Isolated from Intermediate 16 (150.00 mg, 382.78 μmol, 4.14% yield, 93% purity) as off-white gum.

Intermediate 18: tert-butyl (3R)-3,8,10-trimethyl-11-oxo-1,3,4,7,8,9-hexahydropyrido[2,3]pyrazolo[2,4-b][1,4]diazepine-2-carboxylate

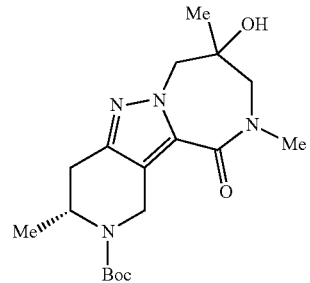 [SMILES: C[C@@H]1Cc2nn3c(c2CN1C(=O)OC(C)(C)C)C(=O)N(C)CC(C)(O)C3]

Isolated from Intermediate 16 (250.00 mg, 645.74 μmol, 6.99% yield, 90% purity) as off-white gum.

Intermediate 19: ethyl 2-[(2,2-difluoroethylamino) methyl]prop-2-enoate

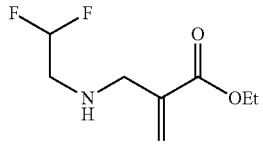

Step 1. tert-butyl N-(2,2-difluoroethyl)carbamate

To a mixture of 2,2-difluoroethanamine (10.00 g, 123.37 mmol, 1.00 eq) and $Et_3N$ (24.97 g, 246.74 mmol, 34.21 mL, 2.00 eq) in DCM (100.00 mL) was added $Boc_2O$ (29.62 g, 135.71 mmol, 31.18 mL, 1.10 eq), and the mixture was stirred at 25° C. for 16 h. TLC indicated no starting material and one major new spot with lower polarity was detected. The mixture was diluted with DCM (150 mL) and washed with brine (150 mL). The organic phase was dried over $Na_2SO_4$, filtered and concentrated in vacuo. The residue was purified by silica gel column to afford the title compound (17.90 g, 98.80 mmol, 80.08% yield) as colorless solid. $^1$H NMR (400 MHz, $CDCl_3$) δ 5.55-6.02 (m, 1H), 4.58-4.88 (m, 1H), 3.26-3.58 (m, 2H), 1.38 (s, 9H).

Step 2. ethyl 2-[[tert-butoxycarbonyl (2,2-difluoroethyl)amino]methyl]prop-2-enoate To a solution of tert-butyl N-(2,2-difluoroethyl)carbamate (2.00 g, 11.04 mmol, 1.00 eq) in THF (30.00 mL) was added NaH (574.08 mg, 14.35 mmol, 60% purity, 1.30 eq) at 0° C. under $N_2$, followed by ethyl 2-(bromomethyl)prop-2-enoate (3.20 g, 16.56 mmol, 1.50 eq) after 0.5 h, and the mixture was stirred at 25° C. for 16 h. LCMS showed desired product was detected mainly. The mixture was quenched with $H_2O$ (100 mL) and extracted with EtOAc (100 mL). The organic phase was concentrated in vacuo, which was purified by silica gel column to afford the title compound (2.30 g, 7.14 mmol, 64.64% yield, 91% purity) as colorless oil.

$^1$H NMR (400 MHz, $CDCl_3$) δ 6.30-6.32 (m, 1H), 5.70-6.15 (m, 1H), 5.30-5.60 (m, 1H), 4.14-4.27 (m, 4H), 3.55-3.59 (m, 2H), 1.44-1.48 (m, 9H), 1.28-1.34 (m, 3H).

Step 3. ethyl 2-[(2,2-difluoroethylamino)methyl] prop-2-enoate

A solution of ethyl 2-[[tert-butoxycarbonyl(2,2-difluoroethyl)amino] methyl] prop-2-enoate (600.00 mg, 2.05 mmol, 1.00 eq) in HCl/dioxane (4 M, 6.00 mL, 11.71 eq) was stirred at 25° C. for 2 h. TLC showed no starting material and one new major spot was detected. The mixture was concentrated in vacuo to afford the title compound as the HCl salt (469.00 mg, 2.04 mmol, 99.62% yield) as colorless solid. $^1$H NMR (400 MHz, $CDCl_3$) δ 10.08-10.26 (m, 1H), 6.60 (m, 1H), 6.31 (m, 2H), 4.24 (m, 2H), 3.91-4.01 (m, 2H), 3.28-3.45 (m, 2H), 1.28 (t, J=7.2 Hz, 3H).

Intermediate 20: 2-tert-butyl 8-ethyl (3R)-10-(2,2-difluoroethyl)-3-methyl-11-oxo-1,3,4,7,8,9-hexahydropyrido[2,3]pyrazolo[2,4-b][1,4]diazepine-2,8-dicarboxylate

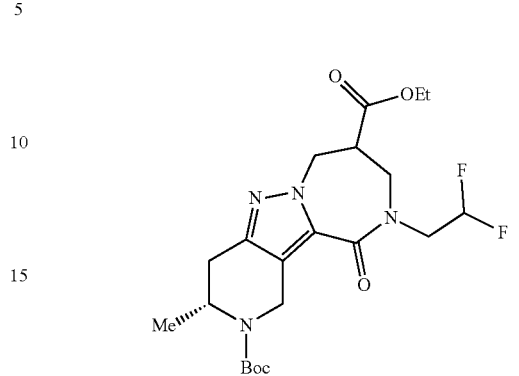

Step 1. tert-butyl (6R)-3-[2,2-difluoroethyl (2-ethoxycarbonylallyl)carbamoyl]-6-methyl-2,4,6,7-tetrahydropyrazolo[4,3-c]pyridine-5-carboxylate A mixture of ethyl 2-[(2,2-difluoroethylamino)methyl] prop-2-enoate (Intermediate 19, 456.54 mg, 1.99 mmol, 1.40 eq), (6R)-5-tert-butoxycarbonyl-6-methyl-2,4,6,7-tetrahydropyrazolo[4,3-c]pyridine-3-carboxylic acid (400.00 mg, 1.42 mmol, 1.00 eq), $T_3P$ (904.85 mg, 2.84 mmol, 845.66 µL, 2.00 eq) and $Et_3N$ (719.42 mg, 7.11 mmol, 985.51 µL, 5.00 eq) in THF (10.00 mL) was heated to 70° C. for 16 h. The mixture was diluted with EtOAc (60 mL) and washed with HCl (1 M, 60 mL). The organic phase was dried over $Na_2SO_4$, filtered and concentrated in vacuo, which was purified by prep-HPLC (FA) to afford the title compound (165.00 mg, 339.77 µmol, 23.93% yield, 94% purity) as colorless oil. LCMS: 457 [M+1].

Step 2. 2-tert-butyl 8-ethyl (3R)-10-(2,2-difluoroethyl)-3-methyl-11-oxo-1,3,4,7,8,9-hexahydropyrido[2,3]pyrazolo[2,4-b][1,4]diazepine-2,8-dicarboxylate To a solution of tert-butyl (6R)-3-[2,2-difluoroethyl(2-ethoxycarbonylallyl) carbamoyl]-6-methyl-2,4,6,7-tetrahydropyrazolo[4,3-c]pyridine-5-carboxylate (165.00 mg, 361.46 µmol, 1.00 eq) in MeCN (6.00 mL) was added DBU (27.51 mg, 180.73 µmol, 27.24 µL, 0.50 eq), and the mixture was heated to 50° C. for 2 h. TLC showed no starting material and major desired product. The mixture was diluted with EtOAc (30 mL) and washed with brine (30 mL). The organic phase was concentrated in vacuo, which was purified by prep-TLC to afford the title compound (103.00 mg, 218.87 µmol, 60.55% yield, 97% purity) as colorless oil. LCMS: 457 [M+1].

Intermediate 21: (2S,3R)-3-((tert-butyldiphenylsilyl)oxy)-2-((methylamino)methyl)pent-4-en-1-ol

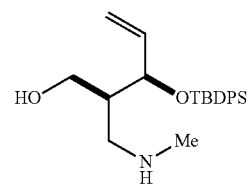

Step 1. ethyl 3-[benzyl(methyl)amino]propanoate

To a solution of N-methyl-1-phenyl-methanamine (50.00 g, 412.61 mmol, 53.19 mL, 1.00 eq) in EtOH (200.00 mL) was added ethyl prop-2-enoate (49.57 g, 495.13 mmol, 53.88 mL, 1.20 eq) under $N_2$, the reaction mixture was stirred at 20° C. for 16 hours. TLC indicated N-methyl-1-phenyl-methanamine was consumed completely, and one major new spot with lower polarity was detected. The reaction mixture was concentrated on a rotary evaporator to afford the title compound (87.00 g, crude) as yellow oil, used in next step directly. $^1$H NMR (400 MHz, $CDCl_3$) δ=7.21-7.35 (m, 5H), 4.15 (q, J=7.17 Hz, 2H), 3.52 (s, 2H), 2.72-2.80 (m, 2H), 2.48-2.56 (m, 2H), 2.22 (s, 3H), 1.26 (t, J=7.15 Hz, 3H).

Step 2. ethyl 3-[tert-butoxycarbonyl(methyl)amino]propanoate

To a mixture of ethyl 3-[benzyl(methyl)amino]propanoate (33.00 g, 149.12 mmol, 1.00 eq) and $(Boc)_2O$ (32.55 g, 149.12 mmol, 34.26 mL, 1.00 eq) in EtOH (200.00 mL) was added Pd/C (3.50 g, 10% purity) under $N_2$, the suspension was degassed under vacuum and purged with $H_2$ three times, the mixture was stirred under $H_2$ (50 psi) at 40° C. for 16 hours. TLC indicated starting material was consumed completely and one major new spot with lower polarity was detected. The reaction mixture was filtered and the filtrate was concentrated. The residue was purified by flash silica gel chromatography to afford the title compound (24.00 g, 103.77 mmol, 69.59% yield) as yellow oil. $^1$H NMR (400 MHz, $CDCl_3$) δ=4.12 (q, J=7.15 Hz, 2H), 3.48 (brs, 2H), 2.85 (s, 3H), 2.52 (t, J=6.78 Hz, 2H), 1.44 (s, 9H), 1.21-1.29 (m, 3H).

Step 3. ethyl 2-[[tert-butoxycarbonyl(methyl)amino]methyl]-3-hydroxy-pent-4-enoate To a solution of ethyl 3-[tert-butoxycarbonyl(methyl)amino]propanoate (25.00 g, 108.09 mmol, 1.00 eq) in THF (200.00 mL) was added LDA (1 M, 162.14 mL, 1.50 eq) dropwise at −78° C. under $N_2$, the reaction mixture was stirred at −78° C. for 30 minutes, then a solution of prop-2-enal (7.88 g, 140.52 mmol, 9.38 mL, 1.30 eq) in THF (20.00 mL) was added dropwise, and the reaction mixture was stirred at 25° C. for another 2 hours. TLC indicated starting material was consumed completely and multiple new spots formed. The reaction was added into aqueous solution of $NH_4Cl$ (200 mL) and then extracted with ethyl acetate (200 mL*2), the combined organic phase was dried over anhydrous $Na_2SO_4$, filtered and concentrated in vacuum. The residue was purified by silica gel chromatography to afford the title compound (18.00 g, 62.64 mmol, 57.95% yield) as yellow oil.

Step 4. ethyl 2-[[tert-butoxycarbonyl(methyl)amino]methyl]-3-[tert-butyl(diphenyl)silyl]oxy-pent-4-enoate To a mixture of ethyl 2-[[tert-butoxycarbonyl(methyl)amino]methyl]-3-hydroxy-pent-4-enoate (25.50 g, 88.74 mmol, 1.00 eq) in DCM (200.00 mL) was added imidazole (6.65 g, 97.62 mmol, 1.10 eq), DMAP (1.08 g, 8.87 mmol, 0.10 eq) and TBDPSCl (26.83 g, 97.62 mmol, 25.08 mL, 1.10 eq) in one portion at 0° C. under $N_2$. The mixture was stirred at 30° C. for 12 hours. TLC showed 30% of starting material was remained. Then added TBDPSCl (24.39 g, 88.74 mmol, 22.80 mL, 1.00 eq) and stirred at 30° C. for another 12 hours. TLC showed the reaction completed. The mixture was poured into water (200 mL). The aqueous phase was extracted with DCM (100 mL*2). The combined organic phase was washed with brine (100 mL*2), dried with anhydrous $Na_2SO_4$, filtered and concentrated in vacuum. The residue was purified by silica gel chromatography to afford the title compound (49.00 g, crude) as yellow oil.

Step 5. tert-butyl ((2S,3S)-3-((tert-butyldiphenylsilyl)oxy)-2-(hydroxymethyl)pent-4-en-1-yl)(methyl) carbamate and tert-butyl ((2S,3R)-3-((tert-butyldiphenylsilyl)oxy)-2-(hydroxymethyl)pent-4-en-1-yl) (methyl)carbamate To a mixture of ethyl 2-[[tert-butoxycarbonyl(methyl)amino]methyl]-3-[tert-butyl (diphenyl)silyl]oxy-pent-4-enoate (17.00 g, 32.33 mmol, 1.00 eq) in THF (200.00 mL) was added $LiBH_4$ (4.22 g, 193.98 mmol, 6.00 eq) in one portion at 0° C. under $N_2$. The mixture was stirred at 30° C. for 60 hours. TLC showed the reaction completed, and two spots were detected. The mixture was poured into water (300 mL). The aqueous phase was extracted with DCM (100 mL*2). The combined organic phase was washed with brine (50 mL*2), dried with anhydrous $Na_2SO_4$, filtered and concentrated in vacuum. The residue was purified by silica gel chromatography to afford tert-butyl ((2S,3S)-3-((tert-butyldiphenylsilyl)oxy)-2-(hydroxymethyl)pent-4-en-1-yl) (methyl)carbamate (3.88 g, 8.02 mmol, 24.81% yield) as yellow oil and tert-butyl ((2S,3R)-3-((tert-butyldiphenylsilyl)oxy)-2-(hydroxymethyl)pent-4-en-1-yl)(methyl)carbamate (940.00 mg, 1.94 mmol, 6.01% yield) as yellow oil.

Step 6. (2S,3R)-3-((tert-butyldiphenylsilyl)oxy)-2-((methylamino)methyl)pent-4-en-1-ol To a solution of tert-butyl ((2S,3R)-3-((tert-butyldiphenylsilyl)oxy)-2-(hydroxymethyl)pent-4-en-1-yl)(methyl) carbamate (1.35 g, 2.79 mmol, 1.00 eq) in DCM (10.00 mL) was added TFA (7.70 g, 67.53 mmol, 5.00 mL, 24.21 eq), the reaction mixture was stirred at 25° C. for 30 minutes. TLC indicated starting material was consumed completely. The reaction mixture was concentrated on a rotary evaporator to afford the title compound (1.35 g, crude, TFA) as yellow oil, used in next step directly. $^1$H NMR (400 MHz, METHANOL-$d_4$) δ=7.62-7.71 (m, 4H), 7.36-7.48 (m, 6H), 5.83 (ddd, J=7.34, 10.30, 17.33 Hz, 1H), 4.97-5.08 (m, 2H), 4.22 (dd, J=4.89, 7.09 Hz, 1H), 3.82 (dd, J=3.55, 10.27 Hz, 1H), 3.60 (t, J=9.90 Hz, 1H), 3.13-3.20 (m, 1H), 2.97-3.06 (m, 1H), 2.60 (s, 3H), 2.04-2.14 (m, 1H), 1.07 (s, 9H).

Intermediate 22: tert-butyl (8Z)-11-methyl-12-oxo-3,4,7,10-tetrahydro-1H-pyrido[2,3]pyrazolo[2,4-b][1,4]diazocine-2-carboxylate

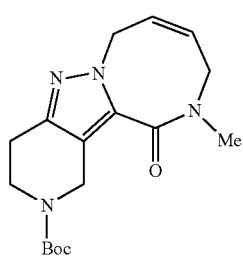 [SMILES: CN1C/C=C\Cn2nc3c(c2C1=O)CN(C(=O)OC(C)(C)C)CC3]

Step 1. 5-tert-butyl 3-ethyl 2-allyl-6,7-dihydro-4H-pyrazolo[4,3-c]pyridine-3,5-dicarboxylate To a solution of 5-tert-butylO3-ethyl 2,4,6,7-tetrahydropyrazolo[4,3-c]pyridine-3,5-dicarboxylate (20.00 g, 67.72 mmol, 1.00 eq) and 3-bromoprop-1-ene (12.29 g, 101.58 mmol, 1.50 eq) in DMF (200.00 mL) was added $Cs_2CO_3$ (55.16 g, 169.30 mmol, 2.50 eq). Then the mixture was stirred at 25° C. for 16 h. TLC (PE:EtOAc=3:1) showed that reactant 5-tert-butylO3-ethyl 2,4,6,7-tetrahydropyrazolo[4,3-c]pyridine-3,5-dicarboxylate was consumed completely and two new spots formed. The mixture was diluted with 100 mL of water and extracted with EtOAc (100 mL*3). The organic phase was washed with brine (100 mL*1) and dried over anhydrous $Na_2SO_4$, filtered and concentrated in vacuo. The residue was purified by column chromatography ($SiO_2$, Petroleum ether/Ethyl acetate=50/1 to 3/1) to afford the title compound (13.50 g, 40.25 mmol, 59.44% yield) was obtained as white solid.

Step 2. 2-allyl-5-tert-butoxycarbonyl-6,7-dihydro-4H-pyrazolo[4,3-c]pyridine-3-carboxylic acid To a solution of 5-tert-butyl 3-ethyl 2-allyl-6,7-dihydro-4H-pyrazolo[4,3-c] pyridine-3,5-dicarboxylate (640.00 mg, 1.91 mmol, 1.00 eq) in THF (20.00 mL) and $H_2O$ (4.00 mL) was added NaOH (152.65 mg, 3.82 mmol, 2.00 eq) at 25° C. Then the mixture was heated to 50° C. for another 16 h. TLC (EtOAc:MeOH=10:1) showed that reactant 5-tert-butyl 3-ethyl 2-allyl-6,7-dihydro-4H-pyrazolo[4,3-c] pyridine-3,5-dicarboxylate remained and one new spot formed. Then 2 mL of MeOH was added and the resulting mixture was still stirred at 50° C. for 3 h. TLC (EtOAc:MeOH=10:1) showed that reactant 5-tert-butyl 3-ethyl 2-allyl-6,7-dihydro-4H-pyrazolo[4,3-c] pyridine-3,5-dicarboxylate was consumed completely and one main new spot formed. The mixture was diluted with 30 mL of water and concentrated in vacuo to remove the organic solvent. Then the pH of the aqueous phase was adjusted to 5 by adding HCl (3N). The aqueous phase was extracted with EtOAc (30 mL*4), and the organic phase was washed with brine (30 mL*1), dried over anhydrous $Na_2SO_4$, filtered and concentrated in vacuo. The title compound (590.00 mg, crude) was obtained as white solid.

Step 3. tert-butyl 2-allyl-3-[allyl(methyl)carbamoyl]-6,7-dihydro-4H-pyrazolo[4,3-c]pyridine-5-carboxylate To a solution of 2-allyl-5-tert-butoxycarbonyl-6,7-dihydro-4H-pyrazolo[4,3-c]pyridine-3-carboxylic acid (590.00 mg, 1.92 mmol, 1.00 eq) and N-methylprop-2-en-1-amine (204.79 mg, 2.88 mmol, 273.06 μL, 1.50 eq) in DMF (10.00 mL) was added PYBOP (1.10 g, 2.11 mmol, 1.10 eq), HOBt (285.33 mg, 2.11 mmol, 1.10 eq) and DIPEA (1.49 g, 11.52 mmol, 2.01 mL, 6.00 eq) with stirring at 25° C. for 1 h. TLC (PE:EtOAc=1:1) showed that reactant 2-allyl-5-tert-butoxycarbonyl-6,7-dihydro-4H-pyrazolo[4,3-c] pyridine-3-carboxylic acid was consumed completely and one new spot formed. LCMS indicated that desired product was detected. The mixture was diluted with 30 mL of water and extracted with EtOAc (30 mL*4). The organic phase was collected and washed with brine (20 mL*1), dried over anhydrous $Na_2SO_4$, filtered and concentrated in vacuo. The residue was purified by column chromatography ($SiO_2$, Petroleum ether/Ethyl acetate=30/1 to 1/1) to afford the title compounds (650.00 mg, 1.80 mmol, 93.76% yield) as colorless oil.

Step 4. tert-butyl (8Z)-11-methyl-12-oxo-3,4,7,10-tetrahydro-1H-pyrido[2,3]pyrazolo[2,4-b][1,4]diazocine-2-carboxylate To a solution of tert-butyl 2-allyl-3-[allyl(methyl)carbamoyl]-6,7-dihydro-4H-pyrazolo[4,3-c]pyridine-5-carboxylate (275.00 mg, 762.94 μmol, 1.00 eq) in DCE (480.00 mL) was added [1,3-bis(2,4,6-trimethylphenyl)imidazolidin-2-ylidene]-dichloro-[(2-isopropoxyphenyl)methylene]ruthenium (95.61 mg, 152.59 μmol, 0.20 eq) in one portion under $N_2$, Then the mixture was stirred at 85° C. for 16 h. TLC (PE:EtOAc=1:3) showed that reactant 5 still remained and two new spots formed. The mixture was concentrated in vacuo. The 600 mg of the residue combined with two batches in parallel was purified by column chromatography ($SiO_2$, Petroleum ether/Ethyl acetate=50/1 to 1/3) to afford the title compound (180.00 mg, 541.52 mol, 35.49% yield) as yellow oil.

Intermediate 23: tert-butyl 11-methyl-12-oxo-3,4,7,8,9,10-hexahydro-1H-pyrido[2,3]pyrazolo[2,4-b][1,4]diazocine-2-carboxylate

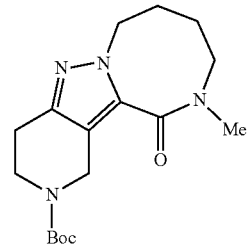 [SMILES: CN1CCCCn2nc3c(c2C1=O)CN(C(=O)OC(C)(C)C)CC3]

To a solution of tert-butyl (8Z)-11-methyl-12-oxo-3,4,7,10-tetrahydro-1H-pyrido[2,3]pyrazolo[2,4-b][1,4]diazocine-2-carboxylate (Intermediate 22, 60.00 mg, 180.51 μmol, 1.00 eq) in MeOH (5.00 mL) was added Pd/C (50.00 mg, 10.00 μL, 10% purity) under $N_2$. The suspension was degassed under vacuum and purged with $H_2$ several times. The mixture was stirred under $H_2$ (15 psi) at 25° C. for 2 hours. TLC (PE:EtOAc=1:3) showed that reactant 6 consumed completely and one main new spot formed. The mixture was diluted with 10 mL of MeOH, filtered and concentrated in vacuo to afford the title compound (61.00 mg, crude) as yellow oil, which was directly used without further purification.

Intermediate 24: tert-butyl 3'-hydroxy-10-methyl-11-oxo-spiro[3,4,7,9-tetrahydro-1H-pyrido[2,3]pyrazolo[2,4-b][1,4]diazepine-8,1'-cyclobutane]-2-carboxylate

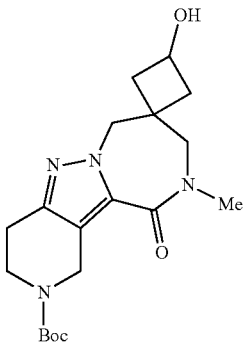 [SMILES: CN1CC2(CC(O)C2)Cn2nc3c(c2C1=O)CN(C(=O)OC(C)(C)C)CC3]

Step 1. [3-benzyloxy-1-(hydroxymethyl)cyclobutyl]methanol

To a suspension of LAH (1.55 g, 40.80 mmol, 2.50 eq) in THF (50.00 mL) was added a solution of diethyl 3-benzyloxycyclobutane-1,1-dicarboxylate (5.00 g, 16.32 mmol, 1.00 eq) in THF (20.00 mL) dropwise at −40° C. The resulting suspension was stirred at 20° C. for 3 hr. TLC (PE:EtOAc=0:1) showed the starting material consumed and one main spot formed. The mixture was diluted with THF (300 mL) and quenched by $H_2O$ (1.5 mL), 15% NaOH (1.5 mL) and $H_2O$ (4.5 mL), filtrated. The filtrate was concentrated in vacuum to afford the title compound (3.30 g, crude) as white solid.

Step 2. 2-(benzyloxy)-6,8-dioxa-7-thiaspiro[3.5]nonane 7-oxide

To a solution of [3-benzyloxy-1-(hydroxymethyl)cyclobutyl]methanol (3.30 g, 14.85 mmol, 1.00 eq) in DCM (90.00 mL) was added TEA (3.31 g, 32.67 mmol, 4.53 mL, 2.20 eq) followed by $SOCl_2$ (2.12 g, 17.82 mmol, 1.29 mL, 1.20 eq) at −10° C. The mixture was stirred at 0° C. for 1 hr. TLC (PE:EtOAc=1:1) showed the starting material consumed, TLC (PE:EtOAc=10:1) showed one main spot appeared. The mixture was diluted with $H_2O$ (50 mL) and extracted with DCM (100 mL*2). The combined organic layer was dried over $Na_2SO_4$, filtrated. The filtrate was concentrated in vacuum. The residue was purified by column chromatography (PE:EtOAc=100:1) to afford the title compound (3.20 g, 11.93 mmol, 80.31% yield) as colorless oil.

Step 3. 2-benzyloxy-6,8-dioxa-7thiaspiro[3.5]nonane 7,7-dioxide 2-benzyloxy-6,8-dioxa-7thiaspiro[3.5]nonane 7-oxide (2.50 g, 9.32 mmol, 1.00 eq) was dissolved in $H_2O$ (7.50 mL), MeCN (5.00 mL) and $CCl_4$ (5.00 mL). $RuCl_3.H_2O$ (210.04 mg, 931.69 μmol, 0.10 eq) was added to the mixture, followed by $NaIO_4$ (3.99 g, 18.63 mmol, 1.03 mL, 2.00 eq). The reaction mixture was then stirred at 20° C. for 1 hr. TLC (PE:EtOAc=5:1) showed the starting material consumed and one main spot appeared. The mixture was diluted with saturated $NaHCO_3$ (80 mL) and extracted with EtOAc (200 mL*2). The combined organic layer was dried over $Na_2SO_4$, filtrated and concentrated in vacuum. The residue was purified by flash chromatography (PE:EtOAc=10%~30%) to afford the title compound (2.40 g, 8.44 mmol, 90.57% yield) as white solid.

Step 4. [3-benzyloxy-1-(methylaminomethyl)cyclobutyl]methyl hydrogen sulfate

To a solution of 2-benzyloxy-6,8-dioxa-7thiaspiro[3.5]nonane 7,7-dioxide (1.00 g, 3.52 mmol, 1.00 eq) in MeCN (2.00 mL) was added $CH_3NH_2$ (2 M in THF, 26.40 mL, 15.00 eq). The mixture was heated to 65° C. for 16 hr. Three peaks showed on LCMS and 40% desired product detected. The mixture was concentrated in vacuum and the residue was washed with methyl tert-butyl (50 mL) to afford the title compound (1.10 g, crude) as white solid.

Step 5. tert-butyl N-[[3-benzyloxy-1-(hydroxymethyl)cyclobutyl]methyl]-N-methyl-carbamate To a solution of [3-benzyloxy-1-(methylaminomethyl)cyclobutyl]methyl hydrogen sulfate (1.10 g, 3.49 mmol, 1.00 eq) in THF (5.00 mL) was added $H_2SO_4$ (68.42 mg, 697.57 μmol, 37.18 μL, 0.20 eq). The mixture was heated to 50° C. for 6 hr. LCMS showed the starting material remained. The mixture was stirred at 70° C. for another 32 hr. LCMS showed a little starting material remained. The pH of the mixture was adjust to 11 with saturated $NaHCO_3$ and added $Boc_2O$ (761.22 mg, 3.49 mmol, 801.29 μL, 1.00 eq). The mixture was stirred at 20° C. for 30 min. TLC (PE:EtOAc=3:1) showed two main spots appeared. The mixture was diluted with $H_2O$ (50 mL) and extracted with EtOAc (80 mL*2). The combined organic layer was dried over $Na_2SO_4$, filtrated and concentrated in vacuum. The residue was purified by flash chromatography (PE:EtOAc:0%~20%) to afford the title compound (519.00 mg, 1.38 mmol, 39.46% yield, 89% purity) as colorless oil.

Step 6. (3-(benzyloxy)-1-((methylamino)methyl)cyclobutyl)methanol

To a solution of tert-butyl N-[[3-benzyloxy-1-(hydroxymethyl)cyclobutyl] methyl]-N-methyl-carbamate (519.00 mg, 1.55 mmol, 1.00 eq) in DCM (5.00 mL) was added TFA (3.00 mL). The mixture was stirred at 20° C. for 0.5 hr. TLC (PE:EtOAc=5:1) showed the starting material consumed. The mixture was concentrated in vacuum to afford the title compound (600.00 mg, crude, TFA) as brown oil.

Step 7. tert-butyl 3-[[3-benzyloxy-1-(hydroxy methyl cyclobutyl]methyl-methyl-carbamoyl]-2,4,6,7-tetrahydropyrazolo[4,3-c]pyridine-5-carboxylate To a solution of 5-tert-butoxycarbonyl-2,4,6,7-tetrahydropyrazolo[4,3-c]pyridine-3-carboxylic acid (400.00 mg, 1.50 mmol, 1.00 eq) and [3-benzyloxy-1-(methyl aminomethyl)cyclobutyl]methanol (524.01 mg, 1.50 mmol, 1.00 eq, TFA) in DMF (5.00 mL) was added PYBOP (780.58 mg, 1.50 mmol, 1.00 eq), HOBt (202.68 mg, 1.50 mmol, 1.00 eq) followed by DIEA (969.30 mg, 7.50 mmol, 1.31 mL, 5.00 eq). The mixture was stirred at 20° C. for 1 hr. LCMS showed one main peak with desired Ms detected. The mixture was extracted with EtOAc (80 mL*3) and $H_2O$ (50 mL). The combined organic layer was washed with $H_2O$ (80 mL*2), 1N HCl (50 mL) and saturated $NaHCO_3$ (50 mL). The combined organic layer was dried over $Na_2SO_4$, filtrated and concentrated in vacuum. The residue was purified by column chromatography (PE:EtOAc=30%~50%) to afford the title compound (300.00 mg, 433.36 µmol, 28.89% yield, 70% purity) as colorless oil.

Step 8. tert-butyl-3-[[3-benzyloxy-1-(methyl sulfonyloxy-methyl)cyclobutyl]methyl-methyl-carbamoyl]-2,4,6,7-tetrahydropyrazolo[4,3-c]pyridine-5-carboxylate To a solution of tert-butyl 3-[[3-benzyloxy-1-(hydroxymethyl)cyclobutyl]methyl-methyl-carbamoyl]-2,4,6,7-tetrahydropyrazolo[4,3-c]pyridine-5-carboxylate (200.00 mg, 288.90 µmol, 1.00 eq) in DCM (1.00 mL) was added pyridine (114.26 mg, 1.44 mmol, 116.59 µL, 5.00 eq) followed by MsCl (49.64 mg, 433.35 µmol, 33.54 µL, 1.50 eq). The mixture was stirred at 20° C. for 2 hr. TLC (PE:EtOAc=1:1) showed the starting material remained and two new main spots appeared. Another batch of MsCl (49.64 mg, 433.35 µmol, 33.54 µL, 1.50 eq) was added and the mixture was stirred at 20° C. for 1 hr. TLC (PE:EtOAc=1:1) showed a little starting material remained and two new main spots appeared. The mixture was extracted with DCM (30 mL*2) and H₂O (20 mL). The combined organic layer was washed saturated Cu₂SO₄ (20 mL*2), dried over Na₂SO₄, filtrated and concentrated in vacuum. The residue was purified by prep-TLC (PE:EtOAc=1:1) to afford the title compound (60.00 mg, 106.63 µmol, 36.91% yield) as colorless oil.

Step 9. tert-butyl 3'-benzyloxy-10-methyl-11-oxo-spiro[3,4,7,9-tetrahydro-1H-pyrido[2,3]pyrazolo[2,4-b][1,4]diazepine-8,1'-cyclobutane]-2-carboxylate To a solution of tert-butyl 3-[[3-benzyloxy-1-(methylsulfonyloxymethyl)cyclobutyl] methyl-methyl-carbamoyl]-2,4,6,7-tetrahydropyrazolo[4,3-c]pyridine-5-carboxylate (60.00 mg, 106.63 µmol, 1.00 eq) in THF (1.00 mL) was added NaH (8.53 mg, 213.27 µmol, 60% purity, 2.00 eq) at 0° C. The mixture was stirred at 0° C. for 0.5 hr. LCMS showed 22% of starting material remained. The mixture was stirred at 20° C. for another 2 hr. LCMS showed one main peak with desired Ms detected. The mixture was quenched by saturated NH₄C₁ (10 mL) and extracted with EtOAc (10 mL*2). The combined organic layer was dried over Na₂SO₄, filtrated and concentrated in vacuum. The residue was purified by prep-TLC (PE:EtOAc=1:1) to afford the title compound (27.00 mg, 57.87 µmol, 54.27% yield) as colorless oil.

Step 10. tert-butyl 3'-hydroxy-10-methyl-1-oxo-spiro[3,4,7,9-tetrahydro-1H-pyrido[2,3]pyrazolo[2,4-b][1,4]diazepine-8,1'-cyclobutane]-2-carboxylate To a solution of tert-butyl 3'-benzyloxy-10-methyl-11-oxo-spiro[3,4,7,9-tetrahydro-1H-pyrido[2,3]pyrazolo[2,4-b][1,4]diazepine-8,1'-cyclobutane]-2-carboxylate (27.00 mg, 57.87 µmol, 1.00 eq) in MeOH (10.00 mL) was added Pd—C (10%, 5 mg) under N₂. The suspension was degassed under vacuum and purged with H₂ several times. The mixture was stirred under H₂ (20 psi) at 40° C. for 16 hours. LCMS showed one main peak with desired MS detected. The mixture was dilute with MeOH (30 mL), filtrated and concentrated in vacuum to afford the title compound (30.00 mg, crude) as brown oil.

Intermediate 25: methyl 2-[tert-butyl(diphenyl)silyl]oxy-4-(methylamino)butanoate

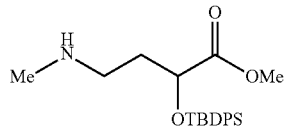

Step 1. 4-(tert-butoxycarbonylamino)-2-hydroxy-butanoic acid

To a solution of 4-amino-2-hydroxy-butanoic acid (10.00 g, 83.95 mmol, 1.00 eq) in H₂O (75.00 mL) was added K₂CO₃ (11.60 g, 83.95 mmol, 1.00 eq) followed by a solution of Boc₂O (18.32 g, 83.95 mmol, 19.29 mL, 1.00 eq) in dioxane (50.00 mL) dropwise at 0° C. The resulting solution was stirred at 20° C. for 16 hr. TLC (PE:EtOAc=0:1) showed one main spot appeared. The mixture was diluted with H₂O (80 mL) and washed with 100 ml DCM to remove the remained Boc₂O. The pH of the aqueous layer was adjusted to 4-5 with 1N hydrochloric acid and the resulting solution was extracted with 4×100 mL of ethyl acetate. The organic layers were combined and concentrated under vacuum to afford the title compound (16.00 g, 72.98 mmol, 86.94% yield) as colorless oil.

Step 2. methyl 4-(tert-butoxycarbonylamino)-2-hydroxy-butanoate

To a solution of 4-(tert-butoxycarbonylamino)-2-hydroxy-butanoic acid (5.00 g, 22.81 mmol, 1.00 eq) in DMF (50.00 mL) was added Cs₂CO₃ (8.92 g, 27.37 mmol, 1.20 eq) and CH₃I (3.24 g, 22.81 mmol, 1.42 mL, 1.00 eq) dropwise at 0° C. The mixture was stirred at 20° C. for 2 hr. TLC (PE:EtOAc=1:1) showed the starting material consumed and one main spot appeared. The mixture was diluted with H₂O (100 mL) and extracted with EtOAc (200 mL*2). The combined organic layer was washed with H₂O (200 mL*2), dried over Na₂SO₄, filtrated and concentrated in vacuum. The residue was purified by column chromatography (PE:EtOAc=30%~50%) to afford the title compound (5.50 g, crude) as colorless oil.

Step 3. methyl 4-(tert-butoxycarbonylamino)-2-[tert-butyl(diphenyl)silyl]oxy-butanoate To a solution of methyl 4-(tert-butoxycarbonylamino)-2-hydroxy-butanoate (5.00 g, 21.44 mmol, 1.00 eq) in DCM (50.00 mL) was added imidazole (2.19 g, 32.16 mmol, 1.50 eq) followed by TBDPSCl (5.89 g, 21.44 mmol, 5.50 mL, 1.00 eq) and DMAP (261.88 mg, 2.14 mmol, 0.10 eq). The mixture was stirred at 20° C. for 16 hr. TLC (PE:EtOAc=1:1) showed the starting material remained and TLC (PE:EtOAc=10:1) showed two main spots appeared. The mixture was diluted with H₂O (50 mL) and extracted with DCM (80 mL*3). The combined organic layer was washed with H₂O (20 mL*3), dried over Na₂SO₄, filtrated and concentrated in vacuum. The residue was purified by flash chromatography (PE:EtOAc:0%~10%) to afford the title compound (6.50 g, 13.78 mmol, 64.28% yield) as colorless oil.

Step 4. methyl 4-[tert-butoxycarbonyl(methyl) amino]-2-[tert-butyl(diphenyl)silyl]oxy-butanoate To a solution of methyl 4-(tert-butoxycarbonylamino)-2-[tert-butyl(diphenyl)silyl]oxy-butanoate (4.40 g, 9.33 mmol, 1.00 eq) in DMF (50.00 mL) was added Ag$_2$O (10.81 g, 46.65 mmol, 5.00 eq) followed by CH$_3$I (6.62 g, 46.65 mmol, 2.90 mL, 5.00 eq). The mixture was stirred at 20° C. for 16 hr. TLC (PE:EtOAc=10:1) showed the starting material remained, additional Ag$_2$O (2.0 g) and CH$_3$I (3 mL) were added and the mixture was stirred at 20° C. for another 120 hr. TLC (PE:EtOAc=10:1) showed a little starting material remained and two main spots appeared. The mixture was diluted with EtOAc (200 mL) and filtrated. The filtrates was diluted with H$_2$O (100 mL) and seperated out the organic layer. The organic layer was washed with H$_2$O (200 mL*2), dried over Na$_2$SO$_4$, filtrated. The filtrate was concentrated in vacuum. The residue was purified by flash chromatography (PE:EtOAc: 0%~10%) to afford the title compound (3.20 g, 6.59 mmol, 70.62% yield) as colorless oil.

Step 5. methyl 2-[tert-butyl(diphenyl)silyl]oxy-4-(methylamino)butanoate

To a solution of methyl 4-[tert-butoxycarbonyl(methyl) amino]-2-[tert-butyl(diphenyl) silyl]oxy-butanoate (1.30 g, 2.68 mmol, 1.00 eq) in DCM (10.00 mL) was added TFA (5.00 mL) at 0° C. The mixture was stirred at 20° C. for 2 hr. TLC (PE:EtOAc=10:1) showed the starting consumed. The mixture was concentrated in vacuum to afford the title compound (2.80 g, crude, TFA) as brown oil.

Intermediate 26: 2-(tert-butoxycarbonyl)-10-methyl-11-oxo-1,3,4,7,8,9,10,11-octahydro-2H-pyrido[4',3':3,4]pyrazolo[1,5-a][1,4]diazepine-7-carboxylic acid

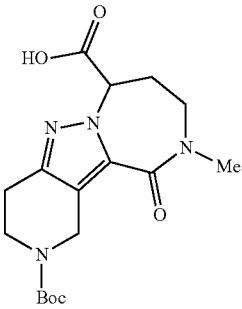 [SMILES: CN1CCC(C(=O)O)n2nc3c(c2C1=O)CN(C(=O)OC(C)(C)C)CC3]

Step 1. tert-butyl 3-[[3-[tert-butyl(diphenyl)silyl]oxy-4-methoxy-4-oxo-butyl]-methyl-carbamoyl]-2,4,6,7-tetrahydropyrazolo[4,3-c]pyridine-5-carboxylate To a solution of 5-tert-butoxycarbonyl-2,4,6,7-tetrahydropyrazolo[4,3-c]pyridine-3-carboxylic acid (800.00 mg, 2.99 mmol, 1.00 eq) and methyl 2-[tert-butyl(diphenyl)silyl]oxy-4-(methylamino)butanoate (Intermediate 25, 2.99 g, 5.98 mmol, 2.00 eq, TFA) in DMF (10.00 mL) was added PYBOP (1.71 g, 3.29 mmol, 1.10 eq), HOBt (444.41 mg, 3.29 mmol, 1.10 eq), followed by DIEA (1.93 g, 14.95 mmol, 2.61 mL, 5.00 eq). The mixture was stirred at 20° C. for 2 hr. LCMS showed one main peak with desired MS detected. The mixture was extracted with EtOAc (50 mL*3) and H$_2$O (50 mL). The combined organic layer was washed H$_2$O (50 mL*3), 1N HCl (50 mL) and saturated NaHCO$_3$ (50 mL), dried over Na$_2$SO$_4$, filtrated and concentrated in vacuum. The residue was re-purified by column chromatography (PE:EtOAc: 20%~100%) to afford the title compound (1.60 g, 2.52 mmol, 84.29% yield) as white solid.

Step 2. tert-butyl 3-[(3-hydroxy-4-methoxy-4-oxo-butyl)-methyl-carbamoyl]-2,4,6,7-tetrahydropyrazolo[4,3-c]pyridine-5-carboxylate To a solution of tert-butyl 3-[[3-[tert-butyl(diphenyl)silyl]oxy-4-methoxy-4-oxo-but-yl]-methyl-carbamoyl]-2,4,6,7-tetrahydropyrazolo[4,3-c]pyridine-5-carboxylate (1.40 g, 2.21 mmol, 1.00 eq) in THF (14.00 mL) was added TBAF (2 M, 2.21 mL, 2.00 eq). The mixture was stirred at 20° C. for 1 hr. TLC (PE:EtOAc=1:2) showed the starting material consumed and two main spots appeared. The mixture was extracted with DCM (50 mL*2) and H$_2$O (30 mL). The combined organic layer was washed with H$_2$O (30 mL*2), 1N HCl (30 mL) and saturated NaHCO$_3$ (30 mL), dried over Na$_2$SO$_4$, filtrated. The filtrate was concentrated in vacuum to afford the title compound (1.5 g crude) as white solid.

Step 3. tert-butyl3-[(4-methoxy-3-methylsulfonyloxy-4-oxo-butyl)-methyl-carbamoyl]-2,4,6,7-tetrahydropyrazolo[4,3-c]pyridine-5-carboxylate and tert-butyl 3-[(4-methoxy-3-methylsulfonyloxy-4-oxo-butyl)-methyl-carbamoyl]-2-methylsulfonyl-6,7-dihydro-4H-pyrazolo[4,3-c]pyridine-5-carboxylate To a solution of tert-butyl 3-[(3-hydroxy-4-methoxy-4-oxo-butyl)-methyl-carbamoyl]-2,4,6,7-tetrahydropyrazolo[4,3-c]pyridine-5-carboxylate (150.00 mg, 378.37 μmol, 1.00 eq) in DCM (5.00 mL) was added Py (29.93 mg, 378.37 μmol, 30.54 μL, 1.00 eq), followed by MsCl (43.34 mg, 378.37 μmol, 29.28 μL, 1.00 eq). The mixture was stirred at 20° C. for 2 hr. TLC (PE:EtOAc=0:1) showed the starting material remained and two new spots appeared. Additional MsCl (43.34 mg, 378.37 μmol, 29.28 μL, 1.00 eq) was added and the mixture was stirred at 20° C. for 1 hr. TLC (PE:EtOAc=0:1) showed the starting material consumed and two new spots appeared. The mixture was extracted with DCM (20 mL*2) and H$_2$O (20 mL). The combined organic layer was washed saturated Cu$_2$SO$_4$ (10 mL*2), dried over Na$_2$SO$_4$, filtrated and concentrated in vacuum. The residue was purified by prep-TLC (PE:EtOAc=0:1) to afford tert-butyl3-[(4-methoxy-3-methylsulfonyloxy-4-oxo-butyl)-methyl-carbamoyl]-2,4,6,7-tetrahydropyrazolo[4,3-c]pyridine-5-carboxylate (20.00 mg, 42.15 mol, 11.14% yield) as white solid and tert-butyl 3-[(4-methoxy-3-methylsulfonyloxy-4-oxo-butyl)-methyl-carbamoyl]-2-methylsulfonyl-6,7-dihydro-4H-pyrazolo[4,3-c]pyridine-5-carboxylate (150.00 mg, 271.43 μmol, 71.74% yield) as white solid.

Step 4. 2-(tert-butoxycarbonyl)-10-methyl-11-oxo-1,3,4,7,8,9,10,11-octahydro-2H-pyrido[4',3':3,4]pyrazolo[1,5-a][1,4]diazepine-7-carboxylic acid To a solution of tert-butyl 3-[(4-methoxy-3-methyl sulfonyloxy-4-oxo-butyl)-methyl-carbamoyl]-2-methylsulfonyl-6,7-dihydro-4H-pyrazolo[4,3-c]pyridine-5-carboxylate (150.00 mg, 271.43 μmol, 1.00 eq) in THF (3.00 mL) was added NaH (21.71 mg, 542.87 μmol, 60% purity, 2.00 eq). The mixture was stirred at 0° C. for 0.5 hr. LCMS showed the starting material and 2-(tert-butoxycarbonyl)-10-methyl- 11-oxo-1,3,4,7,8,9,10,11-octahydro-2H-pyrido[4',3':3,4]pyrazolo[1,5-a][1,4]diazepine-7-carboxylic acid in one peak. The mixture was stirred at 20° C. for another 3 hr. LCMS showed a little starting material remained. Additional NaH (21.71 mg, 542.87 µmol, 60% purity, 2.00 eq) was added and the mixture was stirred at 20° C. for 16 h. LCMS showed 57% of 2-(tert-butoxycarbonyl)-10-methyl-11-oxo-1,3,4,7,8,9,10,11-octahydro-2H-pyrido[4',3':3,4]pyrazolo[1,5-a][1,4]diazepine-7-carboxylic acid and 22% of an unknown compound. The mixture was diluted with H$_2$O (5 mL) and concentrated in vacuum to afford a crude mixture of the title compound (116.00 mg, crude) as brown oil.

Intermediate 27: tert-butyl 8-(1-hydroxyallyl)-10-methyl-11-oxo-1,3,4,7,8,9-hexa hydropyrido[2,3]pyrazolo[2,4-b][1,4]diazepine-2-carboxylate

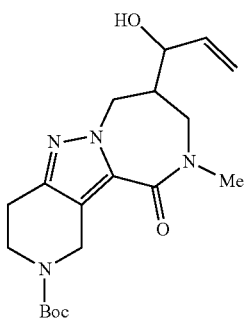 [SMILES: C=CC(O)C1CN(C)C(=O)c2c3c(nn2C1)CCN(C(=O)OC(C)(C)C)C3]

To a mixture of tert-butyl 10-methyl-11-oxo-8-prop-2-enoyl-1,3,4,7,8,9-hexahydropyrido[2,3]pyrazolo[2,4-b][1,4]diazepine-2-carboxylate (3.70 g, 9.88 mmol, 1.00 eq) in MeOH (100.00 mL) was added CeCl$_3$ (4.87 g, 19.76 mmol, 1.24 mL, 2.00 eq) in one portion at 0° C. under N$_2$. The mixture was stirred at 0° C. for 15 min, then NaBH$_4$ (1.50 g, 39.52 mmol, 4.00 eq) was added to the mixture. The mixture was heated to 30° C. and stirred for 2 hours. LCMS and TLC (Dichloromethane:Methanol=10:1) showed the reaction was completed. The mixture was poured into water (20 mL) and concentrated in reduced pressure. The aqueous phase was extracted with ethyl acetate (50 mL*3). The combined organic phase was washed with brine (20 mL*2), dried with anhydrous Na$_2$SO$_4$, filtered and concentrated in vacuum. The residue was purified by silica gel chromatography (Dichloromethane:Methanol=100/1-20:1) to afford the title compound (2.70 g, 6.74 mmol, 68.24% yield, 94% purity) as yellow solid, Which was separated by SFC (Analytical method: IC-3 S_3_5_40_3ML Column: Chiralpak IC-3 100×4.6 mm I.D., 3 um Mobile phase: methanol (0.05% DEA) in CO$_2$ from 5% to 40% Flow rate: 3 mL/min Wavelength: 220 nm. Separation method: Instrument: SFC 80; Column: IC-10 um; Mobile phase: A for CO$_2$ and B for MeOH (0.1% NH$_3$H$_2$O); Gradient: B 35%; Flow rate: 60 mL/min; Back pressure: 100bar; Column temperature: 35° C.; Wavelength: 220 nm) to give four isomers: tert-butyl (S*)-8-((S*)-1-hydroxyallyl)-10-methyl-11-oxo-1,3,4,7,8,9,10,11-octahydro-2H-pyrido[4',3':3,4]pyrazolo[1,5-a][1,4]diazepine-2-carboxylate: 650 mg, tert-butyl (R*)-8-((S*)-1-hydroxyallyl)-10-methyl-11-oxo-1,3,4,7,8,9,10,11-octahydro-2H-pyrido[4',3':3,4]pyrazolo[1,5-a][1,4]diazepine-2-carboxylate 640 mg, tert-butyl (S*)-8-((R*)-1-hydroxyallyl)-10-methyl-11-oxo-1,3,4,7,8,9,10,11-octahydro-2H-pyrido[4',3':3,4]pyrazolo[1,5-a][1,4]diazepine-2-carboxylate: 650 mg and tert-butyl (R*)-8-((R*)-1-hydroxyallyl)-10-methyl-11-oxo-1,3,4,7,8,9,10,11-octahydro-2H-pyrido[4',3':3,4]pyrazolo[1,5-a][1,4]diazepine-2-carboxylate: 650 mg.
*Pure but unknown stereoisomer.

Intermediate 28: tert-butyl 8-(1-benzyloxy-3-hydroxy-propyl)-10-methyl-11-oxo-1,3,4,7,8,9-hexahydropyrido[2,3]pyrazolo[2,4-b][1,4] diazepine-2-carboxylate

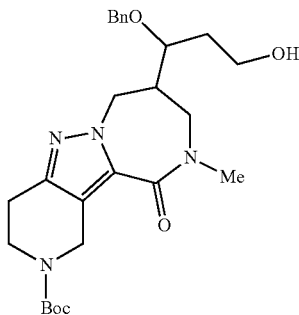 [SMILES: CN1CC(C(CCO)OCc2ccccc2)Cn2nc3c(c2C1=O)CN(C(=O)OC(C)(C)C)CC3]

Step 1. tert-butyl 8-(1-benzyloxyallyl)-10-methyl-11-oxo-1,3,4,7,8,9-hexahydropyrido[2,3]pyrazolo[2,4-b][1,4]diazepine-2-carboxylate To a solution of tert-butyl 8-(1-hydroxyallyl)-10-methyl-11-oxo-1,3,4,7,8,9-hexa hydropyrido[2,3]pyrazolo[2,4-b][1,4]diazepine-2-carboxylate (Intermediate 27, 1.00 g, 2.66 mmol, 1.00 eq) in THF (15.00 mL) was added NaH (425.60 mg, 10.64 mmol, 60% purity, 4.00 eq). The mixture was stirred at 0° C. for 30 min, then BnBr (682.41 mg, 3.99 mmol, 473.90 µL, 1.50 eq) was added. The mixture was stirred at 40° C. for 2 hr. TLC (PE:EtOAc=0:1) showed the starting material consumed and one new spot appeared. The mixture was quenched with H$_2$O (50 mL) and extracted with EtOAc (30 mL*3). The combined organic layer was dried over Na$_2$SO$_4$, filtrated and concentrated in vacuum. The residue was purified by column chromatography (PE:EtOAc=2:1-1:1) to afford the title compound (700.00 mg, 1.47 mmol, 55.44% yield, 98.3% purity) as white solid.

Step 2. tert-butyl 8-(1-benzyloxy-3-hydroxy-propyl)-10-methyl-11-oxo-1,3,4,7,8,9-hexahydropyrido[2,3]pyrazolo[2,4-b][1,4]diazepine-2-carboxylate To a solution of tert-butyl 8-(1-benzyloxyallyl)-10-methyl-11-oxo-1,3,4,7,8,9-hexa hydropyrido[2,3]pyrazolo[2,4-b][1,4]diazepine-2-carboxylate (350.00 mg, 750.16 µmol, 1.00 eq) and chlororhodium triphenylphosphane (69.41 mg, 75.02 µmol, 0.10 eq) in THF (8.00 mL) was added 1,3,2-benzodioxaborole (1 M, 3.75 mL, 5.00 eq) at 0° C. The mixture was stirred at 10° C. for 3 hr. A solution of NaOH (210.04 mg, 5.25 mmol, 7.00 eq) in H$_2$O (4.00 mL) was added at −3° C. dropwise. Then H$_2$O$_2$ (2.38 g, 20.97 mmol, 2.02 mL, 30% purity, 27.96 eq) was added slowly. The mixture was stirred at 25° C. for 2 hr. TLC (PE:EtOAc=0:1) showed the starting material consumed and one main spot appeared. The mixture was extracted with DCM (90 mL*3) and H$_2$O (20 mL). The organic layer was washed with 20% NaOH (80 mL*2), dried over Na$_2$SO$_4$, filtrated and concentrated in vacuum. The residue was purified by column chromatography (PE:EtOAc:50%~100% then to EtOAc:MeOH:10%) to afford the title compound (272.00 mg, 516.40 µmol, 68.84% yield, 92% purity) as brown solid.

Intermediate 29: racemic tert-butyl 8-(((2,2-difluoroethyl)amino)methyl)-10-methyl-1-oxo-1,3,4,7,8,9,10,11-octahydro-2H-pyrido[4',3':3,4]pyrazolo[1,5-a][1,4]diazepine-2-carboxylate

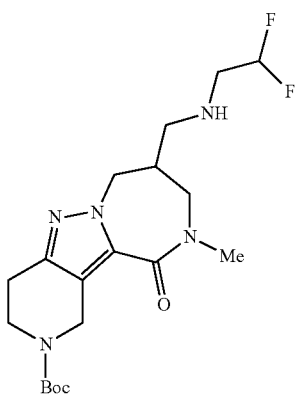 [SMILES: CN1CC(CNCC(F)F)Cn2nc3c(c2C1=O)CN(C(=O)OC(C)(C)C)CC3]

A mixture of tert-butyl 10-methyl-8-(methyl sulfonyloxymethyl)-11-oxo-1,3,4,7,8,9-hexahydropyrido[2,3]pyrazolo[2,4-b][1,4]diazepine-2-carboxylate (150.00 mg, 350.06 µmol, 1.00 eq), 2,2-difluoroethanamine (567.51 mg, 7.00 mmol, 20.00 eq) in DMSO (5.00 mL) was degassed and purged with N₂ for 3 times, and then the mixture was stirred at 88° C. for 16 hour under N₂ atmosphere. LCMS showed the starting material was consumed completely, desired product was major. The mixture was poured into water (20 mL) and extracted with EtOAc (10 mL*2). The combined organic phase was washed with brine (20 mL), dried with anhydrous Na₂SO₄, filtered and concentrated in vacuum. The residue was purified by column chromatography (SiO2, Petroleum ether/Ethyl acetate=100/1 to 1:3) to afford the title compound (82.00 mg, 176.51 µmol, 50.42% yield, 89% purity) as a yellow solid. LCMS: 414 [M+1].

Intermediate 30: 5-tert-butyl3-ethyl 1,4,6,7-tetrahydropyrazolo[4,3-c]pyridine-3,5-dicarboxylate

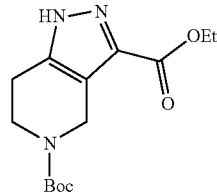 [SMILES: CCOC(=O)c1n[nH]c2c1CN(C(=O)OC(C)(C)C)CC2]

Step 1. tert-butyl 3-(2-ethoxy-2-oxo-acetyl)-4-oxo-piperidine-1-carboxylate

To LiHMDS (1 M, 652.44 mL, 1.30 eq) was added a solution of tert-butyl 4-oxopiperidine-1-carboxylate (100.00 g, 501.88 mmol, 1.00 eq) in THF (1.00 L) dropwise at −78° C. under N₂. The reaction mixture was stirred at −78° C. for 30 minutes under N₂. Then diethyl oxalate (95.35 g, 652.44 mmol, 1.30 eq) was added dropwise. After addition, the reaction mixture was warmed to 15° C. over a period of 30 minutes and stirred at 15° C. for another 2 hours. TLC (PE/EA=3/1, Rf=0.2) showed the reaction was completed. The reaction was quenched with saturated aqueous solution of NH₄Cl (1.5 L) and then neutralized with diluted hydrochloric acid, the aqueous layer was extracted with EtOAc (800 mL×3). The combined organic phase was dried over anhydrous Na₂SO₄, filtered and concentrated in vacuum to afford the title compound (165.00 g, crude) as yellow oil and used directly for next step.

Step 2. 5-tert-butyl3-ethyl 1,4,6,7-tetrahydropyrazolo[4,3-c]pyridine-3,5-dicarboxylate A mixture of tert-butyl 3-(2-ethoxy-2-oxo-acetyl)-4-oxo-piperidine-1-carboxylate (165.00 g, 551.25 mmol, 1.00 eq) and NH₂NH₂·H₂O (35.71 g, 606.37 mmol, 1.10 eq) in AcOH (1.00 L) was degassed and purged with N₂ for 3 times. Then the mixture was stirred at 80° C. for 1 hour under N₂ atmosphere. TLC (PE/EA=1/1, Rf=0.4) and LCMS showed the reaction was completed. The mixture was concentrated under reduced pressure. The residue was dissolved in EtOAc (800 mL) and washed with Na₂CO₃ (1 N, 1.2 L). The aqueous phase was extracted with ethyl acetate (800 mL×2). The combined organic phase was washed with brine (1 L×2), dried with anhydrous Na₂SO₄, filtered and concentrated in vacuum to afford the title compound (130.00 g, 440.19 mmol, 79.85% yield) as a yellow solid. LCMS: 296 [M+1]. ¹H NMR (400 MHz, METHANOL-d₄) δ=4.57-4.65 (m, 2H), 4.36 (d, J=7.03 Hz, 2H), 3.67-3.74 (m, 2H), 2.75 (t, J=5.65 Hz, 2H), 1.49 (s, 9H), 1.36-1.40 (m, 3H).

Compound 001: N-(3-chloro-4-fluorophenyl)-10-methyl-8-methylene-11-oxo-1,3,4,7,8,9,10,11-octahydro-2H-pyrido[4',3':3,4]pyrazolo[1,5-a][1,4]diazepine-2-carboxamide

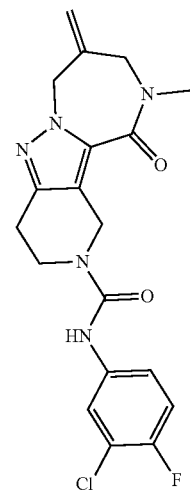 [SMILES: C=C1CN(C)C(=O)c2c3c(nn2C1)CCN(C(=O)Nc1ccc(F)c(Cl)c1)C3]

Step 1. 10-methyl-8-methylene-3,4,7,8,9,10-hexahydro-1H-pyrido[4',3':3,4]pyrazolo[1,5-a][1,4]diazepin-11 (2H)-one To a solution of tert-butyl 10-methyl-8-methylene-11-oxo-3,4,7,9-tetrahydro-1H-pyrido[2,3]pyrazolo[2,4-b][1,4]

diazepine-2-carboxylate (Intermediate 1, 340.00 mg, 1.02 mmol, 1.00 eq) in DCM (2.00 mL) was added TFA (3.08 g, 27.01 mmol, 2.00 mL, 26.48 eq) under $N_2$ and the mixture was stirred at 15° C. for 1 h. The mixture was concentrated in vacuo to afford the title compound as the TFA salt (446.00 mg, crude), which was used directly for the next step.

Step 2: N-(3-chloro-4-fluorophenyl)-10-methyl-8-methylene-11-oxo-1,3,4,7,8,9,10,11-octahydro-2H-pyrido[4',3':3,4]pyrazolo[1,5-a][1,4]diazepine-2-carboxamide A mixture of 10-methyl-8-methylene-1,2,3,4,7,9-hexahydropyrido[2,3]pyrazolo [2,4-b][1,4]diazepin-11-one (446.00 mg, 515.16 μmol, 1.00 eq, TFA), $Et_3N$ (260.65 mg, 2.58 mmol, 357.05 μL, 5.00 eq) and phenyl N-(3-chloro-4-fluorophenyl) carbamate (136.86 mg, 515.16 μmol, 1.00 eq) in DCM (3.00 mL) was stirred at 10° C. for 16 h. The mixture was diluted with DCM (30 mL) and washed with HCl (1 M, 30 mL). The organic phase was dried over $Na_2SO_4$, filtered and concentrated in vacuo to give yellow oil. The oil was purified by silica gel column and prep-HPLC (FA) to afford the title compound (39.00 mg, 96.28 μmol, 18.69% yield, 99.7% purity) as a white solid. LCMS: 404/406 [M+1]. $^1$H NMR (400 MHz, $CDCl_3$) δ 7.60 (dd, J=2.69, 6.48 Hz, 1H), 7.18-7.23 (m, 1H), 7.03-7.11 (m, 1H), 6.55 (s, 1H), 5.18 (d, J=10.39 Hz, 2H), 5.02 (s, 2H), 4.70 (s, 2H), 3.98 (s, 2H), 3.87 (t, J=5.75 Hz, 2H), 3.19 (s, 3H), 2.86 (t, J=5.81 Hz, 2H).

Compound 002: N-(3-chloro-4-fluorophenyl)-8-(hydroxymethyl)-10-methyl-1-oxo-1,3,4,7,8,9,10,11-octahydro-2H-pyrido[4',3':3,4]pyrazolo[1,5-a][1,4]diazepine-2-carboxamide

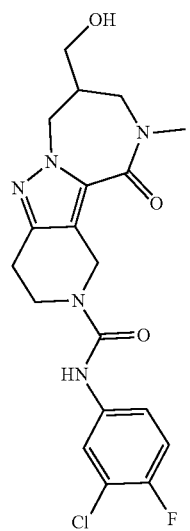 [SMILES: CN1CC(CO)Cn2nc3c(c2C1=O)CN(C(=O)Nc1ccc(F)c(Cl)c1)CC3]

To a solution of N-(3-chloro-4-fluoro-phenyl)-10-methyl-8-methylene-11-oxo-3,4,7,9-tetrahydro-1H-pyrido[2,3]pyrazolo[2,4-b][1,4]diazepine-2-carboxamide (Compound 001; 50.00 mg, 123.81 μmol, 1.00 eq) and chlororhodium triphenylphosphane (4.58 mg, 4.95 μmol, 0.04 eq) in THF (3.00 mL) was added 1,3,2-benzodioxaborole (1 M, 371.43 μL, 3.00 eq) at 0° C. under $N_2$. The mixture was stirred at 0° C. for 3 hr. TLC (DCM:MeOH=15:1) showed the starting material was consumed completely nearly. A solution of NaOH (34.67 mg, 866.67 μmol, 7.00 eq) in $H_2O$ (1.50 mL) was added at −30° C. dropwise. Then $H_2O_2$ (393.01 mg, 3.47 mmol, 333.06 μL, 30% purity, 28.00 eq) was added slowly. The mixture was stirred at 10° C. for 16 hr. LCMS showed the starting material/desire product=1/3. The mixture was quenched with saturated $NaHSO_3$ (50 mL) and extracted with EtOAc (50 mL). The organic phase was washed with NaOH (15%, 30 mL*3) and brine (30 mL), dried over $Na_2SO_4$, filtered and concentrated in vacuo to give brown oil. The oil was purified by prep-HPLC(FA) to afford the title compound (10.00 mg, 23.49 μmol, 18.97% yield, 99.1% purity) as white solid. LCMS: 422/424 [M+1]. $^1$H NMR (400 MHz, $CDCl_3$) δ 7.58 (dd, J=2.63, 6.54 Hz, 1H), 7.14-7.24 (m, 1H), 7.00-7.11 (m, 1H), 6.52 (s, 1H), 4.67 (s, 2H), 4.41 (dd, J=7.09, 14.31 Hz, 1H), 4.20 (dd, J=5.56, 14.24 Hz, 1H), 3.77-3.94 (m, 2H), 3.62-3.77 (m, 2H), 3.43-3.54 (m, 1H), 3.32-3.43 (m, 1H), 3.19 (s, 3H), 2.84 (t, J=5.75 Hz, 2H), 2.61-2.77 (m, 1H), 1.75 (br. s, 1H).

Compound 003: N-(3-chloro-4-fluorophenyl)-8-hydroxy-8-(hydroxymethyl)-10-methyl-1-oxo-1,3,4,7,8,9,10,11-octahydro-2H-pyrido[4',3':3,4]pyrazolo[1,5-a][1,4]diazepine-2-carboxamide

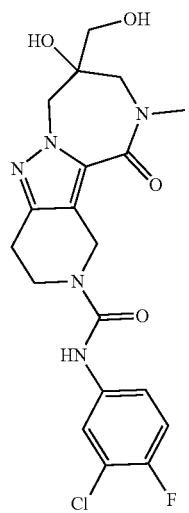 [SMILES: CN1CC(O)(CO)Cn2nc3c(c2C1=O)CN(C(=O)Nc1ccc(F)c(Cl)c1)CC3]

Step 1. 10-methyl-8-methylene-3,4,7,8,9,10-hexahydro-1H-pyrido[4',3':3,4]pyrazolo[1,5-a][1,4]diazepin-11 (2H)-one To a solution of tert-butyl 10-methyl-8-methylene-11-oxo-3,4,7,9-tetrahydro-1H-pyrido[2,3]pyrazolo[2,4-b][1,4]diazepine-2-carboxylate (Intermediate 1, 312.00 mg, 938.63 μmol, 1.00 eq) in DCM (3.00 mL) was added TFA (4.62 g, 40.52 mmol, 3.00 mL, 43.17 eq) under $N_2$ and the mixture was stirred at 15° C. for 1 h. The mixture was concentrated in vacuo to afford the title compound (325.00 mg, crude, TFA) as yellow oil, which was used directly for the next step.

Step 2. N-(3-chloro-4-fluorophenyl)-10-methyl-8-methylene-11-oxo-3,4,8,9,10,11-hexahydro-1H-pyrido[4',3':3,4]pyrazolo[1,5-a][1,4]diazepine-2 (7H)-carboxamide A mixture of 10-methyl-8-methylene-1,2,3,4,7,9-hexahydropyrido[2,3]pyrazolo [2,4-b][1,4]diazepin-11-one (325.00 mg, 938.49 µmol, 1.00 eq, TFA), Et₃N (474.83 mg, 4.69 mmol, 650.45 µL, 5.00 eq) and phenyl N-(3-chloro-4-fluorophenyl)carbamate (249.33 mg, 938.49 µmol, 1.00 eq) in DCM (5.00 mL) was stirred at 10° C. for 16 h. LCMS indicated the starting material/desired product=2/1. The mixture was heated to 30° C. for another 16 h. LCMS indicated the starting material/desired product=1/2. The mixture was heated to 40° C. for another 16 h. TLC (DCM/MeOH=8/1) indicated the starting material was consumed completely. The mixture was diluted with DCM (60 mL) and washed with HCl (1 M, 60 mL). The organic phase was dried over Na₂SO₄, filtered and concentrated in vacuo to give yellow oil. The oil was purified by silica gel column to afford the title compound (320.00 mg, 792.39 µmol, 84.43% yield) as yellow solid. LCMS: 404/406 [M+1].

Step 3. N-(3-chloro-4-fluorophenyl)-8-hydroxy-8-(hydroxymethyl)-10-methyl-11-oxo-1,3,4,7,8,9,10,11-octahydro-2H-pyrido[4',3':3,4]pyrazolo[1,5-a][1,4]diazepine-2-carboxamide To a solution of N-(3-chloro-4-fluoro-phenyl)-10-methyl-8-methylene-11-oxo-3,4,7,9-tetrahydro-1H-pyrido[2,3]pyrazolo[2,4-b][1,4]diazepine-2-carboxamide (50.00 mg, 123.81 µmol, 1.00 eq) in acetone (3.00 mL) and H₂O (1.50 mL) was added K₂OsO₄·2H₂O (2.28 mg, 6.19 µmol, 0.05 eq) and NMO (58.02 mg, 495.24 µmol, 52.27 µL, 4.00 eq) at 0° C. The mixture was stirred at 10° C. for 16 h. The mixture was quenched with saturated NaHSO₃ (40 mL) and extracted with EtOAc (40 mL). The organic phase was dried over Na₂SO₄, filtered and concentrated in vacuo to give black oil. The oil was purified by prep-HPLC(FA) to afford the title compound (26.00 mg, 59.38 µmol, 47.96% yield, 100% purity) as white solid. ¹H NMR (400 MHz, CDCl₃) δ 7.57 (dd, J=2.69, 6.48 Hz, 1H), 7.14-7.22 (m, 1H), 7.02-7.10 (m, 1H), 6.56 (s, 1H), 4.67 (d, J=4.52 Hz, 2H), 4.31-4.41 (m, 1H), 4.18-4.29 (m, 1H), 3.84 (d, J=7.95 Hz, 2H), 3.67-3.74 (m, 1H), 3.58-3.66 (m, 1H), 3.34-3.45 (m, 1H), 3.26-3.34 (m, 1H), 3.22 (s, 3H), 3.02 (br. s., 1H), 2.83 (t, J=5.81 Hz, 2H), 2.32-2.50 (m, 1H). LCMS: 438/440 [M+1].

Compound 004: N-(3-chloro-4-fluorophenyl)-8-hydroxy-10-methyl-11-oxo-1,3,4,7,8,9,10,11-octahydro-2H-pyrido[4',3':3,4]pyrazolo[1,5-a][1,4]diazepine-2-carboxamide Step 1. 8-hydroxy-10-methyl-2,3,4,7,8,9-hexahydro-1H-pyrido[2,3]pyrazolo [2,4-b][1,4]diazepin-11-one To a solution of tert-butyl 8-hydroxy-10-methyl-11-oxo-1,3,4,7,8,9-hexahydropyrido[2,3]pyrazolo[2,4-b][1,4]diazepine-2-carboxylate (Intermediate 3, 49.00 mg, 145.66 µmol, 1.00 eq) in DCM (2.00 mL) was added TFA (3.08 g, 27.01 mmol, 2.00 mL, 185.45 eq) and the mixture was stirred at 15° C. under N₂ for 1 h. LCMS indicated the starting material was consumed completely. The mixture was concentrated in vacuo to afford desired product (51.00 mg, 145.59 µmol, 99.95% yield, TFA) as yellow oil, which was used directly for the next step.

Step 2. N-(3-chloro-4-fluorophenyl)-8-hydroxy-10-methyl-11-oxo-1,3,4,7,8,9,10,11-octahydro-2H-pyrido[4',3':3,4]pyrazolo[1,5-a][1,4]diazepine-2-carboxamide A mixture of 8-hydroxy-10-methyl-2,3,4,7,8,9-hexahydro-1H-pyrido[2,3]pyrazolo [2,4-b][1,4]diazepin-11-one (51.00 mg, 145.59 µmol, 1.00 eq, TFA), Et₃N (73.66 mg, 727.95 µmol, 100.90 µL, 5.00 eq) and phenyl N-(3-chloro-4-fluoro-phenyl) carbamate (38.68 mg, 145.59 µmol, 1.00 eq) in DCM (4.00 mL) was stirred at 10° C. for 16 h. The mixture was diluted with DCM (40 mL) and washed with HCl (1M, 40 mL). The organic phase was dried over Na₂SO₄, filtered and concentrated in vacuo to give yellow oil. The oil was purified by prep-HPLC (FA) to afford the title compound (35.00 mg, 84.10 µmol, 57.77% yield, 98% purity) as white solid. ¹H NMR (400 MHz, CDCl₃) δ 7.58 (dd, J=2.63, 6.54 Hz, 1H), 7.15-7.22 (m, 1H), 7.02-7.10 (m, 1H), 6.51 (s, 1H), 4.68 (d, J=2.69 Hz, 2H), 4.53-4.64 (m, 2H), 4.26 (d, J=9.17 Hz, 1H), 3.85 (t, J=5.81 Hz, 2H), 3.59 (dd, J=4.10, 15.22 Hz, 1H), 3.35 (dd, J=5.44, 15.22 Hz, 1H), 3.22 (s, 3H), 2.85 (t, J=5.75 Hz, 2H), 2.10 (br. s., 1H). LCMS: 408/410 [M+1].

Compound 005: N-(3-chloro-4-fluorophenyl)-8,8-difluoro-10-methyl-11-oxo-1,3,4,7,8,9,10,11-octahydro-2H-pyrido[4',3':3,4]pyrazolo[1,5-a][1,4]diazepine-2-carboxamide

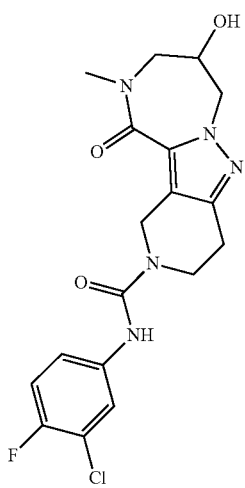 [SMILES: CN1CC(O)Cn2nc3c(c2C1=O)CN(C(=O)Nc1ccc(F)c(Cl)c1)CC3]

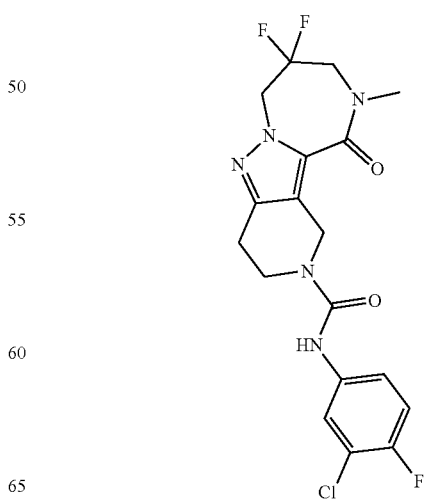

Step 1. tert-butyl 8,8-difluoro-10-methyl-11-oxo-3,4,8,9,10,11-hexahydro-1H-pyrido[4',3':3,4]pyrazolo[1,5-a][1,4]diazepine-2 (7H)-carboxylate To a solution of tert-butyl 10-methyl-8,11-dioxo-3,4,7,9-tetrahydro-1H-pyrido[2,3]pyrazolo[2,4-b][1,4]diazepine-2-carboxylate (Intermediate 2, 80.00 mg, 239.26 μmol, 1.00 eq) in DCM (4.00 mL) was added DAST (115.70 mg, 717.78 μmol, 94.84 μL, 3.00 eq) at −30° C. The mixture was stirred at 15° C. for 16 h. The mixture was diluted with brine (30 mL), extracted with DCM (30 mL*2). The organic phase was dried over Na$_2$SO$_4$, filtered and concentrated in vacuo to give yellow oil. The oil was purified by prep-TLC to afford the title compound (60.00 mg, 153.21 μmol, 64.04% yield, 91% purity) as yellow solid. LCMS: 379[M+23].

Step 2. 8,8-difluoro-10-methyl-3,4,7,8,9,10-hexahydro-1H-pyrido[4',3':3,4]pyrazolo [1,5-a][1,4]diazepin-11 (2H)-one To a solution of tert-butyl 8,8-difluoro-10-methyl-11-oxo-3,4,7,9-tetrahydro-1H-pyrido[2,3]pyrazolo[2,4-b][1,4]diazepine-2-carboxylate (60.00 mg, 168.36 μmol, 1.00 eq) in DCM (2.00 mL) was added TFA (3.08 g, 27.01 mmol, 2.00 mL, 160.45 eq) and the mixture was stirred at 15° C. under N$_2$ for 1 h. The mixture was concentrated in vacuo to afford the title compound (62.00 mg, 150.70 μmol, 89.51% yield, 90% purity, TFA) as yellow oil, which was used directly for the next step. LCMS: 257 [M+1].

Step 3. N-(3-chloro-4-fluorophenyl)-8,8-difluoro-10-methyl-11-oxo-1,3,4,7,8,9,10,11-octahydro-2H-pyrido[4',3':3,4]pyrazolo[1,5-a][1,4]diazepine-2-carboxamide A mixture of 8,8-difluoro-10-methyl-1,2,3,4,7,9-hexahydropyrido[2,3]pyrazolo [2,4-b][1,4]diazepin-11-one (62.00 mg, 167.45 mol, 1.00 eq, TFA), Et$_3$N (84.72 mg, 837.23 μmol, 116.05 μL, 5.00 eq) and phenyl N-(3-chloro-4-fluorophenyl) carbamate (44.49 mg, 167.45 μmol, 1.00 eq) in DCM (4.00 mL) was stirred at 15° C. for 16 h. The mixture was diluted with DCM (40 mL) and washed with HCl (1 M, 40 mL). The organic phase was dried over Na$_2$SO$_4$, filtered and concentrated in vacuo to give yellow oil. The oil was purified by prep-HPLC (FA) to afford the title compound (37.00 mg, 86.31 μmol, 51.55% yield, 99.8% purity) as white solid. $^1$H NMR (400 MHz, CDCl$_3$) δ 7.58 (dd, J=2.57, 6.48 Hz, 1H), 7.16-7.24 (m, 1H), 7.03-7.12 (m, 1H), 6.46 (s, 1H), 4.60-4.80 (m, 4H), 3.86 (t, J=5.75 Hz, 2H), 3.72 (t, J=12.29 Hz, 2H), 3.25 (s, 3H), 2.88 (t, J=5.81 Hz, 2H). LCMS: 428/430[M+1].

Compound 006: N-(3-chloro-4-fluorophenyl)-8-fluoro-10-methyl-11-oxo-1,3,4,7,8,9,10,11-octahydro-2H-pyrido[4',3':3,4]pyrazolo[1,5-a][1,4]diazepine-2-carboxamide

Step 1. tert-butyl 8-fluoro-10-methyl-11-oxo-3,4,8,9,10,11-hexahydro-1H-pyrido[4',3':3,4]pyrazolo[1,5-a][1,4]diazepine-2 (7H)-carboxylate To a solution of tert-butyl 8-hydroxy-10-methyl-11-oxo-1,3,4,7,8,9-hexahydropyrido[2,3]pyrazolo[2,4-b][1,4]diazepine-2-carboxylate (Intermediate 3, 80.00 mg, 237.82 μmol, 1.00 eq) in DCM (4.00 mL) was added DAST (153.34 mg, 951.28 μmol, 125.69 μL, 4.00 eq) at −30° C. The mixture was stirred at 15° C. for 16 h. TLC indicated the starting material was consumed completely and one major new spot with lower polarity was detected. The mixture was diluted with brine (30 mL), extracted with DCM (30 mL*2). The organic phase was dried over Na$_2$SO$_4$, filtered and concentrated in vacuo to give yellow oil. The oil was purified by prep-TLC to afford the title compound (56.00 mg, 162.18 μmol, 68.20% yield, 98% purity) as yellow solid. LCMS: 361[M+23].

Step 2. 8-fluoro-10-methyl-3,4,7,8,9,10-hexahydro-1H-pyrido[4',3':3,4]pyrazolo[1,5-a][1,4]diazepin-11 (2H)-one To a solution of tert-butyl 8-fluoro-10-methyl-11-oxo-1,3,4,7,8,9-hexahydropyrido[2,3]pyrazolo[2,4-b][1,4]diazepine-2-carboxylate (56.00 mg, 165.49 μmol, 1.00 eq) in DCM (1.00 mL) was added TFA (1.54 g, 13.51 mmol, 1.00 mL, 81.61 eq) and the mixture was stirred at 15° C. under N$_2$ for 1 h. TLC showed the reactant was consumed completely and one major new spot with larger polarity was detected. The mixture was concentrated in vacuo to afford 8-fluoro-10-methyl-2,3,4,7,8,9-hexahydro-1H-pyrido[2,3]pyrazolo[2,4-b][1,4]diazepin-11-one (59.00 mg, 150.73 μmol, 91.08% yield, 90% purity, TFA) as yellow oil, which was used directly for the next step. LCMS: 239 [M+1].

Step 3. N-(3-chloro-4-fluorophenyl)-8-fluoro-10-methyl-11-oxo-1,3,4,7,8,9,10,11-octahydro-2H-pyrido[4',3':3,4]pyrazolo[1,5-a][1,4]diazepine-2-carboxamide A mixture of 8-fluoro-10-methyl-2,3,4,7,8,9-hexahydro-1H-pyrido[2,3]pyrazolo [2,4-b][1,4]diazepin-11-one (59.00 mg, 167.48 μmol, 1.00 eq, TFA), Et$_3$N (84.74 mg, 837.40 μmol, 116.08 μL, 5.00 eq) and phenyl N-(3-chloro-4-fluorophenyl) carbamate (44.49 mg, 167.48 μmol, 1.00 eq) in DCM (4.00 mL) was stirred at 15° C. for 16 h. The mixture was diluted with DCM (30 mL) and washed with HCl (1M, 30 mL). The organic phase was dried over Na$_2$SO$_4$, filtered and concentrated in vacuo to give yellow oil, which was purified by prep-HPLC(FA) to afford the title compound (41.00 mg, 99.04 μmol, 59.14% yield, 99% purity) as white solid. LCMS [M+1]: 410. $^1$H NMR (400 MHz, CDCl$_3$) δ 7.59 (dd, J=2.63, 6.54 Hz, 1H), 7.17-7.23 (m, 1H), 7.02-7.10 (m, 1H), 6.63 (s, 1H), 4.64-4.85 (m, 2H), 4.34-4.62 (m, 4H), 3.95-4.08 (m, 1H), 3.86 (q, J=5.42 Hz, 2H), 3.22 (s, 3H), 2.87 (br t, J=5.69 Hz, 2H).

Compounds 007, 008, 009, 010, 011, 012, and 013 were prepared in manner analogous to Compound 006.

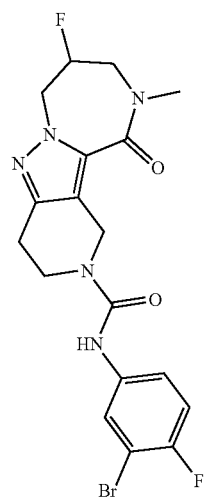 [SMILES: CN1CC(F)(F)Cn2nc3c(c2C1=O)CN(C(=O)Nc1ccc(F)c(Cl)c1)CC3]
007
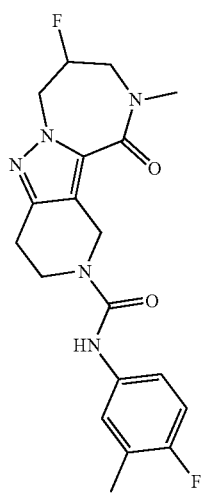
010
-continued
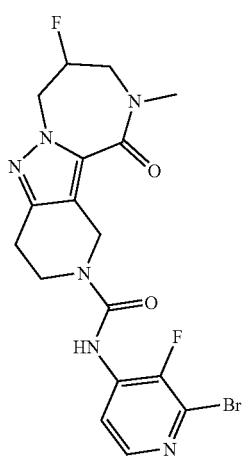
008
011
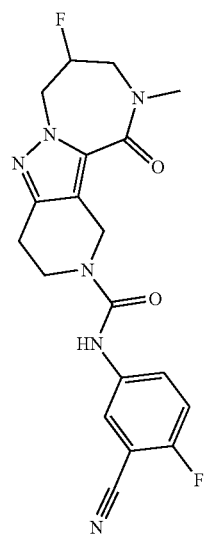
009
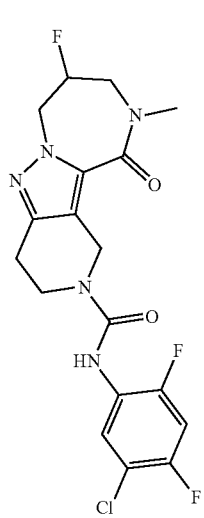
012

161

-continued

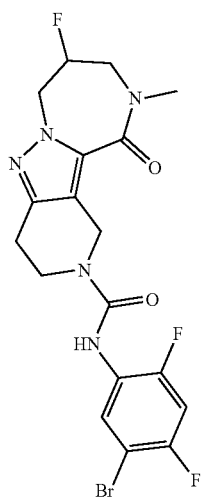
013

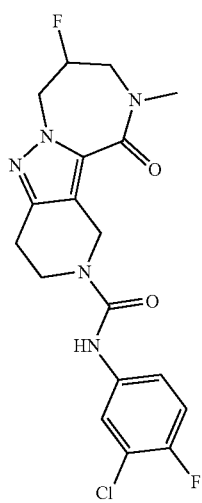
006

Compound 007: N-(3-bromo-4-fluorophenyl)-8-fluoro-10-methyl-11-oxo-1,3,4,7,8,9,10,11-octahydro-2H-pyrido[4',3':3,4]pyrazolo[1,5-a][1,4]diazepine-2-carboxamide LCMS [M+1]: 454. $^1$H NMR (400 MHz, CDCl$_3$) δ=7.71-7.73 (m, 1H) 7.27-7.29 (m, 1H) 7.04 (t, J=8.4 Hz, 1H) 6.71 (s, 1H) 4.66-4.81 (m, 2H) 4.38-4.52 (m, 4H) 3.87-3.89 (m, 1H) 3.83-3.86 (m, 2H) 3.21 (s, 3H) 2.85-2.88 (m, 2H)

162

Compound 008: N-(2-bromo-3-fluoropyridin-4-yl)-8-fluoro-10-methyl-11-oxo-1,3,4,7,8,9,10,11-octahydro-2H-pyrido[4',3':3,4]pyrazolo[1,5-a][1,4]diazepine-2-carboxamide LCMS [M+1]: 455. $^1$H NMR (400 MHz, CDCl$_3$) δ=8.15 (t, J=5.4 Hz, 1H) 8.06 (d, J=5.6 Hz, 1H) 7.06-7.07 (m, 1H) 4.79-4.87 (m, 2H) 4.37-4.51 (m, 4H) 3.87-3.89 (m, 1H) 3.84-3.86 (m, 2H) 3.21 (s, 3H) 2.90 (t, J=5.6 Hz, 2H).

Compound 009: N-(3-cyano-4-fluorophenyl)-8-fluoro-10-methyl-11-oxo-1,3,4,7,8,9,10,11-octahydro-2H-pyrido[4',3':3,4]pyrazolo[1,5-a][1,4]diazepine-2-carboxamide LCMS [M+1]: 401. $^1$H NMR (400 MHz, CDCl$_3$) δ=7.77-7.80 (m, 1H) 7.61-7.62 (m, 1H) 7.13 (t, J=8.6 Hz, 1H) 6.99 (s, 1H) 4.82 (d, J=16 Hz, 1H) 4.68 (d, J=15.6 Hz, 1H) 4.46-4.51 (m, 4H) 3.81-3.90 (m, 2H) 3.21 (s, 3H) 2.85-2.88 (m, 2H).

Compound 010: 8-fluoro-N-(4-fluoro-3-methylphenyl)-10-methyl-11-oxo-1,3,4,7,8,9,10,11-octahydro-2H-pyrido[4',3':3,4]pyrazolo[1,5-a][1,4]diazepine-2-carboxamide LCMS [M+1]: 390. $^1$H NMR (400 MHz, CDCl$_3$) δ=7.24-7.25 (m, 1H) 7.10-7.13 (m, 1H) 6.92 (t, J=9.0 Hz, 1H) 4.67-4.80 (m, 2H) 4.38-4.52 (m, 4H) 3.86-3.87 (m, 1H) 3.84-3.85 (m, 1H) 3.21 (s, 3H) 2.85-2.88 (m, 2H) 2.25 (s, 3H).

Compound 011: 8-fluoro-N-(4-fluoro-3-(trifluoromethyl)phenyl)-10-methyl-11-oxo-1,3,4,7,8,9,10,11-octahydro-2H-pyrido[4',3':3,4]pyrazolo[1,5-a][1,4]diazepine-2-carboxamide LCMS [M+1]: 444. $^1$H NMR (400 MHz, CDCl$_3$) δ=7.68-7.70 (m, 1H) 7.59-7.61 (m, 1H) 7.13 (t, J=9.4 Hz, 1H) 6.8 (s, 1H) 4.82 (d, J=15.6 Hz, 1H) 4.70 (d, J=16 Hz, 1H) 4.39-4.52 (m, 4H) 3.90-3.92 (m, 1H) 3.84-3.89 (m, 2H) 3.22 (s, 3H) 2.87 (t, J=5.4 Hz, 2H).

Compound 012: N-(5-chloro-2,4-difluorophenyl)-8-fluoro-10-methyl-11-oxo-1,3,4,7,8,9,10,11-octahydro-2H-pyrido[4',3':3,4]pyrazolo[1,5-a][1,4]diazepine-2-carboxamide LCMS [M+1]: 428. $^1$H NMR (400 MHz, CDCl$_3$) δ=8.17 (t, J=8.0 Hz, 1H) 6.95 (t, J=5.6 Hz, 1H) 6.6 (s, 1H) 4.75-4.83 (m, 2H) 4.46-4.50 (m, 4H) 3.90-4.00 (m, 1H) 3.83-3.89 (m, 2H) 3.21 (s, 3H) 2.87-2.90 (m, 2H).

Compound 013: N-(5-bromo-2,4-difluorophenyl)-8-fluoro-10-methyl-11-oxo-1,3,4,7,8,9,10,11-octahydro-2H-pyrido[4',3':3,4]pyrazolo[1,5-a][1,4]diazepine-2-carboxamide LCMS [M+1]: 472. $^1$H NMR (400 MHz, CDCl$_3$) δ=8.31 (t, J=7.8 Hz, 1H) 6.91-6.96 (m, 1H) 6.61 (s, 1H) 4.71-4.83 (m, 2H) 4.46-4.51 (m, 4H) 3.87-3.88 (m, 1H) 3.84-3.86 (m, 2H) 3.21 (s, 3H) 2.88 (t, J=5.6 Hz, 2H).

Compound 014: N-(3-chloro-4-fluoro-phenyl)-8,10-dimethyl-11-oxo-1,3,4,7,8,9-hexahydropyrido[2,3]pyrazolo[2,4-b][1,4]diazepine-2-carboxamide

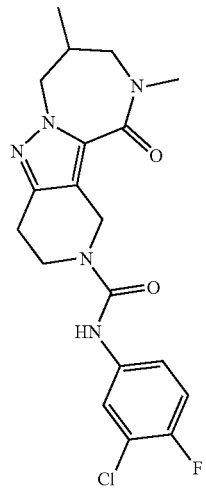 [SMILES: CC1CN(C)C(=O)c2c3c(nn2C1)CCN(C(=O)Nc1ccc(F)c(Cl)c1)C3]

Step 1. tert-butyl 3-[methyl-[2-(methylsulfonyloxymethyl)allyl]carbamoyl]-2,4,6,7-tetrahydropyrazolo[4,3-c]pyridine-5-carboxylate To a solution of tert-butyl 3-[2-(hydroxymethyl)allyl-methyl-carbamoyl]-2,4,6,7-tetrahydropyrazolo[4,3-c]pyridine-5-carboxylate (100.00 mg, 285.38 μmol, 1.00 eq) and Et₃N (57.76 mg, 570.76 μmol, 79.12 μL, 2.00 eq) in DCM (3.00 mL) was added a solution of MsCl (49.04 mg, 428.07 μmol, 33.14 μL, 1.50 eq) in DCM (1.00 mL) at 0° C. under N₂ and the mixture was stirred for another 1 h. The mixture was diluted with EtOAc (40 mL) and washed with brine (30 mL*2). The organic phase was dried over Na₂SO₄, filtered and concentrated in vacuo to afford the title compound (120.00 mg, crude), which was used directly for the next step.

Step 2. tert-butyl 8,10-dimethyl-11-oxo-3,4,10,11-tetrahydro-1H-pyrido[4',3':3,4]pyrazolo[1,5-a][1,4]diazepine-2 (9H)-carboxylate and tert-butyl 8,10-dimethyl-11-oxo-3,4,10,11-tetrahydro-1H-pyrido[4',3':3,4]pyrazolo[1,5-a][1,4]diazepine-2 (7H)-carboxylate To a solution of tert-butyl 3-[methyl-[2-(methylsulfonyloxymethyl)allyl]carbamoyl]-2,4,6,7-tetrahydropyrazolo[4,3-c]pyridine-5-carboxylate (40.00 mg, 93.35 μmol, 1.00 eq) in DMF (2.00 mL) was added t-BuOK (15.71 mg, 140.03 μmol, 1.50 eq) and the mixture was stirred at 50° C. for 16 h. TLC showed the starting material was consumed completely and one major new spot with larger polarity was detected. LCMS indicated two peaks with desired Ms. The mixture was diluted with EtOAc (30 mL) and washed with HCl (1 M, 30 mL). The organic phase was dried over Na₂SO₄, filtered and concentrated in vacuo to give oil. The oil was purified by prep-HPLC (FA) to afford tert-butyl 8,10-dimethyl-11-oxo-1,3,4,7-tetrahydropyrido[2,3]pyrazolo [2,4-b][1,4]diazepine-2-carboxylate (8.00 mg, 24.07 μmol, 25.78% yield). ¹H NMR (400 MHz, CDCl₃) δ 5.89 (s, 1H), 4.63-4.65 (m, 4H), 3.70 (s, 2H), 3.22 (s, 3H), 2.73 (s, 2H), 1.94 (s, 3H), 1.48 (s, 9H) and tert-butyl 8,10-dimethyl-11-oxo-1,3,4,9-tetrahydropyrido[2,3]pyrazolo[2,4-b][1,4]diazepine-2-carboxylate (8.00 mg, 24.07 μmol, 25.78% yield) (8.00 mg). ¹H NMR (400 MHz, CDCl₃) δ 5.91 (s, 1H), 4.64-4.66 (m, 4H), 3.72 (s, 2H), 3.24 (s, 3H), 2.75 (s, 2H), 1.96 (s, 3H), 1.49 (s, 9H).

Step 3. tert-butyl 8,10-dimethyl-11-oxo-3,4,8,9,10,11-hexahydro-1H-pyrido[4',3':3,4]pyrazolo[1,5-a][1,4]diazepine-2 (7H)-carboxylate A mixture of tert-butyl 8,10-dimethyl-11-oxo-1,3,4,9-tetrahydropyrido[2,3] pyrazolo [2,4-b][1,4]diazepine-2-carboxylate (3.00 mg, 9.03 μmol, 0.11 eq), tert-butyl 8,10-dimethyl-11-oxo-1,3,4,7-tetrahydropyrido[2,3]pyrazolo[2,4-b][1,4]diazepine-2-carboxylate (27.00 mg, 81.23 μmol, 1.00 eq) in MeOH (5.00 mL) was Pd/C (10.00 mg, 4.51 μmol, 0.10 eq) under N₂. The suspension was degassed under vacuum and purged with H₂ several times. The mixture was stirred under H₂ (50 psi) at 25° C. for 16 hr. LCMS showed the starting material was consumed completely, the desired product was major. The reaction mixture was diluted with DCM/MeOH=1/1 (50 mL) and filtered. The filtrate was concentrated to give the title compound (15.00 mg, 44.86 μmol, 99.40% yield) as a white solid, which was used directly for the next step. ¹H NMR (400 MHz, CDCl₃) δ 4.61 (br. s., 2H) 4.37 (dd, J=14.05, 6.78 Hz, 1H) 3.95 (dd, J=13.99, 5.58 Hz, 1H) 3.60-3.81 (m, 2H) 3.33-3.46 (m, 1H) 3.17 (s, 3H) 3.03-3.12 (m, 1H) 2.75 (br. s., 2H) 2.52-2.66 (m, 1H) 1.44-1.54 (m, 9H) 1.10 (d, J=6.78 Hz, 3H). LCMS: 335 [M+1].

Step 4. 8,10-dimethyl-3,4,7,8,9,10-hexahydro-1H-pyrido[4',3':3,4]pyrazolo[1,5-a][1,4]diazepin-11 (2H)-one A mixture of tert-butyl 8,10-dimethyl-11-oxo-1,3,4,7,8,9-hexahydropyrido [2,3]pyrazolo[2,4-b][1,4]diazepine-2-carboxylate (38.00 mg, 113.63 μmol, 1.00 eq) in DCM (2.00 mL) was added TFA (1.54 g, 13.51 mmol, 1.00 mL, 118.86 eq), and then the mixture was stirred at 10° C. for 1 hour. TLC showed the starting material was consumed completely and a new spot appeared. The mixture was concentrated in vacuum to give the title compound as the TFA salt (39.58 mg, 113.63 μmol, 100.00% yield) as a yellow oil, which was used directly for the next step.

Step 5. N-(3-chloro-4-fluoro-phenyl)-8,10-dimethyl-11-oxo-1,3,4,7,8,9-hexahydropyrido[2,3]pyrazolo[2,4-b][1,4]diazepine-2-carboxamide A mixture of 8,10-dimethyl-2,3,4,7,8,9-hexahydro-1H-pyrido[2,3]pyrazolo[2,4-b][1,4]diazepin-11-one (39.58 mg, 113.63 μmol, 1.00 eq, TFA), phenyl N-(3-chloro-4-fluoro-phenyl)carbamate (45.28 mg, 170.45 μmol, 1.50 eq), TEA (23.00 mg, 227.26 μmol, 31.51 μL, 2.00 eq) in DCM (3.00 mL) was degassed and purged with N₂ for 3 times, and then the mixture was stirred at 30° C. for 16 hour under N₂ atmosphere. LCMS showed the starting material was consumed completely and desired product was major. The mixture was poured into water (5 mL) and stirred at 5 min. The aqueous phase was extracted with DCM (3 mL*3). The combined organic phase was washed with brine (5 mL), dried with anhydrous Na₂SO₄, filtered and concentrated in vacuum. The residue was purified by prep-HPLC(FA) to give the title compound (15.00 mg, 36.59 μmol, 32.20% yield, 99% purity) as a white solid. ¹H NMR (400 MHz, CDCl$_3$) δ 7.56-7.61 (m, 1H) 7.16-7.23 (m, 1H) 7.01-7.09 (m, 1H) 6.60 (s, 1H) 4.67 (s, 2H) 4.37-4.48 (m, 1H) 3.99 (dd, J=14.06, 5.87 Hz, 1H) 3.79-3.92 (m, 2H) 3.39-3.47 (m, 1H) 3.19 (s, 3H) 3.13 (s, 1H) 2.84 (s, 2H) 2.57-2.69 (m, 1H) 1.13 (d, J=6.85 Hz, 3H). LCMS: 406 [M+1].

Compound 015: N-(3-chloro-4-fluoro-phenyl)-10-methyl-11-oxo-1,3,4,7,8,9-hexahydropyrido [2,3] pyrazolo[2,4-b][1,4]diazepine-2-carboxamide

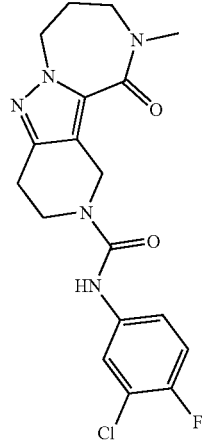 [SMILES: CN1CCCn2nc3c(c2C1=O)CN(C(=O)Nc1ccc(F)c(Cl)c1)CC3]

Step 1. 10-methyl-2,3,4,7,8,9-hexahydro-1H-pyrido[2,3]pyrazolo[2,4-b][1.4]diazepin-11-one Tert-butyl 10-methyl-11-oxo-1,3,4,7,8,9-hexahydro-pyrido[2,3]pyrazolo[2,4-b][1,4] diazepine-2-carboxylate (Intermediate 4, 40.00 mg, 124.85 µmol, 1.00 eq) was dissolved in TFA (2.46 g, 21.61 mmol, 1.60 mL, 173.09 eq) and stirred at 10° C. for 1 hr. TLC (DCM:MeOH=10:1) showed the starting material consumed. The mixture was concentrated in vacuum. The residue was concentrated in vacuum to get 10-methyl-2,3,4,7,8,9-hexahydro-1H-pyrido[2,3]pyrazolo[2,4-b][1,4]diazepin-11-one as the TFA salt (42.00 mg, crude) as colorless oil.

Step 2. N-(3-chloro-4-fluoro-phenyl)-10-methyl-11-oxo-1,3,4,7,8,9-hexahydropyrido [2,3]pyrazolo[2,4-b][1,4]diazepine-2-carboxamide To a solution of 10-methyl-2,3,4,7,8,9-hexahydro-1H-pyrido[2,3]pyrazolo[2,4-b][1,4] diazepin-11-one (42.00 mg, 125.64 µmol, 1.00 eq, TFA) in DCM (3.00 mL) was added phenyl N-(3-chloro-4-fluoro-phenyl)carbamate (33.38 mg, 125.64 µmol, 1.00 eq) followed by TEA (63.57 mg, 628.20 µmol, 87.08 µL, 5.00 eq). The mixture was stirred at 10° C. for 16 hr. LCMS showed one main peak with desired Ms. The mixture was concentrated in vacuum. The residue was purified by prep-HPLC (FA) to afford title compound (33.00 mg, 84.22 µmol, 67.03% yield, 100% purity) as white solid. $^1$H NMR (400 MHz, METHANOL-d$_4$) δ=7.60 (dd, J=2.6, 6.7 Hz, 1H), 7.31 (ddd, J=2.6, 4.1, 9.0 Hz, 1H), 7.11-7.19 (m, 1H), 4.70 (s, 2H), 4.37 (t, J=7.0 Hz, 2H), 3.83 (t, J=5.8 Hz, 2H), 3.45-3.53 (m, 2H), 3.17 (s, 3H), 2.82 (t, J=5.8 Hz, 2H), 2.28-2.38 (m, 2H).

Compound 016A: (S*)—N-(3-chloro-4-fluorophenyl)-8-methoxy-10-methyl-1-oxo-3,4,8,9,10,11-hexahydro-1H-pyrido[4',3':3,4]pyrazolo[1,5-a][1,4]diazepine-2 (7H)-carboxamide

*pure but unknown stereochemistry E1.

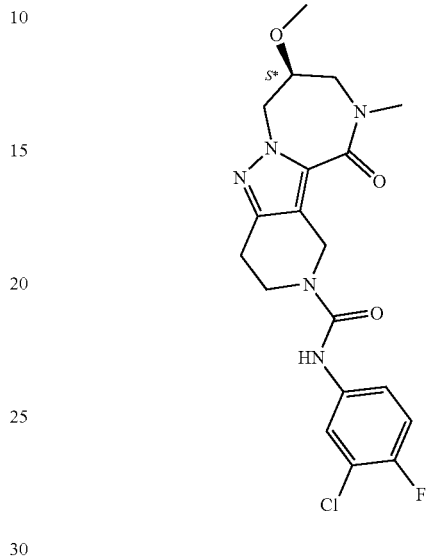

Step 1. tert-butyl 8-methoxy-10-methyl-11-oxo-1,3,4,7,8,9-hexahydropyrido[2,3] pyrazolo[2,4-b][1,4]diazepine-2-carboxylate To a solution of tert-butyl 8-hydroxy-10-methyl-11-oxo-1,3,4,7,8,9-hexahydropyrido[2,3]pyrazolo[2,4-b][1,4]diazepine-2-carboxylate (Intermediate 3, 90.00 mg, 267.55 µmol, 1.00 eq) in THF (4.00 mL) was added NaH (16.05 mg, 401.32 µmol, 60% purity, 1.50 eq) at 0° C., followed by MeI (75.95 mg, 535.09 µmol, 33.31 µL, 2.00 eq) after 0.5 h. The mixture was stirred at 15° C. for 1 h. The mixture was diluted with brine (30 mL), extracted with EtOAc (30 mL, *2). The organic phase was dried over Na$_2$SO$_4$, filtered and concentrated in vacuo to give yellow oil, which was purified by prep-TLC to the title compound (70.00 mg, 184.78 µmol, 69.07% yield, 92.5% purity) as yellow solid. LCMS: 373 [M+23].

Step 2. 8-methoxy-10-methyl-2,3,4,7,8,9-hexahydro-1H-pyrido[2,3]pyrazolo [2,4-b][1,4]diazepin-11-one To a solution of tert-butyl 8-methoxy-10-methyl-11-oxo-1,3,4,7,8,9-hexahydropyrido[2,3]pyrazolo[2,4-b][1,4]diazepine-2-carboxylate (70.00 mg, 199.77 µmol, 1.00 eq) in DCM (2.00 mL) was added TFA (3.08 g, 27.01 mmol, 2.00 mL, 135.22 eq) and the mixture was stirred at 15° C. under N$_2$ for 1 h. The mixture was concentrated in vacuo to afford the title compound as the TFA salt (72.00 mg, 177.87 µmol, 89.04% yield, 90% purity) as yellow oil, which was used directly for the next step. LCMS: 251[M+1].

Step 3. (S*)—N-(3-chloro-4-fluorophenyl)-8-methoxy-10-methyl-11-oxo-3,4,8,9,10,11-hexahydro-1H-pyrido[4',3':3,4]pyrazolo[1,5-a][1,4]diazepine-2 (7H)-carboxamide A mixture of 8-methoxy-10-methyl-2,3,4,7,8,9-hexahydro-1H-pyrido[2,3]pyrazolo[2,4-b][1,4]diazepin-11-one (77.00 mg, 211.35 μmol, 1.00 eq, TFA), Et$_3$N (106.93 mg, 1.06 mmol, 146.48 μL, 5.00 eq) and phenyl N-(3-chloro-4-fluoro-phenyl)carbamate (56.15 mg, 211.35 μmol, 1.00 eq) in DCM (4.00 mL) was stirred at 15° C. for 16 h. The mixture was diluted with DCM (30 mL*2) and washed with HCl (1 N, 30 mL). The organic phase was dried over Na$_2$SO$_4$, filtered and concentrated in vacuo to give yellow oil. The oil was purified by prep-HPLC (FA) to get 48 mg of desired product which was resolved via SFC (OD-3S_4_40_3ML Column: Chiralcel OD-3 100×4.6 mm I.D., 3 um Mobile phase: 40% iso-propanol (0.05% DEA) in CO$_2$ Flow rate: 3 mL/min Wavelength: 220 nm) and further purified by prep-HPLC(FA) to get both enantiomers Compound 016_E1 (17.9 mg) and Compound 016_E2 (15.4 mg). LCMS: 422/424 [M+1]. $^1$H NMR (400 MHz, CDCl$_3$) δ 7.59 (dd, J=2.63, 6.54 Hz, 1H), 7.16-7.23 (m, 1H), 7.03-7.10 (m, 1H), 6.55 (s, 1H), 4.68 (d, J=5.26 Hz, 2H), 4.57 (dd, J=6.24, 14.43 Hz, 1H), 4.29 (dd, J=5.93, 14.37 Hz, 1H), 4.08 (br t, J=5.01 Hz, 1H), 3.86 (q, J=5.75 Hz, 2H), 3.40-3.58 (m, 5H), 3.21 (s, 3H).

Compound 016B: (R*)—N-(3-chloro-4-fluorophenyl)-8-methoxy-10-methyl-11-oxo-3,4,8,9,10,11-hexahydro-1H-pyrido[4',3':3,4]pyrazolo[1,5-a][1,4] diazepine-2 (7H)-carboxamide

*pure but unknown stereochemistry E2.

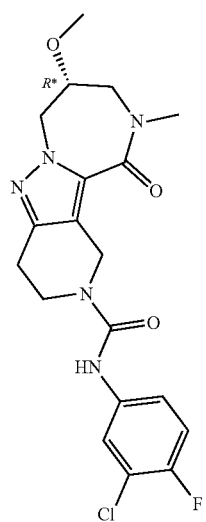 [SMILES: CO[C@@H]1CN(C)C(=O)c2c3c(nn2C1)CCN(C(=O)Nc1ccc(F)c(Cl)c1)C3]

LCMS: 422/424 [M+1]. $^1$H NMR (400 MHz, CDCl$_3$) δ 7.59 (dd, J=2.63, 6.54 Hz, 1H), 7.16-7.23 (m, 1H), 7.03-7.10 (m, 1H), 6.55 (s, 1H), 4.68 (d, J=5.26 Hz, 2H), 4.57 (dd, J=6.24, 14.43 Hz, 1H), 4.29 (dd, J=5.93, 14.37 Hz, 1H), 4.08 (br t, J=5.01 Hz, 1H), 3.86 (q, J=5.75 Hz, 2H), 3.40-3.58 (m, 5H), 3.21 (s, 3H).

Compound 017: N-(3-chloro-4-fluorophenyl)-8-ethoxy-10-methyl-11-oxo-1,3,4,7,8,9,10,11-octahydro-2H-pyrido[4',3':3,4]pyrazolo[1,5-a][1,4]diazepine-2-carboxamide

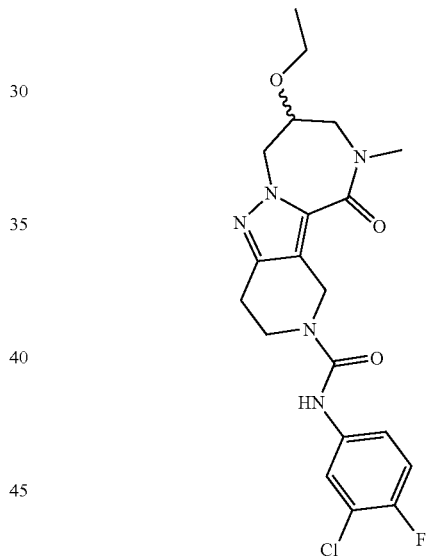

The title compound was prepared in a manner analogous to Compound 016, using EtI instead of MeI in Step 1; to give yellow oil, which was purified by prep-HPLC(FA) to afford the title compound (76.90 mg, 168.13 μmol, 56.80% yield, 95.3% purity) as white solid. $^1$H NMR (400 MHz, CDCl$_3$) δ 7.59 (dd, J=2.64, 6.52 Hz, 1H), 7.20 (ddd, J=2.70, 4.08, 8.91 Hz, 1H), 7.02-7.10 (m, 1H), 6.60 (s, 1H), 4.62-4.76 (m, 2H), 4.57 (dd, J=6.34, 14.24 Hz, 1H), 4.21-4.34 (m, 1H), 4.12-4.21 (m, 1H), 3.86 (t, J=6.27 Hz, 2H), 3.64 (ddt, J=2.13, 7.00, 13.76 Hz, 2H), 3.47 (dq, J=4.58, 15.04 Hz, 2H), 3.21 (s, 3H), 2.85 (q, J=5.48 Hz, 2H), 1.27 (t, J=6.96 Hz, 3H). LCMS: 436/438 [M+1].

Compound 018: N-(3-chloro-4-fluorophenyl)-8-(2,2-difluoroethoxy)-10-methyl-1-oxo-1,3,4,7,8,9,10,11-octahydro-2H-pyrido[4',3':3,4]pyrazolo[1,5-a][1,4]diazepine-2-carboxamide

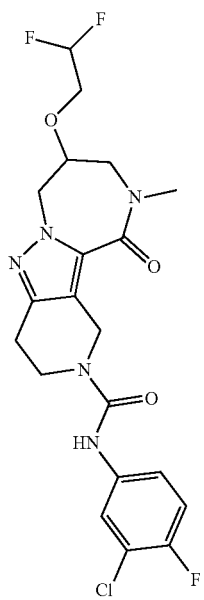 [SMILES: CN1CC(OCC(F)F)Cn2nc3c(c2C1=O)CN(C(=O)Nc1ccc(F)c(Cl)c1)CC3]

The title compound was prepared in a manner analogous to Compound 016, using 2,2-difluoroethyl trifluoromethanesulfonate instead of MeI in Step 1.

Step 1. tert-butyl-8-(2,2-difluoroethoxy)-10-methyl-11-oxo-1,3,4,7,8,9-hexahydropyrido[2,3]pyrazolo[2,4-b][1,4]diazepine-2-carboxylate To a solution of tert-butyl 8-hydroxy-10-methyl-11l-oxo-1,3,4,7,8,9-hexahydropyrido[2,3]pyrazolo[2,4-b][1,4]diazepine-2-carboxylate (100.00 mg, 297.27 µmol, 1.00 eq) in THF (3.00 mL) was added NaH (35.67 mg, 891.82 µmol, 22.70 µL, 60% purity, 3.00 eq) with stirring at 0° C. for 0.5 h under N₂. Then 2,2-difluoroethyl trifluoromethanesulfonate (2.97 mmol, 10.00 eq) in DCM (7.4 mL) was added. The mixture was stirred at 15° C. for 2 h. TLC showed that the starting material was consumed completely and one main spot formed. The mixture was poured into 10 mL of ice water and extracted with EtOAc (10 mL*3). The organic layers was combined and dried over anhydrous Na₂SO₄, filtered and concentrated. The resulting residue combined with another batch reaction mixture (50 mg of starting material) was purified by prep-TLC (PE:EtOAc=1:5) to afford the title compound (140.00 mg, 349.63 µmol, 78.41% yield) as off-white oil.

Step 2. 8-(2,2-difluoroethoxy)-10-methyl-2,3,4,7,8,9-hexahydro-1H-pyrido[2,3]pyrazolo[2,4-b][1,4]diazepin-11-one To a solution of tert-butyl 8-(2,2-difluoroethoxy)-10-methyl-11-oxo-1,3,4,7,8,9-hexahydropyrido[2,3]pyrazolo[2,4-b][1,4]diazepine-2-carboxylate(140.00 mg, 349.63 µmol, 1.00 eq) in DCM (2.00 mL) was added TFA (1.54 g, 13.51 mmol, 1.00 mL, 38.63 eq) with stirring at 15° C. for 1 h. TLC (PE:EtOAc=0:1) showed that the starting material was consumed completely and one major spot formed. The mixture was concentrated in vacuo to give the title compound as the TFA salt (200.00 mg, crude) as yellow oil and directly used in the next step.

Step 3. N-(3-chloro-4-fluorophenyl)-8-(2,2-difluoroethoxy)-10-methyl-11-oxo-1,3,4,7,8,9,10,11-octahydro-2H-pyrido[4',3':3,4]pyrazolo[1,5-a][1,4]diazepine-2-carboxamide To a solution of 8-(2,2-difluoroethoxy)-10-methyl-2,3,4,7,8,9-hexahydro-1H-pyrido[2,3]pyrazolo[2,4-b][1,4]diazepin-11-one (144.86 mg, 349.62 µmol, 1.00 eq, TFA) and phenyl N-(3-chloro-4-fluoro-phenyl)carbamate (102.17 mg, 384.59 µmol, 1.10 eq) in DCM (2.00 mL) was added TEA (283.03 mg, 2.80 mmol, 387.71 µL, 8.00 eq). The mixture was heated to 15° C. with stirring for 16 h. LCMS indicated that reactant 8-(2,2-difluoroethoxy)-10-methyl-2,3,4,7,8,9-hexahydro-1H-pyrido[2,3]pyrazolo[2,4-b][1,4]diazepin-11-one was consumed completely and the desired product was detected. The mixture was diluted with DCM (10 mL) and washed with HCl (1%, 10 mL*2) and brine (10 mL*1). The organic phase was dried over anhydrous Na₂SO₄, filtered and concentrated. The resulting residue was purified by prep-HPLC (FA) to give the title compound (93.60 mg, 189.64 µmol, 54.24% yield, 95.6% purity) as white solid. ¹H NMR (400 MHz, CDCl₃) δ=7.56 (br d, J=5.75 Hz, 1H), 7.14-7.21 (m, 1H), 6.97-7.09 (m, 1H), 6.66 (br s, 1H), 5.73-6.06 (m, 1H), 4.53-4.74 (m, 3H), 4.22-4.32 (m, 2H), 3.70-3.91 (m, 4H), 3.39-3.58 (m, 2H), 3.19 (s, 3H), 2.75-2.89 (m, 2H). LCMS [M+1]: 472.

Compound 019: 8-amino-N-(3-chloro-4-fluorophenyl)-10-methyl-11-oxo-1,3,4,7,8,9,10,11-octahydro-2H-pyrido[4',3':3,4]pyrazolo[1,5-a][1,4]diazepine-2-carboxamide

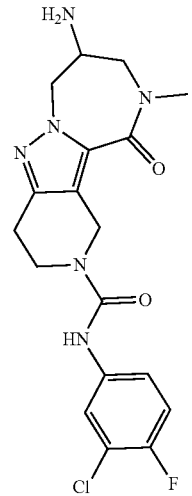 [SMILES: CN1CC(N)Cn2nc3c(c2C1=O)CN(C(=O)Nc1ccc(F)c(Cl)c1)CC3]

Step 1. [2-[(3-chloro-4-fluoro-phenyl)carbamoyl]-10-methyl-11-oxo-1,3,4,7,8,9-hexahydropyrido[2,3]pyrazolo[2,4-b][1,4]diazepin-8-yl]methanesulfonate A mixture of N-(3-chloro-4-fluoro-phenyl)-8-hydroxy-10-methyl-11-oxo-1,3,4,7,8,9-hexahydropyrido[2,3]pyrazolo[2,4-b][1,4]diazepine-2-carboxamide (Compound 004, 200.00 mg, 490.40 µmol, 1.00 eq) and TEA (297.74 mg, 2.94 mmol, 407.87 µL, 6.00 eq) in DCM (5.00 mL) was added MsCl (224.70 mg, 1.96 mmol, 151.83 µL, 4.00 eq) at 0° C. under N₂, and then the mixture was stirred at 15° C. for 16 hours under N₂ atmosphere. The mixture was poured into water (5 mL) and stirred at 5 min. The aqueous phase was extracted with DCM (3 mL*2). The combined organic phase was washed with brine (5 mL), dried with anhydrous Na₂SO₄, filtered and concentrated in vacuum to afford the title compound (200.00 mg, 391.01 µmol, 79.73% yield, 95% purity) as a white solid, which was used directly for the next step. LCMS: 486/488 [M+1].

Step 2. 8-azido-N-(3-chloro-4-fluoro-phenyl)-10-methyl-11-oxo-1,3,4,7,8,9-hexahydro pyrido[2,3]pyrazolo[2,4-b][1,4]diazepine-2-carboxamide To a solution of [2-[(3-chloro-4-fluoro-phenyl)carbamoyl]-10-methyl-11-oxo-1,3,4,7,8,9-hexahydropyrido[2,3]pyrazolo[2,4-b][1,4]diazepin-8-yl]methanesulfonate (120.00 mg, 246.95 µmol, 1.00 eq) in DMF (2.00 mL) was added NaN₃ (32.11 mg, 493.91 µmol, 17.36 µL, 2.00 eq) and the resulting mixture was heated to 65° C. for 32 h. The mixture was diluted with EtOAc (20 mL) and washed with brine (20 mL*3). The organic phase was dried over Na₂SO₄, filtered and concentrated in vacuo to afford the title compound (106.00 mg, crude), which was used directly for the next step. LCMS: 433/435 [M+1].

Step 3. 8-amino-N-(3-chloro-4-fluorophenyl)-10-methyl-11-oxo-1,3,4,7,8,9,10,11-octahydro-2H-pyrido[4',3':3,4]pyrazolo[1,5-a][1,4]diazepine-2-carboxamide A mixture of 8-azido-N-(3-chloro-4-fluoro-phenyl)-10-methyl-11-oxo-1,3,4,7,8,9-hexahydropyrido[2,3]pyrazolo[2,4-b][1,4]diazepine-2-carboxamide (120.00 mg, 277.24 µmol, 1.00 eq), NH₄C₁ (37.07 mg, 693.10 µmol, 24.23 µL, 2.50 eq) and Zn (27.19 mg, 415.86 µmol, 1.50 eq) in H₂O (500.00 uL)/EtOH (5.00 mL) was stirred at 30° C. for 16 hours. The mixture was filtered and the filtrate was concentrated in vacuo. The residue was purified by prep-HPLC(FA) to afford (59.40 mg, 144.54 mol, 52.14% yield, 99% purity) as yellow solid. LCMS: 407/409 [M+1]. ¹H NMR (400 MHz, CDCl₃) δ 8.04 (s, 1H), 7.61 (dd, J=2.64, 6.53 Hz, 1H), 7.18-7.24 (m, 1H), 7.04-7.11 (m, 1H), 6.62 (s, 1H), 4.69 (d, J=3.26 Hz, 2H), 4.54 (dd, J=6.02, 14.30 Hz, 1H), 4.12 (dd, J=4.83, 14.24 Hz, 1H), 3.77-3.92 (m, 3H), 3.54 (dd, J=5.14, 14.81 Hz, 1H), 3.11-3.27 (m, 4H), 2.86 (t, J=5.83 Hz, 2H).

Compound 020: N-(3-chloro-4-fluorophenyl)-8-(dimethylamino)-10-methyl-11-oxo-1,3,4,7,8,9,10,11-octahydro-2H-pyrido[4',3':3,4]pyrazolo[1,5-a][1,4]diazepine-2-carboxamide

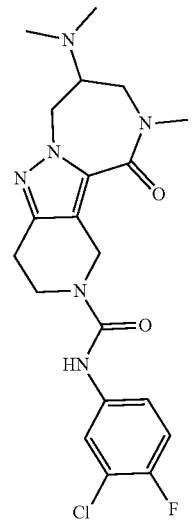 [SMILES: CN1CC(N(C)C)Cn2nc3c(c2C1=O)CN(C(=O)Nc1ccc(F)c(Cl)c1)CC3]

Step 1. tert-butyl 8-(dimethylamino)-10-methyl-11-oxo-1,3,4,7,8,9-hexahydropyrido [2,3]pyrazolo [2,4-b][1,4]diazepine-2-carboxylate To solution of N-methylmethanamine (87.79 mg, 1.08 mmol, 98.64 µL, 3.00 eq, HCl) in THF (3.00 mL) was added AcONa (88.32 mg, 1.08 mmol, 3.00 eq), tert-butyl 10-methyl-8,11-dioxo-3,4,7,9-tetrahydro-1H-pyrido[2,3]pyrazolo[2,4-b][1,4]diazepine-2-carboxylate (Intermediate 2, 120.00 mg, 358.88 µmol, 1.00 eq), tetraethoxytitanium (245.59 mg, 1.08 mmol, 223.26 µL, 3.00 eq) and CH₃COOH (adjusted pH to 6), and the mixture was stirred at 75° C. for 16 h. NaBH₃CN (22.55 mg, 358.88 µmol, 1.00 eq) was added at 15° C. and the mixture was stirred for another 2 h. The mixture was diluted with EtOAc (40 mL) and brine (20 mL) and filtered. The filtrate was washed with brine (40 mL). The organic phase was dried over Na₂SO₄, filtrated and concentrated in vacuo, which was purified by prep-TLC twice to afford the title compound (43.00 mg, 100.56 µmol, 28.02% yield, 85% purity) as yellow oil. ¹H NMR (400 MHz, CDCl₃) δ 4.50-4.60 (m, 2H), 4.46-4.48 (m, 1H), 4.25-4.30 (m, 1H), 3.78-3.82 (m, 1H), 3.52-3.56 (m, 2H), 3.17-3.35 (m, 5H), 2.70-2.80 (m, 2H), 2.35 (s, 6H), 1.49 (s, 9H). LCMS: 364[M+1].

Step 2. 8-(dimethylamino)-10-methyl-2,3,4,7,8,9-hexahydro-1H-pyrido[2,3]pyrazolo[2,4-b][1,4]diazepin-11-one To a solution of tert-butyl8-(dimethylamino)-10-methyl-11-oxo-1,3,4,7,8,9-hexahydropyrido[2,3]pyrazolo[2,4-b][1,4]diazepine-2-carboxylate (43.00 mg, 100.56 µmol, 1.00 eq) in DCM (1.00 mL) was added TFA (1.54 g, 13.51 mmol, 1.00 mL, 134.31 eq) and the mixture was stirred at 15° C. under N₂ for 1 h. TLC showed the reactant was consumed completely and one major new spot with larger polarity was detected. The mixture was concentrated in vacuo to afford the title compound (38.00 mg, crude, TFA) as yellow oil, which was used directly for the next step. LCMS: 264 [M+1].

Step 3. N-(3-chloro-4-fluorophenyl)-8-(dimethylamino)-10-methyl-11-oxo-1,3,4,7,8,9,10,11-octahydro-2H-pyrido[4',3':3,4]pyrazolo[1,5-a][1,4]diazepine-2-carboxamide A mixture of 8-(dimethylamino)-10-methyl-2,3,4,7,8,9-hexahydro-1H-pyrido[2,3]pyrazolo[2,4-b][1,4]diazepin-11-one (38.00 mg, 100.70 µmol, 1.00 eq, TFA), Et$_3$N (50.95 mg, 503.50 µmol, 69.79 µL, 5.00 eq) and phenyl N-(3-chloro-4-fluoro-phenyl)carbamate (26.75 mg, 100.70 µmol, 1.00 eq) in DCM (4.00 mL) was stirred at 15° C. for 16 h. The mixture was diluted with DCM (30 mL) and washed with HCl (1M, 30 mL). The organic phase was dried over Na$_2$SO$_4$, filtered and concentrated in vacuo to give yellow oil. The oil was purified by prep-HPLC (FA) to afford the title compound (33.00 mg, 75.12 µmol, 74.60% yield, 99% purity) as white solid. $^1$H NMR (400 MHz, CDCl$_3$) δ8.10 (s, 1H), 7.60 (dd, J=2.69, 6.48 Hz, 1H), 7.19-7.25 (m, 1H), 7.02-7.11 (m, 1H), 6.71 (s, 1H), 4.53-4.80 (m, 3H), 4.35 (dd, J=6.30, 14.86 Hz, 1H), 3.80-3.93 (m, 2H), 3.54-3.65 (m, 1H), 3.38-3.50 (m, 2H), 3.20 (s, 3H), 2.85 (t, J=5.75 Hz, 2H), 2.42 (s, 6H). LCMS: 435/437[M+1].

Compound 021: N-(3-chloro-4-fluorophenyl)-10-methyl-8-morpholino-11-oxo-1,3,4,7,8,9,10,11-octahydro-2H-pyrido[4',3':3,4]pyrazolo[1,5-a][1,4]diazepine-2-carboxamide

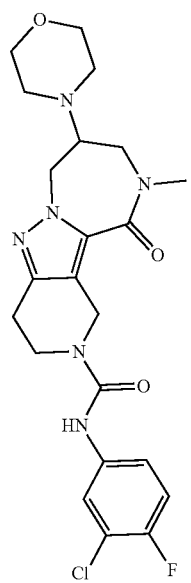 [SMILES: CN1CC(N2CCOCC2)Cn2nc3c(c2C1=O)CN(C(=O)Nc1ccc(F)c(Cl)c1)CC3]

Step 1. tert-butyl 10-methyl-8-morpholino-11-oxo-1,3,4,7,8,9-hexahydropyrido[2,3]pyrazolo[2,4-b][1,4]diazepine-2-carboxylate A mixture of tert-butyl 10-methyl-8,11-dioxo-3,4,7,9-tetrahydro-1H-pyrido[2,3] pyrazolo[2,4-b][1,4]diazepine-2-carboxylate (Intermediate 2, 150.00 mg, 448.60 µmol, 1.00 eq), morpholine (78.16 mg, 897.20 mol, 78.95 µL, 2.00 eq), CH$_3$COOH (26.94 mg, 448.60 µmol, 25.66 µL, 1.00 eq) and 4 A molecular sieve (250.00 mg) in DCE (4.00 mL) was stirred at 20° C. for 3 h. NaBH$_3$CN (140.95 mg, 2.24 mmol, 5.00 eq) was added and the mixture was stirred at 20° C. for 16 h. The mixture was diluted with EtOAc (40 mL) and washed with brine (30 mL). The organic phase was dried over Na$_2$SO$_4$, filtrated and concentrated in vacuo to give oil, which was purified by prep-TLC to afford the title compound (72.00 mg, 174.01 µmol, 38.79% yield, 98% purity) as yellow oil. LCMS: 406[M+1].

Step 2. 10-methyl-8-morpholino-2,3,4,7,8,9-hexahydro-1H-pyrido[2,3]pyrazolo[2,4-b][1,4]diazepin-11-one To a solution of tert-butyl 10-methyl-8-morpholino-11-oxo-1,3,4,7,8,9-hexahydropyrido[2,3]pyrazolo[2,4-b][1,4] diazepine-2-carboxylate (78.00 mg, 192.36 µmol, 1.00 eq) in DCM (2.00 mL) was added TFA (3.08 g, 27.01 mmol, 2.00 mL, 140.43 eq) and the mixture was stirred at 15° C. under N$_2$ for 1 h. The mixture was concentrated in vacuo to afford the title compound as the TFA salt (80.00 mg, 190.75 µmol, 99.16% yield) as yellow oil, which was used directly for the next step.

Step 3. N-(3-chloro-4-fluorophenyl)-10-methyl-8-morpholino-11-oxo-1,3,4,7,8,9,10,11-octahydro-2H-pyrido[4',3':3,4]pyrazolo[1,5-a][1,4]diazepine-2-carboxamide A mixture of 10-methyl-8-morpholino-2,3,4,7,8,9-hexahydro-1H-pyrido[2,3]pyrazolo [2,4-b][1,4]diazepin-11-one (80.00 mg, 190.75 µmol, 1.00 eq, TFA), Et$_3$N (96.51 mg, 953.75 µmol, 132.21 µL, 5.00 eq) and phenyl N-(3-chloro-4-fluoro-phenyl)carbamate (55.74 mg, 209.83 µmol, 1.10 eq) in DCM (5.00 mL) was stirred at 25° C. for 16 h. The mixture was diluted with DCM (30 mL) and washed with HCl (1 M, 30 mL*2). The organic phase was dried over Na$_2$SO$_4$, filtered and concentrated in vacuo. The resulting residue was purified by prep-HPLC(FA) to afford the title compound (53.00 mg, 116.02 µmol, 57.68% yield, 99% purity) as white solid. $^1$H NMR (400 MHz, CDCl$_3$) δ 7.60 (dd, J=2.63, 6.54 Hz, 1H), 7.18-7.25 (m, 1H), 7.03-7.11 (m, 1H), 6.62 (s, 1H), 4.69 (d, J=12.23 Hz, 2H), 4.58 (dd, J=3.91, 14.67 Hz, 1H), 4.36 (dd, J=6.36, 14.67 Hz, 1H), 3.78-3.96 (m, 2H), 3.73 (br t, J=4.10 Hz, 4H), 3.55-3.65 (m, 1H), 3.39 (br d, J=10.88 Hz, 2H), 3.20 (s, 3H), 2.86 (t, J=5.75 Hz, 2H), 2.66-2.76 (m, 2H), 2.52-2.63 (m, 2H). LCMS: 477/479[M+1].

Compound 022: N-(3-chloro-4-fluorophenyl)-8-(3,3-difluoroazetidin-1-yl)-10-methyl-11-oxo-1,3,4,7,8,9,10,11-octahydro-2H-pyrido[4',3':3,4]pyrazolo[1,5-a][1,4]diazepine-2-carboxamide

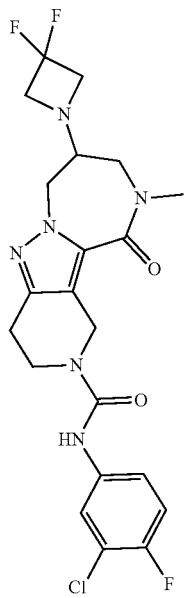 [SMILES: CN1CC(N2CC(F)(F)C2)Cn2nc3c(c2C1=O)CN(C(=O)Nc1ccc(F)c(Cl)c1)CC3]

Step 1. tert-butyl 8-(3,3-difluoroazetidin-1-yl)-10-methyl-1-oxo-1,3,4,7,8,9-hexahydropyrido[2,3]pyrazolo[2,4-b][1,4]diazepine-2-carboxylate A mixture of 3,3-difluoroazetidine; hydrochloride (116.22 mg, 897.20 μmol, 2.00 eq) and NaOAc (73.60 mg, 897.20 μmol, 2.00 eq) in DCE (4.00 mL) was stirred at 25° C. for 0.5 h, tert-butyl 10-methyl-8,11-dioxo-3,4,7,9-tetrahydro-1H-pyrido[2,3] pyrazolo[2,4-b][1,4]diazepine-2-carboxylate (Intermediate 2, 150.00 mg, 448.60 μmol, 1.00 eq) and 4 A molecular sieve (250.00 mg) was added and the mixture was stirred for 3 h. NaBH₃CN (140.95 mg, 2.24 mmol, 5.00 eq) was added and the mixture was stirred at 25° C. for 16 h. The mixture was diluted with EtOAc (40 mL) and washed with brine (30 mL). The organic phase was dried over Na₂SO₄, filtrated and concentrated in vacuo to give oil, which was purified by prep-TLC to afford the title compound (120.00 mg, 288.73 μmol, 64.36% yield, 99% purity) as yellow oil. LCMS: 412[M+1].

Step 2. 8-(3,3-difluoroazetidin-1-yl)-10-methyl-2,3,4,7,8,9-hexahydro-1H-pyrido[2,3]pyrazolo[2,4-b][1,4]diazepin-11-one To a solution of tert-butyl 8-(3,3-difluoroazetidin-1-yl)-10-methyl-11-oxo-1,3,4,7,8,9-hexahydropyrido[2,3]pyrazolo[2,4-b][1,4]diazepine-2-carboxylate (80.00 mg, 194.43 μmol, 1.00 eq) in DCM (2.00 mL) was added TFA (3.08 g, 27.01 mmol, 2.00 mL, 138.93 eq) and the mixture was stirred at 15° C. under N₂ for 1 h. The mixture was concentrated in vacuo to afford the title compound (82.00 mg, 192.78 μmol, 99.15% yield, TFA) as yellow oil, which was used directly for the next step.

Step 3. N-(3-chloro-4-fluorophenyl)-8-(3,3-difluoroazetidin-1-yl)-10-methyl-11-oxo-1,3,4,7,8,9,10,11-octahydro-2H-pyrido[4',3':3,4]pyrazolo[1,5-a][1,4]diazepine-2-carboxamide A mixture of 8-(3,3-difluoroazetidin-1-yl)-10-methyl-2,3,4,7,8,9-hexahydro-1H-pyrido[2,3]pyrazolo[2,4-b][1,4]diazepin-11-one (82.00 mg, 192.78 μmol, 1.00 eq, TFA), Et₃N (97.54 mg, 963.91 μmol, 133.61 μL, 5.00 eq) and phenyl N-(3-chloro-4-fluoro-phenyl)carbamate (56.34 mg, 212.06 μmol, 1.10 eq) in DCM (5.00 mL) was stirred at 22° C. for 16 h. The mixture was diluted with DCM (30 mL) and washed with HCl (1 M, 30 mL*2). The organic phase was dried over Na₂SO₄, filtered and concentrated in vacuo. The resulting residue was purified by prep-HPLC(FA) to afford the title compound (50.00 mg, 102.51 μmol, 53.17% yield, 99% purity) as white solid. $^1$H NMR (400 MHz, CDCl₃) δ 7.59 (dd, J=2.64, 6.53 Hz, 1H), 7.16-7.24 (m, 1H), 7.02-7.11 (m, 1H), 6.56 (s, 1H), 4.68 (d, J=1.76 Hz, 2H), 4.40 (dd, J=6.09, 14.12 Hz, 1H), 4.13 (dd, J=5.96, 14.12 Hz, 1H), 3.82-3.93 (m, 2H), 3.74 (br d, J=4.89 Hz, 4H), 3.36-3.47 (m, 1H), 3.20 (s, 5H), 2.86 (br d, J=5.02 Hz, 2H), 2.03 (s, 1H). LCMS: 483/485 [M+1].

Compound 023: 8-(azetidin-1-yl)-N-(3-chloro-4-fluorophenyl)-10-methyl-11-oxo-1,3,4,7,8,9,10,11-octahydro-2H-pyrido[4',3':3,4]pyrazolo[1,5-a][1,4]diazepine-2-carboxamide

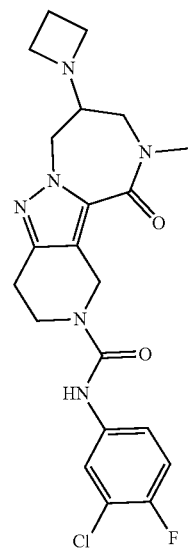 [SMILES: CN1CC(N2CCC2)Cn2nc3c(c2C1=O)CN(C(=O)Nc1ccc(F)c(Cl)c1)CC3]

Step 1. tert-butyl 8-(azetidin-1-yl)-10-methyl-11-oxo-1,3,4,7,8,9-hexahydropyrido[2,3]pyrazolo[2,4-b][1,4]diazepine-2-carboxylate A mixture of azetidine (51.23 mg, 897.20 µmol, 60.27 µL, 2.00 eq) and NaOAc (73.60 mg, 897.20 µmol, 2.00 eq) in DCE (4.00 mL) was stirred at 25° C. for 0.5 h, tert-butyl 10-methyl-8,11-dioxo-3,4,7,9-tetrahydro-1H-pyrido[2,3]pyrazolo[2,4-b][1,4]diazepine-2-carboxylate (Intermediate 2, 150.00 mg, 448.60 µmol, 1.00 eq) and 4 A molecular sieve (250.00 mg) was added and the mixture was stirred for 3 h. NaBH$_3$CN (140.95 mg, 2.24 mmol, 5.00 eq) was added and the mixture was stirred at 25° C. for 16 h. The mixture was diluted with EtOAc (40 mL) and brine (30 mL). The organic phase was dried over Na$_2$SO$_4$, filtrated and concentrated in vacuo. The resulting oil was purified by prep-TLC to afford the title compound (85.00 mg, 181.11 µmol, 40.37% yield, 80% purity) as yellow oil. LCMS: 398[M+23].

Step 2. 8-(azetidin-1-yl)-10-methyl-2,3,4,7,8,9-hexahydro-1H-pyrido[2,3]pyrazolo[2,4-b][1,4]diazepin-11-one To a solution of tert-butyl 8-(azetidin-1-yl)-10-methyl-11-oxo-1,3,4,7,8,9-hexahydropyrido[2,3]pyrazolo[2,4-b][1,4]diazepine-2-carboxylate (106.25 mg, 226.38 µmol, 1.00 eq) in DCM (2.00 mL) was added TFA (3.08 g, 27.01 mmol, 2.00 mL, 119.33 eq) and the mixture was stirred at 15° C. under N$_2$ for 1 h. The mixture was concentrated in vacuo to afford the title compound (88.00 mg, 226.01 µmol, 99.83% yield, TFA) as yellow oil, which was used directly for the next step.

Step 3. 8-(azetidin-1-yl)-N-(3-chloro-4-fluorophenyl)-10-methyl-11-oxo-1,3,4,7,8,9,10,11-octahydro-2H-pyrido[4',3':3,4]pyrazolo[1,5-a][1,4]diazepine-2-carboxamide A mixture of 8-(azetidin-1-yl)-10-methyl-2,3,4,7,8,9-hexahydro-1H-pyrido[2,3] pyrazolo[2,4-b][1,4]diazepin-11-one (88.00 mg, 226.01 µmol, 1.00 eq, TFA), Et$_3$N (114.35 mg, 1.13 mmol, 156.64 µL, 5.00 eq) and phenyl N-(3-chloro-4-fluoro-phenyl) carbamate (66.05 mg, 248.61 µmol, 1.10 eq) in DCM (5.00 mL) was stirred at 15° C. for 16 h. The mixture was diluted with DCM (30 mL) and washed with HCl (1 M, 30 mL*2). The organic phase was dried over Na$_2$SO$_4$, filtered and concentrated in vacuo to give residue, which was purified by prep-HPLC(FA) to afford the title compound (52.80 mg, 118.15 µmol, 52.28% yield) as yellow solid. $^1$H NMR (400 MHz, CDCl$_3$) δ=8.06 (s, 1H), 7.60 (dd, J=2.69, 6.60 Hz, 1H), 7.17-7.25 (m, 1H), 7.03-7.11 (m, 1H), 6.64 (s, 1H), 4.68 (s, 2H), 4.34-4.45 (m, 1H), 4.20-4.33 (m, 1H), 3.76-3.96 (m, 2H), 3.53 (br s, 5H), 3.29 (br s, 2H), 3.19 (s, 3H), 2.80-2.89 (m, 2H), 2.26-2.30 (m, 2H). LCMS: 447/449[M+1].

Compound 024: N-(3-chloro-4-fluorophenyl)-10-methyl-11-oxo-8-(pyrrolidin-1-yl)-1,3,4,7,8,9,10,11-octahydro-2H-pyrido[4',3':3,4]pyrazolo[1,5-a][1,4]diazepine-2-carboxamide

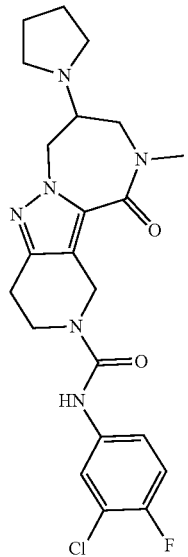 [SMILES: CN1CC(N2CCCC2)Cn2nc3c(c2C1=O)CN(C(=O)Nc1ccc(F)c(Cl)c1)CC3]

Step 1. tert-butyl 10-methyl-11-oxo-8-pyrrolidin-1-yl-1,3,4,7,8,9-hexahydropyrido[2,3]pyrazolo[2,4-b][1,4]diazepine-2-carboxylate A mixture of tert-butyl 10-methyl-8,11-dioxo-3,4,7,9-tetrahydro-1H-pyrido[2,3] pyrazolo[2,4-b][1,4]diazepine-2-carboxylate (Intermediate 2, 150.00 mg, 448.60 µmol, 1.00 eq), pyrrolidine (63.81 mg, 897.20 µmol, 75.07 µL, 2.00 eq), CH$_3$COOH (26.94 mg, 448.60 µmol, 25.66 µL, 1.00 eq) and 4 A molecular sieve (250.00 mg, 448.60 µmol, 1.00 eq) in DCE (4.00 mL) was stirred at 20° C. for 3 h. NaBH$_3$CN (140.95 mg, 2.24 mmol, 5.00 eq) was added and the mixture was stirred at 20° C. for 16 h. The mixture was diluted with EtOAc (40 mL) and washed with brine (60 mL). The organic phase was dried over Na$_2$SO$_4$, filtrated and concentrated in vacuo to give oil, which was purified by prep-TLC to afford the title compound (138.00 mg, 350.77 µmol, 78.19% yield, 99% purity) as yellow oil. LCMS: 390[M+1].

Step 2. 10-methyl-8-pyrrolidin-1-yl-2,3,4,7,8,9-hexahydro-1H-pyrido[2,3]pyrazolo[2,4-b][1,4]diazepin-11-one To a solution of tert-butyl 10-methyl-11-oxo-8-pyrrolidin-1-yl-1,3,4,7,8,9-hexahydropyrido[2,3]pyrazolo[2,4-b][1,4]diazepine-2-carboxylate (80.00 mg, 205.40 µmol, 1.00 eq) in DCM (4.50 mL) was added TFA (6.93 g, 60.78 mmol, 4.50 mL, 295.90 eq) and the mixture was stirred at 20° C. under N$_2$ for 1 h. The mixture was concentrated in vacuo to afford the title compound (82.86 mg, 205.40 µmol, 100.00% yield, TFA) as yellow oil, which was used directly for the next step.

Step 3. N-(3-chloro-4-fluorophenyl)-10-methyl-11-oxo-8-(pyrrolidin-1-yl)-1,3,4,7,8,9,10,11-octahydro-2H-pyrido[4',3':3,4]pyrazolo[1,5-a][1,4]diazepine-2-carboxamide A mixture of 10-methyl-8-pyrrolidin-1-yl-2,3,4,7,8,9-hexahydro-1H-pyrido[2,3] pyrazolo[2,4-b][1,4]diazepin- 11-one (82.86 mg, 205.40 µmol, 1.00 eq, TFA), Et$_3$N (103.92 mg, 1.03 mmol, 142.36 µL, 5.00 eq) and phenyl N-(3-chloro-4-fluoro-phenyl) carbamate (60.03 mg, 225.94 µmol, 1.10 eq) in DCM (5.00 mL) was stirred at 22° C. for 16 h. The mixture was diluted with DCM (30 mL) and washed with HCl (1 M, 30 mL*2). The organic phase was dried over Na$_2$SO$_4$, filtered and concentrated in vacuo. The residue was purified by prep-HPLC(FA) to afford the title compound (21.65 mg, 46.50 µmol, 22.64% yield, 99% purity) as white solid. $^1$H NMR (400 MHz, CDCl$_3$) δ7.56-7.58 (m, 1H), 7.18-7.19 (m, 1H), 7.02-7.06 (m, 1H), 6.71 (s, 1H), 4.66-4.72 (m, 2H), 4.49-4.55 (m, 2H), 3.83-3.88 (m, 2H), 3.63-3.65 (m, 3H), 3.18 (s, 3H), 2.96-3.04 (m, 4H), 2.82-2.85 (m, 2H), 1.95-2.00 (m, 4H). LCMS: 461/463 [M+1].

Compound 025: N-(3-chloro-4-fluorophenyl)-10-methyl-8-(methylthio)-11-oxo-1,3,4,7,8,9,10,11-octahydro-2H-pyrido[4',3':3,4]pyrazolo[1,5-a][1,4]diazepine-2-carboxamide

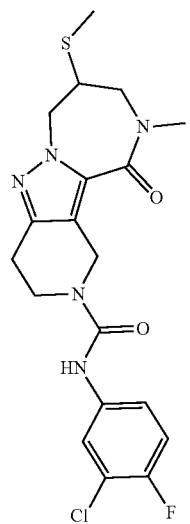 [SMILES: CSC1CN(C)C(=O)c2c3c(nn2C1)CCN(C(=O)Nc1ccc(F)c(Cl)c1)C3]

Step 1. [2-[(3-chloro-4-fluoro-phenyl)carbamoyl]-10-methyl-1-oxo-1,3,4,7,8,9-hexahydropyrido[2,3]pyrazolo[2,4-b][1,4]diazepin-8-yl] methanesulfonate A mixture of N-(3-chloro-4-fluoro-phenyl)-8-hydroxy-10-methyl-11-oxo-1,3,4,7,8,9-hexahydropyrido[2,3]pyrazolo[2,4-b][1,4]diazepine-2-carboxamide (Compound 004, 100.00 mg, 245.20 µmol, 1.00 eq), TEA (49.62 mg, 490.40 µmol, 67.97 µL, 2.00 eq) in DCM (5.00 mL) was added MsCl (42.13 mg, 367.80 µmol, 28.47 µL, 1.50 eq) at 0° C. under N$_2$, and then the mixture was stirred at 15° C. for 16 hr under N$_2$ atmosphere. TLC showed the starting material/desired product=1/3. Then MsCl (14 mg, 122.6 µmol, 9.49 µL, 0.50 eq) was added to the mixture, the mixture was stirred at 15° C. for 4 hr, TLC showed the starting material/desired product=1/3. The mixture was stirred at 50° C. for 2 hr, TLC showed the starting material/desired product=1/3. The mixture was poured into water (5 mL) and stirred at 5 min. The aqueous phase was extracted with ethyl acetate (3 mL*2). The combined organic phase was washed with brine (5 mL), dried with anhydrous Na$_2$SO$_4$, filtered and concentrated in vacuum. The residue was purified by prep-TLC to afford the title compound (82.00 mg, 162.00 µmol, 66.07% yield, 96% purity) as a white solid. LCMS: 486 [M+1]

Step 2: N-(3-chloro-4-fluorophenyl)-10-methyl-8-(methylthio)-11-oxo-1,3,4,7,8,9,10,11-octahydro-2H-pyrido[4',3':3,4]pyrazolo[1,5-a][14]diazepine-2-carboxamide A mixture of [2-[(3-chloro-4-fluoro-phenyl)carbamoyl]-10-methyl-11-oxo-1,3,4,7,8,9-hexahydropyrido[2,3]pyrazolo[2,4-b][1,4]diazepin-8-yl]methanesulfonate (50.00 mg, 102.90 mol, 1.00 eq) in DMF (2.00 mL) was added sodium;methanethiolate (50.48 mg, 720.30 µmol, 45.89 µL, 7.00 eq) at 0° C. under N$_2$, and then the mixture was stirred at 15° C. for 2 hour under N$_2$ atmosphere. LCMS showed the starting material was consumed completely, desired product/byproduct=1/1. The mixture was poured into ice-water (10 mL) and stirred at 5 min. The aqueous phase was extracted with ethyl acetate (5 mL*3). The combined organic phase was washed with brine (10 mL), dried with anhydrous Na$_2$SO$_4$, filtered and concentrated in vacuum. The residue was purified by Prep-HPLC (FA) to afford the title compound (18.00 mg, 40.28 µmol, 39.15% yield, 98% purity) as a white solid. $^1$H NMR (400 MHz, CDCl$_3$) δ 7.58 (dd, J=2.6, 6.5 Hz, 1H), 7.18 (s, 1H), 7.02-7.09 (m, 1H), 6.55 (s, 1H), 4.64-4.74 (m, 3H), 4.22-4.33 (m, 1H), 3.81-3.90 (m, 2H), 3.69 (dd, J=4.5, 14.8 Hz, 1H), 3.36-3.54 (m, 2H), 3.23 (s, 3H), 2.85 (br d, J=4.6 Hz, 2H), 2.24 (s, 3H). LCMS: 438/440 [M+1]; and N-(3-chloro-4-fluorophenyl)-10-methyl-11-oxo-3,4,10,11-tetrahydro-1H-pyrido[4',3':3,4]pyrazolo[1,5-a][1,4]diazepine-2 (7H)-carboxamide as a by-product.

Compound 026A: N-(3-chloro-4-fluoro-phenyl)-10-methyl-8-methylsulfinyl-11-oxo-1,3,4,7,8,9-hexahydropyrido[2,3]pyrazolo[2,4-b][1,4]diazepine-2-carboxamide: Pure but Unknown Diastereomer D1

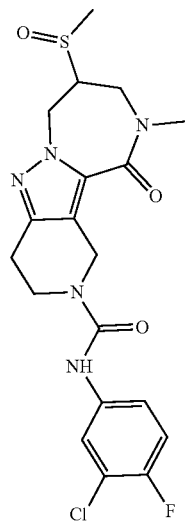 [SMILES: CN1CC(S(C)=O)Cn2nc3c(c2C1=O)CN(C(=O)Nc1ccc(F)c(Cl)c1)CC3]

Step 1. tert-butyl-10-methyl-8-methylsulfonyloxy-11-oxo-1,3,4,7,8,9-hexahydropyrido[2,3]pyrazolo[2,4-b][1,4]diazepine-2-carboxylate To a solution of tert-butyl 8-hydroxy-10-methyl-11-oxo-1,3,4,7,8,9-hexahydropyrido[2,3]pyrazolo[2,4-b][1,4]diazepine-2-carboxylate (220.00 mg, 654.00 µmol, 1.00 eq) in DCM (2.00 mL) was added methanesulfonyl chloride (89.90 mg, 784.80 µmol, 60.74 µL, 1.20 eq). The mixture was stirred at 10° C. for 4 hr. TLC (Dichloromethane:Methanol=10:1) showed the mixture was completed. The mixture was quenched with water(20 mL), extracted with ethyl acetate(10 mL*3), the organic layer was washed with brine (10 mL), dried over anhydrous $Na_2SO_4$ and concentrated in vacuo to afford the title compound (200.00 mg, 482.53 µmol, 73.78% yield) as colorless oil.

Step 2. tert-butyl-8-acetylsulfanyl-10-methyl-11-oxo-1,3,4,7,8,9-hexahydropyrido[2,3]pyrazolo[2,4-b][1,4]diazepine-2-carboxylate To a solution of tert-butyl 10-methyl-8-methylsulfonyloxy-11-oxo-1,3,4,7,8,9-hexahydropyrido[2,3]pyrazolo[2,4-b][1,4]diazepine-2-carboxylate (220.00 mg, 530.79 µmol, 1.00 eq) in DMF (2.00 mL) was added acetylsulfanylpotassium (181.86 mg, 1.59 mmol, 3.00 eq). The mixture was stirred at 80° C. for 16 hr. LCMS showed the reaction was complete. The mixture was quenched by addition water (10 mL), and extracted with ethyl acetate (10 mL*3). The organic layer was washed with water (10 mL) and brine (10 mL) and dried over anhydrous $Na_2SO_4$, concentrated in vacuum to give the residue which was purified by prep-TLC (Dichloromethane:Methanol=10:1) to afford the title compound (170.00 mg, 396.46 µmol, 74.69% yield, 92% purity) as yellow oil.

Step 3. tert-butyl 10-methyl-8-methylsulfanyl-11-oxo-1,3,4,7,8,9-hexahydropyrido[2,3]pyrazolo[2,4-b][1,4]diazepine-2-carboxylate To a solution of tert-butyl 8-acetylsulfanyl-10-methyl-11-oxo-1,3,4,7,8,9-hexahydropyrido[2,3]pyrazolo[2,4-b][1,4]diazepine-2-carboxylate (150.00 mg, 380.24 µmol, 1.00 eq) in MeOH (2.00 mL) was added $K_2CO_3$ (157.66 mg, 1.14 mmol, 3.00 eq). The mixture was stirred at 15° C. for 15 mins, while MeI (59.37 mg, 418.26 µmol, 26.04 µL, 1.10 eq) was added, the mixture was stirred at 15° C. for 15 mins. LCMS showed the reaction complete. The mixture was concentrated in vacuum to give the residue which was washed with DCM (30 mL) and filtered, the filtrate was concentrated in vacuum to afford the title compound (132.00 mg, 356.58 µmol, 93.78% yield, 99% purity) as colorless oil.

Step 4. 10-methyl-8-methylsulfanyl-2,3,4,7,8,9-hexahydro-1H-pyrido[2,3] pyrazolo [2,4-b][1,4]diazepin-11-one To a solution of tert-butyl 10-methyl-8-methylsulfanyl-11-oxo-1,3,4,7,8,9-hexahydropyrido[2,3]pyrazolo[2,4-b][1,4]diazepine-2-carboxylate (150.00 mg, 409.30 µmol, 1.00 eq) in DCM (2.00 mL) was added TFA (3.08 g, 27.01 mmol, 2.00 mL, 66.00 eq), the mixture was stirred at 15° C. for 30 min. TLC (Dichloromethane:Methanol=10:1) showed the reaction was completed. The mixture was concentrated to afford the title compound (140.00 mg, 368.05 µmol, 89.92% yield, TFA) as white solid.

Step 5. N-(3-chloro-4-fluoro-phenyl)-10-methyl-8-methylsulfanyl-11-oxo-1,3,4,7,8,9-hexahydropyrido[2,3]pyrazolo[2,4-b][1,4]diazepine-2-carboxamide To a solution of 10-methyl-8-methylsulfanyl-2,3,4,7,8,9-hexahydro-1H-pyrido[2,3] pyrazolo[2,4-b][1,4]diazepin-11-one (140.00 mg, 368.05 µmol, 1.00 eq, TFA) and phenyl N-(3-chloro-4-fluoro-phenyl)carbamate (97.78 mg, 368.05 µmol, 1.00 eq) in DCM (2.00 mL) was added TEA (93.11 mg, 920.13 µmol, 127.55 µL, 2.50 eq). The mixture was stirred at 15° C. for 16 hr. LCMS showed the reaction was completed. The mixture was quenched by water (10 mL) and extracted with ethyl acetate (30 mL). The organic layer was washed with brine (10 mL), dried over anhydrous $Na_2SO_4$ and concentrated in vacuum to afford the title compound (200.00 mg, 365.36 µmol, 99.27% yield, 80% purity) as white solid.

Step 6. N-(3-chloro-4-fluoro-phenyl)-10-methyl-8-methylsulfinyl-11-oxo-1,3,4,7,8,9-hexahydropyrido[2,3]pyrazolo[2,4-b][1,4]diazepine-2-carboxamide To a solution of N-(3-chloro-4-fluoro-phenyl)-10-methyl-8-methylsulfanyl-11-oxo-1,3,4,7,8,9-hexahydropyrido[2,3]pyrazolo[2,4-b][1,4]diazepine-2-carboxamide (100.00 mg, 228.35 µmol, 1.00 eq) and $(Bu_3Sn)_2O$ (204.18 mg, 342.53 µmol, 174.52 µL, 1.50 eq) in DCM (3.00 mL) was added $Br_2$ (54.74 mg, 342.53 µmol, 17.66 µL, 1.50 eq) in DCM (500.00 uL) for 30 min. The mixture was stirred at 15° C. for 2 hr. LCMS showed the reactant remained, then another batch of$(Bu_3Sn)_2O$ (272.24 mg, 456.70 µmol, 232.69 µL, 2.00 eq) and $Br_2$ (72.99 mg, 456.70 µmol, 23.54 µL, 2.00 eq) was added in turn. The mixture was stirred for another 2 hr. LCMS showed the reaction was completed. The mixture was washed with saturated KF (10 mL), the organic layer was concentrated in vacuum. The residue was purified by prep-HPLC to give N-(3-chloro-4-fluoro-phenyl)-10-methyl-8-methylsulfinyl-11-oxo-1,3,4,7,8,9-hexahydropyrido[2,3]pyrazolo[2,4-b][1,4]diazepine-2-carboxamide (50.00 mg, 106.85 µmol, 46.79% yield, 97% purity) as yellow oil, 35 mg of which was separated by SFC(column: AS (250 mm*30 mm, 10 um); mobile phase: [Neu-ETOH]; Gradient Time (min): 5.5minuinute, 80 minutes), followed by prep-HPLC to afford two isomers Compound 026, D1 (peak1, 14 mg), and Compound 026, D2 (peak 2, 18 mg). Compound 026, D1: $^1H$ NMR (400 MHz, $CDCl_3$) δ 7.58 (dd, J=2.51, 6.42 Hz, 1H), 7.15-7.24 (m, 1H), 7.01-7.11 (m, 1H), 6.64 (s, 1H), 4.18-4.83 (m, 4H), 3.64-4.05 (m, 4H), 3.44-3.58 (m, 1H), 3.23 (d, J=13.94 Hz, 3H), 2.84 (br d, J=4.77 Hz, 2H), 2.63-2.74 (m, 3H).

183

Compound 026B: N-(3-chloro-4-fluoro-phenyl)-10-methyl-8-methylsulfinyl-11-oxo-1,3,4,7,8,9-hexahydropyrido[2,3]pyrazolo[2,4-b][1,4]diazepine-2-carboxamide: Pure but Unknown Diastereomer D2

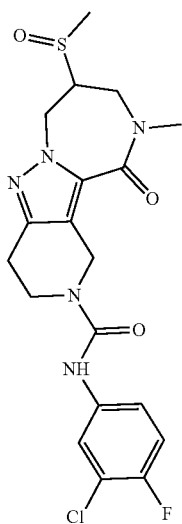 [SMILES: CN1CC(S(C)=O)Cn2nc3c(c2C1=O)CN(C(=O)Nc1ccc(F)c(Cl)c1)CC3]

Compound 026, D2: ¹H NMR (400 MHz, CDCl₃) δ 7.57 (dd, J=2.63, 6.54 Hz, 1H), 7.17-7.24 (m, 1H), 7.01-7.10 (m, 1H), 6.70 (s, 1H), 4.18-4.87 (m, 4H), 3.64-4.02 (m, 4H), 3.42-3.60 (m, 1H), 3.23 (d, J=13.82 Hz, 3H), 2.77-2.91 (m, 2H), 2.62-2.74 (m, 3H).

Compound 027: N-(3-chloro-4-fluoro-phenyl)-10-methyl-8-methylsulfonyl-11-oxo-1,3,4,7,8,9-hexahydropyrido[2,3]pyrazolo[2,4-b][1,4]diazepine-2-carboxamide

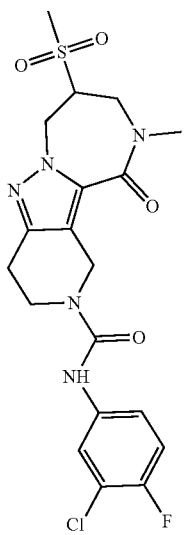 [SMILES: CN1CC(S(C)(=O)=O)Cn2nc3c(c2C1=O)CN(C(=O)Nc1ccc(F)c(Cl)c1)CC3]

184

To a solution of N-(3-chloro-4-fluoro-phenyl)-10-methyl-8-methylsulfanyl-11-oxo-1,3,4,7,8,9-hexahydropyrido[2,3]pyrazolo[2,4-b][1,4]diazepine-2-carboxamide (Compound 26, product from Step 5, 50.00 mg, 114.18 μmol, 1.00 eq) in DCM (2.00 mL) was added m-CPBA (123.15 mg, 570.88 μmol, 80% purity, 5.00 eq). The resulting solution was stirred at 15° C. for 2 hr. LCMS showed the reaction was complete. The mixture was quenched with water (10 mL), the organic layer was washed with sat. NaHCO₃ (10 mL) and brine (10 mL), dried over anhydrous Na₂SO₄ and concentrated in vacuum. The mixture was purified by prep-HPLC to afford the title compound (17.00 mg, 35.81 μmol, 31.37% yield, 99% purity) as the white solid. ¹H NMR (400 MHz, CDCl₃) δ 7.57 (dd, J=2.70, 6.46 Hz, 1H), 7.16-7.23 (m, 1H), 7.02-7.10 (m, 1H), 6.66 (s, 1H), 4.83-4.93 (m, 1H), 4.58-4.79 (m, 3H), 3.74-3.98 (m, 5H), 3.22 (s, 3H), 2.95 (s, 3H), 2.84 (t, J=5.83 Hz, 2H). LCMS: 470/472 [M+1].

Compound 028: methyl 2-(2-((3-chloro-4-fluorophenyl)carbamoyl)-10-methyl-11-oxo-1,3,4,7,8,9,10,11-octahydro-2H-pyrido[4',3':3,4]pyrazolo[1,5-a][1,4]1diazepin-8-yl)acetate

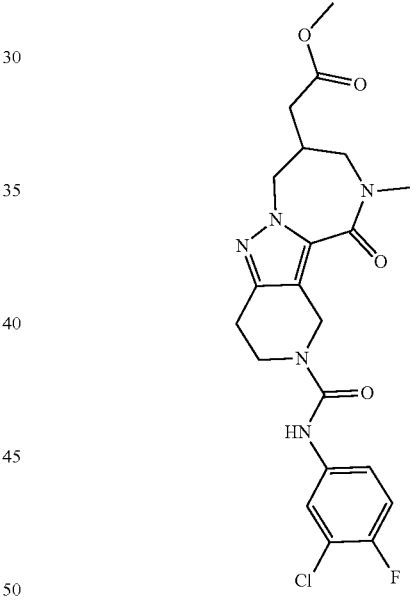

Step 1. tert-butyl (8E)-8-(2-methoxy-2-oxo-ethylidene)-10-methyl-11-oxo-3,4,7,9-tetrahydro-1H-pyrido[2,3]pyrazolo[2,4-b][1,4]diazepine-2-carboxylate To a solution of methyl 2-dimethoxyphosphorylacetate (162.85 mg, 894.22 μmol, 129.25 μL, 1.30 eq) in THF (10.00 mL) was added potassium 2-methylpropan-2-olate (115.78 mg, 1.03 mmol, 1.50 eq) at 0° C. for 10 min. Then the mixture was added tert-butyl 10-methyl-8,11-dioxo-3,4,7,9-tetrahydro-1H-pyrido[2,3]pyrazolo [2,4-b][1,4]diazepine-2-carboxylate (230.00 mg, 687.86 µmol, 1.00 eq) and the mixture was stirred at 15° C. for 4 h. The reaction mixture was quenched with H₂O (10 mL), diluted with brine (40 mL) and extracted with EtOAc (30 mL*2). The combined organic phase was washed with brine (30 mL*2), dried over Na₂SO₄, filtered and concentrated under reduced pressure. The residue was purified by column chromatography to afford the title compound (164.00 mg, 382.25 µmol, 55.57% yield, 91% purity) as a yellow oil. LCMS: 391 [M+1].

Step 2. tert-butyl 8-(2-methoxy-2-oxo-ethyl)-10-methyl-11-oxo-1,3,4,7,8,9-hexahydropyrido[2,3]pyrazolo[2,4-b][1,4]diazepine-2-carboxylate To a solution of tert-butyl (8E)-8-(2-methoxy-2-oxo-ethylidene)-10-methyl-11-oxo-3,4,7,9-tetrahydro-1H-pyrido[2,3]pyrazolo[2,4-b][1,4]diazepine-2-carboxylate (200 mg, 512.26 µmol, 1.00 eq) in MeOH (10.00 mL) was added Pd/C (50.00 mg, 10% purity) and the mixture was stirred at 15° C. under H₂ (15 psi) for 16 h. The reaction mixture was filtered and the filtrate was concentrated in vacuo to afford the title compound (195.00 mg, 472.03 µmol, 92.15% yield, 95% purity) as a oil, which was used directly for the next step. LCMS: 393 [M+1].

Step 3. methyl 2-(10-methyl-11-oxo-2,3,4,7,8,9-hexahydro-1H-pyrido[2,3]pyrazolo[2,4-b][1,4]diazepin-8-yl)acetate To a solution of tert-butyl 8-(2-methoxy-2-oxo-ethyl)-10-methyl-11-oxo-1,3,4,7,8,9-hexahydropyrido[2,3]pyrazolo[2,4-b][1,4]diazepine-2-carboxylate (195.00 mg, 496.88 µmol, 1.00 eq) in DCM (3.00 mL) was added TFA (4.62 g, 40.52 mmol, 3.00 mL, 81.55 eq) and the mixture was stirred at 15° C. for 1 h. The mixture was concentrated in vacuo to afford the title compound (190.00 mg, 448.86 µmol, 90.34% yield, 96% purity, TFA), which was used directly for the next step.

Step 4. methyl 2-(2-((3-chloro-4-fluorophenyl)carbamoyl)-10-methyl-11-oxo-1,3,4,7,8,9,10,11-octahydro-2H-pyrido[4',3':3,4]pyrazolo[1,5-a][1,4]diazepin-8-yl)acetate A mixture of methyl 2-(10-methyl-11-oxo-2,3,4,7,8,9-hexahydro-1H-pyrido[2,3] pyrazolo[2,4-b][1,4]diazepin-8-yl)acetate (195.00 mg, 479.87 µmol, 1.00 eq, TFA), Et₃N (242.79 mg, 2.40 mmol, 332.59 µL, 5.00 eq) and phenyl N-(3-chloro-4-fluoro-phenyl)carbamate (127.49 mg, 479.87 µmol, 1.00 eq) in DCM (5.00 mL) was stirred at 15° C. for 16 h. The mixture was diluted with DCM (30 mL) and washed with HCl (1 M, 30 mL*2). The organic phase was dried over Na₂SO₄, filtered and concentrated in vacuo. The residue was purified by column chromatography to afford desired product (180 mg, 97% purity), 40 mg of which was further purified by prep-HPLC(FA) to afford the title compound (35.7 mg, 99% purity) as white solid. ¹H NMR (400 MHz, CDCl₃) δ 7.57-7.59 (m, 1H), 7.16-7.27 (m, 1H), 7.03-7.07 (t, J=8.8 Hz, 1H), 6.56 (s, 1H), 4.66-4.67 (m, 2H), 4.45-4.47 (m, 1H), 4.12-4.15 (m, 1H), 3.84-3.86 (m, 2H), 3.74 (s, 3H), 3.46-3.48 (m, 1H), 3.18-3.26 (m, 4H), 2.95-3.05 (m, 1H), 2.82-2.85 (m, 2H), 2.39-2.51 (m, 2H). LCMS: 464/466 [M+1].

Compound 029: N-(3-chloro-4-fluorophenyl)-8-(2-hydroxyethyl)-10-methyl-1-oxo-1,3,4,7,8,9,10,11-octahydro-2H-pyrido[4',3':3,4]pyrazolo[1,5-a][1,4]diazepine-2-carboxamide

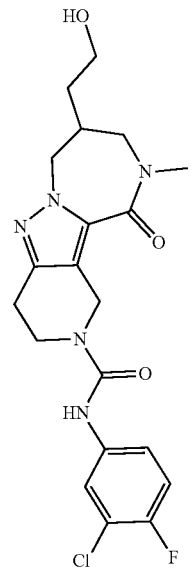 [SMILES: CN1CC(CCO)Cn2nc3c(c2C1=O)CN(C(=O)Nc1ccc(F)c(Cl)c1)CC3]

To a solution of methyl 2-[2-[(3-chloro-4-fluoro-phenyl)carbamoyl]-10-methyl-11-oxo-1,3,4,7,8,9-hexahydropyrido[2,3]pyrazolo[2,4-b][1,4]diazepin-8-yl]acetate (Compound 028, 40.00 mg, 86.23 µmol, 1.00 eq) in THF (3.00 mL) was added LiBH₄ (5.63 mg, 258.69 µmol, 3.00 eq) at 0° C. and the mixture was stirred at 15° C. for 4 h. The reaction mixture was quenched with H₂O (20 mL) at 0° C. and extracted with ethyl acetate (20 mL*2). The combined organic layer was dried over Na₂SO₄, filtered and concentrated under reduced pressure to give a residue, which was purified by prep-HPLC(FA) to afford the title compound (18.50 mg, 42.02 µmol, 48.73% yield, 99% purity) as a white solid. ¹H NMR (400 MHz, CD₃CN) δ 7.64-7.66 (m, 1H), 7.44 (s, 1H), 7.31-7.32 (m, 1H), 7.11-7.15 (t, J=9.0 Hz, 1H), 4.59 (s, 2H), 4.34-4.36 (m, 1H), 4.06-4.10 (m, 1H), 3.73-3.75 (m, 2H), 3.59-3.62 (m, 2H), 3.36-3.39 (m, 1H), 3.08-3.13 (m, 4H), 2.73-2.76 (m, 2H), 2.55-2.65 (m, 1H), 1.52-1.55 (m, 2H). LCMS: 436/438 [M+1].

Compound 030: ethyl 2-((3-chloro-4-fluorophenyl) carbamoyl)-10-methyl-11-oxo-2,3,4,7,8,9,10,11-octahydro-1H-pyrido[4',3':3,4]pyrazolo[1,5-a][1,4] diazepine-8-carboxylate

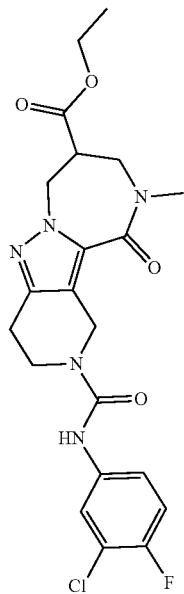 [SMILES: CCOC(=O)C1CN(C)C(=O)c2c3c(nn2C1)CCN(C(=O)Nc1ccc(F)c(Cl)c1)C3]

Step 1. ethyl 2-[[tert-butoxycarbonyl(methyl)amino] methyl]prop-2-enoate

A mixture of tert-butyl N-methylcarbamate (200.00 mg, 1.52 mmol, 1.00 eq) in THF (5.00 mL) was added NaH (91.20 mg, 2.28 mmol, 60% purity, 1.50 eq) at 0° C. for 0.5 hr under $N_2$, then ethyl 2-(bromomethyl)prop-2-enoate (352.10 mg, 1.82 mmol, 1.20 eq) was added to the mixture dropwise at 0° C., and the mixture was stirred at 15° C. for 2 hr under $N_2$ atmosphere. TLC showed the starting material was consumed completely, two new spots appeared. The mixture was poured into ice-water (10 mL) and stirred at 5 min. The aqueous phase was extracted with ethyl acetate (5 mL*3). The combined organic phase was washed with brine (10 mL), dried with anhydrous $Na_2SO_4$, filtered and concentrated in vacuum. The residue was purified by column chromatography ($SiO_2$, Petroleum ether/Ethyl acetate=100/1 to 5/1) to afford the title compound (112.00 mg, 460.34 µmol, 30.29% yield) as a colorless oil. $^1$H NMR (400 MHz, $CDCl_3$) δ 6.28 (s, 1H), 5.55 (s, 1H), 4.23 (q, J=7.1 Hz, 2H), 4.07 (br s, 2H), 2.88 (br s, 3H), 1.45 (br s, 9H), 1.31 (br s, 3H).

Step 2. ethyl2-(methylaminomethyl)prop-2-enoate

A mixture of ethyl 2-[[tert-butoxycarbonyl(methyl) amino]methyl]prop-2-enoate (112.00 mg, 460.34 µmol, 1.00 eq) in dioxane (1.00 mL) was added HCl/dioxane (4 M, 5.00 mL, 43.45 eq), and then the mixture was stirred at 15° C. for 0.5 hour. TLC showed the starting material was consumed completely, a new spot was major. The mixture was concentrated in vacuum to afford the title compound (82.50 mg, 459.25 µmol, 99.76% yield, HCl) as a white solid, which was used directly for next step.

Step 3. tert-butyl 3-[2-ethoxycarbonylallyl (methyl) carbamoyl]-2,4,6,7-tetrahydropyrazolo[4,3-c]pyridine-5-carboxylate A mixture of 5-tert-butoxycarbonyl-2,4,6,7-tetrahydropyrazolo[4,3-c]pyridine-3-carboxylic acid (80.00 mg, 299.31 µmol, 1.00 eq), ethyl 2-(methylaminomethyl) prop-2-enoate (59.14 mg, 329.24 µmol, 1.10 eq, HCl), $T_3P$ (285.70 mg, 897.93 µmol, 267.01 µL, 3.00 eq), TEA (151.44 mg, 1.50 mmol, 207.45 µL, 5.00 eq) in THF (3.00 mL) was degassed and purged with $N_2$ for 3 times, and then the mixture was stirred at 15° C. for 16 hour under $N_2$ atmosphere. TLC showed the starting material was consumed completely and a new spot appeared. The mixture was poured into water (10 mL) and stirred at 5 min. The aqueous phase was extracted with ethyl acetate (5 mL*3). The combined organic phase was washed with brine (10 mL), dried with anhydrous $Na_2SO_4$, filtered and concentrated in vacuum. The residue was purified by Prep-TLC (DCM/MeOH=10/1) to afford the title compound (46.00 mg, 105.49 mol, 35.24% yield, 90% purity) as a white solid. LCMS: 393 [M+1]. $^1$H NMR (400 MHz, $CDCl_3$) δ 6.35 (s, 1H), 5.67 (br s, 1H), 4.63 (s, 4H), 4.18-4.30 (m, 2H), 3.71 (br s, 2H), 2.91-3.47 (m, 3H), 2.74 (br t, J=5.4 Hz, 2H), 1.48 (s, 9H), 1.31 (t, J=7.2 Hz, 3H).

Step 4. 2-tert-butyl 8-ethyl 10-methyl-11-oxo-3,4,8, 9,10,11-hexahydro-1H-pyrido[4',3':3,4]pyrazolo[1,5-a][1,4]diazepine-2,8 (7H)-dicarboxylate A mixture of tert-butyl 3-[2-ethoxycarbonylallyl(methyl) carbamoyl]-2,4,6,7-tetrahydropyrazolo[4,3-c]pyridine-5-carboxylate (36.00 mg, 91.73 µmol, 1.00 eq), DBU (6.98 mg, 45.87 µmol, 6.91 µL, 0.50 eq) in MeCN (1.00 mL) was degassed and purged with $N_2$ for 3 times, and then the mixture was stirred at 50° C. for 2 hour under $N_2$ atmosphere. TLC showed the starting material was consumed completely and desired product was major. The mixture was poured into water (5 mL) and stirred at 5 min. The aqueous phase was extracted with ethyl acetate (3 mL*3). The combined organic phase was washed with brine (5 mL), dried with anhydrous $Na_2SO_4$, filtered and concentrated in vacuum. The residue was purified by Prep-TLC (DCM/MeOH=20/1) to give the title compound (20.00 mg, 50.96 µmol, 55.56% yield) as a white solid. LCMS: 393 [M+1]

Step 5. ethyl 10-methyl-11-oxo-2,3,4,7,8,9,10,11-octahydro-H-pyrido[4',3':3,4]pyrazolo[1,5-a][1,4] diazepine-8-carboxylate A mixture of 2-tert-butyl 8-ethyl 10-methyl-11-oxo-3,4, 8,9,10,11-hexahydro-1H-pyrido[4',3':3,4]pyrazolo[1,5-a][1, 4]diazepine-2,8 (7H)-dicarboxylate (22.00 mg, 56.06 µmol, 1.00 eq) in DCM (1.00 mL) was added TFA (1.54 g, 13.51 mmol, 1.00 mL, 240.93 eq), and then the mixture was stirred at 15° C. for 1 hour. TLC showed the starting material was consumed completely, a new spot appeared. The mixture was concentrated in vacuum to afford the title compound (22.70 mg, 55.86 µmol, 99.65% yield, TFA) as a yellow oil, which was used directly for next step.

Step 6. ethyl 2-((3-chloro-4-fluorophenyl)carbamoyl)-10-methyl-11-oxo-2,3,4,7,8,9,10,11-octahydro-1H-pyrido[4',3':3,4]pyrazolo[1,5-a][1,4]diazepine-8-carboxylate A mixture of ethyl 10-methyl-11-oxo-2,3,4,7,8,9,10,11-octahydro-1H-pyrido[4',3':3,4]pyrazolo[1,5-a][1,4]diazepine-8-carboxylate (22.00 mg, 54.14 μmol, 1.00 eq, TFA), phenyl N-(3-chloro-4-fluoro-phenyl)carbamate (15.82 mg, 59.55 μmol, 1.10 eq) and TEA (10.96 mg, 108.28 μmol, 15.01 μL, 2.00 eq) in DCM (3.00 mL) was degassed and purged with $N_2$ for 3 times, and then the mixture was stirred at 15° C. for 16 hour under $N_2$ atmosphere. LCMS showed the starting material was consumed completely, desired product was major. The mixture was poured into water (5 mL) and stirred at 5 min. The aqueous phase was extracted with DCM (3 mL*3). The combined organic phase was washed with brine (5 mL), dried with anhydrous $Na_2SO_4$, filtered and concentrated in vacuum. The residue was purified by Prep-HPLC (FA) to afford the title compound (15.00 mg, 32.01 μmol, 59.13% yield, 99% purity) as a white solid. $^1$H NMR (400 MHz, $CDCl_3$) δ 7.58 (dd, J=2.6, 6.5 Hz, 1H), 7.16-7.22 (m, 1H), 7.02-7.09 (m, 1H), 6.58 (s, 1H), 4.50-4.76 (m, 4H), 4.27 (d, J=7.1 Hz, 2H), 3.73-3.91 (m, 3H), 3.58-3.70 (m, 1H), 3.33-3.43 (m, 1H), 3.19 (s, 3H), 2.84 (br d, J=5.4 Hz, 2H), 1.33 (t, J=7.2 Hz, 3H). LCMS: 464/466 [M+1].

Compound 031: $N_2$-(3-chloro-4-fluorophenyl)-N8,10-dimethyl-11-oxo-1,3,4,7,8,9,10,11-octahydro-2H-pyrido[4',3':3,4]pyrazolo[1,5-a][1,4]diazepine-2,8-dicarboxamide

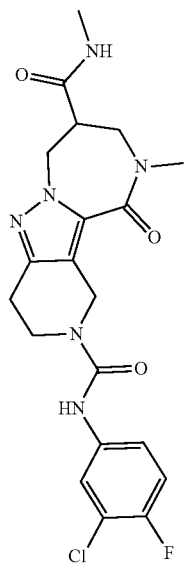 [SMILES: CNC(=O)C1CN(C)C(=O)c2c3c(nn2C1)CCN(C(=O)Nc1ccc(F)c(Cl)c1)C3]

Step 1. 2-((3-chloro-4-fluorophenyl)carbamoyl)-10-methyl-11-oxo-2,3,4,7,8,9,10,11-octahydro-1H-pyrido[4',3':3,4]pyrazolo[1,5-a][1,4]diazepine-8-carboxylic acid To a mixture of ethyl 2-((3-chloro-4-fluorophenyl)carbamoyl)-10-methyl-11-oxo-2,3,4,7,8,9,10,11-octahydro-1H-pyrido[4',3':3,4]pyrazolo[1,5-a][1,4]diazepine-8-carboxylate (Compound 030, 80.00 mg, 172.45 mol, 1.00 eq) in MeOH (5.00 mL) and $H_2O$ (1.00 mL) was added NaOH (10.35 mg, 258.68 mol, 1.50 eq) in one portion. The mixture was stirred at 30° C. for 12 hours. LCMS showed the reaction was completed. The mixture was concentrated in vacuum and adjust to pH=7 with HCl(1 N). The residue was purified by prep-HPLC(FA) to the title compound (28.00 mg, 63.73 mol, 36.96% yield, 99.2% purity) as white solid. $^1$H NMR (400 MHz, $CDCl_3$) δ 7.53-7.59 (m, 1H), 7.16-7.23 (m, 1H), 7.00-7.10 (m, 1H), 6.58-6.67 (m, 1H), 4.54-4.79 (m, 4H), 3.84 (br t, J=5.81 Hz, 3H), 3.58-3.68 (m, 1H), 3.39-3.49 (m, 1H), 3.20 (s, 3H), 2.81-2.91 (m, 2H). LCMS: 436/438 [M+1].

Step 2. N2-(3-chloro-4-fluorophenyl)-N8,10-dimethyl-11-oxo-1,3,4,7,8,9,10,11-octahydro-2H-pyrido[4',3':3,4]pyrazolo[1,5-a][1,4]diazepine-2,8-dicarboxamide To a mixture 2-((3-chloro-4-fluorophenyl)carbamoyl)-10-methyl-11-oxo-2,3,4,7,8,9,10,11-octahydro-1H-pyrido[4',3':3,4]pyrazolo[1,5-a][1,4]diazepine-8-carboxylic acid (70.00 mg, 160.61 μmol, 1.00 eq) and methanamine (43.38 mg, 642.44 μmol, 4.00 eq, HCl) in DMF (5.00 mL) was added HATU (91.60 mg, 240.92 μmol, 1.50 eq) and DIPEA (311.36 mg, 2.41 mmol, 420.76 μL, 15.00 eq) in one portion under $N_2$. The mixture was stirred at 30° C. for 12 hours. LCMS showed the reaction was completed and the desired product was detected. The mixture was poured into water (10 mL), and extracted with ethyl acetate (10 mL*2). The combined organic phase was washed with brine (10 mL*2), dried with anhydrous $Na_2SO_4$, filtered and concentrated in vacuum. The residue was purified by prep-HPLC(FA) to afford N2-(3-chloro-4-fluoro-phenyl)-N8,10-dimethyl-11-oxo-1,3,4,7,8,9-hexahydropyrido[2,3]pyrazolo[2,4-b][1,4]diazepine-2,8-dicarboxamide (25.00 mg, 53.02 μmol, 33.01% yield, 95.2% purity) as white solid. $^1$H NMR (400 MHz, $CDCl_3$) δ 7.54-7.63 (m, 1H), 7.15-7.22 (m, 1H), 7.02-7.10 (m, 1H), 6.52-6.58 (m, 1H), 5.82-5.91 (m, 1H), 4.67 (s, 2H), 4.46-4.64 (m, 2H), 3.81-3.94 (m, 2H), 3.48-3.67 (m, 2H), 3.22 (s, 3H), 2.87 (d, J=4.77 Hz, 5H). LCMS: 449/451 [M+1].

Compound 032: N2-(3-chloro-4-fluorophenyl)-N8,N8,10-trimethyl-11-oxo-1,3,4,7,8,9,10,11-octahydro-2H-pyrido[4',3':3,4]pyrazolo[1,5-a][1,4]diazepine-2,8-dicarboxamide

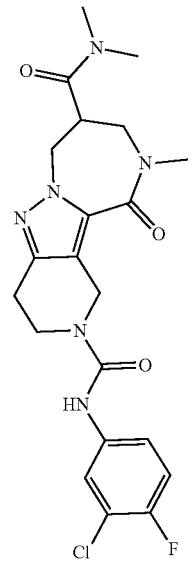 [SMILES: CN(C)C(=O)C1CN(C)C(=O)c2c3c(nn2C1)CCN(C(=O)Nc1ccc(F)c(Cl)c1)C3]

To a mixture of 2-((3-chloro-4-fluorophenyl)carbamoyl)-10-methyl-11-oxo-2,3,4,7,8,9,10,11-octahydro-1H-pyrido[4',3':3,4]pyrazolo[1,5-a][1,4]diazepine-8-carboxylic acid (Compound 030, product from Step 1, 70.00 mg, 160.61 μmol, 1.00 eq) and N-methylmethanamine (65.48 mg, 803.05 μmol, 73.57 μL, 5.00 eq, HCl) in DMF (5.00 mL) was added HATU (91.60 mg, 240.92 μmol, 1.50 eq) and DIPEA (311.36 mg, 2.41 mmol, 420.76 μL, 15.00 eq) in one portion under N2. The mixture was stirred at 30° C. for 12 hours. LCMS showed the reaction was completed and the desired product was detected. The residue was poured into water (10 mL). The aqueous phase was extracted with ethyl acetate (10 mL*2). The combined organic phase was washed with brine (10 mL*2), dried with anhydrous $Na_2SO_4$, filtered and concentrated in vacuum. The residue was purified by prep-HPLC(FA) to afford N2-(3-chloro-4-fluoro-phenyl)-N8,N8,10-trimethyl-11-oxo-1,3,4,7,8,9-hexahydro-pyrido[2,3]pyrazolo[2,4-b][1,4]diazepine-2,8-dicarboxamide (30.00 mg, 63.71 μmol, 39.67% yield, 98.3% purity) as white solid. 1H NMR (400 MHz, $CDCl_3$) δ 7.56-7.63 (m, 1H), 7.15-7.22 (m, 1H), 7.02-7.10 (m, 1H), 6.51-6.60 (m, 1H), 4.40-4.80 (m, 4H), 3.87 (s, 2H), 3.52-3.70 (m, 3H), 3.26 (s, 3H), 3.15 (s, 3H), 3.02 (s, 3H), 2.78-2.91 (m, 2H). LCMS: 463/465 [M+1].

Compound 033: N-(3-chloro-4-fluorophenyl)-8-(2-hydroxypropan-2-yl)-10-methyl-11-oxo-3,4,8,9,10,11-hexahydro-1H-pyrido[4',3':3,4]pyrazolo[1,5-a][1,4]diazepine-2 (7H)-carboxamide

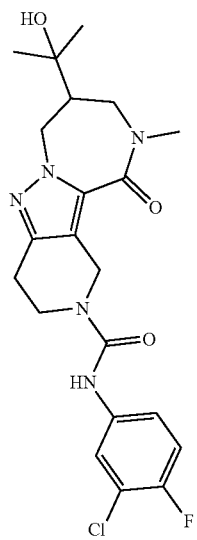 [SMILES: CN1CC(C(C)(C)O)Cn2nc3c(c2C1=O)CN(C(=O)Nc1ccc(F)c(Cl)c1)CC3]

To a mixture of MeMgBr (3 M, 344.90 μL, 6.00 eq) in THF (3.00 mL) was added ethyl 2-[(3-chloro-4-fluoro-phenyl)carbamoyl]-10-methyl-11-oxo-1,3,4,7,8,9-hexahydropyrido[2,3]pyrazolo[2,4-b][1,4]diazepine-8-carboxylate (Compound 030, 80.00 mg, 172.45 μmol, 1.00 eq) in THF (3.00 mL) in one portion at −40° C. under $N_2$. The mixture was stirred at −40° C. for 30 min, then heated to 15° C. and stirred for 2 hours. LCMS showed the reaction was completed. The mixture was poured into sat. $NH_4Cl$ (10 mL) and stirred for 1 min.

The aqueous phase was extracted with ethyl acetate (10 mL*2). The combined organic phase was washed with brine (10 mL*2), dried with anhydrous $Na_2SO_4$, filtered and concentrated in vacuum. The residue was purified by prep-HPLC(FA) to afford the title compound (45.00 mg, 98.91 μmol, 57.36% yield, 98.89% purity) as white solid. LCMS: 450/452 [M+1]. 1H NMR (400 MHz, $CDCl_3$) δ 7.59 (dd, J=2.64, 6.53 Hz, 1H), 7.17-7.22 (m, 1H), 7.05 (t, J=8.78 Hz, 1H), 6.62 (s, 1H), 4.69-4.75 (m, 1H), 4.52-4.65 (m, 2H), 4.33 (dd, J=7.22, 14.62 Hz, 1H), 3.86 (q, J=5.86 Hz, 2H), 3.43-3.58 (m, 2H), 3.19 (s, 3H), 2.83 (t, J=5.77 Hz, 2H), 2.36-2.53 (m, 1H), 1.62 (s, 10H), 1.54 (br s, 1H), 1.31 (d, J=8.66 Hz, 6H).

Compound 034: N-(3-chloro-4-fluorophenyl)-8-(1-hydroxyethyl)-10-methyl-11-oxo-1,3,4,7,8,9,10,11-octahydro-2H-pyrido[4',3':3,4]pyrazolo[1,5-a][1,4]diazepine-2-carboxamide

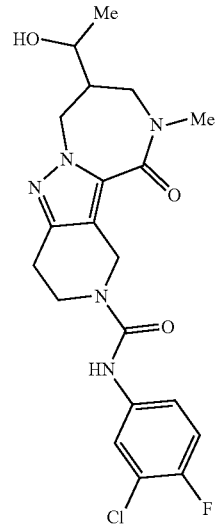 [SMILES: CC(O)C1CN(C)C(=O)c2c3c(nn2C1)CCN(C(=O)Nc1ccc(F)c(Cl)c1)C3]

Step 1. N2-(3-chloro-4-fluoro-phenyl)-N8-methoxy-N8,10-dimethyl-11-oxo-1,3,4,7,8,9-hexahydropyrido[2,3]pyrazolo[2,4-b][1,4]diazepine-2,8-dicarboxamide To a mixture of 2-[(3-chloro-4-fluoro-phenyl)carbamoyl]-10-methyl-11-oxo-1,3,4,7,8,9-hexahydropyrido[2,3]pyrazolo[2,4-b][1,4]diazepine-8-carboxylic acid (Compound 030, product from Step 1, 300.00 mg, 688.33 μmol, 1.00 eq) and N-methoxymethanamine; hydrochloride (268.56 mg, 2.75 mmol, 4.00 eq) in DMF (5.00 mL) was added HATU (392.58 mg, 1.03 mmol, 1.50 eq) and DIPEA (1.33 g, 10.32 mmol, 1.80 mL, 15.00 eq) in one portion under $N_2$. The mixture was stirred at 30° C. for 5 hours. TLC (Dichloromethane:Methanol=10:1) showed the reaction was completed. The mixture was poured into water (15 mL) and extracted with ethyl acetate (20 mL*2). The combined organic phase was washed with brine (10 mL*2), dried with anhydrous Na$_2$SO$_4$, filtered and concentrated in vacuum. The residue was purified by silica gel chromatography (Dichloromethane:Methanol=50:1,20:1) to afford the title compound (310.00 mg, 586.47 µmol, 85.20% yield, 90.6% purity) as white solid. LCMS: 479/481 [M+1].

Step 2. 8-acetyl-N-(3-chloro-4-fluoro-phenyl)-10-methyl-11-oxo-1,3,4,7,8,9-hexahydropyrido[2,3]pyrazolo[2,4-b][1,4]diazepine-2-carboxamide To a mixture of MeMgBr (3 M, 1.11 mL, 20.00 eq) in THF (3.00 mL) was added N2-(3-chloro-4-fluoro-phenyl)-N8-methoxy-N8,10-dimethyl-11-oxo-1,3,4,7,8,9-hexahydropyrido[2,3]pyrazolo[2,4-b][1,4]diazepine-2,8-dicarboxamide (80.00 mg, 167.05 µmol, 1.00 eq) in THF (1.00 mL) drop-wise at 0° C. under N$_2$. The mixture was heated to 30° C. and stirred for 14 hours. TLC (Ethyl acetate:Methanol=20:1) showed the reaction was completed. The mixture was poured into sat. NH$_4$C$_1$ (20 mL) and extracted with ethyl acetate (15 mL*2). The combined organic phase was washed with brine (10 mL*2), dried with anhydrous Na$_2$SO$_4$, filtered and concentrated in vacuum. The residue was purified by prep-TLC (Ethyl acetate:Methanol=20:1) to afford the title compound (25.00 mg, 54.16 µmol, 32.42% yield, 94% purity) as yellow solid. LCMS: 434/436 [M+1].

Step 3. N-(3-chloro-4-fluorophenyl)-8-(1-hydroxyethyl)-10-methyl-11-oxo-1,3,4,7,8,9,10,11-octahydro-2H-pyrido[4',3':3,4]pyrazolo[1,5-a][1,4]diazepine-2-carboxamide To a mixture of 8-acetyl-N-(3-chloro-4-fluoro-phenyl)-10-methyl-11-oxo-1,3,4,7,8,9-hexahydropyrido[2,3]pyrazolo[2,4-b][1,4]diazepine-2-carboxamide (25.00 mg, 57.62 µmol, 1.00 eq) in EtOH (3.00 mL) was added NaBH$_4$ (3.27 mg, 86.43 µmol, 1.50 eq) in one portion at 0° C. under N$_2$. The mixture was stirred at 0° C. for 2 hours. LCMS showed the reaction was completed. The residue was poured into water (10 mL) and extracted with ethyl acetate (10 mL*2). The combined organic phase was washed with brine (10 mL*2), dried with anhydrous Na$_2$SO$_4$, filtered and concentrated in vacuum. The residue was purified by prep-HPLC (FA) to afford the title compound (15.00 mg, 34.31 µmol, 59.55% yield, 99.7% purity) as white solid. $^1$H NMR (400 MHz, CDCl$_3$) δ 7.59 (d, J=6.43 Hz, 1H), 7.17-7.25 (m, 1H), 7.05 (t, J=8.90 Hz, 1H), 6.60 (br d, J=4.03 Hz, 1H), 4.56-4.73 (m, 2H), 4.31-4.44 (m, 1H), 4.10 (dd, J=6.97, 14.31 Hz, 1H), 3.88-3.92 (m, 1H), 3.77-3.88 (m, 1H), 3.75-3.95 (m, 1H), 3.63 (dd, J=6.05, 14.73 Hz, 1H), 3.48 (dd, J=5.14, 14.92 Hz, 1H), 3.31-3.38 (m, 1H), 3.19 (d, J=3.67 Hz, 3H), 2.84 (t, J=5.75 Hz, 2H), 2.36-2.47 (m, 1H), 1.61 (br s, 12H), 1.31 (dd, J=6.30, 11.80 Hz, 3H). LCMS: 436/438 [M+1].

Compound 035: N-(3-chloro-4-fluorophenyl)-8-(1-hydroxypropyl)-10-methyl-1-oxo-1,3,4,7,8,9,10,11-octahydro-2H-pyrido[4',3':3,4]pyrazolo[1,5-a][1,4]diazepine-2-carboxamide

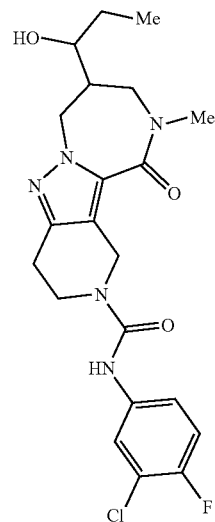 [SMILES: CCC(O)C1CN(C)C(=O)c2c3c(nn2C1)CCN(C(=O)Nc1ccc(F)c(Cl)c1)C3]

Step 1. N-(3-chloro-4-fluoro-phenyl)-10-methyl-11-oxo-8-propanoyl-1,3,4,7,8,9-hexahydropyrido[2,3]pyrazolo[2,4-b][1,4]diazepine-2-carboxamide To a mixture of bromo(ethyl)magnesium (3 M, 1.39 mL, 20.00 eq) in THF (3.00 mL) was added N$_2$-(3-chloro-4-fluoro-phenyl)-N$_8$-methoxy-N$_{8,10}$-dimethyl-11-oxo-1,3,4,7,8,9-hexahydropyrido[2,3]pyrazolo[2,4-b][1,4]diazepine-2,8-dicarboxamide (Compound 034, product from Step 1, 100.00 mg, 208.81 µmol, 1.00 eq) in THF (2.00 mL) drop-wise at 0° C. under N$_2$. The mixture was heated to 30° C. and stirred for 4 hours. LCMS and TLC (Ethyl acetate:Methanol=20:1) showed the reaction was completed. The mixture was poured into water (10 mL) and stirred for 2 min. The aqueous phase was extracted with ethyl acetate (10 mL*2). The combined organic phase was washed with brine (10 mL*2), dried with anhydrous Na$_2$SO$_4$, filtered and concentrated in vacuum. The residue was purified by prep-TLC (Ethyl acetate:Methanol=20:1) to afford the title compound (30.00 mg, 66.98 µmol, 32.08% yield, 100% purity) as yellow solid. LCMS: 448/450 [M+1].

Step 2. N-(3-chloro-4-fluorophenyl)-8-(1-hydroxypropyl)-10-methyl-11-oxo-1,3,4,7,8,9,10,11-octahydro-2H-pyrido[4',3':3,4]pyrazolo[1,5-a][1,4]diazepine-2-carboxamide To a mixture of N-(3-chloro-4-fluoro-phenyl)-10-methyl-11-oxo-8-propanoyl-1,3,4,7,8,9-hexahydropyrido[2,3]pyrazolo[2,4-b][1,4]diazepine-2-carboxamide (30.00 mg, 66.98 µmol, 1.00 eq) in EtOH (3.00 mL) was added NaBH$_4$ (3.80 mg, 100.47 µmol, 1.50 eq) in one portion at 0° C. under N$_2$. The mixture was stirred at 20° C. for 2 hours. LCMS showed the reaction was completed. The residue was poured into water (10 mL). The aqueous phase was extracted with ethyl acetate (10 mL*2). The combined organic phase was washed with brine (10 mL*2), dried with anhydrous Na$_2$SO$_4$, filtered and concentrated in vacuum. The residue was purified by prep-HPLC(FA) to afford the title compound (25.00 mg, 52.90 μmol, 78.98% yield, 95.2% purity) as white solid. $^1$H NMR (400 MHz, CDCl$_3$) δ 7.59 (dd, J=1.96, 6.60 Hz, 1H), 7.17-7.25 (m, 1H), 7.05 (t, J=8.80 Hz, 1H), 6.62 (br d, J=3.79 Hz, 1H), 4.57-4.73 (m, 3H), 4.29-4.44 (m, 1H), 4.15 (br d, J=7.09 Hz, 1H), 3.79-3.92 (m, 2H), 3.64 (br dd, J=5.87, 15.04 Hz, 1H), 3.48 (br d, J=5.14 Hz, 1H), 3.37 (d, J=7.46 Hz, 1H), 3.19 (d, J=2.08 Hz, 3H), 2.84 (br t, J=5.50 Hz, 2H), 2.43-2.53 (m, 1H), 1.85-1.99 (m, 1H), 1.40-1.57 (m, 2H), 0.99-1.07 (m, 3H). LCMS: 450/452 [M+1].

Compound 036: N-(3-chloro-4-fluorophenyl)-8-(cyclopropyl(hydroxy)methyl)-10-methyl-1-oxo-1,3,4,7,8,9,10,11-octahydro-2H-pyrido[4',3': 3,4]pyrazolo[1,5-a][1,4]diazepine-2-carboxamide

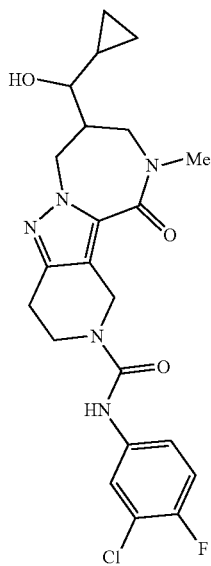 [SMILES: CN1CC(C(O)C2CC2)Cn2nc3c(c2C1=O)CN(C(=O)Nc1ccc(F)c(Cl)c1)CC3]

Step 1. N-(3-chloro-4-fluoro-phenyl)-8-(cyclopropanecarbonyl)-10-methyl-11-oxo-1,3,4,7,8,9-hexahydropyrido[2,3]pyrazolo[2,4-b][1,4]diazepine-2-carboxamide To a mixture of bromo(cyclopropyl)magnesium (0.5 M, 7.52 mL, 15.00 eq) in THF (3.00 mL) was added N2-(3-chloro-4-fluoro-phenyl)-N8-methoxy-N8,10-dimethyl-11-oxo-1,3,4,7,8,9-hexahydropyrido[2,3]pyrazolo[2,4-b][1,4]diazepine-2,8-dicarboxamide (Compound 034, product from Step 1, 120.00 mg, 250.57 μmol, 1.00 eq) in THF (2.00 mL) drop-wise at 0° C. under N2. The mixture was heated to 15° C. and stirred for 14 hours. LCMS and TLC (Ethyl acetate:Methanol=20:1) showed the starting material:desired product=2:3. The mixture was poured into 1N HCl (10 mL) and stirred for 2 min. The aqueous phase was extracted with ethyl acetate (10 mL*2). The combined organic phase was washed with brine (10 mL*2), dried with anhydrous Na$_2$SO$_4$, filtered and concentrated in vacuum. The residue was purified by prep-TLC (Ethyl acetate:Methanol=20:1) to afford the title compound (50.00 mg, 101.11 μmol, 40.35% yield, 93% purity) as yellow solid. LCMS: 460/462 [M+1].

Step 2. N-(3-chloro-4-fluorophenyl)-8-(cyclopropyl(hydroxy)methyl)-10-methyl-1-oxo-1,3,4,7,8,9,10,11-octahydro-2H-pyrido[4',3':3,4]pyrazolo[1,5-a][1,4]diazepine-2-carboxamide To a mixture of N-(3-chloro-4-fluoro-phenyl)-8-(cyclopropanecarbonyl)-10-methyl-11-oxo-1,3,4,7,8,9-hexahydropyrido[2,3]pyrazolo[2,4-b][1,4]diazepine-2-carboxamide (50.00 mg, 108.72 μmol, 1.00 eq) in EtOH (3.00 mL) was added NaBH$_4$ (6.17 mg, 163.08 μmol, 1.50 eq) in one portion at 0° C. under N$_2$. The mixture was stirred at 20° C. for 2 hours. LCMS showed the reaction was completed. The residue was poured into water (10 mL) and extracted with ethyl acetate (10 mL*2). The combined organic phase was washed with brine (10 mL*2), dried with anhydrous Na$_2$SO$_4$, filtered and concentrated in vacuum. The residue was purified by prep-HPLC(FA) to afford the title compound (46.00 mg, 98.29 μmol, 90.41% yield, 98.7% purity) as white solid. $^1$H NMR (400 MHz, CDCl$_3$) δ 7.59 (dd, J=2.32, 6.48 Hz, 1 bH), 7.15-7.23 (m, 1H), 7.05 (t, J=8.80 Hz, 1H), 6.61 (br s, 1H), 4.59-4.74 (m, 3H), 4.44-4.54 (m, 1H), 4.24-4.42 (m, 1H), 3.78-3.92 (m, 2H), 3.60-3.68 (m, 1H), 3.45-3.58 (m, 1H), 3.33-3.43 (m, 1H), 3.19 (d, J=5.50 Hz, 2H), 3.13-3.25 (m, 1H), 2.79-2.90 (m, 2H), 2.79-2.91 (m, 1H), 2.65 (br d, J=6.97 Hz, 1H), 1.74-1.98 (m, 1H), 0.90-1.06 (m, 1H), 0.57-0.78 (m, 2H), 0.40-0.51 (m, 1H), 0.32 (br dd, J=3.55, 7.95 Hz, 2H). LCMS: 462/464 [M+1].

Compound 037: N-(3-chloro-4-fluorophenyl)-8-(difluoromethyl)-10-methyl-11-oxo-1,3,4,7,8,9,10,11-octahydro-2H-pyrido[4',3':3,4]pyrazolo[1,5-a][1,4]diazepine-2-carboxamide

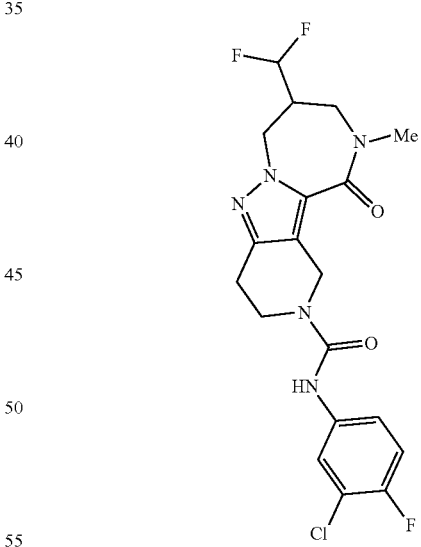

Step 1. N-(3-chloro-4-fluoro-phenyl)-8-(hydroxymethyl)-10-methyl-1-oxo-1,3,4,7,8,9-hexahydropyrido[2,3]pyrazolo[2,4-b][1,4]diazepine-2-carboxamide To a mixture of ethyl 2-[(3-chloro-4-fluoro-phenyl)carbamoyl]-10-methyl-11-oxo-1,3,4,7,8,9-hexahydropyrido[2,3]pyrazolo[2,4-b][1,4]diazepine-8-carboxylate (Compound 030, 500.00 mg, 1.08 mmol, 1.00 eq) in THF (5.00 mL) was added LiAlH$_4$ (61.48 mg, 1.62 mmol, 1.50 eq) in one portion at −40° C. under N$_2$. The mixture was stirred at −40° C. for 30 min, then heated to 0° C. and stirred for 2 hours. TLC (Dichloromethane:Methanol=10:1) showed the reaction was completed. The mixture was poured into HCl (1 N, 10 mL) and stirred for 1 min. The resulting was extracted with ethyl acetate (20 mL*2). The combined organic phase was washed with brine (10 mL*2), dried with anhydrous $Na_2SO_4$, filtered and concentrated in vacuum. The residue was purified by silica gel chromatography (Dichloromethane:Methanol=100:1~20:1) to afford the title compound (330.00 mg, 775.38 μmol, 71.79% yield, 99.12% purity) as yellow solid. LCMS: 422/424 [M+1].

Step 2. N-(3-chloro-4-fluoro-phenyl)-8-formyl-10-methyl-11-oxo-1,3,4,7,8,9-hexahydropyrido[2,3]pyrazolo[2,4-b][1,4]diazepine-2-carboxamide To a mixture of N-(3-chloro-4-fluoro-phenyl)-8-(hydroxymethyl)-10-methyl-11-oxo-1,3,4,7,8,9-hexahydropyrido[2,3]pyrazolo[2,4-b][1,4]diazepine-2-carboxamide (50.00 mg, 118.53 μmol, 1.00 eq) in DCM (3.00 mL) was added Dess-Martin (75.41 mg, 177.79 μmol, 55.04 μL, 1.50 eq) in one portion at 0° C. under $N_2$. The mixture was stirred at 30° C. for 12 hours. LCMS showed the reaction was completed. The mixture was concentrated in vacuum. The residue was purified by silica gel chromatography (Ethyl acetate) to afford the title compound (40.00 mg, 43.83 μmol, 36.97% yield, 46% purity) as yellow solid.

Step 3. N-(3-chloro-4-fluorophenyl)-8-(difluoromethyl)-10-methyl-11-oxo-1,3,4,7,8,9,10,11-octahydro-2H-pyrido[4',3':3,4]pyrazolo[1,5-a][1,4]diazepine-2-carboxamide To a mixture of N-(3-chloro-4-fluoro-phenyl)-8-formyl-10-methyl-11-oxo-1,3,4,7,8,9-hexahydropyrido[2,3]pyrazolo[2,4-b][1,4]diazepine-2-carboxamide (40.00 mg, 95.27 μmol, 1.00 eq) in DCM (4.00 mL) was added DAST (76.78 mg, 476.35 μmol, 62.93 μL, 5.00 eq) in one portion at −78° C. under $N_2$. The mixture was stirred at −78° C. for 2 hours, then heated to 20° C. and stirred for 12 hours. LCMS showed the reaction was completed. The mixture was poured into water (10 mL) and stirred for 2 min. The aqueous phase was extracted with DCM (10 mL*2). The combined organic phase was washed with brine (10 mL*2), dried with anhydrous $Na_2SO_4$, filtered and concentrated in vacuum. The residue was purified by prep-HPLC(FA) to afford the title compound (15.00 mg, 33.58 μmol, 35.24% yield, 98.9% purity) as white solid. $^1H$ NMR (400 MHz, $CDCl_3$) δ 7.58 (dd, J=2.63, 6.54 Hz, 1H), 7.17-7.26 (m, 1H), 7.06 (t, J=8.74 Hz, 1H), 6.57 (br s, 1H), 5.72-6.06 (m, 1H), 4.63-4.72 (m, 2H), 4.52 (dd, J=7.15, 14.49 Hz, 1H), 4.40 (dd, J=6.91, 14.61 Hz, 1H), 3.85 (q, J=5.42 Hz, 2H), 3.55 (dq, J=5.81, 15.39 Hz, 2H), 3.19 (s, 3H), 2.80-2.97 (m, 3H), 1.60 (br s, 11H). LCMS: 442/444 [M+1].

Compound 038: N-(3-chloro-4-fluorophenyl)-10-(2,2-difluoroethyl)-11-oxo-1,3,4,7,8,9,10,11-octahydro-2H-pyrido[4',3':3,4]pyrazolo[1,5-a][1,4]diazepine-2-carboxamide

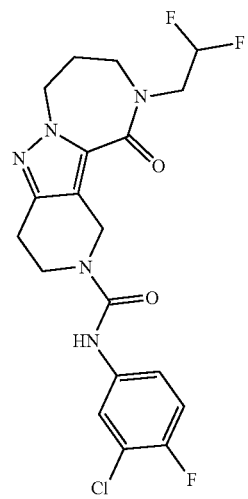 [SMILES: O=C(Nc1ccc(F)c(Cl)c1)N1CCc2nn3c(c2C1)C(=O)N(CC(F)F)CCC3]

Step 1. tert-butyl 10-(2,2-difluoroethyl)-11-oxo-1,3,4,7,8,9-hexahydropyrido[2,3]pyrazolo[2,4-b][1,4]diazepine-2-carboxylate To a solution of tert-butyl 11-oxo-3,4,7,8,9,10-hexahydro-1H-pyrido[2,3]pyrazolo[2,4-b][1,4]diazepine-2-carboxylate (Intermediate 5, 100.00 mg, 326.41 mol, 1.00 eq) in DMF (3.00 mL) was added NaH (19.58 mg, 489.61 μmol, 60% purity, 1.50 eq) at 0° C. under $N_2$. After stirred at 0° C. for 30 minutes, 2,2-difluoroethyl trifluoromethanesulfonate (349.44 mg, 1.63 mmol, 5.00 eq) was added. The reaction mixture was stirred at 15° C. for one hour. LCMS showed compound 5 was consumed completely and about 65% of desired compound was detected. The reaction was quenched with water (30 mL) and then extracted with EtOAc (50 mL*3). The combined organic phase was dried over anhydrous $Na_2SO_4$, filtered and concentrated in vacuum. The residue was purified by silica gel chromatography to afford the title compound (64.00 mg, 172.79 μmol, 52.94% yield) was obtained as yellow oil. LCMS: 371 [M+1].

Step 2. 10-(2,2-difluoroethyl)-2,3,4,7,8,9-hexahydro-1H-pyrido[2,3]pyrazolo[2,4-b][1,4]diazepin-11-one To a solution of tert-butyl 10-(2,2-difluoroethyl)-11-oxo-1,3,4,7,8,9-hexahydropyrido[2,3]pyrazolo[2,4-b][1,4]diazepine-2-carboxylate (62.00 mg, 167.39 μmol, 1.00 eq) in DCM (2.00 mL) was added TFA (1.54 g, 13.51 mmol, 1.00 mL, 80.69 eq), the reaction mixture was stirred at 20° C. for one hour. TLC indicated compound 6 was consumed completely, and one major new spot with larger polarity was detected. The solvent was removed on a rotary evaporator to afford the title compound (64.00 mg, crude, TFA) was obtained as yellow oil, which was used in next step directly without further purification.

Step 3. N-(3-chloro-4-fluorophenyl)-10-(2,2-difluoroethyl)-11-oxo-1,3,4,7,8,9,10,11-octahydro-2H-pyrido[4',3':3,4]pyrazolo[1,5-a][1,4]diazepine-2-carboxamide To a mixture of 10-(2,2-difluoroethyl)-2,3,4,7,8,9-hexahydro-1H-pyrido[2,3]pyrazolo [2,4-b][1,4]diazepin-11-one (64.00 mg, 166.54 μmol, 1.00 eq, TFA) in DCM (5.00 mL) was added TEA (67.41 mg, 666.15 μmol, 92.34 μL, 4.00 eq), followed by phenyl N-(3-chloro-4-fluoro-phenyl)carbamate (44.24 mg, 166.54 μmol, 1.00 eq), the reaction mixture was stirred at 20° C. for 16 hours. LCMS showed a main peak with desired MS was detected. The mixture was extracted with DCM (50 mL*2) and water (30 mL), the organic phase was dried with anhydrous $Na_2SO_4$, filtered and concentrated in vacuum. The residue was purified by prep-HPLC(FA) to afford the title compound (72.00 mg, 161.20 μmol, 96.79% yield, 98.92% purity) was obtained as white solid. $^1$H NMR (400 MHz, $CDCl_3$) δ=7.55-7.57 (dd, J=6.48, 2.69 Hz, 1H) 7.18-7.20 (m, 1H) 7.03-7.07 (m, 1H) 6.54 (s, 1H) 5.89-6.18 (m, 1H) 4.67 (s, 2H) 4.39-4.43 (t, J=6.91 Hz, 2H) 3.83-3.92 (m, 4H) 3.57-3.61 (t, J=6.24 Hz, 2H) 2.83-2.86 (t, J=5.75 Hz, 2H) 2.32-2.38 (m, J=6.57 Hz, 2H). LCMS: 442/444 [M+1]

Compound 039: N-(3-chloro-4-fluorophenyl)-9,10-dimethyl-11-oxo-1,3,4,7,8,9,10,11-octahydro-2H-pyrido[4',3':3,4]pyrazolo[1,5-a][1,4]diazepine-2-carboxamide

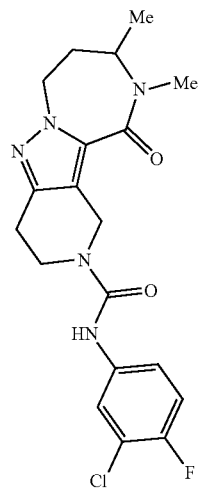 [SMILES: CC1CCn2nc3c(c2C(=O)N1C)CN(C(=O)Nc1ccc(F)c(Cl)c1)CC3]

Step 1. 9,10-dimethyl-2,3,4,7,8,9-hexahydro-1H-pyrido[2,3]pyrazolo[2,4-c][1,4]diazepin-11-one To a mixture of tert-butyl 9,10-dimethyl-11-oxo-1,3,4,7,8,9-hexahydropyrido[2,3]pyrazolo[2,4-c][1,4]diazepine-2-carboxylate (Intermediate 8, 66.00 mg, 197.36 μmol, 1.00 eq) in DCM (2.00 mL) was added TFA (1.54 g, 13.51 mmol, 1.00 mL, 68.44 eq) in one portion under $N_2$. The mixture was stirred at 15° C. for 2 hours. TLC (Dichloromethane: Methanol=10:1) showed the reaction was completed. The mixture was concentrated in vacuum to afford the title compound (68.74 mg, 197.35 μmol, 100.00% yield, TFA) as yellow oil.

Step 2. N-(3-chloro-4-fluorophenyl)-9,10-dimethyl-11-oxo-1,3,4,7,8,9,10,11-octahydro-2H-pyrido[4',3':3,4]pyrazolo[1,5-a][1,4]diazepine-2-carboxamide To a mixture of 9,10-dimethyl-2,3,4,7,8,9-hexahydro-1H-pyrido[2,3]pyrazolo[2,4-c][1,4]diazepin-11-one (68.74 mg, 197.35 mol, 1.00 eq, TFA) and phenyl N-(3-chloro-4-fluorophenyl)carbamate (52.43 mg, 197.35 mol, 1.00 eq) in DCM (6.00 mL) was added TEA (199.70 mg, 1.97 mmol, 273.56 μL, 10.00 eq) under $N_2$. The mixture was stirred at 25° C. for 10 hours. LCMS showed the reaction was completed. The residue was poured into water (10 mL) and stirred for 2 min. The aqueous phase was extracted with ethyl acetate (10 mL*2). The combined organic phase was washed with brine (10 mL*2), dried with anhydrous $Na_2SO_4$, filtered and concentrated in vacuum. The residue was purified by prep-HPLC(FA) to afford the title compound (46.00 mg, 112.20 μmol, 56.85% yield, 98.99% purity) as white solid. $^1$H NMR (400 MHz, $CDCl_3$) δ 7.57-7.61 (m, 1H), 7.16-7.22 (m, 1H), 7.01-7.09 (m, 1H), 6.52-6.59 (m, 1H), 4.71 (s, 2H), 4.44-4.54 (m, 1H), 4.31-4.43 (m, 1H), 3.84 (s, 3H), 3.14 (s, 3H), 2.79-2.89 (m, 2H), 2.36-2.51 (m, 1H), 2.11-2.27 (m, 1H), 1.35 (d, J=6.97 Hz, 3H). LCMS: 406/408 [M+1].

Compound 040: methyl 2-((3-chloro-4-fluorophenyl)carbamoyl)-9-methyl-10-oxo-1,2,3,4,9,10-hexahydropyrido[4',3':3,4]pyrazolo[1,5-a]pyrazine-8-carboxylate

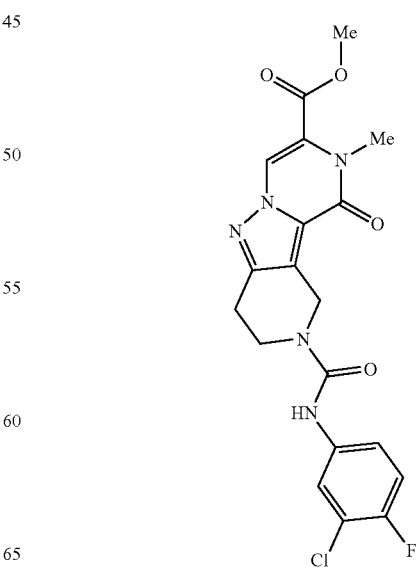

Step 1. methyl 9-methyl-10-oxo-1,2,3,4-tetrahydro-pyrido[2,3]pyrazolo [2,4-b]pyrazine-8-carboxylate A mixture of 2-tert-butyl8-methyl8-methoxy-9-methyl-10-oxo-1,3,4,7-tetrahydro pyrido[2,3]pyrazolo[2,4-c]pyrazine-2,8-dicarboxylate (Intermediate 9, 20.00 mg, 50.71 µmol, 1.00 eq) in HCl/dioxane (4 M, 20.00 mL, 1577.60 eq) was stirred at 20° C. for 2 hours. LCMS showed the reaction was completed. The residue was concentrated in vacuum to afford the title compound (15.15 mg, 50.71 µmol, 100.00% yield, HCl) as yellow solid. LCMS: 263 [M+1].

Step 2. methyl 2-((3-chloro-4-fluorophenyl)carbamoyl)-9-methyl-10-oxo-1,2,3,4,9,10-hexahydropyrido[4',3':3,4]pyrazolo[1,5-a]pyrazine-8-carboxylate To a mixture of methyl 9-methyl-10-oxo-1,2,3,4-tetrahydropyrido[2,3]pyrazolo [2,4-b]pyrazine-8-carboxylate (15.15 mg, 50.71 µmol, 1.00 eq, HCl) and phenyl N-(3-chloro-4-fluoro-phenyl)carbamate (13.47 mg, 50.71 mol, 1.00 eq) in DCM (4.00 mL) was added TEA (51.32 mg, 507.15 µmol, 70.30 µL, 10.00 eq) under $N_2$. The mixture was stirred at 25° C. for 10 hours. LCMS showed the reaction was completed. The residue was poured into water (10 mL) and stirred for 2 min. The aqueous phase was extracted with ethyl acetate (10 mL*2). The combined organic phase was washed with brine (10 mL*2), dried with anhydrous $Na_2SO_4$, filtered and concentrated in vacuum. The residue was purified by prep-HPLC (FA) to afford the title compound (15.00 mg, 32.43 µmol, 63.96% yield, 93.8% purity) as white solid. $^1$H NMR (400 MHz, $CDCl_3$) 8.20 (s, 1H), 7.56-7.63 (m, 1H), 7.14-7.24 (m, 1H), 7.02-7.12 (m, 1H), 6.55 (s, 1H), 4.93 (s, 2H), 3.95 (s, 3H), 3.92 (s, 1H), 3.75 (s, 3H), 2.97-3.05 (m, 1H). LCMS: 434 [M+1].

Compound 041: N-(3-chloro-4-fluorophenyl)-8-(hydroxymethyl)-9-methyl-10-oxo-3,4,9,10-tetrahydropyrido[4',3':3,4]pyrazolo[1,5-a]pyrazine-2 (1H)-carboxamide

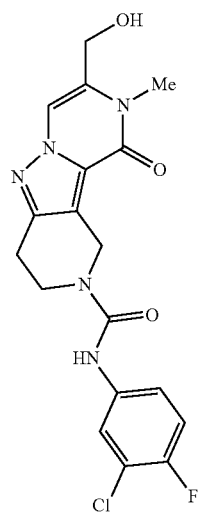 [SMILES: Cn1c(CO)cn2nc3c(c2c1=O)CN(C(=O)Nc1ccc(F)c(Cl)c1)CC3]

To a mixture of methyl 2-[(3-chloro-4-fluoro-phenyl)carbamoyl]-9-methyl-10-oxo-3,4-dihydro-1H-pyrido[2,3]pyrazolo[2,4-b]pyrazine-8-carboxylate (Compound 040, 30.00 mg, 69.15 µmol, 1.00 eq) in THF (2.00 mL) was added $LiBH_4$ (2.26 mg, 103.73 µmol, 1.50 eq) in one portion at 0° C. under $N_2$. The mixture was stirred at 0° C. for 1 hour, then heated to 20° C. and stirred for 2 hours. LCMS showed the reaction was completed. The reaction was quenched with $NH_4Cl$(5 mL). The aqueous phase was extracted with ethyl acetate (10 mL*2). The combined organic phase was washed with brine (10 mL*2), dried with anhydrous $Na_2SO_4$, filtered and concentrated in vacuum. The residue was purified by prep-HPLC(FA) to afford the title compound (18.00 mg, 44.18 µmol, 63.89% yield, 99.6% purity) as white solid. $^1$H NMR (400 MHz, METHANOL-$d_4$) 7.60 (s, 2H), 7.26-7.39 (m, 1H), 7.06-7.20 (m, 1H), 4.94 (s, 2H), 4.56 (s, 2H), 3.82-3.93 (m, 2H), 3.59 (s, 3H), 2.89-2.98 (m, 2H). LCMS: 406 [M+1].

Compound 042: 2-((3-chloro-4-fluorophenyl)carbamoyl)-9-methyl-10-oxo-1,2,3,4,9,10-hexahydropyrido[4',3':3,4]pyrazolo[1,5-a]pyrazine-8-carboxylic acid

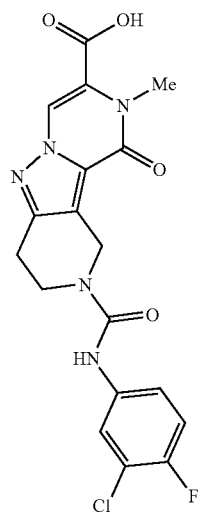 [SMILES: Cn1c(C(=O)O)cn2nc3c(c2c1=O)CN(C(=O)Nc1ccc(F)c(Cl)c1)CC3]

To a mixture of methyl 2-[(3-chloro-4-fluoro-phenyl)carbamoyl]-9-methyl-10-oxo-3,4-dihydro-1H-pyrido[2,3]pyrazolo[2,4-b]pyrazine-8-carboxylate (Compound 040, 36.00 mg, 82.98 µmol, 1.00 eq) in MeOH (4.00 mL) and $H_2O$ (1.00 mL) was added NaOH (6.64 mg, 165.96 µmol, 2.00 eq) in one portion under $N_2$. The mixture was stirred at 30° C. for 5 hours. LCMS showed the reaction was completed. The residue was adjust to pH=7 with 1N HCl and concentrated in vacuum. The residue was purified by prep-HPLC(HCl) to afford the title compound (8.00 mg, 18.77 µmol, 22.62% yield, 98.5% purity) as white solid. $^1$H NMR (400 MHz, METHANOL-$d_4$) 7.81-7.94 (m, 1H), 7.51-7.72 (m, 1H), 7.22-7.38 (m, 1H), 7.04-7.19 (m, 1H), 4.94 (s, 2H), 3.82-3.91 (m, 2H), 3.67 (s, 3H), 2.89-3.01 (m, 2H). LCMS: 420 [M+1].

Compound 043: methyl 2-((3-chloro-4-fluorophenyl)carbamoyl)-9-methyl-10-oxo-1,2,3,4,7,8,9,10-octahydropyrido[4',3':3,4]pyrazolo[1,5-a]pyrazine-8-carboxylate

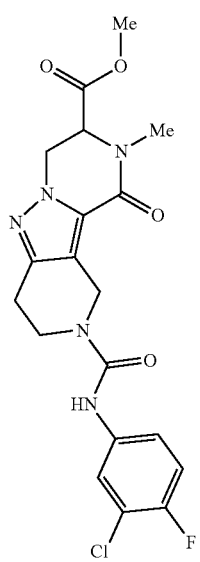 [SMILES: COC(=O)C1Cn2nc3c(c2C(=O)N1C)CN(C(=O)Nc1ccc(F)c(Cl)c1)CC3]

Step 1. methyl 9-methyl-10-oxo-1,2,3,4,7,8-hexahydropyrido[2,3]pyrazolo[2,4-c]pyrazine-8-carboxylate To a solution of methyl 9-methyl-10-oxo-1,2,3,4-tetrahydropyrido[2,3]pyrazolo[2,4-b]pyrazine-8-carboxylate (Intermediate 10, 10.00 mg, 33.48 mol, 1.00 eq, HCl) in AcOH (2.00 mL) was added Pd/C (4.00 mg, 33.48 μmol, 1.00 eq) under $N_2$. The suspension was degassed under vacuum and purged with $H_2$ several times. The mixture was stirred under $H_2$ (50 psi) at 40° C. for 12 hours. LCMS showed little Desired product was detected. The reaction mixture was filtered and the filter was concentrated to afford the title compound (10.86 mg, crude, HOAC) as yellow oil. LCMS: 265 [M+1].

Step 2. methyl 2-((3-chloro-4-fluorophenyl)carbamoyl)-9-methyl-10-oxo-1,2,3,4,7,8,9,10-octahydropyrido[4',3':3,4]pyrazolo[1,5-a]pyrazine-8-carboxylate To a mixture of methyl 9-methyl-10-oxo-1,2,3,4,7,8-hexahydropyrido[2,3]pyrazolo[2,4-c]pyrazine-8-carboxylate (15.57 mg, 41.16 μmol, 1.00 eq, TFA) and phenyl N-(3-chloro-4-fluoro-phenyl)carbamate (10.93 mg, 41.16 μmol, 1.00 eq) in DCM (4.00 mL) was added TEA (41.65 mg, 411.58 μmol, 57.05 μL, 10.00 eq) under $N_2$. The mixture was stirred at 25° C. for 10 hours. LCMS and TLC (Dichloromethane:Methanol=10:1) showed the reaction was completed. The residue was poured into water (10 mL) and stirred for 2 min. The aqueous phase was extracted with ethyl acetate (10 mL*2). The combined organic phase was washed with brine (10 mL*2), dried with anhydrous $Na_2SO_4$, filtered and concentrated in vacuum. The residue was purified by prep-TLC (Dichloromethane:Methanol=10:1) to afford the title compound (16.00 mg, 35.76 μmol, 86.87% yield, 97.4% purity) as white solid. $^1H$ NMR (400 MHz, $CDCl_3$) 7.58-7.65 (m, 1H), 7.17-7.24 (m, 1H), 7.00-7.11 (m, 1H), 6.64-6.72 (m, 1H), 4.65-4.90 (m, 3H), 4.50-4.61 (m, 1H), 4.32-4.39 (m, 1H), 3.83-3.91 (m, 2H), 3.79 (s, 3H), 3.17 (s, 3H), 2.79-2.90 (m, 2H). LCMS: 436 [M+1].

Compound 044: N-(3-chloro-4-fluorophenyl)-8-(hydroxymethyl)-9-methyl-10-oxo-3,4,7,8,9,10-hexahydropyrido[4',3':3,4]pyrazolo[1,5-a]pyrazine-2(1H)-carboxamide

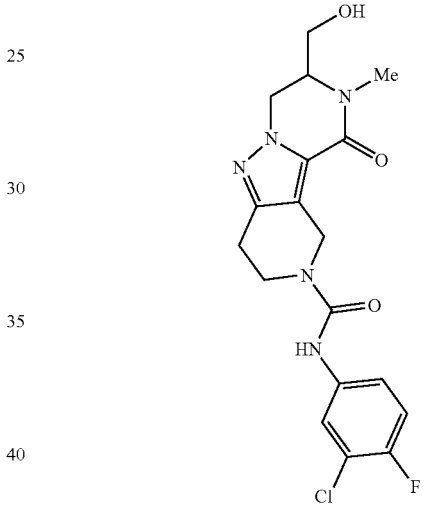

To a mixture of methyl 2-[(3-chloro-4-fluoro-phenyl)carbamoyl]-9-methyl-10-oxo-3,4,7,8-tetrahydro-1H-pyrido[2,3]pyrazolo[2,4-c]pyrazine-8-carboxylate (Compound 043, 13.00 mg, 29.83 μmol, 1.00 eq) in THF (2.00 mL) was added $LiBH_4$ (3.25 mg, 149.14 μmol, 5.00 eq) in one portion at 0° C. under $N_2$. The mixture was stirred at 0° C. for 1 hours, then heated to 20° C. and stirred for 2 hours. LCMS showed the reaction was completed. The reaction was quenched with $NH_4Cl$(5 mL), the aqueous phase was extracted with ethyl acetate (10 mL*2). The combined organic phase was washed with brine (10 mL*2), dried with anhydrous $Na_2SO_4$, filtered and concentrated in vacuum. The residue was purified by prep-HPLC(FA) to afford the title compound (9.00 mg, 21.94 μmol, 73.54% yield, 99.4% purity) as white solid. $^1H$ NMR (400 MHz, METHANOL-$d_4$) 7.55-7.62 (m, 1H), 7.26-7.33 (m, 1H), 7.08-7.19 (m, 1H), 4.75 (d, J=2.32 Hz, 2H), 4.35-4.56 (m, 2H), 3.65-3.93 (m, 4H), 3.43-3.53 (m, 1H), 3.18 (s, 3H), 2.82 (s, 2H). LCMS: 408 [M+1].

205

Compound 045: N-(3-chloro-4-fluorophenyl)-9-methyl-10-oxo-3,4,7,8,9,10-hexahydropyrido[4',3':3,4]pyrazolo [1,5-a]pyrazine-2 (1H)-carboxamide

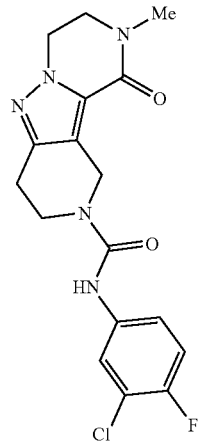 [SMILES: CN1CCn2nc3c(c2C1=O)CN(C(=O)Nc1ccc(F)c(Cl)c1)CC3]

Step 1. 9-methyl-1,2,3,4,7,8-hexahydropyrido[2,3]pyrazolo[2,4-b] pyrazin-10-one To a mixture of tert-butyl 9-methyl-10-oxo-3,4,7,8-tetrahydro-1H-pyrido[2,3] pyrazolo[2,4-b]pyrazine-2-carboxylate (Intermediate 6, 70.00 mg, 228.49 μmol, 1.00 eq) in DCM (1.00 mL) was added TFA (1.54 g, 13.51 mmol, 1.00 mL, 59.11 eq) in one portion under $N_2$. The mixture was stirred at 20° C. for 2 hours. TLC (Dichloromethane:Methanol=10:1) showed the reaction was completed. The mixture was concentrated in vacuum to afford the title compound (73.18 mg, 228.49 μmol, 100.00% yield, TFA) as yellow oil.

Step 2. N-(3-chloro-4-fluorophenyl)-9-methyl-10-oxo-3,4,7,8,9,10-hexahydropyrido[4',3':3,4]pyrazolo [1,5-a]pyrazine-2 (1H)-carboxamide To a mixture of 9-methyl-1,2,3,4,7,8-hexahydropyrido[2,3]pyrazolo[2,4-b]pyrazin-10-one (73.18 mg, 228.49 μmol, 1.00 eq, TFA) and phenyl N-(3-chloro-4-fluoro-phenyl) carbamate (60.70 mg, 228.49 μmol, 1.00 eq) in DCM (6.00 mL) was added TEA (231.21 mg, 2.28 mmol, 316.73 μL, 10.00 eq) under $N_2$. The mixture was stirred at 25° C. for 10 hours. LCMS showed the reaction was completed. The residue was poured into water (10 mL) and stirred for 2 min. The aqueous phase was extracted with ethyl acetate (10 mL*2). The combined organic phase was washed with brine (10 mL*2), dried with anhydrous $Na_2SO_4$, filtered and concentrated in vacuum. The residue was purified by prep-HPLC(FA) to afford the title compound (47.00 mg, 124.16 μmol, 54.34% yield, 99.8% purity) as white solid. $^1$H NMR (400 MHz, $CDCl_3$) δ 7.56-7.63 (m, 1H), 7.14-7.24 (m, 1H), 7.01-7.11 (m, 1H), 6.61 (s, 1H), 4.74 (s, 2H), 4.32-4.44 (m, 2H), 3.87 (t, J=5.75 Hz, 2H), 3.74-3.81 (m, 2H), 3.14 (s, 3H), 2.86 (t, J=5.75 Hz, 2H). LCMS: 378/380 [M+1].

206

Compound 046: N-(3-chloro-4-fluorophenyl)-10-methyl-1,3,4,7,8,9,10,11-octahydro-2H-pyrido[4',3':3,4]pyrazolo[1,5-a][1,4]diazepine-2-carboxamide

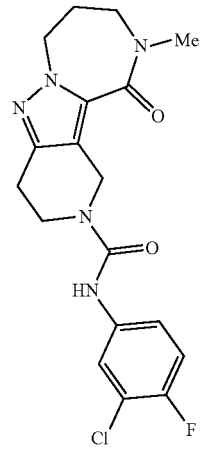 [SMILES: CN1CCCn2nc3c(c2C1=O)CN(C(=O)Nc1ccc(F)c(Cl)c1)CC3]

Step 1. tert-butyl 1,3,4,7,8,9,10,11-octahydropyrido[2,3]pyrazolo[2,4-a][1,4]diazepine-2-carboxylate To a solution of tert-butyl 11-oxo-3,4,7,8,9,10-hexahydro-1H-pyrido[2,3]pyrazolo [2,4-b][1,4]diazepine-2-carboxylate (Intermediate 5, 180.00 mg, 587.54 μmol, 1.00 eq) in toluene (3.00 mL) was added Red-Al® (503.96 mg, 1.76 mmol, 503.96 μL, 70% purity, 3.00 eq). The mixture was stirred at 0° C. for 30 min. Additional 0.05 mL of aliquots of the Red-Al® (sodium bis(2-methoxyethoxy)aluminum dihydride) solution was added every 30 minutes for four times. TLC (EA:MeOH=10:1) and LCMS showed tert-butyl 11-oxo-3,4,7,8,9,10-hexahydro-1H-pyrido[2,3]pyrazolo [2,4-b][1,4]diazepine-2-carboxylate nearly consumed and 60% desired product appeared. The mixture was quenched with 40% NaOH (5 mL), diluted with 50 mL of DCM:MeOH (10:1) and filtrated. The filtrate was concentrated in vacuum. The residue was purified by column chromatography(EtOAc:MeOH, 0%~10%) to afford the title compound (100.00 mg, 249.68 μmol, 42.49% yield, 73% purity) as brown oil.

Step 2. tert-butyl 10-methyl-3,4,7,8,9,11-hexahydro-1H-pyrido[2,3]pyrazolo[2,4-a][1,4]diazepine-2-carboxylate To a solution of tert-butyl 1,3,4,7,8,9,10,11-octahydropyrido[2,3]pyrazolo[2,4-a][1,4]diazepine-2-carboxylate (60.00 mg, 205.21 μmol, 1.00 eq) and HCHO (166.55 mg, 2.05 mmol, 152.80 μL, 37% purity, 10.00 eq) in MeOH (5.00 mL) was added HOAc (1.23 mg, 20.52 μmol, 1.17 μL, 0.10 eq). The mixture was stirred at 20° C. for 0.5 hr. Then $NaBH_3CN$ (51.58 mg, 820.85 μmol, 4.00 eq) was added. The mixture was stirred at 20° C. for 16 hr. TLC (EtOAc:MeOH=10:1) showed one main spot appeared. The mixture was concentrated in vacuum. The residue was extracted with EtOAc (20 mL*2) and $H_2O$ (10 mL). The combined organic layer was dried over $Na_2SO_4$, filtered. The filtrate was concentrated in vacuum to afford the title compound (62.00 mg, crude) as brown oil.

Step 3. 10-methyl-1,2,3,4,7,8,9,11-octahydropyrido [2,3]pyrazolo[2,4-a][1,4]diazepine To a solution of tert-butyl 10-methyl-3,4,7,8,9,11-hexahydro-1H-pyrido[2,3]pyrazolo [2,4-a][1,4]diazepine-2-carboxylate (80.00 mg, 261.10 µmol, 1.00 eq) in DCM (4.00 mL) was added TFA (6.16 g, 54.03 mmol, 4.00 mL, 206.92 eq). The mixture was stirred at 20° C. for 2 hr. TLC (EA:MeOH=10:1) showed Compound 3 consumed. The mixture was concentrated in vacuum to afford the title compound (85.00 mg, crude, TFA) as brown oil.

Step 4. N-(3-chloro-4-fluorophenyl)-10-methyl-1,3,4,7,8,9,10,11-octahydro-2H-pyrido[4',3':3,4]pyrazolo[1,5-a][1,4]diazepine-2-carboxamide To a solution of 10-methyl-1,2,3,4,7,8,9,11-octahydropyrido[2,3]pyrazolo[2,4-a][1,4]diazepine (85.00 mg, 265.37 µmol, 1.00 eq, TFA) and phenyl N-(3-chloro-4-fluoro-phenyl)carbamate (70.50 mg, 265.37 µmol, 1.00 eq) in DCM (3.00 mL) was added TEA (134.26 mg, 1.33 mmol, 183.92 µL, 5.00 eq). The mixture was heated to 20° C. for 16 hr. LCMS showed one main peak with desired Ms. The mixture was concentrated in vacuum. The residue was purified by prep-HPLC(FA), followed by prep-TLC (DCM:MeOH=10:1) and prep-HPLC(Base) to afford the title compound (15.00 mg, 39.58 µmol, 14.92% yield, 99.7% purity) as white solid. $^1$H NMR (400 MHz, CDCl$_3$) δ=7.46 (dd, J=2.69, 6.48 Hz, 1H), 7.07-7.16 (m, 1H), 6.90-7.02 (m, 1H), 6.34 (s, 1H), 4.41 (s, 2H), 4.15-4.25 (m, 2H), 3.67 (t, J=5.81 Hz, 2H), 3.57 (s, 2H), 2.86-2.99 (m, 2H), 2.74 (t, J=5.75 Hz, 2H), 2.30 (s, 3H), 1.82 (br t, J=4.95 Hz, 2H). LCMS [M+1]: 378.

Compound 047: N-(3-chloro-4-fluoro-phenyl)-8-(2-cyclopropyl-1-hydroxy-ethyl)-10-methyl-1-oxo-1,3,4,7,8,9-hexahydropyrido[2,3]pyrazolo[2,4-b][1,4]diazepine-2-carboxamide

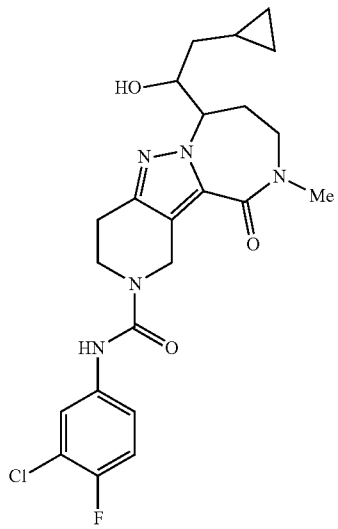 [SMILES: CN1CCC(C(O)CC2CC2)n2nc3c(c2C1=O)CN(C(=O)Nc1ccc(F)c(Cl)c1)CC3]

Step 1. 8-but-3-enoyl-10-methyl-11-oxo-1,3,4,7,8,9-hexahydropyrido[2,3]pyrazolo[2,4-b][1,4]diazepine-2-carboxylate To a solution of allyl(bromo)magnesium (1 M, 2.09 mL, 2.00 eq) in THF (10.00 mL) was added a solution of tert-butyl 8-[methoxy(methyl)carbamoyl]-10-methyl-11-oxo-1,3,4,7,8,9-hexahydropyrido[2,3]pyrazolo[2,4-b][1,4]diazepine-2-carboxylate (Intermediate 11, 500.00 mg, 1.04 mmol, 1.00 eq) in THF (10.00 mL) drop-wise at −30° C. over a period of 10 mins under N$_2$ and stirred for 1 hour. TLC indicated about 35% starting material remained, then another batch of allyl(bromo)magnesium (1 M, 2.09 mL, 2.00 eq) was added into the mixture drop-wise at −30° C. over a period of 10 mins and stirred for 1 hour. TLC indicated the starting material was completely consumed, one new spot was detected. The reaction mixture was poured into 1N HCl (50 ml) at 0° C. and stirred for 10 min. The aqueous phase was extracted with ethyl acetate (10 mL*2). The combined organic layers was washed with brine (10 mL*1), dried over with Na$_2$SO$_4$, filtered and concentrated under reduced pressure to afford the title compound (170.00 mg, crude) as yellow solid, which was used into the next step without further purification.

Step 2. tert-butyl 8-(1-hydroxybut-3-enyl)-10-methyl-11-oxo-1,3,4,7,8,9-hexahydropyrido[2,3]pyrazolo[2,4-b][1,4]diazepine-2-carboxylate To a mixture of tert-butyl 8-but-3-enoyl-10-methyl-11-oxo-1,3,4,7,8,9-hexahydro pyrido[2,3]pyrazolo[2,4-b][1,4]diazepine-2-carboxylate (300.00 mg, 772.28 µmol, 1.00 eq) in MeOH (10.00 mL) was added NaBH$_4$ (58.43 mg, 1.54 mmol, 2.00 eq) in one portion at 0° C. The mixture was stirred at 25° C. for 2 hours. TLC indicated the starting material was consumed completely and one new spot formed.

The reaction mixture was filtered and concentrated in vacuum, then diluted with H$_2$O (20 mL) and extracted with EtOAc (10*3 mL). The combined organic layers was washed with brine (15 mL), dried over Na$_2$SO$_4$, filtered and concentrated under reduced pressure. The residue was purified by column chromatography (SiO$_2$, Petroleum ether/ Ethyl acetate=1/1 to 0:1) to afford the title compound (182.00 mg, 466.09 µmol, 60.35% yield) as yellow oil.

Step 3. tert-butyl 8-(2-cyclopropyl-1-hydroxy-ethyl)-10-methyl-11-oxo-1,3,4,7,8,9-hexahydropyrido[2,3]pyrazolo[2,4-b][1,4]diazepine-2-carboxylate To a stirred suspension of ZnEt$_2$ (1 M, 1.23 mL, 12.00 eq) in toluene (8.00 mL) was added CH$_2$ICl (438.60 mg, 2.49 mmol, 24.27 eq) slowly drop-wise at −20° C. The resulting mixture was stirred for 1 h and added a solution of tert-butyl 8-(1-hydroxybut-3-enyl)-10-methyl-11-oxo-1,3,4,7,8,9-hexahydropyrido[2,3]pyrazolo[2,4-b][1,4]diazepine-2-carboxylate (40.00 mg, 102.44 µmol, 1.00 eq) in toluene (2.00 mL) drop-wise at −20° C. The resulting mixture was stirred at −20° C. for 12 h. TLC indicated one major new spot with larger polarity was detected. LC-MS showed the starting material was consumed completely and one main peak with desired MS was detected. The reaction was cooled to 0° C. and quenched with saturated solution of NH₄Cl (25 mL) and extracted with EtOAc (2*20 mL), dried over sodium sulfate and evaporated under reduced pressure. The residue was purified by prep-TLC (SiO₂, Petroleum ether: Ethyl acetate=1:10) to afford the title compound (30.00 mg, 74.17 μmol, 72.40% yield) as white solid.

LCMS: 405[M+1].

Step 4. 8-(2-cyclopropyl-1-hydroxy-ethyl)-10-methyl-2,3,4,7,8,9-hexahydro-1H-pyrido [2,3]pyrazolo[2,4-b][1,4]diazepin-11-one To a solution of tert-butyl 8-(2-cyclopropyl-1-hydroxy-ethyl)-10-methyl-11-oxo-1,3,4,7,8,9-hexahydropyrido[2,3]pyrazolo[2,4-b][1,4]diazepine-2-carboxylate (30.00 mg, 74.17 μmol, 1.00 eq) in DCM (8.00 mL) was added TFA (6.16 g, 54.03 mmol, 4.00 mL, 728.40 eq). The mixture was stirred at 30° C. for 1h. TLC and LCMS indicated the starting material was consumed completely and one main peak with desired MS was detected. The mixture was concentrated under reduced pressure to afford the title compound (50.00 mg, crude, TFA) as yellow oil. The residue was used into the next step without further purification.

LCMS: 305[M+1].

Step 5. N-(3-chloro-4-fluoro-phenyl)-8-(2-cyclopropyl-1-hydroxy-ethyl)-10-methyl-11-oxo-1,3,4,7,8,9-hexahydropyrido[2,3]pyrazolo[2,4-b][1,4]diazepine-2-carboxamide To a solution of 8-(2-cyclopropyl-1-hydroxy-ethyl)-10-methyl-2,3,4,7,8,9-hexahydro-1H-pyrido[2,3]pyrazolo[2,4-b][1,4]diazepin-11-one (18.00 mg, 43.02 μmol, 1.00 eq, TFA) and TEA (21.77 mg, 215.10 μmol, 29.82 μL, 5.00 eq) in DCM (8.00 mL) was added phenyl N-(3-chloro-4-fluorophenyl)carbamate (13.71 mg, 51.62 μmol, 1.20 eq) with stirring at 30° C. for 1 h. LCMS indicated the desired MS. The mixture was directly evaporated in vacuo and purified by prep-HPLC(FA) to afford the title compound (2.49 mg, 5.23 μmol, 12.16% yield) as white solid. LCMS: 476[M+1]. ¹H NMR (400 MHz, CDCl₃) δ ¹H NMR (400 MHz, CDCl₃) δ 7.59 (dd, J=2.57, 6.60 Hz, 1H), 7.15-7.25 (m, 1H), 7.00-7.11 (m, 1H), 6.60 (br d, J=4.40 Hz, 1H), 4.61-4.72 (m, 2.5H), 4.38-4.39 (m, 1H), 4.10-4.16 (m, 0.5H), 3.81-3.87 (m, 3H), 3.48-3.62 (m, 1H), 3.35-3.38 (m, 1H), 3.18 (s, 3H), 2.82-2.84 (m, 2H), 2.51-2.53 (m, 1H), 2.11-2.13 (m, 1H), 1.35-1.42 (m, 2H), 0.75-0.81 (m, 1H), 0.53-0.61 (m, 2H), 0.10-0.216 (m, 2H).

Compound 048: (3R)—N-(3-chloro-4-fluorophenyl)-10-(2-hydroxy-2-methylpropyl)-3-methyl-1,3,4,7,8,9,10,11-octahydro-2H-pyrido[4',3':3,4]pyrazolo[1,5-a][1,4]diazepine-2-carboxamide

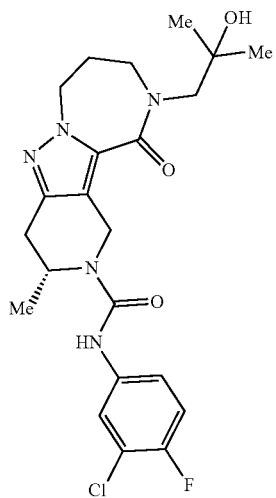 [SMILES: C[C@@H]1Cc2nn3c(c2CN1C(=O)Nc1ccc(F)c(Cl)c1)C(=O)N(CC(C)(C)O)CCC3]

Step 1. tert-butyl (3R)-10-(2-methoxy-2-oxo-ethyl)-3-methyl-11-oxo-1,3,4,7,8,9-hexahydropyrido[2,3]pyrazolo[2,4-b][1,4]diazepine-2-carboxylate To a solution of tert-butyl (3R)-3-methyl-11-oxo-3,4,7,8,9,10-hexahydro-1H-pyrido[2,3]pyrazolo[2,4-b][1,4]diazepine-2-carboxylate (Intermediate 12, 100.00 mg, 312.12 μmol, 1.00 eq) in THF (5.00 mL) was added NaH (24.97 mg, 624.24 μmol, 60% purity, 2.00 eq) at 0° C. with stirring for 0.5 h under N₂.

Then followed by methyl 2-bromoacetate (62.07 mg, 405.76 μmol, 38.32 μL, 1.30 eq). The mixture was stirred at 20° C. for 2 h. TLC (PE:EtOAc=1:3) showed that the tert-butyl (3R)-3-methyl-11-oxo-3,4,7,8,9,10-hexahydro-1H-pyrido[2,3]pyrazolo[2,4-b][1,4]diazepine-2-carboxylate was consumed completely and one main new spot formed. The mixture was quenched with 10 mL of ice-water and extracted with EtOAc (20 mL*3). The organic phase was washed with brine (15 mL*1), dried over anhydrous Na₂SO₄, filtered and concentrated in vacuo. The residue was purified by prep-TLC (PE:EtOAc=1:3) to obtain the title compound (116.00 mg, 280.29 μmol, 89.80% yield) as white solid.

Step 2. tert-butyl(3R)-10-(2-hydroxy-2-methyl-propyl)-3-methyl-11-oxo-1,3,4,7,8,9-hexahydropyrido[2,3]pyrazolo[2,4-b][1,4]diazepine-2-carboxylate To a mixture of MeMgBr (3 M, 1.02 mL, 10.00 eq) in THF (5.00 mL) was added a solution of tert-butyl (3R)-10-(2-methoxy-2-oxo-ethyl)-3-methyl-11-oxo-1,3,4,7,8,9-hexahydropyrido[2,3]pyrazolo[2,4-b][1,4]diazepine-2-carboxylate (120.00 mg, 305.77 μmol, 1.00 eq) in THF (3.00 mL) in one portion at 0° C. under N₂. TLC showed that the tert-butyl (3R)-10-(2-methoxy-2-oxo-ethyl)-3-methyl-11-oxo-1,3,4,7,8,9-hexahydropyrido[2,3]pyrazolo[2,4-b][1,4]diazepine-2-carboxylate was consumed completely and one new spot formed. The mixture was stirred at 0° C. for 0.5 h, then warmed to 20° C. and stirred for 2 h. The mixture was quenched with saturated NH₄Cl aqueous solution and extracted with EtOAc (20 mL*3). The organic phase was washed with brine (20 mL*1), dried over anhydrous Na₂SO₄, filtered and concentrated in vacuo. The residue was purified by prep-TLC and further purified by prep-HPLC (FA) to obtain the title compound (40 mg, 93% purity) as off-white oil. $^1$H NMR (400 MHz, CDCl₃) δ=4.76-5.07 (m, 2H), 4.29-4.50 (m, 2H), 4.07-4.21 (m, 1H), 3.64-3.70 (m, 1H), 3.47-3.62 (m, 3H), 2.92 (br dd, J=5.90, 15.81 Hz, 1H), 2.56 (br d, J=15.81 Hz, 2H), 2.25-2.42 (m, 2H), 2.15-2.23 (m, 1H), 1.47 (s, 9H), 1.28 (d, J=4.64 Hz, 6H), 1.12 (d, J=6.90 Hz, 3H).

Step 3. (3R)-10-(2-hydroxy-2-methyl-propyl)-3-methyl-2,3,4,7,8,9-hexahydro-1H-pyrido[2,3]pyrazolo[2,4-b][1,4]diazepin-11-one To a solution of tert-butyl (3R)-10-(2-hydroxy-2-methyl-propyl)-3-methyl-11-oxo-1,3,4,7,8,9-hexahydropyrido[2,3]pyrazolo[2,4-b][1,4]diazepine-2-carboxylate (40.00 mg, 101.91 μmol, 1.00 eq) in DCM (5.00 mL) was added TFA (770.00 mg, 6.75 mmol, 500.00 μL, 66.27 eq) with stirring at 25° C. for 1 h. LCMS indicated that the tert-butyl(3R)-10-(2-hydroxy-2-methyl-propyl)-3-methyl-11-oxo-1,3,4,7,8,9-hexahydropyrido[2,3]pyrazolo[2,4-b][1,4] diazepine-2-carboxylate was consumed completely and desired product was detected. The mixture was directly evaporated in vacuo. The residue was not purified and used in the next step. (45.00 mg, crude, TFA) was obtained as yellow oil and used in the next step.

Step 4. (3R)— N-(3-chloro-4-fluorophenyl)-10-(2-hydroxy-2-methylpropyl)-3-methyl-1,3,4,7,8,9,10,11-octahydro-2H-pyrido[4',3':3,4]pyrazolo[1,5-a][1,4]diazepine-2-carboxamide To a solution of (3R)-10-(2-hydroxy-2-methyl-propyl)-3-methyl-2,3,4,7,8,9-hexahydro-1H-pyrido[2,3]pyrazolo[2,4-b][1,4]diazepin-11-one (45.00 mg, 116.73 μmol, 1.00 eq, TFA) and TEA (67.23 mg, 664.38 μmol, 92.10 μL, 6.00 eq) in DCM (5.00 mL) was added phenyl N-(3-chloro-4-fluorophenyl)carbamate (32.36 mg, 121.80 μmol, 1.10 eq) with stirring at 25° C. for 16 h. LCMS indicated that the (3R)-10-(2-hydroxy-2-methyl-propyl)-3-methyl-2,3,4,7,8,9-hexahydro-1H-pyrido[2,3]pyrazolo[2,4-b][1,4]diazepin-11-one was consumed completely and desired product was detected. The mixture was directly evaporated in vacuo. The residue was purified by prep-HPLC (FA), following by SFC (Instrument: SFC 80; Column: OD-10 um. Mobile phase: A for CO₂ and B for MeOH (0.1% NH₃H₂O); Gradient: B 30%; Flow rate: 60 mL/min; Back pressure: 100bar; Column temperature: 35° C.; Wavelength: 220 nm.). The title compound (19.00 mg, 40.54 μmol, 36.62% yield, 99% purity) was obtained as white solid. LCMS: 464[M+1]. $^1$H NMR (400 MHz, CDCl₃) δ=7.60 (dd, J=2.63, 6.54 Hz, 1H), 7.18-7.25 (m, 1H), 7.00-7.09 (m, 1H), 6.61 (s, 1H), 5.14 (quin, J=6.57 Hz, 1H), 4.79-4.81 (d, J=15.53 Hz, 1H), 4.37-4.48 (m, 3H), 3.55-3.69 (m, 4H), 3.00-3.03 (m, 1H), 2.64-2.67 (d, J=15.89 Hz, 1H), 2.32-2.48 (m, 2H), 1.32 (s, 6H), 1.18 (d, J=6.85 Hz, 3H).

Compound 049: (3R)— N-(3-chloro-4-fluorophenyl)-10-(2-hydroxyethyl)-3-methyl-11-oxo-1,3,4,7,8,9,10,11-octahydro-2H-pyrido[4',3':3,4]pyrazolo[1,5-a][1,4]diazepine-2-carboxamide

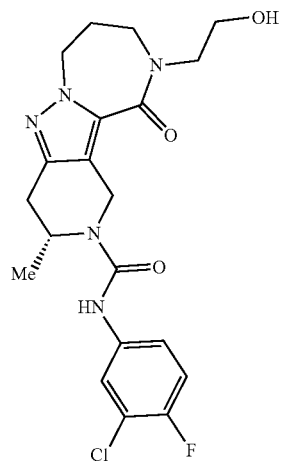

Step 1. tert-butyl (3R)-10-(2-hydroxyethyl)-3-methyl-11-oxo-1,3,4,7,8,9-hexahydropyrido[2,3]pyrazolo[2,4-b][1,4]diazepine-2-carboxylate To a solution of tert-butyl (3R)-10-(2-methoxy-2-oxo-ethyl)-3-methyl-11-oxo-1,3,4,7,8,9-hexahydropyrido[2,3]pyrazolo[2,4-b][1,4]diazepine-2-carboxylate (Compound 048, product from Step 1, 50.00 mg, 127.40 μmol, 1.00 eq) in THF (5.00 mL) was added LiAlH₄ (9.67 mg, 254.80 μmol, 2.00 eq) at −78° C. with stirring under N₂. The mixture was warmed to 0° C. with stirring for 2 h. TLC (PE:EtOAc=1:3) showed that the tert-butyl (3R)-10-(2-methoxy-2-oxo-ethyl)-3-methyl-11-oxo-1,3,4,7,8,9-hexahydropyrido[2,3]pyrazolo[2,4-b][1,4]diazepine-2-carboxylate consumed completely and one main new spot formed. LCMS indicated desired product was detected. The mixture was quenched with 20 mL of water and extracted with EtOAc (20 mL*3). The organic phase was washed with brine (20 mL*1), dried over anhydrous Na₂SO₄, filtered and concentrated in vacuo. The residue was purified by prep-TLC (PE:EtOAc=1:3). The title compound (35.00 mg, 96.04 μmol, 75.38% yield) was obtained as light-yellow oil.

Step 2. (3R)-10-(2-hydroxyethyl)-3-methyl-2,3,4,7,8,9-hexahydro-1H-pyrido[2,3]pyrazolo[2,4-b][1,4]diazepin-11-one To a solution of tert-butyl (3R)-10-(2-hydroxyethyl)-3-methyl-11-oxo-1,3,4,7,8,9-hexahydropyrido[2,3]pyrazolo[2,4-b][1,4]diazepine-2-carboxylate (35.00 mg, 96.04 mol, 1.00 eq) in DCM (3.00 mL) was added TFA (770.00 mg, 6.75 mmol, 500.00 μL, 70.32 eq) at 20° C. with stirring for 1 h. TLC (PE:EtOAc=1:1) showed that the tert-butyl (3R)-10-(2-hydroxyethyl)-3-methyl-11-oxo-1,3,4,7,8,9-hexahydropyrido[2,3]pyrazolo[2,4-b][1,4]diazepine-2-carboxylate consumed completely and one new spot formed. The mixture was concentrated in vacuo to afford the title compound (40.00 mg, crude, TFA) as yellow oil and directly used in the next step.

Step 3. (3R)—N-(3-chloro-4-fluorophenyl)-10-(2-hydroxyethyl)-3-methyl-11-oxo-1,3,4,7,8,9,10,11-octahydro-2H-pyrido[4',3':3,4]pyrazolo[1,5-a][1,4]diazepine-2-carboxamide To a solution of (3R)-10-(2-hydroxyethyl)-3-methyl-2,3,4,7,8,9-hexahydro-1H-pyrido [2,3]pyrazolo[2,4-b][1,4]diazepin-11-one (40.00 mg, 105.72 µmol, 1.00 eq, TFA) and phenyl N-(3-chloro-4-fluoro-phenyl)carbamate (30.90 mg, 116.29 µmol, 1.10 eq) in DCM (3.00 mL) was added TEA (32.09 mg, 317.17 µmol, 43.96 µL, 3.00 eq) with stirring at 20° C. for 16 h. LCMS indicated that reactant was consumed completely and 55% of desired product. The mixture was concentrated invacuo, and the residue was purified by prep-HPLC (FA). The title compound (17.50 mg, 38.14 µmol, 36.08% yield, 95% purity) was obtained as white solid. LCMS: 436[M+1]. $^1$H NMR (400 MHz, CDCl$_3$) δ=7.60 (dd, J=2.63, 6.54 Hz, 1H), 7.18-7.25 (m, 1H), 7.00-7.09 (m, 1H), 6.61 (s, 1H), 5.12-5.15 (m, 1H), 4.09-4.85 (m, 1H), 4.37-4.48 (m, 3H), 3.89-3.92 (m, 2H), 3.76-3.78 (m, 2H), 3.54-3.56 (m., 2H), 3.00-3.04 (m, 1H), 2.65-2.69 (m, 1H), 2.34-2.37 (m, 2H), 1.17 (d, J=6.85 Hz, 3H).

Compound 050: N-(3-chloro-4-fluorophenyl)-10-methyl-8-(methylamino)-11-oxo-1,3,4,7,8,9,10,11-octahydro-2H-pyrido[4',3':3,4]pyrazolo[1,5-a][1,4]diazepine-2-carboxamide

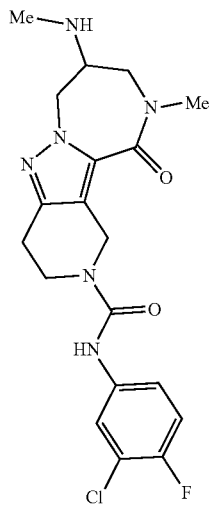 [SMILES: CNC1CN(C)C(=O)c2c3c(nn2C1)CCN(C(=O)Nc1ccc(F)c(Cl)c1)C3]

Step 1. tert-butyl10-methyl-8-(methylamino)-11-oxo-1,3,4,7,8,9-hexahydropyrido[2,3]pyrazolo[2,4-b][1,4]diazepine-2-carboxylate A mixture of tert-butyl 10-methyl-8,11-dioxo-3,4,8,9,10,11-hexahydro-1H-pyrido[4',3':3,4]pyrazolo[1,5-a][1,4]diazepine-2 (7H)-carboxylate (Intermediate 2, 300.00 mg, 897.21 µmol, 1.00 eq), methylamine (7.5 M, 239.26 µL, 2.00 eq, EtOH solution), CH$_3$COOH (53.88 mg, 897.21 µmol, 51.31 µL, 1.00 eq) and 4 A molecular sieve (400.00 mg) in DCE (8.00 mL) was stirred at 20° C. for 16 h. NaBH$_3$CN (281.90 mg, 4.49 mmol, 5.00 eq) was added and the mixture was stirred at 20° C. for 3 h. The mixture was diluted with EtOAc (40 mL) and washed with brine (40 mL). The organic phase was dried over Na$_2$SO$_4$, filtered and concentrated in vacuo, which was purified by silica gel column to afford the title compound (120.00 mg, 309.07 µmol, 34.45% yield, 90% purity) as yellow oil.
LCMS: 350 [M+1].

Step 2. tert-butyl 8-[allyloxycarbonyl(methyl)amino]-10-methyl-11-oxo-1,3,4,7,8,9-hexahydro-pyrido[2,3]pyrazolo[2,4-b][1,4]diazepine-2-carboxylate To a solution of tert-butyl 10-methyl-8-(methylamino)-11-oxo-1,3,4,7,8,9-hexahydropyrido[2,3]pyrazolo[2,4-b][1,4]diazepine-2-carboxylate (116.00 mg, 314.80 µmol, 1.00 eq) and NaHCO$_3$ (79.34 mg, 944.40 µmol, 36.73 µL, 3.00 eq) in THF (4.00 mL) and H$_2$O (1.00 mL) was added allyl carbonochloridate (49.33 mg, 409.24 µmol, 43.27 µL, 1.30 eq), and the mixture was stirred at 20° C. for 16 h. The mixture was diluted with EtOAc (40 mL) and washed with HCl (1 M, 40 mL). The organic phase was dried over Na$_2$SO$_4$, filtered and concentrated in vacuo, which was purified by prep-TLC to afford the title compound (99.00 mg, 228.37 µmol, 72.55% yield) as yellow oil.

Step 3. allyl N-methyl-N-(10-methyl-11-oxo-2,3,4,7,8,9-hexahydro-1H-pyrido[2,3]pyrazolo[2,4-b][1,4]diazepin-8-yl)carbamate To a solution of tert-butyl 8-[allyloxycarbonyl(methyl)amino]-10-methyl-11-oxo-1,3,4,7,8,9-hexahydropyrido[2,3]pyrazolo[2,4-b][1,4]diazepine-2-carboxylate (108.00 mg, 249.13 µmol, 1.00 eq) in DCM (2.00 mL) was added TFA (3.08 g, 27.01 mmol, 2.00 mL, 108.43 eq) and the mixture was stirred at 25° C. under N$_2$ for 1 h. The mixture was concentrated in vacuo to afford the title compound (111.00 mg, 248.09 µmol, 99.58% yield, TFA) as yellow oil, which was used directly for the next step.

Step 4. allyl N-[2-[(3-chloro-4-fluoro-phenyl)carbamoyl]-10-methyl-11-oxo-1,3,4,7,8,9-hexahydro-pyrido[2,3]pyrazolo[2,4-b][1,4]diazepin-8-yl]-N-methyl-carbamate A mixture of allyl N-methyl-N-(10-methyl-11-oxo-2,3,4,7,8,9-hexahydro-1H-pyrido[2,3]pyrazolo[2,4-b][1,4]diazepin-8-yl)carbamate (111.00 mg, 248.09 µmol, 1.00 eq, TFA), Et$_3$N (125.52 mg, 1.24 mmol, 171.95 µL, 5.00 eq) and phenyl N-(3-chloro-4-fluoro-phenyl)carbamate (72.50 mg, 272.90 µmol, 1.10 eq) in DCM (5.00 mL) was stirred at 25° C. for 16 h. The mixture was diluted with DCM (30 mL) and washed with HCl (1 M, 30 mL*2). The organic phase was dried over Na$_2$SO$_4$, filtered and concentrated in vacuo, which was purified by prep-TLC to afford (108.00 mg, 213.89 mol, 86.21% yield) as yellow solid.
LCMS: 505/507 [M+1].

Step 5. N-(3-chloro-4-fluorophenyl)-10-methyl-8-(methylamino)-11-oxo-1,3,4,7,8,9,10,11-octahydro-2H-pyrido[4',3':3,4]pyrazolo[1,5-a][1,4]diazepine-2-carboxamide A mixture of allyl N-[2-[(3-chloro-4-fluoro-phenyl)carbamoyl]-10-methyl-11l-oxo-1,3,4,7,8,9-hexahydropyrido[2,3]pyrazolo[2,4-b][1,4]diazepin-8-yl]-N-methyl-carbamate (98.00 mg, 194.08 mol, 1.00 eq), 1,3-dimethylhexahydropyrimidine-2,4,6-trione (151.52 mg, 970.41 µmol, 5.00 eq) and Pd(PPh$_3$)$_4$ (22.43 mg, 19.41 µmol, 0.10 eq) in THF (3.00 mL) was stirred at 25° C. for 16 h. The mixture was diluted with EtOAc (30 mL) and washed with brine (30 mL). The organic phase was dried over Na$_2$SO$_4$, filtered and concentrated in vacuo, which was purified by silica gel column and prep-HPLC(HCl) to afford the title compound (55.00 mg, 119.06 μmol, 61.35% yield, 99% purity, HCl) as yellow solid. $^1$H NMR (400 MHz, METHANOL-d$_4$) δ 7.60 (dd, J=2.57, 6.72 Hz, 1H), 7.24-7.37 (m, 1H), 7.15 (t, J=8.99 Hz, 1H), 4.76-4.88 (m, 2H), 4.55 (s, 2H), 4.25-4.36 (m, 1H), 3.86-3.97 (m, 1H), 3.71-3.82 (m, 1H), 3.23 (s, 5H), 2.83-2.89 (m, 1H), 2.82-2.83 (m, 1H), 2.77 (s, 3H). LCMS: 421/423 [M+1].

Compound 051: N-(3-chloro-4-fluorophenyl)-8-(hydroxymethyl)-11-oxo-10-(2,2,2-trifluoroethyl)-1,3,4,7,8,9,10,11-octahydro-2H-pyrido[4',3': 3,4]pyrazolo[1,5-a][1,4]diazepine-2-carboxamide

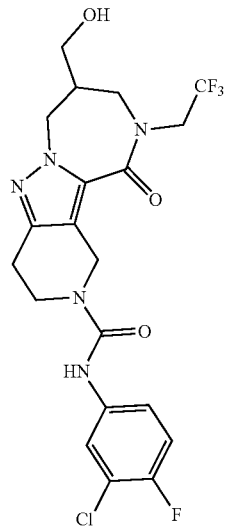 [SMILES: O=C(Nc1ccc(F)c(Cl)c1)N1CCc2nn3c(c2C1)C(=O)N(CC(F)(F)F)CC(CO)C3]

Step 1. 5-tert-butyl 3-ethyl 2-[2-[(2,2,2-trifluoroethylamino) methyl]allyl]-6,7-dihydro-4H-pyrazolo[4,3-c]pyridine-3,5-dicarboxylate A solution of 5-tert-butyl 3-ethyl 2-[2-(chloromethyl)allyl]-6,7-dihydro-4H-pyrazolo[4,3-c]pyridine-3,5-dicarboxylate (500.00 mg, 1.30 mmol, 1.00 eq) and 2,2,2-trifluoroethanamine (3.86 g, 39.00 mmol, 3.06 mL, 30.00 eq) in EtOH (50.00 mL) was stirred at 90° C. for 32 h. The mixture was diluted with EtOAc (120 mL) and washed with saturated NaHCO$_3$ solution (120 mL). The organic phase was dried over Na$_2$SO$_4$, filtered and concentrated in vacuo which was purified by silica gel column to afford the title compound (460.00 mg, 1.03 mmol, 79.26% yield) as yellow oil. LCMS: 447 [M+1].

Step 2. tert-butyl 8-methylene-11-oxo-10-(2,2,2-trifluoroethyl)-3,4,7,9-tetrahydro-1H-pyrido[2,3]pyrazolo[2,4-b][1,4]diazepine-2-carboxylate To a solution of 5-tert-butyl 3-ethyl 2-[2-[(2,2,2-trifluoroethylamino)methyl]allyl]-6,7-dihydro-4H-pyrazolo[4,3-c]pyridine-3,5-dicarboxylate (460.00 mg, 1.03 mmol, 1.00 eq) in toluene (10.00 mL) was added Al(CH$_3$)$_3$ (2 M, 2.06 mL, 4.00 eq) at −30° C. and the mixture was stirred at 60° C. for 16 h. The mixture was quenched with H$_2$O (10.00 mL). Na$_2$CO$_3$ (109.20 mg, 1.03 mmol, 1.00 eq) and Boc$_2$O (269.84 mg, 1.24 mmol, 284.04 μL, 1.20 eq) was added and the mixture was stirred at 20° C. for 16 h. The mixture was diluted with EtOAc (50 mL) and washed with HCl (1M, 50 mL). The organic phase was dried over Na$_2$SO$_4$, filtered and concentrated in vacuo, which was purified by silica gel column to afford the title compound (390.00 mg, 974.05 μmol, 94.57% yield) as yellow solid. $^1$H NMR (400 MHz, CDCl$_3$) δ 5.07 (br d, J=4.16 Hz, 2H), 4.91 (s, 2H), 4.48-4.59 (m, 2H), 4.08-4.20 (m, 2H), 3.97-4.05 (m, 2H), 3.56-3.73 (m, 2H), 2.59-2.75 (m, 2H), 1.44-1.50 (m, 5H), 1.41 (s, 9H). LCMS: 401 [M+1].

Step 3. tert-butyl 8-(hydroxymethyl)-11-oxo-10-(2,2,2-trifluoroethyl)-1,3,4,7,8,9-hexahydropyrido[2,3]pyrazolo[2,4-b][1,4]diazepine-2-carboxylate To a solution of tert-butyl 8-methylene-11-oxo-10-(2,2,2-trifluoroethyl)-3,4,7,9-tetrahydro-1H-pyrido[2,3]pyrazolo[2,4-b][1,4]diazepine-2-carboxylate (150.00 mg, 374.63 μmol, 1.00 eq) in THF (3.00 mL) was added BH$_3$.DMS (10 M, 149.85 μL, 4.00 eq) at 0° C. and the mixture was stirred at 20° C. for 16 h. TLC indicated the starting material was consumed completely. H$_2$O$_2$ (297.30 mg, 2.62 mmol, 251.95 μL, 30% purity, 7.00 eq) and a solution of NaOH (74.93 mg, 1.87 mmol, 5.00 eq) in H$_2$O (500.00 uL) was added at −30° C., and the mixture was stirred at 20° C. for 2 h. The mixture was diluted with EtOAc (40 mL) and washed with saturated Na$_2$SO$_3$ (30 mL), brine (30 mL). The organic phase was dried over Na$_2$SO$_4$, filtered and concentrated in vacuo, which was purified by prep-TLC to afford the title compound (86.00 mg, 199.37 μmol, 53.22% yield, 97% purity) as yellow oil.
LCMS: 419 [M+1].

Step 4. 8-(hydroxymethyl)-10-(2,2,2-trifluoroethyl)-2,3,4,7,8,9-hexahydro-1H-pyrido[2,3]pyrazolo[2,4-b][1,4]diazepin-11-one To a solution of tert-butyl 8-(hydroxymethyl)-11-oxo-10-(2,2,2-trifluoroethyl)-1,3,4,7,8,9-hexahydropyrido[2,3]pyrazolo[2,4-b][1,4]diazepine-2-carboxylate (106.00 mg, 253.34 μmol, 1.00 eq) in DCM (2.00 mL) was added TFA (3.08 g, 27.01 mmol, 2.00 mL, 106.63 eq) and the mixture was stirred at 25° C. under N$_2$ for 1 h. The mixture was concentrated in vacuo to afford the title compound (109.00 mg, 252.13 mol, 99.52% yield, TFA) as yellow oil, which was used directly for the next step.

Step 5. N-(3-chloro-4-fluorophenyl)-8-(hydroxymethyl)-11-oxo-10-(2,2,2-trifluoroethyl)-1,3,4,7,8,9,10,11-octahydro-2H-pyrido[4',3':3,4]pyrazolo[1,5-a][1,4]diazepine-2-carboxamide A mixture of 8-(hydroxymethyl)-10-(2,2,2-trifluoroethyl)-2,3,4,7,8,9-hexahydro-1H-pyrido[2,3]pyrazolo[2,4-b][1,4]diazepin-11-one (109.00 mg, 252.13 μmol, 1.00 eq, TFA), Et$_3$N (127.56 mg, 1.26 mmol, 174.74 μL, 5.00 eq) and phenyl N-(3-chloro-4-fluoro-phenyl)carbamate (73.68 mg, 277.34 μmol, 1.10 eq) in DCM (5.00 mL) was stirred at 25° C. for 16 h. The mixture was diluted with DCM (30 mL) and washed with HCl (1 M, 30 mL). The organic phase was dried over Na$_2$SO$_4$, filtered and concentrated in vacuo, which was purified by prep-HPLC(FA) to afford the title compound (56.00 mg, 113.18 μmol, 44.89% yield, 99% purity) as yellow solid. H NMR (400 MHz, CDCl$_3$) δ 7.59 (dd, J=2.63, 6.54 Hz, 1H), 7.17-7.24 (m, 1H), 7.03-7.12 (m, 1H), 6.56 (s, 1H), 4.76-4.92 (m, 1H), 4.65-4.72 (m, 2H), 4.30-4.49 (m, 2H), 3.78-3.95 (m, 2H), 3.63-3.76 (m, 3H), 3.46-3.61 (m, 2H), 2.82-2.92 (m, 2H), 2.71-2.81 (m, 1H). LCMS: 490/492 [M+1].

Compound 052: ethyl 2-((3-chloro-4-fluorophenyl)carbamoyl)-8,10-dimethyl-11-oxo-1,3,4,7,8,9,10,11-octahydro-2H-pyrido[4',3':3,4]pyrazolo[1,5-a][1,4]diazepine-8-carboxylate

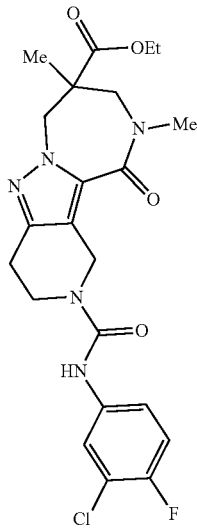 [SMILES: CCOC(=O)C1(C)CN(C)C(=O)c2c3c(nn2C1)CCN(C(=O)Nc1ccc(F)c(Cl)c1)C3]

Step 1. 2-tert-butyl 8-ethyl 8,10-dimethyl-11-oxo-3,4,7,9-tetrahydro-1H-pyrido[2,3]pyrazolo[2,4-b][1,4]diazepine-2,8-dicarboxylate To a solution of 2-tert-butyl 8-ethyl 10-methyl-11-oxo-1,3,4,7,8,9-hexahydropyrido[2,3]pyrazolo[2,4-b][1,4]diazepine-2,8-dicarboxylate (Intermediate 14, 200.00 mg, 509.62 µmol, 1.00 eq) in THF (6.00 mL) was added LDA (1 M, 1.53 mL, 3.00 eq) at −65° C. under $N_2$, followed by MeI (217.01 mg, 1.53 mmol, 95.18 µL, 3.00 eq) after 0.5 h and the mixture was stirred at 25° C. for 2 h. The mixture was quenched with HCl (1M, 40 mL) and extracted with EtOAc (40 mL). The organic phase was dried over $Na_2SO_4$, filtered and concentrated in vacuo. The residue was purified by prep-TLC to afford the title compound (140.00 mg, 309.99 µmol, 60.83% yield, 90% purity) as yellow oil. LCMS: 407 [M+1].

Step 2. ethyl 8,10-dimethyl-11-oxo-1,2,3,4,7,9-hexahydropyrido[2,3] pyrazolo[2,4-b][1,4]diazepine-8-carboxylate To a solution of 2-tert-butyl 8-ethyl 8,10-dimethyl-11-oxo-3,4,7,9-tetrahydro-1H-pyrido[2,3]pyrazolo[2,4-b][1,4]diazepine-2,8-dicarboxylate (210.00 mg, 516.63 µmol, 1.00 eq) in DCM (3.00 mL) was added TFA (4.62 g, 40.52 mmol, 3.00 mL, 78.43 eq) and the mixture was stirred at 25° C. under $N_2$ for 1 h. The mixture was concentrated in vacuo to afford the title compound (217.00 mg, 516.20 µmol, 99.92% yield, TFA) as yellow oil, which was used directly for the next step.

Step 3. ethyl 2-((3-chloro-4-fluorophenyl)carbamoyl)-8,10-dimethyl-11-oxo-1,3,4,7,8,9,10,11-octahydro-2H-pyrido[4',3':3,4]pyrazolo[1,5-a][1,4]diazepine-8-carboxylate A mixture of ethyl 8,10-dimethyl-11-oxo-1,2,3,4,7,9-hexahydropyrido[2,3]pyrazolo [2,4-b][1,4]diazepine-8-carboxylate (217.00 mg, 516.20 µmol, 1.00 eq, TFA), $Et_3N$ (261.17 mg, 2.58 mmol, 357.77 µL, 5.00 eq) and phenyl N-(3-chloro-4-fluoro-phenyl)carbamate (150.85 mg, 567.82 µmol, 1.10 eq) in DCM (7.00 mL) was stirred at 25° C. for 16 h. The mixture was diluted with DCM (30 mL) and washed with HCl (1 M, 30 mL). The organic phase was dried over $Na_2SO_4$, filtered and concentrated in vacuo, which was purified by prep-HPLC(FA) to afford the title compound (175.00 mg, 362.51 µmol, 70.23% yield, 99% purity) as white solid.

$^1$H NMR (400 MHz, $CDCl_3$) δ 7.58 (dd, J=2.69, 6.48 Hz, 1H), 7.15-7.23 (m, 1H), 7.01-7.09 (m, 1H), 6.63 (s, 1H), 4.70 (s, 1H), 4.54-4.65 (m, 2H), 4.21-4.32 (m, 3H), 3.79-3.91 (m, 2H), 3.70-3.78 (m, 1H), 3.22 (d, J=15.04 Hz, 1H), 3.17 (s, 3H), 2.79-2.88 (m, 2H), 1.31-1.36 (m, 6H). LCMS: 478/480 [M+1].

Compound 053: N-(3-chloro-4-fluorophenyl)-8-(hydroxymethyl)-8,10-dimethyl-11-oxo-1,3,4,7,8,9,10,11-octahydro-2H-pyrido[4',3':3,4]pyrazolo[1,5-a][1,4]diazepine-2-carboxamide

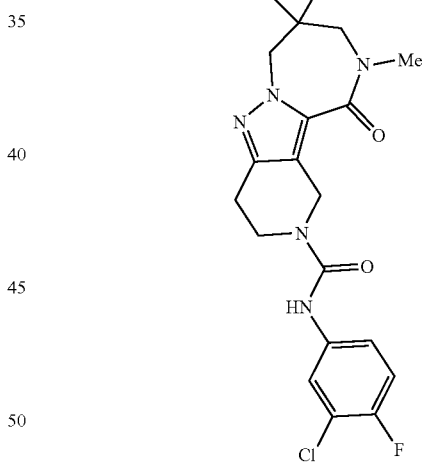

To a solution of ethyl 2-[(3-chloro-4-fluoro-phenyl)carbamoyl]-8,10-dimethyl-11-oxo-3,4,7,9-tetrahydro-1H-pyrido[2,3]pyrazolo[2,4-b][1,4]diazepine-8-carboxylate (Compound 052, 60.00 mg, 125.54 µmol, 1.00 eq) in THF (5.00 mL) was added $LiBH_4$ (8.20 mg, 376.62 µmol, 3.00 eq) at 0° C. and the mixture was stirred at 25° C. for 2 h. The mixture was quenched with $H_2O$ (30 mL) and extracted with EtOAc (30 mL). The organic phase was dried over $Na_2SO_4$, filtered and concentrated in vacuo. The residue was purified by prep-HPLC(FA) to afford the title compound (34.00 mg, 77.22 µmol, 61.51% yield, 99% purity) as white solid. $^1$H NMR (400 MHz, $CDCl_3$) δ 7.60 (dd, J=2.63, 6.54 Hz, 1H), 7.20 (br d, J=1.34 Hz, 1H), 7.07 (s, 1H), 6.62 (s, 1H), 4.64-4.74 (m, 2H), 4.19 (s, 1H), 4.01 (s, 1H), 3.87 (s, 1H), 3.50-3.66 (m, 2H), 3.37 (d, J=14.79 Hz, 1H), 3.22 (s, 3H), 3.03-3.11 (m, 1H), 2.85 (s, 1H), 1.88-1.97 (m, 1H), 1.16 (s, 3H). LCMS: 436/438 [M+1].

Compound 054: N-(3-chloro-4-fluorophenyl)-8-(3,3-difluoropyrrolidin-1-yl)-10-methyl-11-oxo-1,3,4,7,8,9,10,11-octahydro-2H-pyrido[4',3':3,4]pyrazolo[1,5-a][1,4]diazepine-2-carboxamide

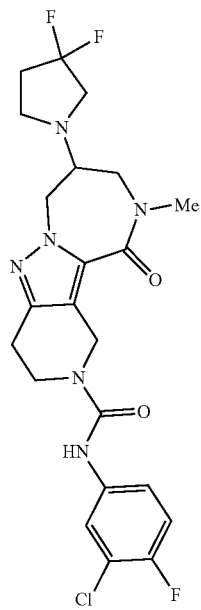 [SMILES: CN1CC(N2CCC(F)(F)C2)Cn2nc3c(c2C1=O)CN(C(=O)Nc1ccc(F)c(Cl)c1)CC3]

Step 1. tert-butyl 8-(3,3-difluoropyrrolidin-1-yl)-10-methyl-1-oxo-1,3,4,7,8,9-hexahydropyrido[2,3]pyrazolo[2,4-b][1,4]diazepine-2-carboxylate To a solution of 3,3-difluoropyrrolidine (96.09 mg, 669.34 μmol, 1.49 eq, HCl) in DCE (4.00 mL) was added NaOAc (73.60 mg, 897.20 μmol, 2.00 eq). After stirring for 1 hr, tert-butyl 10-methyl-8,11-dioxo-3,4,7,9-tetrahydro-1H-pyrido[2,3]pyrazolo [2,4-b][1,4]diazepine-2-carboxylate (150.00 mg, 448.60 μmol, 1.00 eq) and 4 A MS (300.00 mg) was added. The mixture was stirred at 20° C. for 4 hr. NaBH₃CN (112.76 mg, 1.79 mmol, 4.00 eq) was added. Then the mixture was stirred at 20° C. for 12 hr. LCMS showed the reaction completed. The mixture was poured into saturated NH₄Cl (20 mL), extracted with DCM (10 mL*2). The organic layer was washed with brine (20 mL*2), dried over anhydrous Na₂SO₄ and concentrated in vacuum to give the crude, which was purified by prep.TLC (100% Ethyl acetate) to afford the title compound (120.00 mg, 282.04 mol, 62.87% yield) as colorless oil.

LCMS: 426 [M+1].

Step 2. 8-(3,3-difluoropyrrolidin-1-yl)-10-methyl-2,3,4,7,8,9-hexahydro-1H-pyrido[2,3]pyrazolo[2,4-b][1,4]diazepin-11-one To a solution tert-butyl 8-(3,3-difluoropyrrolidin-1-yl)-10-methyl-11-oxo-1,3,4,7,8,9-hexahydropyrido[2,3]pyrazolo[2,4-b][1,4]diazepine-2-carboxylate (90.00 mg, 211.53 μmol, 1.00 eq) in DCM (2.00 mL) was added TFA (3.08 g, 27.01 mmol, 2.00 mL, 127.70 eq). The mixture was stirred at 20° C. for 1 hr. TLC showed the reaction completed. The mixture was concentrated to afford the title compound (90.00 mg, 204.83 μmol, 96.83% yield, TFA) as the colorless oil, which was used directly.

Step 3. N-(3-chloro-4-fluorophenyl)-8-(3,3-difluoropyrrolidin-1-yl)-10-methyl-11-oxo-1,3,4,7,8,9,10,11-octahydro-2H-pyrido[4',3':3,4]pyrazolo[1,5-a][1,4]diazepine-2-carboxamide To a solution of 8-(3,3-difluoropyrrolidin-1-yl)-10-methyl-2,3,4,7,8,9-hexahydro-1H-pyrido[2,3]pyrazolo[2,4-b][1,4]diazepin-11-one (90.00 mg, 204.83 μmol, 1.00 eq, TFA) and phenyl N-(3-chloro-4-fluoro-phenyl)carbamate (55.52 mg, 209.00 μmol, 1.00 eq) in DCM (2.00 mL) was added TEA (62.18 mg, 614.50 μmol, 85.18 μL, 3.00 eq). The mixture was stirred at 20° C. for 12 h. LCMS showed the reaction was completed. The mixture was concentrated in vacuum to give the crude, which was purified by prep-HPLC to afford the title compound (57.00 mg, 113.56 μmol, 55.44% yield, 99% purity) as white solid. LCMS: 497/499 [M+1]. ¹H NMR (400 MHz, CDCl₃) δ 7.58 (dd, J=2.57, 6.48 Hz, 1H), 7.15-7.22 (m, 1H), 6.99-7.09 (m, 1H), 6.58 (s, 1H), 4.67 (s, 2H), 4.31-4.46 (m, 2H), 3.79-3.98 (m, 2H), 3.44 (d, J=5.38 Hz, 2H), 3.29-3.31 (m, 1H), 3.20 (s, 3H), 2.81-3.12 (m, 6H), 2.28-2.33 (m, 2H).

Compound 055: N-(3-chloro-4-fluorophenyl)-10-methyl-11-oxo-8-(piperidin-1-yl)-1,3,4,7,8,9,10,11-octahydro-2H-pyrido[4',3':3,4]pyrazolo[1,5-a][1,4]diazepine-2-carboxamide

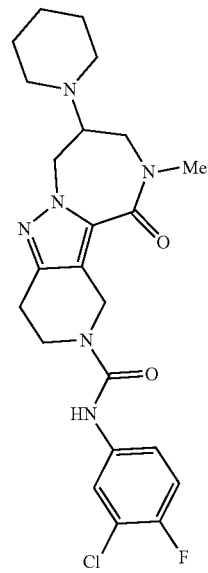 [SMILES: CN1CC(N2CCCCC2)Cn2nc3c(c2C1=O)CN(C(=O)Nc1ccc(F)c(Cl)c1)CC3]

Step 1. tert-butyl 10-methyl-11l-oxo-8-(1-piperidyl)-1,3,4,7,8,9-hexahydropyrido[2,3]pyrazolo[2,4-b][1,4]diazepine-2-carboxylate To a solution of tert-butyl 10-methyl-8,11-dioxo-3,4,7,9-tetrahydro-1H-pyrido[2,3] pyrazolo[2,4-b][1,4]diazepine-2-carboxylate (120.00 mg, 358.88 µmol, 1.00 eq) and piperidine (61.12 mg, 717.76 µmol, 71.07 µL, 2.00 eq) in DCE (2.00 mL) was added HOAc (21.55 mg, 358.88 µmol, 20.52 µL, 1.00 eq), 4 A MS (300.00 mg), the mixture was stirred at 20° C. for 3 hr. NaBH$_3$CN (112.76 mg, 1.79 mmol, 5.00 eq) was added and the mixture was stirred at 20° C. for 12 hr. TLC showed the reaction was completed. The mixture was poured into saturated NH$_4$C$_1$ (20 mL), extracted with Ethyl acetate (15 mL*2). The organic layer was washed with brine (20 mL*2), dried over anhydrous Na$_2$SO$_4$ and concentrated in vacuum. The crude was purified by prep.TLC to afford the title compound (50.00 mg, 111.52 µmol, 31.07% yield, 90% purity) as colorless oil.

Step 2. 10-methyl-8-(1-piperidyl)-2,3,4,7,8,9-hexahydro-1H-pyrido[2,3]pyrazolo[2,4-b][1,4]diazepin-11-one To a solution of tert-butyl 10-methyl-11-oxo-8-(1-piperidyl)-1,3,4,7,8,9-hexahydropyrido[2,3]pyrazolo[2,4-b][1,4]diazepine-2-carboxylate (50.00 mg, 123.91 µmol, 1.00 eq) in DCM (2.00 mL) was added TFA (14.13 mg, 123.91 µmol, 9.17 µL, 1.00 eq). The mixture was stirred at 20° C. for 1 hr. TLC showed the reaction was completed. The mixture was concentrated in vacuum to afford the title compound (50.00 mg, 119.78 µmol, 96.67% yield, TFA) as colorless oil, which was used for the next step without purification.

Step 3. N-(3-chloro-4-fluorophenyl)-10-methyl-11-oxo-8-(piperidin-1-yl)-1,3,4,7,8,9,10,11-octahydro-2H-pyrido[4',3':3,4]pyrazolo[1,5-a][1,4]diazepine-2-carboxamide To a solution of 10-methyl-8-(1-piperidyl)-2,3,4,7,8,9-hexahydro-H-pyrido[2,3] pyrazolo[2,4-b][1,4]diazepin-11-one (50.00 mg, 119.78 µmol, 1.00 eq, TFA) and phenyl N-(3-chloro-4-fluoro-phenyl)carbamate (31.82 mg, 119.78 µmol, 1.00 eq) in DCM (2.00 mL) was added TEA (36.36 mg, 359.35 µmol, 49.81 µL, 3.00 eq). The mixture was stirred at 20° C. for 16 hr. LCMS showed the reaction was completed. The mixture was concentrated in vacuum to give the crude. The crude was purified by prep-HPLC to afford the title compound (22.00 mg, 45.86 µmol, 38.28% yield, 99% purity) as white solid. LCMS: 475/477 [M+1]. $^1$H NMR (400 MHz, CDCl$_3$) δ 8.13 (s, 1H), 7.58 (dd, J=2.63, 6.54 Hz, 1H), 7.17-7.24 (m, 1H), 7.05 (t, J=8.80 Hz, 1H), 6.73 (s, 1H), 4.67-4.76 (m, 2H), 4.58-4.67 (m, 1H), 4.35 (dd, J=6.54, 15.34 Hz, 1H), 3.87-3.95 (m, 1H), 3.67-3.82 (m, 3H), 3.54-3.59 (m, 1H), 3.18 (s, 3H), 2.79-2.93 (m, 4H), 2.65-2.78 (m, 2H), 1.66-1.80 (m, 4H), 1.47-1.64 (m, 2H).

Compound 056: N-(3-chloro-4-fluorophenyl)-8-(4,4-difluoropiperidin-1-yl)-10-methyl-11-oxo-1,3,4,7,8,9,10,11-octahydro-2H-pyrido[4',3':3,4]pyrazolo[1,5-a][1,4]diazepine-2-carboxamide

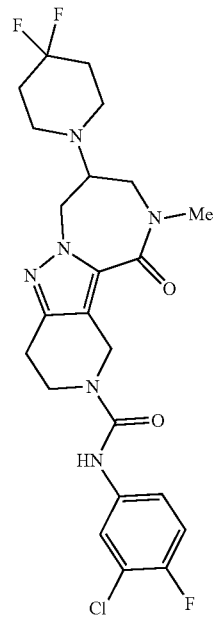

Step 1. tert-butyl 8-(4,4-difluoro-1-piperidyl)-10-methyl-11-oxo-1,3,4,7,8,9-hexahydropyrido[2,3]pyrazolo[2,4-b][1,4] diazepine-2-carboxylate To a solution of tert-butyl 10-methyl-8,11-dioxo-3,4,7,9-tetrahydro-1H-pyrido[2,3] pyrazolo[2,4-b][1,4]diazepine-2-carboxylate (150.00 mg, 448.60 µmol, 1.00 eq) and 4,4-difluoropiperidine (108.68 mg, 897.22 mol, 2.00 eq) in DCE (2.00 mL) was added 4 A MS (300.00 mg) and HOAc (26.94 mg, 448.60 mol, 25.66 µL, 1.00 eq), the mixture was stirred at 20° C. for 16 hr. NaBH$_3$CN (140.95 mg, 2.24 mmol, 5.00 eq) was added. The mixture was stirred at 20° C. for 3 hr. TLC showed the reaction was completed. The mixture was poured into saturated NH$_4$C$_1$ (20 mL), extracted with Ethyl acetate (15 mL*2), the organic layer was washed with brine (20 mL*2), dried over anhydrous Na$_2$SO$_4$ and concentrated in vacuum. The crude was purified by prep-TLC to afford the title compound (53.00 mg, 114.56 µmol, 25.54% yield, 95% purity) as colorless oil.

Step 2. 8-(4,4-difluoro-1-piperidyl)-10-methyl-2,3,4,7,8,9-hexahydro-1H-pyrido[2,3]pyrazolo[2,4-b][1,4]diazepin-11-one To a solution of tert-butyl 8-(4,4-difluoro-1-piperidyl)-10-methyl-11-oxo-1,3,4,7,8,9-hexahydropyrido[2,3]pyrazolo[2,4-b][1,4]diazepine-2-carboxylate (53.00 mg, 120.59 µmol, 1.00 eq) in DCM (2.00 mL) was added TFA (3.08 g, 27.01 mmol, 2.00 mL, 224.01 eq), the mixture was stirred at 20° C. for 1 hr. TLC showed the reaction complete. The mixture was concentrated in vacuum to afford the title compound (54.00 mg, 119.10 µmol, 98.76% yield, TFA) as colorless oil, which was used for the next step without purification.

Step 3. N-(3-chloro-4-fluorophenyl)-8-(4,4-difluoropiperidin-1-yl)-10-methyl-11-oxo-1,3,4,7,8,9,10,11-octahydro-2H-pyrido[4',3':3,4]pyrazolo[1,5-a][1,4]diazepine-2-carboxamide To a solution of 8-(4,4-difluoro-1-piperidyl)-10-methyl-2,3,4,7,8,9-hexahydro-1H-pyrido[2,3]pyrazolo[2,4-b][1,4]diazepin-11-one (54.00 mg, 119.10 µmol, 1.00 eq, TFA) and phenyl N-(3-chloro-4-fluoro-phenyl)carbamate (31.64 mg, 119.10 µmol, 1.00 eq) in DCM (2.00 mL) was added TEA (36.15 mg, 357.29 µmol, 49.53 µL, 3.00 eq). The mixture was stirred at 20° C. for 16 hr. LCMS showed the reaction complete. The mixture was concentrated in vacuum. The crude was purified by prep-HPLC to afford the title compound (24.00 mg, 45.09 mol, 37.86% yield, 96% purity) as white solid. LCMS: 511/513 [M+1]. $^1$H NMR (400 MHz, CDCl$_3$) δ 7.58 (dd, J=2.64, 6.53 Hz, 1H), 7.18-7.20 (m, 1H), 7.02-7.08 (m, 1H), 6.65 (s, 1H), 4.51-4.80 (m, 3H), 4.28-4.39 (m, 1H), 3.76-3.93 (m, 2H), 3.47-3.63 (m, 2H), 3.28-3.40 (m, 1H), 3.18 (s, 3H), 2.74-2.89 (m, 4H), 2.63-2.67 (m, 2H), 1.92-2.10 (m, 4H).

Compound 057: methyl 2-((3-chloro-4-fluorophenyl)carbamoyl)-10-methyl-11-oxo-1,3,4,7,8,9,10,11-octahydro-2H-pyrido[4',3':3,4]pyrazolo[1,5-a][1,4]diazepine-9-carboxylate

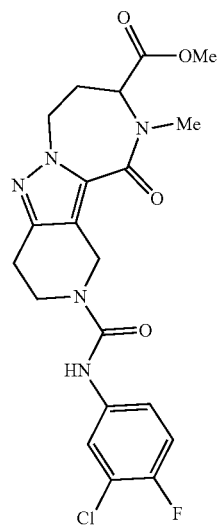 [SMILES: COC(=O)C1CCn2nc3c(c2C(=O)N1C)CN(C(=O)Nc1ccc(F)c(Cl)c1)CC3]

Step 1. 2-tert-butyl 9-methyl 10-methyl-11-oxo-1,3,4,7,8,9-hexahydropyrido[2,3]pyrazolo[2,4-c][1,4]diazepine-2,9-dicarboxylate and 2-tert-butyl 9-methyl 9,10-dimethyl-11-oxo-3,4,7,8-tetrahydro-1H-pyrido[2,3]pyrazolo[2,4-c][1,4]diazepine-2,9-dicarboxylate To a solution of 2-tert-butyl 9-methyl 11-oxo-3,4,7,8,9,10-hexahydro-1H-pyrido[2,3]pyrazolo[2,4-c][1,4]diazepine-2,9-dicarboxylate (Intermediate 13, 1.10 g, 3.02 mmol, 1.00 eq) in DMF (20.00 mL) was added NaH (144.90 mg, 3.62 mmol, 60% purity, 1.20 eq) at −30° C., stirring for 30 min MeI (557.01 mg, 3.93 mmol, 244.30 µL, 1.30 eq) was added and the mixture was stirred at 20° C. for 2 hr. LCMS showed the reactant consumed and 70% of 2-tert-butyl 9-methyl 10-methyl-11-oxo-1,3,4,7,8,9-hexahydropyrido[2,3]pyrazolo[2,4-c][1,4]diazepine-2,9-dicarboxylate and 18% of 2-tert-butyl 9-methyl 9,10-dimethyl-11-oxo-3,4,7,8-tetrahydro-1H-pyrido[2,3]pyrazolo[2,4-c][1,4]diazepine-2,9-dicarboxylate were detected. The mixture was poured into water (100 mL), extracted with ethyl acetate (50 mL*3), the organic layer was washed with brine (50 mL*3), dried over anhydrous Na$_2$SO$_4$ and concentrated in vacuum. The crude was purified by prep-HPLC to afford 2-tert-butyl 9-methyl 10-methyl-11-oxo-1,3,4,7,8,9-hexahydropyrido[2,3]pyrazolo[2,4-c][1,4]diazepine-2,9-dicarboxylate (680.00 mg, 1.80 mmol, 59.60% yield) and 2-tert-butyl 9-methyl 9,10-dimethyl-11-oxo-3,4,7,8-tetrahydro-1H-pyrido[2,3]pyrazolo[2,4-c][1,4]diazepine-2,9-dicarboxylate (120.00 mg, 305.77 µmol, 10.12% yield) as colorless oil.

Step 2. methyl-10-methyl-11-oxo-2,3,4,7,8,9-hexahydro-1H-pyrido[2,3]pyrazolo[2,4-c][1,4]diazepine-9-carboxylate To a solution of 2-tert-butyl 9-methyl 10-methyl-11-oxo-1,3,4,7,8,9-hexahydropyrido[2,3]pyrazolo[2,4-c][1,4]diazepine-2,9-dicarboxylate (200.00 mg, 528.51 µmol, 1.00 eq) in DCM (3.00 mL) was added TFA (4.62 g, 40.52 mmol, 3.00 mL, 76.67 eq). The mixture was stirred at 20° C. for 1 hr. TLC (Petroleum ether: ethyl acetate=1:1) showed the reaction was completed. The mixture was concentrated in vacuum to afford the title compound (200.00 mg, 509.77 µmol, 96.46% yield, TFA) as colorless oil.

Step 3. methyl 2-((3-chloro-4-fluorophenyl)carbamoyl)-10-methyl-11-oxo-1,3,4,7,8,9,10,11-octahydro-2H-pyrido[4',3':3,4]pyrazolo[1,5-a][1,4]diazepine-9-carboxylate To a solution of methyl 10-methyl-11-oxo-2,3,4,7,8,9-hexahydro-1H-pyrido[2,3] pyrazolo[2,4-c][1,4]diazepine-9-carboxylate (190.00 mg, 484.29 µmol, 1.00 eq, TFA) and phenyl N-(3-chloro-4-fluoro-phenyl)carbamate (128.66 mg, 484.29 µmol, 1.00 eq) in DCM (3.00 mL) was added TEA (98.01 mg, 968.57 µmol, 134.26 µL, 2.00 eq). The mixture was stirred at 20° C. for 16 hr. LCMS showed the reaction was completed. The mixture was poured into water (20 mL), extracted with ethyl acetate (20 mL*2), the organic layer was washed with brine (20 mL), dried over anhydrous Na$_2$SO$_4$ and concentrated in vacuum. The crude was purified by prep-HPLC to afford the title compound (150.00 mg, 323.43 µmol, 66.79% yield, 97% purity) as white solid.

LCMS: 450/452 [M+1]. $^1$H NMR (400 MHz, CDCl$_3$) δ 7.60 (dd, J=2.63, 6.54 Hz, 1H), 7.18-7.24 (m, 1H), 7.00-7.09 (m, 1H), 6.64 (s, 1H), 4.59-4.80 (m, 2H), 4.28-4.47 (m, 3H), 3.74-3.95 (m, 2H), 3.67 (s, 3H), 3.20 (s, 3H), 2.88-2.99 (m, 1H), 2.81 (t, J=5.81 Hz, 2H), 2.49-2.65 (m, 1H).

Compound 058: 2-((3-chloro-4-fluorophenyl)carbamoyl)-10-methyl-11-oxo-1,3,4,7,8,9,10,11-octahydro-2H-pyrido[4',3':3,4]pyrazolo[1,5-a][1,4]diazepine-9-carboxylic acid

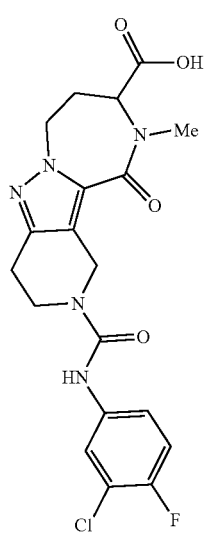 [SMILES: CN1C(=O)c2c3c(nn2CCC1C(=O)O)CCN(C(=O)Nc1ccc(F)c(Cl)c1)C3]

To a solution of methyl 2-[(3-chloro-4-fluoro-phenyl)carbamoyl]-10-methyl-11-oxo-1,3,4,7,8,9-hexahydropyrido[2,3]pyrazolo[2,4-c][1,4]diazepine-9-carboxylate (Compound 057, 30.00 mg, 66.69 μmol, 1.00 eq) in MeOH (2.00 mL) and H$_2$O (2.00 mL) was added NaOH (8.00 mg, 200.07 μmol, 3.00 eq), the mixture was stirred at 20° C. for 16 hr. LCMS showed the reaction was completed. The mixture was acidified by HCl (1N) to pH 4. The residue was purified by prep-HPLC to afford the title compound (24.00 mg, 54.52 μmol, 81.74% yield, 99% purity) as white solid LCMS: 436/438 [M+1]. $^1$H NMR (400 MHz, METHANOL-d$_4$) δ 7.56-7.64 (m, 1H), 7.25-7.35 (m, 1H), 7.13 (t, J=8.93 Hz, 1H), 4.60 (br s, 2H), 4.37 (br d, J=5.01 Hz, 3H), 3.84-3.99 (m, 1H), 3.59-3.75 (m, 1H), 3.17 (s, 3H), 2.93 (br d, J=14.43 Hz, 1H), 2.75 (br t, J=5.32 Hz, 2H), 2.53 (br dd, J=5.93, 14.61 Hz, 1H).

Compound 059: N2-(3-chloro-4-fluorophenyl)-N9,N9,10-trimethyl-11-oxo-1,3,4,7,8,9,10,11-octahydro-2H-pyrido[4',3':3,4]pyrazolo[1,5-a][1,4]diazepine-2,9-dicarboxamide

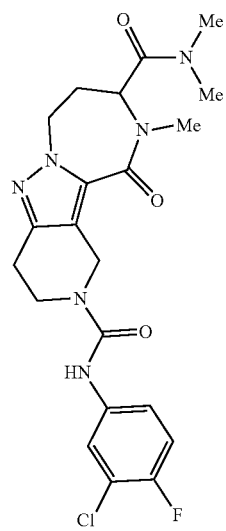 [SMILES: CN(C)C(=O)C1CCn2nc3c(c2C(=O)N1C)CN(C(=O)Nc1ccc(F)c(Cl)c1)CC3]

To a solution of 2-[(3-chloro-4-fluoro-phenyl)carbamoyl]-10-methyl-11-oxo-1,3,4,7,8,9-hexahydropyrido[2,3]pyrazolo[2,4-c][1,4]diazepine-9-carboxylic acid (Compound 058, 100.00 mg, 229.44 μmol, 1.00 eq) and Me$_2$NH (187.09 mg, 2.29 mmol, 210.21 μL, 10.00 eq, HCl) in DMF (3.00 mL) was added DIPEA (593.06 mg, 4.59 mmol, 801.43 μL, 20.00 eq) and HATU (104.69 mg, 275.33 μmol, 1.20 eq). The mixture was stirred at 20° C. for 16 hr. LCMS showed the reaction was completed. The mixture was poured into water (20 mL), extracted with ethyl acetate (20 mL*2), the organic layer was washed with brine (20 mL*3), dried over anhydrous Na$_2$SO$_4$ and concentrated in vacuum. The residue was purified by prep-HPLC to afford the title compound (50.00 mg, 106.93 μmol, 46.61% yield, 99% purity) as white solid. LCMS: 463/465 [M+1]. $^1$H NMR (400 MHz, CDCl$_3$) δ 7.60 (dd, J=2.63, 6.54 Hz, 1H), 7.18-7.25 (m, 1H), 7.04 (t, J=8.80 Hz, 1H), 6.77 (s, 1H), 4.75 (q, J=15.89 Hz, 2H), 4.61 (dd, J=4.52, 7.58 Hz, 1H), 4.51 (td, J=4.52, 14.31 Hz, 1H), 4.18 (ddd, J=4.71, 10.33, 14.55 Hz, 1H), 3.76-3.94 (m, 2H), 3.07 (s, 3H), 3.03 (d, J=8.31 Hz, 6H), 2.75-2.84 (m, 2H), 2.50-2.64 (m, 2H).

Compound 060: N-(3-chloro-4-fluorophenyl)-9-(hydroxymethyl)-10-methyl-1-oxo-1,3,4,7,8,9,10,11-octahydro-2H-pyrido[4',3':3,4]pyrazolo[1,5-a][1,4]diazepine-2-carboxamide

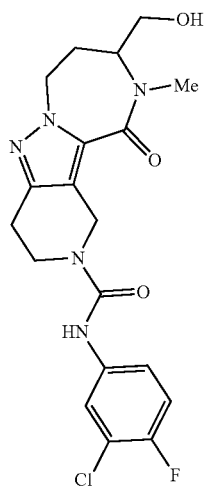 [SMILES: CN1C(=O)c2c3c(nn2CCC1CO)CCN(C(=O)Nc1ccc(F)c(Cl)c1)C3]

To a solution of methyl 2-[(3-chloro-4-fluoro-phenyl)carbamoyl]-10-methyl-11-oxo-1,3,4,7,8,9-hexahydropyrido[2,3]pyrazolo[2,4-c][1,4]diazepine-9-carboxylate (Compound 057, 100.00 mg, 222.29 µmol, 1.00 eq) in THF (3.00 mL) was added LiBH$_4$ (14.52 mg, 666.87 µmol, 3.00 eq) at 10° C. The mixture was stirred at 20° C. for 16 hr. LCMS showed the reaction was completed. The mixture was poured into aqueous HCl (0.5 M), extracted with DCM (20 mL*2), the organic layer was washed with brine (20 mL), dried over anhydrous Na$_2$SO$_4$ and concentrated in vacuum. The crude was purified by prep-HPLC to afford the title compound (43.00 mg, 100.91 µmol, 45.40% yield, 99% purity) as white solid. LCMS: 422/424 [M+1]. $^1$H NMR (400 MHz, CDCl$_3$) δ 7.57 (dd, J=2.63, 6.54 Hz, 1H), 7.18-7.25 (m, 1H), 7.04 (t, J=8.80 Hz, 1H), 6.90 (s, 1H), 4.66 (s, 2H), 4.32-4.52 (m, 2H), 3.90 (td, J=5.61, 13.36 Hz, 1H), 3.69-3.83 (m, 4H), 3.21 (s, 3H), 2.80 (t, J=5.75 Hz, 2H), 2.21-2.57 (m, 3H).

Compound 061: N-(3-chloro-4-fluorophenyl)-9-(hydroxymethyl)-9,10-dimethyl-11-oxo-1,3,4,7,8,9,10,11-octahydro-2H-pyrido[4',3':3,4]pyrazolo[1,5-a][1,4]diazepine-2-carboxamide

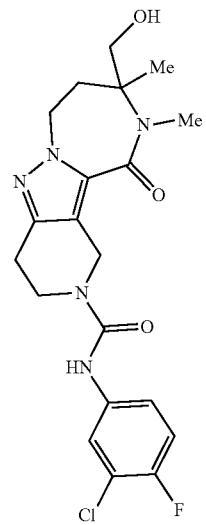 [SMILES: CN1C(=O)c2c3c(nn2CCC1(C)CO)CCN(C(=O)Nc1ccc(F)c(Cl)c1)C3]

Step 1. 2-tert-butyl 9-methyl 9,10-dimethyl-11-oxo-3,4,7,8-tetrahydro-1H-pyrido[2,3]pyrazolo[2,4-c][1,4]diazepine-2,9-dicarboxylate To a solution of methyl 2-[(3-chloro-4-fluoro-phenyl)carbamoyl]-9,10-dimethyl-11-oxo-3,4,7,8-tetrahydro-1H-pyrido[2,3]pyrazolo[2,4-c][1,4]diazepine-9-carboxylate (100.00 mg, 285.41 µmol, 1.00 eq) in DMF (3.00 mL) was added NaH (34.25 mg, 856.23 µmol, 60% purity, 3.00 eq), stirring for 30 min, MeI (202.56 mg, 1.43 mmol, 88.84 µL, 5.00 eq) was added and the mixture was stirred at 20° C. for 2 hr. LCMS showed the reactant consumed and the major product was detected. The mixture was poured into water(10 mL), extracted with ethyl acetate(10 mL*2). The combined organic layer was washed with brine(10 mL*2), dried over anhydrous Na$_2$SO$_4$ and concentrated in vacuum to afford the title compound (120.00 mg, crude) as the yellow oil.

Step 2. methyl 9,10-dimethyl-11-oxo-1,3,4,7,8,9,10,11-octahydro-2H-pyrido[4',3':3,4]pyrazolo[1,5-a][1,4]diazepine-9-carboxylate To a solution of 2-tert-butyl 9-methyl 9,10-dimethyl-11-oxo-3,4,7,8-tetrahydro-1H-pyrido[2,3]pyrazolo[2,4-c][1,4]diazepine-2,9-dicarboxylate (120.00 mg, 305.77 µmol, 1.00 eq) in DCM (3.00 mL) was added TFA (4.62 g, 40.52 mmol, 3.00 mL, 132.52 eq). The mixture was stirred at 20° C. for 1 hr. TLC showed the reaction was completed. The mixture was concentrated in vacuum to give methyl9,10-dimethyl-11-oxo-1,2,3,4,7,8-hexahydropyrido[2,3]pyrazolo [2,4-c][1,4] diazepine-9-carboxylate (120.00 mg, 295.30 µmol, 96.58% yield, TFA) as the colorless oil, which was used for the next step without purification.

Step 3. methyl 2-((3-chloro-4-fluorophenyl)carbamoyl)-9,10-dimethyl-11-oxo-1,3,4,7,8,9,10,11-octahydro-2H-pyrido[4',3':3,4]pyrazolo[1,5-a][1,4]diazepine-9-carboxylate To a solution of methyl 9,10-dimethyl-11-oxo-1,2,3,4,7,8-hexahydropyrido[2,3] pyrazolo[2,4-c][1,4]diazepine-9- carboxylate (120.00 mg, 295.30 μmol, 1.00 eq, TFA) and phenyl N-(3-chloro-4-fluoro-phenyl)carbamate (78.45 mg, 295.30 μmol, 1.00 eq) in DCM (3.00 mL) was added TEA (365.00 mg, 3.61 mmol, 500.00 μL, 12.21 eq). The mixture was stirred at 20° C. for 16 hr. TLC showed the reaction was completed. The reaction mixture was partitioned between ethyl acetate (20 mL) and water (20 mL) and extracted with ethyl acetate (20 mL*2), the organic layer was washed with brine (20 mL), dried over anhydrous $Na_2SO_4$ and concentrated in vacuum. The crude was purified by prep-TLC to afford the title compound (90.00 mg, 188.19 μmol, 63.73% yield, 97% purity) as white solid.

Step 4. N-(3-chloro-4-fluorophenyl)-9-(hydroxymethyl)-9,10-dimethyl-11-oxo-1,3,4,7,8,9,10,11-octahydro-2H-pyrido[4',3':3,4]pyrazolo[1,5-a][1,4]diazepine-2-carboxamide To a solution of methyl 2-[(3-chloro-4-fluoro-phenyl)carbamoyl]-9,10-dimethyl-11-oxo-3,4,7,8-tetrahydro-1H-pyrido[2,3]pyrazolo[2,4-c][1,4]diazepine-9-carboxylate (45.00 mg, 97.01 μmol, 1.00 eq) in THF (2.00 mL) was added $LiBH_4$ (4.23 mg, 194.02 μmol, 2.00 eq) at 0° C. The mixture was stirred at 20° C. for 16 hr. LCMS showed 15% recatant remained and $LiBH_4$ (4.23 mg, 194.02 μmol, 2.00 eq) was added, the mixture was stirred at 20° C. for 4 hr. LCMS showed the reaction was completed. The mixture was poured into aqeuous HCl (0.5M), extracted with DCM (20 mL*2), the organic layer was washed with brine (20 mL), dried over anhydrous $Na_2SO_4$ and concentrated in vacuum. The crude was purified by prep-HPLC to afford the title compound (22.00 mg, 49.46 μmol, 50.99% yield, 98% purity) as white solid. LCMS: 436/438 [M+1]. $^1$H NMR (400 MHz, $CDCl_3$) δ 7.57 (dd, J=2.64, 6.53 Hz, 1H), 7.22 (ddd, J=2.76, 4.08, 8.97 Hz, 1H), 7.00-7.09 (m, 1H), 6.79 (s, 1H), 4.64-4.75 (m, 2H), 4.51-4.59 (m, 1H), 4.38-4.47 (m, 1H), 3.77-3.92 (m, 3H), 3.55 (d, J=11.29 Hz, 1H), 3.12 (s, 3H), 2.80 (t, J=5.77 Hz, 2H), 2.49-2.63 (m, 1H), 2.27 (ddd, J=2.38, 8.28, 15.56 Hz, 2H), 1.44 (s, 3H).

Compound 062: 2-((3-chloro-4-fluorophenyl)carbamoyl)-9,10-dimethyl-11-oxo-1,3,4,7,8,9,10,11-octahydro-2H-pyrido[4',3':3,4]pyrazolo[1,5-a][1,4]diazepine-9-carboxylic acid

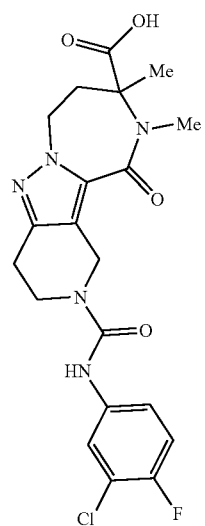 [SMILES: CN1C(=O)c2c3c(nn2CCC1(C)C(=O)O)CCN(C(=O)Nc1ccc(F)c(Cl)c1)C3]

To a solution of methyl 2-[(3-chloro-4-fluoro-phenyl)carbamoyl]-9,10-dimethyl-11-oxo-3,4,7,8-tetrahydro-1H-pyrido[2,3]pyrazolo[2,4-c][1,4]diazepine-9-carboxylate (10.00 mg, 21.56 μmol, 1.00 eq) in MeOH (1.00 mL) and $H_2O$ (1.00 mL) was added NaOH (1.29 mg, 32.34 μmol, 1.50 eq). The mixture was stirred at 20° C. for 16 hrs. LCMS showed 60% reactant remained, NaOH (2.59 mg, 64.67 μmol, 3.00 eq) was added. The mixture was heated to 40° C. and stirred at 40° C. for 16 hr. LCMS showed the reaction completed. The mixture was acidified to pH 3 by HCl (3 M). The resulting mixture was purified by prep-HPLC to afford the title compound (7.00 mg, 15.09 μmol, 70.01% yield, 97% purity) as white solid. LCMS: 450/452 [M+1]. $^1$H NMR (400 MHz, $CDCl_3$) δ 7.45 (dd, J=2.51, 6.27 Hz, 1H), 7.11-7.20 (m, 1H), 7.01-7.08 (m, 1H), 6.80 (br s, 1H), 6.74-6.86 (m, 1H), 4.70-4.75 (m, 1H), 4.21-4.45 (m, 3H), 3.93.396 (m, 1H), 3.56 (br s, 1H), 3.17 (s, 4H), 2.70-2.92 (m, 2H), 2.08-2.23 (m, 1H), 1.66 (s, 3H).

Compound 063: N-(3-chloro-4-fluorophenyl)-10-methyl-8-(morpholinomethyl)-11-oxo-1,3,4,7,8,9,10,11-octahydro-2H-pyrido[4',3':3,4]pyrazolo[1,5-a][1,4]diazepine-2-carboxamide

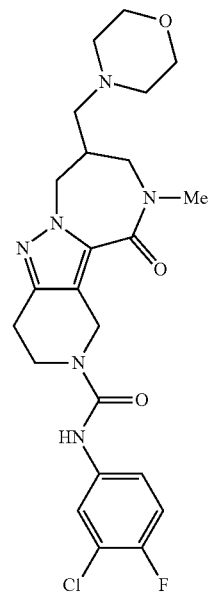 [SMILES: CN1CC(CN2CCOCC2)Cn2nc3c(c2C1=O)CN(C(=O)Nc1ccc(F)c(Cl)c1)CC3]

Step 1. tert-butyl 8-(hydroxymethyl)-10-methyl-11-oxo-1,3,4,7,8,9-hexahydropyrido[2,3]pyrazolo[2,4-b][1,4]diazepine-2-carboxylate A mixture of 2-tert-butyl8-ethyl10-methyl-11-oxo-1,3,4,7,8,9-hexahydropyrido[2,3]pyrazolo[2,4-b][1,4]diazepine-2,8-dicarboxylate (Intermediate 14, 500.00 mg, 1.27 mmol, 1.00 eq) in THF (10.00 mL) was added $LiAlH_4$ (96.39 mg, 2.54 mmol, 2.00 eq) at −40° C. under $N_2$, then the mixture was stirred at −40° C. for 2 hr under $N_2$ atmosphere. The mixture was poured into ice-water (20 mL) and stirred at 5 min. The aqueous phase was extracted with ethyl acetate (10 mL*3). The combined organic phase was washed with HCl (1N, 20 mL*2), dried with anhydrous $Na_2SO_4$, filtered and concentrated in vacuum. The residue was purified by column chromatography (SiO2, Petroleum ether/Ethyl acetate=100/1 to 1:2) to afford the title compound (120.00 mg, 342.46 µmol, 26.97% yield) as a white solid. LCMS: 351 [M+1].

Step 2. tert-butyl 10-methyl-8-(methylsulfonyloxymethyl)-11-oxo-1,3,4,7,8,9-hexahydropyrido[2,3]pyrazolo[2,4-b][1,4]diazepine-2-carboxylate A mixture of tert-butyl 8-(hydroxymethyl)-10-methyl-11-oxo-1,3,4,7,8,9-hexahydropyrido[2,3]pyrazolo[2,4-b][1,4]diazepine-2-carboxylate (100.00 mg, 285.38 µmol, 1.00 eq), TEA (144.39 mg, 1.43 mmol, 197.79 µL, 5.00 eq) in DCM (3.00 mL) was added MsCl (130.76 mg, 1.14 mmol, 88.35 µL, 4.00 eq) at 0° C. under $N_2$, and then the mixture was stirred at 15° C. for 2 hour under $N_2$ atmosphere. LCMS and TLC showed the starting material was consumed completely, a new spot appeared. The mixture was poured into ice-water (20 mL) and stirred at 5 min. The aqueous phase was extracted with DCM (10 mL*2). The combined organic phase was washed with brine (20 mL), dried with anhydrous $Na_2SO_4$, filtered and concentrated in vacuum to afford the title compound (102.00 mg, 238.04 µmol, 83.41% yield) as a white solid, which was used directly for next step. LCMS 429 [M+1].

Step 3. tert-butyl 10-methyl-8-(morpholinomethyl)-1-oxo-1,3,4,7,8,9-hexahydropyrido[2,3]pyrazolo[2,4-b][1,4] diazepine-2-carboxylate A mixture of tert-butyl 10-methyl-8-(methylsulfonyloxymethyl)-11-oxo-1,3,4,7,8,9-hexahydropyrido[2,3]pyrazolo[2,4-b][1,4]diazepine-2-carboxylate (100.00 mg, 233.37 µmol, 1.00 eq), morpholine (203.31 mg, 2.33 mmol, 205.37 µL, 10.00 eq) in DMSO (2.00 mL) was degassed and purged with $N_2$ for 3 times, and then the mixture was stirred at 88° C. for 16 hour under $N_2$ atmosphere. LCMS showed the starting material was consumed completely, desired product was major. The mixture was poured into water (10 mL) and extracted with EtOAc (5 mL*3). The combined organic phase was washed with brine (10 mL), dried with anhydrous $Na_2SO_4$, filtered and concentrated in vacuum. The residue was purified by Prep-TLC (DCM/MeOH=20/1) to afford the title compound (65.00 mg, 147.19 µmol, 63.07% yield, 95% purity) as a white solid.
LCMS: 420 [M+1].

Step 4. 10-methyl-8-(morpholinomethyl)-2,3,4,7,8,9-hexahydro-1H-pyrido[2,3]pyrazolo[2,4-b][1,4]diazepin-11-one A mixture of tert-butyl 10-methyl-8-(morpholinomethyl)-11-oxo-1,3,4,7,8,9-hexahydropyrido[2,3]pyrazolo[2,4-b][1,4]diazepine-2-carboxylate (65.00 mg, 154.94 µmol, 1.00 eq), TFA (1.54 g, 13.51 mmol, 1.00 mL, 87.17 eq) in DCM (2.00 mL) was degassed and purged with $N_2$ for 3 times, and then the mixture was stirred at 20° C. for 1 hour under $N_2$ atmosphere. TLC showed the starting material was consumed completely, a new spot appeared. The mixture was concentrated in vacuum to afford the title compound (67.00 mg, 154.58 µmol, 99.77% yield, TFA) as a yellow oil, which was used directly for next step.

Step 5. N-(3-chloro-4-fluorophenyl)-10-methyl-8-(morpholinomethyl)-11-oxo-1,3,4,7,8,9,10,11-octahydro-2H-pyrido[4',3':3,4]pyrazolo[1,5-a][1,4]diazepine-2-carboxamide A mixture of 10-methyl-8-(morpholinomethyl)-2,3,4,7,8,9-hexahydro-1H-pyrido[2,3]pyrazolo[2,4-b][1,4]diazepin-11-one (67.00 mg, 209.77 µmol, 1.00 eq), phenyl N-(3-chloro-4-fluoro-phenyl)carbamate (66.88 mg, 251.72 µmol, 1.20 eq), TEA (42.45 mg, 419.54 µmol, 58.15 µL, 2.00 eq) in DCM (5.00 mL) was degassed and purged with $N_2$ for 3 times, and then the mixture was stirred at 20° C. for 16 hour under $N_2$ atmosphere. LCMS showed the starting material was consumed completely, desired product was major. The mixture was poured into water (10 mL) and stirred at 5 min. The aqueous phase was extracted with DCM (5 mL*3). The combined organic phase was washed with brine (10 mL), dried with anhydrous $Na_2SO_4$, filtered and concentrated in vacuum. The residue was purified by Prep-HPLC (FA) to afford the title compound (60.00 mg, 120.99 µmol, 57.68% yield, 99% purity) as a white solid. LCMS: 491/493 [M+1].
$^1$H NMR (400 MHz, $CDCl_3$) δ 7.58 (dd, J=2.63, 6.54 Hz, 1H), 7.18-7.24 (m, 1H), 7.01-7.09 (m, 1H), 6.72 (s, 1H), 4.67 (s, 2H), 4.38-4.47 (m, 1H), 4.11-4.20 (m, 1H), 3.74-3.92 (m, 6H), 3.49 (m, 1H), 3.28 (m, 1H), 3.17 (s, 3H), 2.75-2.91 (m, 4H), 2.67 (m, 4H), 2.48-2.56 (m, 1H).

Compound 064: N-(3-chloro-4-fluorophenyl)-10-methyl-11-oxo-8-(piperidin-1-ylmethyl)-1,3,4,7,8,9,10,11-octahydro-2H-pyrido[4',3':3,4]pyrazolo[1,5-a][1,4]diazepine-2-carboxamide

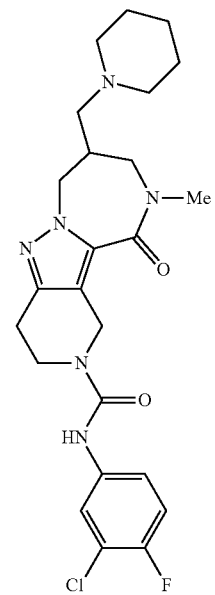 [SMILES: CN1CC(CN2CCCCC2)Cn2nc3c(c2C1=O)CN(C(=O)Nc1ccc(F)c(Cl)c1)CC3]

Step 1. tert-butyl 8-(hydroxymethyl)-10-methyl-11-oxo-1,3,4,7,8,9-hexahydropyrido[2,3]pyrazolo[2,4-b][1,4]diazepine-2-carboxylate A mixture of tert-butyl 10-methyl-8-methylene-11-oxo-3,4,7,9-tetrahydro-1H-pyrido[2,3]pyrazolo[2,4-b][1,4]diazepine-2-carboxylate (Intermediate 1, 800.00 mg, 2.41 mmol, 1.00 eq), chlororhodium; triphenylphosphane (89.19 mg, 96.40 µmol, 0.04 eq) in THF (10.00 mL) was added 1,3,2-benzodioxaborole (1 M, 7.23 mL, 3.00 eq) at 0° C. under $N_2$, and then the mixture was stirred at 20° C. for 3 hr under $N_2$ atmosphere. TLC showed the starting material was consumed completely. A solution of sodium; hydroxide (482.00 mg, 12.05 mmol, 5.00 eq) in $H_2O$ (5.00 mL) was added at −30° C. dropwise, then hydrogen peroxide (1.91 g, 16.87 mmol, 1.62 mL, 30% purity, 7.00 eq) was added slowly. The mixture was stirred at 20° C. for 16 hr. TLC showed no starting material, desired product was major. The mixture was quenched with NaHSO₃ (saturated, 40 mL) and extracted with EtOAc (20 mL). The organic phase was washed with NaOH (15%, 40 mL*3) and brine, dried over Na₂SO₄, filtered and concentrated in vacuo to give brown oil. The residue was purified by column chromatography (SiO₂, Petroleum ether/Ethyl acetate=100/1 to 1/4) to afford the title compound (522.00 mg, 1.42 mmol, 58.72% yield, 95% purity) as a white solid.

LCMS: 351 [M+1].

Step 2. tert-butyl10-methyl-8-(methylsulfonyloxymethyl)-11-oxo-1,3,4,7,8,9-hexahydropyrido[2,3]pyrazolo[2,4-b][1,4]diazepine-2-carboxylate A mixture of tert-butyl 8-(hydroxymethyl)-10-methyl-11-oxo-1,3,4,7,8,9-hexahydropyrido[2,3]pyrazolo[2,4-b][1,4]diazepine-2-carboxylate (500.00 mg, 1.43 mmol, 1.00 eq), TEA (723.51 mg, 7.15 mmol, 991.11 µL, 5.00 eq) in DCM (10.00 mL) was added MsCl (655.23 mg, 5.72 mmol, 442.72 µL, 4.00 eq) at 0° C. under N₂, and then the mixture was stirred at 20° C. for 2 hour under N₂ atmosphere. TLC showed the starting material was consumed completely, a new spot appeared. The mixture was poured into ice-water (20 mL) and stirred at 5 min. The aqueous phase was extracted with DCM (10 mL*2). The combined organic phase was washed with brine (20 mL), dried with anhydrous Na₂SO₄, filtered and concentrated in vacuum to afford the title compound (550.00 mg, 1.09 mmol, 76.29% yield, 85% purity) as a colorless oil.

LCMS: 429 [M+1].

Step 3. tert-butyl10-methyl-11-oxo-8-(1-pipenridylmethyl)-1,3,4,7,8,9-hexahydropyrido[2,3]pyrazolo[2,4-b][1,4]diazepine-2-carboxylate A mixture of tert-butyl 10-methyl-8-(methylsulfonyloxymethyl)-11-oxo-1,3,4,7,8,9-hexahydropyrido[2,3]pyrazolo[2,4-b][1,4]diazepine-2-carboxylate (120.00 mg, 280.05 µmol, 1.00 eq), piperidine (238.46 mg, 2.80 mmol, 277.28 µL, 10.00 eq) in DMSO (2.00 mL) was degassed and purged with N₂ for 3 times, and then the mixture was stirred at 88° C. for 16 hour under N₂ atmosphere. LCMS showed the starting material was consumed completely, desired product was major. The mixture was poured into water (10 mL). The aqueous phase was extracted with ethyl acetate (5 mL*2). The combined organic phase was washed with brine (10 mL*2), dried with anhydrous Na₂SO₄, filtered and concentrated in vacuum. The residue was purified by Prep-TLC (DCM/MeOH=10/1) to afford the title compound (60.00 mg, 143.70 µmol, 51.31% yield) as a white solid. LCMS: 418 [M+1]

Step 4. 10-methyl-8-(1-piperidylmethyl)-2,3,4,7,8,9-hexahydro-1H-pyrido[2,3]pyrazolo[2,4-b][1,4]diazepin-11-one A mixture of tert-butyl 10-methyl-1-oxo-8-(1-piperidyl-methyl)-1,3,4,7,8,9-hexahydropyrido[2,3]pyrazolo[2,4-b][1,4]diazepine-2-carboxylate (54.00 mg, 129.33 µmol, 1.00 eq) in DCM (2.00 mL) was added TFA (1.54 g, 13.51 mmol, 1.00 mL, 104.43 eq), and then the mixture was stirred at 20° C. for 1 hour under N₂ atmosphere. TLC showed the starting material was consumed completely, a new spot appeared. The mixture was concentrated in vacuum to afford the title compound (55.80 mg, 129.33 µmol, 100.00% yield, TFA) as a yellow oil, which was used directly for next step.

Step 5. N-(3-chloro-4-fluorophenyl)-10-methyl-11-oxo-8-(piperidin-1-ylmethyl)-1,3,4,7,8,9,10,11-octahydro-2H-pyrido[4',3':3,4]pyrazolo[1,5-a][1,4]diazepine-2-carboxamide A mixture of 10-methyl-8-(1-piperidylmethyl)-2,3,4,7,8,9-hexahydro-1H-pyri do[2,3]pyrazolo[2,4-b][1,4]diazepin-11-one (55.80 mg, 129.33 µmol, 1.00 eq, TFA), phenyl N-(3-chloro-4-fluoro-phenyl)carbamate (41.23 mg, 155.20 µmol, 1.20 eq), TEA (26.17 mg, 258.66 µmol, 35.85 µL, 2.00 eq) in DCM (5.00 mL) was degassed and purged with N₂ for 3 times, and then the mixture was stirred at 20° C. for 16 hour under N₂ atmosphere. LCMS showed the starting material was consumed completely, desired product was major. The mixture was poured into water (10 mL) and stirred at 5 min. The aqueous phase was extracted with DCM (5 mL*3). The combined organic phase was washed with brine (10 mL), dried with anhydrous Na₂SO₄, filtered and concentrated in vacuum. The residue was purified by Prep-HPLC (HCl) to afford the title compound (40.00 mg, 80.98 µmol, 62.62% yield, 99% purity) as a white solid. LCMS: 489/491 [M+1]. ¹H NMR (400 MHz, CDCl₃) δ 7.60 (m, 1H), 7.18 (m, 1H), 7.02-7.10 (m, 1H), 6.60 (br s, 1H), 4.57-4.77 (m, 2H), 4.48 (m, 1H), 4.35 (m, 1H), 3.84 (m, 3H), 3.68 (m, 1H), 3.32-3.58 (m, 3H), 3.24 (m, 3H), 2.63-3.08 (m, 6H), 2.37 (m, 2H), 1.81-2.02 (m, 3H), 1.48 (m, 1H).

Compound 065: N-(3-chloro-4-fluorophenyl)-8-((dimethylamino)methyl)-10-methyl-1-oxo-1,3,4,7,8,9,10,11-octahydro-2H-pyrido[4',3':3,4]pyrazolo[1,5-a][1,4]diazepine-2-carboxamide

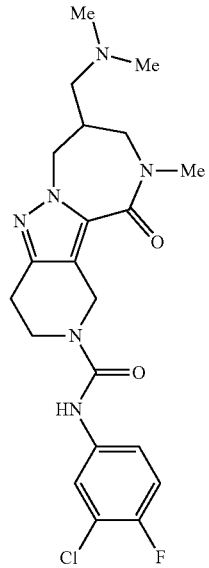 [SMILES: CN(C)CC1CN(C)C(=O)c2c3c(nn2C1)CCN(C(=O)Nc1ccc(F)c(Cl)c1)C3]

Step 1. tert-butyl8-[(dimethylamino)methyl]-10-methyl-11-oxo-1,3,4,7,8,9-hexahydropyrido [2,3] pyrazolo[2,4-b][1,4]diazepine-2-carboxylate A mixture of tert-butyl 10-methyl-8-(methylsulfonyloxymethyl)-11-oxo-1,3,4,7,8,9-hexahydropyrido[2,3]pyrazolo[2,4-b][1,4]diazepine-2-carboxylate (Compound 064, product from Step 2, 120.00 mg, 280.05 μmol, 1.00 eq), N-methylmethanamine (2 M, 1.40 mL, 10.00 eq) in DMSO (5.00 mL) was degassed and purged with N₂ for 3 times, and then the mixture was stirred at 88° C. for 16 hour under N₂ atmosphere. TLC showed the starting material was consumed completely, desired product was major. The mixture was poured into water (10 mL) and extracted with EtOAc (5 mL*3). The combined organic phase was washed with brine (10 mL), dried with anhydrous Na₂SO₄, filtered and concentrated in vacuum. The residue was purified by Prep-TLC (DCM/MeOH=10/1) to afford the title compound (65.00 mg, 165.31 μmol, 59.03% yield, 96% purity) as a white solid. LCMS: 378 [M+1]

Step 2. 8-[(dimethylamino)methyl]-10-methyl-2,3,4,7,8,9-hexahydro-1H-pyrido[2,3]pyrazolo[2,4-b][1,4]diazepin-11-one A mixture of tert-butyl8-[(dimethylamino)methyl]-10-methyl-11-oxo-1,3,4,7,8,9-hexahydropyrido[2,3]pyrazolo[2,4-b][1,4]diazepine-2-carboxylate (55.00 mg, 145.70 μmol, 1.00 eq) in DCM (2.00 mL) was added TFA (1.69 g, 14.86 mmol, 1.10 mL, 101.97 eq) and then the mixture was stirred at 20° C. for 1 hour under N₂ atmosphere. TLC showed the starting material was consumed completely, a new spot appeared. The mixture was concentrated in vacuum to afford the title compound (57.00 mg, 145.63 μmol, 99.96% yield, TFA) as yellow oil, which was used directly for next step.

Step 3. N-(3-chloro-4-fluorophenyl)-8-((dimethylamino)methyl)-10-methyl-11-oxo-1,3,4,7,8,9,10,11-octahydro-2H-pyrido[4',3':3,4]pyrazolo[1,5-a][1,4]diazepine-2-carboxamide A mixture of 8-[(dimethylamino)methyl]-10-methyl-2,3,4,7,8,9-hexahydro-1H-pyrid o[2,3]pyrazolo[2,4-b][1,4]diazepin-11-one (57.00 mg, 145.63 μmol, 1.00 eq, TFA), phenyl N-(3-amino-4-fluoro-phenyl)carbamate (43.03 mg, 174.76 μmol, 1.20 eq), TEA (29.47 mg, 291.27 mol, 40.37 μL, 2.00 eq) in DCM (5.00 mL) was degassed and purged with N₂ for 3 times, and then the mixture was stirred at 20° C. for 16 hour under N₂ atmosphere. LCMS showed the starting material was consumed completely, desired product was major. The mixture was poured into water (10 mL) and stirred at 5 min. The aqueous phase was extracted with DCM (5 mL*2). The combined organic phase was washed with brine (10 mL), dried with anhydrous Na₂SO₄, filtered and concentrated in vacuum. The residue was purified by Prep-HPLC (HCl) to afford the title compound (59.00 mg, 130.11 μmol, 89.34% yield, 99% purity) as a white solid. LCMS: 449/451 [M+1]. ¹H NMR (400 MHz, CDCl₃) δ 7.57-7.63 (m, 1H), 7.15-7.22 (m, 1H), 7.02-7.10 (m, 1H), 6.51-6.57 (m, 1H), 4.58-4.77 (m, 2H), 4.46-4.56 (m, 1H), 4.31 (s, 1H), 3.84-3.89 (m, 3H), 3.47-3.61 (m, 1H), 3.25 (s, 3H), 3.12-3.20 (m, 1H), 3.04 (m, 2H), 2.83-2.92 (m, 6H), 2.80-2.86 (m, 2H).

Compound 066: N-(3-chloro-4-fluorophenyl)-8-((3,3-difluoropyrrolidin-1-yl)methyl)-10-methyl-11-oxo-1,3,4,7,8,9,10,11-octahydro-2H-pyrido[4',3':3,4]pyrazolo[1,5-a][1,4]diazepine-2-carboxamide

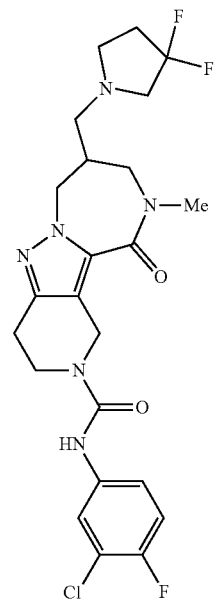 [SMILES: CN1CC(CN2CCC(F)(F)C2)Cn2nc3c(c2C1=O)CN(C(=O)Nc1ccc(F)c(Cl)c1)CC3]

Step 1. tert-butyl 8-[(3,3-difluoropyrrolidin-1-yl)methyl]-10-methyl-1-oxo-1,3,4,7,8,9-hexahydropyrido[2,3]pyrazolo[2,4-b][1,4]diazepine-2-carboxylate A mixture of tert-butyl 10-methyl-8-(methylsulfonyloxymethyl)-11-oxo-1,3,4,7,8,9-hexahydropyrido[2,3]pyrazolo[2,4-b][1,4]diazepine-2-carboxylate (Compound 064, product from Step 2, 20.00 mg, 46.67 μmol, 1.00 eq), 3,3-difluoropyrrolidine (49.99 mg, 466.74 μmol, 10.00 eq) in DMSO (1.00 mL) was degassed and purged with N₂ for 3 times, and then the mixture was stirred at 88° C. for 16 hr under N₂ atmosphere. TLC showed the starting material/desired product/byproduct=3/2/1. Then 3,3-difluoropyrrolidine (49.99 mg, 466.74 μmol, 10.00 eq) was added to the mixture, and the mixture was stirred at 90° C. for 16 hr. TLC showed the starting material was consumed completely, desired product/byproduct=3/1. The mixture was poured into water (10 mL) and stirred at 5 min. The aqueous phase was extracted with ethyl acetate (5 mL*2). The combined organic phase was washed with brine (10 mL), dried with anhydrous Na₂SO₄, filtered and concentrated in vacuum. The residue was purified by Prep-TLC (DCM/MeOH=10/1) to afford the title compound (8.00 mg, 16.20 μmol, 34.71% yield, 89% purity) as a white solid.
LCMS: 440 [M+1].

Step 2. 8-[(3,3-difluoropyrrolidin-1-yl)methyl]-10-methyl-2,3,4,7,8,9-hexahydro-1H-pyrido[2,3]pyrazolo[2,4-b][1,4]diazepin-11-one A mixture of tert-butyl8-[(3,3-difluoropyrrolidin-1-yl)methyl]-10-methyl-11-oxo-1,3,4,7,8,9-hexahydropyrido[2,3]pyrazolo[2,4-b][1,4]diazepine-2-carboxylate (8.00 mg, 18.20 μmol, 1.00 eq) in DCM (2.00 mL) was added TFA (821.32 mg, 7.20 mmol, 533.32 µL, 395.73 eq), and then the mixture was stirred at 20° C. for 1 hour. TLC showed the starting material was consumed completely, and a new spot formed. The mixture was concentrated in vacuum to afford the title compound (8.25 mg, 18.20 µmol, 100.00% yield, TFA) as a yellow oil, which was used directly for next step.

Step 3. N-(3-chloro-4-fluorophenyl)-8-((3,3-difluoropyrrolidin-1-yl)methyl)-10-methyl-11-oxo-1,3,4,7,8,9,10,11-octahydro-2H-pyrido[4',3':3,4]pyrazolo[1,5-a][1,4]diazepine-2-carboxamide A mixture of 8-[(3,3-difluoropyrrolidin-1-yl)methyl]-10-methyl-2,3,4,7,8,9-hexahydro-1H-pyrido[2,3]pyrazolo[2,4-b][1,4]diazepin-11-one (8.25 mg, 18.20 µmol, 1.00 eq, TFA), phenyl N-(3-chloro-4-fluoro-phenyl)carbamate (5.32 mg, 20.01 µmol, 1.10 eq), TEA (3.68 mg, 36.39 mol, 5.04 µL, 2.00 eq) in DCM (3.00 mL) was degassed and purged with $N_2$ for 3 times, and then the mixture was stirred at 20° C. for 16 hours under $N_2$ atmosphere. LCMS showed the starting material was consumed completely, and the desired product was major. The mixture was poured into water (10 mL) and extracted with DCM (5 mL*2). The combined organic phase was washed with brine (10 mL), dried with anhydrous $Na_2SO_4$, filtered and concentrated in vacuum. The residue was purified by Prep-HPLC (HCl) to afford the title compound (8.50 mg, 16.47 µmol, 90.49% yield, 99% purity) as a light yellow solid. LCMS: 511/513 [M+1]. $^1$H NMR (400 MHz, METHANOL-$d_4$) δ=7.58 (dd, J=2.6, 6.7 Hz, 1H), 7.31-7.25 (m, 1H), 7.14 (s, 1H), 4.68 (d, J=3.0 Hz, 2H), 4.56-4.47 (m, 1H), 4.36-4.27 (m, 1H), 4.04-3.53 (m, 7H), 3.35 (br s, 3H), 3.19 (d, J=1.6 Hz, 3H), 3.09-2.97 (m, 1H), 2.82 (s, 4H).

Compound 067: N-(3-cyano-4-fluorophenyl)-8-((3,3-difluoropyrrolidin-1-yl)methyl)-10-methyl-11-oxo-1,3,4,7,8,9,10,11-octahydro-2H-pyrido[4',3':3,4]pyrazolo[1,5-a][1,4]diazepine-2-carboxamide

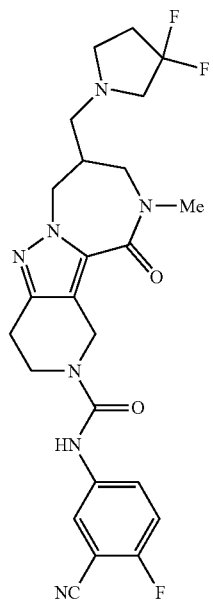 [SMILES: CN1CC(CN2CCC(F)(F)C2)Cn2nc3c(c2C1=O)CN(C(=O)Nc1ccc(F)c(C#N)c1)CC3]

A mixture of 8-[(3,3-difluoropyrrolidin-1-yl)methyl]-10-methyl-2,3,4,7,8,9-hexahydro-1H-pyrido[2,3]pyrazolo[2,4-b][1,4]diazepin-11-one (Compound 066, product from Step 2, 62.00 mg, 136.74 µmol, 1.00 eq, TFA), $Et_3N$ (69.18 mg, 683.70 µmol, 94.77 µL, 5.00 eq) and phenyl N-(3-cyano-4-fluoro-phenyl)carbamate (42.04 mg, 164.09 µmol, 1.20 eq) in DCM (6.00 mL) was stirred at 30° C. for 2 h. LCMS indicated the starting material was consumed completely and major desired product. The mixture was concentrated in vacuo, which was purified by prep-HPLC (FA) to afford (43.00 mg, 81.46 µmol, 59.57% yield, 95% purity) as yellow solid. LCMS: 502[M+1]. $^1$H NMR (400 MHz, CDCl$_3$) δ 7.78 (m, 1H), 7.60 (m, 1H), 7.13 (t, J=8.74 Hz, 1H), 6.93 (s, 1H), 4.68 (s, 2H), 4.41 (m, 1H), 4.13 (d, J=5.87 Hz, 1H), 3.87 (m, 2H), 3.46 (m, 1H), 3.26-3.37 (m, 1H), 3.18 (s, 3H), 2.93 (m, 2H), 2.73-2.87 (m, 4H), 2.56-2.66 (m, 1H), 2.47-2.55 (m, 2H), 2.30 (m, 2H).

Compound 068: 8-((3,3-difluoropyrrolidin-1-yl)methyl)-N-(4-fluoro-3-(trifluoromethyl)phenyl)-10-methyl-11-oxo-1,3,4,7,8,9,10,11-octahydro-2H-pyrido[4',3':3,4]pyrazolo[1,5-a][1,4] diazepine-2-carboxamide

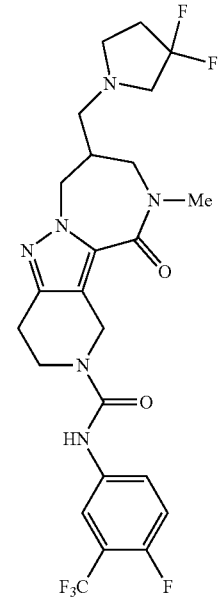 [SMILES: CN1CC(CN2CCC(F)(F)C2)Cn2nc3c(c2C1=O)CN(C(=O)Nc1ccc(F)c(C(F)(F)F)c1)CC3]

A mixture of 8-[(3,3-difluoropyrrolidin-1-yl)methyl]-10-methyl-2,3,4,7,8,9-hexahydro-1H-pyrido[2,3]pyrazolo[2,4-b][1,4]diazepin-11-one (Compound 066, product from Step 2, 62.00 mg, 136.74 µmol, 1.00 eq, TFA), $Et_3N$ (69.18 mg, 683.70 µmol, 94.77 µL, 5.00 eq) and phenyl N-[4-fluoro-3-(trifluoromethyl)phenyl]carbamate (49.10 mg, 164.09 µmol, 1.20 eq) in DCM (6.00 mL) was stirred at 30° C. for 2 h. LCMS indicated the starting material was consumed completely and major desired product. The mixture was concentrated in vacuo, which was purified by prep-HPLC (FA) to afford the title compound (42.00 mg, 76.37 µmol, 55.85% yield, 99% purity) as white solid. LCMS: 545 [M+1$^1$H NMR (400 MHz, CDCl$_3$) δ 7.70 (m, 1H), 7.57-7.64 (m, 1H), 7.11-7.16 (m, 1H), 6.83 (s, 1H), 4.71 (s, 2H), 4.42 (m, 1H), 4.13 (m, 1H), 3.89 (m, 2H), 3.42-3.54 (m, 1H), 3.27-3.39 (m, 1H), 3.19 (s, 3H), 2.95 (m, 2H), 2.86 (m, 4H), 2.58-2.69 (m, 1H), 2.49-2.56 (m, 2H), 2.32 (m, 2H).

Compound 069: N-(3-chloro-4-fluorophenyl)-10-methyl-11-oxo-8-(pyrrolidin-1-ylmethyl)-1,3,4,7,8,9,10,11-octahydro-2H-pyrido[4',3':3,4]pyrazolo[1,5-a][1,4]diazepine-2-carboxamide

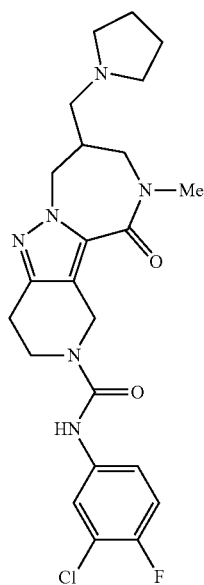 [SMILES: CN1CC(CN2CCCC2)Cn2nc3c(c2C1=O)CN(C(=O)Nc1ccc(F)c(Cl)c1)CC3]

Step 1. tert-butyl 10-methyl-11-oxo-8-(pyrrolidin-1-ylmethyl)-1,3,4,7,8,9-hexahydropyrido[2,3]pyrazolo[24-b][14]diazepine-2-carboxylate To a solution of tert-butyl 10-methyl-8-(methylsulfonyloxymethyl)-11-oxo-1,3,4,7,8,9-hexahydropyrido[2,3]pyrazolo[2,4-b][1,4]diazepine-2-carboxylate (Compound 064, product from Step 2, 150.00 mg, 350.06 µmol, 1.00 eq) in DMSO (3.00 mL) was added pyrrolidine (248.96 mg, 3.50 mmol, 292.89 µL, 10.00 eq), the mixture was stirred at 88° C. for 16 h. The reaction mixture was diluted with brine (40 mL) and extracted with EtOAc (30 mL*2). The combined organic was washed with H$_2$O (60 mL*3), dried over Na$_2$SO$_4$, filtered and concentrated under reduced pressure. The residue was purified by prep-TLC (DCM:MeOH=10:1) to afford the title compound (91.00 mg, 221.01 µmol, 63.13% yield, 98% purity) as yellow oil, which was used directly for the next step.

LCMS: 404 [M+1].

Step 2. 10-methyl-8-(pyrrolidin-1-ylmethyl)-2,3,4,7,8,9-hexahydro-1H-pyrido[2,3]pyrazolo[2,4-b][1,4]diazepin-11-one To a solution of tert-butyl 10-methyl-1-oxo-8-(pyrrolidin-1-ylmethyl)-1,3,4,7,8,9-hexahydropyrido[2,3]pyrazolo[2,4-b][1,4]diazepine-2-carboxylate (91.00 mg, 225.52 µmol, 1.00 eq) in DCM (2.00 mL) was added TFA (3.96 g, 34.76 mmol, 2.57 mL, 154.14 eq), the mixture was stirred at 25° C. for 1 h. The mixture was directly evaporated to afford the title compound (94.14 mg, 225.53 µmol, 100.00% yield, TFA) as yellow oil, which was used directly for the next step.

LCMS: 304 [M+1].

Step 3. N-(3-chloro-4-fluorophenyl)-10-methyl-11-oxo-8-(pyrrolidin-1-ylmethyl)-1,3,4,7,8,9,10,11-octahydro-2H-pyrido[4',3':3,4]pyrazolo[1,5-a][1,4]diazepine-2-carboxamide To a solution of 10-methyl-8-(pyrrolidin-1-ylmethyl)-2,3,4,7,8,9-hexahydro-1H-pyrido[2,3]pyrazolo[2,4-b][1,4]diazepin-11-one (94.14 mg, 225.53 µmol, 1.00 eq, TFA) and Et$_3$N (114.11 mg, 1.13 mmol, 156.31 µL, 5.00 eq) in DCM (3.00 mL) was added phenyl N-(3-chloro-4-fluoro-phenyl) carbamate (59.92 mg, 225.53 µmol, 1.00 eq), the mixture was stirred at 25° C. for 16 h. The mixture was concentrated under reduced pressure. The residue was purified by prep-HPLC(Base) to afford the title compound (61.00 mg, 127.15 µmol, 56.38% yield, 99% purity) as white solid. LCMS: 475/477 [M+1]. $^1$H NMR (400 MHz, CDCl$_3$) δ 7.58-7.61 (m, 1H), 7.17-7.19 (m, 1H), 7.03-7.07 (m, 1H), 6.61 (s, 1H), 4.67 (s, 2H), 4.39-4.44 (m, 1H), 4.0-4.2 (m, 1H), 3.84-3.87 (m, 2H), 3.36-3.45 (m, 1H), 3.34-3.35 (m, 1H), 3.17 (s, 3H), 2.82-2.85 (m, 2H), 2.65-2.67 (m, 1H), 2.48-2.55 (m, 6H), 1.79 (m, 4H).

Compound 070: 8-(aminomethyl)-N-(3-chloro-4-fluorophenyl)-10-methyl-11-oxo-1,3,4,7,8,9,10,11-octahydro-2H-pyrido[4',3':3,4]pyrazolo[1,5-a][1,4]diazepine-2-carboxamide

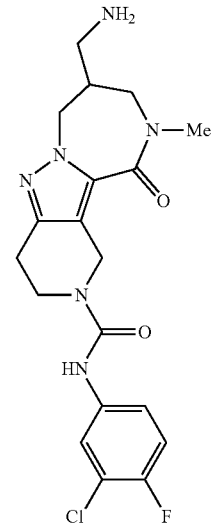 [SMILES: CN1CC(CN)Cn2nc3c(c2C1=O)CN(C(=O)Nc1ccc(F)c(Cl)c1)CC3]

Step 1. 8-(azidomethyl)-N-(3-chloro-4-fluoro-phenyl)-10-methyl-11-oxo-1,3,4,7,8,9-hexahydropyrido[2,3]pyrazolo[2,4-b][1,4]diazepine-2-carboxamide A mixture of [2-[(3-chloro-4-fluoro-phenyl)carbamoyl]-10-methyl-11-oxo-1,3,4,7,8,9-hexahydropyrido[2,3]pyrazolo[2,4-b][1,4]diazepin-8-yl]methylmethanesulfonate (80.00 mg, 160.02 µmol, 1.00 eq) in DMF (5.00 mL) was added NaN₃ (20.81 mg, 320.04 µmol, 11.25 µL, 2.00 eq) at 0° C. under N₂, and then the mixture was stirred at 50° C. for 16 hr under N₂ atmosphere. LCMS showed starting material/desired product=1/8. Then NaN₃ (20.81 mg, 320.04 µmol, 11.25 µL, 2.00 eq) was added to the mixture at 0° C. under N₂, and the mixture was stirred at 50° C. for another 16 hr. The mixture was diluted with EtOAc(20 mL) and washed with brine(20 mL*3). The organic phase was dried over Na₂SO₄, filtered and concentrated in vacuum to afford the title compound (50.00 mg, 111.89 µmol, 69.92% yield) as a yellow oil, which was used directly for next step. LCMS: 447 [M+1].

Step 3. 8-(aminomethyl)-N-(3-chloro-4-fluorophenyl)-10-methyl-11-oxo-1,3,4,7,8,9,10,11-octahydro-2H-pyrido[4',3':3,4]pyrazolo[1,5-a][1,4]diazepine-2-carboxamide A mixture of 8-(azidomethyl)-N-(3-chloro-4-fluoro-phenyl)-10-methyl-11-oxo-1,3,4,7,8,9-hexahydropyrido[2,3]pyrazolo[2,4-b][1,4]diazepine-2-carboxamide (40.00 mg, 89.51 µmol, 1.00 eq), NH₄Cl (14.36 mg, 268.53 µmol, 9.39 µL, 3.00 eq) and Zn (11.71 mg, 179.02 µmol, 2.00 eq) in EtOH (5.00 mL) and H₂O (500.00 uL) was degassed and purged with N₂ for 3 times, and then the mixture was stirred at 30° C. for 16 hour under N₂ atmosphere. LCMS showed the starting material was consumed completely, desired product was major. The mixture was filtered and the filtrate was concentrated in vacuo. The residue was purified by Prep-HPLC (FA) to afford the title compound (32.00 mg, 74.51 µmol, 83.24% yield, 98% purity) as a white solid. LCMS: 421 [M+1]. ¹H NMR (400 MHz, CDCl₃) δ 7.57-7.62 (m, 1H), 7.17-7.23 (m, 1H), 7.05 (s, 1H), 6.60-6.64 (m, 1H), 4.67 (d, J=2.51 Hz, 2H), 4.37-4.47 (m, 1H), 4.13-4.25 (m, 1H), 3.86 (d, J=6.90 Hz, 2H), 3.44 (d, J=5.40 Hz, 1H), 3.38 (d, J=7.53 Hz, 1H), 3.19 (s, 3H), 2.83 (d, J=5.65 Hz, 4H), 2.43-2.57 (m, 1H).

Compound 071: (R)—N-(2-bromo-5-chloro-4-fluorophenyl)-10-(2,2-difluoroethyl)-3-methyl-11-oxo-1,3,4,7,8,9,10,11-octahydro-2H-pyrido[4',3':3,4]pyrazolo[1,5-a][1,4]diazepine-2-carboxamide The title compound was prepared in a manner analogous to Compound 072, using phenyl (2-bromo-5-chloro-4-fluorophenyl)carbamate in Step 3. LCMS [M+1]: 534/536. ¹H NMR (400 MHz, CDCl₃) δ=8.32 (d, J=7.5 Hz, 1H), 7.35 (d, J=8.0 Hz, 1H), 6.93-6.98 (m, 1H), 5.88-6.24 (m, 1H), 5.00-5.09 (m, 1H), 4.91 (s, 1H), 4.35-4.53 (m, 3H), 3.79-4.07 (m, 2H), 3.59 (s, 2H), 3.00-3.09 (m, 1H), 2.66-2.75 (m, 1H), 2.36 (s, 2H), 1.23 (d, J=6.9 Hz, 3H).

Compound 072: (3R)—N-(3-chloro-4-fluorophenyl)-10-(2,2-difluoroethyl)-3-methyl-11-oxo-1,3,4,7,8,9,10,11-octahydro-2H-pyrido[4',3':3,4]pyrazolo[1,5-a][1,4]diazepine-2-carboxamide

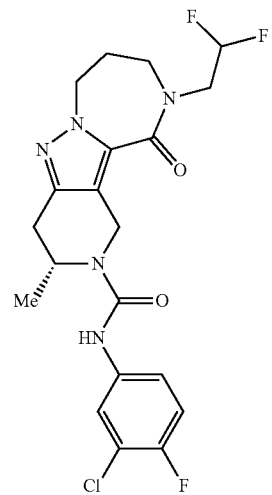 [SMILES: C[C@@H]1Cc2nn3c(c2CN1C(=O)Nc1ccc(F)c(Cl)c1)C(=O)N(CC(F)F)CCC3]

Step 1. tert-butyl (3R)-10-(2,2-difluoroethyl)-3-methyl-11-oxo-1,3,4,7,8,9-hexahydropyrido[2,3]pyrazolo[2,4-b][1,4]diazepine-2-carboxylate To a solution of tert-butyl (3R)-3-methyl-11-oxo-3,4,7,8,9,10-hexahydro-1H-pyrido[2,3]pyrazolo[2,4-b][1,4]diazepine-2-carboxylate (700.00 mg, 2.18 mmol, 1.00 eq) in DMF (7.00 mL) was added NaH (261.60 mg, 6.54 mmol, 60% purity, 3.00 eq) at −10° C. The mixture was stirred at −10° C. for 30 min. Then a solution of 2,2-difluoroethyl trifluoromethanesulfonate (1.40 g, 6.54 mmol, 3.00 eq) in DMF (800.00 uL) was added dropwise at −10° C. The mixture was stirred at 0° C. for 1 hr. TLC (PE:EtOAc=1:1) showed one main spot appeared. The mixture was added into ice-water (50 mL) and extracted with EtOAc (50 mL*3). The combined organic layer was washed with H₂O (50 mL*3), dried over Na₂SO₄, filtrated. The filtrate was concentrated in vacuum. The residue was purified by column chromatography (PE:EtOAc=30%~50%) to afford the title compound (800.00 mg, 2.08 mmol, 95.41% yield) as colorless oil.

Step 2. (3R)-10-(2,2-difluoroethyl)-3-methyl-2,3,4,7,8,9-hexahydro-1H-pyrido[2,3]pyrazolo[2,4-b][1,4]diazepin-11-one To a solution of tert-butyl (3R)-10-(2,2-difluoroethyl)-3-methyl-11-oxo-1,3,4,7,8,9-hexahydropyrido[2,3]pyrazolo[2,4-b][1,4]diazepine-2-carboxylate (350.00 mg, 910.46 µmol, 1.00 eq) in DCM (5.00 mL) was added TFA (7.70 g, 67.53 mmol, 5.00 mL, 74.17 eq). The mixture was stirred at 20° C. for 1 hr. TLC (PE:EtOAc=1:1) showed the starting material consumed. The mixture was concentrated in vacuum to afford the title compound (380.00 mg, crude, TFA) as brown oil.

Step 3. (3R)—N-(3-chloro-4-fluorophenyl)-10-(2,2-difluoroethyl)-3-methyl-11-oxo-1,3,4,7,8,9,10,11-octahydro-2H-pyrido[4',3':3,4]pyrazolo[1,5-a][1,4]diazepine-2-carboxamide To a solution of (3R)-10-(2,2-difluoroethyl)-3-methyl-2,3,4,7,8,9-hexahydro-1H-pyrido[2,3]pyrazolo[2,4-b][1,4]diazepin-11-one (55.00 mg, 138.08 µmol, 1.00 eq, TFA) and Et₃N (69.86 mg, 690.40 µmol, 95.70 µL, 5.00 eq) in DCM (2.00 mL) was added phenyl N-(3-chloro-4-fluoro-phenyl) carbamate (36.68 mg, 138.08 µmol, 1.00 eq). The mixture was stirred at 25° C. for 16 h. The mixture was directly evaporated. The residue was purified by prep-HPLC (FA) to afford the title compound (31.70 mg, 69.33 µmol, 50.21% yield, 99.7% purity) as white solid. LCMS [M+1]: 456
Compounds 073, 074, 075, 076, 077, 078, and 071 were prepared in a manner analogous to Compound 072.
073
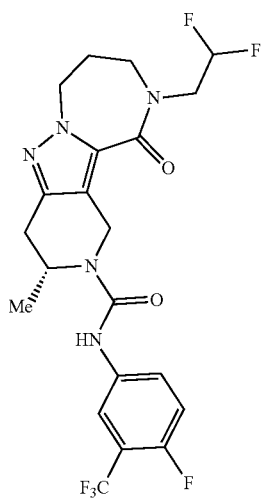
074
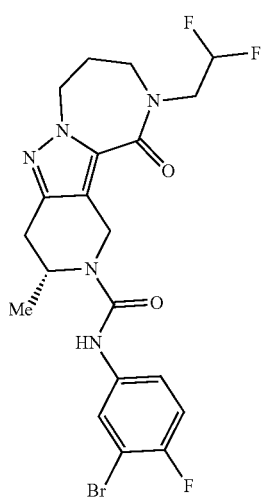
075
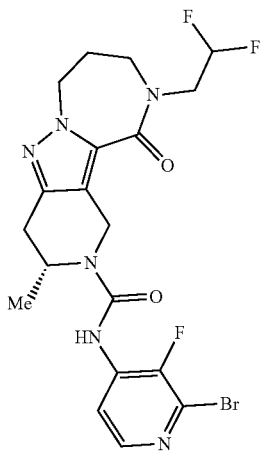
076
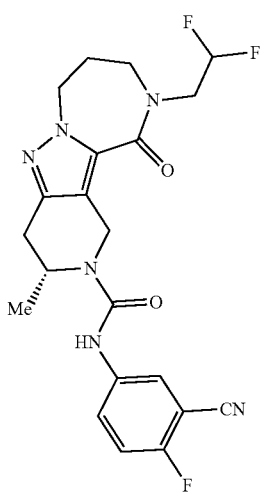
077
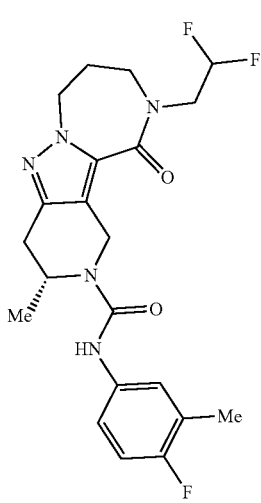

-continued

078

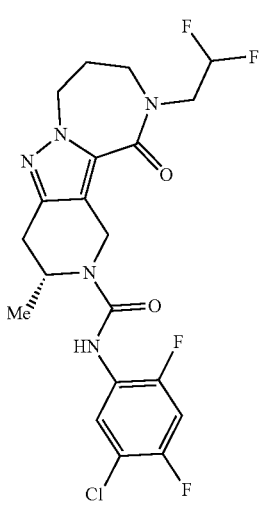

071

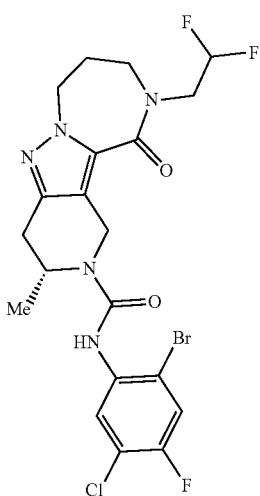

Compound 073: (R)-10-(2,2-difluoroethyl)-N-(4-fluoro-3-(trifluoromethyl)phenyl)-3-methyl-11-oxo-1,3,4,7,8,9,10,11-octahydro-2H-pyrido[4',3':3,4]pyrazolo[1,5-a][1,4]diazepine-2-carboxamide The title compound was prepared in a manner analogous to Compound 072, using phenyl (4-fluoro-3-(trifluoromethyl)phenyl)carbamate in Step 3. LCMS [M+1]:489. $^1$H NMR (400 MHz, CDCl$_3$) δ=7.65-7.71 (m, 1H), 7.56-7.63 (m, 1H), 7.13 (s, 1H), 6.61 (s, 1H), 6.05 (s, 1H), 5.13 (m, 1H), 4.84 (m, 1H), 4.38-4.51 (m, 3H), 3.81-4.07 (m, 2H), 3.55-3.68 (m, 2H), 3.03 (m, 1H), 2.68 (m, 1H), 2.37 (m, 2H), 1.19 (d, J=6.8 Hz, 3H).

Compound 074: (R)—N-(3-bromo-4-fluorophenyl)-10-(2,2-difluoroethyl)-3-methyl-11-oxo-1,3,4,7,8,9,10,11-octahydro-2H-pyrido[4',3':3,4]pyrazolo[1,5-a][1,4]diazepine-2-carboxamide The title compound was prepared in a manner analogous to Compound 072, using phenyl (3-bromo-4-fluorophenyl)carbamate in Step 3. LCMS [M+1]: 500/502. $^1$H NMR (400 MHz, CDCl$_3$) δ=7.69-7.74 (m, 1H), 7.27-7.30 (m, 1H), 7.04 (br d, J=2.4 Hz, 1H), 6.46-6.58 (m, 1H), 5.86-6.24 (m, 1H), 5.05-5.18 (m, 1H), 4.82 (m, 1H), 4.35-4.52 (m, 3H), 3.77-4.08 (m, 2H), 3.59-3.61 (m, 2H), 2.93-3.09 (m, 1H), 2.69 (s, 1H), 2.36 (m, 2H), 1.18 (dd, J=2.2, 6.8 Hz, 3H).

Compound 075: (R)—N-(2-bromo-3-fluoropyridin-4-yl)-10-(2,2-difluoroethyl)-3-methyl-1-oxo-1,3,4,7,8,9,10,11-octahydro-2H-pyrido[4',3':3,4]pyrazolo[1,5-a][1,4]diazepine-2-carboxamide The title compound was prepared in a manner analogous to Compound 072, using phenyl (2-bromo-3-fluoropyridin-4-yl)carbamate in Step 3. LCMS [M+1]: 501. $^1$H NMR (400 MHz, CDCl$_3$) δ=8.14-8.18 (m, 1H), 8.06 (d, J=5.5 Hz, 1H), 6.96-7.07 (m, 1H), 5.87-6.23 (m, 1H), 5.00-5.10 (m, 1H), 4.85-4.96 (m, 1H), 4.35-4.56 (m, 3H), 3.77-4.09 (m, 2H), 3.58-3.63 (m, 2H), 2.99-3.10 (m, 1H), 2.66-2.77 (m, 1H), 2.31-2.44 (m, 2H), 1.23 (d, J=6.9 Hz, 3H).

Compound 076: (R)—N-(3-cyano-4-fluorophenyl)-10-(2,2-difluoroethyl)-3-methyl-11-oxo-1,3,4,7,8,9,10,11-octahydro-2H-pyrido[4',3':3,4]pyrazolo[1,5-a][1,4]diazepine-2-carboxamide The title compound was prepared in a manner analogous to Compound 072, using phenyl (3-cyano-4-fluorophenyl)carbamate in Step 3. LCMS [M+1]: 446. $^1$H NMR (400 MHz, CDCl$_3$) δ=7.78 (s, 1H), 7.58-7.65 (m, 1H), 7.13 (s, 1H), 6.79-6.89 (m, 1H), 5.87-6.24 (m, 1H), 5.07-5.18 (m, 1H), 4.84-4.92 (m, 1H), 4.39-4.51 (m, 3H), 3.93 (br s, 2H), 3.57-3.68 (m, 2H), 2.96-3.08 (m, 1H), 2.66-2.77 (m, 1H), 2.32-2.44 (m, 2H), 1.19 (d, J=6.9 Hz, 3H).

Compound 077: (R)-10-(2,2-difluoroethyl)-N-(4-fluoro-3-methylphenyl)-3-methyl-11-oxo-1,3,4,7,8,9,10,11-octahydro-2H-pyrido[4',3':3,4]pyrazolo[1,5-a][1,4]diazepine-2-carboxamide The title compound was prepared in a manner analogous to Compound 072, using phenyl (4-fluoro-3-methylphenyl)carbamate in Step 3. LCMS [M+1]: 435. $^1$H NMR (400 MHz, CDCl$_3$) δ=7.24-7.27 (m, 1H), 7.08-7.16 (m, 1H), 6.88-6.97 (m, 1H), 6.46 (s, 1H), 6.05 (s, 1H), 5.12 (s, 1H), 4.83-4.89 (m, 1H), 4.35-4.50 (m, 3H), 3.80-4.05 (m, 2H), 3.52-3.69 (m, 2H), 2.98-3.07 (m, 1H), 2.62-2.70 (m, 1H), 2.36 (s, 2H), 2.25 (d, J=1.5 Hz, 3H), 1.18 (d, J=6.9 Hz, 3H).

Compound 078: (R)—N-(5-chloro-2,4-difluorophenyl)-10-(2,2-difluoroethyl)-3-methyl-11-oxo-1,3,4,7,8,9,10,11-octahydro-2H-pyrido[4',3':3,4]pyrazolo[1,5-a][1,4]diazepine-2-carboxamide The title compound was prepared in a manner analogous to Compound 072, using phenyl (5-chloro-2,4-difluorophenyl)carbamate in Step 3. LCMS [M+1]: 474. $^1$H NMR (400 MHz, CDCl$_3$) δ=8.19 (s, 1H), 6.95 (dd, J=8.5, 10.6 Hz, 1H), 6.53-6.59 (m, 1H), 6.05 (s, 1H), 5.02-5.13 (m, 1H), 4.80-4.91 (m, 1H), 4.44 (s, 3H), 3.78-4.08 (m, 2H), 3.49-3.69 (m, 2H), 2.99-3.09 (m, 1H), 2.71 (s, 1H), 2.36 (br s, 2H), 1.21 (d, J=6.8 Hz, 3H).

Compound 079_D1: (3R,8R*)—N-(3-chloro-4-fluorophenyl)-8-fluoro-3,8,10-trimethyl-11-oxo-1,3,4,7,8,9,10,11-octahydro-2H-pyrido[4',3':3,4]pyrazolo[1,5-a][1,4]diazepine-2-carboxamide

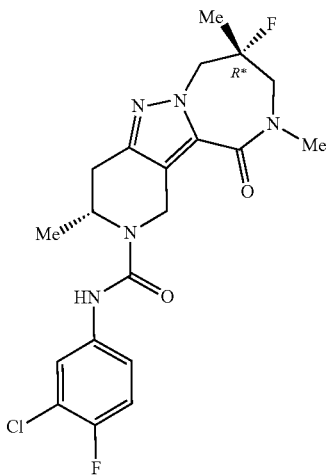 [SMILES: C[C@@H]1Cc2nn3c(c2CN1C(=O)Nc1ccc(F)c(Cl)c1)C(=O)N(C)C[C@@](C)(F)C3]

Step 1. tert-butyl (3R)-8-fluoro-3,8,10-trimethyl-11-oxo-1,3,4,7,8,9,10,11-octahydro-2H-pyrido[4',3':3,4]pyrazolo[1,5-a][1,4]diazepine-2-carboxylate To a solution of tert-butyl (3R)-8-hydroxy-3,8,10-trimethyl-11-oxo-3,4,7,9-tetrahydro-1H-pyrido[2,3]pyrazolo[2,4-b][1,4]diazepine-2-carboxylate (Intermediate 18, 65.00 mg, 178.36 µmol, 1.00 eq) in DCM (5.00 mL) was added BAST (236.76 mg, 1.07 mmol, 234.42 µL, 6.00 eq) at −30° C. under N$_2$, and the mixture was stirred at 20° C. for 2 hours. TLC (PE:EtOAc=1:1) showed that starting material was consumed completely and two main new spots formed. The mixture was diluted with 10 mL and extracted with DCM (15 mL*3). The combined organic phase was dried over anhydrous Na$_2$SO$_4$, filtered and concentrated in vacuo. The combined residue of two batches of reaction was purified by prep-TLC (PE:EtOAc=1:1) to give two diastereomers of the title compound D1: 40.00 mg, 109.16 µmol, 30.60% yield and D2: 35.00 mg, 95.52 µmol, 26.78% yield as white solid.

Step 2. (3R)-8-fluoro-3,8,10-trimethyl-1,2,3,4,7,9-hexahydropyrido[2,3]pyrazolo[2,4-b][1,4]diazepin-11-one_D1

To a solution of tert-butyl (3R)-8-fluoro-3,8,10-trimethyl-11-oxo-1,3,4,7,8,9,10,11-octahydro-2H-pyrido[4',3':3,4]pyrazolo[1,5-a][1,4]diazepine-2-carboxylate_D1 (40.00 mg, 109.16 µmol, 1.00 eq) in DCM (3.00 mL) was added TFA (1.23 g, 10.80 mmol, 799.73 µL, 98.95 eq) at 20° C. with stirring for 1 h. LC-MS showed that reactant starting material was consumed completely and desired product was detected. The mixture was directly evaporated in vacuo to afford the title compound (45.00 mg, crude, TFA) as yellow oil.

The other diastereomer was made by an analogous method.
*Pure but unknown diastereomer D1.

Step 3. (3R,8R*)—N-(3-chloro-4-fluorophenyl)-8-fluoro-3,8,10-trimethyl-11-oxo-1,3,4,7,8,9,10,11-octahydro-2H-pyrido[4',3':3,4]pyrazolo[1,5-a][1,4]diazepine-2-carboxamide To a solution of (3R)-8-fluoro-3,8,10-trimethyl-1,2,3,4,7,9-hexahydropyrido[2,3]pyrazolo[2,4-b][1,4]diazepin-11-one_D1 (50.00 mg, 131.46 µmol, 1.00 eq, TFA) and phenyl N-(3-chloro-4-fluoro-phenyl)carbamate (38.42 mg, 144.61 µmol, 1.10 eq) in DCM (3.00 mL) was added TEA (106.42 mg, 1.05 mmol, 145.78 µL, 8.00 eq) at 20° C. for 16 h. LC-MS indicated that reactant consumed completely and desired product was detected. The reaction mixture was concentrated in vacuo. The resulting residue was purified by prep-HPLC (FA) to afford the title compound (33.00 mg, 75.36 µmol, 57.33% yield, 100% purity) as white solid.

LCMS: 438 [M+1]. $^1$H NMR (400 MHz, CDCl$_3$) δ=7.58 (dd, J=2.69, 6.48 Hz, 1H), 7.14-7.22 (m, 1H), 7.00-7.10 (m, 1H), 6.52 (s, 1H), 5.10 (m, 1H), 4.78 (d, J=15.65 Hz, 1H), 4.35-4.53 (m, 3H), 3.48 (m, 1H), 3.37-3.45 (m, 1H), 3.18-3.26 (m, 3H), 2.94-3.06 (m, 1H), 2.68 (m, 1H), 1.51-1.59 (m, 3H), 1.19 (d, J=6.85 Hz, 3H). 079_D2 was prepared by an analogous method.

Compound 079_D2: (3R,8S*)—N-(3-chloro-4-fluorophenyl)-8-fluoro-3,8,10-trimethyl-11-oxo-1,3,4,7,8,9,10,11-octahydro-2H-pyrido[4',3':3,4]pyrazolo[1,5-a][1,4]diazepine-2-carboxamide

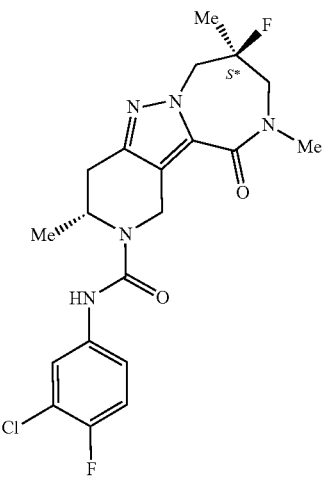 [SMILES: C[C@@H]1Cc2nn3c(c2CN1C(=O)Nc1ccc(F)c(Cl)c1)C(=O)N(C)C[C@](C)(F)C3]

The title compound was prepared in a manner analogous to Compound 079 D1, *Pure but unknown diastereomer D2.
LCMS: 438 [M+1]. $^1$H NMR (400 MHz, CDCl$_3$) δ=7.60 (dd, J=2.63, 6.54 Hz, 1H), 7.17-7.23 (m, 1H), 7.03-7.09 (m, 1H), 6.60 (s, 1H), 5.13 (m, 1H), 4.88 (d, J=15.41 Hz, 1H), 4.34-4.54 (m, 3H), 3.47-3.58 (m, 1H), 3.35-3.46 (m, 1H), 3.22 (s, 3H), 3.03 (m, 1H), 2.66 (m, 1H), 1.55-1.62 (m, 3H), 1.18 (d, J=6.85 Hz, 3H).

249

Compound 080_D1: (3R,8S*)—N-(3-chloro-4-fluorophenyl)-3,8,10-trimethyl-11-oxo-3,4,8,9,10,11-hexahydro-1H-pyrido[4',3':3,4]pyrazolo[1,5-a][1,4]diazepine-2 (7H)-carboxamide

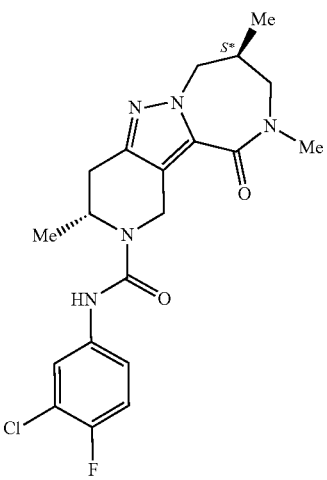 [SMILES: C[C@H]1CN(C)C(=O)c2c3c(nn2C1)C[C@@H](C)N(C(=O)Nc1ccc(F)c(Cl)c1)C3]

Step 1. (3R)-3,8,10-trimethyl-2,3,4,7,8,9-hexahydro-1H-pyrido[2,3]pyrazolo[2,4-b][1,4]diazepin-11-one To a solution of tert-butyl (3R)-3,8,10-trimethyl-11-oxo-1,3,4,7,8,9-hexahydro pyrido[2,3]pyrazolo[2,4-b][1,4]diazepine-2-carboxylate (Intermediate 17, 60.00 mg, 172.20 µmol, 1.00 eq) in DCM (3.00 mL) was added TFA (770.00 mg, 6.75 mmol, 500.00 µL, 39.22 eq) at 20° C. with stirring for 1 h. TLC (PE:EtOAc=0:1) showed that starting material consumed completely and one main spot formed. The mixture was concentrated to afford the title compound (65.00 mg, crude, TFA) as yellow oil.

Step 2. (3R,8S*)—N-(3-chloro-4-fluorophenyl)-3,8,10-trimethyl-11-oxo-3,4,8,9,10,11-hexahydro-1H-pyrido[4',3':3,4]pyrazolo[1,5-a][1,4]diazepine-2 (7H)-carboxamide, *Pure but unknown diastereomer D1

To a solution of (3R)-3,8,10-trimethyl-2,3,4,7,8,9-hexahydro-1H-pyrido[2,3]pyrazolo [2,4-b][1,4]diazepin-11-one (65.00 mg, 179.38 mol, 1.00 eq, TFA) and phenyl N-(3-chloro-4-fluoro-phenyl)carbamate (50.04 mg, 188.35 µmol, 1.05 eq) in DCM (3.00 mL) was added TEA (145.22 mg, 1.44 mmol, 198.93 µL, 8.00 eq) at 20° C. for 16 h. LCMS indicated that reactant 7 was consumed completely and desired product was detected. The residue was directly evaporated. The residue was purified by prep-HPLC (FA), followed by SFC to give two diastereomers: 080_D1 (15.50 mg, 36.92 µmol, 20.58% yield) as white solid and 080_D2 (17.24 mg, 40.24 µmol, 22.43% yield, 98% purity) as white solid.

SFC separation condition: Instrument: SFC 80; Column: AD-10 um; Mobile phase: A for $CO_2$ and B for EtOH (0.1% $NH_3H_2O$); Gradient: B 30%; Flow rate: 60 mL/min; Back pressure: 100bar; Column temperature: 35° C.; Wavelength: 220 nm. LCMS: 420 [M+1]. $^1$H NMR (400 MHz, $CDCl_3$) δ=7.61 (dd, J=2.63, 6.54 Hz, 1H), 7.17-7.23 (m, 1H), 7.02-7.08 (m, 1H), 6.61 (s, 1H), 5.14 (m, 1H), 4.81 (d, J=15.28 Hz, 1H), 4.39-4.49 (m, 2H), 3.98-4.03 (m, 1H), 3.89-3.42 (m, 1H), 3.19 (s, 3H), 3.13-3.16 (m, 1H), 3.02-3.08 (m, 1H), 2.61-2.70 (m, 2H), 1.17 (d, J=6.85 Hz, 3H), 1.12 (d, J=6.72 Hz, 3H).

Compound 080_D2: (3R,8R*)—N-(3-chloro-4-fluorophenyl)-3,8,10-trimethyl-11-oxo-3,4,8,9,10,11-hexahydro-1H-pyrido[4',3':3,4]pyrazolo[1,5-a][1,4]diazepine-2 (7H)-carboxamide

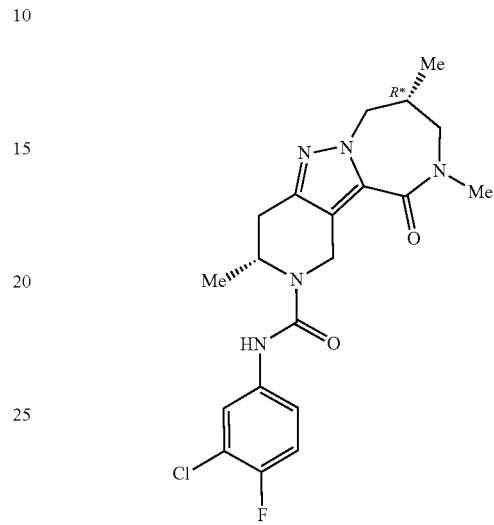

The title compound was prepared in a manner analogous to Compound 080D1, *Pure but unknown diastereomer D2. LCMS: 420 [M+1]. $^1$H NMR (400 MHz, $CDCl_3$) δ=7.61 (dd, J=2.69, 6.60 Hz, 1H), 7.16-7.23 (m, 1H), 7.01-7.08 (m, 1H), 6.59 (s, 1H), 5.14 (m, 1H), 4.81 (d, J=15.41 Hz, 1H), 4.40-4.50 (m, 2H), 3.98 (m, 1H), 3.45-3.47 (m, 1H), 3.20 (s, 3H), 3.13-3.16 (m, 1H), 3.01-3.08 (m, 1H), 2.58-2.69 (m, 2H), 1.17 (dd, J=6.91, 12.78 Hz, 6H).

Compound 081: (3R,8S*)—N-(4-fluoro-3-(trifluoromethyl)phenyl)-8-(hydroxymethyl)-3,10-dimethyl-11-oxo-3,4,8,9,10,11-hexahydro-1H-pyrido[4',3':3,4]pyrazolo[1,5-a][14]diazepine-2 (7H)-carboxamide Step 1. (3R,S*)-8-(hydroxymethyl)-3,10-dimethyl-1,2,3,4,7,8,9,10-octahydro-11H-pyrido[4',3':3,4]pyrazolo[1,5-a][1,4]diazepin-11-one To a solution of tert-butyl (3R)-8-(hydroxymethyl)-3,10-dimethyl-11-oxo-1,3,4,7,8,9-hexahydropyrido[2,3]pyrazolo [2,4-b][1,4]diazepine-2-carboxylate (Intermediate 16, 2.00 g, 4.72 mmol, 1.00 eq) in MeOH (20.00 mL) was added HCl/MeOH (4 M, 10.00 mL, 8.47 eq) at 25° C. with stirring for 3 h. TLC (PE:EtOAc=0:1) showed that reactant tert-butyl (3R)-8-(hydroxymethyl)-3,10-dimethyl-11-oxo-1,3,4,7,8,9-hexahydropyrido[2,3]pyrazolo[2,4-b][1,4]diazepine-2-carboxylate was consumed completely. The mixture was concentrated in vacuo. The residue with 92% purity was resolved by SFC (Analytic condition: AD-3S_4_5_40_3ML Column: Chiralpak AD-3 100×4.6 mm I.D., 3 um Mobile phase: iso-propanol (0.05% DEA) in $C_{02}$ from 5% to 40%. Flow rate: 3 mL/min Wavelength: 220 nm. Separation condition: Instrument: SFC 80; Column: AD-5 um Mobile phase: A for $CO_2$ and B for IPA (0.10% $NH_3H_2O$); Gradient: B 25%; Flow rate: 55 mL/min; Back pressure: 100bar; Column temperature: 35; Wavelength: 220 nm) to give both diastereomers: (3R,8 S*)-8-(hydroxymethyl)-3,10-dimethyl-1,2,3,4,7,8,9,10-octahydro-11H-pyrido[4',3':3,4]pyrazolo[1,5-a][1,4]diazepin-11-one (520 mg) and (3R,8R*)-8-(hydroxymethyl)-3,10-dimethyl-1,2,3,4,7,8,9,10-octahydro-11H-pyrido[4',3':3,4]pyrazolo[1,5-a][1,4]diazepin-11-one (670 mg) as white solid.

Step 2. (3R,8S*)—N-(4-fluoro-3-(trifluoromethyl)phenyl)-8-(hydroxymethyl)-3,10-dimethyl-11-oxo-3,4,8,9,10,11-hexahydro-1H-pyrido[4',3':3,4]pyrazolo[1,5-a][1,4]diazepine-2 (7H)-carboxamide To a solution of (3R,8S*)-8-(hydroxymethyl)-3,10-dimethyl-2,3,4,7,8,9-hexahydro-1H-pyrido[2,3] pyrazolo[2,4-b][1,4]diazepin-11-one (40.00 mg, 151.33 μmol, 1.00 eq) in DCM (3.00 mL) was added phenyl N-[4-fluoro-3-(trifluoromethyl)phenyl] carbamate (54.34 mg, 181.60 μmol, 1.20 eq) and Et$_3$N (76.57 mg, 756.65 μmol, 104.89 μL, 5.00 eq). The mixture was stirred at 25° C. for 16 h. The mixture was concentrated under reduced pressure. The resulting residue was purified by prep-HPLC(FA) to afford (24.10 mg, 50.83 μmol, 33.59% yield, 99% purity) as white solid. *Pure but unknown diastereomer. LCMS: 470 [M+1]. $^1$H NMR (400 MHz, CDCl$_3$) δ 7.70 (m, 1H), 7.55-7.64 (m, 1H), 7.12 (t, J=9.35 Hz, 1H), 6.82 (s, 1H), 5.14-5.17 (m, 1H), 4.84-4.88 (m, 1H), 4.36-4.49 (m, 2H), 4.19-4.23 (m, 1H), 3.65-3.77 (m, 2H), 3.32-3.54 (m, 2H), 3.20 (s, 3H), 3.01-3.05 (m, 1H), 2.61-2.77 (m, 2H), 1.18 (d, J=6.90 Hz, 3H).

Compounds 082, 083, 084, 085, 086, 087, 088, 089, and 090 were prepared in a manner analogous to compound 081 from the corresponding diastereomer.

081

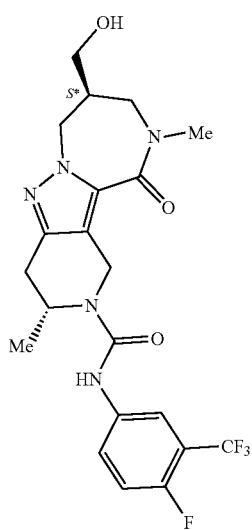

081 D2

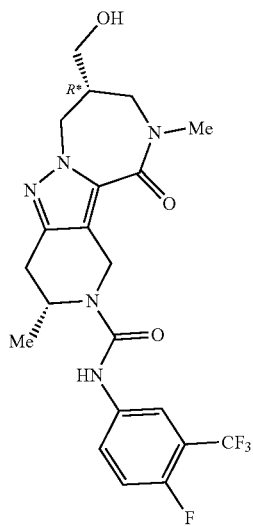

082 D1

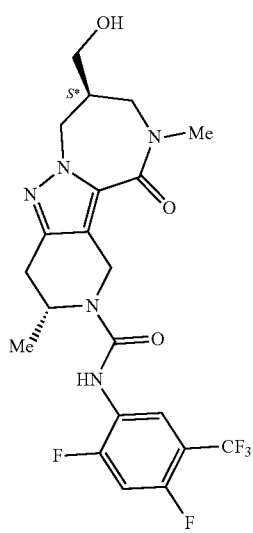

082 D2

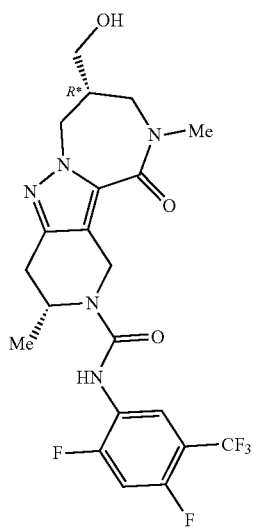

-continued
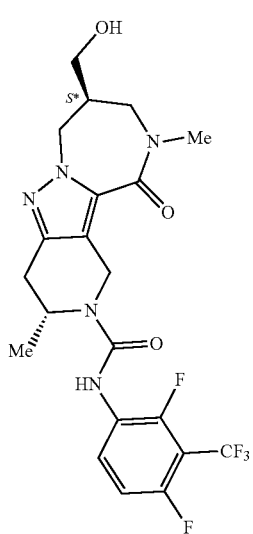
083 D1
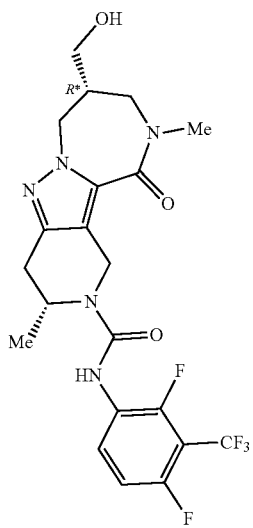
083 D2
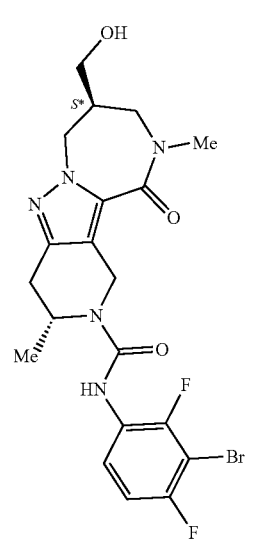
084 D1
-continued
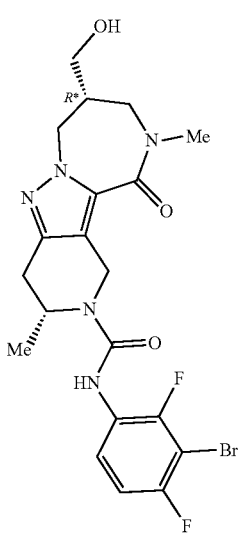
084 D2
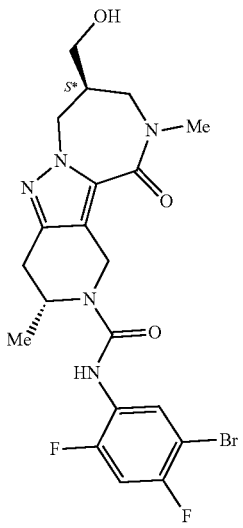
085 D1
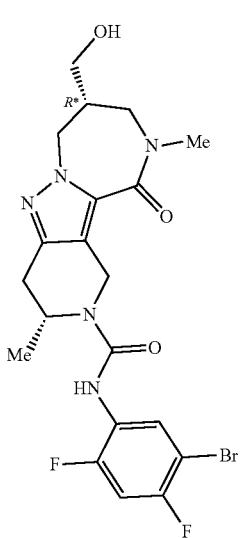
085 D2

255
-continued
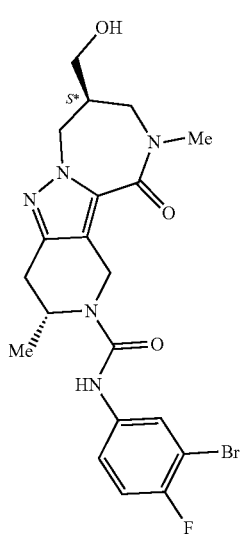
086 D1
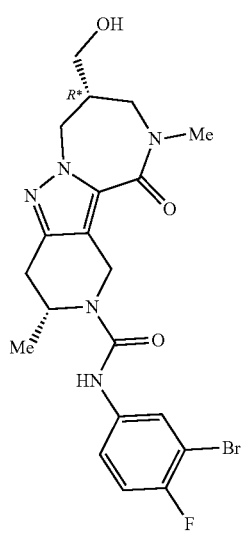
086 D2
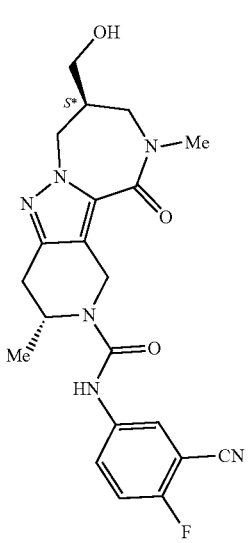
087 D1
256
-continued
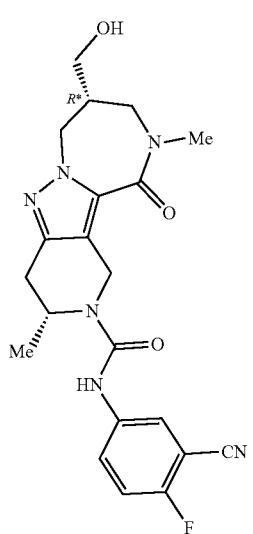
087 D2
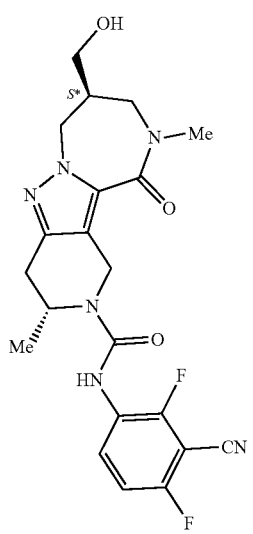
088 D1
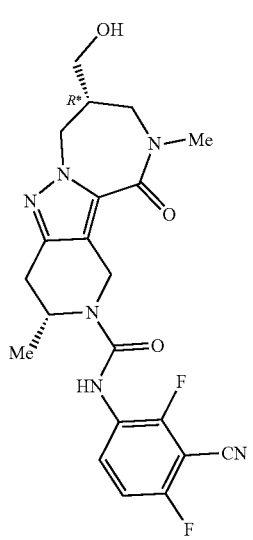
088 D2

-continued

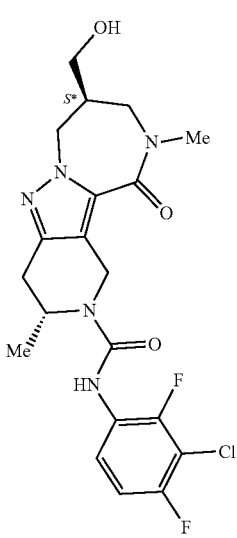
089 D1

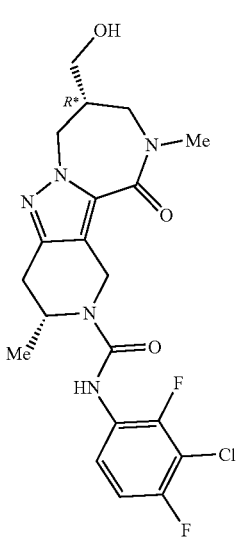
089 D2

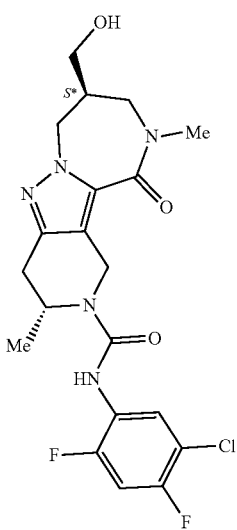
090 D1

-continued

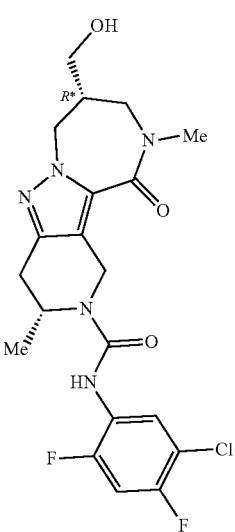
090 D2

Compound 081_D2: (3R,8R*)—N-(4-fluoro-3-(trifluoromethyl)phenyl)-8-(hydroxymethyl)-3,10-dimethyl-11-oxo-3,4,8,9,10,11-hexahydro-1H-pyrido[4',3':3,4]pyrazolo[1,5-a][1,4]diazepine-2 (7H)-carboxamide The title compound was prepared in a manner analogous to Compound 081, *Pure but unknown diastereomer. LCMS: 470 [M+1] ¹H NMR (400 MHz, CDCl₃) δ 7.69-7.10 (m, 1H), 7.59-7.61 (m, 1H), 7.12 (t, J=9.41 Hz, 1H), 6.77 (s, 1H), 5.15 (t, J=6.53 Hz, 1H), 4.80-4.84 (m, 1H), 4.36-4.52 (m, 2H), 4.25-4.27 (m, 1H), 3.64-3.76 (m, 2H), 3.32-3.52 (m, 2H), 3.20 (s, 3H), 3.00-3.04 (m, 1H), 2.61-2.78 (m, 2H), 1.19 (d, J=6.90 Hz, 3H).

Compound 082_D1: (3R,8S*)—N-(2,4-difluoro-5-(trifluoromethyl)phenyl)-8-(hydroxmethyl)-3,10-dimethyl-11-oxo-1,3,4,7,8,9,10,11-octahydro-2H-pyrido[4',3':3,4]pyrazolo[1,5-a][1,4]diazepine-2-carboxamide The title compound was prepared in a manner analogous to Compound 081, *Pure but unknown diastereomer. LCMS:488 [M+1] ¹H NMR (400 MHz, CDCl₃) δ 8.38 (t, J=7.97 Hz, 1H), 6.99 (t, J=10.04 Hz, 1H), 6.66 (br d, J=2.89 Hz, 1H), 5.10-5.30 (m, 1H), 4.84-4.88 (m, 1H), 4.39-4.52 (m, 2H), 4.16-4.20 (m, 1H), 3.67-3.77 (m, 2H), 3.33-3.55 (m, 2H), 3.20 (s, 3H), 3.00-3.04 (m, 1H), 2.63-2.76 (m, 2H), 1.20 (d, J=6.90 Hz, 3H).

Compound 082_D2: (3R,8R*)—N-(2,4-difluoro-5-(trifluoromethyl)phenyl)-8-(hydroxymethyl)-3,10-dimethyl-11-oxo-1,3,4,7,8,9,10,11-octahydro-2H-pyrido[4',3':3,4]pyrazolo[1,5-a][1,4]diazepine-2-carboxamide The title compound was prepared in a manner analogous to Compound 081*Pure but unknown diastereomer. LCMS: 488 [M+1] ¹H NMR (400 MHz, CDCl₃) δ 8.38 (t, J=8.03 Hz, 1H), 6.99 (t, J=10.10 Hz, 1H), 6.63 (s, 1H), 5.08-5.12 (m, 1H), 4.81-4.85 (m, 1H), 4.52 (d, J=15.56 Hz, 1H), 4.22-4.45 (m, 2H), 3.60-3.76 (m, 2H), 3.30-3.50 (m, 2H), 3.20 (s, 3H), 3.00-3.05 (m, 1H), 2.61-2.79 (m, 2H), 1.21 (d, J=6.90 Hz, 3H).

Compound 083_D1: (3R,8S*)—N-(2,4-difluoro-3-(trifluoromethyl)phenyl)-8-(hydroxymethyl)-3,10-dimethyl-11-oxo-1,3,4,7,8,9,10,11-octahydro-2H-pyrido[4',3':3,4]pyrazolo[1,5-a][1,4] diazepine-2-carboxamide The title compound was prepared in a manner analogous to Compound 081*Pure but unknown diastereomer. LCMS: 488 [M+1] $^1$H NMR (400 MHz, CDCl$_3$) δ 8.17-8.23 (m, 1H), 6.98 (t, J=9.16 Hz, 1H), 6.67 (s, 1H), 5.08-5.10 (m, 1H), 4.85-4.89 (m, 1H), 4.39-4.53 (m, 2H), 4.17-4.19 (m, 1H), 3.66-3.78 (m, 2H), 3.32-3.55 (m, 2H), 3.20 (s, 3H), 3.01-3.05 (m, 16.06 Hz, 1H), 2.63-2.76 (m, 2H), 1.20 (d, J=6.90 Hz, 3H).

Compound 083_D2: (3R,8R*)—N-(2,4-difluoro-3-(trifluoromethyl)phenyl)-8-(hydroxymethyl)-3,10-dimethyl-11-oxo-1,3,4,7,8,9,10,11-octahydro-2H-pyrido[4',3':3,4]pyrazolo[1,5-a][1,4] diazepine-2-carboxamide The title compound was prepared in a manner analogous to Compound 081*Pure but unknown diastereomer. LCMS: 488 [M+1] $^1$H NMR (400 MHz, CDCl$_3$) δ 8.19-8.25 (m, 1H), 6.99 (t, J=9.41 Hz, 1H), 6.61 (s, 1H), 5.06-5.09 (m, 1H), 4.83-4.86 (m, 1H), 4.49-4.51 (m, 1H), 4.22-4.44 (m, 2H), 3.62-3.74 (m, 2H), 3.31-3.50 (m, 2H), 3.20 (s, 3H), 3.01-3.05 (m, 1H), 2.64-2.77 (m, 2H), 1.21 (d, J=6.85 Hz, 3H).

Compound 084_D1: (3R,8S*)—N-(3-bromo-2,4-difluorophenyl)-8-(hydroxymethyl)-3,10-dimethyl-11-oxo-1,3,4,7,8,9,10,11-octahydro-2H-pyrido[4',3':3,4]pyrazolo[1,5-a][1,4]diazepine-2-carboxamide The title compound was prepared in a manner analogous to Compound 081*Pure but unknown diastereomer. LCMS: 498/500 [M+1] $^1$H NMR (400 MHz, CDCl$_3$) δ 7.89-7.95 (m, 1H), 6.94 (t, J=7.6 Hz, 1H), 6.58 (s, 1H), 5.08-5.10 (m 1H), 4.85-4.88 (m, 1H), 4.38-4.53 (m, 2H), 4.14-4.18 (m, 1H), 3.66-3.79 (m, 2H), 3.32-3.56 (m, 2H), 3.20 (s, 3H), 3.01-3.05 (m, 1H), 2.61-2.76 (m, 2H), 1.20 (d, J=6.90 Hz, 3H).

Compound 084_D2: (3R,8R*)—N-(3-bromo-2,4-difluorophenyl)-8-(hydroxymethyl)-3,10-dimethyl-11-oxo-1,3,4,7,8,9,10,11-octahydro-2H-pyrido[4',3':3,4]pyrazolo[1,5-a][1,4]diazepine-2-carboxamide The title compound was prepared in a manner analogous to Compound 081, *Pure but unknown diastereomer. LCMS: 498/500 [M+1] $^1$H NMR (400 MHz, CDCl$_3$) δ 7.90-7.96 (m, 1H), 6.91-6.96 (m, 1H), 6.55 (s, 1H), 5.02-5.13 (m, 1H), 4.82-4.86 (m, 1H), 4.49-4.53 (m, 1H), 4.22-4.45 (m, 2H), 3.62-3.74 (m, 2H), 3.30-3.50 (m, 2H), 3.20 (s, 3H), 3.01-3.05 (m, 1H), 2.63-2.77 (m, 2H), 1.21 (d, J=6.90 Hz, 3H).

Compound 085_D1: (3R,8 S*)—N-(5-bromo-2,4-difluorophenyl)-8-(hydroxymethyl)-3,10-dimethyl-11-oxo-1,3,4,7,8,9,10,11-octahydro-2H-pyrido[4',3':3,4]pyrazolo[1,5-a][1,4]diazepine-2-carboxamide The title compound was prepared in a manner analogous to Compound 081,*Pure but unknown diastereomer. LCMS: 498/500 [M+1] $^1$H NMR (400 MHz, CDCl$_3$) δ 8.23-8.39 (m, 1H), 6.93 (t, J=7.97 Hz, 1H), 6.57 (s, 1H), 5.09-5.11 (m 1H), 4.82-4.86 (m, 1H), 4.37-4.52 (m, 2H), 4.17-4.19 (m, 1H), 3.64-3.80 (m, 2H), 3.33-3.54 (m, 2H), 3.20 (s, 3H), 2.98-3.02 (m, 1H), 2.63-2.77 (m, 2H), 1.20 (d, J=6.78 Hz, 3H).

Compound 085_D2: (3R,8R*)—N-(5-bromo-2,4-difluorophenyl)-8-(hydroxymethyl)-3,10-dimethyl-11-oxo-1,3,4,7,8,9,10,11-octahydro-2H-pyrido[4',3':3,4]pyrazolo[1,5-a][1,4]diazepine-2-carboxamide The title compound was prepared in a manner analogous to Compound 081,*Pure but unknown diastereomer. LCMS: 498/500 [M+1] $^1$H NMR (400 MHz, CDCl$_3$) δ 8.25-8.37 (m, 1H), 6.91-6.95 (m, 1H), 6.55 (s, 1H), 5.09-5.11 (m, 1H), 4.79-4.83 (m, 1H), 4.48-4.52 (m, 1H), 4.20-4.44 (m, 2H), 3.63-3.73 (m, 2H), 3.29-3.51 (m, 2H), 3.20 (s, 3H), 3.01-3.05 (m, 1H), 2.62-2.77 (m, 2H), 1.20 (d, J=6.90 Hz, 3H).

Compound 086_D1: (3R,8S*)—N-(3-bromo-4-fluorophenyl)-8-(hydroxymethyl)-3,10-dimethyl-11-oxo-1,3,4,7,8,9,10,11-octahydro-2H-pyrido[4',3':3,4]pyrazolo[1,5-a][1,4]diazepine-2-carboxamide The title compound was prepared in a manner analogous to Compound 081,*Pure but unknown diastereomer. LCMS: 480/482 [M+1] $^1$H NMR (400 MHz, CDCl$_3$) δ 7.73-7.75 (m, 1H), 7.24-7.27 (m, 1H), 6.95-7.09 (m, 1H), 6.65 (s, 1H), 5.06-5.20 (m, 1H), 4.83 (d, J=15.18 Hz, 1H), 4.36-4.48 (m, 2H), 4.20-4.22 (m, 1H), 3.70-3.74 (m, 2H), 3.33-3.54 (m, 2H), 3.20 (s, 3H), 3.00-3.05 (m, 1H), 2.58-2.78 (m, 2H), 1.18 (d, J=6.90 Hz, 3H).

Compound 086 D2: (3R,8R*)—N-(3-bromo-4-fluorophenyl)-8-(hydroxymethyl)-3,10-dimethyl-11-oxo-1,3,4,7,8,9,10,11-octahydro-2H-pyrido[4',3':3,4]pyrazolo[1,5-a][1,4]diazepine-2-carboxamide The title compound was prepared in a manner analogous to Compound 081, *Pure but unknown diastereomer. LCMS: 480/482 [M+1] $^1$H NMR (400 MHz, CDCl$_3$) δ 7.72-7.75 (m, 1H), 7.25-7.26 (m, 1H), 7.04 (t, J=8.53 Hz, 1H), 6.61 (s, 1H), 5.13-5.15 (m, 1H), 4.78-4.81 (m, 1H), 4.37-4.51 (m, 2H), 4.24-4.27 (m, 1H), 3.62-3.75 (m, 2H), 3.30-3.50 (m, 2H), 3.20 (s, 3H), 3.01-3.04 (m, 1H), 2.59-2.79 (m, 2H), 1.18 (d, J=6.78 Hz, 3H).

Compound 087_D1: (3R,8S*)—N-(3-cyano-4-fluorophenyl)-8-(hydroxymethyl)-3,10-dimethyl-11-oxo-1,3,4,7,8,9,10,11-octahydro-2H-pyrido[4',3':3,4]pyrazolo[1,5-a][1,4]diazepine-2-carboxamide The title compound was prepared in a manner analogous to Compound 081, *Pure but unknown diastereomer. LCMS: 427 [M+1] $^1$H NMR (400 MHz, CDCl$_3$) δ 7.79-7.81 (m, 1H), 7.59-7.61 (m, 1H), 7.07-7.17 (m, 1H), 6.93 (s, 1H), 5.07-5.19 (m, 1H), 4.86 (d, J=15.43 Hz, 1H), 4.36-4.49 (m, 2H), 4.19-4.24 (m, 1H), 3.66-3.80 (m, 2H), 3.30-3.55 (m, 2H), 3.20 (s, 3H), 3.01-3.05 (m, 1H), 2.58-2.76 (m, 2H), 1.18 (d, J=6.90 Hz, 3H).

Compound 087_D2: (3R,8R*)—N-(3-cyano-4-fluorophenyl)-8-(hydroxymethyl)-3,10-dimethyl-11-oxo-1,3,4,7,8,9,10,11-octahydro-2H-pyrido[4',3':3,4]pyrazolo[1,5-a][1,4]diazepine-2-carboxamide The title compound was prepared in a manner analogous to Compound 081, *Pure but unknown diastereomer.

LCMS: 427 [M+1] ¹H NMR (400 MHz, CDCl₃) δ 7.78-7.80 (m, 1H), 7.59-7.62 (m, 1H), 7.13 (t, J=8.68 Hz, 1H), 6.88 (s, 1H), 5.13-5.15 (m, 1H), 4.80-4.85 (m, 1H), 4.37-4.53 (m, 2H), 4.22-4.25 (m, 1H), 3.62-3.76 (m, 2H), 3.31-3.53 (m, 2H), 3.20 (s, 3H), 3.00-3.03 (m, 1H), 2.62-2.76 (m, 2H), 1.19 (d, J=6.97 Hz, 3H).

Compound 088_D1: (3R,8S*)—N-(3-cyano-2,4-difluorophenyl)-8-(hydroxymethyl)-3,10-dimethyl-11-oxo-1,3,4,7,8,9,10,11-octahydro-2H-pyrido[4',3':3,4]pyrazolo[1,5-a][1,4]diazepine-2-carboxamide The title compound was prepared in a manner analogous to Compound 081, *Pure but unknown diastereomer. LCMS: 445 [M+1] ¹H NMR (400 MHz, CDCl₃) δ 8.23-8.29 (m, 1H), 7.01 (t, J=7.97 Hz, 1H), 6.69 (s, 1H), 5.08 (m, 1H), 4.86-4.89 (m, 1H), 4.38-4.54 (m, 2H), 4.18-4.20 (m, 1H), 3.65 –0.78 (m, 2H), 3.33-3.55 (m, 2H), 3.20 (s, 3H), 3.01-3.06 (m, 1H), 2.62-2.78 (m, 2H), 1.21 (d, J=6.90 Hz, 3H).

Compound 088_D2: (3R,8R*)—N-(3-cyano-2,4-difluorophenyl)-8-(hydroxymethyl)-3,10-dimethyl-11-oxo-1,3,4,7,8,9,10,11-octahydro-2H-pyrido[4',3':3,4]pyrazolo[1,5-a][1,4]diazepine-2-carboxamide The title compound was prepared in a manner analogous to Compound 081, *Pure but unknown diastereomer. LCMS: 445 [M+1] ¹H NMR (400 MHz, CDCl₃) δ 8.24-8.30 (m, 1H), 6.99-7.27 (m, 1H), 6.63 (s, 1H), 5.07-5.09 (m, 1H), 4.82-4.86 (m, 1H), 4.50-4.54 (m, 1H), 4.20-4.45 (m, 2H), 3.64-3.75 (m, 2H), 3.31-3.52 (m, 2H), 3.20 (s, 3H), 3.01-3.05 (m, 1H), 2.61-2.76 (m, 2H), 1.21 (d, J=6.90 Hz, 3H).

Compound 089_D1: (3R,8S*)—N-(3-chloro-2,4-difluorophenyl)-8-(hydroxymethyl)-3,10-dimethyl-11-oxo-1,3,4,7,8,9,10,11-octahydro-2H-pyrido[4',3':3,4]pyrazolo[1,5-a][1,4]diazepine-2-carboxamide The title compound was prepared in a manner analogous to Compound 081,*Pure but unknown diastereomer. LCMS: 454/456 [M+1] ¹H NMR (400 MHz, CDCl₃) δ 7.83-7.89 (m, 1H), 6.92-6.97 (m, 9.25 Hz, 1H), 6.58 (s, 1H), 5.08-5.10 (m, 1H), 4.85-4.89 (m, 1H), 4.39-4.54 (m, 2H), 4.17-4.19 (m, 1H), 3.64-3.78 (m, 2H), 3.33-3.56 (m, 2H), 3.20 (s, 3H), 3.01-3.05 (m, 1H), 2.61-2.76 (m, 2H), 1.20 (d, J=6.90 Hz, 3H).

Compound 089_D2: (3R,8R*)—N-(3-chloro-2,4-difluorophenyl)-8-(hydroxymethyl)-3,10-dimethyl-11-oxo-1,3,4,7,8,9,10,11-octahydro-2H-pyrido[4',3':3,4]pyrazolo[1,5-a][1,4]diazepine-2-carboxamide The title compound was prepared in a manner analogous to Compound 081, *Pure but unknown diastereomer. LCMS: 454/456 [M+1] ¹H NMR (400 MHz, CDCl₃) δ 7.84-7.90 (m, 1H), 6.92-6.97 (m, 1H), 6.55 (s, 1H), 5.01-5.14 (m, 1H), 4.82-4.86 (m, 1H), 4.49-4.53 (m, 1H), 4.22-4.44 (m, 2H), 3.67-3.69 (m, 2H), 3.30-3.49 (m, 2H), 3.20 (s, 3H), 3.01-3.05 (m, 1H), 2.62-2.76 (m, 2H), 1.21 (d, J=6.85 Hz, 3H).

Compound 090_D1: (3R,8S*)—N-(5-chloro-2,4-difluorophenyl)-8-(hydroxymethyl)-3,10-dimethyl-11-oxo-1,3,4,7,8,9,10,11-octahydro-2H-pyrido[4',3':3,4]pyrazolo[1,5-a][1,4]diazepine-2-carboxamide The title compound was prepared in a manner analogous to Compound 081, *Pure but unknown diastereomer. LCMS: 454/456 [M+1] ¹H NMR (400 MHz, CDCl₃) δ 8.18 (t, J=8.09 Hz, 1H), 6.92-6.97 (m, 1H), 6.58 (s, 1H), 5.08-5.10 (m, 1H), 4.83-4.87 (m, 1H), 4.38-4.54 (m, 2H), 4.17-4.19 (m, 1H), 3.65-3.79 (m, 2H), 3.32-3.57 (m, 2H), 3.20 (s, 3H), 3.01-3.04 (m, 1H), 2.61-2.74 (m, 2H), 1.20 (d, J=6.78 Hz, 3H).

Compound 090_D2: (3R,8R*)—N-(5-chloro-2,4-difluorophenyl)-8-(hydroxymethyl)-3,10-dimethyl-11-oxo-1,3,4,7,8,9,10,11-octahydro-2H-pyrido[4',3':3,4]pyrazolo[1,5-a][1,4]diazepine-2-carboxamide The title compound was prepared in a manner analogous to Compound 081, *Pure but unknown diastereomer. LCMS: 454/456 [M+1] ¹H NMR (400 MHz, CDCl₃) δ 8.16-8.20 (m, 1H), 6.92-6.97 (m, 1H), 6.55 (s, 1H), 5.08-5.12 m, 1H), 4.80-4.84 (m, 1H), 4.48-4.52 (m, 1H), 4.22-4.43 (m, 2H), 3.60-3.75 (m, 2H), 3.30-3.50 (m, 2H), 3.20 (s, 3H), 3.01-3.05 (m, 1H), 2.62-2.77 (m, 2H), 1.20 (d, J=6.90 Hz, 3H).

Compound 091: N-(3-chloro-4-fluorophenyl)-8-(2,2-difluoroethyl)-8-(hydroxmethyl)-10-methyl-11-oxo-1,3,4,7,8,9,10,11-octahydro-2H-pyrido[4',3':3,4]pyrazolo[1,5-a][1,4]diazepine-2-carboxamide

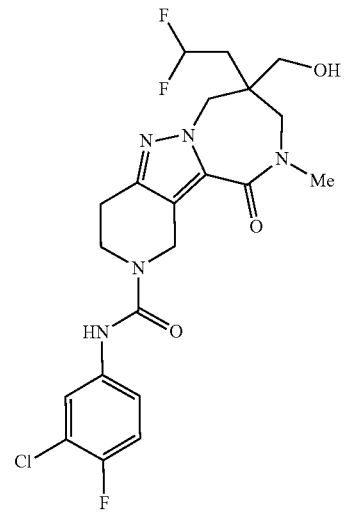 [SMILES: CN1CC(CO)(CC(F)F)Cn2nc3c(c2C1=O)CN(C(=O)Nc1ccc(F)c(Cl)c1)CC3]

Step 1. 2-tert-butyl 8-ethyl 8-(2,2-difluoroethyl)-10-methyl-11-oxo-3,4,7,9-tetrahydro-1H-pyrido[2,3]pyrazolo[2,4-b][1,4]diazepine-2,8-dicarboxylate To a solution of 2-tert-butyl 8-ethyl 10-methyl-11-oxo-1,3,4,7,8,9-hexahydropyrido[2,3]pyrazolo[2,4-b][1,4]diazepine-2,8-dicarboxylate (Intermediate 14, 400.00 mg, 1.02 mmol, 1.00 eq) in THF (8.00 mL) was added LDA (1 M, 3.06 mL, 3.00 eq) at −65° C. under N₂, followed by 2,2-difluoroethyl trifluoromethanesulfonate (1.09 g, 5.10 mmol, 5.00 eq) after 0.5 h, and the mixture was stirred at 25° C. for another 5 h. LCMS indicated ~45% desired product and multiple peaks. The mixture combine with another batch and was diluted with EtOAc (60 mL) and washed with HCl (1 M, 60 mL). The organic phase was dried over Na₂SO₄, filtered and concentrated in vacuo, which was purified by prep-HPLC(FA) to afford the title compound (185.00 mg, 405.28 μmol, 39.73% yield) as yellow solid. LCMS: 457 [M+1].

Step 2. ethyl 8-(2,2-difluoroethyl)-10-methyl-11-oxo-1,2,3,4,7,9-hexahydropyrido[2,3]pyrazolo[2,4-b][1,4]diazepine-8-carboxylate To a solution of 2-tert-butyl 8-ethyl 8-(2,2-difluoroethyl)-10-methyl-11l-oxo-3,4,7,9-tetrahydro-1H-pyrido[2,3]pyrazolo[2,4-b][1,4]diazepine-2,8-dicarboxylate (215.00 mg, 471.00 μmol, 1.00 eq) in DCM (3.00 mL) was added TFA (4.62 g, 40.52 mmol, 3.00 mL, 86.03 eq), and the mixture was stirred at 25° C. under $N_2$ for 1 h. TLC showed no starting material and one major new spot was detected. The mixture was concentrated in vacuo to afford the title compound (221.00 mg, 469.82 μmol, 99.75% yield, TFA) as yellow oil, which was used directly for the next step.

Step 3. ethyl 2-[(3-chloro-4-fluoro-phenyl)carbamoyl]-8-(2,2-difluoroethyl)-10-methyl-11-oxo-3,4,7,9-tetrahydro-1H-pyrido[2,3]pyrazolo[2,4-b][1,4]diazepine-8-carboxylate A mixture of ethyl 8-(2,2-difluoroethyl)-10-methyl-11-oxo-1,2,3,4,7,9-hexahydro pyrido[2,3]pyrazolo[2,4-b][1,4]diazepine-8-carboxylate (221.00 mg, 469.82 μmol, 1.00 eq, TFA), $Et_3N$ (237.71 mg, 2.35 mmol, 325.63 μL, 5.00 eq) and phenyl N-(3-chloro-4-fluoro-phenyl)carbamate (137.30 mg, 516.80 μmol, 1.10 eq) in DCM (10.00 mL) was stirred at 25° C. for 16 h. LCMS indicated the starting material was consumed completely and major desired product. The mixture was diluted with DCM (40 mL) and washed with HCl (1 M, 40 mL). The organic phase was dried over $Na_2SO_4$, filtered and concentrated in vacuo, which was purified by silica gel column to afford the title compound (195.00 mg, 361.99 μmol, 77.05% yield, 98% purity) as yellow solid. LCMS: 528 [M+1].

Step 4. N-(3-chloro-4-fluorophenyl)-8-(2,2-difluoroethyl)-8-(hydroxmethyl)-10-methyl-1-oxo-1,3,4,7,8,9,10,11-octahydro-2H-pyrido[4',3':3,4]pyrazolo[1,5-a][1,4]diazepine-2-carboxamide To a solution of ethyl 2-[(3-chloro-4-fluoro-phenyl)carbamoyl]-8-(2,2-difluoroethyl)-10-methyl-11-oxo-3,4,7,9-tetrahydro-1H-pyrido[2,3]pyrazolo[2,4-b][1,4]diazepine-8-carboxylate (90.00 mg, 170.48 μmol, 1.00 eq) in THF (5.00 mL) was added $LiBH_4$ (11.14 mg, 511.44 μmol, 3.00 eq) at 0° C. and the mixture was stirred at 25° C. for 2 h. LCMS indicated starting material consumed and desired product was detected. The mixture was quenched with $H_2O$ (30 mL) and extracted with EtOAc (30 mL). The organic phase was dried over $Na_2SO_4$, filtered and concentrated in vacuo, which was purified by prep-HPLC(FA) to afford the title compound (50.00 mg, 101.87 μmol, 59.76% yield, 99% purity) as white solid. LCMS: 486 [M+1]. $^1$H NMR (400 MHz, $CDCl_3$) δ 7.58-7.61 (m, 1H), 7.21-7.28 (m, 1H), 7.05-7.09 (t, J=8.8 Hz, 1H), 6.68 (s, 1H), 6.06-6.34 (m, 1H), 4.68-4.73 (m, 2H), 4.24-4.28 (m, 1H), 4.05-4.09 (m, 1H), 3.85-3.88 (m, 2H), 3.67-3.70 (m, 2H), 3.19-3.28 (m, 5H), 2.84-2.87 (m, 2H), 2.05-2.09 (m, 2H).

Compound 092_D1: (3R,8R*)—N-(3-chloro-4-fluorophenyl)-10-(2,2-difluoroethyl)-8-(hydroxymethyl)-3-methyl-11-oxo-1,3,4,7,8,9,10,11-octahydro-2H-pyrido[4',3':3,4]pyrazolo[1,5-a][1,4]diazepine-2-carboxamide

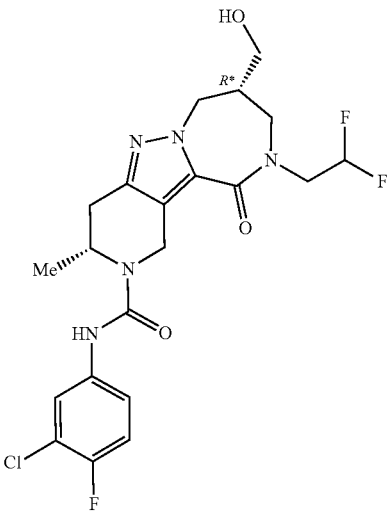 [SMILES: C[C@@H]1Cc2nn3c(c2CN1C(=O)Nc1ccc(F)c(Cl)c1)C(=O)N(CC(F)F)C[C@@H](CO)C3]

Step 1. ethyl (3R)-10-(2,2-difluoroethyl)-3-methyl-11-oxo-2,3,4,7,8,9-hexahydro-1H-pyrido[2,3]pyrazolo[2,4-b][1,4]diazepine-8-carboxylate To a solution of 2-tert-butyl 8-ethyl (3R)-10-(2,2-difluoroethyl)-3-methyl-11-oxo-1,3,4,7,8,9-hexahydropyrido[2,3]pyrazolo[2,4-b][1,4]diazepine-2,8-dicarboxylate (Intermediate 20, 130.00 mg, 284.79 μmol, 1.00 eq) in DCM (3.00 mL) was added TFA (4.62 g, 40.52 mmol, 3.00 mL, 142.28 eq), and the mixture was stirred at 25° C. under $N_2$ for 1 h. TLC showed no starting material and one major new spot was detected. The mixture was concentrated in vacuo to afford the title compound (133.00 mg, 282.74 μmol, 99.28% yield, TFA) as yellow oil, which was used directly for the next step.

Step 2. ethyl (16S)-12-chloro-26-(2,2-difluoroethyl)-11-fluoro-18,19-dioxo-22,23,24,25,26-pentazapentacyclodocosa-1 (11),2 (12),9,13 (22),14-pentaene-17-carboxylate A mixture of ethyl (3R)-10-(2,2-difluoroethyl)-3-methyl-1-oxo-2,3,4,7,8,9-hexahydro-1H-pyrido[2,3]pyrazolo[2,4-b][1,4]diazepine-8-carboxylate (133.00 mg, 282.74 μmol, 1.00 eq, TFA), $Et_3N$ (143.05 mg, 1.41 mmol, 195.96 μL, 5.00 eq) and phenyl N-(3-chloro-4-fluoro-phenyl)carbamate (90.14 mg, 339.29 μmol, 1.20 eq) in DCM (10.00 mL) was stirred at 25° C. for 16 h. TLC indicated the starting material was consumed completely and major desired product.

The mixture was diluted with DCM (40 mL) and washed with HCl (1 M, 40 mL). The organic phase was dried over $Na_2SO_4$, filtered and concentrated in vacuo, which was purified by silica gel column to afford the title compound (120.00 mg, 229.74 μmol, 81.26% yield, 98% purity) as yellow solid. LCMS: 528 [M+1].

Step 3. (3R,8R*)—N-(3-chloro-4-fluorophenyl)-10-(2,2-difluoroethyl)-8-(hydroxymethyl)-3-methyl-11-oxo-1,3,4,7,8,9,10,11-octahydro-2H-pyrido[4',3':3,4]pyrazolo[1,5-a][1,4]diazepine-2-carboxamide, *Pure but unknown diastereomer D1

To a solution of ethyl (3R)-2-[(3-chloro-4-fluoro-phenyl)carbamoyl]-10-(2,2-difluoroethyl)-3-methyl-11-oxo-1,3,4,7,8,9-hexahydropyrido[2,3]pyrazolo[2,4-b][1,4]diazepine-8-carboxylate (30.00 mg, 56.83 μmol, 1.00 eq) in THF (2.00 mL) was added LiBH$_4$ (3.71 mg, 170.48 μmol, 3.00 eq) at 0° C. and the mixture was stirred at 25° C. for 2 h. LCMS showed no starting material and major desired product. The mixture was quenched with H$_2$O (20 mL) and extracted with EtOAc (30 mL). The organic phase was dried over Na$_2$SO$_4$, filtered and concentrated in vacuo. The residue combined another batch (EW645-046) was purified by prep-TLC to give 10 mg of product, which was resolved by SFC ("AD-3S_3_5_40_3ML Column: Chiralpak AD-3 100×4.6 mm I.D., 3 um Mobile phase: methanol (0.05% DEA) in CO$_2$ from 5% to 40% Flow rate: 3 mL/min Wavelength: 220 nm"), following by prep-HPLC (FA) to afford each 24 mg of the title compound.

LCMS: 486/488 [M+1]. $^1$H NMR (400 MHz, CDCl$_3$) δ 7.60 (m, 1H), 7.18-7.25 (m, 1H), 7.02-7.11 (m, 1H), 6.59 (s, 1H), 5.91-6.28 (m, 1H), 5.13 (m, 1H), 4.87 (m, 1H), 4.12-4.48 (m, 3H), 3.43-3.81 (m, 4H), 3.03 (m, 1H), 2.58-2.80 (m, 1H), 1.18 (m, 3H).

Compound 092_D2: (3R,8 S*)—N-(3-chloro-4-fluorophenyl)-10-(2,2-difluoroethyl)-8-(hydroxymethyl)-3-methyl-11-oxo-1,3,4,7,8,9,10,11-octahydro-2H-pyrido[4',3':3,4]pyrazolo[1,5-a][1,4]diazepine-2-carboxamide

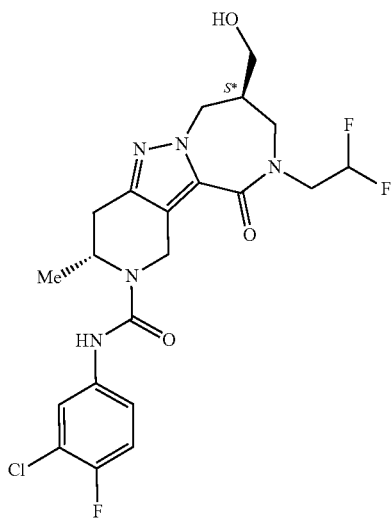 [SMILES: C[C@@H]1Cc2nn3c(c2CN1C(=O)Nc1ccc(F)c(Cl)c1)C(=O)N(CC(F)F)C[C@H](CO)C3]

The title compound was prepared in a manner analogous to Compound 092_D 1 was synthesized by an analogous method. *Pure but unknown diastereomer D2.LCMS: 486/488 [M+1]. $^1$H NMR (400 MHz, CDCl$_3$) δ 7.59 (m, 1H), 7.17-7.25 (m, 1H), 7.04-7.12 (m, 1H), 6.51 (s, 1H), 5.90-6.29 (m, 1H), 5.10 (s, 1H), 4.79 (m, 1H), 4.19-4.54 (m, 4H), 3.42-3.76 (m, 5H), 2.99-3.09 (m, 1H), 2.71 (s, 2H), 1.21 (m, 3H).

Compound 93: 8-(aminomethyl)-N-[4-fluoro-3-(trifluoromethyl)phenyl]-10-methyl-11-oxo-1,3,4,7,8,9-hexahydropyrido[2,3]pyrazolo[2,4-b][1,4]diazepine-2-carboxamide

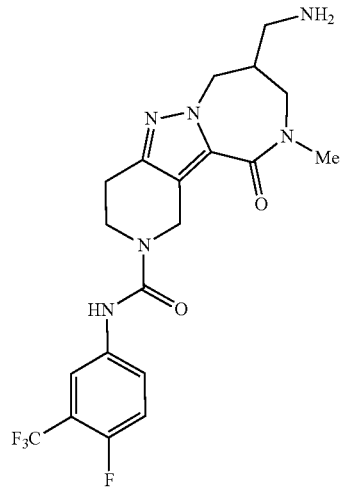 [SMILES: CN1CC(CN)Cn2nc3c(c2C1=O)CN(C(=O)Nc1ccc(F)c(C(F)(F)F)c1)CC3]

Step 1. 8-(hydroxymethyl)-10-methyl-2,3,4,7,8,9-hexahydro-1H-pyrido[2,3]pyrazolo[2,4-b][1,4]diazepin-11-one To a solution of tert-butyl 8-(hydroxymethyl)-10-methyl-1-oxo-1,3,4,7,8,9-hexahydropyrido[2,3]pyrazolo[2,4-b][1,4]diazepine-2-carboxylate (Compound 064, product from Step 1, 200.00 mg, 570.76 μmol, 1.00 eq) in DCM (2.00 mL) was added TFA (3.08 g, 27.01 mmol, 2.00 mL, 47.33 eq) at 0° C. The mixture was stirred at 25° C. for 1 h. LCMS showed that the reactant was consumed completely and the desired product was major. The mixture was concentrated under reduced pressure to afford the title compound (207.00 mg, 568.18 μmol, 99.55% yield, TFA) as yellow oil which was used directly for the next step.

Step 2. N-[4-fluoro-3-(trifluoromethyl)phenyl]-4-(hydroxymethyl)-2-methyl-1-oxo-5,8,9,11-tetrahydro-4H-pyrido[2,3]pyrazolo[2,4-d][1,2,5]oxadiazepine-10-carboxamide To a solution of 4-(hydroxymethyl)-2-methyl-4,5,8,9,10,11-hexahydropyrido[2,3]pyrazolo[2,4-d][1,2,5]oxadiazepin-1-one (100.00 mg, 273.01 μmol, 1.00 eq, TFA) in DCM (3.00 mL) was added phenyl N-[4-fluoro-3-(trifluoromethyl)phenyl]carbamate (98.03 mg, 327.61 μmol, 1.20 eq) and Et$_3$N (138.13 mg, 1.37 mmol, 189.22 μL, 5.00 eq). The mixture was stirred at 25° C. for 16 h. LCMS showed the reactant was consumed completely and the desired product was major. The mixture was diluted with Ethyl acetate (30 mL) and extracted with brine (30 mL*3). The combined organic layers were dried over Na$_2$SO$_4$, filtered and concentrated under reduced pressure which was purified by prep-TLC to afford the title compound (120.00 mg, 259.74 μmol, 95.14% yield, 99% purity) as white solid.

Step 3. [2-[[4-fluoro-3-(trifluoromethyl)phenyl]carbamoyl]-10-methyl-11-oxo-1,3,4,7,8,9-hexahydropyrido[2,3]pyrazolo[2,4-b][1,4]diazepin-8-yl]methyl methanesulfonate To a solution of N-[4-fluoro-3-(trifluoromethyl)phenyl]-8-(hydroxymethyl)-10-methyl-11-oxo-1,3,4,7,8,9-hexahydropyrido[2,3]pyrazolo[2,4-b][1,4]diazepine-2-carboxamide (120.00 mg, 263.50 µmol, 1.00 eq) in DCM (2.00 mL) was added TEA (133.32 mg, 1.32 mmol, 182.63 µL, 5.00 eq) and MsCl (90.55 mg, 790.50 µmol, 61.18 µL, 3.00 eq) at 0° C. The mixture was stirred at 25° C. for 2 hr. TLC (Dichloromethane:Methanol=10:1) showed the reaction was completed. The mixture was poured into water (20 mL), and extracted with ethyl acetate (20 mL*2). The organic layer was washed with brine (10 mL), dried over anhydrous $Na_2SO_4$ and concentrated in vacuum to afford the title compound (140.00 mg, 262.42 µmol, 99.59% yield) as colorless oil.

Step 4. 8-(azidomethyl)-N-[4-fluoro-3-(trifluoromethyl)phenyl]-10-methyl-11-oxo-1,3,4,7,8,9-hexahydropyrido[2,3]pyrazolo[2,4-b][1,4]diazepine-2-carboxamide To a solution of [2-[[4-fluoro-3-(trifluoromethyl)phenyl]carbamoyl]-10-methyl-11-oxo-1,3,4,7,8,9-hexahydropyrido[2,3]pyrazolo[2,4-b][1,4]diazepin-8-yl]methyl methanesulfonate (140.00 mg, 262.42 µmol, 1.00 eq) in DMF (3.00 mL) was added NaN3 (68.24 mg, 1.05 mmol, 4.00 eq) at 0° C. The mixture was stirred at 50° C. for 16 hr. LCMS showed the reaction was completed. The reaction mixture was quenched by addition water (20 mL), and then extracted with ethyl acetate (20 mL*3). The combined organic layers were washed with brine (20 mL), dried over anhydrous $Na_2SO_4$, filtered and concentrated under reduced pressure to afford the title compound (120.00 mg, 249.78 µmol, 95.18% yield) as colorless oil.

Step 5. 8-(aminomethyl)-N-[4-fluoro-3-(trifluoromethyl)phenyl]-10-methyl-11-oxo-1,3,4,7,8,9-hexahydropyrido[2,3]pyrazolo[2,4-b][1,4]diazepine-2-carboxamide and N-[4-fluoro-3-(trifluoromethyl)phenyl]-10-methyl-8-(methylaminomethyl)-11-oxo-1,3,4,7,8,9-hexahydropyrido[2,3]pyrazolo[2,4-b][1,4]diazepine-2-carboxamide To a solution of 8-(azidomethyl)-N-[4-fluoro-3-(trifluoromethyl)phenyl]-10-methyl-11-oxo-1,3,4,7,8,9-hexahydropyrido[2,3]pyrazolo[2,4-b][1,4]diazepine-2-carboxamide (120.00 mg, 249.78 µmol, 1.00 eq) in MeOH (5.00 mL) was added Pd/C (20.00 mg, 10% purity). The mixture was stirred under $H_2$ (15 PSi) at 25° C. for 3 hr. TLC showed the reactant consumed, LCMS showed 32% Compound 093 and 39% Compound 094 (N-[4-fluoro-3-(trifluoromethyl)phenyl]-10-methyl-8-(methylaminomethyl)-11-oxo-1,3,4,7,8,9-hexahydropyrido[2,3]pyrazolo[2,4-b][1,4]diazepine-2-carboxamide). The mixture was filtered and the filtrate was concentrated in vacuum which was purified by prep-HPLC to afford Compound 93: 8-(aminomethyl)-N-[4-fluoro-3-(trifluoromethyl)phenyl]-10-methyl-11-oxo-1,3,4,7,8,9-hexahydropyrido[2,3]pyrazolo[2,4-b][1,4]diazepine-2-carboxamide (20.00 mg, 41.81 µmol, 16.74% yield, 95% purity) as white solid and Compound 94: N-[4-fluoro-3-(trifluoromethyl)phenyl]-10-methyl-8-(methylaminomethyl)-11-oxo-1,3,4,7,8,9-hexahydropyrido[2,3]pyrazolo[2,4-b][1,4]diazepine-2-carboxamide(9.00 mg, 18.25 µmol, 7.31% yield, 95% purity) was obtained as white solid.

LCMS: 455 [M+1]. $^1$H NMR (400 MHz, CDCl$_3$) δ 7.69 (dd, J=2.63, 6.05 Hz, 1H), 7.56-7.63 (m, 1H), 7.12 (t, J=9.41 Hz, 1H), 6.86 (s, 1H), 4.62-4.78 (m, 2H), 4.40-4.44 (m, 1H), 4.21-4.38 (m, 1H), 3.78-3.96 (m, 2H), 3.32-3.55 (m, 2H), 3.19 (s, 3H), 2.71-2.88 (m, 4H), 2.38-2.59 (m, 1H).

Compound 94: N-[4-fluoro-3-(trifluoromethyl)phenyl]-10-methyl-8-(methylaminomethyl)-11-oxo-1,3,4,7,8,9-hexahydropyrido[2,3]pyrazolo[2,4-b][1,4]diazepine-2-carboxamide

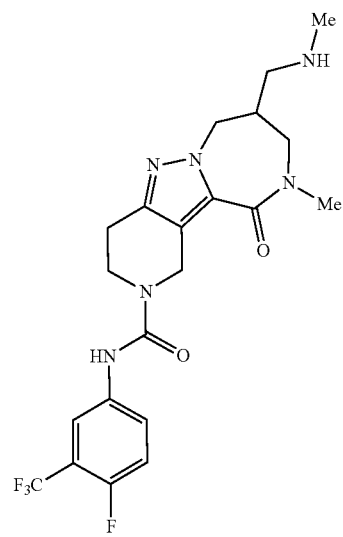 [SMILES: CNCC1CN(C)C(=O)c2c3c(nn2C1)CCN(C(=O)Nc1ccc(F)c(C(F)(F)F)c1)C3]

LCMS: 469 [M+1]. $^1$H NMR (400 MHz, CDCl$_3$) δ 7.69 (dd, J=2.70, 6.09 Hz, 1H), 7.56-7.64 (m, 1H), 7.11 (t, J=9.35 Hz, 1H), 6.98 (s, 1H), 4.57-4.75 (m, 2H), 4.40-4.42 (m, 1H), 4.13-4.15 (m, 1H), 3.78-3.95 (m, 2H), 3.30-3.53 (m, 2H), 3.17 (s, 3H), 2.84 (t, J=5.77 Hz, 2H), 2.53-2.75 (m, 3H), 2.46 (s, 3H).

Compound 095: 8-(aminomethyl)-N-(3-cyano-4-fluorophenyl)-10-methyl-11-oxo-1,3,4,7,8,9,10,11-octahydro-2H-pyrido[4',3':3,4]pyrazolo[1,5-a][1,4]diazepine-2-carboxamide

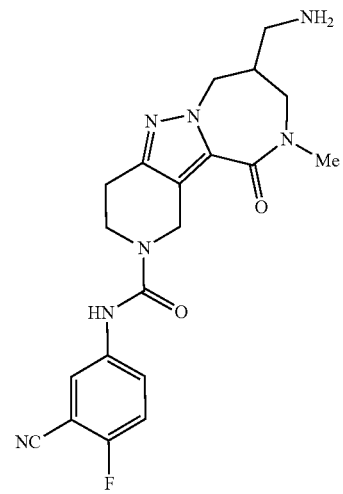 [SMILES: CN1CC(CN)Cn2nc3c(c2C1=O)CN(C(=O)Nc1ccc(F)c(C#N)c1)CC3]

Step 1. N-(3-cyano-4-fluoro-phenyl)-4-(hydroxymethyl)-2-methyl-1-oxo-5,8,9,11-tetrahydro-4H-pyrido[2,3]pyrazolo[2,4-d][1,2,5]oxadiazepine-10-carboxamide To a solution of 4-(hydroxymethyl)-2-methyl-4,5,8,9,10,11-hexahydropyrido[2,3]pyrazolo[2,4-d][1,2,5]oxadiazepin-1-one (Compound 093, product from Step 1, 100.00 mg, 273.01 µmol, 1.00 eq, TFA) in DCM (3.00 mL) was added phenyl N-(3-cyano-4-fluoro-phenyl)carbamate (83.94 mg, 327.61 µmol, 1.20 eq) and Et$_3$N (138.13 mg, 1.37 mmol, 189.22 µL, 5.00 eq). The mixture was stirred at 25° C. for 16 h. LCMS showed that the reactant was consumed completely and the desired product was major. The mixture was diluted with Ethyl acetate (30 mL) and extracted with brine (30 mL*3). The combined organic layers were dried over Na$_2$SO$_4$, filtered and concentrated under reduced pressure to give a residue which was purified by prep-TLC to afford the title compound (80.00 mg, 189.19 µmol, 69.30% yield, 98% purity) as white solid.

Step 2. [2-[(3-cyano-4-fluoro-phenyl)carbamoyl]-10-methyl-11-oxo-1,3,4,7,8,9-hexahydropyrido[2,3]pyrazolo[2,4-b][1,4]diazepin-8-yl]methyl methanesulfonate To a solution of N-(3-cyano-4-fluoro-phenyl)-8-(hydroxymethyl)-10-methyl-11-oxo-1,3,4,7,8,9-hexahydropyrido[2,3]pyrazolo[2,4-b][1,4]diazepine-2-carboxamide (80.00 mg, 193.98 µmol, 1.00 eq) in DCM (3.00 mL) was added TEA (98.14 mg, 969.90 µmol, 134.44 µL, 5.00 eq) and MsCl (66.66 mg, 581.94 µmol, 45.04 µL, 3.00 eq). The mixture was stirred at 20° C. for 4 hr. TLC showed the reactant consumed and a mew spot detected. The mixture was poured into water(10 mL), extracted with ethyl acetate (10 mL*3), the organic layer was washed with brine(10 mL), dried over anhydrous Na$_2$SO$_4$, filtered and concentrated in vacuum to afford the title compound (95.00 mg, 193.68 µmol, 99.84% yield) as white solid.

Step 3. 8-(azidomethyl)-N-(3-cyano-4-fluoro-phenyl)-10-methyl-11-oxo-1,3,4,7,8,9-hexahydropyrido[2,3]pyrazolo[2,4-b][1,4]diazepine-2-carboxamide To a solution of [2-[(3-cyano-4-fluoro-phenyl)carbamoyl]-10-methyl-11-oxo-1,3,4,7,8,9-hexahydropyrido[2,3]pyrazolo[2,4-b][1,4]diazepin-8-yl]methyl methanesulfonate (100.00 mg, 203.87 µmol, 1.00 eq) in DMF (3.00 mL) was added NaN$_3$ (53.01 mg, 815.48 µmol, 4.00 eq) at 0° C. The mixture was stirred at 50° C. for 16 hr. LCMS showed the reaction was completed. The reaction mixture was quenched by addition water (20 mL), and extracted with ethyl acetate (20 mL*3). The combined organic layers were washed with brine (20 mL), dried over anhydrous Na$_2$SO$_4$, filtered and concentrated under reduced pressure to afford the title compound (80.00 mg, 182.89 µmol, 89.71% yield) as colorless oil.

Step 4. 8-(aminomethyl)-N-(3-cyano-4-fluorophenyl)-10-methyl-11-oxo-1,3,4,7,8,9,10,11-octahydro-2H-pyrido[4',3':3,4]pyrazolo[1,5-a][1,4]diazepine-2-carboxamide To a mixture of 8-(azidomethyl)-N-(3-cyano-4-fluoro-phenyl)-10-methyl-11-oxo-1,3,4,7,8,9-hexahydropyrido[2,3]pyrazolo[2,4-b][1,4]diazepine-2-carboxamide (80.00 mg, 182.89 µmol, 1.00 eq) in EtOH (5.00 mL) and H$_2$O (500.00 uL) was added Zn (47.84 mg, 731.56 µmol, 4.00 eq) and NH$_4$Cl (58.70 mg, 1.10 mmol, 38.37 µL, 6.00 eq). The mixture was stirred at 25° C. for 16 hr. LCMS showed the reactant consumed and the desired product detected. The mixture was filtered and the filtrate was purified by prep-HPLC to afford (30.00 mg, 69.27 µmol, 37.88% yield, 95% purity) as white solid. LCMS: 412 [M+1]. $^1$H NMR (400 MHz, CDCl$_3$) δ 7.78 (dd, J=2.75, 5.44 Hz, 1H), 7.60 (ddd, J=2.87, 4.52, 9.11 Hz, 1H), 7.13 (t, J=8.74 Hz, 1H), 6.93 (s, 1H), 4.58-4.75 (m, 2H), 4.40-4.42 (m, 1H), 4.18-4.20 (m, 1H), 3.87 (t, J=5.87 Hz, 2H), 3.31-3.53 (m, 2H), 3.13-3.26 (m, 3H), 2.72-2.89 (m, 4H), 2.39-2.57 (m, 1H).

Compound 096_E1: (R*)—N-(5-chloro-2,4-difluorophenyl)-8-((S*)-1-hydroxypropyl)-10-methyl-11-oxo-1,3,4,7,8,9,10,11-octahydro-2H-pyrido[4',3':3,4]pyrazolo[1,5-a][1,4]diazepine-2-carboxamide

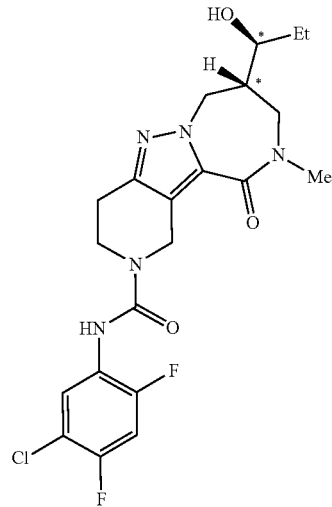 [SMILES: CC[C@H](O)[C@@H]1CN(C)C(=O)c2c3c(nn2C1)CCN(C(=O)Nc1cc(Cl)c(F)cc1F)C3]

Step 1. 2-tert-butoxycarbonyl-10-methyl-11-oxo-1,3,4,7,8,9-hexahydropyrido[2,3]pyrazolo[2,4-b][1,4]diazepine-8-carboxylic acid To a mixture of 2-tert-butyl 8-ethyl 10-methyl-11-oxo-1,3,4,7,8,9-hexahydropyrido[2,3]pyrazolo[2,4-b][1,4]diazepine-2,8-dicarboxylate (Intermediate 14, 4.80 g, 12.23 mmol, 1.00 eq) in MeOH (20.00 mL) and H$_2$O (4.00 mL) was added NaOH (978.47 mg, 24.46 mmol, 2.00 eq) in one portion. The mixture was stirred at 30° C. for 5 hours. LCMS and TLC (Dichloromethane:Methanol=10:1) showed the reaction was completed. The mixture was concentrated in vacuum to remove MeOH. The residue poured into water (10 mL) and stirred for 1 min. The aqueous phase was extracted with DCM (30 mL*2). The aqueous phase was adjust to pH=3 with 1N HCl and extracted with ethyl acetate(30 mL*2), The combined organic phase was washed with brine (10 mL*2), dried with anhydrous Na$_2$SO$_4$, filtered and concentrated in vacuum to afford the title compound (4.40 g, 12.07 mmol, 98.73% yield, 100% purity) as white solid. LCMS[M+1]: 365

Step 2. tert-butyl 8-[methoxy(methyl) carbamoyl]-10-methyl-11-oxo-1,3,4,7,8,9-hexahydropyrido[2,3]pyrazolo[2,4-b][1,4]diazepine-2-carboxylate To a mixture of 2-tert-butoxycarbonyl-10-methyl-11-oxo-1,3,4,7,8,9-hexahydropyrido[2,3]pyrazolo[2,4-b][1,4]diazepine-8-carboxylic acid (500.00 mg, 1.37 mmol, 1.00 eq) and N-methoxymethanamine hydrochloride (534.52 mg, 5.48 mmol, 4.00 eq) in THF (10.00 mL) was added T$_3$P (1.74 g, 2.74 mmol, 1.63 mL, 50% purity, 2.00 eq) and TEA (2.08 g, 20.55 mmol, 2.85 mL, 15.00 eq) in one portion under N$_2$. The mixture was stirred at 30° C. for 12 hours. LCMS and TLC (Dichloromethane:Methanol=10:1) showed the reaction was completed. The mixture was poured into water (15 mL) and stirred for 2 min. The aqueous phase was extracted with ethyl acetate (20 mL*2). The combined organic phase was washed with brine (10 mL*2), dried with anhydrous Na$_2$SO$_4$, filtered and concentrated in vacuum. The residue was purified by silica gel chromatography (Dichloromethane:Methanol=50:1-20:1) to afford the title compound (510.00 mg, 1.24 mmol, 90.45% yield, 99% purity) as white solid. LCMS[M+1]: 408.

Step 3. tert-butyl 10-methyl-11-oxo-8-prop-2-enoyl-1,3,4,7,8,9-hexahydropyrido[2,3]pyrazolo[2,4-b][1,4]diazepine-2-carboxylate To a mixture of vinylmagnesium bromide (1 M, 4.91 mL, 5.00 eq) in THF (4.00 mL) was added tert-butyl 8-[methoxy(methyl)carbamoyl]-10-methyl-11-oxo-1,3,4,7,8,9-hexahydropyrido[2,3]pyrazolo[2,4-b][1,4]diazepine-2-carboxylate (400.00 mg, 981.69 µmol, 1.00 eq) in THF (2.00 mL) drop-wise at –30° C. under N$_2$. The mixture was heated to 0° C. and stirred for 1 hours. LCMS and TLC (Ethyl acetate) showed the reaction was completed and the desired product was detected. The mixture was poured into 1N HCl (30 mL) and stirred for 2 min. The aqueous phase was extracted with ethyl acetate (10 mL*2). The combined organic phase was washed with brine (10 mL*2), dried with anhydrous Na$_2$SO$_4$, filtered and concentrated in vacuum to afford the title compound (288.00 mg, 769.17 µmol, 78.35% yield) as yellow solid. LCMS[M+1]: 375.

Step 4. tert-butyl 8-(1-hydroxyallyl)-10-methyl-11-oxo-1,3,4,7,8,9-hexahydropyrido[2,3]pyrazolo[2,4-b][1,4]diazepine-2-carboxylate_E1-E4

To a mixture of tert-butyl 10-methyl-11-oxo-8-prop-2-enoyl-1,3,4,7,8,9-hexahydropyrido[2,3]pyrazolo[2,4-b][1,4]diazepine-2-carboxylate (3.70 g, 9.88 mmol, 1.00 eq) in MeOH (100.00 mL) was added CeCl$_3$ (4.87 g, 19.76 mmol, 1.24 mL, 2.00 eq) in one portion at 0° C. under N$_2$. The mixture was stirred at 0° C. for 15 min, then NaBH$_4$ (1.50 g, 39.52 mmol, 4.00 eq) was added to the mixture. The mixture was heated to 30° C. and stirred for 2 hours. LCMS and TLC (Dichloromethane:Methanol=10:1) showed the reaction was completed. The mixture was poured into water (20 mL) and concentrated in reduced pressure. The aqueous phase was extracted with ethyl acetate (50 mL*3). The combined organic phase was washed with brine (20 mL*2), dried with anhydrous Na$_2$SO$_4$, filtered and concentrated in vacuum. The residue was purified by silica gel chromatography (Dichloromethane:Methanol=100/1-20:1) to afford racemic title compound (2.70 g, 6.74 mmol, 68.24% yield, 94% purity) as yellow solid, Which was separated by SFC (Analytical method: IC-3S_3_5_40_3ML Column: Chiralpak IC-3 100×4.6 mm I.D., 3 um Mobile phase: methanol (0.05% DEA) in CO$_2$ from 5% to 40% Flow rate: 3 mL/min Wavelength: 220 nm. Separation method: Instrument: SFC 80; Column: IC-10 um; Mobile phase: A for CO$_2$ and B for MeOH (0.1% NH$_3$H$_2$O); Gradient: B 35%; Flow rate: 60 mL/min; Back pressure: 100bar; Column temperature: 35 □; Wavelength: 220 nm) to give four isomers: E1: 650 mg, E2: 640 mg, E3: 650 mg and E4: 650 mg.

Step 5. tert-butyl 8-(1-hydroxypropyl)-10-methyl-11-oxo-1,3,4,7,8,9-hexahydropyrido[2,3]pyrazolo[2,4-b][1,4]diazepine-2-carboxylate_E1

To a solution of tert-butyl 8-(1-hydroxyallyl)-10-methyl-11-oxo-1,3,4,7,8,9-hexahydropyrido[2,3]pyrazolo[2,4-b][1,4]diazepine-2-carboxylate (550.00 mg, 1.46 mmol, 1.00 eq) in MeOH (20.00 mL) was added Pd/C (100.00 mg) under N$_2$. The suspension was degassed under vacuum and purged with H$_2$ several times. The mixture was stirred under H$_2$ (15 psi) at 30° C. for 5 hours LCMS showed the starting material was consumed completely. The reaction mixture was filtered and the filtrate was concentrated to afford the title compound (520.00 mg, 1.37 mmol, 94.11% yield) as yellow solid. LCMS[M+1]: 379.

Step 6. 8-(1-hydroxypropyl)-10-methyl-2,3,4,7,8,9-hexahydro-1H-pyrido[2,3]pyrazolo[2,4-b][1,4]diazepin-11-one_E1

To a mixture of tert-butyl 8-(1-hydroxypropyl)-10-methyl-11-oxo-1,3,4,7,8,9-hexahydropyrido[2,3]pyrazolo[2,4-b][1,4]diazepine-2-carboxylate (200.00 mg, 528.46 µmol, 1.00 eq) in DCM (2.00 mL) was added TFA (3.08 g, 27.01 mmol, 2.00 mL, 51.12 eq) in one portion at 30° C. under N$_2$. The mixture was stirred at 30° C. for 2 hours. LCMS showed the reaction was completed. The mixture was concentrated in vacuum to afford the title compound (207.00 mg, 527.56 µmol, 99.83% yield, TFA) as yellow oil.

Step 7. (R*)—N-(5-chloro-2,4-difluorophenyl)-8-((S*)-1-hydroxypropyl)-10-methyl-11-oxo-1,3,4,7,8,9,10,11-octahydro-2H-pyrido[4',3':3,4]pyrazolo[1,5-a][1,4]diazepine-2-carboxamide *Pure but Unknown Diastereomer E1

To a mixture of 8-(1-hydroxypropyl)-10-methyl-2,3,4,7,8,9-hexahydro-1H-pyrido[2,3]pyrazolo[2,4-b][1,4]diazepin-11-one (50.00 mg, 127.43 mol, 1.00 eq, TFA) and phenyl N-(5-chloro-2,4-difluoro-phenyl)carbamate (46.99 mg, 165.66 mol, 1.30 eq) in DCM (6.00 mL) was added TEA (128.95 mg, 1.27 mmol, 176.64 µL, 10.00 eq) under N$_2$. The mixture was stirred at 25° C. for 10 hours. LCMS showed the reaction was completed. The residue was poured into water (10 mL). The aqueous phase was extracted with ethyl acetate (10 mL*2). The combined organic phase was washed with brine (10 mL*2), dried with anhydrous Na$_2$SO$_4$, filtered and concentrated in vacuum. The residue was purified by prep-HPLC(FA) to afforded the title compound (40.00 mg, 84.89 µmol, 66.62% yield, 99.3% purity) as white solid. LCMS [M+1]: 468 $^1$H NMR (400 MHz, CDCl$_3$) δ 8.17 (t, J=8.03 Hz, 1H), 6.94 (dd, J=8.47, 10.60 Hz, 1H), 6.59 (d, J=2.89 Hz, 1H), 4.70 (s, 2H), 4.40-4.42 (m, 1H), 4.13-4.16 (m, 1H), 3.82-3.89 (m, 2H), 3.64-3.66 (m, 2H), 3.46-3.48 (m, 1H), 3.19 (s, 3H), 2.85 (t, J=5.77 Hz, 2H), 2.46-2.47 (m, 1H), 1.70-1.77 (m, 1H), 1.44-1.55 (m, 2H), 1.04 (t, J=7.40 Hz, 3H).

Compounds 096,097,098,099,100,101,102,103,104, and 105 were prepared from the corresponding enantiomer separately through an analogous method.

| 273 | 274 -continued |
|---|---|
| 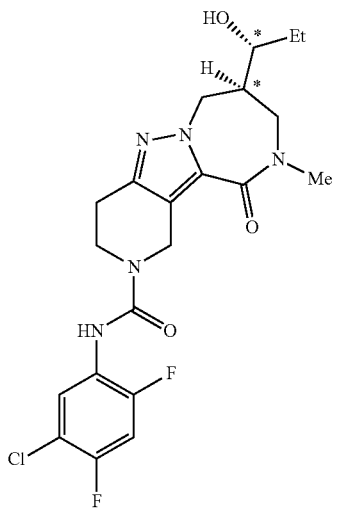 | 096 E2 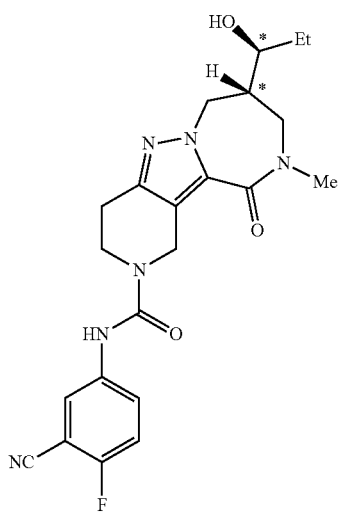 097 E1 |
| 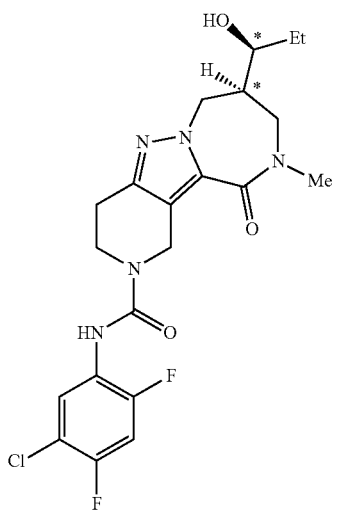 096 E3 | 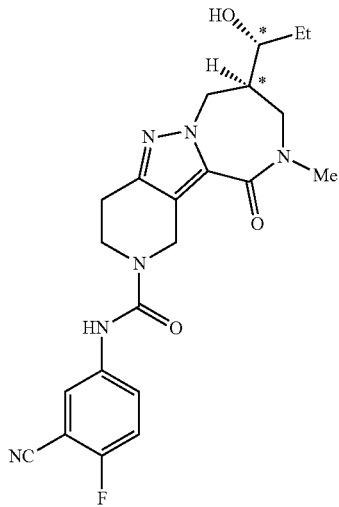 097 E2 |
| 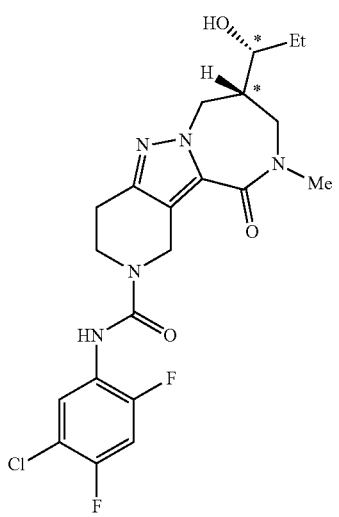 096 E4 | 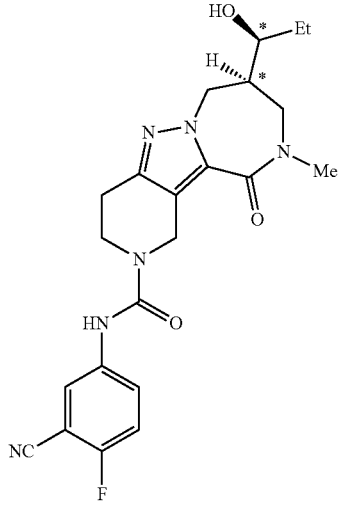 097 E3 |

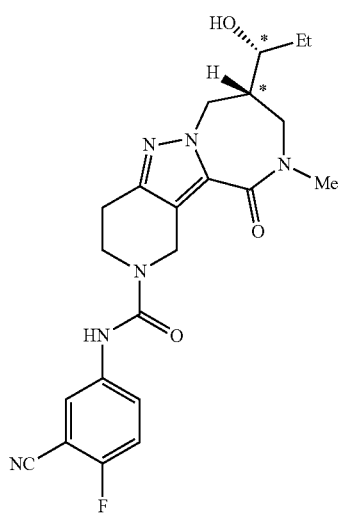
097 E4
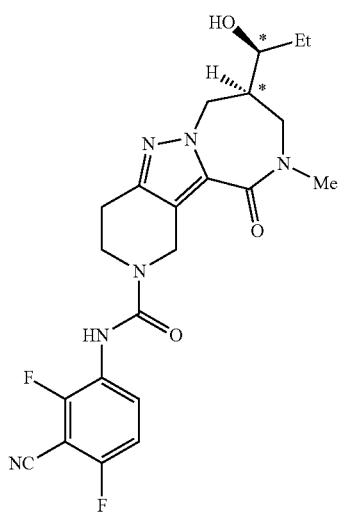
098 E3
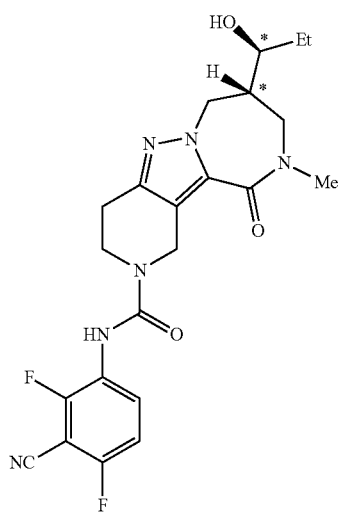
098 E1
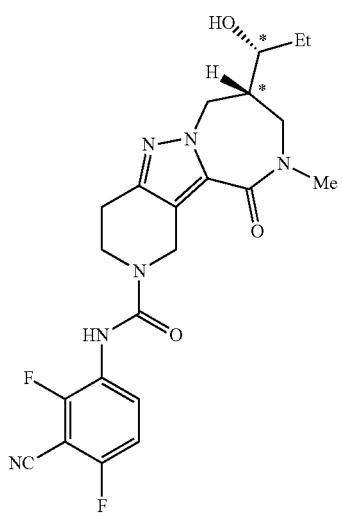
098 E4
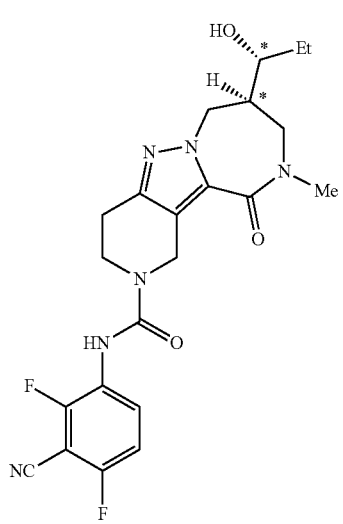
098 E2
099 E1

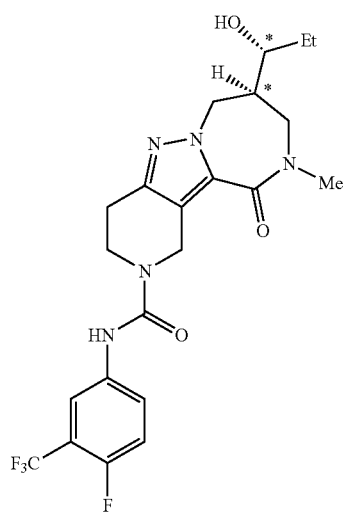
099 E2
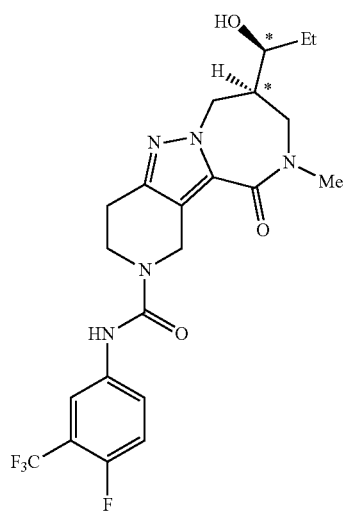
099 E3
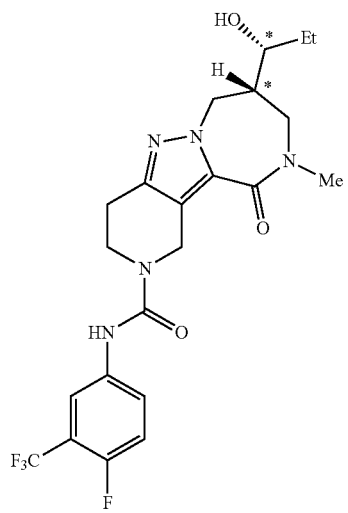
099 E4
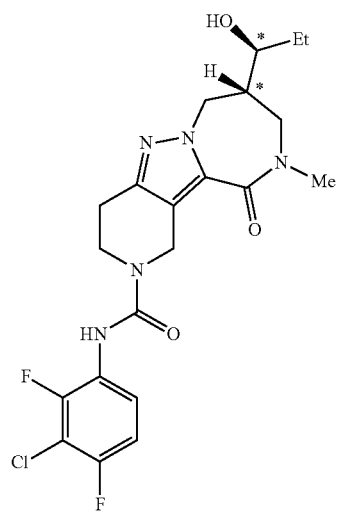
100 E1
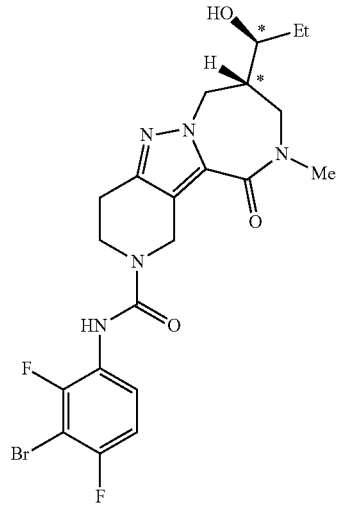
101 E1
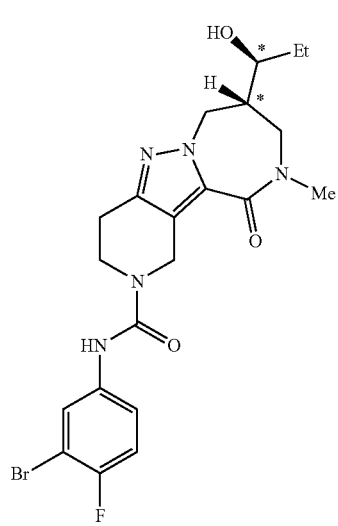
102 E1

279
-continued

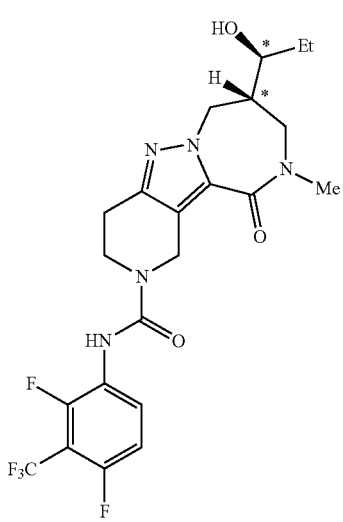

103 E1

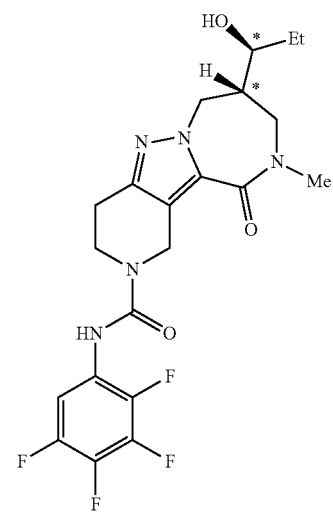

104 E1

105 E1

280

Compound 096_E2: (S*)—N-(5-chloro-2,4-difluorophenyl)-8-((R*)-1-hydroxypropyl)-10-methyl-11-oxo-1,3,4,7,8,9,10,11-octahydro-2H-pyrido[4',3':3,4]pyrazolo[1,5-a][1,4]diazepine-2-carboxamide

*Pure but unknown diastereomer E2.
LCMS [M+1]: 468 $^1$H NMR (400 MHz, CDCl$_3$) δ 8.18 (t, J=8.03 Hz, 1H), 6.96 (dd, J=8.47, 10.60 Hz, 1H), 6.61 (s, 1H), 4.71 (s, 2H), 4.40-4.42 (m, 1H), 4.14-4.16 (m, 1H), 3.83-3.91 (m, 2H), 3.62-3.69 (m, 2H), 3.47-3.48 (m, 1H), 3.20 (s, 3H), 2.86 (t, J=5.71 Hz, 2H), 2.47-2.49 (m, 1H), 1.71-1.79 (m, 1H), 1.45-1.56 (m, 2H), 1.05 (t, J=7.34 Hz, 3H).

Compound 096_E3: (S*)—N-(5-chloro-2,4-difluorophenyl)-8-((S*)-1-hydroxypropyl)-10-methyl-11-oxo-1,3,4,7,8,9,10,11-octahydro-2H-pyrido[4',3':3,4]pyrazolo[1,5-a][1,4]diazepine-2-carboxamide

*Pure but unknown diastereomer E3.
LCMS [M+1]: 468 $^1$H NMR (400 MHz, CDCl$_3$) δ 8.18 (t, J=8.07 Hz, 1H), 6.96 (dd, J=8.50, 10.45 Hz, 1H), 6.63 (br d, J=2.69 Hz, 1H), 4.59-4.77 (m, 3H), 4.32 (m, 1H), 3.79-3.95 (m, 2H), 3.49-3.56 (m, 1H), 3.36-3.37 (m, 2H), 3.20 (s, 3H), 2.87 (t, J=5.81 Hz, 2H), 2.46-2.54 (m, 1H), 1.90-2.20 (m, 1H), 1.44-1.54 (m, 2H), 1.03 (t, J=7.40 Hz, 3H).

Compound 096_E4: (R*)—N-(5-chloro-2,4-difluorophenyl)-8-((R*)-1-hydroxypropyl)-10-methyl-1-oxo-1,3,4,7,8,9,10,11-octahydro-2H-pyrido[4',3':3,4]pyrazolo[1,5-a][1,4]diazepine-2-carboxamide

*Pure but unknown diastereomer E4.
LCMS [M+1]: 468 $^1$H NMR (400 MHz, CDCl$_3$) δ 8.18 (t, J=8.07 Hz, 1H), 6.96 (dd, J=8.50, 10.58 Hz, 1H), 6.63 (s, 1H), 4.59-4.77 (m, 3H), 4.32 (m, 1H), 3.79-3.95 (m, 2H), 3.50-3.56 (m, 1H), 3.36 (m, 2H), 3.20 (s, 3H), 2.87 (t, J=5.81 Hz, 2H), 2.46-2.54 (m, 1H), 2.03 (s, 1H), 1.75 (br s, 1H), 1.66 (m, 19H), 1.42-1.55 (m, 2H), 1.03 (t, J=7.34 Hz, 3H).

Compound 097_E1: (R*)—N-(3-cyano-4-fluorophenyl)-8-((S*)-1-hydroxypropyl)-10-methyl-11-oxo-1,3,4,7,8,9,10,11-octahydro-2H-pyrido[4',3':3,4]pyrazolo[1,5-a][1,4]diazepine-2-carboxamide

*Pure but unknown diastereomer E1.
LCMS [M+1]: 441. $^1$H NMR (400 MHz, CDCl$_3$) δ 7.80 (dd, J=2.76, 5.52 Hz, 1H), 7.60-7.63 (m, 1H), 7.14 (t, J=8.72 Hz, 1H), 6.99-7.04 (m, 1H), 4.64-4.75 (m, 2H), 4.43 (m, 1H), 4.15 (m, 1H), 3.81-3.95 (m, 2H), 3.66 (m, 2H), 3.48 (m, 1H), 3.21 (s, 3H), 2.85 (t, J=5.71 Hz, 2H), 2.45-2.53 (m, 1H), 1.79 (m, 1H), 1.44-1.59 (m, 2H), 1.05 (t, J=7.40 Hz, 3H).

Compound 097_E2: (S*)—N-(3-cyano-4-fluorophenyl)-8-((R*)-1-hydroxypropyl)-10-methyl-11-oxo-1,3,4,7,8,9,10,11-octahydro-2H-pyrido[4',3': 3,4]pyrazolo[1,5-a][1,4]diazepine-2-carboxamide

*Pure but unknown diastereomer E2.
LCMS [M+1]: 441. $^1$H NMR (400 MHz, CDCl$_3$) δ 7.80 (dd, J=2.76, 5.40 Hz, 1H), 7.60-7.63 (m, 1H), 7.14 (t, J=8.72 Hz, 1H), 6.99 (br s, 1H), 4.64-4.75 (m, 2H), 4.43 (dd, J=7.28, 14.18 Hz, 1H), 4.15 (m, 1H), 3.81-3.95 (m, 2H), 3.66 (m, 2H), 3.48 (m, 14.87 Hz, 1H), 3.21 (s, 3H), 2.85 (t, J=5.83 Hz, 2H), 2.49 (m, 1H), 1.79 (br s, 1H), 1.60-1.71 (m, 18H), 1.52 (m, 2H), 1.05 (t, J=7.40 Hz, 3H).

Compound 097_E3: (S*)—N-(3-cyano-4-fluorophenyl)-8-((S*)-1-hydroxypropyl)-10-methyl-11-oxo-1,3,4,7,8,9,10,11-octahydro-2H-pyrido[4',3': 3,4]pyrazolo[1,5-a][1,4]diazepine-2-carboxamide

*Pure but unknown diastereomer E3.
LCMS [M+1]: 441. $^1$H NMR (400 MHz, CDCl$_3$) δ 7.79 (dd, J=2.69, 5.38 Hz, 1H), 7.60-7.63 (m, 1H), 7.14 (t, J=8.68 Hz, 1H), 7.04 (s, 1H), 4.70-4.79 (m, 1H), 4.59-4.69 (m, 2H), 4.33 (m, 1H), 3.81-3.95 (m, 2H), 3.50-3.58 (m, 1H), 3.38 (m, 2H), 3.20 (s, 3H), 2.85 (t, J=5.81 Hz, 2H), 2.51 (m, 1H), 1.97-2.18 (m, 1H), 1.46-1.57 (m, 1H), 1.45-1.56 (m, 1H), 1.04 (t, J=7.40 Hz, 3H).

Compound 097_E4: (R*)—N-(3-cyano-4-fluorophenyl)-8-((R*)-1-hydroxypropyl)-10-methyl-11-oxo-1,3,4,7,8,9,10,11-octahydro-2H-pyrido[4',3': 3,4]pyrazolo[1,5-a][1,4]diazepine-2-carboxamide

*Pure but unknown diastereomer E4.
LCMS [M+1]: 441. $^1$H NMR (400 MHz, CDCl$_3$) δ 7.79 (dd, J=2.75, 5.44 Hz, 1H), 7.61-7.63 (m, 1H), 7.05-7.17 (m, 2H), 4.71-4.79 (m, 1H), 4.58-4.67 (m, 2H), 4.33 (m, 1H), 3.81-3.95 (m, 2H), 3.51-3.57 (m, 1H), 3.38 (d, J=7.46 Hz, 2H), 3.20 (s, 3H), 2.85 (t, J=5.81 Hz, 2H), 2.47-2.55 (m, 1H), 2.03 (s, 1H), 1.62-1.74 (m, 1H), 1.45-1.58 (m, 2H), 1.04 (t, J=7.40 Hz, 3H).

Compound 098_E1: (R*)—N-(3-cyano-2,4-difluorophenyl)-8-((S*)-1-hydroxypropyl)-10-methyl-11-oxo-1,3,4,7,8,9,10,11-octahydro-2H-pyrido[4',3':3,4]pyrazolo[1,5-a][1,4]diazepine-2-carboxamide

*Pure but unknown diastereomer E1.
LCMS [M+1]: 459. $^1$H NMR (400 MHz, CDCl$_3$) δ 8.25 (dt, J=5.84, 9.13 Hz, 1H), 7.01 (ddd, J=1.76, 7.97, 9.47 Hz, 1H), 6.73 (d, J=2.26 Hz, 1H), 4.72 (d, J=3.51 Hz, 2H), 4.41 (m, 1H), 4.14 (m, 1H), 3.78-3.95 (m, 2H), 3.59-3.71 (m, 2H), 3.46 (m, 1H), 3.19 (s, 3H), 2.85 (t, J=5.71 Hz, 2H), 2.40-2.54 (m, 1H), 1.43-1.59 (m, 2H), 1.03 (t, J=7.40 Hz, 3H).

Compound 098_E2: (S*)—N-(3-cyano-2,4-difluorophenyl)-8-((R*)-1-hydroxypropyl)-10-methyl-11-oxo-1,3,4,7,8,9,10,11-octahydro-2H-pyrido[4',3':3,4]pyrazolo[1,5-a][1,4]diazepine-2-carboxamide

*Pure but unknown diastereomer E2.
LCMS [M+1]: 459 $^1$H NMR (400 MHz, CDCl$_3$) δ 8.25 (dt, J=5.90, 9.10 Hz, 1H), 7.01 (ddd, J=1.69, 7.94, 9.44 Hz, 1H), 6.73 (d, J=2.01 Hz, 1H), 4.72 (d, J=3.64 Hz, 2H), 4.41 (m, 1H), 4.14 (m, 1H), 3.86 (m, 2H), 3.57-3.71 (m, 2H), 3.46 (m, 1H), 3.19 (s, 3H), 2.85 (t, J=5.71 Hz, 2H), 2.37-2.57 (m, 1H), 1.51 (dt, J=7.40, 14.93 Hz, 2H), 1.04 (t, J=7.40 Hz, 3H).

Compound 098_E3: (S*)—N-(3-cyano-2,4-difluorophenyl)-8-((S*)-1-hydroxypropyl)-10-methyl-11-oxo-1,3,4,7,8,9,10,11-octahydro-2H-pyrido[4',3':3,4]pyrazolo[1,5-a][1,4]diazepine-2-carboxamide

*Pure but unknown diastereomer E3.
LCMS [M+1]: 459. $^1$H NMR (400 MHz, CDCl$_3$) δ 8.26 (dt, J=5.83, 9.13 Hz, 1H), 7.01 (ddd, J=1.76, 7.97, 9.47 Hz, 1H), 6.72 (d, J=2.26 Hz, 1H), 4.53-4.85 (m, 3H), 4.31 (m, 1H), 3.77-3.95 (m, 2H), 3.52 (m, 1H), 3.36 (m, 2H), 3.19 (s, 3H), 2.86 (t, J=5.77 Hz, 2H), 2.42-2.56 (m, 1H), 1.44-1.58 (m, 2H), 1.02 (t, J=7.40 Hz, 3H).

Compound 098_E4: (R*)—N-(3-cyano-2,4-difluorophenyl)-8-((R*)-1-hydroxypropyl)-10-methyl-11-oxo-1,3,4,7,8,9,10,11-octahydro-2H-pyrido[4',3':3,4]pyrazolo[1,5-a][1,4]diazepine-2-carboxamide

*Pure but unknown diastereomer E4.
LCMS [M+1]: 459. $^1$H NMR (400 MHz, CDCl$_3$) δ 8.18-8.35 (m, 1H), 7.02 (ddd, J=1.76, 8.03, 9.54 Hz, 1H), 6.65-6.80 (m, 1H), 4.54-4.83 (m, 3H), 4.20-4.37 (m, 1H), 3.75-3.96 (m, 2H), 3.47-3.59 (m, 1H), 3.36 (m, 2H), 3.19 (s, 3H), 2.86 (s, 2H), 2.41-2.58 (m, 1H), 1.42-1.56 (m, 2H), 1.02 (t, J=7.40 Hz, 3H).

Compound 099_E1: (R*)—N-(4-fluoro-3-(trifluoromethyl)phenyl)-8-((S*)-1-hydroxypropyl)-10-methyl-11-oxo-1,3,4,7,8,9,10,11-octahydro-2H-pyrido[4',3':3,4]pyrazolo[1,5-a][1,4]diazepine-2-carboxamide

*Pure but unknown diastereomer E1.
LCMS [M+1]: 484. $^1$H NMR (400 MHz, CDCl$_3$) δ 7.69 (dd, J=2.63, 6.05 Hz, 1H), 7.59 (td, J=3.38, 9.02 Hz, 1H), 7.12 (t, J=9.35 Hz, 1H), 6.87 (s, 1H), 4.60-4.77 (m, 2H), 4.41 (m, 1H), 4.13 (m, 1H), 3.78-3.96 (m, 2H), 3.64 (m, 2H), 3.47 (m, 1H), 3.19 (s, 3H), 2.84 (t, J=5.93 Hz, 2H), 2.40-2.53 (m, 1H), 1.72-1.82 (m, 1H), 1.46-1.57 (m, 2H), 1.04 (t, J=7.40 Hz, 3H).

Compound 099_E2: (S*)—N-(4-fluoro-3-(trifluoromethyl)phenyl)-8-((R*)-1-hydroxypropyl)-10-methyl-11-oxo-1,3,4,7,8,9,10,11-octahydro-2H-pyrido[4',3':3,4]pyrazolo[1,5-a][1,4]diazepine-2-carboxamide

*Pure but unknown diastereomer E2.
LCMS [M+1]: 484. $^1$H NMR (400 MHz, CDCl$_3$) δ 7.69 (dd, J=2.75, 6.17 Hz, 1H), 7.56-7.63 (m, 1H), 7.12 (t, J=9.35 Hz, 1H), 6.87 (s, 1H), 4.61-4.78 (m, 2H), 4.41 (m, 1H), 4.13 (m, 1H), 3.79-3.96 (m, 2H), 3.59-3.71 (m, 2H), 3.47 (m, 1H), 3.19 (s, 3H), 2.84 (t, J=5.93 Hz, 2H), 2.38-2.54 (m, 1H), 1.74 (br dd, J=3.24, 7.27 Hz, 1H), 1.71-1.81 (m, 1H), 1.51 (dt, J=7.64, 14.95 Hz, 2H), 1.04 (t, J=7.34 Hz, 3H).

Compound 099_E3: (S*)—N-(4-fluoro-3-(trifluoromethyl)phenyl)-8-((S*)-1-hydroxypropyl)-10-methyl-11-oxo-1,3,4,7,8,9,10,11-octahydro-2H-pyrido[4',3':3,4]pyrazolo[1,5-a][1,4]diazepine-2-carboxamide

*Pure but unknown diastereomer E3.
LCMS [M+1]: 484. $^1$H NMR (400 MHz, CDCl$_3$) δ 7.69 (dd, J=2.57, 5.87 Hz, 1H), 7.55-7.62 (m, 1H), 7.12 (t, J=9.41 Hz, 1H), 6.86 (s, 1H), 4.55-4.80 (m, 3H), 4.31 (m, 14.37 Hz, 1H), 3.82-3.93 (m, 2H), 3.48-3.57 (m, 1H), 3.36 (m, 2H), 3.19 (s, 3H), 2.84 (t, J=5.75 Hz, 2H), 2.39-2.54 (m, 1H), 1.95-2.10 (m, 1H), 1.45-1.55 (m, 2H), 1.02 (t, J=7.40 Hz, 3H).

Compound 099_E4: (R*)—N-(4-fluoro-3-(trifluoromethyl)phenyl)-8-((R*)-1-hydroxypropyl)-10-methyl-11-oxo-1,3,4,7,8,9,10,11-octahydro-2H-pyrido[4',3':3,4]pyrazolo[1,5-a][1,4]diazepine-2-carboxamide

*Pure but unknown diastereomer E4.
LCMS [M+1]: 484. ¹H NMR (400 MHz, CDCl₃) δ 7.66-7.72 (m, 1H), 7.55-7.63 (m, 1H), 7.12 (s, 1H), 6.86 (s, 1H), 4.55-4.79 (m, 3H), 4.24-4.37 (m, 1H), 3.87 (s, 2H), 3.47-3.59 (m, 1H), 3.36 (d, J=7.46 Hz, 2H), 3.19 (s, 3H), 2.80-2.89 (m, 2H), 2.44-2.55 (m, 1H), 1.99-2.13 (m, 1H), 1.44-1.55 (m, 2H), 1.02 (t, J=7.40 Hz, 3H).

Compound 100_E1: (R*)—N-(3-chloro-2,4-difluorophenyl)-8-((S*)-1-hydroxypropyl)-10-methyl-11-oxo-1,3,4,7,8,9,10,11-octahydro-2H-pyrido[4',3':3,4]pyrazolo[1,5-a][1,4]diazepine-2-carboxamide

*Pure but unknown diastereomer E1.
LCMS [M+1]: 468 ¹H NMR (400 MHz, CDCl₃) δ 7.86 (dt, J=5.56, 8.89 Hz, 1H), 6.90-7.00 (m, 1H), 6.60 (br s, 1H), 4.71 (d, J=1.34 Hz, 2H), 4.41 (m, 1H), 4.13 (m, 1H), 3.80-3.92 (m, 2H), 3.56-3.70 (m, 2H), 3.46 (m, 1H), 3.19 (s, 3H), 2.85 (t, J=5.62 Hz, 2H), 2.40-2.52 (m, 1H), 1.44-1.57 (m, 2H), 1.04 (t, J=7.40 Hz, 3H).

Compound 101_E1: (R*)—N-(3-bromo-2,4-difluorophenyl)-8-((S*)-1-hydroxypropyl)-10-methyl-11-oxo-1,3,4,7,8,9,10,11-octahydro-2H-pyrido[4',3':3,4]pyrazolo[1,5-a][1,4]diazepine-2-carboxamide

*Pure but unknown diastereomer E1.
LCMS [M+1]:512. ¹H NMR (400 MHz, CDCl₃) δ 7.92 (dt, J=5.62, 8.93 Hz, 1H), 6.93 (dt, J=2.08, 8.62 Hz, 1H), 6.61 (br s, 1H), 4.67-4.76 (m, 2H), 4.41 (m, 1H), 4.13 (m, 1H), 3.80-3.89 (m, 1H), 3.58-3.70 (m, 2H), 3.46 (m, 1H), 3.19 (s, 3H), 2.85 (t, J=5.81 Hz, 2H), 2.46 (m, 1H), 1.44-1.57 (m, 2H), 1.03 (t, J=7.40 Hz, 3H).

Compound 102_E1: (R*)—N-(3-bromo-4-fluorophenyl)-8-((S)-1-hydroxypropyl)-10-methyl-11-oxo-1,3,4,7,8,9,10,11-octahydro-2H-pyrido[4',3':3,4]pyrazolo[1,5-a][1,4]diazepine-2-carboxamide

*Pure but unknown diastereomer E1.
LCMS [M+1]: 494. ¹H NMR (400 MHz, CDCl₃) δ 7.72 (dd, J=2.69, 6.11 Hz, 1H), 7.24-7.27 (m, 1H), 7.03 (t, J=8.56 Hz, 1H), 6.68 (s, 1H), 4.60-4.73 (m, 2H), 4.41 (m, 1H), 4.13 (m, 1H), 3.76-3.93 (m, 2H), 3.64 (m, 2H), 3.46 (m, 1H), 3.19 (s, 3H), 2.83 (t, J=5.75 Hz, 2H), 2.41-2.52 (m, 1H), 1.76 (m, 1H), 1.43-1.57 (m, 2H), 1.04 (t, J=7.40 Hz, 3H).

Compound 103_E1: (R*)—N-(2,4-difluoro-3-(trifluoromethyl)phenyl)-8-((S*)-1-hydroxypropyl)-10-methyl-11-oxo-1,3,4,7,8,9,10,11-octahydro-2H-pyrido[4',3':3,4]pyrazolo[1,5-a][1,4] diazepine-2-carboxamide

*Pure but unknown diastereomer E1.
LCMS [M+1]: 502. ¹H NMR (400 MHz, CDCl₃) δ 8.13-8.28 (m, 1H), 6.90-7.10 (m, 1H), 6.69 (br s, 1H), 4.63-4.80 (m, 2H), 4.05-4.47 (m, 2H), 3.86 (m, 2H), 3.64 (m, 2H), 3.39-3.50 (m, 1H), 3.19 (s, 3H), 2.85 (br t, J=5.50 Hz, 2H), 2.40-2.52 (m, 1H), 1.44-1.55 (m, 2H), 1.04 (t, J=7.40 Hz, 3H).

Compound 104_E1: (R*)-8-((S*)-1-hydroxypropyl)-10-methyl-11-oxo-N-(3,4,5-trifluorophenyl)-1,3,4,7,8,9,10,11-octahydro-2H-pyrido[4',3':3,4]pyrazolo[1,5-a][1,4] diazepine-2-carboxamide

*Pure but unknown diastereomer E1.
LCMS [M+1]: 452. ¹H NMR (400 MHz, CDCl₃) δ 7.14 (dd, J=6.09, 9.60 Hz, 2H), 6.74-6.86 (m, 1H), 4.58-4.73 (m, 2H), 4.41 (m, 1H), 4.13 (m, 1H), 3.76-3.93 (m, 2H), 3.64 (m, 2H), 3.46 (m, 1H), 3.19 (s, 3H), 2.83 (br t, J=5.65 Hz, 2H), 2.40-2.53 (m, 1H), 1.41-1.57 (m, 2H), 1.04 (t, J=7.40 Hz, 3H).

Compound 105_E1: (R*)-8-((S*)-1-hydroxypropyl)-10-methyl-11-oxo-N-(2,3,4,5-tetrafluorophenyl)-1,3,4,7,8,9,10,11-octahydro-2H-pyrido[4',3':3,4]pyrazolo[1,5-a][1,4]diazepine-2-carboxamide

*Pure but unknown diastereomer E1.
LCMS [M+1]: 470. ¹H NMR (400 MHz, CDCl₃) δ 7.82 (m, 1H), 6.71 (br s, 1H), 4.70 (d, J=2.57 Hz, 2H), 4.41 (m, 1H), 4.13 (m, 1H), 3.78-3.92 (m, 2H), 3.60-3.67 (m, 2H), 3.46 (m, 1H), 3.19 (s, 3H), 2.85 (t, J=5.75 Hz, 2H), 2.40-2.52 (m, 1H), 1.42-1.57 (m, 2H), 1.03 (t, J=7.40 Hz, 3H).

Compound 106: N-(3-chloro-4-fluoro-phenyl)-8-(1-hydroxybutyl)-10-methyl-1-oxo-1,3,4,7,8,9-hexahydropyrido[2,3]pyrazolo[2,4-b][1,4]diazepine-2-carboxamide

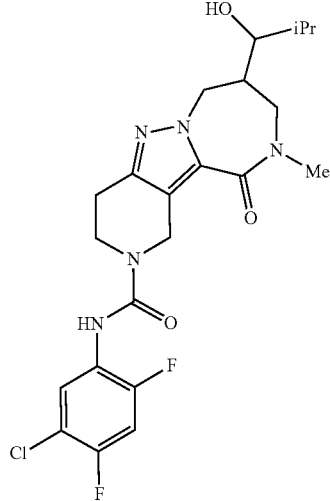 [SMILES: CC(C)C(O)C1CN(C)C(=O)c2c3c(nn2C1)CCN(C(=O)Nc1cc(Cl)c(F)cc1F)C3]

Step 1. tert-butyl 8-butanoyl-10-methyl-11-oxo-1,3,4,7,8,9-hexahydropyrido[2,3]pyrazolo[2,4-b][1,4]diazepine-2-carboxylate To a mixture of propylmagnesium bromide (2 M, 490.85 µL, 2.00 eq) in THF (3.00 mL) was added tert-butyl 8-[methoxy(methyl)carbamoyl]-10-methyl-11-oxo-1,3,4,7,8,9-hexahydropyrido[2,3]pyrazolo[2,4-b][1,4]diazepine-2-carboxylate (Compound 096, Product from Step 2, 200.00 mg, 490.85 µmol, 1.00 eq) in THF (3.00 mL) drop-wise at −10° C. under N₂. The mixture was heated to 0° C. and stirred for 1 hours. LCMS showed the starting material/Desired product=1:2, then added bromo(propyl)magnesium (2 M, 1.23 mL, 5.00 eq) at 0° C. and stirred for 1 hours. TLC (Ethyl acetate) showed the reaction was completed and mainly the desired product was detected. The mixture was poured into 1N HCl (50 mL) and stirred for 2 min. The aqueous phase was extracted with ethyl acetate (10 mL*2). The combined organic phase was washed with brine (10 mL*2), dried with anhydrous Na$_2$SO$_4$, filtered and concentrated in vacuum to afford the title compound (170.00 mg, 217.68 μmol, 44.35% yield, 50% purity) as yellow solid. LCMS[M+I]: 391.

Step 2. tert-butyl 8-(1-hydroxybutyl)-10-methyl-11-oxo-1,3,4,7,8,9-hexahydropyrido [2,3]pyrazolo[2,4-b][1,4]diazepine-2-carboxylate To a mixture of tert-butyl 8-butanoyl-10-methyl-11-oxo-1,3,4,7,8,9-hexahydropyrido[2,3]pyrazolo[2,4-b][1,4]diazepine-2-carboxylate (170.00 mg, 435.36 μmol, 1.00 eq) in MeOH (5.00 mL) was added NaBH$_4$ (32.94 mg, 870.72 μmol, 2.00 eq) in one portion at −10° C. under N$_2$. The mixture was stirred at −10° C. for 30 min, then heated to 25° C. and stirred for 1 hours. LCMS and TLC (Petroleum ether: Ethyl acetate=0:1) showed the reaction was completed. The mixture was poured into water (10 mL) and stirred for 2 min. The aqueous phase was extracted with ethyl acetate (10 mL*2). The combined organic phase was washed with brine (10 mL*2), dried with anhydrous Na$_2$SO$_4$, filtered and concentrated in vacuum. The residue was purified by prep-TLC (ethyl acetate) to afford the title compound (75.00 mg, 185.36 μmol, 42.58% yield, 97% purity) as yellow solid. LCMS [M+1]: 393.

Step 3. 8-(1-hydroxybutyl)-10-methyl-2,3,4,7,8,9-hexahydro-1H-pyrido[2,3]pyrazolo[2,4-b][1,4]diazepin-11-one To a mixture of tert-butyl 8-(1-hydroxybutyl)-10-methyl-11-oxo-1,3,4,7,8,9-hexahydropyrido[2,3]pyrazolo[2,4-b][1,4]diazepine-2-carboxylate (75.00 mg, 191.09 μmol, 1.00 eq) in DCM (2.00 mL) was added TFA (1.54 g, 13.51 mmol, 1.00 mL, 70.68 eq) in one portion at 30° C. under N$_2$. The mixture was stirred at 30° C. for 2 hours. TLC (Ethyl acetate) showed the reaction was completed. The mixture was concentrated in vacuum to afford the title compound (77.66 mg, 191.09 μmol, 100.00% yield, TFA) as yellow oil.

Step 4. N-(3-chloro-4-fluoro-phenyl)-8-(1-hydroxybutyl)-10-methyl-11-oxo-1,3,4,7,8,9-hexahydro-pyrido[2,3]pyrazolo[2,4-b][1,4]diazepine-2-carboxamide To a mixture of 8-(1-hydroxybutyl)-10-methyl-2,3,4,7,8,9-hexahydro-1H-pyrido[2,3]pyrazolo[2,4-b][1,4]diazepin-11-one (77.66 mg, 191.09 μmol, 1.00 eq, TFA) and phenyl N-(3-chloro-4-fluoro-phenyl)carbamate (50.77 mg, 191.09 μmol, 1.00 eq) in DCM (6.00 mL) was added TEA (193.37 mg, 1.91 mmol, 264.89 μL, 10.00 eq) under N$_2$. The mixture was stirred at 25° C. for 10 hours. LCMS showed the reaction was completed. The residue was poured into water (10 mL) and stirred for 2 min. The aqueous phase was extracted with ethyl acetate (10 mL*2). The combined organic phase was washed with brine (10 mL*2), dried with anhydrous Na$_2$SO$_4$, filtered and concentrated in vacuum. The residue was purified by prep-HPLC(FA) to afford the title compound (49.00 mg, 105.62 μmol, 55.27% yield) as white solid.

LCMS [M+1]: 464. $^1$H NMR (400 MHz, CDCl$_3$) δ 7.60 (dd, J=2.32, 6.36 Hz, 1H), 7.22 (m, 1H), 7.01-7.11 (m, 1H), 6.73 (m, 1H), 4.54-4.78 (m, 3H), 4.27-4.48 (m, 1H), 4.26-4.50 (m, 1H), 4.09-4.22 (m, 1H), 3.81-3.95 (m, 2H), 3.58-3.79 (m, 2H), 3.43-3.51 (m, 1H), 3.35-3.42 (m, 1H), 3.20 (s, 3H), 2.85 (br t, J=5.01 Hz, 2H), 2.41-2.53 (m, 1H), 1.40-1.55 (m, 4H), 0.99 (q, J=7.05 Hz, 3H).

Compound 107_D1: (3R,8S*)—N-(4-fluoro-3-(trifluoromethyl)phenyl)-8-((R)-1-hydroxypropyl)-3,10-dimethyl-11-oxo-1,3,4,7,8,9,10,11-octahydro-2H-pyrido[4',3':3,4]pyrazolo[1,5-a][1,4] diazepine-2-carboxamide

*Pure but unknown diastereomer D1.

To a solution of (3R,8 S*)—N-(4-fluoro-3-(trifluoromethyl)phenyl)-8-((R)-1-hydroxyallyl)-3,10-dimethyl-11-oxo-1,3,4,7,8,9,10,11-octahydro-2H-pyrido[4',3':3,4]pyrazolo[1,5-a][1,4]diazepine-2-carboxamide (Compound 122_D1, 45.00 mg, 90.82 μmol, 1.00 eq) in MeOH (5.00 mL) was added Pd/C (5.00 mg, 10% purity) under N$_2$, the suspension was degassed under vacuum and purged with H$_2$ three times, the mixture was stirred under H$_2$ (15 psi) at 20° C. for 30 minutes. LCMS showed one main peak with desired MS was detected. The reaction mixture was filtered and the filtrate was concentrated. The residue was purified by prep-HPLC(FA) to afford the title compound (44.00 mg, 86.68 μmol, 95.44% yield, 98% purity) as white solid. LCMS (M+1): 498. $^1$H NMR (400 MHz, CDCl$_3$) δ=7.69 (dd, J=2.75, 6.05 Hz, 1H), 7.55-7.62 (m, 1H), 7.13 (t, J=9.41 Hz, 1H), 6.64 (s, 1H), 5.15 (m, 1H), 4.80 (m, 1H), 4.39-4.54 (m, 2H), 4.12 (m, 1H), 3.62-3.71 (m, 2H), 3.48 (m, 1H), 3.20 (s, 3H), 3.01 (m, 1H), 2.67 (m, 1H), 2.41-2.52 (m, 1H), 1.45-1.57 (m, 2H), 1.19 (d, J=6.97 Hz, 3H), 1.05 (t, J=7.40 Hz, 3H).

Compounds 107~109_D1&D2 were prepared in a manner analogous to Compound 107.

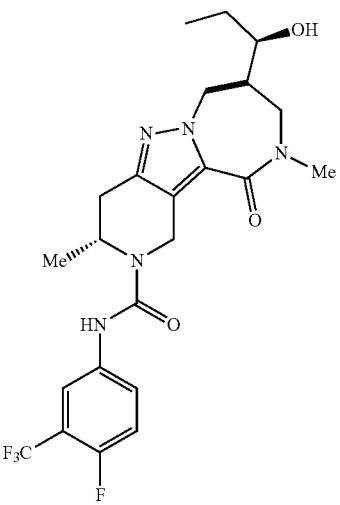

107 D1

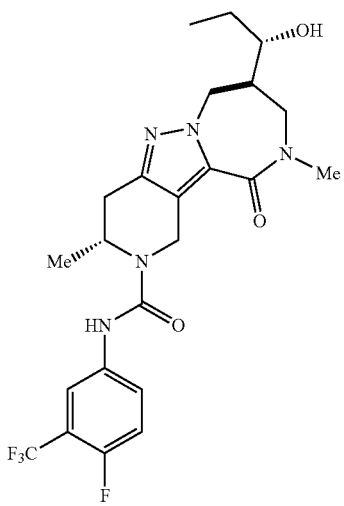

107 D2

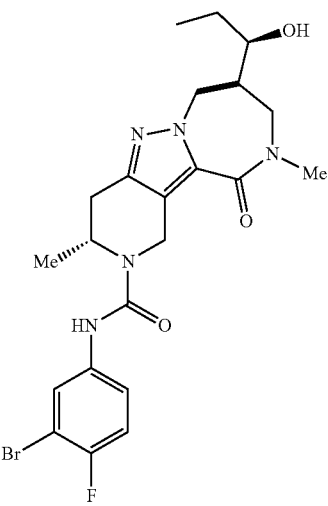

109 D1

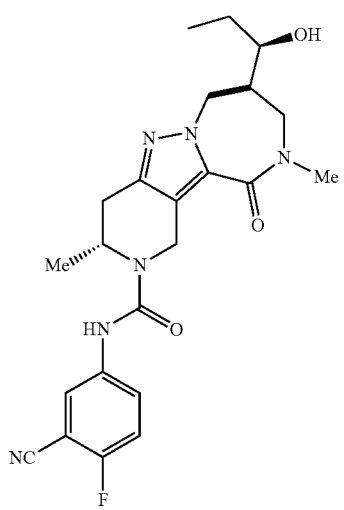

108 D1

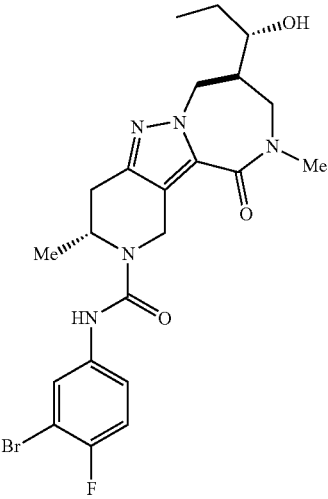

109 D2

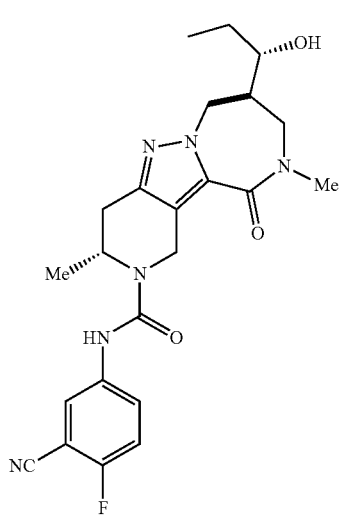

108 D2

Compound 107_D2: (3R,8R*)—N-(4-fluoro-3-(trifluoromethyl)phenyl)-8-((R)-1-hydroxypropyl)-3,10-dimethyl-11-oxo-1,3,4,7,8,9,10,11-octahydro-2H-pyrido[4',3':3,4]pyrazolo[1,5-a][1,4]diazepine-2-carboxamide The title compound was prepared in a manner analogous to Compound 107_D1, using Compound 122_D2. *Pure but unknown diastereomer D2.

LCMS (M+1): 498. $^1$H NMR (400 MHz, CDCl$_3$) δ=7.70 (dd, J=2.75, 6.17 Hz, 1H), 7.55-7.62 (m, 1H), 7.13 (t, J=9.35 Hz, 1H), 6.66 (s, 1H), 5.16 (br t, J=6.36 Hz, 1H), 4.84 (m, 1H), 4.39-4.49 (m, 2H), 4.16 (m, 1H), 3.65 (m, 2H), 3.48 (m, 1H), 3.20 (s, 3H), 3.03 (m, 1H), 2.65 (m, 1H), 2.45-2.55 (m, 1H), 1.44-1.56 (m, 2H), 1.18 (d, J=6.85 Hz, 3H), 1.04 (t, J=7.40 Hz, 3H).

Compound 108_D1: (3R,8S*)—N-(3-cyano-4-fluorophenyl)-8-((R)-1-hydroxypropyl)-3,10-dimethyl-11-oxo-1,3,4,7,8,9,10,11-octahydro-2H-pyrido[4',3':3,4]pyrazolo[1,5-a][1,4]diazepine-2-carboxamide The title compound was prepared in a manner analogous to Compound 107_D1, using Compound 123_D1. *Pure but unknown diastereomer D1.

LCMS (M+1): 455. $^1$H NMR (400 MHz, CDCl$_3$) δ=7.79 (dd, J=2.81, 5.38 Hz, 1H), 7.59 (m, 1H), 7.13 (t, J=8.74 Hz,

1H), 6.80 (s, 1H), 5.14 (m, 1H), 4.80 (m, 1H), 4.39-4.52 (m, 2H), 4.13 (m, 1H), 3.61-3.70 (m, 2H), 3.48 (m, 1H), 3.20 (s, 3H), 3.01 (dd, J=5.81, 15.83 Hz, 1 H), 2.67 (m, 1H), 2.43-2.53 (m, 1H), 1.44-1.60 (m, 2H), 1.19 (d, J=6.97 Hz, 3H), 1.04 (t, J=7.40 Hz, 3H).

Compound 108_D2: (3R,8R*)—N-(3-cyano-4-fluorophenyl)-8-((R)-1-hydroxypropyl)-3,10-dimethyl-11-oxo-1,3,4,7,8,9,10,11-octahydro-2H-pyrido[4',3':3,4]pyrazolo[1,5-a][1,4]diazepine-2-carboxamide The title compound was prepared in a manner analogous to Compound 107_D 1, using Compound 123_D2. *Pure but unknown diastereomer D2.

LCMS (M+1): 455. $^1$H NMR (400 MHz, CDCl$_3$) δ=7.80 (dd, J=2.81, 5.50 Hz, 1H), 7.59 (m, 1H), 7.13 (t, J=8.74 Hz, 1H), 6.82 (s, 1H), 5.09-5.20 (m, 1H), 4.84 (m, 1H), 4.39-4.48 (m, 2H), 4.15 (m, 1H), 3.65 (m, 2H), 3.48 (m, 1H), 3.20 (s, 3H), 3.02 (m, 1H), 2.65 (m, 1H), 2.45-2.55 (m, 1H), 1.43-1.60 (m, 2H), 1.18 (d, J=6.85 Hz, 3H), 1.04 (t, J=7.40 Hz, 3H).

Compound 109_D1: (3R,8 S*)—N-(3-bromo-4-fluorophenyl)-8-((R)-1-hydroxypropyl)-3,10-dimethyl-11-oxo-1,3,4,7,8,9,10,11-octahydro-2H-pyrido[4',3':3,4]pyrazolo[1,5-a][1,4]diazepine-2-carboxamide The title compound was prepared in a manner analogous to Compound 107_D 1, Compound 124 D1. *Pure but unknown diastereomer D1.

LCMS (M+1): 508/510. $^1$H NMR (400 MHz, CDCl$_3$) δ=7.74 (dd, J=2.70, 6.09 Hz, 1H), 7.22-7.27 (m, 1H), 7.00-7.07 (m, 1H), 6.55 (s, 1H), 5.08-5.19 (m, 1H), 4.78 (m, 1H), 4.39-4.51 (m, 2H), 4.11 (m, 1H), 3.61-3.71 (m, 2H), 3.48 (m, 1H), 3.20 (s, 3H), 3.01 (m, 1H), 2.66 (m, 1H), 2.41-2.52 (m, 1H), 1.42-1.57 (m, 2H), 1.18 (d, J=6.90 Hz, 3H), 1.05 (t, J=7.40 Hz, 3H).

Compound 109_D2: (3R,8R*)—N-(3-bromo-4-fluorophenyl)-8-((R)-1-hydroxypropyl)-3,10-dimethyl-11-oxo-1,3,4,7,8,9,10,11-octahydro-2H-pyrido[4',3':3,4]pyrazolo[1,5-a][1,4]diazepine-2-carboxamide The title compound was prepared in a manner analogous to Compound 107_D 1, Compound 124_D2. *Pure but unknown diastereomer D2.

LCMS (M+1): 508/510. $^1$H NMR (400 MHz, CDCl$_3$) δ=7.75 (dd, J=2.70, 6.09 Hz, 1H), 7.25 (m, 1H), 7.04 (t, J=8.53 Hz, 1H), 6.61 (s, 1H), 5.15 (m, 1H), 4.82 (d, J=15.43 Hz, 1H), 4.38-4.48 (m, 2H), 4.15 (m, 1H), 3.64 (m, 2H), 3.47 (m, 1H), 3.19 (s, 3H), 3.02 (m, 1H), 2.64 (m, 1H), 2.45-2.55 (m, 1H), 1.44-1.59 (m, 2H), 1.17 (d, J=6.90 Hz, 3H), 1.04 (t, J=7.40 Hz, 3H).

Compound 110: N-(3-chloro-4-fluorophenyl)-11-methyl-12-oxo-3,4,7,8,9,10,11,12-octahydropyrido[4',3':3,4]pyrazolo[1,5-a][1,4]diazocine-2 (1H)-carboxamide

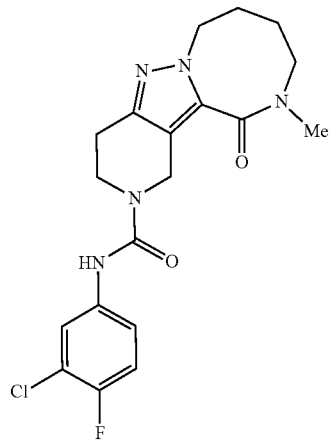 [SMILES: CN1CCCCn2nc3c(c2C1=O)CN(C(=O)Nc1ccc(F)c(Cl)c1)CC3]

Step 1. 11-methyl-1,2,3,4,7,8,9,10-octahydropyrido[2,3]pyrazolo[2,4-b][1,4]diazocin-12-one To a solution of tert-butyl 11-methyl-12-oxo-3,4,7,8,9,10-hexahydro-1H-pyrido[2,3]pyrazolo[2,4-b][1,4]diazocine-2-carboxylate (Intermediate 23, 61.00 mg, 182.41 μmol, 1.00 eq) in DCM (5.00 mL) was added TFA (308.00 mg, 2.70 mmol, 200.00 μL, 14.81 eq), then the mixture was stirring at 25° C. for 1 h. TLC (PE:EtOAc=1:3) showed that compound 7 consumed completely and one new spot formed. The mixture was concentrated in vacuo to afford the title compound (65.00 mg, crude, TFA) as yellow oil, without further purification and directly used in the next step.

Step 2. N-(3-chloro-4-fluorophenyl)-11-methyl-12-oxo-3,4,7,8,9,10,11,12-octahydropyrido[4',3':3,4]pyrazolo[1,5-a][1,4]diazocine-2 (1H)-carboxamide To a solution of 11-methyl-1,2,3,4,7,8,9,10-octahydropyrido[2,3]pyrazolo[2,4-b][1,4]diazocin-12-one (65.00 mg, 186.61 μmol, 1.00 eq, TFA) and phenyl N-(3-chloro-4-fluoro-phenyl)carbamate (54.53 mg, 205.27 μmol, 1.10 eq) in DCM (3.00 mL) was added TEA (151.06 mg, 1.49 mmol, 206.94 μL, 8.00 eq), then the mixture was stirring at 25° C. for 16 h. LCMS indicated that 11-methyl-1,2,3,4,7,8,9,10-octahydropyrido[2,3]pyrazolo[2,4-b][1,4]diazocin-12-one was consumed completely and desired product was detected. The mixture was concentrated in vacuo. The residue was purified by prep-HPLC (FA) to afford the title compound (33.32 mg, 81.61 μmol, 43.73% yield, 99.4% purity) as a yellow solid. LCMS: 406[M+1]. $^1$H NMR (400 MHz, CDCl$_3$) δ=7.58 (dd, J=2.69, 6.60 Hz, 1H), 7.16-7.22 (m, 1H), 7.02-7.09 (m, 1H), 6.55 (s, 1H), 4.60 (s, 2H), 4.29 (br s, 2H), 3.85 (t, J=5.75 Hz, 2H), 3.31 (br d, J=8.80 Hz, 2H), 3.14 (s, 3H), 2.84 (t, J=5.81 Hz, 2H), 1.97 (br s, 2H), 1.86 (br s, 2H).

291

Compound 111: (Z)—N-(3-chloro-4-fluorophenyl)-11-methyl-12-oxo-3,4,7,10,11,12-hexahydropyrido[4',3':3,4]pyrazolo[1,5-a][1,4]diazocine-2 (1H)-carboxamide

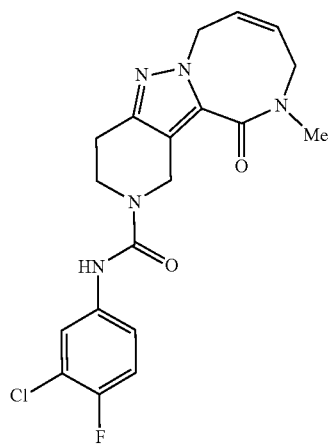 [SMILES: CN1C/C=C\Cn2nc3c(c2C1=O)CN(C(=O)Nc1ccc(F)c(Cl)c1)CC3]

Step 1. (8Z)-11-methyl-1,2,3,4,7,10-hexahydro-pyrido[2,3]pyrazolo[2,4-b][1,4]diazocin-12-one To a solution of tert-butyl (8Z)-11-methyl-12-oxo-3,4,7,10-tetrahydro-1H-pyrido[2,3]pyrazolo[2,4-b][1,4]diazocine-2-carboxylate (Intermediate 22, 50.00 mg, 150.42 μmol, 1.00 eq) in DCM (3.00 mL) was added TFA (329.99 mg, 2.89 mmol, 214.28 μL, 19.24 eq), then the mixture was stirring at 25° C. for 1 h. TLC (PE:EtOAc=1:3) showed that the reactant 6 consumed completely and one new spot formed. The mixture was concentrated in vacuum. The title compound (55.00 mg, crude, TFA) was obtained as yellow oil.

Step 2. (Z)—N-(3-chloro-4-fluorophenyl)-11-methyl-12-oxo-3,4,7,10,11,12-hexahydropyrido[4',3':3,4]pyrazolo[1,5-a][1,4]diazocine-2 (1H)-carboxamide To a solution of (8Z)-11-methyl-1,2,3,4,7,10-hexahydro-pyrido[2,3]pyrazolo [2,4-b][1,4]diazocin-12-one (55.00 mg, 158.82 μmol, 1.00 eq, TFA) and phenyl N-(3-chloro-4-fluoro-phenyl)carbamate (46.41 mg, 174.70 μmol, 1.10 eq) in DCM (3.00 mL) was added TEA (128.57 mg, 1.27 mmol, 176.12 μL, 8.00 eq), then the mixture was stirring at 25° C. for 16 h. LCMS indicated that (8Z)-11-methyl-1,2,3,4,7,10-hexahydropyrido[2,3]pyrazolo[2,4-b][1,4]diazocin-12-one was consumed completely and desired product was detected. The mixture was concentrated in vacuo. The residue was purified by prep-HPLC(FA) to afford the title compound (25.57 mg, 62.68 μmol, 39.47% yield, 99% purity) as yellow solid. LCMS: 404[M+1]. $^1$H NMR (400 MHz, CDCl$_3$) δ=7.57 (dd, J=2.63, 6.54 Hz, 1H), 7.16-7.21 (m, 1H), 7.03-7.09 (m, 1H), 6.54 (s, 1H), 5.91-6.05 (m, 2H), 4.89 (d, J=3.79 Hz, 2H), 4.61 (s, 2H), 3.85 (t, J=5.87 Hz, 2H), 3.80 (br d, J=5.38 Hz, 2H), 3.12 (s, 3H), 2.85 (t, J=5.81 Hz, 2H).

292

Compound 112: N-(3-cyano-4-fluorophenyl)-7-(3,3-difluoro-1-hydroxypropyl)-10-methyl-11-oxo-1,3,4,7,8,9,10,11-octahydro-2H-pyrido[4',3':3,4]pyrazolo[1,5-a][1,4]diazepine-2-carboxamide

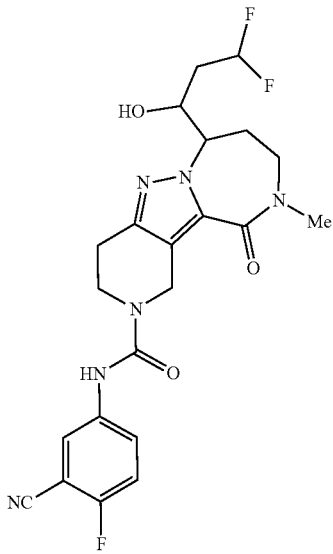 [SMILES: CN1CCC(C(O)CC(F)F)n2nc3c(c2C1=O)CN(C(=O)Nc1ccc(F)c(C#N)c1)CC3]

The title compound was prepared in a manner analogous to Compound 116, using phenyl (3-cyano-4-fluorophenyl)carbamate in Step 5. LCMS: 477[M+1]. $^1$H NMR (400 MHz, CDCl$_3$) δ=7.79 (dd, J=2.7, 5.4 Hz, 1H), 7.60 (br d, J=9.8 Hz, 1H), 7.15 (t, J=8.6 Hz, 1H), 6.79 (brs, 1H), 5.92-6.28 (m, 1H), 4.58-4.80 (m, 3H), 4.22-4.49 (m, 2H), 4.13 (brs, 1H), 3.84-3.95 (m, 3H), 3.63 (m, 1H), 3.29-3.50 (m, 2H), 3.21 (d, J=2.6 Hz, 3H), 2.86 (br t, J=5.5 Hz, 2H), 2.70 (brs, 1H), 2.56 (brd, J=6.2 Hz, 1H), 2.25 (brs, 1H), 2.00-2.13 (m, 2H).

Compound 113: 2-((3-chloro-4-fluorophenyl)carbamoyl)-10-methyl-11-oxo-1,3,4,7,8,9,10,11-octahydro-2H-pyrido[4',3':3,4]pyrazolo[1,5-a][1,4]diazepine-7-carboxylic acid

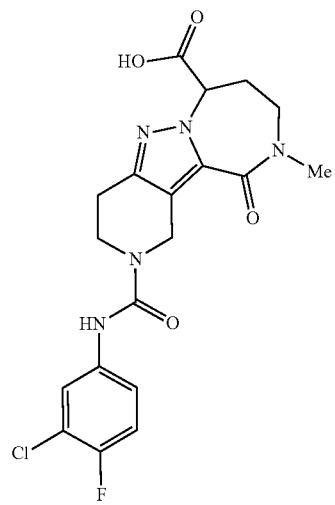 [SMILES: CN1CCC(C(=O)O)n2nc3c(c2C1=O)CN(C(=O)Nc1ccc(F)c(Cl)c1)CC3]

Step 1. methyl 2-((3-chloro-4-fluorophenyl)carbamoyl)-10-methyl-11-oxo-1,3,4,7,8,9,10,11-octahydro-2H-pyrido[4',3':3,4]pyrazolo[1,5-a][1,4]diazepine-7-carboxylate and 2-((3-chloro-4-fluorophenyl)carbamoyl)-10-methyl-11-oxo-1,3,4,7,8,9,10,11-octahydro-2H-pyrido[4',3':3,4]pyrazolo[1,5-a][1,4]diazepine-7-carboxylic acid To a solution of 2-(tert-butoxycarbonyl)-10-methyl-11-oxo-1,3,4,7,8,9,10,11-octahydro-2H-pyrido[4',3':3,4]pyrazolo[1,5-a][1,4]diazepine-7-carboxylic acid (Intermediate 26, 116.00 mg) in MeOH (2.00 mL) was added HCl/MeOH (4 M, 2.00 mL). The mixture was stirred at 20° C. for 2 hr. TLC (DCM:MeOH=10:1) showed one main spot appeared. The mixture was concentrated in vacuum a residue (96.00 mg, crude, HCl) as brown oil.

Step 2. 2-((3-chloro-4-fluorophenyl)carbamoyl)-10-methyl-11-oxo-1,3,4,7,8,9,10,11-octahydro-2H-pyrido[4',3':3,4]pyrazolo[1,5-a][1,4]diazepine-7-carboxylic acid To a solution of methyl above oil (95.00 mg, 301.81 µmol, 1.00 eq, HCl) and phenyl N-(3-chloro-4-fluoro-phenyl)carbamate (80.18 mg, 301.81 µmol, 1.00 eq) in DCM (3.00 mL) was added TEA (152.70 mg, 1.51 mmol, 209.18 µL, 5.00 eq). The mixture was stirred at 20° C. for 5 hr. Several peaks showed on LCMS, 24% 2-((3-chloro-4-fluorophenyl)carbamoyl)-10-methyl-11-oxo-1,3,4,7,8,9,10,11-octahydro-2H-pyrido[4',3':3,4]pyrazolo[1,5-a][1,4]diazepine-7-carboxylic acid and 22% methyl 2-((3-chloro-4-fluorophenyl)carbamoyl)-10-methyl-11-oxo-1,3,4,7,8,9,10,11-octahydro-2H-pyrido[4',3':3,4]pyrazolo[1,5-a][1,4]diazepine-7-carboxylate were detected. The mixture was extracted with EtOAc (10 mL*2) and H₂O (10 mL). The combined organic layer was washed 1N HCl (10 mL), dried over Na₂SO₄, filtrated and concentrated in vacuum. The residue was purified by prep-TLC (PE:EtOAc=0:1) and prep-HPLC(FA) to afford methyl 2-((3-chloro-4-fluorophenyl)carbamoyl)-10-methyl-11-oxo-1,3,4,7,8,9,10,11-octahydro-2H-pyrido[4',3':3,4]pyrazolo[1,5-a][1,4]diazepine-7-carboxylate (40.00 mg, 88.92 µmol, 29.46% yield) as colorless oil and 2-((3-chloro-4-fluorophenyl)carbamoyl)-10-methyl-11-oxo-1,3,4,7,8,9,10,11-octahydro-2H-pyrido[4',3':3,4]pyrazolo[1,5-a][1,4]diazepine-7-carboxylic acid (9.00 mg, 19.25 µmol, 6.38% yield, 93.2% purity) as white solid. LCMS: 436[M+1]. $^1$H NMR (400 MHz, METHANOL-d₄) δ=7.61 (dd, J=2.63, 6.66 Hz, 1H), 7.26-7.38 (m, 1H), 7.06-7.20 (m, 1H), 5.32 (br d, J=9.54 Hz, 1H), 4.65-4.73 (m, 1H), 4.54-4.80 (m, 1H), 4.69 (brs, 3H), 3.71-3.97 (m, 2H), 3.54-3.65 (m, 1H), 3.52-3.65 (m, 1H), 3.37-3.52 (m, 1H), 3.36-3.52 (m, 1H), 3.66 (s, 1H), 3.36-3.53 (m, 1H), 3.34-3.70 (m, 1H), 3.15 (brs, 1H), 3.08 (s, 2H), 2.98-3.00 (m, 1H), 2.90-2.99 (m, 1H), 2.89-2.99 (m, 1H), 2.89-2.99 (m, 1H), 2.89-2.99 (m, 1H), 2.88-3.00 (m, 1H), 2.74-2.86 (m, 2H), 2.41-2.60 (m, 1H), 2.41-2.60 (m, 1H).

Compound 114: N-(3-chloro-4-fluorophenyl)-7-(hydroxymethyl)-10-methyl-11-oxo-1,3,4,7,8,9,10,11-octahydro-2H-pyrido[4',3':3,4]pyrazolo[1,5-a][1,4]diazepine-2-carboxamide

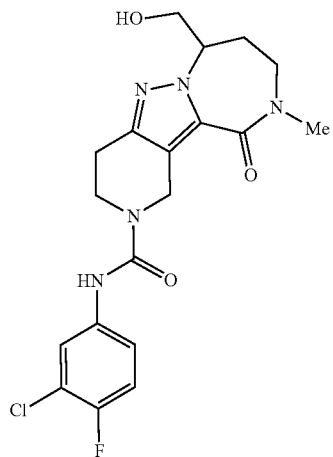 [SMILES: CN1CCC(CO)n2nc3c(c2C1=O)CN(C(=O)Nc1ccc(F)c(Cl)c1)CC3]

Step 1. methyl 10-methyl-11-oxo-2,3,4,7,8,9-hexahydro-1H-pyrido[2,3]pyrazolo[2,4-c][1,4]diazepine-7-carboxylate To a solution of 2-(tert-butoxycarbonyl)-10-methyl-11-oxo-1,3,4,7,8,9,10,11-octahydro-2H-pyrido[4',3':3,4]pyrazolo[1,5-a][1,4]diazepine-7-carboxylic acid (Intermediate 26, 370.00 mg, 1.02 mmol, 1.00 eq) in MeOH (10.00 mL) was added HCl/MeOH (4 M, 10.00 mL, 39.22 eq). The mixture was heated to 45° C. for 1 hr. TLC (DCM:MeOH=10:1) showed the starting material consumed and one main spot appeared. The mixture was concentrated in vacuum to afford methyl 10-methyl-11-oxo-2,3,4,7,8,9-hexahydro-1H-pyrido[2,3]pyrazolo[2,4-c][1,4]diazepine-7-carboxylate (340.00 mg, crude, HCl) as brown solid.

Step 2. 2-tert-butyl 7-methyl 10-methyl-11-oxo-1,3,4,7,8,9-hexahydro pyrido[2,3]pyrazolo[2,4-c][1,4]diazepine-2,7-dicarboxylate To a solution of methyl 10-methyl-11-oxo-2,3,4,7,8,9-hexahydro-1H-pyrido[2,3]pyra-zolo[2,4-c][1,4]diazepine-7-carboxylate (240.00 mg, 762.46 mol, 1.00 eq, HCl) in DCM (10.00 mL) was added TEA (385.77 mg, 3.81 mmol, 528.45 µL, 5.00 eq) followed by Boc₂O (332.81 mg, 1.52 mmol, 350.33 µL, 2.00 eq). The mixture was heated to 20° C. for 16 hr. LCMS showed one main peak with desired Ms detected. The mixture was extracted with EtOAc (20 mL*3) and H₂O (10 mL). The combined organic layer was washed with 1N HCl (10 mL), dried over Na₂SO₄, filtrated and concentrated in vacuum. The residue was purified by column chromatography (PE:EtOAc=70%~100%) to afford the title compound (160.00 mg, 422.81 µmol, 55.45% yield) as colorless oil.

Step 3. tert-butyl 7-(hydroxymethyl)-10-methyl-11-oxo-1,3,4,7,8,9-hexahydropyrido[2,3]pyrazolo[2,4-c][1,4]diazepine-2-carboxylate To a solution of 2-tert-butyl 7-methyl 10-methyl-11-oxo-1,3,4,7,8,9-hexahydro pyrido[2,3]pyrazolo[2,4-c][1,4]diazepine-2,7-dicarboxylate (60.00 mg, 158.55 μmol, 1.00 eq) in THF (3.00 mL) was added LiBH$_4$ (13.81 mg, 634.20 μmol, 4.00 eq) at 0° C. The mixture was stirred at 25° C. for 1 hr. TLC (PE:EtOAc=0:1) showed the starting material consumed and three new spots formed. LCMS showed one main peak with desired Ms detected. The mixture was quenched with saturated NH$_4$C$_1$ (20 mL) and extracted with EtOAc(20 mL*3). The combined organic layer was dried over Na$_2$SO$_4$, filtrated and concentrated in vacuum to afford the title compound (45.00 mg, crude) as colorless oil.

Step 5. N-(3-chloro-4-fluorophenyl)-7-(hydroxymethyl)-10-methyl-11-oxo-1,3,4,7,8,9,10,11-octahydro-2H-pyrido[4',3':3,4]pyrazolo[1,5-a][1,4]diazepine-2-carboxamide To a solution of tert-butyl 7-(hydroxymethyl)-10-methyl-11-oxo-1,3,4,7,8,9-hexahydropyrido[2,3]pyrazolo[2,4-c][1,4]diazepine-2-carboxylate (60.00 mg, 171.23 μmol, 1.00 eq) in DCM (3.00 mL) was added TFA (4.62 g, 40.52 mmol, 3.00 mL, 236.64 eq). The mixture was stirred at 25° C. for 1 hr. TLC (PE:EtOAc=0:1) showed the starting material consumed. The mixture was concentrated in vacuum to get 7-(hydroxymethyl)-10-methyl-2,3,4,7,8,9-hexahydro-1H-pyrido[2,3]pyrazolo[2,4-c][1,4]diazepin-11-one (63.00 mg, crude, TFA) as brown oil.

Step 6. N-(3-chloro-4-fluorophenyl)-7-(hydroxymethyl)-10-methyl-11-oxo-1,3,4,7,8,9,10,11-octahydro-2H-pyrido[4',3':3,4]pyrazolo[1,5-a][1,4]diazepine-2-carboxamide To a solution of 7-(hydroxymethyl)-10-methyl-2,3,4,7,8,9-hexahydro-1H-pyrido[2,3]pyrazolo[2,4-c][1,4]diazepin-11-one (62.00 mg, 170.18 μmol, 1.00 eq, TFA) and phenyl N-(3-chloro-4-fluoro-phenyl)carbamate (45.21 mg, 170.18 μmol, 1.00 eq) in DCM (3.00 mL) was added TEA (86.10 mg, 850.90 μmol, 117.95 μL, 5.00 eq). The mixture was stirred at 20° C. for 5 hr. TLC (DCM:MeOH=10:1) showed one main spot appeared. The mixture was extracted with EtOAc (10 mL*2) and H$_2$O (10 mL). The combined organic layer was washed 1N HCl (10 mL), dried over Na$_2$SO$_4$, filtrated and concentrated in vacuum. The residue was purified by prep-TLC (DCM:MeOH=10:1) to get 40 mg product, which was combined with another batch (EW619-1536, 15 mg with 80% purity) to further purify by prep-HPLC(FA) to afford the title compound (40.00 mg, 65.51 μmol, 38.50% yield, 98.7% purity) as colorless oil. LCMS: 422[M+1]. $^1$H NMR (400 MHz, METHANOL-d$_4$) δ=7.60 (dd, J=2.57, 6.60 Hz, 1H), 7.27-7.35 (m, 1H), 7.11-7.19 (m, 1H), 4.59-4.73 (m, 3H), 3.84-3.94 (m, 3H), 3.72-3.83 (m, 3H), 3.53-3.63 (m, 1H), 3.36-3.46 (m, 1H), 3.15 (s, 3H), 2.83 (t, J=5.75 Hz, 2H), 2.40-2.52 (m, 2H), 2.23-2.35 (m, 1H).

Compound 115: N-(3-chloro-4-fluoro-phenyl)-8-(3-fluoro-1-hydroxy-propyl)-10-methyl-1-oxo-1,3,4,7,8,9-hexahydropyrido[2,3]pyrazolo[2,4-b][1,4]diazepine-2-carboxamide

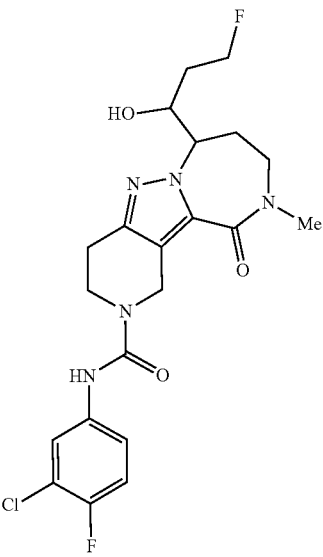 [SMILES: CN1CCC(C(O)CCF)n2nc3c(c2C1=O)CN(C(=O)Nc1ccc(F)c(Cl)c1)CC3]

Step 1. tert-butyl 8-(1-benzyloxy-3-fluoro-propyl)-10-methyl-11-oxo-1,3,4,7,8,9-hexahydropyrido[2,3]pyrazolo[2,4-b][1,4]diazepine-2-carboxylate To a solution of tert-butyl 8-(1-benzyloxy-3-hydroxy-propyl)-10-methyl-11-oxo-1,3,4,7,8,9-hexahydropyrido[2,3]pyrazolo[2,4-b][1,4]diazepine-2-carboxylate (Intermediate 28, 90.00 mg, 185.72 μmol, 1.00 eq) in THF (1.00 mL) was added DAST (119.75 mg, 742.88 μmol, 98.16 μL, 4.00 eq) at −40° C. The mixture was stirred at −40° C. for 1 hr. TLC (PE:EtOAc=1:2) showed the starting material consumed and one main spot appeared. The mixture was extracted with DCM (10 mL*2) and H$_2$O (10 mL). The combined organic layer was washed saturated NaHCO$_3$ (10 mL), dried over Na$_2$SO$_4$, filtrated and concentrated in vacuum. The residue was purified by prep-TLC (PE:EtOAc=1:2) to afford the title compound (55.00 mg, 91.56 μmol, 49.30% yield, 81% purity) as yellow oil.

Step 2. tert-butyl 8-(3-fluoro-1-hydroxy-propyl)-10-methyl-11-oxo-1,3,4,7,8,9-hexahydropyrido[2,3]pyrazolo[2,4-b][1,4]diazepine-2-carboxylate To a solution of tert-butyl 8-(1-benzyloxy-3-fluoro-propyl)-10-methyl-11l-oxo-1,3,4,7,8,9-hexahydropyrido[2,3]pyrazolo[2,4-b][1,4]diazepine-2-carboxylate (55.00 mg, 113.03 μmol, 1.00 eq) in MeOH (10.00 mL) was added Pd/C (50.00 mg) under N₂. The suspension was degassed under vacuum and purged with H₂ several times. The mixture was stirred under H₂ (50 Psi) at 30° C. for 32 hours. LCMS indicated that 70% of the starting material still remained and 13% of desired product was detected. Then the mixture was filtered and the filtrate was added Pd/C (50.00 mg) under N₂. The suspension was degassed under vacuum and purged with H₂ several times. The mixture was stirred under H₂ (50 Psi) at 30° C. for 48 hours. LCMS indicated that 8% of the starting material still remained and 70% of desired product was detected. The mixture was filtered and concentrated in vacuum. The title compound (45.00 mg, crude) was obtained as colorless oil.

Step 3. 8-(3-fluoro-1-hydroxy-propyl)-10-methyl-2,3,4,7,8,9-hexahydro-1H-pyrido[2,3]pyrazolo[2,4-b][1,4]diazepin-11-one To a solution of tert-butyl 8-(3-fluoro-1-hydroxy-propyl)-10-methyl-11-oxo-1,3,4,7,8,9-hexahydropyrido[2,3]pyrazolo[2,4-b][1,4]diazepine-2-carboxylate (45.00 mg, 113.50 µmol, 1.00 eq) in DCM (2.00 mL) was added TFA (308.00 mg, 2.70 mmol, 200.00 µL, 23.80 eq) with stirring at 20° C. for 1 h. TLC (PE:EtOAc=0:1) showed that the reactant 9 consumed completely and one main new spot formed. The mixture was concentrated in vacuum. The title compound (47.00 mg, crude, TFA) was obtained as yellow oil and used in the next step.

Step 4. N-(3-chloro-4-fluoro-phenyl)-8-(3-fluoro-1-hydroxy-propyl)-10-methyl-1-oxo-1,3,4,7,8,9-hexahydropyrido[2,3]pyrazolo[2,4-b][1,4]diazepine-2-carboxamide To a solution of 8-(3-fluoro-1-hydroxy-propyl)-10-methyl-2,3,4,7,8,9-hexahydro-1H-pyrido[2,3]pyrazolo[2,4-b][1,4]diazepin-11-one (47.00 mg, 114.53 µmol, 1.00 eq, TFA) and TEA (69.54 mg, 687.18 µmol, 95.26 µL, 6.00 eq) in DCM (2.00 mL) was added phenyl N-(3-chloro-4-fluoro-phenyl)carbamate (30.43 mg, 114.53 µmol, 1.00 eq) with stirring at 20° C. for 16 h. LCMS indicated that the starting material was consumed completely and desired product was detected. The mixture was concentrated in vacuum. The resulting residue was purified by prep-HPLC (FA) to afford the title compound (10.00 mg, 21.16 µmol, 18.47% yield, 99% purity) as white solid. LCMS: 468[M+1]. ¹H NMR (400 MHz, CDCl₃) δ=7.59 (dd, J=2.64, 6.53 Hz, 1H), 7.15-7.22 (m, 1H), 7.03-7.09 (m, 1H), 6.56 (s, 1H), 4.71-4.84 (m, 1H), 4.61-4.71 (m, 3H), 4.39-4.61 (m, 1H), 4.15-4.39 (m, 1H), 3.99 (br s, 1H), 3.79-4.03 (m, 3H), 3.30-3.68 (m, 2H), 3.19 (d, J=4.02 Hz, 3H), 2.84 (t, J=5.65 Hz, 2H), 2.50-2.61 (m, 1H), 2.16-2.43 (m, 1H), 1.78-2.00 (m, 2H).

Compound 116: N-(3-chloro-4-fluoro-phenyl)-8-(3,3-difluoro-1-hydroxy-propyl)-10-methyl-1-oxo-1,3,4,7,8,9-hexahydropyrido[2,3]pyrazolo[2,4-b][1,4]diazepine-2-carboxamide

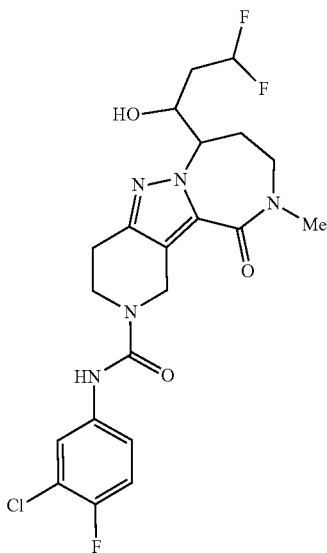 [SMILES: CN1CCC(C(O)CC(F)F)n2nc3c(c2C1=O)CN(C(=O)Nc1ccc(F)c(Cl)c1)CC3]

Step 1. tert-butyl 8-(1-benzyloxy-3-oxo-propyl)-10-methyl-11-oxo-1,3,4,7,8,9-hexahydropyrido[2,3]pyrazolo[2,4-b][1,4]diazepine-2-carboxylate To a solution of tert-butyl 8-(1-benzyloxy-3-hydroxy-propyl)-10-methyl-11-oxo-1,3,4,7,8,9-hexahydropyrido[2,3]pyrazolo[2,4-b][1,4]diazepine-2-carboxylate (Intermediate 28, 200.00 mg, 412.72 µmol, 1.00 eq) in DCM (4.00 mL) was added Dess-Martin (525.15 mg, 1.24 mmol, 383.32 µL, 3.00 eq) at 0° C. The mixture was stirred at 25° C. for 1 hr. TLC (PE:EtOAc=0:1) showed the starting material consumed and one main new spot formed. The reaction mixture was diluted with DCM (50 mL) and filtrated. The filtrate was concentrated in vacuum. The residue was purified by prep-TLC (PE:EtOAc=0:1) to afford the title compound (160.00 mg, 331.56 µmol, 80.34% yield) as white solid.

Step 2. tert-butyl 8-(1-benzyloxy-3,3-difluoro-propyl)-10-methyl-11-oxo-1,3,4,7,8,9-hexa hydropyrido[2,3]pyrazolo[2,4-b][1,4]diazepine-2-carboxylate To a solution of tert-butyl 8-(1-benzyloxy-3-oxo-propyl)-10-methyl-11-oxo-1,3,4,7,8,9-hexahydropyrido[2,3]pyrazolo[2,4-b][1,4]diazepine-2-carboxylate (116.00 mg, 227.95 µmol, 1.00 eq) in DCM (1.00 mL) was added DAST (146.97 mg, 911.80 µmol, 120.47 µL, 4.00 eq) at -40° C. The mixture was stirred at 20° C. for 1 hr. TLC (PE:EtOAc=1:1) showed the starting material consumed and one main spot formed. The mixture was extracted with DCM (10 mL*2) and H₂O (10 mL). The combined organic layer was dried over Na₂SO₄, filtrated and concentrated in vacuum. The residue was purified by prep-TLC (PE:EtOAc=1:1) to get tert-butyl 8-(1-benzyloxy-3,3-difluoro-propyl)-10-methyl-11-oxo-1,3,4,7,8,9-hexahydropyrido[2,3]pyrazolo[2,4-b][1,4]diazepine-2-carboxylate (75.00 mg, 123.37 µmol, 54.12% yield, 83% purity) as yellow oil. The residue was purified by prep-HPLC (FA) to afford the title compound (56.00 mg, 109.54 μmol, 69.09% yield, 98.7% purity) as yellow oil.

Step 3. tert-butyl 8-(3,3-difluoro-1-hydroxy-propyl)-10-methyl-11-oxo-1,3,4,7,8,9-hexahydropyrido[2,3]pyrazolo[2,4-b][1,4]diazepine-2-carboxylate To a solution of tert-butyl 8-(1-benzyloxy-3,3-difluoro-propyl)-10-methyl-11-oxo-1,3,4,7,8,9-hexahydropyrido[2,3]pyrazolo[2,4-b][1,4]diazepine-2-carboxylate (50.00 mg, 99.09 μmol, 1.00 eq) in MeOH (15.00 mL) was added Pd/C (10.00 mg, 99.09 μmol, 10% purity, 1.00 eq) and HOAc (595.06 ug, 9.91 μmol, 0.57 μL, 0.10 eq) under N₂. The suspension was degassed under vacuum and purged with H₂ several times. The mixture was stirred under H₂ (15 psi) at 25° C. for 24 hours. TLC (PE:EtOAc=0:1) showed the starting material remained, the mixture was diluted with MeOH (20 mL), filtrated. The filtrate was added Pd/C (20 mg) under N₂. The suspension was degassed under vacuum and purged with H₂ several times. The mixture was stirred under H₂ (40 psi) at 30° C. for 20 hours. LCMS showed the starting material remained and 60% desired product. The mixture was stirred under H₂ (45 psi) at 30° C. for another 16 hours. LCMS showed the starting material consumed completely. The mixture was diluted with MeOH (30 mL) and filtrated. The filtrate was concentrated in vacuum to afford the title compound (60.00 mg, crude) as yellow oil.

Step 4. 8-(3,3-difluoro-1-hydroxy-propyl)-10-methyl-2,3,4,7,8,9-hexahydro-1H-pyrido [2,3]pyrazolo[2,4-b][1,4]diazepin-11-one To a solution of tert-butyl 8-(3,3-difluoro-1-hydroxy-propyl)-10-methyl-11l-oxo-1,3,4,7,8,9-hexahydropyrido[2,3]pyrazolo[2,4-b][1,4]diazepine-2-carboxylate (60.00 mg, 144.77 μmol, 1.00 eq) in DCM (5.00 mL) was added TFA (40.52 mmol, 3.00 mL, 279.89 eq). The mixture was stirred at 20° C. for 0.5 hr. TLC (PE:EtOAc=0:1) showed the starting material consumed. The mixture was concentrated in vacuum to afford the title compound (64.00 mg, crude, TFA) as yellow oil.

Step 5. N-(3-chloro-4-fluoro-phenyl)-8-(3,3-difluoro-1-hydroxy-propyl)-10-methyl-11-oxo-1,3,4,7,8,9-hexahydropyrido[2,3]pyrazolo[2,4-b][1,4]diazepine-2-carboxamide To a solution of 8-(3,3-difluoro-1-hydroxy-propyl)-10-methyl-2,3,4,7,8,9-hexahydro-1H-pyrido[2,3]pyrazolo[2,4-b][1,4]diazepin-11-one (30.00 mg, 70.04 μmol, 1.00 eq, TFA) and phenyl N-(3-chloro-4-fluoro-phenyl)carbamate (18.61 mg, 70.04 μmol, 1.00 eq) in DCM (5.00 mL) was added TEA (35.44 mg, 350.20 μmol, 48.55 μL, 5.00 eq). The mixture was stirred at 20° C. for 16 hr. LCMS showed one main peak (254 nm) with desired Ms detected. The mixture was concentrated in vacuum. The residue was purified by prep-HPLC (FA) to afford the title compound (14.00 mg, 28.32 μmol, 40.44% yield, 98.3% purity) as white solid.

LCMS: 486[M+1]. ¹H NMR (400 MHz, CDCl₃) δ=7.79 (dd, J=2.7, 5.4 Hz, 1H), 7.60 (br d, J=9.8 Hz, 1H), 7.15 (t, J=8.6 Hz, 1H), 6.79 (brs, 1H), 5.92-6.28 (m, 1H), 4.58-4.80 (m, 3H), 4.22-4.49 (m, 2H), 4.13 (brs, 1H), 3.84-3.95 (m, 3H), 3.63 (m, 1H), 3.29-3.50 (m, 2H), 3.21 (d, J=2.6 Hz, 3H), 2.86 (br t, J=5.5 Hz, 2H), 2.70 (brs, 1H), 2.56 (br d, J=6.2 Hz, 1H), 2.25 (brs, 1H), 2.00-2.13 (m, 2H).

Compound 117: 8-(acetamidomethyl)-N-(3-chloro-4-fluorophenyl)-10-methyl-11-oxo-1,3,4,7,8,9,10,11-octahydro-2H-pyrido[4',3':3,4]pyrazolo[1,5-a][1,4]diazepine-2-carboxamide

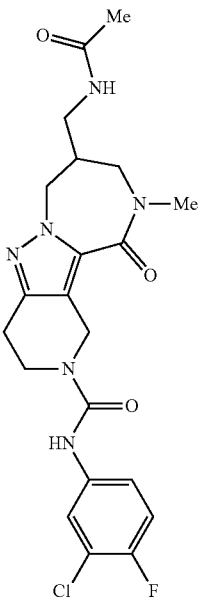 [SMILES: CC(=O)NCC1CN(C)C(=O)c2c3c(nn2C1)CCN(C(=O)Nc1ccc(F)c(Cl)c1)C3]

A mixture of 8-(aminomethyl)-N-(3-chloro-4-fluoro-phenyl)-10-methyl-11-oxo-1,3,4,7,8,9-hexahydropyrido[2,3]pyrazolo[2,4-b][1,4]diazepine-2-carboxamide (Compound 070, 30.00 mg, 71.28 μmol, 1.00 eq), TEA (10.82 mg, 106.92 μmol, 14.82 μL, 1.50 eq) and Ac₂O (8.73 mg, 85.54 μmol, 8.01 μL, 1.20 eq) in DCM (3.00 mL) was degassed and purged with N₂ for 3 times, and then the mixture was stirred at 20° C. for 1 hour under N₂ atmosphere. LCMS showed the starting material was consumed completely, desired product was major. The mixture was poured into water (10 mL) and stirred at 5 min. The aqueous phase was extracted with DCM (5 mL*3). The combined organic phase was washed with brine (10 mL), dried with anhydrous Na₂SO₄, filtered and concentrated in vacuum. The residue was purified by Prep-HPLC (HCl) to afford the title compound (25.00 mg, 53.47 μmol, 75.01% yield, 99% purity) as a white solid. LCMS: 463/465 [M+1]. ¹H NMR (400 MHz, CDCl₃) δ 7.55-7.61 (m, 1H), 7.15-7.22 (m, 1H), 7.04-7.10 (m, 1H), 6.47 (s, 1H), 6.12-6.20 (m, 1H), 4.67 (m, 2H), 4.29-4.45 (m, 2H), 3.87 (m, 2H), 3.41 (m, 2H), 3.19 (s, 4H), 3.01-3.13 (m, 1H), 2.88 (m, 3H), 2.00 (s, 3H).

Compound 118: N-(3-cyano-4-fluorophenyl)-8-(((2,2-difluoroethyl)amino)methyl)-10-methyl-11-oxo-1,3,4,7,8,9,10,11-octahydro-2H-pyrido[4',3':3,4]pyrazolo[1,5-a][1,4]diazepine-2-carboxamide

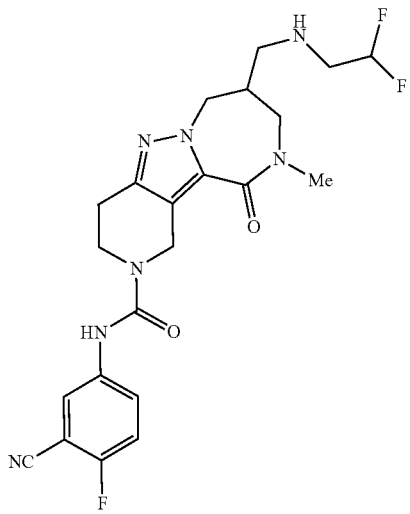 [SMILES: CN1CC(CNCC(F)F)Cn2nc3c(c2C1=O)CN(C(=O)Nc1ccc(F)c(C#N)c1)CC3]

Step 1. 8-[(2,2-difluoroethylamino)methyl]-10-methyl-2,3,4,7,8,9-hexahydro-1H-pyrido[2,3]pyrazolo[2,4-b][1,4]diazepin-11-one A solution of tert-butyl8-[(2,2-difluoroethylamino)methyl]-10-methyl-11l-oxo-1,3,4,7,8,9-hexahydropyrido[2,3]pyrazolo[2,4-b][1,4]diazepine-2-carboxylate (Intermediate 29, 80.00 mg, 193.49 µmol, 1.00 eq) in DCM (2.00 mL) was added TFA (6.16 g, 54.03 mmol, 4.00 mL, 279.23 eq), and then the mixture was stirred at 20° C. for 1 hour. TLC showed the starting material was consumed completely and a new spot formed. The mixture was concentrated in vacuum to afford the title compound (104.75 mg, 193.48 µmol, 100.00% yield, 2TFA) as a yellow oil, which was used directly for next step.

Step 2. N-(3-cyano-4-fluorophenyl)-8-(((2,2-difluoroethyl)amino)methyl)-10-methyl-1-oxo-1,3,4,7,8,9,10,11-octahydro-2H-pyrido[4',3':3,4]pyrazolo[1,5-a][1,4]diazepine-2-carboxamide A mixture of 8-[(2,2-difluoroethylamino)methyl]-10-methyl-2,3,4,7,8,9-hexahydro-1H-pyrido[2,3]pyrazolo[2,4-b][1,4]diazepin-11-one (80.00 mg, 147.77 µmol, 1.00 eq, 2TFA), phenyl N-(3-cyano-4-fluoro-phenyl)carbamate (34.08 mg, 132.99 µmol, 0.90 eq), TEA (29.91 mg, 295.54 µmol, 40.97 µL, 2.00 eq) in DCM (3.00 mL) was degassed and purged with $N_2$ for 3 times, and then the mixture was stirred at 30° C. for 16 hour under $N_2$ atmosphere. LCMS showed the starting material was consumed completely, desired product was major. The mixture was poured into water (10 mL) and extracted with DCM (5 mL). The combined organic phase was washed with brine (10 mL), dried with anhydrous $Na_2SO_4$, filtered and concentrated in vacuum. The residue was purified by Prep-HPLC (HCl), following by Prep-HPLC (BASE) to afford the title compound (51.00 mg, 106.19 µmol, 71.86% yield, 99% purity) as a white solid. $^1$H NMR (400 MHz, CDCl$_3$) δ 7.77 (dd, J=2.75, 5.44 Hz, 1H), 7.55-7.62 (m, 1H), 7.09-7.16 (m, 1H), 6.79 (s, 1H), 5.70-5.98 (m, 1H), 4.68 (s, 2H), 4.36-4.47 (m, 1H), 4.17 (dd, J=5.62, 14.31 Hz, 1H), 3.80-3.92 (m, 2H), 3.42-3.50 (m, 1H), 3.30-3.40 (m, 1H), 3.18 (s, 3H), 2.94-3.07 (m, 2H), 2.69-2.87 (m, 4H), 2.50-2.62 (m, 1H), 1.14-1.31 (m, 1H).

Compound 118_E1: (R*)—N-(3-cyano-4-fluorophenyl)-8-(((2,2-difluoroethyl)amino)methyl)-10-methyl-11-oxo-1,3,4,7,8,9,10,11-octahydro-2H-pyrido[4',3':3,4]pyrazolo[1,5-a][1,4]diazepine-2-carboxamide

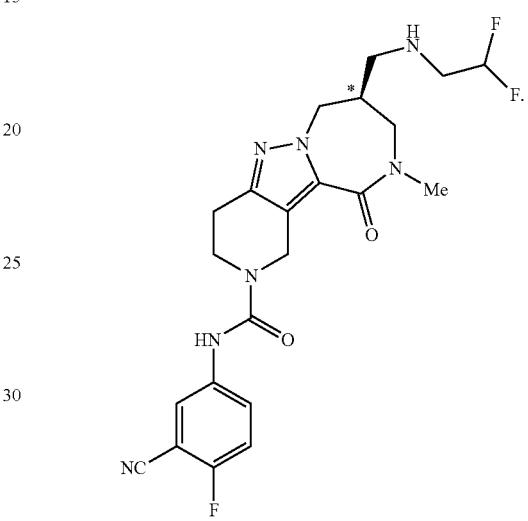

*Pure but unknown diastereomer E1

Step 1. tert-butyl 8-[[tert-butoxycarbonyl(2,2-difluoroethyl)amino]methyl]-10-methyl-11-oxo-1,3,4,7,8,9-hexahydropyrido[2,3]pyrazolo[2,4-b][1,4]diazepine-2-carboxylate A mixture of racemic tert-butyl 8-[(2,2-difluoroethylamino)methyl]-10-methyl-11-oxo-1,3,4,7,8,9-hexahydropyrido[2,3]pyrazolo[2,4-b][1,4]diazepine-2-carboxylate (Intermediate 29, 1.60 g, 3.87 mmol, 1.00 eq), Boc$_2$0 (2.53 g, 11.61 mmol, 2.67 mL, 3.00 eq), TEA (1.37 g, 13.54 mmol, 1.88 mL, 3.50 eq) in DCM (20.00 mL) was degassed and purged with $N_2$ for 3 times, and then the mixture was stirred at 30° C. for 72 hour under $N_2$ atmosphere. TLC showed the starting material was consumed completely, and a new spot formed. The mixture was concentrated in vacuum. The residue was purified by column chromatography (SiO$_2$, Petroleum ether/Ethyl acetate=100/1 to 1:1) to afford the title compound (1.88 g, 3.51 mmol, 90.81% yield, 96% purity) as a yellow solid, which was separated by SFC (column: IC (250 mm*30 mm, 10 um); mobile phase: [0.1% NH$_3$H$_2$O IPA]; B %: 40%~40%,4.7 min; 500minmin) to give each 930 mg of both enantiomers.

Step 2. 8-[(2,2-difluoroethylamino)methyl]-10-methyl-2,3,4,7,8,9-hexahydro-1H-pyrido[2,3]pyrazolo[2,4-b][1,4]diazepin-11-one To a solution of tert-butyl 8-[[tert-butoxycarbonyl(2,2-difluoroethyl)amino] methyl]-10-methyl-11-oxo-1,3,4,7,8, 9-hexahydropyrido[2,3]pyrazolo[2,4-b][1,4]diazepine-2-carboxylate (630.00 mg, 1.23 mmol, 1.00 eq) in DCM (4.00 mL) was added TFA (3.08 g, 27.01 mmol, 2.00 mL, 21.96 eq) at 0° C. The mixture was stirred at 25° C. for 1 h. The mixture was concentrated under reduced pressure to afford the title compound (665.00 mg, 1.17 mmol, 94.87% yield, 95% purity, 2TFA) as yellow oil, the crude product was used directly for the next step.

Step 3. (R*)—N-(3-cyano-4-fluorophenyl)-8-(((2,2-difluoroethyl)amino)methyl)-10-methyl-11-oxo-1,3,4,7,8,9,10,11-octahydro-2H-pyrido[4',3': 3,4]pyrazolo[1,5-a][1,4]diazepine-2-carboxamide To a solution of 8-[(2,2-difluoroethylamino)methyl]-10-methyl-2,3,4,7,8,9-hexahydro-1H-pyrido[2,3]pyrazolo[2,4-b][1,4]diazepin-11-one (52.00 mg, 96.05 μmol, 1.00 eq, 2TFA) in DCM (3.00 mL) was added phenyl N-(3-cyano-4-fluoro-phenyl)carbamate (24.61 mg, 96.05 μmol, 1.00 eq) and Et₃N (48.60 mg, 480.25 μmol, 66.57 μL, 5.00 eq). The mixture was stirred at 25° C. for 16 h. The mixture was concentrated under reduced pressure. The residue combined with EW5335-130 was purified by prep-HPLC(HCl) to afford the title compound (37.50 mg, 71.05 μmol, 97% purity, HCl) as yellow solid. LCMS:476 [M+1]. ¹H NMR (400 MHz, METHANOL-d₄) δ 7.81 (dd, J=2.81, 5.62 Hz, 1H), 7.69 (m, 1H), 7.27 (t, J=8.99 Hz, 1H), 6.21-6.52 (m, 1H), 4.69 (s, 2H), 4.52 (m, 1H), 4.33 (m, 1H), 3.73-3.94 (m, 2H), 3.53-3.72 (m, 3H), 3.09-3.26 (m, 5H), 2.97 (br d, J=6.48 Hz, 1H), 2.77-2.88 (m, 2H).

118/119/127-125_E1, 118/119/127-125_E2 were prepared through an analogous procedure to Compound 118

118 E2

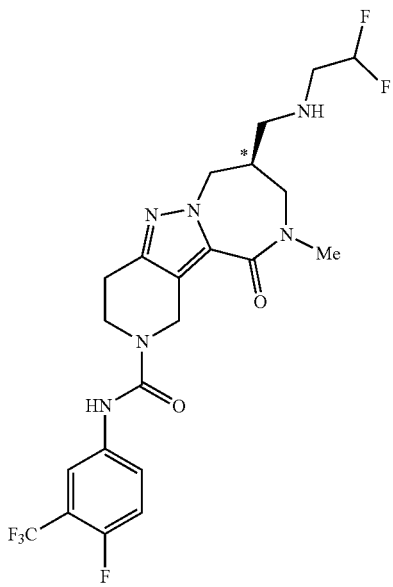

119 E1

119 E2

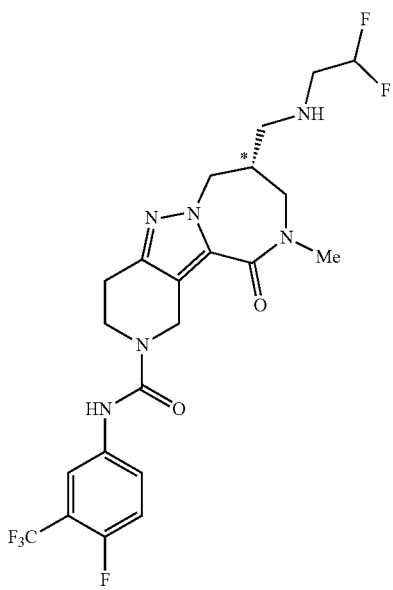

305
-continued
126 E1
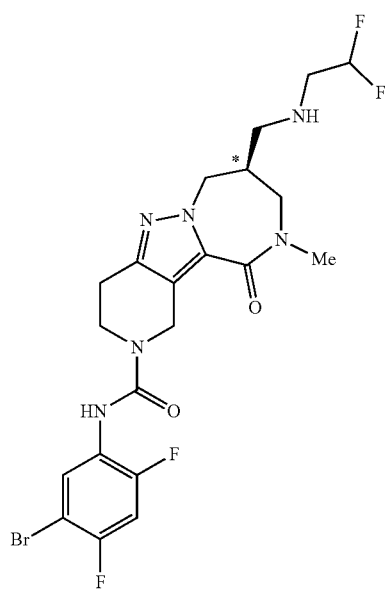
306
-continued
125 E1
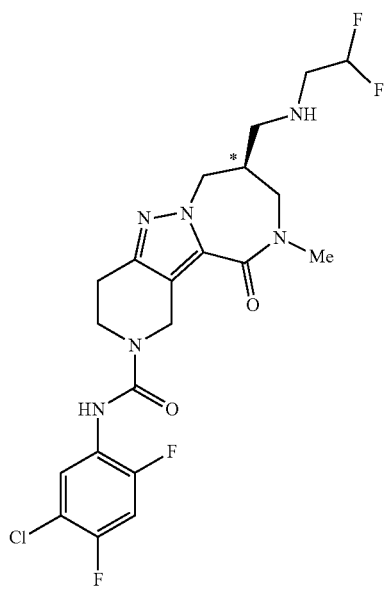
125 E2
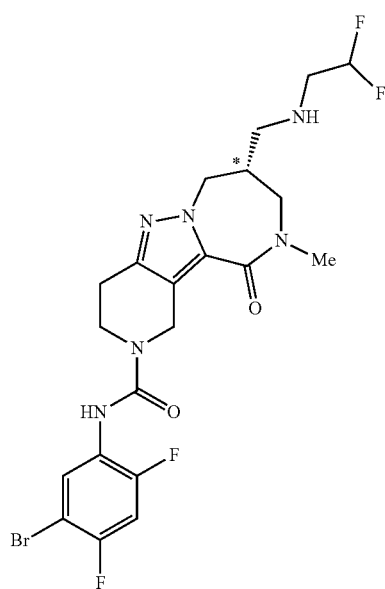
126 E2
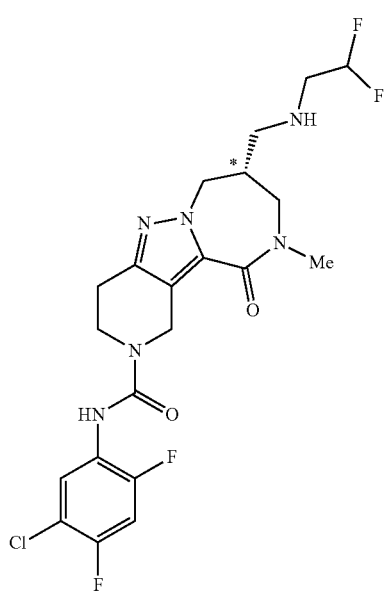

307

-continued

127 E1

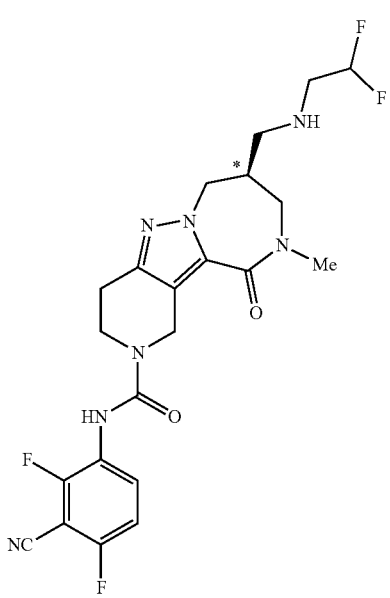

127 E2

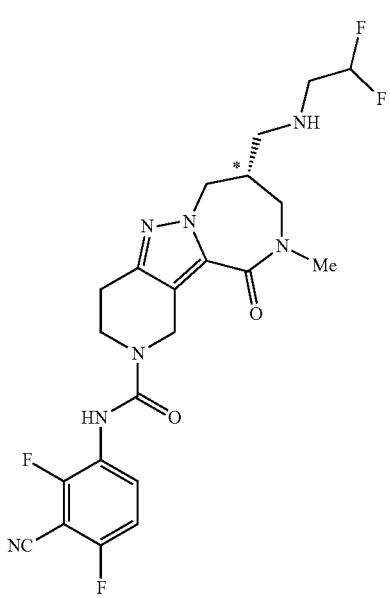

Compound 118_E2: (S*)—N-(3-cyano-4-fluorophenyl)-8-(((2,2-difluoroethyl)amino)methyl)-10-methyl-11-oxo-1,3,4,7,8,9,10,11-octahydro-2H-pyrido[4',3':3,4]pyrazolo[1,5-a][1,4]diazepine-2-carboxamide The title compound was prepared in a manner analogous to Compound 118_E1. *Pure but unknown diastereomer E2. LCMS:476 [M+1]. $^1$H NMR (400 MHz, CDCl$_3$) δ 7.77 (dd, J=2.76, 5.40 Hz, 1H), 7.61 (m, 1H), 7.12 (t, J=8.72 Hz, 1H), 7.06 (s, 1H), 5.65-6.01 (m, 1H), 4.61-4.74 (m, 2H), 4.40 (m, 1H), 4.17 (m, 1H), 3.86 (t, J=5.83 Hz, 2H), 3.30-3.52 (m, 2 H), 3.17 (s, 3H), 2.93-3.07 (m, 2H), 2.84 (t, J=5.77 Hz, 2H), 2.67-2.79 (m, 2H), 2.50-2.61 (m, 1H).

308

Compound 119: 8-(((2,2-difluoroethyl)amino)methyl)-N-(4-fluoro-3-(trifluoromethyl)phenyl)-10-methyl-11-oxo-1,3,4,7,8,9,10,11-octahydro-2H-pyrido[4',3':3,4]pyrazolo[1,5-a][1,4] diazepine-2-carboxamide

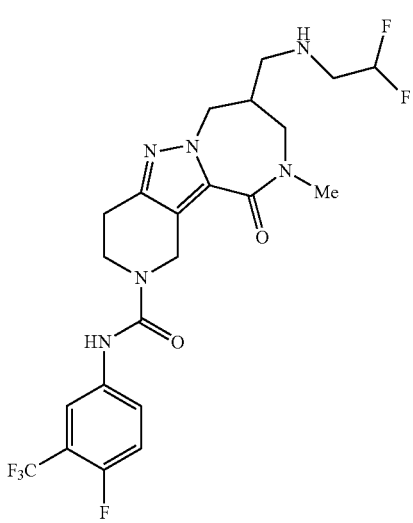 [SMILES: CN1CC(CNCC(F)F)Cn2nc3c(c2C1=O)CN(C(=O)Nc1ccc(F)c(C(F)(F)F)c1)CC3]

Step 1. tert-butyl 8-[[2,2-difluoroethyl-(2,2,2-trifluoroacetyl)amino]methyl]-10-methyl-1-ox o-1,3,4,7,8,9-hexahydropyrido[2,3]pyrazolo[2,4-b][1,4]diazepine-2-carboxylate A mixture of tert-butyl8-[(2,2-difluoroethylamino)methyl]-10-methyl-11-oxo-1,3,4,7,8,9-hexahydropyrido[2,3]pyrazolo[2,4-b][1,4]diazepine-2-carboxylate (Intermediate 29, 89.00 mg, 215.26 μmol, 1.00 eq), TEA (43.56 mg, 430.52 μmol, 59.67 μL, 2.00 eq) in DCM (5.00 mL) was added (2,2,2-trifluoroacetyl) 2,2,2-trifluoroacetate (67.82 mg, 322.89 μmol, 44.91 μL, 1.50 eq) dropwise at 0° C. under N$_2$. Then the mixture was stirred at 30° C. for 1 hour under N$_2$ atmosphere. TLC showed the starting material was consumed completely, desired product was major. The mixture was poured into water (10 mL) and extracted with DCM (5 mL*3). The combined organic phase was washed with brine (10 mL), dried with anhydrous Na$_2$SO$_4$, filtered and concentrated in vacuum. The residue was purified by Prep-TLC (DCM/MeOH=10/1) to afford the title compound (85.00 mg, 158.50 μmol, 73.63% yield, 95% purity) as a white solid. LCMS: 509 [M+1].

Step 2. N-(2,2-difluoroethyl)-2,2,2-trifluoro-N-[(10-methyl-11-oxo-2,3,4,7,8,9-hexahydro-1H-pyrido[2,3]pyrazolo[2,4-b][1,4]diazepin-8-yl)methyl]acetamide A solution of tert-butyl8-[[2,2-difluoroethyl-(2,2,2-trifluoroacetyl)amino]methyl]-10-methyl-11-oxo-1,3,4,7,8,9-hexahydropyrido[2,3]pyrazolo[2,4-b][1,4]diazepine-2-carboxylate (85.00 mg, 166.84 μmol, 1.00 eq) in DCM (2.00 mL) was added TFA (2.62 g, 22.96 mmol, 1.70 mL, 137.62 eq), and then the mixture was stirred at 30° C. for 1 hour. TLC showed the starting material was consumed completely, a new spot appeared. The mixture was concentrated in vacuum to afford the title compound (87.00 mg, 166.23 µmol, 99.63% yield, TFA) as a yellow oil, which was used directly for next step.

Step 3. 8-[[2,2-difluoroethyl-(2,2,2-trifluoroacetyl) amino]methyl]-N-[4-fluoro-3-(trifluoromethyl)phenyl]-10-methyl-11-oxo-1,3,4,7,8,9-hexahydropyrido [2,3]pyrazolo[2,4-b][1,4]diazepine-2-carboxamide A mixture of N-(2,2-difluoroethyl)-2,2,2-trifluoro-N-[(10-methyl-11-oxo-2,3,4,7,8,9-hexahydro-1H-pyrido[2,3] pyrazolo[2,4-b][1,4]diazepin-8-yl)methyl]acetamide (85.00 mg, 162.41 µmol, 1.00 eq, TFA), phenyl N-[4-fluoro-3-(trifluoromethyl)phenyl] carbamate (58.31 mg, 194.89 µmol, 1.20 eq), TEA (82.17 mg, 812.03 mol, 112.56 µL, 5.00 eq) in DCM (5.00 mL) was degassed and purged with N₂ for 3 times, and then the mixture was stirred at 30° C. for 16 hour under N₂ atmosphere. LCMS showed the starting material was consumed completely, desired product was major. The mixture was poured into water (10 mL) and stirred at 5 min. The aqueous phase was extracted with DCM (5 mL*3). The combined organic phase was washed with brine (10 mL), dried with anhydrous Na₂SO₄, filtered and concentrated in vacuum. The residue was purified by Prep-TLC (PE/EtOAc=0/1) to afford the title compound (74.00 mg, 115.61 µmol, 71.19% yield, 96% purity) as a white solid. LCMS: 614 [M+1].

Step 4. 8-(((2,2-difluoroethyl)amino)methyl)-N-(4-fluoro-3-(trifluoromethyl)phenyl)-10-methyl-11-oxo-1,3,4,7,8,9,10,11-octahydro-2H-pyrido[4',3':3,4] pyrazolo[1,5-a][1,4]diazepine-2-carboxamide A mixture of 8-[[2,2-difluoroethyl-(2,2,2-trifluoroacetyl) amino]methyl]-N-[4-fluoro-3-(trifluoromethyl)phenyl]-10-methyl-11-oxo-1,3,4,7,8,9-hexahydropyrido[2,3]pyrazolo [2,4-b][1,4]diazepine-2-carboxamide (74.00 mg, 120.43 µmol, 1.00 eq), K₂CO₃ (49.93 mg, 361.29 µmol, 3.00 eq) in MeOH (5.00 mL) and H₂O (1.00 mL) was degassed and purged with N₂ for 3 times, and then the mixture was stirred at 50° C. for 1 hour under N₂ atmosphere. LCMS showed the starting material was consumed completely, and desired product was major. The mixture was poured into water (10 mL) and extracted with DCM (5 mL*3). The combined organic phase was washed with brine (10 mL), dried with anhydrous Na₂SO₄, filtered and concentrated in vacuum. The residue was purified by Prep-HPLC (Base) to afford the title compound (32.00 mg, 59.25 µmol, 49.20% yield, 96% purity) as a white solid. ¹H NMR (400 MHz, CDCl₃) δ 7.66-7.71 (m, 1H), 7.56-7.62 (m, 1H), 7.09-7.16 (m, 1H), 6.75-6.80 (m, 1H), 5.67-6.03 (m, 1H), 4.69 (s, 2H), 4.35-4.47 (m, 1H), 4.12-4.23 (m, 1H), 3.87 (m, 2H), 3.42-3.50 (m, 1H), 3.35-3.37 (d, J=7.28 Hz, 1H), 3.18 (s, 3H), 2.95-3.06 (m, 2H), 2.68-2.88 (m, 4H), 2.50-2.62 (m, 1H), 1.11-1.34 (m, 1H).

Compound 119_E1: (R*)-8-(((2,2-difluoroethyl) amino)methyl)-N-(4-fluoro-3-(trifluoromethyl)phenyl)-10-methyl-11-oxo-1,3,4,7,8,9,10,11-octahydro-2H-pyrido[4',3':3,4]pyrazolo[1,5-a][1,4]diazepine-2-carboxamide

*Pure but unknown diastereomer E1.
LCMS: 519 [M+1]. ¹H NMR (400 MHz, CDCl₃) δ 7.68 (dd, J=2.70, 6.09 Hz, 1H), 7.55-7.63 (m, 1H), 7.12 (t, J=9.41 Hz, 1H), 6.87 (s, 1H), 5.67-6.01 (m, 1H), 4.69 (d, J=1.51 Hz, 2H), 4.40 (dd, J=6.78, 14.31 Hz, 1H), 4.17 (m, 1H), 3.81-3.92 (m, 2H), 3.30-3.50 (m, 2H), 3.12-3.22 (m, 3H), 2.94-3.06 (m, 2H), 2.84 (t, J=5.77 Hz, 2H), 2.67-2.80 (m, 2H), 2.50-2.63 (m, 1H).

Compound 119_E2: (S*)-8-(((2,2-difluoroethyl) amino)methyl)-N-(4-fluoro-3-(trifluoromethyl)phenyl)-10-methyl-11-oxo-1,3,4,7,8,9,10,11-octahydro-2H-pyrido[4',3':3,4]pyrazolo[1,5-a][1,4]diazepine-2-carboxamide

*Pure but unknown diastereomer E2.
LCMS: 519 [M+1]. ¹H NMR (400 MHz, CDCl₃) δ 7.68 (dd, J=2.70, 6.09 Hz, 1H), 7.54-7.63 (m, 1H), 7.12 (t, J=9.35 Hz, 1H), 6.78 (s, 1H), 5.66-6.02 (m, 1H), 4.64-4.75 (m, 2H), 4.41 (m, 1H), 4.17 (m, 1H), 3.79-3.93 (m, 2H), 3.29-3.50 (m, 2H), 3.18 (s, 3H), 3.01 (m, 2H), 2.84 (t, J=5.77 Hz, 2H), 2.68-2.80 (m, 2H), 2.50-2.61 (m, 1H).

Compound 120: N-(3-cyano-4-fluorophenyl)-10-methyl-11-oxo-8-(((2,2,2-trifluoroethyl)amino) methyl)-1,3,4,7,8,9,10,11-octahydro-2H-pyrido[4',3': 3,4]pyrazolo [1,5-a][1,4]diazepine-2-carboxamide

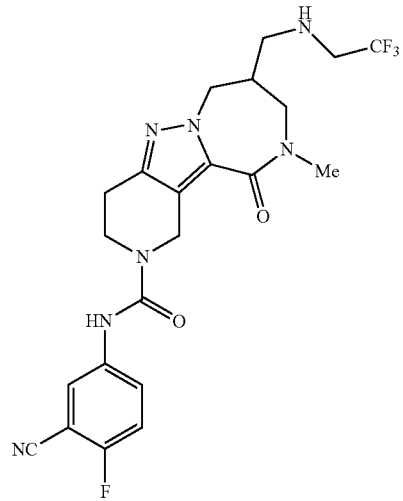 [SMILES: CN1CC(CNCC(F)(F)F)Cn2nc3c(c2C1=O)CN(C(=O)Nc1ccc(F)c(C#N)c1)CC3]

Step 1. tert-butyl 10-methyl-11-oxo-8-[(2,2,2-trifluoroethylamino)methyl]-1,3,4,7,8,9-hexahydropyrido[2,3]pyrazolo[2,4-b][1,4]diazepine-2-carboxylate A mixture of tert-butyl 10-methyl-8-(methylsulfonyloxymethyl)-11-oxo-1,3,4,7,8,9-hexahydropyrido[2,3]pyrazolo[2,4-b][1,4]diazepine-2-carboxylate (300.00 mg, 700.12 µmol, 1.00 eq) and 2,2,2-trifluoroethanamine (1.39 g, 14.00 mmol, 1.10 mL, 20.00 eq) in DMSO (8.00 mL) was heated to 116° C. in sealed tube for 16 h. LCMS showed starting material/desired product: ~1/2. another batch of 2,2,2-trifluoroethanamine (1.39 g, 14.00 mmol, 1.10 mL, 20.00 eq) was added and the mixture was heated to 116° C. in sealed tube for another 16 h. LCMS showed no starting material and major desired product. The mixture was diluted with EtOAc (50 mL) and washed with brine (50 mL, three times). The organic phase was dried over Na₂SO₄, filtered and concentrated in vacuo, which was purified by prep-TLC to afford the title compound (164.00 mg, 372.51 µmol, 53.21% yield, 98% purity) as white solid. LCMS: 454 [M+23].

Step 2. 10-methyl-8-[(2,2,2-trifluoroethylamino) methyl]-2,3,4,7,8,9-hexahydro-1H-pyrido[2,3]pyrazolo[2,4-b][1,4]diazepin-11-one To a solution of tert-butyl 10-methyl-11-oxo-8-[(2,2,2-trifluoroethylamino)methyl]-1,3,4,7,8,9-hexahydropyrido[2,3]pyrazolo[2,4-b][(R*)-1,4]diazepine-2-carboxylate (174.00 mg, 403.29 µmol, 1.00 eq) in DCM (2.00 mL) was added TFA (3.08 g, 27.01 mmol, 2.00 mL, 66.98 eq), and the mixture was stirred at 30° C. for 1 h. The mixture was concentrated in vacuo to afford the title compound (228.00 mg, 407.59 µmol, 101.07% yield, 2TFA) as yellow oil, which was used directly for the next step.

Step 3. N-(3-cyano-4-fluorophenyl)-10-methyl-11-oxo-8-(((2,2,2-trifluoroethyl)amino)methyl)-1,3,4,7,8,9,10,11-octahydro-2H-pyrido[4',3':3,4]pyrazolo[1,5-a][1,4]diazepine-2-carboxamide A mixture of 10-methyl-8-[(2,2,2-trifluoroethylamino)methyl]-2,3,4,7,8,9-hexahydro-1H-pyrido[2,3]pyrazolo[2,4-b][1,4]diazepin-11-one (114.00 mg, 203.80 µmol, 1.00 eq, 2TFA), Et₃N (123.74 mg, 1.22 mmol, 169.51 µL, 6.00 eq) and phenyl N-(3-cyano-4-fluoro-phenyl)carbamate (44.39 mg, 173.23 µmol, 0.85 eq) in DCM (4.00 mL) was stirred at 30° C. for 2 h. LCMS indicated the starting material was consumed completely and major desired product. The mixture was concentrated in vacuo, which was purified by prep-HPLC (base) two times to afford the title compound (36.00 mg, 72.95 µmol, 35.80% yield) as yellow solid.
LCMS: 494 [M+1]. ¹H NMR (400 MHz, CDCl₃) δ 7.79 (m, 1H), 7.60 (m, 1H), 7.15 (t, J=8.8 Hz, 1H), 6.83 (s, 1H), 4.70 (s, 2H), 4.37-4.51 (m, 1H), 4.10-4.25 (m, 1H), 3.82-3.97 (m, 2H), 3.31-3.54 (m, 2H), 3.16-3.30 (m, 5H), 2.86 (m, 4H), 2.50-2.63 (m, 1H), 1.32-1.42 (m, 1H).

Compound 121: N-(4-fluoro-3-(trifluoromethyl) phenyl)-10-methyl-11-oxo-8-(((2,2,2-trifluoroethyl) amino)methyl)-1,3,4,7,8,9,10,11-octahydro-2H-pyrido[4',3':3,4]pyrazolo[1,5-a][1,4]diazepine-2-carboxamide

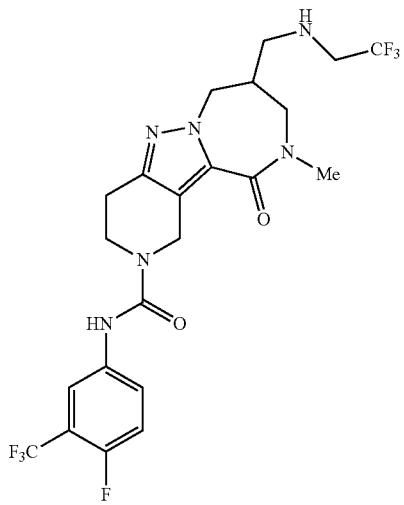 [SMILES: CN1CC(CNCC(F)(F)F)Cn2nc3c(c2C1=O)CN(C(=O)Nc1ccc(F)c(C(F)(F)F)c1)CC3]

The title compound was prepared in a manner analogous to Compound 120, using phenyl (4-fluoro-3-(trifluoromethyl)phenyl)carbamate in Step 3. LCMS: 537 [M+1]. ¹H NMR (400 MHz, CDCl₃) δ 7.70 (m, 1H), 7.56-7.64 (m, 1H), 7.14 (t, J=9.4 Hz, 1H), 6.78 (s, 1H), 4.70 (s, 2H), 4.43 (m, 1H), 4.17 (m, 1H), 3.82-3.98 (m, 2H), 3.43-3.55 (m, 1H), 3.32-3.43 (m, 1H), 3.19 (s, 5H), 2.71-2.93 (m, 4H), 2.48-2.64 (m, 1H), 1.28-1.45 (m, 1H).

Compound 122_D1: (3R,8S*)—N-(4-fluoro-3-(trifluoromethyl)phenyl)-8-((R*)-1-hydroxyallyl)-3,10-dimethyl-11-oxo-1,3,4,7,8,9,10,11-octahydro-2H-pyrido[4',3':3,4]pyrazolo[1,5-a][1,4]diazepine-2-carboxamide

*Pure but unknown diastereomer D1.

Step 1. tert-butyl(6R)-3-[[(2R,3 S)-3-[tert-butyl(diphenyl)silyl]oxy-2-(hydroxymethyl)pent-4-enyl]-methyl-carbamoyl]-6-methyl-2,4,6,7-tetrahydropyrazolo[4,3-c]pyridine-5-carboxylate To a mixture of (2S,3R)-3-[tert-butyl(diphenyl)silyl]oxy-2-(methylaminomethyl)pent-4-en-1-ol (Intermediate 21, 1.35 g, 2.71 mmol, 1.00 eq, TFA) and (6R)-5-tert-butoxycarbonyl-6-methyl-2,4,6,7-tetrahydropyrazolo[4,3-c]pyridine-3-carboxylic acid (763.17 mg, 2.71 mmol, 1.00 eq) in DMF (8.00 mL) was added PYBOP (1.69 g, 3.26 mmol, 1.20 eq), HOBt (439.88 mg, 3.26 mmol, 1.20 eq) and DIPEA (1.40 g, 10.85 mmol, 1.90 mL, 4.00 eq), the reaction mixture was stirred at 25° C. for 2 hours. Several new peaks were shown on LCMS and about 30% of desired compound was detected. The reaction mixture was diluted with ethyl acetate (100 mL) and washed with water (80 mL*2), the organic phase was dried with anhydrous Na₂SO₄, filtered and concentrated in vacuum. The residue was purified by silica gel chromatography to afford the title compound (1.00 g, 3.09 mmol, 57.04% yield) as white solid.

Step 2. tert-butyl (R)-3-(((2S,3R)-3-((tert-butyldiphenylsilyl)oxy)-2-(((methylsulfonyl)oxy)methyl) pent-4-en-1-yl)(methyl)carbamoyl)-6-methyl-2,4,6,7-tetrahydro-5H-pyrazolo[4,3-c]pyridine-5-carboxylate To a mixture of tert-butyl (6R)-3-[[(2R,3 S)-3-[tert-butyl (diphenyl)silyl] oxy-2-(hydroxymethyl)pent-4-enyl]-methylcarbamoyl]-6-methyl-2,4,6,7-tetrahydropyrazolo[4,3-c] pyridine-5-carboxylate (350.00 mg, 541.05 µmol, 1.00 eq) and TEA (164.25 mg, 1.62 mmol, 225.00 µL, 3.00 eq) in DCM (8.00 mL) was added MsCl (185.93 mg, 1.62 mmol, 125.63 µL, 3.00 eq) at 0° C. under N₂, the reaction mixture was stirred at 25° C. for 30 minutes. TLC indicated starting material was consumed completely, and two major new spots with lower polarity was detected. The reaction was quenched with water (20 mL) and then extracted with DCM (50 mL*2), the combined organic phase was dried over anhydrous Na₂SO₄, filtered and concentrated in vacuum to afford the title compound (700.00 mg, crude) and as yellow oil, used in next step directly.

Step 3. tert-butyl (3R,8 S)-8-((R)-1-((tert-butyldiphenylsilyl)oxy)allyl)-3,10-dimethyl-11-oxo-1,3,4,7,8,9,10,11-octahydro-2H-pyrido[4',3':3,4]pyrazolo[1,5-a][1,4]diazepine-2-carboxylate To a mixture of tert-butyl (6R)-3-[[(2R,3 S)-3-[tert-butyl (diphenyl)silyl]oxy-2-(methylsulfonyloxymethyl)pent-4- enyl]-methylcarbamoyl]-6-methyl-2,4,6,7-tetrahydropyrazolo[4,3-c]pyridine-5-carboxylate (700.00 mg, 965.54 µmol, 1.00 eq) and tert-butyl (6R)-3-[[(2R,3 S)-3-[tert-butyl (diphenyl)silyl]oxy-2-(methylsulfonyloxy methyl)pent-4-enyl]-methyl-carbamoyl]-6-methyl-2-methylsulfonyl-6,7-dihydro-4H-pyrazolo[4,3-c]pyridine-5-carboxylate (965.54 µmol, 1.00 eq) in DMF (5.00 mL) was added $Cs_2CO_3$ (629.18 mg, 1.93 mmol, 2.00 eq) and TBAI (35.66 mg, 96.55 µmol, 0.10 eq) under $N_2$, the reaction mixture was stirred at 25° C. for 16 hours. LCMS showed one main peak with desired MS was detected. The reaction mixture was diluted with ethyl acetate (100 mL) and washed with water (50 mL*2), the organic phase was dried with anhydrous $Na_2SO_4$, filtered and concentrated in vacuum. The residue was purified by silica gel chromatography to afford the title compound (350.00 mg, 556.55 µmol, 57.64% yield) as white solid.

Step 4. tert-butyl (3R,8S)-8-((R)-1-hydroxyallyl)-3,10-dimethyl-11-oxo-1,3,4,7,8,9,10,11-octahydro-2H-pyrido[4',3':3,4]pyrazolo[1,5-a][1,4]diazepine-2-carboxylate To a solution of tert-butyl (3R,8 S)-8-((R)-1-((tert-butyldiphenylsilyl)oxy)allyl)-3,10-dimethyl-11-oxo-1,3,4,7,8,9,10,11-octahydro-2H-pyrido[4',3':3,4]pyrazolo[1,5-a][1,4]diazepine-2-carboxylate (700.00 mg, 1.11 mmol, 1.00 eq) in THF (10.00 mL) was added TBAF (1 M, 2.22 mL, 2.00 eq), the reaction mixture was stirred at 25° C. for one hour. TLC indicated starting material was consumed completely and one major new spot with larger polarity was detected. The reaction mixture was diluted with ethyl acetate (100 mL) and washed with water (50 mL*2), the organic phase was dried with anhydrous $Na_2SO_4$, filtered and concentrated in vacuum. The residue was purified by silica gel chromatography to afford the title compound (375.00 mg, 931.55 µmol, 83.92% yield, 97% purity) as white solid.

Step 5. tert-butyl (3R,8 S)-8-((R)-1-((tert-butyldiphenylsilyl)oxy)allyl)-3,10-dimethyl-11-oxo-1,3,4,7,8,9,10,11-octahydro-2H-pyrido[4',3':3,4]pyrazolo[1,5-a][1,4]diazepine-2-carboxylate_D1 and D2

Compound tert-butyl (3R,8S*)-8-((R*)-1-((tert-butyldiphenylsilyl)oxy)allyl)-3,10-dimethyl-11-oxo-1,3,4,7,8,9,10,11-octahydro-2H-pyrido[4',3':3,4]pyrazolo[1,5-a][1,4]diazepine-2-carboxylate (500.00 mg, 97% purity) was separated by SFC to get both diastereomers (D1: 190 mg and D2: 190 mg). SFC separation condition: Instrument: SFC 80; Column: AD-10 um; Mobile phase: A for $CO_2$ and B for MeOH (0.1% $NH_3H_2O$); Gradient: B 30%; Flow rate: 60 mL/min; Back pressure: 100 bar; Column temperature: 35° C.; Wavelength: 220 nm.

D1: $^1$H NMR (400 MHz, $CDCl_3$) δ=5.85 (ddd, J=7.15, 10.16, 17.19 Hz, 1H), 5.39 (d, J=17.19 Hz, 1H), 5.28-5.34 (m, 1H), 4.78-5.08 (m, 2H), 4.33 (dd, J=7.47, 14.24 Hz, 1H), 4.09-4.22 (m, 2H), 4.02 (br dd, J=8.66, 14.18 Hz, 1H), 3.56-3.64 (m, 1H), 3.46-3.55 (m, 1H), 3.19 (s, 3H), 2.91 (br dd, J=5.77, 15.69 Hz, 1H), 2.56 (d, J=15.69 Hz, 1H), 2.42-2.52 (m, 1H), 1.48 (s, 9H), 1.13 (d, J=7.03 Hz, 3H).

*Pure but unknown diastereomer D1.

D2: $^1$H NMR (400 MHz, $CDCl_3$) δ=5.87 (ddd, J=7.09, 10.23, 17.19 Hz, 1H), 5.41 (d, J=17.19 Hz, 1H), 5.32 (d, J=10.29 Hz, 1H), 4.79-5.08 (m, 2H), 4.25-4.34 (m, 1H), 4.10-4.25 (m, 3H), 3.40-3.58 (m, 2H), 3.18 (s, 3H), 2.93 (dd, J=5.83, 15.75 Hz, 1H), 2.47-2.59 (m, 2H), 1.48 (s, 9H), 1.12 (d, J=6.90 Hz, 3H).

*Pure but unknown diastereomer D2.

Step 6. (3R,8S*)-8-((R*)-1-hydroxyallyl)-3,10-dimethyl-1,2,3,4,7,8,9,10-octahydro-11H-pyrido[4',3':3,4]pyrazolo[1,5-a][1,4]diazepin-11-one_D1

To a solution of tert-butyl (3R,8S*)-8-((R*)-1-((tert-butyldiphenylsilyl)oxy)allyl)-3,10-dimethyl-11-oxo-1,3,4,7,8,9,10,11-octahydro-2H-pyrido[4',3':3,4]pyrazolo[1,5-a][1,4]diazepine-2-carboxylate_D1 (190.00 mg, 471.98 µmol, 1.00 eq) in DCM (5.00 mL) was added TFA (2.99 g, 26.20 mmol, 1.94 mL, 55.52 eq), the reaction mixture was stirred at 25° C. for one hour. TLC indicated starting material was consumed completely. The reaction mixture was concentrated on a rotary evaporator to afford the title compound (190.00 mg, crude, TFA) as yellow oil, used in next step directly.

*Pure but unknown diastereomer D1.

Step 7. D1: (3R,8 S*)—N-(4-fluoro-3-(trifluoromethyl)phenyl)-8-((R*)-1-hydroxyallyl)-3,10-dimethyl-11-oxo-1,3,4,7,8,9,10,11-octahydro-2H-pyrido[4',3':3,4]pyrazolo[1,5-a][1,4]diazepine-2-carboxamide To a mixture of (3R,8 S*)-8-((R*)-1-hydroxyallyl)-3,10-dimethyl-1,2,3,4,7,8,9,10-octahydro-11H-pyrido[4',3':3,4]pyrazolo[1,5-a][1,4]diazepin-11-one_D1 (63.00 mg, 155.79 µmol, 1.00 eq, TFA) in DCM (2.00 mL) was added TEA (63.06 mg, 623.16 µmol, 86.38 µL, 4.00 eq), followed by phenyl N-[4-fluoro-3-(trifluoromethyl)phenyl] carbamate (46.62 mg, 155.79 µmol, 1.00 eq), the reaction mixture was stirred at 25° C. for 4 hours. LCMS showed one main peak with desired MS was detected. Removed the solvent on a rotary evaporator. The residue was purified by prep-HPLC (FA) to afford the title compound (56.00 mg, 111.89 µmol, 71.82% yield, 99% purity) as white solid. LCMS (M+1): 496. $^1$H NMR (400 MHz, $CDCl_3$) δ=7.69 (dd, J=2.69, 6.11 Hz, 1H), 7.56-7.61 (m, 1H), 7.13 (t, J=9.35 Hz, 1 H), 6.62 (s, 1H), 5.88 (ddd, J=7.15, 10.24, 17.21 Hz, 1H), 5.42 (d, J=17.12 Hz, 1H), 5.34 (d, J=10.27 Hz, 1H), 5.15 (t, J=6.42 Hz, 1H), 4.80 (d, J=15.16 Hz, 1H), 4.50 (d, J=15.28 Hz, 1H), 4.36 (dd, J=7.46, 14.43 Hz, 1H), 4.10-4.18 (m, 2H), 3.49-3.65 (m, 2H), 3.20 (s, 3H), 3.01 (dd, J=5.93, 15.71 Hz, 1H), 2.67 (d, J=16.14 Hz, 1H), 2.49-2.57 (m, 1H), 1.79 (br s, 1H), 1.19 (d, J=6.85 Hz, 3H).

122~124_D1 and D2 were prepared in a manner analogous to Compound 122.

315 316
-continued
| | |
|---|---|
| 122 D1 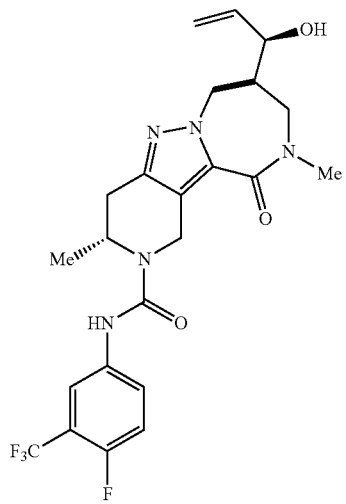 | 123 D2 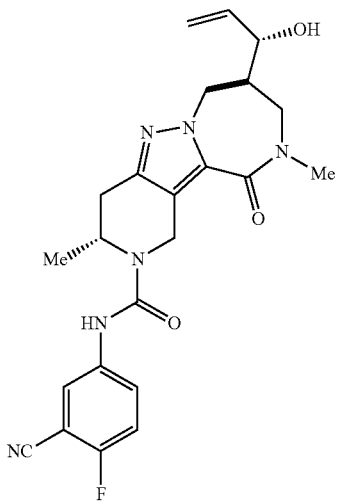 |
| 122 D2 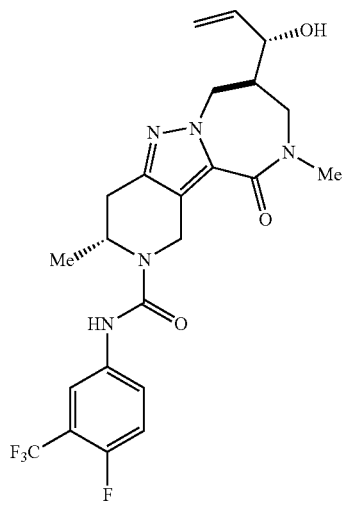 | 124 D1 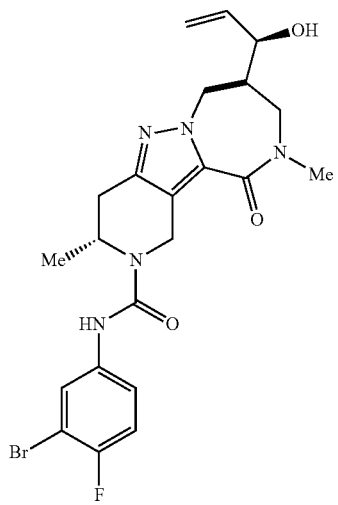 |
| 123 D1 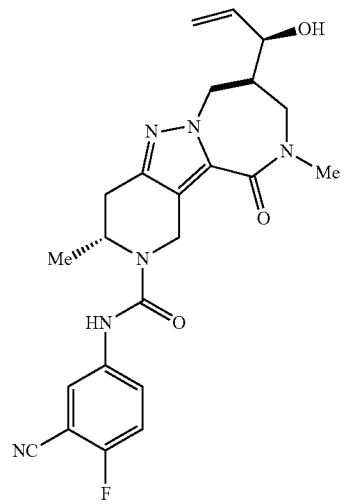 | 124 D2 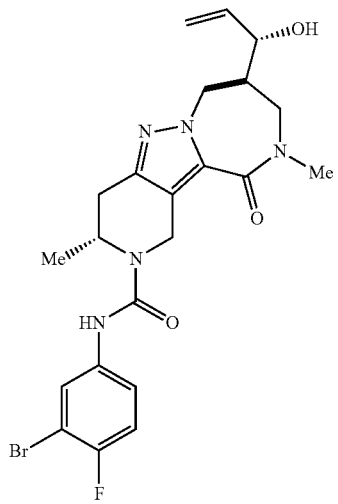 |

Compound 122_D2: (3R,8S*)—N-(4-fluoro-3-(trifluoromethyl)phenyl)-8-((S*)-1-hydroxyallyl)-3,10-dimethyl-11-oxo-1,3,4,7,8,9,10,11-octahydro-2H-pyrido[4',3':3,4]pyrazolo[1,5-a][1,4]diazepine-2-carboxamide

*Pure but unknown diastereomer D2.

LCMS (M+1): 496. $^1$H NMR (400 MHz, CDCl$_3$) δ=7.70 (dd, J=2.69, 5.99 Hz, 1H), 7.56-7.62 (m, 1H), 7.13 (t, J=9.41 Hz, 1H), 6.68 (br s, 1H), 5.88 (ddd, J=7.09, 10.21, 17.18 Hz, 1H), 5.42 (d, J=17.12 Hz, 1H), 5.34 (d, J=10.27 Hz, 1H), 5.16 (quin, J=6.39 Hz, 1H), 4.84 (d, J=15.28 Hz, 1H), 4.46 (d, J=15.16 Hz, 1H), 4.36 (dd, J=7.27, 14.37 Hz, 1H), 4.11-4.22 (m, 2H), 3.47-3.63 (m, 2H), 3.20 (s, 3H), 3.03 (dd, J=6.05, 15.96 Hz, 1H), 2.66 (d, J=15.77 Hz, 1H), 2.51-2.61 (m, 1H), 1.83 (br s, 1H), 1.18 (d, J=6.97 Hz, 3H).

Compound 123_D1: (3R,8S*)—N-(3-cyano-4-fluorophenyl)-8-((R*)-1-hydroxyallyl)-3,10-dimethyl-11-oxo-1,3,4,7,8,9,10,11-octahydro-2H-pyrido[4',3':3,4]pyrazolo[1,5-a][1,4]diazepine-2-carboxamide

*Pure but unknown diastereomer D1.

LCMS (M+1): 453. $^1$H NMR (400 MHz, CDCl$_3$) δ=7.80 (dd, J=2.75, 5.44 Hz, 1H), 7.58 (ddd, J=2.87, 4.49, 9.02 Hz, 1H), 7.13 (t, J=8.68 Hz, 1H), 6.71 (s, 1H), 5.88 (ddd, J=7.15, 10.15, 17.18 Hz, 1H), 5.42 (d, J=17.12 Hz, 1H), 5.35 (d, J=10.27 Hz, 1H), 5.14 (quin, J=6.66 Hz, 1H), 4.80 (d, J=15.41 Hz, 1H), 4.49 (d, J=15.28 Hz, 1H), 4.36 (dd, J=7.40, 14.37 Hz, 1H), 4.12-4.19 (m, 2H), 3.49-3.65 (m, 2H), 3.20 (s, 3H), 3.01 (dd, J=5.69, 15.96 Hz, 1H), 2.67 (d, J=15.77 Hz, 1H), 2.49-2.57 (m, 1H), 1.81 (br s, 1H), 1.19 (d, J=6.97 Hz, 3H).

Compound 123_D2: (3R,8S*)—N-(3-cyano-4-fluorophenyl)-8-((S*)-1-hydroxyallyl)-3,10-dimethyl-11-oxo-1,3,4,7,8,9,10,11-octahydro-2H-pyrido[4',3':3,4]pyrazolo[1,5-a][1,4]diazepine-2-carboxamide

*Pure but unknown diastereomer D2.

LCMS (M+1): 453. $^1$H NMR (400 MHz, CDCl$_3$) δ=7.80 (dd, J=2.81, 5.50 Hz, 1H), 7.58 (ddd, J=2.87, 4.55, 9.08 Hz, 1H), 7.13 (t, J=8.74 Hz, 1H), 6.74 (s, 1H), 5.88 (ddd, J=7.03, 10.18, 17.15 Hz, 1H), 5.42 (d, J=17.12 Hz, 1H), 5.34 (d, J=10.27 Hz, 1H), 5.14 (quin, J=6.30 Hz, 1H), 4.83 (d, J=15.28 Hz, 1H), 4.45 (d, J=15.28 Hz, 1H), 4.36 (dd, J=7.27, 14.37 Hz, 1H), 4.12-4.22 (m, 2H), 3.48-3.63 (m, 2H), 3.20 (s, 3H), 3.02 (dd, J=5.81, 15.71 Hz, 1H), 2.66 (d, J=15.53 Hz, 1H), 2.52-2.60 (m, 1H), 1.82 (br s, 1H), 1.18 (d, J=6.97 Hz, 3H).

Compound 124_D1: (3R,8S*)—N-(3-bromo-4-fluorophenyl)-8-((R*)-1-hydroxyallyl)-3,10-dimethyl-11-oxo-1,3,4,7,8,9,10,11-octahydro-2H-pyrido[4',3':3,4]pyrazolo[1,5-a][1,4]diazepine-2-carboxamide

*Pure but unknown diastereomer D1.

LCMS (M+1): 506/508. $^1$H NMR (400 MHz, CDCl$_3$) δ=7.74 (dd, J=2.63, 6.05 Hz, 1H), 7.23-7.26 (m, 1H), 7.04 (t, J=8.56 Hz, 1H), 6.52 (s, 1H), 5.87 (ddd, J=7.15, 10.24, 17.21 Hz, 1H), 5.42 (d, J=17.24 Hz, 1H), 5.34 (d, J=10.39 Hz, 1H), 5.10-5.17 (m, 1H), 4.78 (d, J=15.41 Hz, 1H), 4.48 (d, J=15.16 Hz, 1H), 4.36 (dd, J=7.46, 14.31 Hz, 1H), 4.09-4.18 (m, 2H), 3.48-3.65 (m, 2H), 3.20 (s, 3H), 3.00 (dd, J=5.75, 15.53 Hz, 1H), 2.66 (d, J=16.02 Hz, 1H), 2.48-2.57 (m, 1H), 1.79 (br s, 1H), 1.18 (d, J=6.97 Hz, 3H).

Compound 124_D2: (3R,8S*)—N-(3-bromo-4-fluorophenyl)-8-((S*)-1-hydroxyallyl)-3,10-dimethyl-11-oxo-1,3,4,7,8,9,10,11-octahydro-2H-pyrido[4',3':3,4]pyrazolo[1,5-a][1,4]diazepine-2-carboxamide

*Pure but unknown diastereomer D2.

LCMS (M+1): 506/508. $^1$H NMR (400 MHz, CDCl$_3$) δ=7.75 (dd, J=2.69, 6.11 Hz, 1H), 7.23-7.27 (m, 1H), 7.04 (t, J=8.50 Hz, 1H), 6.53 (s, 1H), 5.88 (ddd, J=7.03, 10.15, 17.18 Hz, 1H), 5.42 (d, J=17.12 Hz, 1H), 5.34 (d, J=10.27 Hz, 1H), 5.11-5.18 (m, 1H), 4.81 (d, J=15.28 Hz, 1H), 4.45 (d, J=15.16 Hz, 1H), 4.32-4.39 (m, 1H), 4.12-4.23 (m, 2H), 3.48-3.62 (m, 2H), 3.20 (s, 3H), 3.02 (dd, J=5.87, 15.89 Hz, 1H), 2.65 (d, J=15.53 Hz, 1H), 2.51-2.60 (m, 1H), 1.81 (br s, 1H), 1.17 (d, J=6.97 Hz, 3H).

Compound 125_E1: (R*)—N-(5-bromo-2,4-difluorophenyl)-8-(((2,2-difluoroethyl)amino)methyl)-10-methyl-11-oxo-1,3,4,7,8,9,10,11-octahydro-2H-pyrido[4',3':3,4]pyrazolo[1,5-a][1,4]diazepine-2-carboxamide

*Pure but unknown diastereomer E1.

LCMS: 547/549 [M+l]. $^1$H NMR (400 MHz, CDCl$_3$) δ 8.31 (t, J=7.95 Hz, 1H), 6.93 (m, 1H), 6.58 (br d, J=2.81 Hz, 1H), 5.67-6.02 (m, 1H), 4.70 (s, 2H), 4.12-4.45 (m, 2H), 3.74-3.94 (m, 2H), 3.28-3.50 (m, 2H), 3.18 (s, 3H), 2.93-3.06 (m, 2H), 2.85 (t, J=5.75 Hz, 2H), 2.67-2.80 (m, 2H), 2.49-2.61 (m, 1H).

Compound 125_E2: (S*)—N-(5-bromo-2,4-difluorophenyl)-8-(((2,2-difluoroethyl)amino)methyl)-10-methyl-11-oxo-1,3,4,7,8,9,10,11-octahydro-2H-pyrido[4',3':3,4]pyrazolo[1,5-a][1,4]diazepine-2-carboxamide

*Pure but unknown diastereomer E2.

LCMS: 547/549 [M+l]. $^1$H NMR (400 MHz, CDCl$_3$) δ 8.32 (t, J=7.89 Hz, 1H), 6.93 (dd, J=7.95, 10.64 Hz, 1H), 6.57 (br d, J=2.93 Hz, 1H), 5.67-6.02 (m, 1H), 4.70 (s, 2H), 4.14-4.45 (m, 2H), 3.76-3.93 (m, 2H), 3.28-3.49 (m, 2H), 3.18 (s, 3H), 2.93-3.08 (m, 1H), 2.91-3.00 (m, 1H), 2.85 (t, J=5.81 Hz, 2H), 2.75 (m, 2H), 2.46-2.60 (m, 1H).

Compound 126_E1: (R*)—N-(5-chloro-2,4-difluorophenyl)-8-(((2,2-difluoroethyl)amino)methyl)-10-methyl-11-oxo-1,3,4,7,8,9,10,11-octahydro-2H-pyrido[4',3':3,4]pyrazolo[1,5-a][1,4]diazepine-2-carboxamide

*Pure but unknown diastereomer E1.

LCMS: 503/505 [M+l]. $^1$H NMR (400 MHz, CDCl$_3$) δ 8.17 (t, J=8.03 Hz, 1H), 6.94 (m, 1H), 6.59 (br d, J=3.01 Hz, 1H), 5.65-6.02 (m, 1H), 4.70 (s, 2H), 4.40 (m, 1H), 4.17 (m, 1H), 3.76-3.93 (m, 2H), 3.28-3.50 (m, 2H), 3.18 (s, 3H), 2.93-3.08 (m, 2H), 2.85 (t, J=5.77 Hz, 2H), 2.75 (dq, J=7.47, 11.94 Hz, 2H), 2.48-2.62 (m, 1H).

Compound 126_E2: (S*)—N-(5-chloro-2,4-difluorophenyl)-8-(((2,2-difluoroethyl)amino)methyl)-10-methyl-11-oxo-1,3,4,7,8,9,10,11-octahydro-2H-pyrido[4',3':3,4]pyrazolo[1,5-a][1,4]diazepine-2-carboxamide

*Pure but unknown diastereomer E2.

LCMS: 503/505 [M+l]. $^1$H NMR (400 MHz, CDCl$_3$) δ 8.16 (t, J=8.03 Hz, 1H), 6.94 (dd, J=8.41, 10.54 Hz, 1H), 6.61 (br d, J=2.89 Hz, 1H), 5.67-6.02 (m, 1H), 4.70 (s, 2H), 4.40 (m, 1H), 4.17 (m, 1H), 3.77-3.94 (m, 2H), 3.28-3.50 (m, 2H), 3.17 (s, 3H), 2.92-3.06 (m, 2H), 2.85 (t, J=5.77 Hz, 2H), 2.65-2.80 (m, 2H), 2.48-2.62 (m, 1H).

Compound 127_E1: (R*)—N-(3-cyano-2,4-difluorophenyl)-8-(((2,2-difluoroethyl)amino)methyl)-10-methyl-11-oxo-1,3,4,7,8,9,10,11-octahydro-2H-pyrido[4',3':3,4]pyrazolo[1,5-a][1,4]diazepine-2-carboxamide

*Pure but unknown diastereomer E1.

LCMS: 494 [M+1]. ¹H NMR (400 MHz, CDCl₃) δ 8.27 (dt, J=5.77, 9.16 Hz, 1H), 6.97-7.05 (m, 1H), 6.66 (br d, J=2.51 Hz, 1H), 5.67-6.02 (m, 1H), 4.72 (s, 2H), 4.40 (m, 1H), 4.17 (m, 1H), 3.78-3.94 (m, 2H), 3.29-3.50 (m, 2H), 3.18 (s, 3H), 2.92-3.07 (m, 2H), 2.86 (t, J=5.84 Hz, 2H), 2.67-2.80 (m, 2H), 2.50-2.62 (m, 1H).

Compound 127_E2: (S*)—N-(3-cyano-2,4-difluorophenyl)-8-(((2,2-difluoroethyl)amino)methyl)-10-methyl-11-oxo-1,3,4,7,8,9,10,11-octahydro-2H-pyrido[4',3':3,4]pyrazolo[1,5-a][1,4]diazepine-2-carboxamide

*Pure but unknown diastereomer E2.

LCMS: 494 [M+1]. ¹H NMR (400 MHz, METHANOL-d₄) δ 7.76 (dt, J=5.99, 8.93 Hz, 1H), 7.17-7.26 (m, 1H), 6.21-6.57 (m, 1H), 4.72 (s, 2H), 4.54 (m, 1H), 4.36 (m, 1H), 3.76-3.97 (m, 2H), 3.54-3.74 (m, 3H), 3.08-3.27 (m, 5H), 3.00 (br s, 1H), 2.86 (br t, J=5.56 Hz, 2H).

Compound 128_E1: (R*)—N-(3-chloro-2,4-difluorophenyl)-8-(((2,2-difluoroethyl)amino)methyl)-10-methyl-11-oxo-1,3,4,7,8,9,10,11-octahydro-2H-pyrido[4',3':3,4]pyrazolo[1,5-a][1,4]diazepine-2-carboxamide

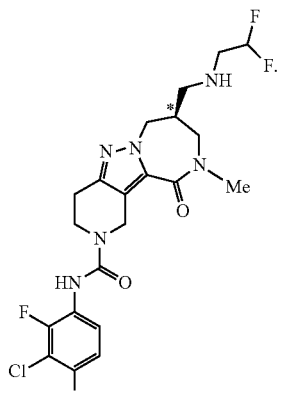

*Pure but unknown diastereomer E1

LCMS: 503/505 [M+1]. ¹H NMR (400 MHz, METHANOL-d₄) δ 7.34 (dt, J=5.62, 8.74 Hz, 1H), 7.08 (dt, J=1.90, 8.83 Hz, 1H), 6.21-6.54 (m, 1H), 4.63-4.77 (m, 2H), 4.53 (m, 1H), 4.34 (m, 1H), 3.75-3.95 (m, 2H), 3.53-3.72 (m, 3H), 3.08-3.27 (m, 5H), 2.98 (br s, 1H), 2.84 (t, J=5.75 Hz, 2H).

Compound 128_E2: (S*)—N-(3-chloro-2,4-difluorophenyl)-8-(((2,2-difluoroethyl)amino)methyl)-10-methyl-11-oxo-1,3,4,7,8,9,10,11-octahydro-2H-pyrido[4',3':3,4]pyrazolo[1,5-a][1,4]diazepine-2-carboxamide

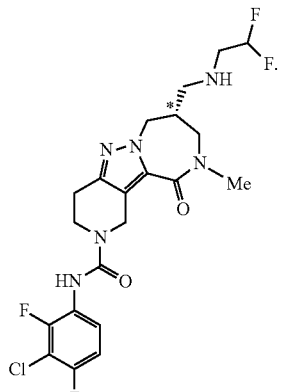

*Pure but unknown diastereomer E2

LCMS: 503/505 [M+1]. ¹H NMR (400 MHz, CDCl₃) δ 7.86 (dt, J=5.50, 8.93 Hz, 1H), 6.90-7.00 (m, 1H), 6.62 (br d, J=2.32 Hz, 1H), 5.66-6.01 (m, 1H), 4.71 (s, 2H), 4.40 (dd, J=6.85, 14.31 Hz, 1H), 4.17 (m, 1H), 3.74-3.94 (m, 2H), 3.26-3.49 (m, 2H), 3.06-3.22 (m, 3H), 2.91-3.05 (m, 2H), 2.85 (t, J=5.75 Hz, 2H), 2.65-2.80 (m, 2H), 2.49-2.59 (m, 1H).

Compound 129_E1: (R*)—N-(3-bromo-2,4-difluorophenyl)-8-(((2,2-difluoroethyl)amino)methyl)-10-methyl-11-oxo-1,3,4,7,8,9,10,11-octahydro-2H-pyrido[4',3':3,4]pyrazolo[1,5-a][1,4]diazepine-2-carboxamide

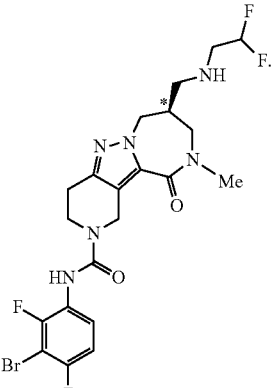

*Pure but unknown diastereomer E1

LCMS: 547/549 [M+1]. ¹H NMR (400 MHz, CDCl₃) δ 7.93 (dt, J=5.58, 8.94 Hz, 1H), 6.94 (m, 1H), 6.59 (d, J=2.76 Hz, 1H), 5.66-6.03 (m, 1H), 4.71 (s, 2H), 4.40 (m, 1H), 4.17 (m, 1H), 3.77-3.93 (m, 2H), 3.28-3.49 (m, 2H), 3.18 (s, 3H), 2.91-3.08 (m, 2H), 2.85 (t, J=5.77 Hz, 2H), 2.75 (m, 2H), 2.49-2.61 (m, 1H).

Compound 129_E2: (S*)—N-(3-bromo-2,4-difluorophenyl)-8-(((2,2-difluoroethyl)amino)methyl)-10-methyl-11-oxo-1,3,4,7,8,9,10,11-octahydro-2H-pyrido[4',3':3,4]pyrazolo[1,5-a][1,4]diazepine-2-carboxamide

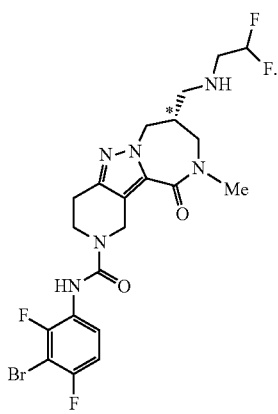

*Pure but unknown diastereomer E2

LCMS: 547/549 [M+1]. $^1$H NMR (400 MHz, CDCl$_3$) δ 8.00 (s, 1H), 7.93 (dt, J=5.75, 8.86 Hz, 1H), 6.89-7.00 (m, 1H), 6.58 (br s, 1H), 5.68-6.02 (m, 1H), 4.71 (s, 2H), 4.12-4.44 (m, 2H), 3.77-3.93 (m, 2H), 3.28-3.50 (m, 2H), 3.18 (s, 3H), 2.95-3.08 (m, 2H), 2.85 (t, J=5.81 Hz, 2H), 2.70-2.82 (m, 2H), 2.51-2.63 (m, 1H).

Compound 130_E1: (R*)—N-(3-bromo-4-fluorophenyl)-8-(((2,2-difluoroethyl)amino)methyl)-10-methyl-11-oxo-1,3,4,7,8,9,10,11-octahydro-2H-pyrido[4',3':3,4]pyrazolo[1,5-a][1,4]diazepine-2-carboxamide

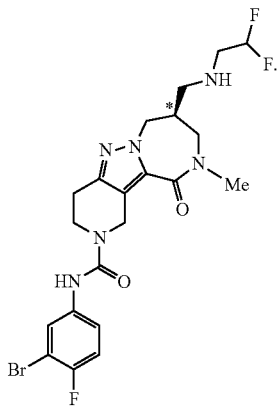

*Pure but unknown diastereomer E1

*Pure but unknown diastereomer E1.

LCMS: 529/531 [M+1]. $^1$H NMR (400 MHz, METHANOL-d$_4$) δ 7.68-7.75 (m, 1H), 7.33 (m, 1H), 7.11 (t, J=8.74 Hz, 1H), 6.19-6.52 (m, 1H), 4.67 (d, J=1.96 Hz, 2H), 4.51 (m, 1H), 4.33 (mz, 1H), 3.71-3.93 (m, 2H), 3.51-3.70 (m, 3H), 3.07-3.26 (m, 5H), 2.90-3.03 (m, 1H), 2.82 (br t, J=5.62 Hz, 2H).

Compound 130_E2: (S*)—N-(3-bromo-4-fluorophenyl)-8-(((2,2-difluoroethyl)amino)methyl)-10-methyl-11-oxo-1,3,4,7,8,9,10,11-octahydro-2H-pyrido[4',3':3,4]pyrazolo[1,5-a][1,4]diazepine-2-carboxamide

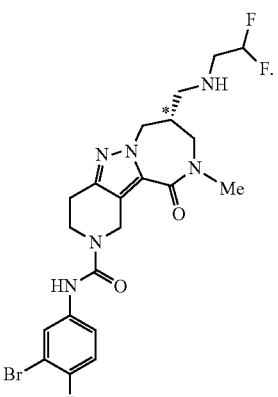

*Pure but unknown diastereomer E2

LCMS: 529/531 [M+1]. $^1$H NMR (400 MHz, CDCl$_3$) δ 8.01 (s, 1H), 7.72 (dd, J=2.64, 6.02 Hz, 1H), 7.23-7.26 (m, 1H), 7.00-7.07 (m, 1H), 6.52-6.64 (m, 1H), 6.58 (s, 1H), 5.66-6.05 (m, 1H), 4.67 (s, 2H), 4.41 (m, 1H), 4.18 (dd, J=5.40, 14.56 Hz, 1H), 3.77-3.93 (m, 2H), 3.26-3.51 (m, 2H), 3.18 (s, 3H), 2.94-3.09 (m, 2H), 2.84 (t, J=5.71 Hz, 2H), 2.65-2.80 (m, 2H), 2.52-2.63 (m, 1H).

Compound 131_E1: (R*)—N-(2,4-difluoro-3-(trifluoromethyl)phenyl)-8-(((2,2-difluoroethyl)amino)methyl)-10-methyl-11-oxo-1,3,4,7,8,9,10,11-octahydro-2H-pyrido[4',3':3,4]pyrazolo[1,5-a][1,4]diazepine-2-carboxamide

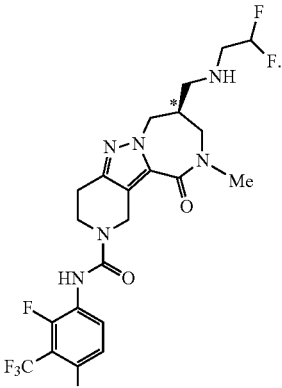

*Pure but unknown diastereomer E1

LCMS: 537 [M+1]. $^1$H NMR (400 MHz, METHANOL-d$_4$) δ 7.68 (dt, J=5.62, 8.68 Hz, 1H), 7.14 (t, J=9.72 Hz, 1H), 6.19-6.52 (m, 1H), 4.70 (d, J=2.32 Hz, 2H), 4.51 (m, 1H), 4.33 (m, 1H), 3.73-3.95 (m, 2H), 3.52-3.70 (m, 3H), 3.09-3.27 (m, 5H), 2.98 (br s, 1H), 2.83 (br t, J=5.75 Hz, 2H).

323

Compound 131_E2: (S*)—N-(2,4-difluoro-3-(trifluoromethyl)phenyl)-8-(((2,2-difluoroethyl)amino)methyl)-10-methyl-11-oxo-1,3,4,7,8,9,10,11-octahydro-2H-pyrido[4',3':3,4]pyrazolo[1,5-a][1,4]diazepine-2-carboxamide

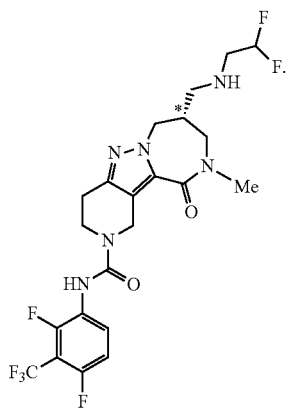

*Pure but unknown diastereomer E2

LCMS: 537 [M+1]. ¹H NMR (400 MHz, CDCl₃) δ 8.21 (dt, J=5.46, 8.94 Hz, 1H), 6.98 (t, J=8.85 Hz, 1H), 6.65 (br d, J=3.01 Hz, 1H), 5.66-6.01 (m, 1H), 4.72 (s, 2H), 4.40 (m, 1H), 4.17 (m, 1H), 3.77-3.95 (m, 2H), 3.29-3.49 (m, 2H), 3.18 (s, 3H), 3.00 (m, 2H), 2.86 (t, J=5.71 Hz, 2H), 2.67-2.80 (m, 2H), 2.50-2.60 (m, 1H).

Compound 132: N-(3-chloro-4-fluorophenyl)-3-hydroxy-10'-methyl-11'-oxo-1',3',4',9',10',11'-hexahydro-2'H,7'H-spiro[cyclobutane-1,8'-pyrido[4',3':3,4]pyrazolo [1,5-a][1,4]diazepine]-2'-carboxamide

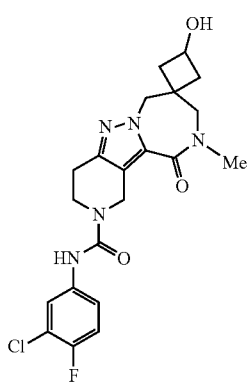 [SMILES: CN1CC2(CC(O)C2)Cn2nc3c(c2C1=O)CN(C(=O)Nc1ccc(F)c(Cl)c1)CC3]

To a solution of 3'-hydroxy-10-methyl-spiro[1,2,3,4,7,9-hexahydropyrido[2,3]pyrazolo[2,4-b][1,4]diazepine-8,1'-cyclobutane]-11-one (Intermediate 24, 30.00 mg, 76.85 μmol, 1.00 eq, TFA) in DCM (4.00 mL) was added TEA (38.88 mg, 384.25 μmol, 53.26 μL, 5.00 eq), followed by phenyl N-(3-chloro-4-fluoro-phenyl)carbamate (20.42 mg, 76.85 μmol, 1.00 eq). The mixture was stirred at 20° C. for 1 hr. LCMS showed one main peak with desired Ms detected. The mixture was concentrated in vacuum. The residue was purified by prep-HPLC (FA) to afford the title compound (24.00 mg, 53.58 μmol, 69.73% yield) as white solid. LCMS: 448[M+1]. ¹H NMR (400 MHz, METHANOL-d₄) δ=7.60 (dd, J=2.63, 6.66 Hz, 1H), 7.27-7.33 (m, 1H), 7.09-7.18 (m, 1H), 4.68 (s, 2H), 4.34-4.42 (m, 1H), 4.32 (s, 2H), 3.83 (t, J=5.81 Hz, 2H), 3.41 (s, 2H), 3.18 (s, 3H), 2.82 (t, J=5.81 Hz, 2H), 2.38-2.49 (m, 2H), 1.87-1.98 (m, 2H).

Compound 133_D1: (3R,8R*)-8-fluoro-N-(4-fluoro-3-(trifluoromethyl)phenyl)-8-(hydroxymethyl)-3,10-dimethyl-11-oxo-1,3,4,7,8,9,10,11-octahydro-2H-pyrido[4',3':3,4]pyrazolo[1,5-a][1,4]diazepine-2-carboxamide_D1

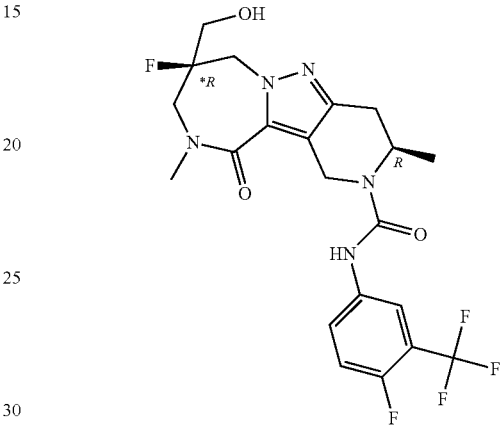

Step 1. 2-(tert-butyl) 8-ethyl (3R)-8-fluoro-3,10-dimethyl-11-oxo-1,3,4,7,8,9,10,11-octahydro-2H-pyrido[4',3':3,4]pyrazolo[1,5-a][1,4]diazepine-2,8-dicarboxylate To a solution of LDA (1 M, 959.45 μL, 1.30 eq) in THF (2.00 mL) was added a solution of 2-(tert-butyl) 8-ethyl (3R)-3,10-dimethyl-11-oxo-1,3,4,7,8,9,10,11-octahydro-2H-pyrido[4',3':3,4]pyrazolo[1,5-a][1,4]diazepine-2,8-dicarboxylate (300.00 mg, 738.04 μmol, 1.00 eq) in THF (2.00 mL) at −78° C. The mixture was stirred at −78° C. for 30 min. Then a solution of NFSI (279.28 mg, 885.65 μmol, 1.20 eq) in THF (2.00 mL) was added at −78° C. Then the mixture was stirred at −78° C. for 1 hr. The reaction mixture was quenched with saturated NH₄Cl(10 mL) and extracted with EtOAc(80 mL*2). The combined organic layers were dried over Na₂SO₄, filtrated and concentrated in vacuum. The residue was purified column chromatography (PE:EA: 30%~50%) to afford the title compound (250.00 mg, 512.40 μmol, 69.43% yield, 87% purity) as a white solid. ¹H NMR (400 MHz, CHLOROFORM-d) δ=4.72 (dd, J=15.1, 17.8 Hz, 1H), 4.59-4.42 (m, 3H), 4.33-4.21 (m, 2H), 3.86-3.73 (m, 1H), 3.70-3.49 (m, 3H), 3.11 (s, 3H), 2.69 (br s, 2H), 1.41 (s, 9H), 1.29 (t, J=7.2 Hz, 3H).

Step 2. tert-Butyl (3R)-8-fluoro-8-(hydroxymethyl)-3,10-dimethyl-11-oxo-1,3,4,7,8,9,10,11-octahydro-2H-pyrido[4',3':3,4]pyrazolo[1,5-a][1,4]diazepine-2-carboxylate_D1 and tert-Butyl (3R)-8-fluoro-8-(hydroxymethyl)-3,10-dimethyl-11-oxo-1,3,4,7,8,9,10,11-octahydro-2H-pyrido[4',3':3,4]pyrazolo[1,5-a][1,4]diazepine-2-carboxylate_D2

To a solution of 2-(tert-butyl) 8-ethyl (3R)-8-fluoro-3,10-dimethyl-11-oxo-1,3,4,7,8,9,10,11-octahydro-2H-pyrido[4', 3':3,4]pyrazolo[1,5-a][1,4]diazepine-2,8-dicarboxylate (230.00 mg, 541.85 µmol, 1.00 eq) in THF (6.00 mL) was added LiBH$_4$ (35.40 mg, 1.63 mmol, 3.00 eq) with stirring at 0° C. for 1 h. The mixture was poured into the 20 mL of saturated NH$_4$Cl and extracted with EtOAc (20 mL*3), and then the combined organic phase was washed with brine (20 mL*1), dried over anhydrous Na$_2$SO$_4$, filtered and concentrated in vacuo. The residue was combined with a 30 mg (pilot reaction) and purified by prep-TLC (PE:EtOAc=1:2) to obtain two diastereomers of the title compound: 45 mg tert-butyl (3R)-8-fluoro-8-(hydroxymethyl)-3,10-dimethyl-11-oxo-1,3,4,7,8,9,10,11-octahydro-2H-pyrido[4',3':3,4]pyrazolo[1,5-a][1,4]diazepine-2-carboxylate as colorless oil and 120 mg of and tert-Butyl (3R)-8-fluoro-8-(hydroxymethyl)-3,10-dimethyl-11-oxo-1,3,4,7,8,9,10,11-octahydro-2H-pyrido[4',3':3,4]pyrazolo[1,5-a][1,4]diazepine-2-carboxylate D2 as a white solid.

Step 3. (3R)-8-fluoro-8-(hydroxymethyl)-3,10-dimethyl-1,2,3,4,7,8,9,10-octahydro-11H-pyrido[4',3':3,4]pyrazolo[1,5-a][1,4]diazepin-11-one_D1 and (3R)-8-fluoro-8-(hydroxymethyl)-3,10-dimethyl-1,2,3,4,7,8,9,10-octahydro-11H-pyrido[4',3':3,4]pyrazolo[1,5-a][1,4]diazepin-11-one_D2

To a solution of tert-butyl (3R)-8-fluoro-8-(hydroxymethyl)-3,10-dimethyl-11-oxo-1,3,4,7,8,9,10,11-octahydro-2H-pyrido[4',3':3,4]pyrazolo[1,5-a][1,4]diazepine-2-carboxylate (45.00 mg, 117.67 µmol, 1.00 eq) in DCM (3.00 mL) was added TFA (462.00 mg, 4.05 mmol, 300.00 µL, 34.43 eq) at 15° C. with stirring for 1 h. The mixture was concentrated in vacuo. The residue was not purified. The title compound (47.00 mg, crude, TFA) was obtained as yellow oil and directly used in the next step.

Step 4. (3R,8R*)-8-fluoro-N-(4-fluoro-3-(trifluoromethyl)phenyl)-8-(hydroxymethyl)-3,10-dimethyl-11-oxo-1,3,4,7,8,9,10,11-octahydro-2H-pyrido[4',3':3,4]pyrazolo[1,5-a][1,4]diazepine-2-carboxamide_D1

To a solution of (3R)-8-fluoro-8-(hydroxymethyl)-3,10-dimethyl-1,2,3,4,7,8,9,10-octahydro-11H-pyrido[4',3':3,4]pyrazolo[1,5-a][1,4]diazepin-11-one_D1 (47.00 mg, 118.59 µmol, 1.00 eq, TFA) and phenyl N-[4-fluoro-3-(trifluoromethyl)phenyl]carbamate (35.48 mg, 118.59 µmol, 1.00 eq) in DCM (5.00 mL) was added TEA (72.00 mg, 711.54 µmol, 98.63 µL, 6.00 eq) at 20° C. with stirring for 2 h. The mixture was concentrated in vacuo. The residue was purified by prep-HPLC(FA) to obtain the title compound (34.00 mg, 69.76 µmol, 58.82% yield) as white solid. LCMS: 488 [M+1]; $^1$H NMR (400 MHz, CHLOROFORM-d) δ 7.67 (dd, J=2.76, 6.15 Hz, 1H), 7.54-7.62 (m, 1H), 7.13 (t, J=9.35 Hz, 1H), 6.55 (s, 1H), 5.07-5.17 (m, 1H), 4.81 (d, J=15.56 Hz, 1H), 4.39-4.58 (m, 3H), 3.75-3.97 (m, 2H), 3.63 (d, J=5.90 Hz, 1H), 3.59 (s, 1H), 3.23 (s, 3H), 3.01 (dd, J=5.83, 16.12 Hz, 1H), 2.69 (d, J=16.06 Hz, 1H), 2.01-2.12 (m, 1H), 1.20 (d, J=6.90 Hz, 3H).

Compound 133_D2: (3R,8S*)-8-fluoro-N-(4-fluoro-3-(trifluoromethyl)phenyl)-8-(hydroxymethyl)-3,10-dimethyl-11-oxo-1,3,4,7,8,9,10,11-octahydro-2H-pyrido[4',3':3,4]pyrazolo[1,5-a][1,4]diazepine-2-carboxamide_D2

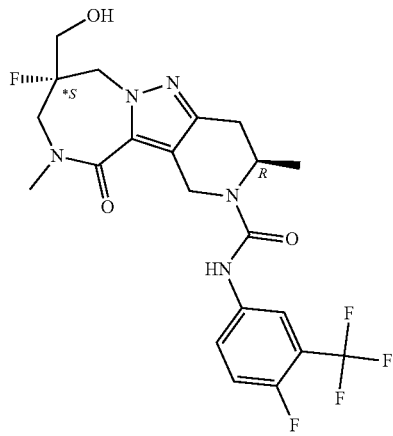

The title compound was prepared in a manner analogous to Compound 133_D1. LCMS: 488 [M+1]. $^1$H NMR (400 MHz, CHLOROFORM-d) δ=7.70 (dd, J=2.70, 6.09 Hz, 1H), 7.56-7.64 (m, 1H), 7.27 (s, 3H), 7.13 (t, J=9.35 Hz, 1H), 6.74 (br s, 1H), 5.10-5.20 (m, 1H), 4.89 (d, J=15.56 Hz, 1H), 4.40-4.52 (m, 3H), 3.77-3.98 (m, 2H), 3.64 (d, J=2.89 Hz, 1H), 3.60 (s, 1H), 3.22 (s, 3H), 3.03 (dd, J=6.02, 15.94 Hz, 1H), 2.67 (d, J=16.19 Hz, 1H), 2.20 (br s, 1H), 1.18 (d, J=6.90 Hz, 3H).

Compound 134_D1: (3R,8R)—N-(3-Cyano-4-fluorophenyl)-8-((2,2-difluoroethoxy)methyl)-3,10-dimethyl-11-oxo-1,3,4,7,8,9,10,11-octahydro-2H-pyrido[4',3':3,4]pyrazolo[1,5-a][1,4]diazepine-2-carboxamide

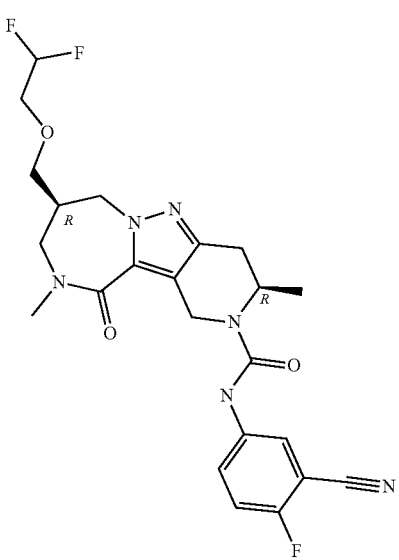

Step 1. tert-Butyl (3R,8R)-8-(hydroxymethyl)-3,10-dimethyl-11-oxo-1,3,4,7,8,9,10,11-octahydro-2H-pyrido[4',3':3,4]pyrazolo[1,5-a][1,4]diazepine-2-carboxylate To a mixture of tert-butyl (3R,8R)-8-(methoxy(methyl)carbamoyl)-3,10-dimethyl-11-oxo-1,3,4,7,8,9,10,11-octahydro-2H-pyrido[4',3':3,4]pyrazolo[1,5-a][1,4]diazepine-2-carboxylate (400.00 mg, 901.56 µmol, 1 eq) in THF (6 mL) and MeOH (6 mL) was added NaBH$_4$ (68.21 mg, 1.80 mmol, 2 eq) in one portion at 0° C. under N$_2$. The mixture was stirred at 0° C. for 3 hours. The mixture was poured into water (10 mL) and stirred for 1 min. The aqueous phase was extracted with DCM (20 mL*2). The combined organic layers were washed with brine (15 mL*2), dried with anhydrous Na$_2$SO$_4$, filtered and concentrated in vacuum. The residue was purified by silica gel chromatography (100-200 mesh silica gel, Dichloromethane: Methanol=100/1, 20/1) to afford the title compound (328 mg, 900.01 µmol, 99.83% yield, 100% purity) as yellow solid. LCMS: 365 [M+1].

Step 2. tert-Butyl (3R,8R)-8-((2,2-difluoroethoxy)methyl)-3,10-dimethyl-11-oxo-1,3,4,7,8,9,10,11-octahydro-2H-pyrido[4',3':3,4]pyrazolo[1,5-a][1,4]diazepine-2-carboxylate To a mixture of tert-butyl (3R,8R)-8-(hydroxymethyl)-3,10-dimethyl-11-oxo-1,3,4,7,8,9,10,11-octahydro-2H-pyrido[4',3':3,4]pyrazolo[1,5-a][1,4]diazepine-2-carboxylate (100.00 mg, 274.39 µmol, 1 eq) in THF (1 mL) was added NaH (21.95 mg, 548.79 µmol, 60% purity, 2 eq) in one portion at −20° C. under N$_2$. The mixture was stirred at −20° C. for 30 min, then 2,2-difluoroethyl trifluoromethanesulfonate (176.25 mg, 823.18 µmol, 3 eq) was added to the mixture. The mixture was stirred at −20° C. for 2 hours. The mixture was poured into water (15 mL) and stirred for 1 min. The aqueous phase was extracted with ethyl acetate (25 mL*2). The combined organic layers were washed with brine (10 mL*2), dried with anhydrous Na$_2$SO$_4$, filtered and concentrated in vacuum. The residue was purified by prep-TLC (Ethyl acetate: Petroleum ether=2/1) to afford the title compound (107 mg, 249.72 µmol, 91.01% yield, 100% purity) as a yellow solid. LCMS: 429 [M+1].

Step 3. (3R,8R)-8-((2,2-Difluoroethoxy)methyl)-3,10-dimethyl-1,2,3,4,7,8,9,10-octahydro-11H-pyrido[4',3':3,4]pyrazolo[1,5-a][1,4]diazepin-11-one To a solution of tert-butyl (3R,8R)-8-((2,2-difluoroethoxy)methyl)-3,10-dimethyl-11-oxo-1,3,4,7,8,9,10,11-octahydro-2H-pyrido[4',3':3,4]pyrazolo[1,5-a][1,4]diazepine-2-carboxylate (160.00 mg, 373.42 µmol, 1.00 eq) in DCM (2 mL) was added TFA (4.39 g, 38.48 mmol, 2.85 mL, 103.04 eq) under N$_2$. The mixture was stirred at 30° C. for 2 hours. The mixture was concentrated in vacuum to afford the title compound (166 mg, crude) as yellow oil.

Step 4. (3R,8R)—N-(3-Cyano-4-fluorophenyl)-8-((2,2-difluoroethoxy)methyl)-3,10-dimethyl-11-oxo-1,3,4,7,8,9,10,11-octahydro-2H-pyrido[4',3':3,4]pyrazolo[1,5-a][1,4]diazepine-2-carboxamide To a mixture of (3R,8R)-8-((2,2-difluoroethoxy)methyl)-3,10-dimethyl-1,2,3,4,7,8,9,10-octahydro-11H-pyrido[4',3':3,4]pyrazolo[1,5-a][1,4]diazepin-11-one (61.61 mg, 187.62 µmol, 1 eq, TFA) and phenyl N-(3-cyano-4-fluoro-phenyl) carbamate (53.42 mg, 187.62 µmol, 1 eq) in DCM (6.00 mL) was added TEA (189.85 mg, 1.88 mmol, 261.15 µL, 10.00 eq) under N$_2$. The mixture was stirred at 30° C. for 10 hours. The residue was poured into water (10 mL) and stirred for 2 min. The aqueous phase was extracted with ethyl acetate (10 mL*2). The combined organic layers were washed with brine (5 mL*2), dried with anhydrous Na$_2$SO$_4$, filtered and concentrated in vacuum. The residue was purified by prep-HPLC(FA) to afford the title compound (76 mg, 152.63 µmol, 81.35% yield, 98.5% purity) as a white solid. LCMS: 491 [M+1]. $^1$H NMR (400 MHz, CHLOROFORM-d) δ 7.79 (dd, J=2.81, 5.50 Hz, 1H), 7.51-7.60 (m, 1H), 7.14 (t, J=8.74 Hz, 1H), 6.60 (s, 1H), 5.72-6.08 (m, 1H), 5.08-5.19 (m, 1H), 4.80 (d, J=15.41 Hz, 1H), 4.38-4.53 (m, 2H), 4.13 (dd, J=6.97, 14.31 Hz, 1H), 3.49-3.84 (m, 5H), 3.37 (d, J=6.24 Hz, 1H), 3.18 (s, 3H), 3.00 (d, J=5.99 Hz, 1H), 2.82 (br d, J=6.36 Hz, 1H), 2.68 (d, J=16.26 Hz, 1H), 1.19 (d, J=6.97 Hz, 3H).

Compound 135 D1: (3R,8R)-8-((2,2-difluoroethoxy)methyl)-N-(4-fluoro-3-(trifluoromethyl)phenyl)-3,10-dimethyl-11-oxo-1,3,4,7,8,9,10,11-octahydro-2H-pyrido[4',3':3,4]pyrazolo[1,5-a][1,4]diazepine-2-carboxamide

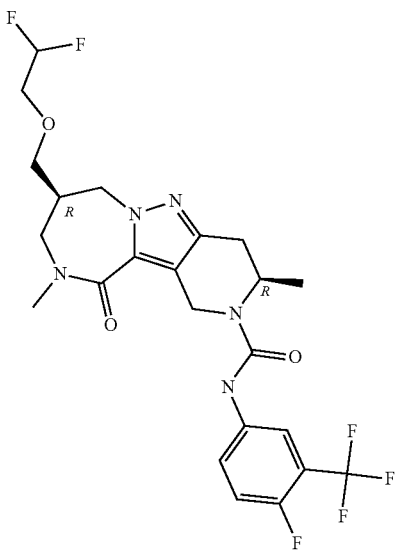

To a mixture of (3R,8R)-8-((2,2-difluoroethoxy)methyl)-3,10-dimethyl-1,2,3,4,7,8,9,10-octahydro-11H-pyrido[4',3':3,4]pyrazolo[1,5-a][1,4]diazepin-11-one (61.61 mg, 187.62 µmol, 1 eq, TFA) and phenyl N-[4-fluoro-3-(trifluoromethyl)phenyl]carbamate (56.14 mg, 187.62 µmol, 1 eq) in DCM (6.00 mL) was added TEA (189.85 mg, 1.88 mmol, 261.15 µL, 10.00 eq) under N$_2$. The mixture was stirred at 30° C. for 10 hours. The residue was poured into water (10 mL) and stirred for 2 min. The aqueous phase was extracted with ethyl acetate (10 mL*2). The combined organic layers were washed with brine (5 mL*2), dried with anhydrous Na$_2$SO$_4$, filtered and concentrated in vacuum. The residue was purified by prep-HPLC(FA) to afford the title compound (71 mg, 133.09 µmol, 70.94% yield, 100% purity) as a white solid. LCMS: 534 [M+1] $^1$H NMR (400 MHz, CHLOROFORM-d) δ 7.68 (dd, J=2.75, 6.17 Hz, 1H), 7.55-7.62 (m, 1H), 7.13 (t, J=9.41 Hz, 1H), 6.55 (s, 1H), 5.72-6.08 (m, 1H), 5.15 (t, J=6.30 Hz, 1H), 4.81 (d, J=15.41 Hz, 1H), 4.40-4.53 (m, 2H), 4.12 (dd, J=7.15, 14.24 Hz, 1H), 3.49-3.82 (m, 5H), 3.35 (dd, J=5.93, 14.98 Hz, 1H), 3.02 (dd, J=5.87, 15.65 Hz, 1H), 2.75-2.87 (m, 1H), 2.67 (d, J=15.89 Hz, 1H), 1.19 (d, J=6.85 Hz, 3H).

Compound 134 D2: (3R,8S)—N-(3-cyano-4-fluorophenyl)-8-((2,2-difluoroethoxy)methyl)-3,10-dimethyl-11-oxo-1,3,4,7,8,9,10,11-octahydro-2H-pyrido[4',3':3,4]pyrazolo[1,5-a][1,4]diazepine-2-carboxamide

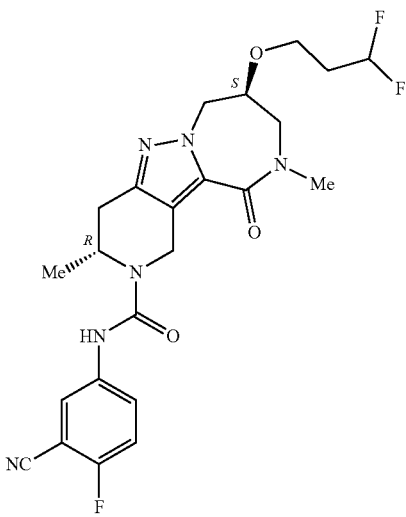

Step 1. tert-Butyl (3R,8 S)-8-(hydroxymethyl)-3,10-dimethyl-11-oxo-1,3,4,7,8,9,10,11-octahydro-2H-pyrido[4',3':3,4]pyrazolo[1,5-a][1,4]diazepine-2-carboxylate To a solution of tert-butyl (3R,8S)-8-(methoxy(methyl)carbamoyl)-3,10-dimethyl-11-oxo-1,3,4,7,8,9,10,11-octahydro-2H-pyrido[4',3':3,4]pyrazolo[1,5-a][1,4]diazepine-2-carboxylate (300 mg, 711.76 μmol, 1 eq) in THF (6 mL) and MeOH (6 mL) was added NaBH₄ (53.85 mg, 1.42 mmol, 2 eq) at 0° C. The solution was stirred at 25° C. for 16 hr. The solution was poured into water (30 mL). The mixture extracted with ethyl acetate (20 mL*2). The combined organic layers were washed with brine (20 mL), dried with anhydrous Na₂SO₄, filtered and concentrated. The residue was purified by column chromatography. The title compound (230 mg, 602.71 μmol, 84.68% yield, 95.5% purity) was obtained as yellow oil. LCMS: 365 [M+1].

Step 2. tert-Butyl (3R,8 S)-8-((2,2-difluoroethoxy)methyl)-3,10-dimethyl-11-oxo-1,3,4,7,8,9,10,11-octahydro-2H-pyrido[4',3':3,4]pyrazolo[1,5-a][1,4]diazepine-2-carboxylate To a solution of tert-butyl (3R,8S)-8-(hydroxymethyl)-3,10-dimethyl-11-oxo-1,3,4,7,8,9,10,11-octahydro-2H-pyrido[4',3':3,4]pyrazolo[1,5-a][1,4]diazepine-2-carboxylate (230 mg, 631.11 μmol, 1 eq) in THF (10 mL) was added NaH (50.49 mg, 1.26 mmol, 60% purity, 2 eq) at −20° C. The solution was stirred at −20° C. for 30 min. Then 2,2,2-difluoroethyl trifluoromethanesulfonate (405.38 mg, 1.89 mmol, 3 eq) was added, the solution was stirred at −15° C. for 2 hr. The solution was poured into water (30 mL). The mixture extracted with ethyl acetate (20 mL*2). The combined organic layers were washed with brine (20 mL*3), dried with anhydrous Na₂SO₄, filtered and concentrated. The residue was purified by prep-TLC. The title compound (190 mg, 443.44 μmol, 70.26% yield) was obtained as yellow oil.

Step 3. (3R,8S)-8-((2,2-Difluoroethoxy)methyl)-3,10-dimethyl-1,2,3,4,7,8,9,10-octahydro-11H-pyrido[4',3':3,4]pyrazolo[1,5-a][1,4]diazepin-11-one To a solution of tert-butyl (3R,8S)-8-((2,2-difluoroethoxy)methyl)-3,10-dimethyl-11-oxo-1,3,4,7,8,9,10,11-octahydro-2H-pyrido[4',3':3,4]pyrazolo[1,5-a][1,4]diazepine-2-carboxylate (190 mg, 443.44 μmol, 1 eq) in DCM (5 mL) was added TFA (7.70 g, 67.53 mmol, 5.00 mL, 152.29 eq). The solution was stirred at 25° C. for 30 min. The solution was concentrated. The title compound (196 mg, crude, TFA) was obtained as yellow oil.

Step 4. (3R,8S)—N-(3-Cyano-4-fluorophenyl)-8-((2,2-difluoroethoxy)methyl)-3,10-dimethyl-11-oxo-1,3,4,7,8,9,10,11-octahydro-2H-pyrido[4',3': 3,4]pyrazolo[1,5-a][1,4]diazepine-2-carboxamide To a solution of (3R,8S)-8-((2,2-difluoroethoxy)methyl)-3,10-dimethyl-1,2,3,4,7,8,9,10-octahydro-11H-pyrido[4',3':3,4]pyrazolo[1,5-a][1,4]diazepin-11-one (98 mg, 221.53 μmol, 1 eq, TFA) in DCM (2 mL) was added TEA (67.25 mg, 664.59 μmol, 92.50 μL, 3 eq) and phenyl N-(3-cyano-4-fluoro-phenyl)carbamate (56.76 mg, 221.53 μmol, 1 eq). The solution was stirred at 25° C. for 16 hr. TEA (67.25 mg, 664.59 μmol, 92.50 μL, 3 eq) was added. The solution was stirred at 25° C. for 16 hr. The solution was concentrated. The residue was purified by prep-HPLC (FA). The title compound (47.37 mg, 94.32 μmol, 42.58% yield, 97.66% purity) was obtained as white solid. LCMS: 491 [M+1]; ¹H NMR (400 MHz, CHLOROFORM-d) δ 7.79 (dd, J=2.81, 5.38 Hz, 1H), 7.60 (ddd, J=2.87, 4.55, 9.08 Hz, 1H), 7.13 (t, J=8.68 Hz, 1H), 6.86 (s, 1H), 5.68-6.07 (m, 1H), 5.13 (quin, J=6.57 Hz, 1H), 4.84 (d, J=15.41 Hz, 1H), 4.36-4.52 (m, 2H), 4.15 (dd, J=5.93, 14.37 Hz, 1H), 3.48-3.83 (m, 5H), 3.33 (dd, J=7.09, 15.04 Hz, 1H), 3.18 (s, 3H), 3.01 (dd, J=5.75, 16.02 Hz, 1H), 2.82 (td, J=6.40, 12.75 Hz, 1H), 2.66 (d, J=15.89 Hz, 1H), 1.18 (d, J=6.85 Hz, 3H).

331

Compound 135_D2: (3R,8S)-8-((2,2-difluoroeth-oxy)methyl)-N-(4-fluoro-3-(trifluoromethyl)phenyl)-3,10-dimethyl-11-oxo-1,3,4,7,8,9,10,11-octahydro-2H-pyrido[4',3':3,4]pyrazolo[1,5-a][1,4]diazepine-2-carboxamide

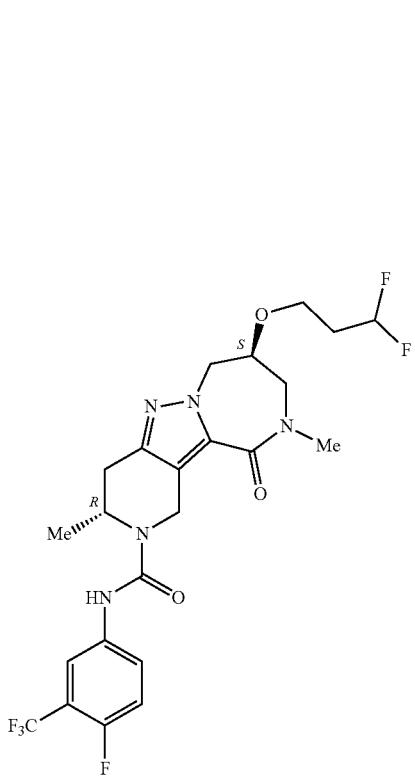

To a solution of (3R,8S)-8-((2,2-difluoroethoxy)methyl)-3,10-dimethyl-1,2,3,4,7,8,9,10-octahydro-1H-pyrido[4',3': 3,4]pyrazolo[1,5-a][1,4]diazepin-11-one (98 mg, 221.53 μmol, 1 eq, TFA) in DCM (2 mL) was added TEA (67.25 mg, 664.59 μmol, 92.50 μL, 3 eq) and phenyl N-[4-fluoro-3-(trifluoromethyl)phenyl]carbamate (66.29 mg, 221.53 μmol, 1 eq). The solution was stirred at 25° C. for 16 hr. TEA (67.25 mg, 664.59 μmol, 92.50 μL, 3 eq) was added. The solution was stirred at 25° C. for 16 hr. The solution was concentrated. The residue was purified by prep-HPLC (FA). The title compound (68.35 mg, 122.53 μmol, 55.31% yield, 95.63% purity) was obtained as a white solid. LCMS: 534 [M+1]; $^1$H NMR (400 MHz, CHLOROFORM-d) δ 7.69 (dd, J=2.63, 6.05 Hz, 1H), 7.54-7.64 (m, 1H), 7.12 (t, J=9.41 Hz, 1H), 6.81 (s, 1H), 5.70-6.08 (m, 1H), 5.14 (quin, J=6.42 Hz, 1H), 4.84 (d, J=15.41 Hz, 1H), 4.33-4.53 (m, 2H), 4.16 (dd, J=5.75, 14.31 Hz, 1H), 3.43-3.88 (m, 5H), 3.32 (dd, J=7.27, 14.98 Hz, 1H), 3.17 (s, 3H), 3.02 (dd, J=5.81, 15.83 Hz, 1H), 2.74-2.89 (m, 1H), 2.66 (d, J=15.77 Hz, 1H), 1.17 (d, J=6.97 Hz, 3H).

332

Compound 136: (R)—N-(3-cyano-4-fluorophenyl)-8,8-difluoro-3,10-dimethyl-11-oxo-1,3,4,7,8,9,10,11-octahydro-2H-pyrido[4',3':3,4]pyrazolo[1,5-a][1,4]diazepine-2-carboxamide

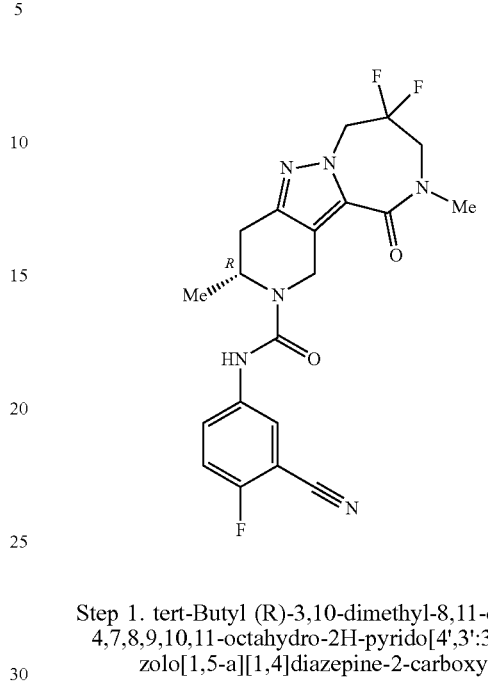

Step 1. tert-Butyl (R)-3,10-dimethyl-8,11-dioxo-1,3,4,7,8,9,10,11-octahydro-2H-pyrido[4',3':3,4]pyrazolo[1,5-a][1,4]diazepine-2-carboxylate To a solution of tert-butyl (R)-3,10-dimethyl-8-methylene-11-oxo-1,3,4,7,8,9,10,11-octahydro-2H-pyrido[4',3':3,4]pyrazolo[1,5-a][1,4]diazepine-2-carboxylate (370.00 mg, 1.07 mmol, 1.00 eq) in THF (10.00 mL) and H$_2$O (5.00 mL) was added OsO4 (27.20 mg, 107.00 μmol, 5.55 μL, 0.10 eq) and NaIO$_4$ (686.59 mg, 3.21 mmol, 177.87 μL, 3.00 eq) at 0° C. The mixture was stirred at 15° C. for 16 hr. The mixture was diluted with EtOAc (60 mL) and washed with saturated Na$_2$SO$_3$ (60 mL). The organic phase was dried over Na$_2$SO$_4$, filtered and concentrated in vacuo to give brown oil. The resulting oil was purified via silica gel column (EA/PE=5/1) to afford the title compound (200.00 mg, 539.61 μmol, 50.43% yield, 94% purity).

Step 2. tert-Butyl (R)-8,8-difluoro-3,10-dimethyl-11-oxo-1,3,4,7,8,9,10,11-octahydro-2H-pyrido[4',3': 3,4]pyrazolo[1,5-a][1,4]diazepine-2-carboxylate To a solution of tert-butyl (R)-3,10-dimethyl-8,11-dioxo-1,3,4,7,8,9,10,11-octahydro-2H-pyrido[4',3':3,4]pyrazolo[1,5-a][1,4]diazepine-2-carboxylate (80.00 mg, 229.62 μmol, 1.00 eq) in DCM (3.00 mL) was added DAST (222.08 mg, 1.38 mmol, 182.03 μL, 6.00 eq) slowly with stirring at −30° C. under N$_2$. The mixture was warmed to 15° C. with stirring for 16 h. The mixture was quenched with 10 mL of water and extracted with DCM (15 mL*3). The combined organic layers were washed with brine (15 mL), dried over anhydrous Na$_2$SO$_4$, filtered and concentrated in vacuum. The residue was purified by prep-TLC (DCM:MeOH=10:1) to afford the title compound (40.00 mg, 97.19 μmol, 42.33% yield, 90% purity) as colorless oil.

Step 3. (R)-8,8-Difluoro-3,10-dimethyl-1,2,3,4,7,8,9,10-octahydro-11H-pyrido[4',3':3,4]pyrazolo[1,5-a][1,4]diazepin-11-one To a solution of tert-butyl (R)-8,8-difluoro-3,10-dimethyl-11-oxo-1,3,4,7,8,9,10,11-octahydro-2H-pyrido[4',3':3, 4]pyrazolo[1,5-a][1,4]diazepine-2-carboxylate (40.00 mg, 97.19 µmol, 1.00 eq) in DCM (3.00 mL) was added TFA (462.00 mg, 4.05 mmol, 300.00 µL, 41.69 eq) at 15° C., and the mixture was stirring for 2 h. The mixture was concentrated in vacuum to afford the title compound (40.00 mg, crude, TFA) was obtained as yellow oil, which was not purified and directly used in the next step.

Step 4. (R)—N-(3-Cyano-4-fluorophenyl)-8,8-difluoro-3,10-dimethyl-11-oxo-1,3,4,7,8,9,10,11-octahydro-2H-pyrido[4',3':3,4]pyrazolo[1,5-a][1,4]diazepine-2-carboxamide To a solution of (R)-8,8-difluoro-3,10-dimethyl-1,2,3,4,7,8,9,10-octahydro-11H-pyrido[4',3':3,4]pyrazolo[1,5-a][1,4]diazepin-11-one (40.00 mg, 104.09 µmol, 1.00 eq, TFA) in DCM (2.00 mL) was added TEA (63.20 mg, 624.54 µmol, 86.58 µL, 6.00 eq) and phenyl N-(3-cyano-4-fluoro-phenyl)carbamate (32.00 mg, 124.91 µmol, 1.20 eq) at 15° C., and then the mixture was stirring for 16 h. The mixture was concentrated in vacuum and purified by prep-HPLC (TFA) twice to give the title compound (18 mg, 39.96 µmol, 38.39% yield, 96% purity) as a white solid. LCMS: 433 [M+1]; $^1$H NMR (400 MHz, CHLOROFORM-d) δ=7.76 (dd, J=2.82, 5.33 Hz, 1H), 7.60 (m, 1H), 7.15 (t, J=8.72 Hz, 1H), 6.67 (s, 1H), 5.07-5.16 (m, 1H), 4.87 (d, J=15.69 Hz, 1H), 4.72 (t, J=12.42 Hz, 2H), 4.47 (d, J=15.69 Hz, 1H), 3.68-3.79 (m, 2H), 3.25 (s, 3H), 3.04 (dd, J=5.58, 16.12 Hz, 1H), 2.72 (d, J=15.56 Hz, 1H), 1.20 (d, J=6.90 Hz, 3H).

Compound 137 D1: (3R,8R*)—N-(3-cyano-4-fluorophenyl)-8-fluoro-3,10-dimethyl-11-oxo-1,3,4,7,8,9,10,11-octahydro-2H-pyrido[4',3':3,4]pyrazolo[1,5-a][1,4]diazepine-2-carboxamide_D1

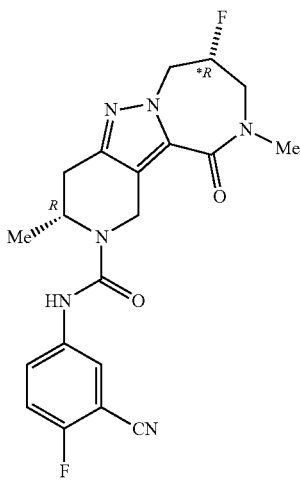

Step 1. tert-Butyl (3R)-8-hydroxy-3,10-dimethyl-11-oxo-1,3,4,7,8,9,10,11-octahydro-2H-pyrido[4',3':3,4]pyrazolo[1,5-a][1,4]diazepine-2-carboxylate To a solution of tert-butyl (R)-3,10-dimethyl-8,11-dioxo-1,3,4,7,8,9,10,11-octahydro-2H-pyrido[4',3':3,4]pyrazolo[1,5-a][1,4]diazepine-2-carboxylate (120.00 mg, 344.43 µmol, 1.00 eq) in MeOH (5.00 mL) was added NaBH$_4$ (39.09 mg, 1.03 mmol, 3.00 eq) at 0° C., and then the mixture was warmed to 15° C. with stirring for 1 h under N$_2$ atmosphere. The mixture was poured into ice-water (20 mL) and stirred at 5 min. The aqueous phase was extracted with ethyl acetate (10 mL*3). The combined organic layers were washed with brine (20 mL), dried with anhydrous Na$_2$SO$_4$, filtered and concentrated in vacuum. The residue was purified by prep-TLC (DCM:MeOH=10:1) to give the title compound (78.00 mg, 222.60 µmol, 64.63% yield) as colorless oil.

Step 2. tert-Butyl (3R)-8-fluoro-3,10-dimethyl-11-oxo-1,3,4,7,8,9,10,11-octahydro-2H-pyrido[4',3':3,4]pyrazolo[1,5-a][1,4]diazepine-2-carboxylate_D1 and tert-butyl (3R)-8-fluoro-3,10-dimethyl-11-oxo-1,3,4,7,8,9,10,11-octahydro-2H-pyrido[4',3':3,4]pyrazolo[1,5-a][1,4]diazepine-2-carboxylate_D2

To a solution of tert-butyl (3R)-8-hydroxy-3,10-dimethyl-11-oxo-1,3,4,7,8,9,10,11-octahydro-2H-pyrido[4',3':3,4]pyrazolo[1,5-a][1,4]diazepine-2-carboxylate (60.00 mg, 171.23 µmol, 1.00 eq) in DCM (1.00 mL) was added DAST (82.80 mg, 513.68 µmol, 67.87 µL, 3.00 eq) drop wise at -30° C., and then the mixture was warmed to 15° C. with stirring for 1 h. The mixture was continued to stir at 15° C. for another 1 h. The mixture was quenched with 10 mL of water and extracted with DCM (15 mL*3). The combined organic layers were washed with brine (15 mL), dried over anhydrous Na$_2$SO$_4$, filtered and concentrated in vacuum. The residue with was purified by prep-TLC (DCM:MeOH=10:1), following by SFC (SFC separation condition: column: IC (250 mm*30 mm, 10 um); mobile phase: [0.1% NH$_3$H$_2$O MEOH]; B %: 25%~25%,4.35 min; 90 min) separation to give two diastereomers: 20 mg of tert-butyl (3R)-8-fluoro-3,10-dimethyl-11-oxo-1,3,4,7,8,9,10,11-octahydro-2H-pyrido[4',3':3,4]pyrazolo[1,5-a][1,4]diazepine-2-carboxylate_D1 and 18 mg of tert-butyl (3R)-8-fluoro-3,10-dimethyl-11-oxo-1,3,4,7,8,9,10,11-octahydro-2H-pyrido[4',3':3,4]pyrazolo[1,5-a][1,4]diazepine-2-carboxylate_D2 as colorless oil.

Step 3. (3R)-8-Fluoro-3,10-dimethyl-1,2,3,4,7,8,9,10-octahydro-11H-pyrido[4',3':3,4]pyrazolo[1,5-a][1,4]diazepin-11-one_D1

To a solution of tert-butyl (3R)-8-fluoro-3,10-dimethyl-11-oxo-1,3,4,7,8,9,10,11-octahydro-2H-pyrido[4',3':3,4]pyrazolo[1,5-a][1,4]diazepine-2-carboxylate_D1 (20 mg, 56.75 µmol, 1 eq) in DCM (1 mL) was added TFA (307.99 mg, 2.70 mmol, 199.99 µL, 47.60 eq) dropwise at 15° C., and the mixture was stirred for 1 h. The mixture was concentrated in vacuum to give the title compound (20.79 mg, crude, TFA) as yellow oil, which was not further purified and directly used in the next step.

Step 4. (3R,8R*)—N-(3-cyano-4-fluorophenyl)-8-fluoro-3,10-dimethyl-11-oxo-1,3,4,7,8,9,10,11-octahydro-2H-pyrido[4',3':3,4]pyrazolo[1,5-a][1,4]diazepine-2-carboxamide_D1

To a solution of (3R)-8-fluoro-3,10-dimethyl-1,2,3,4,7,8,9,10-octahydro-11H-pyrido[4',3':3,4]pyrazolo[1,5-a][1,4]diazepin-11-one_D1 (20.79 mg, 56.75 µmol, 1 eq, TFA) and TEA (34.46 mg, 340.52 µmol, 47.40 µL, 6 eq) in DCM (1 mL) was added phenyl N-(3-cyano-4-fluoro-phenyl)carbamate (18.91 mg, 73.78 µmol, 1.3 eq), and stirred at 15° C. for 16 h. The mixture was concentrated in vacuum, and was purified by prep-HPLC(FA) to give the title compound (7.5 mg, 18.03 µmol, 31.76% yield, 99.6% purity) as a white solid. LCMS: 415 [M+1]. $^1$H NMR (400 MHz, CHLORO- FORM-d) δ=7.80 (dd, J=2.82, 5.46 Hz, 1H), 7.56 (m, 1H), 7.15 (t, J=8.66 Hz, 1H), 6.58 (s, 1H), 5.11-5.19 (m, 1H), 4.83 (d, J=15.69 Hz, 1H), 4.36-4.59 (m, 5H), 3.97-4.07 (m, 1H), 3.23 (s, 3H), 3.04 (dd, J=6.21, 16.00 Hz, 1H), 2.72 (d, J=16.19 Hz, 1H), 1.19 (d, J=6.90 Hz, 3H).

Compound 137_D2: (3R,8S*)—N-(3-Cyano-4-fluorophenyl)-8-fluoro-3,10-dimethyl-11-oxo-1,3,4,7,8,9,10,11-octahydro-2H-pyrido[4',3':3,4]pyrazolo[1,5-a][1,4]diazepine-2-carboxamide_D2

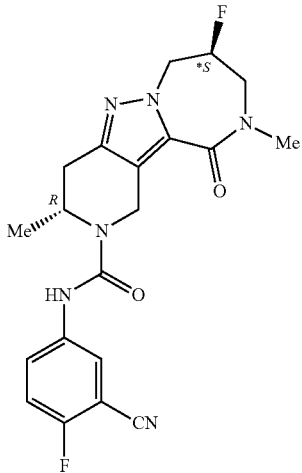

The title compound was prepared in a manner analogous to Compound 246 tert-butyl (3R)-8-fluoro-3,10-dimethyl-11-oxo-1,3,4,7,8,9,10,11-octahydro-2H-pyrido[4',3':3,4]pyrazolo[1,5-a][1,4]diazepine-2-carboxylate_D2. LCMS: 415 [M+1]. ¹H NMR (400 MHz, CHLOROFORM-d) δ=7.81 (dd, J=2.76, 5.40 Hz, 1H), 7.59 (m, 1H), 7.27 (s, 2H), 7.15 (t, J=8.72 Hz, 1H), 6.67 (s, 1H), 5.11-5.21 (m, 1H), 4.93 (d, J=15.56 Hz, 1H), 4.36-4.64 (m, 5H), 3.95-4.09 (m, 1H), 3.23 (s, 3H), 3.06 (dd, J=5.58, 15.87 Hz, 1H), 2.70 (d, J=15.81 Hz, 1H), 1.16 (d, J=6.90 Hz, 3H).

Compound 138: (3R,8R*)-8-fluoro-N-(4-fluoro-3-(trifluoromethyl)phenyl)-3,10-dimethyl-11-oxo-1,3,4,7,8,9,10,11-octahydro-2H-pyrido[4',3':3,4]pyrazolo[1,5-a][1,4]diazepine-2-carboxamide

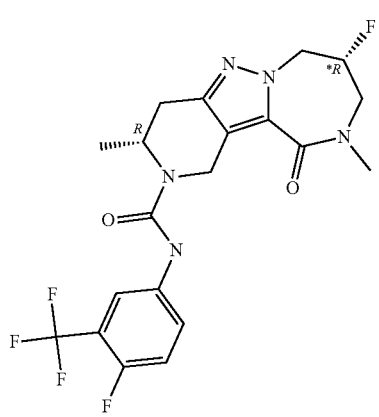

Step 1. tert-Butyl (3R,8R)-8-hydroxy-3,10-dimethyl-11-oxo-1,3,4,7,8,9,10,11-octahydro-2H-pyrido[4',3':3,4]pyrazolo[1,5-a][1,4]diazepine-2-carboxylate Tert-butyl (5R)-11-hydroxy-5,13-dimethyl-14-oxo-4,8,9,13-tetrazatricyclo[7.5.0.0²,⁷] tetradeca-1,7-diene-4-carboxylate (674 mg, 1.92 mmol, 1 eq) was separated via SFC to give both diastereomers: tert-butyl (3R,8R)-8-hydroxy-3,10-dimethyl-11-oxo-1,3,4,7,8,9,10,11-octahydro-2H-pyrido[4',3':3,4]pyrazolo[1,5-a][1,4]diazepine-2-carboxylate_D1 and (345 mg, 936.31 µmol, 95.1% purity, t=1.66 min) and tert-butyl (3R,8R)-8-hydroxy-3,10-dimethyl-11-oxo-1,3,4,7,8,9,10,11-octahydro-2H-pyrido[4',3':3,4]pyrazolo[1,5-a][1,4]diazepine-2-carboxylate_D2 (310 mg, 874.94 µmol, 45.49% yield, 98.9% purity, t=1.89 min) as white solid. SFC analysis condition: AD-3S_4_5_40_3ML. Column: Chiralpak AD-3 100×4.6 mm I.D., 3 um; Mobile phase: isopropanol (0.05% DEA) in CO₂ from 5% to 40%; Flow rate: 3 mL/min Wavelength: 220 nm. SFC separation condition: Column: AD (250 mm*30 mm, 10 um); Mobile phase: [0.1% NH₃H₂O IPA]; B %: 20%~20%, 2.3 min; 150 min.

Step 2. tert-Butyl (3R,8S)-8-fluoro-3,10-dimethyl-11-oxo-1,3,4,7,8,9,10,11-octahydro-2H-pyrido[4',3':3,4]pyrazolo[1,5-a][1,4]diazepine-2-carboxylate_D1

To a solution of resulting tert-butyl (3R,8R)-8-hydroxy-3,10-dimethyl-11-oxo-1,3,4,7,8,9,10,11-octahydro-2H-pyrido[4',3':3,4]pyrazolo[1,5-a][1,4]diazepine-2-carboxylate_D1 (150.00 mg, 428.07 µmol, 1 eq) in DCM (2 mL) was added DAST (207.00 mg, 1.28 mmol, 169.67 µL, 3 eq) at −30° C. The mixture was stirred at −30° C. for 2 hr. The mixture was diluted with H₂O (20 mL) and extracted with DCM (20 mL*3). The combined organic layers were dried over Na₂SO₄, filtered and concentrated under reduced pressure. The residue was purified by prep-TLC (SiO₂, EA:MeOH=10:1) to afford the title compound (89 mg, 250.78 µmol, 58.58% yield, 99.3% purity) as yellow oil and checked by HPLC. SFC (IC-3S_3_5_40_3ML Column: Chiralpak IC-3 100×4.6 mm I.D., 3 um Mobile phase: methanol (0.05% DEA) in CO₂ from 5% to 40% Flow rate: 3 mL/min Wavelength: 220 nm) indicated that the resulting product was corresponding to first diastereomer D1.

Step 3. (3R,8 S)-8-Fluoro-3,10-dimethyl-1,2,3,4,7,8,9,10-octahydro-11H-pyrido[4',3':3,4]pyrazolo[1,5-a][1,4]diazepin-11-one_D1

To a solution of tert-butyl (3R,8S)-8-fluoro-3,10-dimethyl-11-oxo-1,3,4,7,8,9,10,11-octahydro-2H-pyrido[4',3':3,4]pyrazolo[1,5-a][1,4]diazepine-2-carboxylate_D1 (85.00 mg, 241.20 µmol, 1 eq) in DCM (5 mL) was added TFA (770.00 mg, 6.75 mmol, 500.00 µL, 28.00 eq). The mixture was stirred at 16° C. for 2 hr. The mixture was concentrated under reduced pressure to give the title compound (89 mg, crude, TFA) as yellow oil, which without further purified and directly used in the next step.

Step 4. (3R,8R*)-8-fluoro-N-(4-fluoro-3-(trifluoromethyl)phenyl)-3,10-dimethyl-11-oxo-1,3,4,7,8,9,10,11-octahydro-2H-pyrido[4',3':3,4]pyrazolo[1,5-a][1,4]diazepine-2-carboxamide To a solution of (3R,8 S)-8-fluoro-3,10-dimethyl-1,2,3,4,7,8,9,10-octahydro-11H-pyrido[4',3':3,4]pyrazolo[1,5-a][1,4]diazepin-11-one_D1 (70 mg, 277.46 µmol, 1 eq, TFA) in DCM (5 mL) were added TEA (140.38 mg, 1.39 mmol, 193.10 µL, 5 eq) and phenyl N-[4-fluoro-3-(trifluoromethyl)phenyl]carbamate (83.02 mg, 277.46 µmol, 1 eq). The mixture was stirred at 16° C. for 10 hr. The mixture was concentrated under reduced pressure. The residue was purified by prep-HPLC (FA) to give the title compound (54 mg, 118.06 µmol, 42.55% yield, 100% purity) as white solid. LCMS: 458 [M+1]. ¹H NMR (400 MHz, CHLOROFORM-d) δ 7.70 (dd, J=2.64, 6.15 Hz, 1H), 7.55-7.62 (m, 1H), 7.14 (t, J=9.35 Hz, 1H), 6.62 (s, 1H), 5.17 (quin, J=6.84 Hz, 1H), 4.85 (d, J=15.69 Hz, 1H), 4.31-4.63 (m, 5H), 3.93-4.10 (m, 1H), 3.23 (s, 3H), 3.05 (dd, J=6.02, 15.69 Hz, 1H), 2.71 (d, J=16.19 Hz, 1H), 1.19 (d, J=6.90 Hz, 3H).

Compound 139: (R)—N-(3-cyano-4-fluorophenyl)-3,8,8,10-tetramethyl-11-oxo-1,3,4,7,8,9,10,11-octahydro-2H-pyrido[4',3':3,4]pyrazolo[1,5-a][1,4]diazepine-2-carboxamide

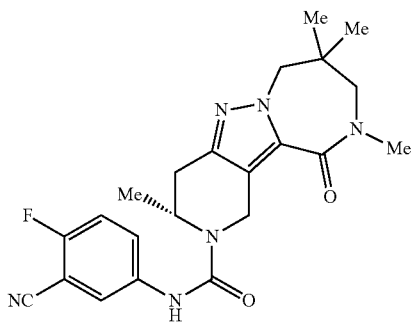 [SMILES: C[C@@H]1Cc2nn3c(c2CN1C(=O)Nc1ccc(F)c(C#N)c1)C(=O)N(C)CC(C)(C)C3]

Step 1.
N-(3-Hydroxy-2,2-dimethylpropyl)formamide

To a solution of 3-amino-2,2-dimethyl-propan-1-ol (3.3 g, 31.99 mmol, 1 eq) in EtOH (60 mL) was added HCOOEt (4.73 g, 63.98 mmol, 2 eq). The mixture was stirred at 80° C. for 6 hr. The mixture was concentrated in vacuum to afford the title compound (4.1 g, crude) as colorless oil, used in the next step directly.

Step 2. 2,2-Dimethyl-3-(methylamino)propan-1-ol

To a solution of N-(3-hydroxy-2,2-dimethyl-propyl)formamide (4 g, 30.49 mmol, 1 eq) in THF (50 mL) at −40° C. was added LAH (1.50 g, 39.64 mmol, 1.3 eq) portionwise. Then the mixture was heated to 20° C. for 16 hr. The mixture was quenched by H₂O (1.5 mL), 15% NaOH (1.5 mL) and H₂O (3 mL). The mixture was filtered and concentrated in vacuum to afford the title compound (3.5 g, crude) as a white solid, used in the next step directly.

Step 3. tert-Butyl (R)-3-((3-hydroxy-2,2-dimethylpropyl)(methyl)carbamoyl)-6-methyl-1,4,6,7-tetrahydro-5H-pyrazolo[4,3-c]pyridine-5-carboxylate To a solution of (R)-5-(tert-butoxycarbonyl)-6-methyl-4,5,6,7-tetrahydro-1H-pyrazolo[4,3-c]pyridine-3-carboxylic acid (1.5 g, 5.33 mmol, 1 eq) and 2,2-dimethyl-3-(methylamino)propan-1-ol (812.34 mg, 6.93 mmol, 1.3 eq) in pyridine (15 mL) was added EDCI (1.23 g, 6.40 mmol, 1.2 eq). The mixture was heated to 40° C. for 16 hr. The mixture was extracted with EA (100 mL*3) and H₂O (100 mL). The combined organic layers were washed with 1N HCl (60 mL*3), filtered, dried over Na₂SO₄, concentrated in vacuum. The residue was purified by flash silica chromatography (PE:EA:50%-100%) to afford the title compound (1.0 g, 2.63 mmol, 49.29% yield) as a white solid.

Step 4. tert-Butyl (R)-3-((2,2-dimethyl-3-((methylsulfonyl)oxy)propyl)(methyl)carbamoyl)-6-methyl-1,4,6,7-tetrahydro-5H-pyrazolo[4,3-c]pyridine-5-carboxylate To a solution of tert-butyl (R)-3-((3-hydroxy-2,2-dimethylpropyl)(methyl)carbamoyl)-6-methyl-1,4,6,7-tetrahydro-5H-pyrazolo[4,3-c]pyridine-5-carboxylate (800 mg, 2.10 mmol, 1 eq) in DCM (8 mL) was added DIEA (815.24 mg, 6.31 mmol, 1.10 mL, 3 eq), followed by MsCl (289.03 mg, 2.52 mmol, 195.29 µL, 1.2 eq) slowly at −10° C. The mixture was stirred at 10° C. for 10 min. Additional MsCl (240.85 mg, 2.10 mmol, 162.74 µL, 1 eq) was added and the mixture was stirred at 10° C. for 10 min. The mixture was diluted with H₂O (20 mL) and extracted with DCM (20 mL). The organic layer was washed with 0.5N HCl (10 mL), dried over Na₂SO₄, filtered and concentrated in vacuum to give the title compound (1.0 g, crude) as a white solid used in the next step directly.

Step 5. tert-Butyl (R)-3,8,8,10-tetramethyl-11-oxo-1,3,4,7,8,9,10,11-octahydro-2H-pyrido[4',3':3,4]pyrazolo[1,5-a][1,4]diazepine-2-carboxylate To a solution of tert-butyl (R)-3-((2,2-dimethyl-3-((methylsulfonyl)oxy)propyl)(methyl)carbamoyl)-6-methyl-1,4,6,7-tetrahydro-5H-pyrazolo[4,3-c]pyridine-5-carboxylate (1.0 g, 1.86 mmol, 1 eq) in THF (10 mL) was added NaH (149.07 mg, 3.73 mmol, 60% purity, 2 eq) at 0° C. The mixture was stirred at 40° C. for 16 hr. The mixture was heated to 40° C. for an additional 32 hr. Additional NaH (111.79 mg, 2.80 mmol, 60% purity, 1.5 eq) was added and the mixture was heated to 40° C. for 48 hr. The mixture was poured into water (10 mL) and extracted with EA (30 mL*3). The combined organic layers were dried over Na₂SO₄, filtered and concentrated in vacuum. The residue was purified by silica gel column chromatography (PE:EA:30%~50%) to afford the title compound (670 mg, 1.85 mmol, 99.20% yield) as a white solid.

Step 6. (R)-3,8,8,10-Tetramethyl-1,2,3,4,7,8,9,10-octahydro-11H-pyrido[4',3':3,4]pyrazolo[1,5-a][1,4]diazepin-11-one To a solution of tert-butyl (R)-3,8,8,10-tetramethyl-11-oxo-1,3,4,7,8,9,10,11-octahydro-2H-pyrido[4',3':3,4]pyrazolo[1,5-a][1,4]diazepine-2-carboxylate (160 mg, 441.42 µmol, 1 eq) in DCM (2 mL) was added TFA (3.08 g, 27.01 mmol, 2 mL, 61.19 eq). The mixture was stirred at 15° C. for 1 hr. The mixture was concentrated in vacuum to afford the title compound (172 mg, crude, TFA) as brown oil, used in the next step directly.

Step 7. (R)—N-(3-Cyano-4-fluorophenyl)-3,8,8,10-tetramethyl-11-oxo-1,3,4,7,8,9,10,11-octahydro-2H-pyrido[4',3':3,4]pyrazolo[1,5-a][1,4]diazepine-2-carboxamide To a solution of (R)-3,8,8,10-tetramethyl-1,2,3,4,7,8,9,10-octahydro-11H-pyrido[4',3':3,4]pyrazolo[1,5-a][1,4]diazepin-11-one (85 mg, 225.84 μmol, 1 eq, TFA) in DCM (2 mL) was added TEA (114.26 mg, 1.13 mmol, 157.17 μL, 5 eq) and phenyl N-(3-cyano-4-fluoro-phenyl)carbamate (57.87 mg, 225.84 μmol, 1 eq). The mixture was stirred at 15° C. for 16 hr. The mixture was concentrated in vacuum. The residue was purified by prep-HPLC (FA) to afford the title compound (51.44 mg, 118.04 μmol, 52.27% yield, 97.4% purity) as a white solid.

LCMS: 425 [M+1]. $^1$H NMR (400 MHz, CHLOROFORM-d) δ=7.81 (dd, J=2.76, 5.52 Hz, 1H), 7.53-7.61 (m, 1H), 7.15 (t, J=8.72 Hz, 1H), 6.57 (s, 1H), 5.14 (br t, J=6.90 Hz, 1H), 4.81 (d, J=15.43 Hz, 1H), 4.51 (d, J=15.31 Hz, 1H), 4.04 (s, 2H), 3.22 (s, 3H), 3.00-3.17 (m, 3H), 2.70 (d, J=15.94 Hz, 1H), 1.11-1.24 (m, 9H).

Compound 140: (R)—N-(4-Fluoro-3-(trifluoromethyl)phenyl)-3,8,8,10-tetramethyl-11-oxo-1,3,4,7,8,9,10,11-octahydro-2H-pyrido[4',3':3,4]pyrazolo[1,5-a][1,4]diazepine-2-carboxamide

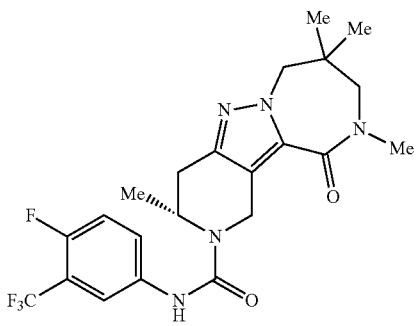

The title compound was prepared in a manner analogous to Compound 139, substituting phenyl (4-fluoro-3-(trifluoromethyl)phenyl)carbamate for phenyl N-(3-cyano-4-fluoro-phenyl)carbamate in Step 7. LCMS: 468 [M+1]. $^1$H NMR (400 MHz, CHLOROFORM-d) δ=7.70 (dd, J=2.57, 6.21 Hz, 1H), 7.56-7.63 (m, 1H), 7.15 (t, J=9.35 Hz, 1H), 6.54 (s, 1H), 5.08-5.21 (m, 1H), 4.81 (d, J=15.31 Hz, 1H), 4.52 (d, J=15.18 Hz, 1H), 4.04 (s, 2H), 3.22 (s, 3H), 3.11-3.18 (m, 1H), 2.99-3.09 (m, 2H), 2.70 (d, J=16.19 Hz, 1H), 1.11-1.23 (m, 9H).

Compound 141: (R)—N-(3-Cyano-4-fluorophenyl)-3-hydroxy-3',10'-dimethyl-11'-oxo-1',3',4',9',10',11'-hexahydro-2'H,7'H-spiro[cyclobutane-1,8'-pyrido[4',3':3,4]pyrazolo[1,5-a][1,4]diazepine]-2'-carboxamide

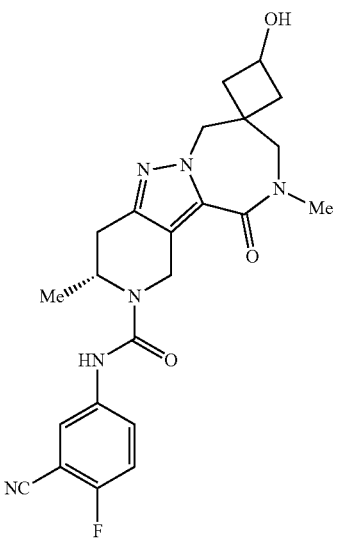 [SMILES: C[C@@H]1Cc2nn3c(c2CN1C(=O)Nc1ccc(F)c(C#N)c1)C(=O)N(C)CC1(CC(O)C1)C3]

Step 1. tert-Butyl (R)-3-(((3-(benzyloxy)-1-(hydroxymethyl)cyclobutyl)methyl)(methyl)carbamoyl)-6-methyl-2,4,6,7-tetrahydro-5H-pyrazolo[4,3-c]pyridine-5-carboxylate To a mixture of [3-benzyloxy-1-(methylaminomethyl)cyclobutyl]methanol (1.6 g, 4.58 mmol, 1 eq, TFA) and (R)-5-(tert-butoxycarbonyl)-6-methyl-4,5,6,7-tetrahydro-2H-pyrazolo[4,3-c]pyridine-3-carboxylic acid (1.03 g, 3.66 mmol, 0.8 eq) in pyridine (10 mL) was added EDCI (1.05 g, 5.50 mmol, 1.2 eq), the reaction mixture was stirred at 40° C. for 16 hours. The reaction mixture was diluted with ethyl acetate (100 mL) and washed with diluted HCl (1N, 80 mL*3), the organic phase was dried with anhydrous Na$_2$SO$_4$, filtered and concentrated in vacuum. The residue was purified by silica gel chromatography. The title compound (835 mg, 98% purity) was obtained as yellow solid.

Step 2. tert-Butyl (R)-3-(((3-(benzyloxy)-1-(((methylsulfonyl)oxy)methyl)cyclobutyl)methyl)(methyl)carbamoyl)-6-methyl-2,4,6,7-tetrahydro-5H-pyrazolo[4,3-c]pyridine-5-carboxylate and tert-butyl (R)-3-(((3-(benzyloxy)-1-(((methyl sulfonyl)oxy)methyl)cyclobutyl)methyl)methyl)(carbamoyl)-6-methyl-2-(methylsulfonyl)-2,4,6,7-tetrahydro-5H-pyrazolo[4,3-c]pyridine-5-carboxylate To a solution of tert-butyl (R)-3-(((3-(benzyloxy)-1-(hydroxymethyl)cyclobutyl)methyl)(methyl)carbamoyl)-6-methyl-2,4,6,7-tetrahydro-5H-pyrazolo[4,3-c]pyridine-5-carboxylate (612.24 mg, 1.20 mmol, 1.00 eq) in DCM (6 mL) were added DIEA (466.56 mg, 3.61 mmol, 628.78 μL, 3 eq) and MsCl (206.76 mg, 1.81 mmol, 139.71 μL, 1.5 eq). The mixture was stirred at 20° C. for 2 hr. Additional MsCl (206.76 mg, 1.81 mmol, 139.71 μL, 1.5 eq) was added and the mixture was stirred at 20° C. for 1 hr. The mixture was extracted with DCM (30 mL*2) and H$_2$O (20 mL). The combined organic layers were washed 0.5 N HCl (10 mL), dried over $Na_2SO_4$, filtered and concentrated in vacuum. To afford a mixture of the title compounds as brown oil, used in the next step directly.

Step 3. tert-Butyl (R)-3-(benzyloxy)-3',10'-dimethyl-11'-oxo-1',3',4',9',10',11'-hexahydro-2'H,7'H-spiro[cyclobutane-18'-pyrido[4',3':3,4]pyrazolo[1,5-a][1,4]diazepine]-2'-carboxylate To a solution of tert-butyl (R)-3-(((3-(benzyloxy)-1-(((methylsulfonyl)oxy)methyl)cyclobutyl)methyl)(methyl) carbamoyl)-6-methyl-2,4,6,7-tetrahydro-5H-pyrazolo[4,3-c]pyridine-5-carboxylate and tert-butyl (R)-3-(((3-(benzyloxy)-1-(((methylsulfonyl)oxy)methyl)cyclobutyl) methyl)(methyl)carbamoyl)-6-methyl-2-(methylsulfonyl)-2,4,6,7-tetrahydro-5H-pyrazolo[4,3-c]pyridine-5-carboxylate (900 mg, 1.46 mmol, 1 eq) in THF (10 mL) was added NaH (234.15 mg, 5.85 mmol, 60% purity, 4 eq) and NaI (43.87 mg, 292.68 μmol, 0.2 eq) at 0° C. The mixture was stirred at 40° C. for 16 hr. Additional NaH (234.12 mg, 5.85 mmol, 60% purity, 4 eq) was added and the mixture was stirred at 40° C. for 48 hr. The mixture was stirred at 40° C. for 16 hr. The mixture was combined with another batch and was quenched with $H_2O$ (40 mL) and extracted with EA (80 mL*3). The combined organic layer was dried over $Na_2SO_4$, filtrated and concentrated in vacuum. The resulting residue s combined with another batch of crude product and purified by column chromatography ($SiO_2$, PE:EA=30%~60%) to give 350 mg desired product totally as colorless oil.

Step 4. tert-Butyl (R)-3-hydroxy-3',10'-dimethyl-11'-oxo-1',3',4',9',10',11'-hexahydro-2'H,7'H-spiro [cyclobutane-1,8'-pyrido[4',3':3,4]pyrazolo[1,5-a][1,4]diazepine]-2'-carboxylate To a solution of tert-butyl (R)-3-(benzyloxy)-3',10'-dimethyl-11'-oxo-1',3',4',9',10',11'-hexahydro-2'H,7'H-spiro[cyclobutane-1,8'-pyrido[4',3':3,4]pyrazolo[1,5-a][1,4]diazepine]-2'-carboxylate (350 mg, 728.26 μmol, 1.00 eq) in MeOH (10.00 mL) was added Pd/C (50 mg, 728.26 μmol, 10% purity, 1.00 eq) under $N_2$. The suspension was degassed under vacuum and purged with $H_2$ several times. The mixture was stirred under $H_2$ (20 psi) at 40° C. for 3 hours. The mixture was stirred under $H_2$ (20 psi) at 40° C. for 16 hours. The mixture was stirred under $H_2$ (50 psi) at 25° C. for 16 hours. The mixture was diluted with MeOH (80 mL), filtrated and concentrated in vacuum to give the title compound (290 mg, crude) as white solid, which was used in the next step directly.

Step 5. (R)-3-Hydroxy-3',10'-dimethyl-1',2',3',4',9',10'-hexahydro-7'H,11'H-spiro[cyclobutane-1,8'-pyrido[4',3':3,4]pyrazolo[1,5-a][1,4]diazepin]-11'-one To a solution of tert-butyl (R)-3-hydroxy-3',10'-dimethyl-11'-oxo-1',3',4',9',10', 11'-hexahydro-2'H,7'H-spiro[cyclobutane-1,8'-pyrido[4',3':3,4]pyrazolo[1,5-a][1,4]diazepine]-2'-carboxylate (55 mg, 140.85 μmol, 1 eq) in DCM (2 mL) was added TFA (2.82 g, 24.76 mmol, 1.83 mL, 175.79 eq). The mixture was stirred at 15° C. for 0.5 hr. The mixture was concentrated in vacuo. The title compound (60 mg, crude, TFA) was obtained as brown oil, which was used in the next step directly.

Step 6. (R)—N-(3-Cyano-4-fluorophenyl)-3-hydroxy-3',10'-dimethyl-11'-oxo-1',3',4',9',10',11'-hexahydro-2'H,7'H-spiro[cyclobutane-1,8'-pyrido[4',3':3,4]pyrazolo[1,5-a][1,4]diazepine]-2'-carboxamide To a solution of (R)-3-hydroxy-3',10'-dimethyl-1',2',3',4',9',10'-hexahydro-7'H, 11'H-spiro[cyclobutane-1,8'-pyrido [4',3':3,4]pyrazolo[1,5-a][1,4]diazepin]-11'-one (58 mg, 143.43 μmol, 1 eq, TFA) and phenyl N-(3-cyano-4-fluorophenyl)carbamate (36.75 mg, 143.43 μmol, 1 eq) in DCM (2 mL) was added TEA (72.57 mg, 717.14 μmol, 99.82 μL, 5 eq). The mixture was stirred at 15° C. for 30 min. The mixture was concentrated in vacuo. The residue was purified by prep-HPLC (FA). The title compound (25.02 mg, 54.65 μmol, 38.11% yield, 98.84% purity) was obtained as white solid. LCMS: 453 [M+1]. $^1$H NMR (400 MHz, METHANOL-$d_4$) δ=7.82 (dd, J 2.76, 5.65 Hz, 1H), 7.70 (ddd, J 2.76, 4.74, 9.19 Hz, 1H), 7.28 (t, J=8.97 Hz, 1H), 4.94-5.04 (m, 2H), 4.31-4.41 (m, 4H), 3.43 (s, 2H), 3.19 (s, 3H), 3.01 (dd, J 5.90, 15.81 Hz, 1H), 2.67 (d, J 15.94 Hz, 1H), 2.40-2.50 (m, 2H), 1.98 (dd, J 7.84, 12.11 Hz, 1H), 1.89 (dd, J=7.15, 12.67 Hz, 1H), 1.22 (d, J=6.90 Hz, 3H).

Compound 142: (R)—N-(3-Cyano-4-fluorophenyl)-3-fluoro-3',10'-dimethyl-11'-oxo-1',3',4',9',10',11'-hexahydro-2'H,7'H-spiro[cyclobutane-1,8'-pyrido[4',3':3,4]pyrazolo[1,5-a][1,4]diazepine]-2'-carboxamide

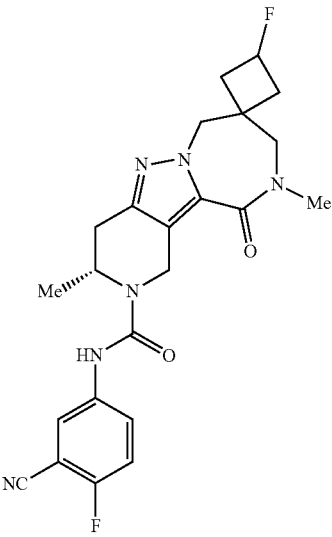 [SMILES: C[C@@H]1Cc2nn3c(c2CN1C(=O)Nc1ccc(F)c(C#N)c1)C(=O)N(C)CC1(CC(F)C1)C3]

Step 1. tert-Butyl (R)-3-fluoro-3',10'-dimethyl-1'-oxo-1',3',4',9',10',11'-hexahydro-2'H,7'H-spiro[cyclobutane-1,8'-pyrido[4',3':3,4]pyrazolo[1,5-a][1,4]diazepine]-2'-carboxylate To a solution of tert-butyl (R)-3-hydroxy-3',10'-dimethyl-11'-oxo-1',3',4',9',10',11'-hexahydro-2'H,7'H-spiro[cyclobutane-1,8'-pyrido[4',3':3,4]pyrazolo[1,5-a][1,4]diazepine]-2'-carboxylate (70 mg, 179.27 μmol, 1 eq) in DCM (1.5 mL) was added DAST (86.69 mg, 537.81 μmol, 71.06 μL, 3 eq) at −40° C. The mixture was stirred at 0° C. for 1 hr. The mixture was combined with another batch of the crude reaction. Diluted with $H_2O$ (30 mL) and extracted with DCM (20 mL*2). The combined organic layers were dried over Na$_2$SO$_4$, filtered and concentrated in vacuo to afford 100 mg of the title compound was obtained as brown oil.

Step 2. (R)-3-Fluoro-3',10'-dimethyl-1',2',3',4',9',10'-hexahydro-7'H, 11'H-spiro[cyclobutane-1,8'-pyrido[4',3':3,4]pyrazolo[1,5-a][1,4]diazepin]-11'-one To a solution of tert-butyl (R)-3-fluoro-3',10'-dimethyl-11'-oxo-1',3',4',9',10',11'-hexahydro-2'H,7'H-spiro[cyclobutane-1,8'-pyrido[4',3':3,4]pyrazolo[1,5-a][1,4]diazepine]-2'-carboxylate (80 mg, 203.84 µmol, 1 eq) in DCM (1.5 mL) was added TFA (3.50 g, 30.71 mmol, 2.27 mL, 150.68 eq). The mixture was stirred at 10° C. for 1 hr. The mixture was concentrated in vacuo. The title compound (85 mg, crude, TFA) was obtained as brown oil.

Step 3. (R)—N-(3-Cyano-4-fluorophenyl)-3-fluoro-3',10'-dimethyl-1'-oxo-1',3',4',9',10',11'-hexahydro-2'H,7'H-spiro[cyclobutane-1,8'-pyrido[4',3':3,4]pyrazolo [1,5-a][1,4]diazepine]-2'-carboxamide To a solution of (R)-3-fluoro-3',10'-dimethyl-1',2',3',4',9',10'-hexahydro-7'H, 11'H-spiro[cyclobutane-1,8'-pyrido[4',3':3,4]pyrazolo[1,5-a][1,4]diazepin]-11'-one (80 mg, 196.86 µmol, 1 eq, TFA) and phenyl N-(3-cyano-4-fluoro-phenyl) carbamate (50.44 mg, 196.86 µmol, 1 eq) in DCM (2 mL) was added TEA (99.60 mg, 984.31 µmol, 137.01 µL, 5 eq). The mixture was stirred at 15° C. for 30 min. The mixture was concentrated in vacuo. The residue was purified by prep-TLC (PE:EA=0:1), Further purification by prep-HPLC (FA). The title compound (16.53 mg, 35.97 µmol, 18.27% yield, 98.9% purity) was obtained as white solid. LCMS: 455 [M+1]. $^1$H NMR (400 MHz, METHANOL-d$_4$) δ=7.82 (dd, J=2.76, 5.65 Hz, 1H), 7.70 (ddd, J=2.76, 4.71, 9.10 Hz, 1H), 7.28 (t, J=8.97 Hz, 1H), 5.21 (quin, J=6.21 Hz, 1H), 5.05-5.24 (m, 1H), 5.04-5.12 (m, 1H), 4.93-5.04 (m, 2H), 4.41 (d, J=2.01 Hz, 2H), 4.35 (d, J=16.69 Hz, 1H), 3.44 (s, 2H), 3.21 (s, 3H), 3.01 (dd, J=5.83, 15.75 Hz, 1H), 2.66 (d, J=15.81 Hz, 1H), 2.42-2.62 (m, 2H), 2.22-2.36 (m, 2H), 1.23 (d, J=6.90 Hz, 3H).

Compound 143: (R)—N-(3-Cyano-4-fluorophenyl)-3,3-difluoro-3',10'-dimethyl-11'-oxo-1',3',4',9',10',11'-hexahydro-2'H,7'H-spiro[cyclobutane-1,8'-pyrido[4',3':3,4]pyrazolo[1,5-a][1,4]diazepine]-2'-carboxamide

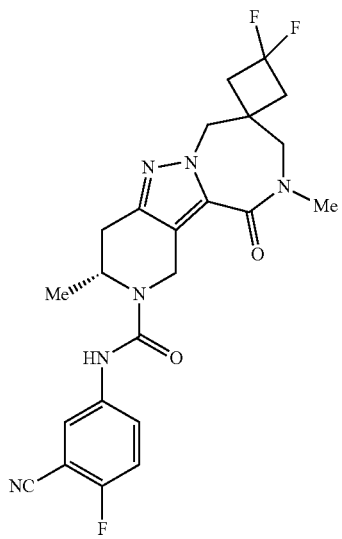 [SMILES: C[C@@H]1Cc2nn3c(c2CN1C(=O)Nc1ccc(F)c(C#N)c1)C(=O)N(C)CC1(C3)CC(F)(F)C1]

Step 1. tert-Butyl (R)-3',10'-dimethyl-3,11'-dioxo-1',3',4',9',10',11'-hexahydro-2'H,7'H-spiro[cyclobutane-1,8'-pyrido[4',3':3,4]pyrazolo[1,5-a][1,4]diazepine]-2'-carboxylate To a solution of tert-butyl (R)-3-hydroxy-3',10'-dimethyl-11'-oxo-1',3',4',9',10',11'-hexahydro-2'H,7'H-spiro[cyclobutane-1,8'-pyrido[4',3':3,4]pyrazolo[1,5-a][1,4]diazepine]-2'-carboxylate (130 mg, 332.93 µmol, 1 eq) in DCM (2 mL) was added DMP (282.42 mg, 665.86 µmol, 206.14 µL, 2 eq). The mixture was stirred at 15° C. for 1 hr. The mixture was combined with another batch to dilute with DCM (30 mL) and filtered, the filtrates was concentrated in vacuo. The residue was purified by column chromatography(SiO2, PE:EA:2:1-1:2) to give 100 mg of desired product as white solid.

Step 2. tert-butyl (R)-3,3-difluoro-3',10'-dimethyl-1'-oxo-1',3',4',9',10',11'-hexahydro-2'H,7'H-spiro [cyclobutane-1,8'-pyrido[4',3':3,4]pyrazolo[1,5-a][1,4]diazepine]-2'-carboxylate To a solution of tert-butyl (R)-3',10'-dimethyl-3,11'-dioxo-1',3',4',9',10',11'-hexahydro-2'H,7'H-spiro[cyclobutane-1,8'-pyrido[4',3':3,4]pyrazolo[1,5-a][1,4]diazepine]-2'-carboxylate (90 mg, 231.68 µmol, 1 eq) in DCM (2 mL) was added DAST (186.72 mg, 1.16 mmol, 153.05 µL, 5 eq) at -40° C. The mixture was stirred at 0° C. for 1 hr. The mixture was combined with another batch (EW619-1976) to dilute with H$_2$O (30 mL) and extracted with DCM (20 mL*2). The combined organic layer was dried over Na$_2$SO$_4$, filtered and concentrated in vacuo. 100 mg crude product was obtained as brown oil, which was used in the next step directly.

Step 3. (R)-3,3-Difluoro-3',10'-dimethyl-1',2',3',4',9',10'-hexahydro-7'H,11'H-spiro[cyclobutane-1,8'-pyrido[4',3':3,4]pyrazolo[1,5-a][1,4]diazepin]-11'-one To a solution of tert-butyl (R)-3,3-difluoro-3',10'-dimethyl-11'-oxo-1',3',4',9',10',11'-hexahydro-2'H,7'H-spiro[cyclobutane-1,8'-pyrido[4',3':3,4]pyrazolo[1,5-a][1,4]diazepine]-2'-carboxylate (100 mg, 243.63 µmol, 1 eq) in DCM (2 mL) was added TFA (3.08 g, 27.01 mmol, 2 mL, 110.87 eq). The mixture was stirred at 20° C. for 0.5 hr. The mixture was concentrated in vacuo to give the title compound (110 mg, crude, TFA) as brown oil.

Step 4. (R)—N-(3-Cyano-4-fluorophenyl)-3,3-difluoro-3',10'-dimethyl-11'-oxo-1',3',4',9',10',11'-hexahydro-2'H,7'H-spiro[cyclobutane-1,8'-pyrido[4',3':3,4]pyrazolo[1,5-a][1,4]diazepine]-2'-carboxamide To a solution of (R)-3,3-Difluoro-3',10'-dimethyl-1',2',3',4',9',10'-hexahydro-7'H, 11'H-spiro[cyclobutane-1,8'-pyrido[4',3':3,4]pyrazolo[1,5-a][1,4]diazepin]-11'-one (100 mg, 322.23 µmol, 1 eq, TFA) and phenyl N-(3-cyano-4-fluorophenyl)carbamate (82.56 mg, 322.23 µmol, 1 eq) in DCM (2 mL) was added TEA (163.03 mg, 1.61 mmol, 224.25 µL, 5 eq). The mixture was stirred at 15° C. for 30 min. The residue was purified by prep-HPLC (FA). The title compound (35.85 mg, 73.15 µmol, 22.70% yield, 96.4% purity) was obtained as white solid. LCMS: 473 [M+1]. $^1$H NMR (400 MHz, CHLOROFORM-d) δ=7.79 (dd, J 2.75, 5.44 Hz, 1H), 7.59 (ddd, J=2.87, 4.52, 9.11 Hz, 1H), 7.15 (t, J=8.74 Hz, 1H), 6.69 (s, 1H), 5.14 (quin, J 6.51 Hz, 1H), 4.84 (d, J 15.53 Hz, 1H), 4.41-4.52 (m, 3H), 3.46-3.58 (m, 2H), 3.24 (s, 3H), 3.03 (dd, J 5.87, 16.02 Hz, 1H), 2.51-2.78 (m, 5H), 1.20 (d, J 6.97 Hz, 3H).

Compound 144_E1: (S)—N-(3-Cyano-4-fluorophenyl)-8-fluoro-10-methyl-11-oxo-1,3,4,7,8,9,10,11-octahydro-2H-pyrido[4',3':3,4]pyrazolo[1,5-a][1,4]diazepine-2-carboxamide E1

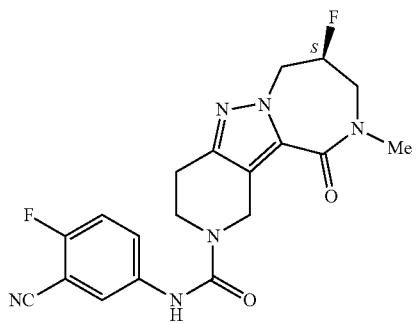

Step 1. 5-(tert-Butyl) 3-ethyl 2-(2-(chloromethyl)allyl)-2,4,6,7-tetrahydro-5H-pyrazolo[4,3-c]pyridine-3,5-dicarboxylate To a solution of 5-(tert-butyl) 3-ethyl 2,4,6,7-tetrahydro-5H-pyrazolo[4,3-c]pyridine-3,5-dicarboxylate (10 g, 33.86 mmol, 1 eq) in DMF (130 mL) was added $Cs_2CO_3$ (16.55 g, 50.79 mmol, 1.5 eq) and 3-chloro-2-(chloromethyl)prop-1-ene (21.16 g, 169.30 mmol, 19.59 mL, 5 eq). The solution was stirred at 50° C. for 3 hr. The mixture was diluted with EtOAc (100 mL) and filtered. The filtrate was poured into 0.5 N HCl (300 mL). The solution was extracted with ethyl acetate (200 mL*2). The combined organic layers were washed with brine (200 mL*3), dried with anhydrous $Na_2SO_4$, filtered and concentrated. The residue was purified by column chromatography. The title compound (5.3 g, 13.53 mmol, 39.96% yield, 98% purity) was obtained as white solid. LCMS: 384 [M+1].

Step 2. tert-Butyl 10-methyl-8-methylene-11-oxo-1,3,4,7,8,9,10,11-octahydro-2H-pyrido[4',3':3,4]pyrazolo[1,5-a][1,4]diazepine-2-carboxylate To a solution of 5-(tert-butyl) 3-ethyl 2-(2-(chloromethyl)allyl)-2,4,6,7-tetrahydro-5H-pyrazolo[4,3-c]pyridine-3,5-dicarboxylate (5.3 g, 13.81 mmol, 1 eq) in EtOH (21 mL) was added $MeNH_2$ (42.88 g, 414.20 mmol, 30 eq, 30% $MeNH_2$ in EtOH). The mixture was heated to 80° C. for 16 hr in a sealed tube. The solution was concentrated. The residue was purified by column chromatography. The title compound (2.6 g, 7.82 mmol, 56.65% yield) was obtained as white solid. LCMS: 333 [M+1].

Step 3. tert-Butyl 10-methyl-8,11-dioxo-1,3,4,7,8,9,10,11-octahydro-2H-pyrido[4',3':3,4]pyrazolo[1,5-a][1,4]diazepine-2-carboxylate To a solution of tert-butyl 10-methyl-8-methylene-11-oxo-1,3,4,7,8,9,10,11-octahydro-2H-pyrido[4',3':3,4]pyrazolo[1,5-a][1,4]diazepine-2-carboxylate (1.2 g, 3.61 mmol, 1 eq) in THF (30 mL) and $H_2O$ (15 mL) was added $OsO_4$ (275.34 mg, 1.08 mmol, 56.19 µL, 0.3 eq) and $NaIO_4$ (2.32 g, 10.83 mmol, 600.14 L, 3 eq) at 0° C. The mixture was stirred at 10° C. for 7 hr. The solution was poured into ice sat. $NaHSO_3$ (100 mL). The mixture extracted with ethyl acetate (50 mL*2). The combined organic layers were washed with brine (50 mL), dried with anhydrous $Na_2SO_4$, filtered and concentrated. The residue was purified by column chromatography. The title compound (580 mg, 1.56 mmol, 43.21% yield, 90% purity) was obtained as white solid. LCMS: 353 [M+19].

Step 4. tert-Butyl 8-hydroxy-10-methyl-11-oxo-1,3,4,7,8,9,10,11-octahydro-2H-pyrido[4',3':3,4]pyrazolo[1,5-a][1,4]diazepine-2-carboxylate To a solution of tert-butyl 10-methyl-8,11-dioxo-1,3,4,7,8,9,10,11-octahydro-2H-pyrido[4',3':3,4]pyrazolo[1,5-a][1,4]diazepine-2-carboxylate (580 mg, 1.56 mmol, 1 eq) in MeOH (15 mL) was added $NaBH_4$ (107.62 mg, 2.84 mmol, 1.82 eq) at 0° C. The solution was stirred at 0° C. for 1 hr. The solution was poured into water (30 mL). The mixture extracted with ethyl acetate (20 mL*2). The combined organic layers were washed with brine (20 mL), dried with anhydrous $Na_2SO_4$, filtered and concentrated. The title compound (550 mg, crude) was obtained as white solid. LCMS: 337 [M+1].

Step 5. tert-Butyl 8-hydroxy-10-methyl-11-oxo-1,3,4,7,8,9,10,11-octahydro-2H-pyrido[4',3':3,4]pyrazolo[1,5-a][1,4]diazepine-2-carboxylate_E1 and tert-butyl 8-hydroxy-10-methyl-11-oxo-1,3,4,7,8,9,10,11-octahydro-2H-pyrido[4',3':3,4]pyrazolo[1,5-a][1,4]diazepine-2-carboxylate_E2

Racemate of tert-butyl 8-hydroxy-10-methyl-11-oxo-1,3,4,7,8,9,10,11-octahydro-2H-pyrido[4',3':3,4]pyrazolo[1,5-a][1,4]diazepine-2-carboxylate (580 mg, 1.53 mmol) was resolved via SFC to give both enantiomers: tert-Butyl 8-hydroxy-10-methyl-11-oxo-1,3,4,7,8,9,10,11-octahydro-2H-pyrido[4',3':3,4]pyrazolo[1,5-a][1,4]diazepine-2-carboxylate_E1 (200 mg, 558.29 µmol, 36.38% yield, 93.9% purity, t=3.176 min) and tert-Butyl 8-hydroxy-10-methyl-1-oxo-1,3,4,7,8,9,10,11-octahydro-2H-pyrido[4',3':3,4]pyrazolo[1,5-a][1,4]diazepine-2-carboxylate_E2 (250 mg, 684.48 µmol, 44.60% yield, 92.1% purity, t=3.401 min) as white solid. SFC analytical method: IC-3S_4_5_40_3ML Column: Chiralpak IC-3 100×4.6 mm I.D., 3 um Mobile phase: iso-propanol (0.05% DEA) in $CO_2$ from 5% to 40% Flow rate: 3 mL/min Wavelength: 254 nm.

SFC separation method: column: IC (250 mm*30 mm, 10 um); mobile phase: [0.1% $NH_3H_2O$ IPA]; B %: 35%~35%, 4.35 min; 100 min.

Step 6. tert-Butyl (S)-8-fluoro-10-methyl-11-oxo-1,3,4,7,8,9,10,11-octahydro-2H-pyrido[4',3':3,4]pyrazolo[1,5-a][1,4]diazepine-2-carboxylate_E1

To a solution of tert-Butyl 8-hydroxy-10-methyl-11-oxo-1,3,4,7,8,9,10,11-octahydro-2H-pyrido[4',3':3,4]pyrazolo[1,5-a][1,4]diazepine-2-carboxylate_E1 (140.00 mg, 390.80 µmol, 1 eq) in DCM (2 mL) was added DAST (201.26 mg, 1.25 mmol, 164.97 µL, 3.19 eq) at −20° C. The solution was stirred at 0° C. for 0.5 hr. The solution was poured into ice sat. $NaHCO_3$ (30 mL). The mixture extracted with ethyl acetate (20 mL*2). The combined organic layers were washed with brine (20 mL), dried with anhydrous $Na_2SO_4$, filtered and concentrated. The residue was purified by prep- TLC. The title compound (75 mg, 221.65 μmol, 56.72% yield) was obtained as yellow oil.

Step 7. (S)-8-Fluoro-10-methyl-1,2,3,4,7,8,9,10-octahydro-11H-pyrido[4',3':3,4]pyrazolo[1,5-a][1,4]diazepin-11-one_E1

To a solution of tert-butyl (S)-8-fluoro-10-methyl-11-oxo-1,3,4,7,8,9,10,11-octahydro-2H-pyrido[4',3':3,4]pyrazolo[1,5-a][1,4]diazepine-2-carboxylate_E1 (75.00 mg, 221.65 μmol, 1 eq) in DCM (5 mL) was added TFA (7.70 g, 67.53 mmol, 5.00 mL, 304.68 eq). The solution was stirred at 25° C. for 0.5 hr. The solution was concentrated. The title compound (80 mg, crude, TFA) was obtained as yellow oil.

Step 8. (S)—N-(3-Cyano-4-fluorophenyl)-8-fluoro-10-methyl-11-oxo-1,3,4,7,8,9,10,11-octahydro-2H-pyrido[4',3':3,4]pyrazolo[1,5-a][1,4]diazepine-2-carboxamide E1

To a solution of (S)-8-fluoro-10-methyl-1,2,3,4,7,8,9,10-octahydro-11H-pyrido[4',3':3,4]pyrazolo[1,5-a][1,4]diazepin-11-one_E1 (78 mg, 1 eq, TFA) in DCM (5 mL) was added TEA (112.02 mg, 1.11 mmol, 154.09 μL, 5 eq) and phenyl N-(3-cyano-4-fluoro-phenyl)carbamate (56.73 mg, 221.40 μmol, 1 eq). The solution was stirred at 25° C. for 16 hr. The solution was concentrated. The residue was purified by prep-HPLC. The title compound (52.09 mg, 129.06 μmol, 99.2% purity) was obtained as white solid. LCMS: 401 [M+1]. $^1$H NMR (400 MHz, CHLOROFORM-d) δ 7.79 (dd, J=2.76, 5.52 Hz, 1H), 7.59 (ddd, J=2.76, 4.52, 9.03 Hz, 1H), 7.14 (t, J=8.66 Hz, 1H), 6.78 (s, 1H), 4.65-4.86 (m, 2H), 4.35-4.63 (m, 1H), 3.97-4.07 (m, 1H), 3.79-3.95 (m, 2H), 3.22 (s, 3H), 2.88 (br t, J=5.71 Hz, 2H).

Compound 144_E2: (R)—N-(3-Cyano-4-fluorophenyl)-8-fluoro-10-methyl-11-oxo-1,3,4,7,8,9,10,11-octahydro-2H-pyrido[4',3':3,4]pyrazolo[1,5-a][1,4]diazepine-2-carboxamide E2

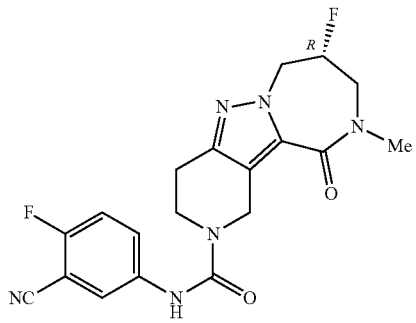

The title compound was prepared in a manner analogous to Compound 144_E1 substituting tert-Butyl 8-hydroxy-10-methyl-11-oxo-1,3,4,7,8,9,10,11-octahydro-2H-pyrido[4',3':3,4]pyrazolo[1,5-a][1,4]diazepine-2-carboxylate_E2 for tert-butyl 8-hydroxy-10-methyl-11-oxo-1,3,4,7,8,9,10,11-octahydro-2H-pyrido[4',3':3,4]pyrazolo[1,5-a][1,4]diazepine-2-carboxylate_E1. LCMS: 401 [M+1]. $^1$H NMR (400 MHz, CHLOROFORM-d) δ 7.78 (dd, J=2.76, 5.27 Hz, 1H), 7.56-7.63 (m, 1H), 7.14 (t, J=8.72 Hz, 1H), 6.81 (s, 1H), 4.65-4.89 (m, 2H), 4.32-4.62 (m, 4H), 4.01 (br dd, J=5.21, 10.85 Hz, 1H), 3.77-3.95 (m, 2H), 3.22 (s, 3H), 2.82-2.94 (m, 2H).

Compound 145_D1: (R)—N-(3-Cyano-4-fluorophenyl)-8-(2,2-difluoroethoxy)-10-methyl-11-oxo-1,3,4,7,8,9,10,11-octahydro-2H-pyrido[4',3':3,4]pyrazolo[1,5-a][1,4]diazepine-2-carboxamide

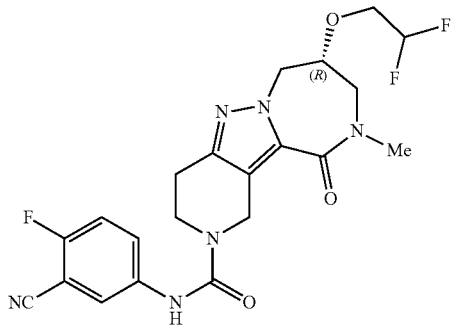

Step 1. tert-Butyl (R)-8-(2,2-difluoroethoxy)-10-methyl-11-oxo-1,3,4,7,8,9,10,11-octahydro-2H-pyrido[4',3':3,4]pyrazolo[1,5-a][1,4]diazepine-2-carboxylate To a suspension of NaH (24.97 mg, 624.28 μmol, 60% purity, 3 eq) in THF (0.6 mL) was added a solution of tert-butyl (R)-8-hydroxy-10-methyl-11-oxo-1,3,4,7,8,9,10,11-octahydro-2H-pyrido[4',3':3,4]pyrazolo[1,5-a][1,4]diazepine-2-carboxylate_E1 (70 mg, 208.09 μmol, 1 eq) in THF (0.6 mL) at −40° C., the mixture was stirred at −40° C. for 30 min. Then a solution of 2,2-difluoroethyl trifluoromethanesulfonate (133.67 mg, 624.28 μmol, 3 eq) in THF (0.4 mL) was added at −40° C. dropwise. The mixture was stirred at 5° C. for 1 hr. The mixture was quenched with H$_2$O (20 mL) at 0° C. and extracted with EA (30 mL*2). The combined organic layers were dried over Na$_2$SO$_4$, filtered and concentrated in vacuo to give the title compound (85 mg, crude) as yellow oil, which was used in the next step directly.

Step 2. (R)-8-(2,2-Difluoroethoxy)-10-methyl-1,2,3,4,7,8,9,10-octahydro-11H-pyrido[4',3':3,4]pyrazolo[1,5-a][1,4]diazepin-11-one To a solution of tert-butyl (R)-8-(2,2-difluoroethoxy)-10-methyl-11-oxo-1,3,4,7,8,9,10,11-octahydro-2H-pyrido[4',3':3,4]pyrazolo[1,5-a][1,4]diazepine-2-carboxylate (120 mg, 299.69 μmol, 1 eq) in DCM (2 mL) was added TFA (3.08 g, 27.01 mmol, 2.00 mL, 90.13 eq). The mixture was stirred at 15° C. for 0.5 hr. The mixture was concentrated in vacuo to give the title compound (126 mg, crude, TFA) as yellow oil.

Step 3. (R)—N-(3-Cyano-4-fluorophenyl)-8-(2,2-difluoroethoxy)-10-methyl-11-oxo-1,3,4,7,8,9,10,11-octahydro-2H-pyrido[4',3':3,4]pyrazolo[1,5-a][1,4]diazepine-2-carboxamide To a solution of (R)-8-(2,2-difluoroethoxy)-10-methyl-1,2,3,4,7,8,9,10-octahydro-11H-pyrido[4',3':3,4]pyrazolo[1,5-a][1,4]diazepin-11-one (125 mg, 301.69 μmol, 1 eq, TFA) and phenyl N-(3-cyano-4-fluoro-phenyl)carbamate (77.30 mg, 301.69 μmol, 1 eq) in DCM (5 mL) was added TEA (152.64 mg, 1.51 mmol, 209.96 μL, 5 eq). The mixture was stirred at 15° C. for 3 hr. The mixture was concentrated in vacuo. The residue was purified by prep-HPLC(FA) to give the title compound (65.88 mg, 140.76 μmol, 46.66% yield, 98.8% purity) was obtained a white solid. LCMS: 463 [M+1]. ¹H NMR (400 MHz, CHLOROFORM-d) 6=7.78 (dd, J=2.76, 5.40 Hz, 1H), 7.60 (ddd, J=2.82, 4.55, 9.07 Hz, 1H), 7.15 (t, J=8.72 Hz, 1H), 6.79 (s, 1H), 5.75-6.08 (m, 1H), 4.57-4.78 (m, 3H), 4.25-4.35 (m, 2H), 3.73-3.95 (m, 4H), 3.42-3.60 (m, 2H), 3.22 (s, 3H), 2.79-2.92 (m, 2H).

Compound 145_D2: (S)—N-(3-Cyano-4-fluorophenyl)-8-(2,2-difluoroethoxy)-10-methyl-1-oxo-1,3,4,7,8,9,10,11-octahydro-2H-pyrido[4',3':3,4]pyrazolo[1,5-a][1,4]diazepine-2-carboxamide

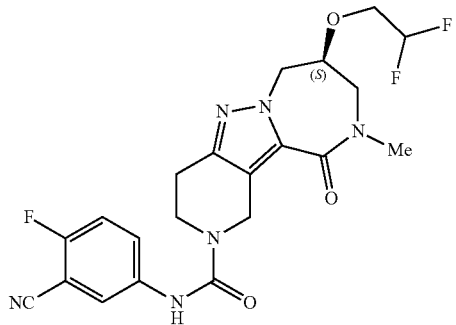

The title compound was prepared in a manner analogous to Compound 145_D1 substituting tert-butyl (S)-8-hydroxy-10-methyl-11-oxo-1,3,4,7,8,9,10,11-octahydro-2H-pyrido[4',3':3,4]pyrazolo[1,5-a][1,4]diazepine-2-carboxylate for tert-butyl (R)-8-hydroxy-10-methyl-11-oxo-1,3,4,7,8,9,10,11-octahydro-2H-pyrido[4',3':3,4]pyrazolo[1,5-a][1,4]diazepine-2-carboxylate. LCMS: 463 [M+1]. ¹H NMR (400 MHz, CHLOROFORM-d) 6=7.78 (dd, J=2.76, 5.52 Hz, 1H), 7.60 (ddd, J=2.76, 4.58, 9.10 Hz, 1H), 7.14 (t, J=8.72 Hz, 1H), 6.84 (s, 1H), 5.75-6.10 (m, 1H), 4.55-4.77 (m, 3H), 4.25-4.36 (m, 2H), 3.72-3.95 (m, 4H), 3.43-3.61 (m, 2H), 3.22 (s, 3H), 2.79-2.93 (m, 2H).

Compound 146: (R)—N-(3-Cyano-4-fluorophenyl)-3-methyl-11-oxo-1,3,4,7,8,9,10,11-octahydro-2H-pyrido[4',3':3,4]pyrazolo[1,5-a][1,4]diazepine-2-carboxamide

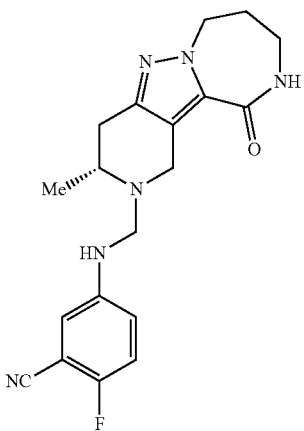 [SMILES: C[C@@H]1Cc2nn3c(c2CN1CNc1ccc(F)c(C#N)c1)C(=O)NCCC3]

Step 1. (R)-3-Methyl-1,2,3,4,7,8,9,10-octahydro-11H-pyrido[4',3':3,4]pyrazolo[1,5-a][1,4]diazepin-11-one To a solution of tert-butyl (R)-3-methyl-11-oxo-1,3,4,7,8,9,10,11-octahydro-2H-pyrido[4',3':3,4]pyrazolo[1,5-a][1,4]diazepine-2-carboxylate (140 mg, 436.97 μmol, 1 eq) in DCM (10 mL) was added TFA (7.70 g, 67.53 mmol, 5 mL, 154.54 eq). The solution was stirred at 20° C. for 1 hr. TLC (ethyl acetate) indicated starting material was consumed completely. The solution was concentrated. The title compound (146 mg, crude, TFA) was obtained as yellow oil.

Step 2. (R)—N-(3-Cyano-4-fluorophenyl)-3-methyl-11-oxo-1,3,4,7,8,9,10,11-octahydro-2H-pyrido[4',3':3,4]pyrazolo[1,5-a][1,4]diazepine-2-carboxamide To a solution of (R)-3-methyl-1,2,3,4,7,8,9,10-octahydro-11H-pyrido[4',3':3,4]pyrazolo[1,5-a][1,4]diazepin-11-one (73 mg, 218.37 μmol, 1 eq, TFA) in DCM (5 mL) was added TEA (66.29 mg, 655.11 μmol, 91.18 μL, 3 eq) and phenyl N-(3-cyano-4-fluoro-phenyl)carbamate (50.36 mg, 196.53 μmol, 0.9 eq). The solution was stirred at 20° C. for 16 hr. The solution was concentrated. The residue was purified by prep-HPLC(FA). The title compound (55 mg, 143.11 μmol, 65.54% yield, 99.5% purity) was obtained as a white solid. LCMS: 383 [M+1]. ¹H NMR (400 MHz, CHLOROFORM-d) δ 7.81 (dd, J=2.76, 5.52 Hz, 1H), 7.63 (ddd, J=2.89, 4.55, 9.13 Hz, 1H), 7.12 (t, J=8.78 Hz, 1H), 7.02 (s, 1H), 6.20 (br s, 1H), 5.15 (quin, J=6.40 Hz, 1H), 4.88 (d, J=15.94 Hz, 1H), 4.42-4.55 (m, 3H), 3.43-3.53 (m, 2H), 3.02 (dd, J=5.83, 15.75 Hz, 1H), 2.67 (d, J=15.81 Hz, 1H), 2.27-2.38 (m, 2H), 1.17 (d, J=6.90 Hz, 3H).

Compound 147: (R)—N-(4-Fluoro-3-(trifluoromethyl)phenyl)-3-methyl-11-oxo-1,3,4,7,8,9,10,11-octahydro-2H-pyrido[4',3':3,4]pyrazolo[1,5-a][1,4]diazepine-2-carboxamide

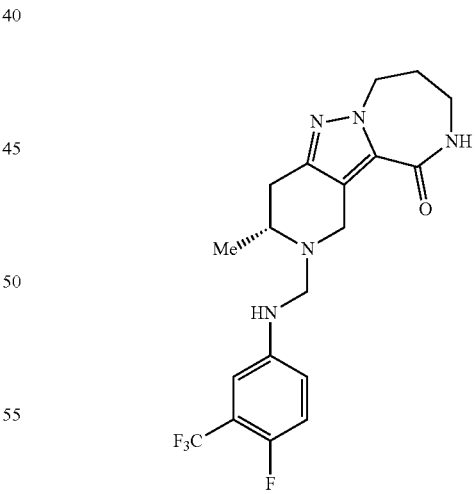

To a solution of (R)-3-methyl-1,2,3,4,7,8,9,10-octahydro-11H-pyrido[4',3':3,4]pyrazolo[1,5-a][1,4]diazepin-11-one (73 mg, 218.37 μmol, 1 eq, TFA) in DCM (5 mL) was added TEA (66.29 mg, 655.11 μmol, 91.18 μL, 3 eq) and phenyl N-[4-fluoro-3-(trifluoromethyl)phenyl]carbamate (58.81 mg, 196.53 μmol, 0.9 eq). The solution was stirred at 20° C. for 16 hr. The solution was concentrated. The residue was purified by prep-HPLC(FA). The title compound (47.8 mg, 112.02 μmol, 51.30% yield, 99.69% purity) was obtained as white solid. LCMS: 426 [M+1]. 1H NMR (400 MHz, CHLOROFORM-d) δ 7.71 (dd, J=2.70, 6.09 Hz, 1H), 7.55-7.64 (m, 1H), 7.12 (t, J=9.47 Hz, 1H), 6.87 (s, 1H), 6.12 (br s, 1H), 5.17 (quin, J=6.40 Hz, 1H), 4.88 (d, J=15.81 Hz, 1H), 4.43-4.56 (m, 3H), 3.45-3.53 (m, 2H), 3.03 (dd, J=5.90, 15.81 Hz, 1H), 2.67 (d, J=15.81 Hz, 1H), 2.28-2.39 (m, 2H), 1.17 (d, J=6.90 Hz, 3H).

Compound 148: (3R,8S)—N-(3-Cyano-4-fluorophenyl)-8-(hydroxymethyl)-3,9-dimethyl-10-oxo-3,4,7,8,9,10-hexahydropyrido[4',3':3,4]pyrazolo [1,5-a]pyrazine-2 (1H)-carboxamide

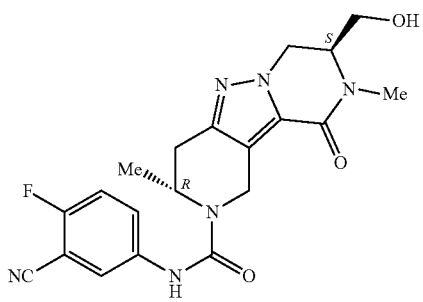

Step 1. (2S)-1-allyloxy-3-[tert-butyl (dimethyl)silyl] oxy-propan-2-ol

To a solution of (2R)-3-allyloxypropane-1,2-diol (8 g, 60.53 mmol, 1 eq) and Imid (6.18 g, 90.80 mmol, 1.5 eq) in DCM (50 mL) was added TBSCl (9.12 g, 60.53 mmol, 7.42 mL, 1 eq) dropwise at 0° C. with stirring for 1 h. The mixture was quenched with aqueous saturated NH₄Cl solution (50 mL*1) and extracted with EtOAc (50 mL*3). The organic layers were washed with brine (50 mL*1), dried over anhydrous Na₂SO₄, filtered and concentrated in vacuum. The residue was purified by column chromatography (SiO₂, Petroleum ether/Ethyl acetate=50/1 to 20/1). The title compound (12 g, 48.70 mmol, 80.45% yield) was obtained as colorless liquid.

Step 2. [(1S)-1-(Allyloxymethyl)-2-[tert-butyl(dimethyl)silyl]oxy-ethyl] methanesulfonate To a solution of (2S)-1-allyloxy-3-[tert-butyl(dimethyl)silyl]oxy-propan-2-ol (12 g, 48.70 mmol, 1 eq) and DIEA (18.88 g, 146.09 mmol, 25.45 mL, 3 eq) in DCM (80 mL) was added MsCl (8.37 g, 73.05 mmol, 5.65 mL, 1.5 eq) at 0° C. with stirring for 2 h. The mixture was quenched with aqueous 1 N HCl solution (100 mL*1) and extracted with EtOAc (60 mL*3). The organic layers were washed with brine (60 mL*1), dried over anhydrous Na₂SO₄, filtered and concentrated in vacuum to afford the title compound (15.9 g, crude) was obtained as yellow oil, which was directly used in the next step without purification.

Step 3. (2R)-1-Allyloxy-3-[tert-butyl (dimethyl) silyl] oxy-N-methyl-propan-2-amine A mixture of [(1S)-1-(allyloxymethyl)-2-[tert-butyl (dimethyl) silyl] oxy-ethyl] methanesulfonate (15.9 g, 49.00 mmol, 1 eq) and methanamine (49.00 mmol, 30%, 50 mL EtOH solution) was stirred at 80° C. for 32 h. Then the mixture was stirred at 80° C. for another 16 h. The mixture was concentrated under vacuum. The residue was purified by column chromatography (SiO₂, Petroleum ether/Ethyl acetate=50/1 to 10/1) to give the title compound (8.0 g, 30.83 mmol, 62.93% yield) as yellow oil.

Step 4. tert-Butyl (6R)-3-[[(1R)-1-(allyloxymethyl)-2-[tert-butyl (dimethyl) silyl] oxy-ethyl]-methyl-carbamoyl]-6-methyl-2,4,6,7-tetrahydropyrazolo[4,3-c]pyridine-5-carboxylate To a solution of (6R)-5-tert-butoxycarbonyl-6-methyl-2,4,6,7-tetrahydropyrazolo[4,3-c]pyridine-3-carboxylic acid (2 g, 7.11 mmol, 1 eq) and (2R)-1-allyloxy-3-[tert-butyl (dimethyl)silyl]oxy-N-methyl-propan-2-amine (2.21 g, 8.53 mmol, 1.2 eq) in Py (15 mL) was added EDCI (1.64 g, 8.53 mmol, 1.2 eq). The solution was stirred at 40° C. for 16 hr. The solution was diluted with ethyl acetate (100 mL). The organic phase was washed with 1N HCl (100 mL*3) and brine (80 mL), dried with anhydrous Na₂SO₄, filtered and concentrated. The residue was purified by column chromatography to give the title compound (1.9 g, 3.63 mmol, 51.12% yield) as yellow solid. LCMS: 523 [M+1].

Step 5. tert-Butyl (6R)-3-[[(1S)-1-(allyloxymethyl)-2-hydroxy-ethyl]-methyl-carbamoyl]-6-methyl-2,4,6,7-tetrahydropyrazolo [4,3-c] pyridine-5-carboxylate To a solution of tert-butyl (6R)-3-[[(1R)-1-(allyloxymethyl)-2-[tert-butyl(dimethyl) silyl]oxy-ethyl]-methyl-carbamoyl]-6-methyl-2,4,6,7-tetrahydropyrazolo[4,3-c]pyridine-5-carboxylate (1.9 g, 3.63 mmol, 1 eq) in THF (30 mL) was added TBAF (1 M, 4.36 mL, 1.2 eq). The solution was stirred at 25° C. for 0.5 hr. The solution was poured into water (30 mL). The mixture extracted with ethyl acetate (20 mL*2). The combined organic layers were washed with brine (20 mL*3), dried with anhydrous Na₂SO₄, filtered and concentrated. The residue was purified by column chromatography to give the title compound (1.23 g, 3.01 mmol, 82.84% yield) as white solid.

Step 6. tert-Butyl (3R,8S)-8-(allyloxymethyl)-3,9-dimethyl-10-oxo-3,4,7,8-tetrahydro-1H-pyrido[2,3] pyrazolo[2,4-c]pyrazine-2-carboxylate To a solution of tert-butyl (6R)-3-[[(1S)-1-(allyloxymethyl)-2-hydroxy-ethyl]-methyl-carbamoyl]-6-methyl-2,4,6,7-tetrahydropyrazolo [4,3-c] pyridine-5-carboxylate (1.13 g, 2.77 mmol, 1 eq) in THF (60 mL) was added tributylphosphane (1.68 g, 8.30 mmol, 2.05 mL, 3 eq). The solution was stirred at 25° C. for 15 min. Then ADDP (2.09 g, 8.30 mmol, 3 eq) was added. The solution was stirred at 70° C. for 16 hr. The solution was diluted with ethyl acetate (50 mL). The organic phase was washed with 1N HCl (30 mL*3) and brine (50 mL), dried with anhydrous Na₂SO₄, filtered and concentrated. The residue was purified by column chromatography to give the title compound (818 mg, 2.07 mmol, 74.97% yield, 99% purity) as white solid. LCMS: 391 [M+1].

Step 7. give tert-Butyl (3R,8S)-8-(hydroxymethyl)-3,9-dimethyl-10-oxo-3,4,7,8-tetrahydro-1H-pyrido [2,3]pyrazolo[2,4-c]pyrazine-2-carboxylate A solution of tert-butyl (3R,8S)-8-(allyloxymethyl)-3,9-dimethyl-10-oxo-3,4,7,8-tetrahydro-1H-pyrido[2,3]pyrazolo[2,4-c]pyrazine-2-carboxylate (900 mg, 2.30 mmol, 1 eq), OsO₄ (175.79 mg, 691.46 µmol, 35.88 µL, 0.3 eq), NaIO₄ (2.46 g, 11.52 mmol, 638.59 µL, 5 eq), and NMO (1.35 g, 11.52 mmol, 1.22 mL, 5 eq) in dioxane (30 mL) and H₂O (10 mL) was stirred at 60° C. for 16 hr. The mixture was poured into water (30 mL). The solution was extracted with EtOAc (30 mL*2). The combined organic layers were washed with Na₂S₂O₃ (30 mL) and brine (30 mL), dried with anhydrous Na₂SO₄, filtered and concentrated. The residue was purified by column chromatography to give the desired product (600 mg, 1.67 mmol, 72.43% yield, 97.5% purity) as white solid, which was 86% de from SFC. The product was re-purified by SFC (Analysis condition: OJ-3S_3_5_40_3ML; Column: Chiralcel OJ-3 100×4.6 mm I.D., 3 um Mobile phase: methanol (0.05% DEA) in C$_{O2}$ from 5% to 40% Flow). Separation condition: Column: OJ (250 mm*30 mm, 5 um); mobile phase: [0.1% NH₃H₂O MeOH]; B %: 15%~15%, 1.8 min; 90 min) to give tert-butyl (3R,8S)-8-(hydroxymethyl)-3,9-dimethyl-10-oxo-3,4,7,8-tetrahydro-1H-pyrido[2,3]pyrazolo[2,4-c]pyrazine-2-carboxylate (410 mg, 1.17 mmol, 68.33% yield) was obtained as white solid. LCMS: 351 [M+1].

Step 8. (3R,8S)-8-(hydroxymethyl)-3,9-dimethyl-1,2,3,4,7,8-hexahydropyrido[2,3] pyrazolo[2,4-c]pyrazin-10-one To a solution of tert-butyl (3R,8 S)-8-(hydroxymethyl)-3,9-dimethyl-10-oxo-3,4,7,8-tetrahydro-1H-pyrido[2,3]pyrazolo[2,4-c]pyrazine-2-carboxylate (40 mg, 107.30 µmol, 1 eq) in DCM (5 mL) was added TFA (7.70 g, 67.53 mmol, 5 mL, 629.35 eq). The solution was stirred at 20° C. for 0.5 hr. The solution was concentrated to afford the title compound (40 mg, crude, TFA) was obtained as yellow oil.

Step 9. (3R,8S)—N-(3-Cyano-4-fluorophenyl)-8-(hydroxymethyl)-3,9-dimethyl-10-oxo-3,4,7,8,9,10-hexahydropyrido[4',3':3,4]pyrazolo[1,5-a]pyrazine-2 (1H)-carboxamide To a solution of (3R,8S)-8-(hydroxymethyl)-3,9-dimethyl-1,2,3,4,7,8-hexahydropyrido[2,3]pyrazolo[2,4-c]pyrazin-10-one (39 mg, 1 eq, TFA) in DCM (6 mL) was added TEA (45.98 mg, 454.39 µmol, 63.25 µL, 5 eq) and phenyl N-(3-cyano-4-fluoro-phenyl)carbamate (20.96 mg, 81.80 µmol, 0.9 eq). The solution was stirred at 20° C. for 16 hr. The solution was concentrated. The residue was purified by prep-HPLC (column: Phenomenex Synergi C18 150*30 mm*4 um; mobile phase: [water (0.225% FA)-ACN]; B %: 18%~48%, 10.5 min). The title compound (27.27 mg, 65.40 µmol, 98.9% purity) was obtained as white solid. LCMS: 413 [M+1]. ¹H NMR (400 MHz, CHLOROFORM-d) δ 7.82 (ddd, J=2.76, 4.58, 9.10 Hz, 1H), 7.66 (dd, J=2.64, 5.40 Hz, 1H), 7.18 (t, J=8.78 Hz, 1H), 6.89 (s, 1H), 4.99-5.14 (m, 1H), 4.45-4.54 (m, 1H), 4.31-4.41 (m, 1H), 4.03-4.26 (m, 3H), 3.74-3.89 (m, 2H), 3.26 (s, 3H), 2.89 (dd, J=5.65, 15.69 Hz, 1H), 2.61 (d, J=15.81 Hz, 1H), 1.04 (d, J=6.90 Hz, 3H).

Compound 149: (3R,8S)—N-(3-cyano-4-fluorophenyl)-8-(fluoromethyl)-3,9-dimethyl-10-oxo-3,4,7,8,9,10-hexahydropyrido[4',3':3,4]pyrazolo[1,5-a]pyrazine-2 (1H)-carboxamide

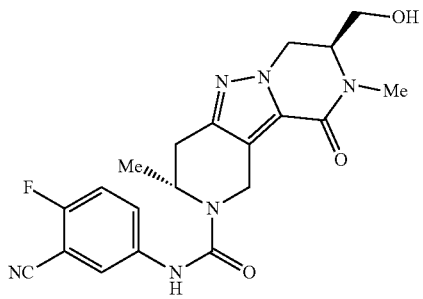 [SMILES: C[C@@H]1Cc2nn3c(c2CN1C(=O)Nc1ccc(F)c(C#N)c1)C(=O)N(C)[C@H](CO)C3]

Step 1. tert-Butyl (3R,8S)-8-(fluoromethyl)-3,9-dimethyl-10-oxo-3,4,7,8-tetrahydro-1H-pyrido[2,3]pyrazolo[2,4-c]pyrazine-2-carboxylate To a solution of tert-butyl (3R,8S)-8-(hydroxymethyl)-3,9-dimethyl-10-oxo-3,4,7,8-tetrahydro-1H-pyrido[2,3]pyrazolo[2,4-c]pyrazine-2-carboxylate (120 mg, 342.45 µmol, 1 eq) in DCM (6 mL) was added DAST (165.60 mg, 1.03 mmol, 135.74 µL, 3 eq) at 0° C. The solution was stirred at 20° C. for 0.5 hr. The solution was poured into sat. NaHCO₃ (30 mL). The mixture extracted with ethyl acetate (20 mL*2). The combined organic layers were washed with brine (20 mL), dried with anhydrous Na₂SO₄, filtered and concentrated. The residue was purified by prep-TLC (SiO₂, Ethyl acetate, Rf=0.51) to give the title compound (75 mg, 212.82 µmol, 49.72% yield) as white solid.

Step 2. (3R,8S)-8-(Fluoromethyl)-3,9-dimethyl-1,2,3,4,78-hexahydropyrido[2,3]pyrazolo[2,4-c]pyrazin-10-one To a solution of tert-butyl (3R,8 S)-8-(fluoromethyl)-3,9-dimethyl-10-oxo-3,4,7,8-tetrahydro-1H-pyrido[2,3]pyrazolo[2,4-c]pyrazine-2-carboxylate (70 mg, 198.64 µmol, 1 eq) in DCM (5 mL) was added TFA (7.70 g, 67.53 mmol, 5 mL, 339.97 eq). The solution was stirred at 25° C. for 0.5 hr. The solution was concentrated to give the title compound (73 mg, crude, TFA) as yellow oil.

Step 3. (3R,8S)—N-(3-cyano-4-fluorophenyl)-8-(fluoromethyl)-3,9-dimethyl-10-oxo-3,4,7,8,9,10-hexahydropyrido[4',3':3,4]pyrazolo[1,5-a]pyrazine-2 (1H)-carboxamide To a solution of (3R,8S)-8-(fluoromethyl)-3,9-dimethyl-1,2,3,4,7,8-hexahydropyrido[2,3]pyrazolo[2,4-c]pyrazin-10-one (73 mg, 289.35 µmol, 1 eq) in DCM (5 mL) was added phenyl N-(3-cyano-4-fluoro-phenyl)carbamate (74.14 mg, 289.35 µmol, 1 eq) and TEA (146.40 mg, 1.45 mmol, 201.37 µL, 5 eq). The solution was stirred at 25° C. for 16 hr. LC—The mixture was concentrated and purified by prep-HPLC to give the title compound (46.27 mg, 111.03 µmol, 38.37% yield, 99.44% purity) as white solid. LCMS: 415 [M+1].

1H NMR (400 MHz, CHLOROFORM-d) δ 7.79 (dd, J=2.69, 5.38 Hz, 1H), 7.62 (m, 1H), 7.13 (t, J=8.74 Hz, 1H), 6.97 (s, 1H), 5.15 (m, 1H), 4.87 (d, J=15.77 Hz, 1H), 4.33-4.62 (m, 5H), 3.94-4.09 (m, 1H), 3.17-3.29 (m, 3H), 3.03 (dd, J=5.69, 15.96 Hz, 1H), 2.70 (d, J=16.02 Hz, 1H), 1.17 (d, J=6.97 Hz, 3H).

Compound 150: (3R,8S)—N-(3-cyano-4-fluorophenyl)-8-((2,2-difluoroethoxy)methyl)-3,9-dimethyl-10-oxo-3,4,7,8,9,10-hexahydropyrido[4',3':3,4]pyrazolo[1,5-a]pyrazine-2 (1H)-carboxamide

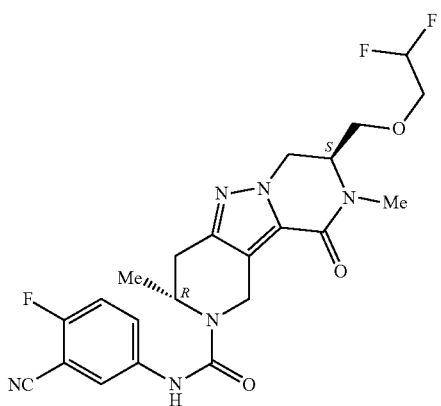

Step 1. tert-Butyl (3R,8S)-8-(2,2-difluoroethoxymethyl)-3,9-dimethyl-10-oxo-3,4,7,8-tetrahydro-1H-pyrido[2,3]pyrazolo[2,4-c]pyrazine-2-carboxylate To a solution of tert-butyl (3R,8S)-8-(hydroxymethyl)-3,9-dimethyl-10-oxo-3,4,7,8-tetrahydro-1H-pyrido[2,3]pyrazolo[2,4-c]pyrazine-2-carboxylate (100 mg, 285.38 μmol, 1 eq) in THF (2 mL) was added NaH (22.83 mg, 570.76 μmol, 60% purity, 2 eq) at −20° C. The solution was stirred at −20° C. for 30 min. Then 2,2,2-difluoroethyl trifluoromethanesulfonate (183.31 mg, 856.13 μmol, 3 eq) was added, the solution was stirred at 25° C. for 2 hr. The solution was poured into water (30 mL). The mixture extracted with ethyl acetate (20 mL*2). The combined organic layers were washed with brine (20 mL*3), dried with anhydrous $Na_2SO_4$, filtered and concentrated to give the title compound (120 mg, crude) as yellow oil.

Step 2. (3R,8S)-8-(2,2-Difluoroethoxymethyl)-3,9-dimethyl-1,2,3,4,7,8-hexahydropyrido[2,3]pyrazolo[2,4-c]pyrazin-10-one To a solution of tert-butyl (3R,8 S)-8-(2,2-difluoroethoxymethyl)-3,9-dimethyl-10-oxo-3,4,7,8-tetrahydro-1H-pyrido[2,3]pyrazolo[2,4-c]pyrazine-2-carboxylate (110 mg, 265.41 μmol, 1 eq) in DCM (5 mL) was added TFA (7.70 g, 67.53 mmol, 5 mL, 254.43 eq). The solution was stirred at 25° C. for 0.5 hr. The solution was concentrated to afford the title compound (120 mg, crude, TFA) as yellow oil.

Step 3. (3R,8S)—N-(3-Cyano-4-fluorophenyl)-8-((2,2-difluoroethoxy)methyl)-3,9-dimethyl-10-oxo-3,4,7,8,9,10-hexahydropyrido[4',3':3,4]pyrazolo[1,5-a]pyrazine-2 (1H)-carboxamide To a solution of(3R,8S)-8-(2,2-difluoroethoxymethyl)-3,9-dimethyl-1,2,3,4,7,8-hexahydropyrido[2,3]pyrazolo[2,4-c]pyrazin-10-one (110 mg, 349.95 μmol, 1 eq) in DCM (5 mL) was added phenyl N-(3-cyano-4-fluoro-phenyl)carbamate (89.67 mg, 349.95 μmol, 1 eq) and TEA (106.23 mg, 1.05 mmol, 146.13 μL, 3 eq). The solution was stirred at 25° C. for 16 hr. The solution was concentrated. The residue was purified by prep-HPLC to give the title compound (80.53 mg, 165.22 μmol, 47.21% yield, 97.75% purity) as a white solid. LCMS: 477 [M+1]. $^1$H NMR (400 MHz, CHLOROFORM-d) δ 7.80 (dd, J=2.51, 5.14 Hz, 1H), 7.54-7.69 (m, 1H), 7.13 (t, J=8.66 Hz, 1H), 6.87 (s, 1H), 5.60-6.01 (m, 1H), 5.15 (br t, J=6.21 Hz, 1H), 4.85 (br d, J=15.56 Hz, 1H), 4.49-4.65 (m, 2H), 4.33-4.47 (m, 1H), 3.83-3.99 (m, 1H), 3.46-3.80 (m, 4H), 3.19 (s, 3H), 3.03 (br dd, J=5.52, 15.81 Hz, 1H), 2.71 (br d, J=16.06 Hz, 1H), 1.18 (br d, J=6.90 Hz, 3H).

Compound 151: ((3R,8S)-3,10-Dimethyl-2-(4-nitrobenzoyl)-11-oxo-1,3,4,7,8,9,10,11-octahydro-2H-pyrido[4',3':3,4]pyrazolo[1,5-a][1,4]diazepin-8-yl) methyl 4-nitrobenzoate

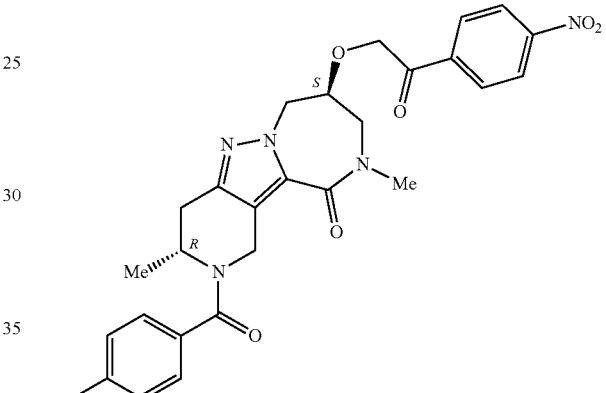

Step 1. (3R,8S)-8-(hydroxymethyl)-3,10-dimethyl-1,2,3,4,7,8,9,10-octahydro-11H-pyrido[4',3':3,4]pyrazolo[1,5-a][1,4]diazepin-11-one A mixture of tert-butyl (3R,8S)-8-(hydroxymethyl)-3,10-dimethyl-11-oxo-1,3,4,7,8,9,10,11-octahydro-2H-pyrido[4',3':3,4]pyrazolo[1,5-a][1,4]diazepine-2-carboxylate (100.00 mg, 274.39 μmol, 1 eq) and TFA (3.08 g, 27.01 mmol, 2.00 mL, 98.44 eq) in DCM (4 mL) was stirred at 15° C. for 1 hr under $N_2$ atmosphere. The mixture was concentrated in vacuum to give the title compound (103.8 mg, 274.35 μmol, 99.98% yield, TFA) as a yellow oil, which was used directly for next step.

Step 2. ((3R,8S)-3,10-Dimethyl-2-(4-nitrobenzoyl)-11-oxo-1,3,4,7,8,9,10,11-octahydro-2H-pyrido[4',3':3,4]pyrazolo[1,5-a][14]diazepin-8-yl)methyl 4-nitrobenzoate A mixture of ((3R,8S)-8-(hydroxymethyl)-3,10-dimethyl-1,2,3,4,7,8,9,10-octahydro-11H-pyrido[4',3':3,4]pyrazolo[1,5-a][1,4]diazepin-11-one (103 mg, 272.24 μmol, 1 eq, TFA), 4-nitrobenzoyl chloride (325.33 mg, 1.75 mmol, 6.44 eq) and TEA (220.38 mg, 2.18 mmol, 303.14 μL, 8 eq) in DCM (6 mL) was stirred at 15° C. for 16 hr under $N_2$ atmosphere. MeOH (6 mL) was added to the mixture and stirred for 30 min. The mixture was washed by cool $Na_2CO_3$ (aq. 1N, 20 mL*3). The organic phase was dried with anhydrous Na₂SO₄, filtered and concentrated in vacuum to give title compound (180 mg, crude) as a yellow oil.

A mixture of resulting ((3R,8S)-8-(hydroxymethyl)-3,10-dimethyl-1,2,3,4,7,8,9,10-octahydro-11H-pyrido[4',3':3,4]pyrazolo[1,5-a][1,4]diazepin-11-one (180.00 mg, crude), and 4-nitrobenzoyl chloride (80.79 mg, 435.39 µmol, 1 eq), TEA (88.11 mg, 870.77 µmol, 121.20 µL, 2 eq), DMAP (2.66 mg, 21.77 µmol, 0.05 eq) in DCM (5 mL) was degassed and purged with N₂ for 3 times, and then the mixture was stirred at 15° C. for 16 hr under N₂ atmosphere. LCMS showed the desired product was form mainly. The mixture was poured into ice-water (10 mL) and stirred for 1 min. The aqueous phase was extracted with DCM (20 mL). The combined organic phase was washed with brine (10 mL), dried with anhydrous Na₂SO₄, filtered and concentrated in vacuum. The residue was purified by prep-HPLC to give the title compound (85 mg, 146.57 µmol, 33.66% yield, 97% purity) as a white solid. LCMS: 563 [M+1]. ¹H NMR (400 MHz, CHLOROFORM-d) δ 8.32 (br d, J=8.78 Hz, 4H), 8.19 (d, J=8.78 Hz, 2H), 7.60 (d, J=8.78 Hz, 2H), 5.43-5.71 (m, 1H), 4.15-4.59 (m, 6H), 2.94-3.53 (m, 7H), 2.56-2.82 (m, 1H), 1.23-1.35 (m, 3H).

Example 1: HBV Assembly Assay

The interference of compounds from this invention with HBV capsid assembly could be measured using an in vitro assembly assay based on fluorescence quenching, which was developed according to a method described by Zlotnick and coworkers (Nature Biotechnology 2006, 24:358). In a typical assay, a mutant HBV C150 protein (amino acids 1-150, C49A, C61A, C107A, 150C) is cloned into a T7 RNA-polymerase based expression vector, expressed in *E. coli* and purified to homogeneity as a dimer. The purified HBV core protein is desalted and labeled with BODIPY-FL Dye.

In a non-limiting embodiment, the assembly assay is conducted in 96-well plate format. The assembly reactions are carried out in 50 mM Hepes buffer, pH 7.5 and 150 mM NaCl. The compounds are pre-incubated with the HBV CA protein for 15 min, and the assembly reactions are initiated by addition of NaCl. The reaction is allowed to continue for 1 hour at room temperature. The changes in fluorescence between DMSO treated and compound treated samples are recorded and analyzed for assembly modulation.

Example 2: HBV Replication Inhibition Assay

HBV replication inhibition by the disclosed compounds were determined in cells infected or transfected with HBV, or cells with stably integrated HBV, such as HepG2.2.15 cells (Sells et al. 1987). In this example, HepG2.2.15 cells were maintained in cell culture medium containing 10% fetal bovine serum (FBS), Geneticin, L-glutamine, penicillin and streptomycin. HepG2.2.15 cells were seeded in 96-well plates at a density of 40,000 cells/well and were treated with serially diluted compounds at a final DMSO concentration of 0.5% either alone or in combination by adding drugs in a checker box format. Cells were incubated with compounds for three days, after which medium was removed and fresh medium containing compounds was added to cells and incubated for another three days. At day 6, supernatant was removed and treated with DNase at 37° C. for 60 minutes, followed by enzyme inactivation at 75° C. for 15 minutes. Encapsidated HBV DNA was released from the virions and covalently linked HBV polymerase by incubating in lysis buffer (Affymetrix QS0010) containing 2.5 µg proteinase K at 50° C. for 40 minutes. HBV DNA was denatured by addition of 0.2 M NaOH and detected using a branched DNA (BDNA) QuantiGene assay kit according to manufacturer recommendation (Affymetrix). HBV DNA levels were also quantified using qPCR, based on amplification of encapsidated HBV DNA extraction with QuickExtraction Solution (Epicentre Biotechnologies) and amplification of HBV DNA using HBV specific PCR probes that can hybridize to HBV DNA and a fluorescently labeled probe for quantitation. In addition, cell viability of HepG2.2.15 cells incubated with test compounds alone or in combination was determined by using CellTitre-Glo reagent according to the manufacturer protocol (Promega). The mean background signal from wells containing only culture medium was subtracted from all other samples, and percent inhibition at each compound concentration was calculated by normalizing to signals from HepG2.2.15 cells treated with 0.5% DMSO using equation E1.

$$\% \text{ inhibition} = (DMSOave - Xi)/DMSOave \times 100\% \quad \text{E1:}$$

where DMSOave is the mean signal calculated from the wells that were treated with DMSO control (0% inhibition control) and Xi is the signal measured from the individual wells. EC50 values, effective concentrations that achieved 50% inhibitory effect, were determined by non-linear fitting using Graphpad Prism software (San Diego, Calif.) and equation E2:

$$Y = Y\min + (Y\max - Y\min)/(1 + 10(\text{Log EC50} - X) \times \text{HillSlope}) \quad \text{E2:}$$

where Y represents percent inhibition values and X represents the logarithm of compound concentrations.

Selected disclosed compounds were assayed in the HBV replication assay (BDNA assay), as described above and a representative group of these active compounds is shown in Table 6.

Table 6 shows $EC_{50}$ values obtained by the BDNA assay for a group of select compounds. In Table 6, "A" represents $1 < EC_{50} \leq 100$; "B" represents $100 < EC_{50} \leq 500$; "C" represents $500 < EC_{50} \leq 1000$; and "D" represents $EC_{50} > 1000$.

TABLE 6

Activity in BDNA-assay ($EC_{50}$)

| Compound ID | Compound Name | DNA $EC_{50}$ (nM) |
|---|---|---|
| 001 | N-(3-chloro-4-fluorophenyl)-10-methyl-8-methylene-11-oxo-1,3,4,7,8,9,10,11-octahydro-2H-pyrido[4',3':3,4]pyrazolo[1,5-a][1,4]diazepine-2-carboxamide | A |
| 002 | N-(3-chloro-4-fluorophenyl)-8-(hydroxymethyl)-10-methyl-11-oxo-1,3,4,7,8,9,10,11-octahydro-2H-pyrido[4',3':3,4]pyrazolo[1,5-a][1,4]diazepine-2-carboxamide | A |
| 003 | N-(3-chloro-4-fluorophenyl)-8-hydroxy-8-(hydroxymethyl)-10-methyl-11-oxo-1,3,4,7,8,9,10,11-octahydro-2H-pyrido[4',3':3,4]pyrazolo[1,5-a][1,4]diazepine-2-carboxamide | C |
| 004 | N-(3-chloro-4-fluorophenyl)-8-hydroxy-10-methyl-11-oxo-1,3,4,7,8,9,10,11-octahydro-2H-pyrido[4',3':3,4]pyrazolo[1,5-a][1,4]diazepine-2-carboxamide | A |
| 005 | N-(3-chloro-4-fluorophenyl)-8,8-difluoro-10-methyl-11-oxo-1,3,4,7,8,9,10,11-octahydro-2H-pyrido[4',3':3,4]pyrazolo[1,5-a][1,4]diazepine-2-carboxamide | A |

TABLE 6-continued

Activity in BDNA-assay (EC$_{50}$)

| Compound ID | Compound Name | DNA EC$_{50}$ (nM) |
|---|---|---|
| 006 | N-(3-chloro-4-fluorophenyl)-8-fluoro-10-methyl-11-oxo-1,3,4,7,8,9,10,11-octahydro-2H-pyrido[4',3':3,4]pyrazolo[1,5-a][1,4]diazepine-2-carboxamide | A |
| 007 | N-(3-bromo-4-fluorophenyl)-8-fluoro-10-methyl-11-oxo-1,3,4,7,8,9,10,11-octahydro-2H-pyrido[4',3':3,4]pyrazolo[1,5-a][1,4]diazepine-2-carboxamide | A |
| 008 | N-(2-bromo-3-fluoropyridin-4-yl)-8-fluoro-10-methyl-11-oxo-1,3,4,7,8,9,10,11-octahydro-2H-pyrido[4',3':3,4]pyrazolo[1,5-a][1,4]diazepine-2-carboxamide | A |
| 009 | N-(3-cyano-4-fluorophenyl)-8-fluoro-10-methyl-11-oxo-1,3,4,7,8,9,10,11-octahydro-2H-pyrido[4',3':3,4]pyrazolo[1,5-a][1,4]diazepine-2-carboxamide | A |
| 010 | 8-fluoro-N-(4-fluoro-3-methylphenyl)-10-methyl-11-oxo-1,3,4,7,8,9,10,11-octahydro-2H-pyrido[4',3':3,4]pyrazolo[1,5-a][1,4]diazepine-2-carboxamide | A |
| 011 | 8-fluoro-N-(4-fluoro-3-(trifluoromethyl)phenyl)-10-methyl-11-oxo-1,3,4,7,8,9,10,11-octahydro-2H-pyrido[4',3':3,4]pyrazolo[1,5-a][1,4]diazepine-2-carboxamide | A |
| 012 | N-(5-chloro-2,4-difluorophenyl)-8-fluoro-10-methyl-11-oxo-1,3,4,7,8,9,10,11-octahydro-2H-pyrido[4',3':3,4]pyrazolo[1,5-a][1,4]diazepine-2-carboxamide | A |
| 013 | N-(5-bromo-2,4-difluorophenyl)-8-fluoro-10-methyl-11-oxo-1,3,4,7,8,9,10,11-octahydro-2H-pyrido[4',3':3,4]pyrazolo[1,5-a][1,4]diazepine-2-carboxamide | A |
| 014 | N-(3-chloro-4-fluoro-phenyl)-8,10-dimethyl-11-oxo-1,3,4,7,8,9-hexahydropyrido[2,3]pyrazolo[2,4-b][1,4]diazepine-2-carboxamide | A |
| 015 | N-(3-chloro-4-fluoro-phenyl)-10-methyl-11-oxo-1,3,4,7,8,9-hexahydropyrido[2,3]pyrazolo[2,4-b][1,4]diazepine-2-carboxamide | A |
| 016A | (S*)-N-(3-chloro-4-fluorophenyl)-8-methoxy-10-methyl-11-oxo-3,4,8,9,10,11-hexahydro-1H-pyrido[4',3':3,4]pyrazolo[1,5-a][1,4]diazepine-2(7H)-carboxamide | A |
| 016B | (R*)-N-(3-chloro-4-fluorophenyl)-8-methoxy-10-methyl-11-oxo-3,4,8,9,10,11-hexahydro-1H-pyrido[4',3':3,4]pyrazolo[1,5-a][1,4]diazepine-2(7H)-carboxamide | A |
| 017 | N-(3-chloro-4-fluorophenyl)-8-ethoxy-10-methyl-11-oxo-1,3,4,7,8,9,10,11-octahydro-2H-pyrido[4',3':3,4]pyrazolo[1,5-a][1,4]diazepine-2-carboxamide | A |
| 018 | N-(3-chloro-4-fluorophenyl)-8-(2,2-difluoroethoxy)-10-methyl-11-oxo-1,3,4,7,8,9,10,11-octahydro-2H-pyrido[4',3':3,4]pyrazolo[1,5-a][1,4]diazepine-2-carboxamide | A |
| 019 | 8-amino-N-(3-chloro-4-fluorophenyl)-10-methyl-11-oxo-1,3,4,7,8,9,10,11-octahydro-2H-pyrido[4',3':3,4]pyrazolo[1,5-a][1,4]diazepine-2-carboxamide | B |
| 020 | N-(3-chloro-4-fluorophenyl)-8-(dimethylamino)-10-methyl-11-oxo-1,3,4,7,8,9,10,11-octahydro-2H-pyrido[4',3':3,4]pyrazolo[1,5-a][1,4]diazepine-2-carboxamide | A |
| 021 | N-(3-chloro-4-fluorophenyl)-10-methyl-8-morpholino-11-oxo-11,3,4,7,8,9,10,11-octahydro-2H-pyrido[4',3':3,4]pyrazolo[1,5-a][1,4]diazepine-2-carboxamide | B |
| 022 | N-(3-chloro-4-fluorophenyl)-8-(3,3-difluoroazetidin-1-yl)-10-methyl-11-oxo-1,3,4,7,8,9,10,11-octahydro-2H-pyrido[4',3':3,4]pyrazolo[1,5-a][1,4]diazepine-2-carboxamide | B |
| 023 | 8-(azetidin-1-yl)-N-(3-chloro-4-fluorophenyl)-10-methyl-11-oxo-1,3,4,7,8,9,10,11-octahydro-2H-pyrido[4',3':3,4]pyrazolo[1,5-a][1,4]diazepine-2-carboxamide | A |
| 024 | N-(3-chloro-4-fluorophenyl)-10-methyl-11-oxo-8-(pyrrolidin-1-yl)-1,3,4,7,8,9,10,11-octahydro-2H-pyrido[4',3':3,4]pyrazolo[1,5-a][1,4]diazepine-2-carboxamide | A |
| 025 | N-(3-chloro-4-fluorophenyl)-10-methyl-8-(methylthio)-11-oxo-1,3,4,7,8,9,10,11-octahydro-2H-pyrido[4',3':3,4]pyrazolo[1,5-a][1,4]diazepine-2-carboxamide | A |
| 026A | N-(3-chloro-4-fluorophenyl)-10-methyl-8-(methylsulfinyl)-11-oxo-1,3,4,7,8,9,10,11-octahydro-2H-pyrido[4',3':3,4]pyrazolo[1,5-a][1,4]diazepine-2-carboxamide | D |
| 026B | N-(3-chloro-4-fluorophenyl)-10-methyl-8-(methylsulfinyl)-11-oxo-1,3,4,7,8,9,10,11-octahydro-2H-pyrido[4',3':3,4]pyrazolo[1,5-a][1,4]diazepine-2-carboxamide | C |
| 027 | N-(3-chloro-4-fluoro-phenyl)-10-methyl-8-methylsulfonyl-11-oxo-1,3,4,7,8,9-hexahydropyrido[2,3]pyrazolo[2,4-b][1,4]diazepine-2-carboxamide | A |
| 028 | methyl 2-(2-((3-chloro-4-fluorophenyl)carbamoyl)-10-methyl-11-oxo-1,3,4,7,8,9,10,11-octahydro-2H-pyrido[4',3':3,4]pyrazolo[1,5-a][1,4]diazepin-8-yl)acetate | B |
| 029 | N-(3-chloro-4-fluorophenyl)-8-(2-hydroxyethyl)-10-methyl-11-oxo-1,3,4,7,8,9,10,11-octahydro-2H-pyrido[4',3':3,4]pyrazolo[1,5-a][1,4]diazepine-2-carboxamide | B |
| 030 | ethyl 2-((3-chloro-4-fluorophenyl)carbamoyl)-10-methyl-11-oxo-2,3,4,7,8,9,10,11-octahydro-1H-pyrido[4',3':3,4]pyrazolo[1,5-a][1,4]diazepine-8-carboxylate | D |
| 031 | N2-(3-chloro-4-fluorophenyl)-N8,10-dimethyl-11-oxo-1,3,4,7,8,9,10,11-octahydro-2H-pyrido[4',3':3,4]pyrazolo[1,5-a][1,4]diazepine-2,8-dicarboxamide | A |
| 032 | N2-(3-chloro-4-fluorophenyl)-N8,N8,10-trimethyl-11-oxo-1,3,4,7,8,9,10,11-octahydro-2H-pyrido[4',3':3,4]pyrazolo[1,5-a][1,4]diazepine-2,8-dicarboxamide | B |
| 033 | N-(3-chloro-4-fluorophenyl)-8-(2-hydroxypropan-2-yl)-10-methyl-11-oxo-3,4,8,9,10,11-hexahydro-1H-pyrido[4',3':3,4]pyrazolo[1,5-a][1,4]diazepine-2(7H)-carboxamide | A |
| 034 | N-(3-chloro-4-fluorophenyl)-8-(1-hydroxyethyl)-10-methyl-11-oxo-1,3,4,7,8,9,10,11-octahydro-2H-pyrido[4',3':3,4]pyrazolo[1,5-a][1,4]diazepine-2-carboxamide | B |
| 035 | N-(3-chloro-4-fluorophenyl)-8-(1-hydroxypropyl)-10-methyl-11-oxo-1,3,4,7,8,9,10,11-octahydro-2H-pyrido[4',3':3,4]pyrazolo[1,5-a][1,4]diazepine-2-carboxamide | A |
| 036 | N-(3-chloro-4-fluorophenyl)-8-(cyclopropyl(hydroxy)methyl)-10-methyl-11-oxo-1,3,4,7,8,9,10,11-octahydro-2H-pyrido[4',3':3,4]pyrazolo[1,5-a][1,4]diazepine-2-carboxamide | A |
| 037 | N-(3-chloro-4-fluorophenyl)-8-(difluoromethyl)-10-methyl-11-oxo-1,3,4,7,8,9,10,11-octahydro-2H-pyrido[4',3':3,4]pyrazolo[1,5-a][1,4]diazepine-2-carboxamide | A |
| 038 | N-(3-chloro-4-fluorophenyl)-10-(2,2-difluoroethyl)-11-oxo-1,3,4,7,8,9,10,11-octahydro-2H-pyrido[4',3':3,4]pyrazolo[1,5-a][1,4]diazepine-2-carboxamide | A |
| 039 | N-(3-chloro-4-fluorophenyl)-9,10-dimethyl-11-oxo-1,3,4,7,8,9,10,11-octahydro-2H-pyrido[4',3':3,4]pyrazolo[1,5-a][1,4]diazepine-2-carboxamide | A |
| 040 | methyl 2-((3-chloro-4-fluorophenyl)carbamoyl)-9-methyl-10-oxo-1,2,3,4,9,10-hexahydropyrido[4',3':3,4]pyrazolo[1,5-a]pyrazine-8-carboxylate | B |

TABLE 6-continued

Activity in BDNA-assay (EC$_{50}$)

| Compound ID | Compound Name | DNA EC$_{50}$ (nM) |
|---|---|---|
| 041 | N-(3-chloro-4-fluorophenyl)-8-(hydroxymethyl)-9-methyl-10-oxo-3,4,9,10-tetrahydropyrido[4',3':3,4]pyrazolo[1,5-a]pyrazine-2(1H)-carboxamide | A |
| 042 | 2-((3-chloro-4-fluorophenyl)carbamoyl)-9-methyl-10-oxo-1,2,3,4,9,10-hexahydropyrido[4',3':3,4]pyrazolo[1,5-a]pyrazine-8-carboxylic acid | D |
| 043 | methyl 2-((3-chloro-4-fluorophenyl)carbamoyl)-9-methyl-10-oxo-1,2,3,4,7,8,9,10-octahydropyrido[4',3':3,4]pyrazolo[1,5-a]pyrazine-8-carboxylate | B |
| 044 | N-(3-chloro-4-fluorophenyl)-8-(hydroxymethyl)-9-methyl-10-oxo-3,4,7,8,9,10-hexahydropyrido[4',3':3,4]pyrazolo[1,5-a]pyrazine-2(1H)-carboxamide | A |
| 045 | N-(3-chloro-4-fluorophenyl)-9-methyl-10-oxo-3,4,7,8,9,10-hexahydropyrido[4',3':3,4]pyrazolo[1,5-a]pyrazine-2(1H)-carboxamide | A |
| 046 | N-(3-chloro-4-fluorophenyl)-10-methyl-1,3,4,7,8,9,10,11-octahydro-2H-pyrido[4',3':3,4]pyrazolo[1,5-a][1,4]diazepine-2-carboxamide | D |
| 047 | N-(3-chloro-4-fluorophenyl)-8-(2-cyclopropyl-1-hydroxyethyl)-10-methyl-11-oxo-1,3,4,7,8,9,10,11-octahydro-2H-pyrido[4',3':3,4]pyrazolo[1,5-a][1,4]diazepine-2-carboxamide | A |
| 048 | (3R)-N-(3-chloro-4-fluorophenyl)-10-(2-hydroxy-2-methylpropyl)-3-methyl-1,3,4,7,8,9,10,11-octahydro-2H-pyrido[4',3':3,4]pyrazolo[1,5-a][1,4]diazepine-2-carboxamide | B |
| 049 | (3R)-N-(3-chloro-4-fluorophenyl)-10-(2-hydroxyethyl)-3-methyl-11-oxo-1,3,4,7,8,9,10,11-octahydro-2H-pyrido[4',3':3,4]pyrazolo[1,5-a][1,4]diazepine-2-carboxamide | A |
| 050 | N-(3-chloro-4-fluorophenyl)-10-methyl-8-(methylamino)-11-oxo-1,3,4,7,8,9,10,11-octahydro-2H-pyrido[4',3':3,4]pyrazolo[1,5-a][1,4]diazepine-2-carboxamide | B |
| 051 | N-(3-chloro-4-fluorophenyl)-8-(hydroxymethyl)-11-oxo-10-(2,2,2-trifluoroethyl)-1,3,4,7,8,9,10,11-octahydro-2H-pyrido[4',3':3,4]pyrazolo[1,5-a][1,4]diazepine-2-carboxamide | A |
| 052 | ethyl 2-((3-chloro-4-fluorophenyl)carbamoyl)-8,10-dimethyl-11-oxo-1,3,4,7,8,9,10,11-octahydro-2H-pyrido[4',3':3,4]pyrazolo[1,5-a][1,4]diazepine-8-carboxylate | B |
| 053 | N-(3-chloro-4-fluorophenyl)-8-(hydroxymethyl)-8,10-dimethyl-11-oxo-1,3,4,7,8,9,10,11-octahydro-2H-pyrido[4',3':3,4]pyrazolo[1,5-a][1,4]diazepine-2-carboxamide | A |
| 054 | N-(3-chloro-4-fluorophenyl)-8-(3,3-difluoropyrrolidin-1-yl)-10-methyl-11-oxo-1,3,4,7,8,9,10,11-octahydro-2H-pyrido[4',3':3,4]pyrazolo[1,5-a][1,4]diazepine-2-carboxamide | B |
| 055 | N-(3-chloro-4-fluorophenyl)-10-methyl-11-oxo-8-(piperidin-1-yl)-1,3,4,7,8,9,10,11-octahydro-2H-pyrido[4',3':3,4]pyrazolo[1,5-a][1,4]diazepine-2-carboxamide | B |
| 056 | N-(3-chloro-4-fluorophenyl)-8-(4,4-difluoropiperidin-1-yl)-10-methyl-11-oxo-1,3,4,7,8,9,10,11-octahydro-2H-pyrido[4',3':3,4]pyrazolo[1,5-a][1,4]diazepine-2-carboxamide | B |
| 057 | methyl 2-((3-chloro-4-fluorophenyl)carbamoyl)-10-methyl-11-oxo-1,3,4,7,8,9,10,11-octahydro-2H-pyrido[4',3':3,4]pyrazolo[1,5-a][1,4]diazepine-9-carboxylate | B |
| 058 | 2-((3-chloro-4-fluorophenyl)carbamoyl)-10-methyl-11-oxo-1,3,4,7,8,9,10,11-octahydro-2H-pyrido[4',3':3,4]pyrazolo[1,5-a][1,4]diazepine-9-carboxylic acid | D |
| 059 | N2-(3-chloro-4-fluorophenyl)-N9,N9,10-trimethyl-11-oxo-1,3,4,7,8,9,10,11-octahydro-2H-pyrido[4',3':3,4]pyrazolo[1,5-a][1,4]diazepine-2,9-dicarboxamide | B |
| 060 | N-(3-chloro-4-fluorophenyl)-9-(hydroxymethyl)-10-methyl-11-oxo-1,3,4,7,8,9,10,11-octahydro-2H-pyrido[4',3':3,4]pyrazolo[1,5-a][1,4]diazepine-2-carboxamide | A |
| 061 | N-(3-chloro-4-fluorophenyl)-9-(hydroxymethyl)-9,10-dimethyl-11-oxo-1,3,4,7,8,9,10,11-octahydro-2H-pyrido[4',3':3,4]pyrazolo[1,5-a][1,4]diazepine-2-carboxamide | A |
| 062 | 2-((3-chloro-4-fluorophenyl)carbamoyl)-9,10-dimethyl-11-oxo-1,3,4,7,8,9,10,11-octahydro-2H-pyrido[4',3':3,4]pyrazolo[1,5-a][1,4]diazepine-9-carboxylic acid | D |
| 063 | N-(3-chloro-4-fluorophenyl)-10-methyl-8-(morpholinomethyl)-11-oxo-1,3,4,7,8,9,10,11-octahydro-2H-pyrido[4',3':3,4]pyrazolo[1,5-a][1,4]diazepine-2-carboxamide | A |
| 064 | N-(3-chloro-4-fluorophenyl)-10-methyl-11-oxo-8-(piperidin-1-ylmethyl)-1,3,4,7,8,9,10,11-octahydro-2H-pyrido[4',3':3,4]pyrazolo[1,5-a][1,4]diazepine-2-carboxamide | B |
| 065 | N-(3-chloro-4-fluorophenyl)-8-((dimethylamino)methyl)-10-methyl-11-oxo-1,3,4,7,8,9,10,11-octahydro-2H-pyrido[4',3':3,4]pyrazolo[1,5-a][1,4]diazepine-2-carboxamide | B |
| 066 | N-(3-chloro-4-fluorophenyl)-8-((3,3-difluoropyrrolidin-1-yl)methyl)-10-methyl-11-oxo-1,3,4,7,8,9,10,11-octahydro-2H-pyrido[4',3':3,4]pyrazolo[1,5-a][1,4]diazepine-2-carboxamide | A |
| 067 | N-(3-cyano-4-fluorophenyl)-8-((3,3-difluoropyrrolidin-1-yl)methyl)-10-methyl-11-oxo-1,3,4,7,8,9,10,11-octahydro-2H-pyrido[4',3':3,4]pyrazolo[1,5-a][1,4]diazepine-2-carboxamide | B |
| 068 | 8-((3,3-difluoropyrrolidin-1-yl)methyl)-N-(4-fluoro-3-(trifluoromethyl)phenyl)-10-methyl-11-oxo-1,3,4,7,8,9,10,11-octahydro-2H-pyrido[4',3':3,4]pyrazolo[1,5-a][1,4]diazepine-2-carboxamide | B |
| 069 | N-(3-chloro-4-fluorophenyl)-10-methyl-11-oxo-8-(pyrrolidin-1ylmethyl)-1,3,4,7,8,9,10,11-octahydro-2H-pyrido[4',3':3,4]pyrazolo[1,5-a][1,4]diazepine-2-carboxamide | A |
| 070 | 8-(aminomethyl)-N-(3-chloro-4-fluorophenyl)-10-methyl-11-oxo-1,3,4,7,8,9,10,11-octahydro-2H-pyrido[4',3':3,4]pyrazolo[1,5-a][1,4]diazepine-2-carboxamide | A |
| 071 | (R)-N-(2-bromo-5-chloro-4-fluorophenyl)-10-(2,2-difluoroethyl)-3-methyl-11-oxo-3,4,8,9,10,11-hexahydro-1H-pyrido[4',3':3,4]pyrazolo[1,5-a][1,4]diazepine-2(7H)-carboxamide | A |
| 072 | (3R)-N-(3-chloro-4-fluorophenyl)-10-(2,2-difluoroethyl)-3-methyl-11-oxo-1,3,4,7,8,9,10,11-octahydro-2H-pyrido[4',3':3,4]pyrazolo[1,5-a][1,4]diazepine-2-carboxamide | A |
| 073 | (R)-10-(2,2-difluoroethyl)-N-(4-fluoro-3-(trifluoromethyl)phenyl)-3-methyl-11-oxo-3,4,8,9,10,11-hexahydro-1H-pyrido[4',3':3,4]pyrazolo[1,5-a][1,4]diazepine-2(7H)-carboxamide | A |
| 074 | (R)-N-(3-bromo-4-fluorophenyl)-10-(2,2-difluoroethyl)-3-methyl-11-oxo-3,4,8,9,10,11-hexahydro-1H-pyrido[4',3':3,4]pyrazolo[1,5-a][1,4]diazepine-2(7H)-carboxamide | A |
| 075 | (R)-N-(2-bromo-3-fluoropyridin-4-yl)-10-(2,2-difluoroethyl)-3-methyl-11-oxo-3,4,8,9,10,11-hexahydro-1H-pyrido[4',3':3,4]pyrazolo[1,5-a][1,4]diazepine-2(7H)-carboxamide | A |

TABLE 6-continued

Activity in BDNA-assay (EC$_{50}$)

| Compound ID | Compound Name | DNA EC$_{50}$ (nM) |
|---|---|---|
| 076 | (R)-N-(3-cyano-4-fluorophenyl)-10-(2,2-difluoroethyl)-3-methyl-11-oxo-3,4,8,9,10,11-hexahydro-1H-pyrido[4',3':3,4]pyrazolo[1,5-a][1,4]diazepine-2(7H)-carboxamide | A |
| 077 | (R)-10-(2,2-difluoroethyl)-N-(4-fluoro-3-methylphenyl)-3-methyl-11-oxo-3,4,8,9,10,11-hexahydro-1H-pyrido[4',3':3,4]pyrazolo[1,5-a][1,4]diazepine-2(7H)-carboxamide | A |
| 078 | (R)-N-(5-chloro-2,4-difluorophenyl)-110-(2,2-difluoroethyl)-3-methyl-11-oxo-3,4,8,9,10,11-hexahydro-1H-pyrido[4',3':3,4]pyrazolo[1,5-a][1,4]diazepine-2(7H)-carboxamide | B |
| 079_D1 | (3R,8R*)-N-(3-chloro-4-fluorophenyl)-8-fluoro-3,8,10-trimethyl-11-oxo-3,4,8,9,10,11-hexahydro-1H-pyrido[4',3':3,4]pyrazolo[1,5-a][1,4]diazepine-2(7H)-carboxamide | A |
| 079_D2 | (3R,8S*)-N-(3-chloro-4-fluorophenyl)-8-fluoro-3,8,10-trimethyl-11-oxo-3,4,8,9,10,11-hexahydro-1H-pyrido[4',3':3,4]pyrazolo[1,5-a][1,4]diazepine-2(7H)-carboxamide | A |
| 080_D1 | (3R,8S*)-N-(3-chloro-4-fluorophenyl)-3,8,10-trimethyl-11-oxo-3,4,8,9,10,11-hexahydro-1H-pyrido[4',3':3,4]pyrazolo[1,5-a][1,4]diazepine-2(7H)-carboxamide | A |
| 080_D2 | (3R,8R*)-N-(3-chloro-4-fluorophenyl)-3,8,10-trimethyl-11-oxo-3,4,8,9,10,11-hexahydro-1H-pyrido[4',3':3,4]pyrazolo[1,5-a][1,4]diazepine-2(7H)-carboxamide | A |
| 081_D1 | (3R,8S*)-N-(4-fluoro-3-(trifluoromethyl)phenyl)-8-(hydroxymethyl)-3,10-dimethyl-11-oxo-3,4,8,9,10,11-hexahydro-1H-pyrido[4',3':3,4]pyrazolo[1,5-a][1,4]diazepine-2(7H)-carboxamide | A |
| 081_D2 | (3R,8R*)-N-(4-fluoro-3-(trifluoromethyl)phenyl)-8-(hydroxymethyl)-3,10-dimethyl-11-oxo-3,4,8,9,10,11-hexahydro-1H-pyrido[4',3':3,4]pyrazolo[1,5-a][1,4]diazepine-2(7H)-carboxamide | A |
| 082_D1 | (3R,8S*)-N-(2,4-difluoro-5-(trifluoromethyl)phenyl)-8-(hydroxymethyl)-3,10-dimethyl-11-oxo-3,4,8,9,10,11-hexahydro-1H-pyrido[4',3':3,4]pyrazolo[1,5-a][1,4]diazepine-2(7H)-carboxamide | A |
| 082_D2 | (3R,8R*)-N-(2,4-difluoro-5-(trifluoromethyl)phenyl)-8-(hydroxymethyl)-3,10-dimethyl-11-oxo-3,4,8,9,10,11-hexahydro-1H-pyrido[4',3':3,4]pyrazolo[1,5-a][1,4]diazepine-2(7H)-carboxamide | B |
| 083_D1 | (3R,8S*)-N-(2,4-difluoro-3-(trifluoromethyl)phenyl)-8-(hydroxymethyl)-3,10-dimethyl-11-oxo-3,4,8,9,10,11-hexahydro-1H-pyrido[4',3':3,4]pyrazolo[1,5-a][1,4]diazepine-2(7H)-carboxamide | A |
| 083_D2 | (3R,8R*)-N-(2,4-difluoro-3-(trifluoromethyl)phenyl)-8-(hydroxymethyl)-3,10-dimethyl-11-oxo-3,4,8,9,10,11-hexahydro-1H-pyrido[4',3':3,4]pyrazolo[1,5-a][1,4]diazepine-2(7H)-carboxamide | A |
| 084_D1 | (3R,8S*)-N-(3-bromo-2,4-difluorophenyl)-8-(hydroxymethyl)-3,10-dimethyl-11-oxo-3,4,8,9,10,11-hexahydro-1H-pyrido[4',3':3,4]pyrazolo[1,5-a][1,4]diazepine-2(7H)-carboxamide | B |
| 084_D2 | (3R,8R*)-N-(3-bromo-2,4-difluorophenyl)-8-(hydroxymethyl)-3,10-dimethyl-11-oxo-3,4,8,9,10,11-hexahydro-1H-pyrido[4',3':3,4]pyrazolo[1,5-a][1,4]diazepine-2(7H)-carboxamide | A |
| 085_D1 | (3R,8S*)-N-(5-bromo-2,4-difluorophenyl)-8-(hydroxymethyl)-3,10-dimethyl-11-oxo-3,4,8,9,10,11-hexahydro-1H-pyrido[4',3':3,4]pyrazolo[1,5-a][1,4]diazepine-2(7H)-carboxamide | A |
| 085_D2 | (3R,8R*)-N-(5-bromo-2,4-difluorophenyl)-8-(hydroxymethyl)-3,10-dimethyl-11-oxo-3,4,8,9,10,11-hexahydro-1H-pyrido[4',3':3,4]pyrazolo[1,5-a][1,4]diazepine-2(7H)-carboxamide | A |
| 086_D1 | (3R,8S*)-N-(3-bromo-4-fluorophenyl)-8-(hydroxymethyl)-3,10-dimethyl-11-oxo-3,4,8,9,10,11-hexahydro-11H-pyrido[4',3':3,4]pyrazolo[1,5-a][1,4]diazepine-2(7H)-carboxamide | A |
| 086_D2 | (3R,8R*)-N-(3-bromo-4-fluorophenyl)-8-(hydroxymethyl)-3,10-dimethyl-11-oxo-3,4,8,9,10,11-hexahydro-11H-pyrido[4',3':3,4]pyrazolo[1,5-a][1,4]diazepine-2(7H)-carboxamide | A |
| 087_D1 | (3R,8S*)-N-(3-cyano-4-fluorophenyl)-8-(hydroxymethyl)-3,10-dimethyl-11-oxo-3,4,8,9,10,11-hexahydro-1H-pyrido[4',3':3,4]pyrazolo[1,5-a][1,4]diazepine-2(7H)-carboxamide | A |
| 087_D2 | (3R,8R*)-N-(3-cyano-4-fluorophenyl)-8-(hydroxymethyl)-3,10-dimethyl-11-oxo-3,4,8,9,10,11-hexahydro-1H-pyrido[4',3':3,4]pyrazolo[1,5-a][1,4]diazepine-2(7H)-carboxamide | A |
| 088_D1 | (3R,8S*)-N-(3-cyano-2,4-difluorophenyl)-8-(hydroxymethyl)-3,10-dimethyl-11-oxo-3,4,8,9,10,11-hexahydro-1H-pyrido[4',3':3,4]pyrazolo[1,5-a][1,4]diazepine-2(7H)-carboxamide | A |
| 088_D2 | (3R,8R*)-N-(3-cyano-2,4-difluorophenyl)-8-(hydroxymethyl)-3,10-dimethyl-11-oxo-3,4,8,9,10,11-hexahydro-1H-pyrido[4',3':3,4]pyrazolo[1,5-a][1,4]diazepine-2(7H)-carboxamide | A |
| 089_D1 | (3R,8S*)-N-(3-chloro-2,4-difluorophenyl)-8-(hydroxymethyl)-3,10-dimethyl-11-oxo-3,4,8,9,10,11-hexahydro-1H-pyrido[4',3':3,4]pyrazolo[1,5-a][1,4]diazepine-2(7H)-carboxamide | A |
| 089_D2 | (3R,8R*)-N-(3-chloro-2,4-difluorophenyl)-8-(hydroxymethyl)-3,10-dimethyl-11-oxo-3,4,8,9,10,11-hexahydro-1H-pyrido[4',3':3,4]pyrazolo[1,5-a][1,4]diazepine-2(7H)-carboxamide | A |
| 090_D1 | (3R,8S*)-N-(5-chloro-2,4-difluorophenyl)-8-(hydroxymethyl)-3,10-dimethyl-11-oxo-3,4,8,9,10,11-hexahydro-1H-pyrido[4',3':3,4]pyrazolo[1,5-a][1,4]diazepine-2(7H)-carboxamide | A |
| 090_D2 | (3R,8R*)-N-(5-chloro-2,4-difluorophenyl)-8-(hydroxymethyl)-3,10-dimethyl-11-oxo-3,4,8,9,10,11-hexahydro-1H-pyrido[4',3':3,4]pyrazolo[1,5-a][1,4]diazepine-2(7H)-carboxamide | A |
| 091 | N-(3-chloro-4-fluorophenyl)-8-(2,2-difluoroethyl)-8-(hydroxymethyl)-10-methyl-11-oxo-1,3,4,7,8,9,10,11-octahydro-2H-pyrido[4',3':3,4]pyrazolo[1,5-a][1,4]diazepine-2-carboxamide | B |
| 092_D1 | (3R,8R*)-N-(3-chloro-4-fluorophenyl)-10-(2,2-difluoroethyl)-8-(hydroxymethyl)-3-methyl-11-oxo-3,4,8,9,10,11-hexahydro-1H-pyrido[4',3':3,4]pyrazolo[1,5-a][1,4]diazepine-2(7H)-carboxamide | A |
| 092_D2 | (3R,8S*)-N-(3-chloro-4-fluorophenyl)-10-(2,2-difluoroethyl)-8-(hydroxymethyl)-3-methyl-11-oxo-3,4,8,9,10,11-hexahydro-1H-pyrido[4',3':3,4]pyrazolo[1,5-a][1,4]diazepine-2(7H)-carboxamide | A |

TABLE 6-continued

Activity in BDNA-assay (EC$_{50}$)

| Compound ID | Compound Name | DNA EC$_{50}$ (nM) |
|---|---|---|
| 093 | 8-(aminomethyl)-N-(4-fluoro-3-(trifluoromethyl)phenyl)-10-methyl-11-oxo-1,3,4,7,8,9,10,11-octahydro-2H-pyrido[4',3':3,4]pyrazolo[1,5-a][1,4]diazepine-2-carboxamide | B |
| 094 | N-(4-fluoro-3-(trifluoromethyl)phenyl)-10-methyl-8-((methylamino)methyl)-11-oxo-1,3,4,7,8,9,10,11-octahydro-2H-pyrido[4',3':3,4]pyrazolo[1,5-a][1,4]diazepine-2-carboxamide | B |
| 095 | 8-(aminomethyl)-N-(3-cyano-4-fluorophenyl)-10-methyl-11-oxo-1,3,4,7,8,9,10,11-octahydro-2H-pyrido[4',3':3,4]pyrazolo[1,5-a][1,4]diazepine-2-carboxamide | A |
| 096_E1 | (R*)-N-(5-chloro-2,4-difluorophenyl)-8-((S*)-1-hydroxypropyl)-10-methyl-11-oxo-3,4,8,9,10,11-hexahydro-1H-pyrido[4',3':3,4]pyrazolo[1,5-a][1,4]diazepine-2(7H)-carboxamide | A |
| 096_E2 | (S*)-N-(5-chloro-2,4-difluorophenyl)-8-((R*)-1-hydroxypropyl)-10-methyl-11-oxo-3,4,8,9,10,11-hexahydro-1H-pyrido[4',3':3,4]pyrazolo[1,5-a][1,4]diazepine-2(7H)-carboxamide | B |
| 096_E3 | (S*)-N-(5-chloro-2,4-difluorophenyl)-8-((S*)-1-hydroxypropyl)-10-methyl-11-oxo-3,4,8,9,10,11-hexahydro-1H-pyrido[4',3':3,4]pyrazolo[1,5-a][1,4]diazepine-2(7H)-carboxamide | B |
| 096_E4 | (R*)-N-(5-chloro-2,4-difluorophenyl)-8-((R*)-1-hydroxypropyl)-10-methyl-11-oxo-3,4,8,9,10,11-hexahydro-1H-pyrido[4',3':3,4]pyrazolo[1,5-a][1,4]diazepine-2(7H)-carboxamide | A |
| 097_E1 | (R*)-N-(3-cyano-4-fluorophenyl)-8-((S*)-1-hydroxypropyl)-10-methyl-11-oxo-1,3,4,7,8,9,10,11-octahydro-2H-pyrido[4',3':3,4]pyrazolo[1,5-a][1,4]diazepine-2-carboxamide | A |
| 097_E2 | (S*)-N-(3-cyano-4-fluorophenyl)-8-((R*)-1-hydroxypropyl)-10-methyl-11-oxo-1,3,4,7,8,9,10,11-octahydro-2H-pyrido[4',3':3,4]pyrazolo[1,5-a][1,4]diazepine-2-carboxamide | B |
| 097_E3 | (S*)-N-(3-cyano-4-fluorophenyl)-8-((S*)-1-hydroxypropyl)-10-methyl-11-oxo-1,3,4,7,8,9,10,11-octahydro-2H-pyrido[4',3':3,4]pyrazolo[1,5-a][1,4]diazepine-2-carboxamide | B |
| 097_E4 | (R*)-N-(3-cyano-4-fluorophenyl)-8-((R*)-1-hydroxypropyl)-10-methyl-11-oxo-1,3,4,7,8,9,10,11-octahydro-2H-pyrido[4',3':3,4]pyrazolo[1,5-a][1,4]diazepine-2-carboxamide | A |
| 098_E1 | (R*)-N-(3-cyano-2,4-difluorophenyl)-8-((S*)-1-hydroxypropyl)-10-methyl-11-oxo-1,3,4,7,8,9,10,11-octahydro-2H-pyrido[4',3':3,4]pyrazolo[1,5-a][1,4]diazepine-2-carboxamide | A |
| 098_E2 | (S*)-N-(3-cyano-2,4-difluorophenyl)-8-((R*)-1-hydroxypropyl)-10-methyl-11-oxo-1,3,4,7,8,9,10,11-octahydro-2H-pyrido[4',3':3,4]pyrazolo[1,5-a][1,4]diazepine-2-carboxamide | C |
| 098_E3 | (S*)-N-(3-cyano-2,4-difluorophenyl)-8-((S*)-1-hydroxypropyl)-10-methyl-11-oxo-1,3,4,7,8,9,10,11-octahydro-2H-pyrido[4',3':3,4]pyrazolo[1,5-a][1,4]diazepine-2-carboxamide | B |
| 098_E4 | (R*)-N-(3-cyano-2,4-difluorophenyl)-8-((R*)-1-hydroxypropyl)-10-methyl-11-oxo-1,3,4,7,8,9,10,11-octahydro-2H-pyrido[4',3':3,4]pyrazolo[1,5-a][1,4]diazepine-2-carboxamide | C |
| 099_E1 | (R*)-N-(4-fluoro-3-(trifluoromethyl)phenyl)-8-((S*)-1-hydroxypropyl)-10-methyl-11-oxo-1,3,4,7,8,9,10,11-octahydro-2H-pyrido[4',3':3,4]pyrazolo[1,5-a][1,4]diazepine-2-carboxamide | A |
| 099_E2 | (S*)-N-(4-fluoro-3-(trifluoromethyl)phenyl)-8-((R*)-1-hydroxypropyl)-10-methyl-11-oxo-1,3,4,7,8,9,10,11-octahydro-2H-pyrido[4',3':3,4]pyrazolo[1,5-a][1,4]diazepine-2-carboxamide | B |
| 099_E3 | (S*)-N-(4-fluoro-3-(trifluoromethyl)phenyl)-8-((S*)-1-hydroxypropyl)-10-methyl-11-oxo-1,3,4,7,8,9,10,11-octahydro-2H-pyrido[4',3':3,4]pyrazolo[1,5-a][1,4]diazepine-2-carboxamide | A |
| 099_E4 | (R*)-N-(4-fluoro-3-(trifluoromethyl)phenyl)-8-((R*)-1-hydroxypropyl)-10-methyl-11-oxo-1,3,4,7,8,9,10,11-octahydro-2H-pyrido[4',3':3,4]pyrazolo[1,5-a][1,4]diazepine-2-carboxamide | B |
| 100_E1 | N-(3-chloro-2,4-difluorophenyl)-8-(1-hydroxypropyl)-10-methyl-11-oxo-1,3,4,7,8,9,10,11-octahydro-2H-pyrido[4',3':3,4]pyrazolo[1,5-a][1,4]diazepine-2-carboxamide | A |
| 101_E1 | N-(3-bromo-2,4-difluorophenyl)-8-(1-hydroxypropyl)-10-methyl-11-oxo-1,3,4,7,8,9,10,11-octahydro-2H-pyrido[4',3':3,4]pyrazolo[1,5-a][1,4]diazepine-2-carboxamide | A |
| 102_E1 | N-(3-bromo-4-fluorophenyl)-8-(1-hydroxypropyl)-10-methyl-11-oxo-1,3,4,7,8,9,10,11-octahydro-2H-pyrido[4',3':3,4]pyrazolo[1,5-a][1,4]diazepine-2-carboxamide | A |
| 103_E1 | N-(2,4-difluoro-3-(trifluoromethyl)phenyl)-8-(1-hydroxypropyl)-10-methyl-11-oxo-1,3,4,7,8,9,10,11-octahydro-2H-pyrido[4',3':3,4]pyrazolo[1,5-a][1,4]diazepine-2-carboxamide | A |
| 104_E1 | 8-(1-hydroxypropyl)-10-methyl-11-oxo-N-(3,4,5-trifluorophenyl)-1,3,4,7,8,9,10,11-octahydro-2H-pyrido[4',3':3,4]pyrazolo[1,5-a][1,4]diazepine-2-carboxamide | A |
| 105_E1 | 8-(1-hydroxypropyl)-10-methyl-11-oxo-N-(2,3,4,5-tetrafluorophenyl)-1,3,4,7,8,9,10,11-octahydro-2H-pyrido[4',3':3,4]pyrazolo[1,5-a][1,4]diazepine-2-carboxamide | A |
| 106 | N-(3-chloro-4-fluorophenyl)-8-(1-hydroxybutyl)-10-methyl-11-oxo-1,3,4,7,8,9,10,11-octahydro-2H-pyrido[4',3':3,4]pyrazolo[1,5-a][1,4]diazepine-2-carboxamide | A |
| 107_D1 | (3R,8S*)-N-(4-fluoro-3-(trifluoromethyl)phenyl)-8-((R)-1-hydroxypropyl)-3,10-dimethyl-11-oxo-3,4,8,9,10,11-hexahydro-1H-pyrido[4',3':3,4]pyrazolo[1,5-a][1,4]diazepine-2(7H)-carboxamide | A |
| 107_D2 | (3R,8R*)-N-(4-fluoro-3-(trifluoromethyl)phenyl)-8-((R)-1-hydroxypropyl)-3,10-dimethyl-11-oxo-3,4,8,9,10,11-hexahydro-1H-pyrido[4',3':3,4]pyrazolo[1,5-a][1,4]diazepine-2(7H)-carboxamide | A |
| 108_D1 | (3R,8S*)-N-(3-cyano-4-fluorophenyl)-8-((R)-1-hydroxypropyl)-3,10-dimethyl-11-oxo-3,4,8,9,10,11-hexahydro-1H-pyrido[4',3':3,4]pyrazolo[1,5-a][1,4]diazepine-2(7H)-carboxamide | A |
| 108_D2 | (3R,8R*)-N-(3-cyano-4-fluorophenyl)-8-((R)-1-hydroxypropyl)-3,10-dimethyl-11-oxo-3,4,8,9,10,11-hexahydro-1H-pyrido[4',3':3,4]pyrazolo[1,5-a][1,4]diazepine-2(7H)-carboxamide | B |
| 109_D1 | (3R,8S*)-N-(3-bromo-4-fluorophenyl)-8-((R)-1-hydroxypropyl)-3,10-dimethyl-11-oxo-3,4,8,9,10,11-hexahydro-1H-pyrido[4',3':3,4]pyrazolo[1,5-a][1,4]diazepine-2(7H)-carboxamide | A |

TABLE 6-continued

Activity in BDNA-assay (EC$_{50}$)

| Compound ID | Compound Name | DNA EC$_{50}$ (nM) |
|---|---|---|
| 109_D2 | (3R,8R*)-N-(3-bromo-4-fluorophenyl)-8-((R)-1-hydroxypropyl)-3,10-dimethyl-11-oxo-3,4,8,9,10,11-hexahydro-1H-pyrido[4',3':3,4]pyrazolo[1,5-a][1,4]diazepine-2(7H)-carboxamide | A |
| 110 | N-(3-chloro-4-fluorophenyl)-11-methyl-12-oxo-3,4,7,8,9,10,11,12-octahydropyrido[4',3':3,4]pyrazolo[1,5-a][1,4]diazocine-2(1H)-carboxamide | A |
| 111 | (Z)-N-(3-chloro-4-fluorophenyl)-11-methyl-12-oxo-3,4,7,10,11,12-hexahydropyrido[4',3':3,4]pyrazolo[1,5-a][1,4]diazocine-2(1H)-carboxamide | A |
| 112 | N-(3-cyano-4-fluorophenyl)-8-(3,3-difluoro-1-hydroxypropyl)-10-methyl-11-oxo-1,3,4,7,8,9,10,11-octahydro-2H-pyrido[4',3':3,4]pyrazolo[1,5-a][1,4]diazepine-2-carboxamide | A |
| 113 | 2-((3-chloro-4-fluorophenyl)carbamoyl)-10-methyl-11-oxo-1,3,4,7,8,9,10,11-octahydro-2H-pyrido[4',3':3,4]pyrazolo[1,5-a][1,4]diazepine-7-carboxylic acid | D |
| 114 | N-(3-chloro-4-fluorophenyl)-7-(hydroxymethyl)-10-methyl-11-oxo-1,3,4,7,8,9,10,11-octahydro-2H-pyrido[4',3':3,4]pyrazolo[1,5-a][1,4]diazepine-2-carboxamide | A |
| 115 | N-(3-chloro-4-fluorophenyl)-8-(3-fluoro-1-hydroxypropyl)-10-methyl-11-oxo-1,3,4,7,8,9,10,11-octahydro-2H-pyrido[4',3':3,4]pyrazolo[1,5-a][1,4]diazepine-2-carboxamide | A |
| 116 | N-(3-chloro-4-fluorophenyl)-8-(3,3-difluoro-1-hydroxypropyl)-10-methyl-1-oxo-1,3,4,7,8,9,10,11-octahydro-2H-pyrido[4',3':3,4]pyrazolo[1,5-a][1,4]diazepine-2-carboxamide | A |
| 117 | 8-(acetamidomethyl)-N-(3-chloro-4-fluorophenyl)-10-methyl-11-oxo-1,3,4,7,8,9,10,11-octahydro-2H-pyrido[4',3':3,4]pyrazolo[1,5-a][1,4]diazepine-2-carboxamide | A |
| 118 | N-(3-cyano-4-fluorophenyl)-8-(((2,2-difluoroethyl)amino)methyl)-10-methyl-11-oxo-1,3,4,7,8,9,10,11-octahydro-2H-pyrido[4',3':3,4]pyrazolo[1,5-a][1,4]diazepine-2-carboxamide | A |
| 118_E1 | (R*)-N-(3-cyano-4-fluorophenyl)-8-(((2,2-difluoroethyl)amino)methyl)-10-methyl-11-oxo-3,4,8,9,10,11-hexahydro-1H-pyrido[4',3':3,4]pyrazolo[1,5-a][1,4]diazepine-2(7H)-carboxamide | B |
| 118_E2 | (S*)-N-(3-cyano-4-fluorophenyl)-8-(((2,2-difluoroethyl)amino)methyl)-10-methyl-11-oxo-3,4,8,9,10,11-hexahydro-1H-pyrido[4',3':3,4]pyrazolo[1,5-a][1,4]diazepine-2(7H)-carboxamide | A |
| 119 | 8-(((2,2-difluoroethyl)amino)methyl)-N-(4-fluoro-3-(trifluoromethyl)phenyl)-10-methyl-11-oxo-1,3,4,7,8,9,10,11-octahydro-2H-pyrido[4',3':3,4]pyrazolo[1,5-a][1,4]diazepine-2-carboxamide | A |
| 119_E1 | (R*)-8-(((2,2-difluoroethyl)amino)methyl)-N-(4-fluoro-3-(trifluoromethyl)phenyl)-10-methyl-11-oxo-3,4,8,9,10,11-hexahydro-1H-pyrido[4',3':3,4]pyrazolo[1,5-a][1,4]diazepine-2(7H)-carboxamide | B |
| 119_E2 | (S*)-8-(((2,2-difluoroethyl)amino)methyl)-N-(4-fluoro-3-(trifluoromethyl)phenyl)-10-methyl-11-oxo-3,4,8,9,10,11-hexahydro-1H-pyrido[4',3':3,4]pyrazolo[1,5-a][1,4]diazepine-2(7H)-carboxamide | A |
| 120 | N-(3-cyano-4-fluorophenyl)-10-methyl-11-oxo-8-(((2,2,2-trifluoroethyl)amino)methyl)-1,3,4,7,8,9,10,11-octahydro-2H-pyrido[4',3':3,4]pyrazolo[1,5-a][1,4]diazepine-2-carboxamide | A |
| 121 | N-(4-fluoro-3-(trifluoromethyl)phenyl)-10-methyl-11-oxo-8-(((2,2,2-trifluoroethyl)amino)methyl)-1,3,4,7,8,9,10,11-octahydro-2H-pyrido[4',3':3,4]pyrazolo[1,5-a][1,4]diazepine-2-carboxamide | A |
| 122_D1 | (3R,8S*)-N-(4-fluoro-3-(trifluoromethyl)phenyl)-8-((R)-1-hydroxyallyl)-3,10-dimethyl-11-oxo-3,4,8,9,10,11-hexahydro-1H-pyrido[4',3':3,4]pyrazolo[1,5-a][1,4]diazepine-2(7H)-carboxamide | A |
| 122_D2 | (3R,8R*)-N-(4-fluoro-3-(trifluoromethyl)phenyl)-8-((R)-1-hydroxyallyl)-3,10-dimethyl-11-oxo-3,4,8,9,10,11-hexahydro-1H-pyrido[4',3':3,4]pyrazolo[1,5-a][1,4]diazepine-2(7H)-carboxamide | B |
| 123_D1 | (3R,8S*)-N-(3-cyano-4-fluorophenyl)-8-((R)-1-hydroxyallyl)-3,10-dimethyl-11-oxo-3,4,8,9,10,11-hexahydro-1H-pyrido[4',3':3,4]pyrazolo[1,5-a][1,4]diazepine-2(7H)-carboxamide | A |
| 123_D2 | (3R,8R*)-N-(3-cyano-4-fluorophenyl)-8-((R)-1-hydroxyallyl)-3,10-dimethyl-11-oxo-3,4,8,9,10,11-hexahydro-1H-pyrido[4',3':3,4]pyrazolo[1,5-a][1,4]diazepine-2(7H)-carboxamide | B |
| 124_D1 | (3R,8S*)-N-(3-bromo-4-fluorophenyl)-8-((R)-1-hydroxyallyl)-3,10-dimethyl-11-oxo-3,4,8,9,10,11-hexahydro-1H-pyrido[4',3':3,4]pyrazolo[1,5-a][1,4]diazepine-2(7H)-carboxamide | A |
| 124_D2 | (3R,8R*)-N-(3-bromo-4-fluorophenyl)-8-((R)-1-hydroxyallyl)-3,10-dimethyl-11-oxo-3,4,8,9,10,11-hexahydro-1H-pyrido[4',3':3,4]pyrazolo[1,5-a][1,4]diazepine-2(7H)-carboxamide | A |
| 125_E1 | (R*)-N-(5-bromo-2,4-difluorophenyl)-8-(((2,2-difluoroethyl)amino)methyl)-10-methyl-11-oxo-3,4,8,9,10,11-hexahydro-1H-pyrido[4',3':3,4]pyrazolo[1,5-a][1,4]diazepine-2(7H)-carboxamide | B |
| 125_E2 | (S*)-N-(5-bromo-2,4-difluorophenyl)-8-(((2,2-difluoroethyl)amino)methyl)-10-methyl-11-oxo-3,4,8,9,10,11-hexahydro-1H-pyrido[4',3':3,4]pyrazolo[1,5-a][1,4]diazepine-2(7H)-carboxamide | A |
| 126_E1 | (R*)-N-(5-chloro-2,4-difluorophenyl)-8-(((2,2-difluoroethyl)amino)methyl)-10-methyl-11-oxo-3,4,8,9,10,11-hexahydro-1H-pyrido[4',3':3,4]pyrazolo[1,5-a][1,4]diazepine-2(7H)-carboxamide | B |
| 126_E2 | (S*)-N-(5-chloro-2,4-difluorophenyl)-8-(((2,2-difluoroethyl)amino)methyl)-10-methyl-11-oxo-3,4,8,9,10,11-hexahydro-1H-pyrido[4',3':3,4]pyrazolo[1,5-a][1,4]diazepine-2(7H)-carboxamide | B |
| 127_E1 | (R*)-N-(3-cyano-2,4-difluorophenyl)-8-(((2,2-difluoroethyl)amino)methyl)-10-methyl-11-oxo-3,4,8,9,10,11-hexahydro-1H-pyrido[4',3':3,4]pyrazolo[1,5-a][1,4]diazepine-2(7H)-carboxamide | C |
| 127_E2 | (S*)-N-(3-cyano-2,4-difluorophenyl)-8-(((2,2-difluoroethyl)amino)methyl)-10-methyl-11-oxo-3,4,8,9,10,11-hexahydro-1H-pyrido[4',3':3,4]pyrazolo[1,5-a][1,4]diazepine-2(7H)-carboxamide | A |
| 128_E1 | (R*)-N-(3-chloro-2,4-difluorophenyl)-8-(((2,2-difluoroethyl)amino)methyl)-10-methyl-11-oxo-3,4,8,9,10,11-hexahydro-1H-pyrido[4',3':3,4]pyrazolo[1,5-a][1,4]diazepine-2(7H)-carboxamide | B |

TABLE 6-continued

Activity in BDNA-assay ($EC_{50}$)

| Compound ID | Compound Name | DNA $EC_{50}$ (nM) |
|---|---|---|
| 128_E2 | (S*)-N-(3-chloro-2,4-difluorophenyl)-8-(((2,2-difluoroethyl)amino)methyl)-10-methyl-11-oxo-3,4,8,9,10,11-hexahydro-1H-pyrido[4',3':3,4]pyrazolo[1,5-a][1,4]diazepine-2(7H)-carboxamide | A |
| 129_E1 | (R*)-N-(3-bromo-2,4-difluorophenyl)-8-(((2,2-difluoroethyl)amino)methyl)-10-methyl-11-oxo-3,4,8,9,10,11-hexahydro-1H-pyrido[4',3':3,4]pyrazolo[1,5-a][1,4]diazepine-2(7H)-carboxamide | B |
| 129_E2 | (S*)-N-(3-bromo-2,4-difluorophenyl)-8-(((2,2-difluoroethyl)amino)methyl)-10-methyl-11-oxo-3,4,8,9,10,11-hexahydro-1H-pyrido[4',3':3,4]pyrazolo[1,5-a][1,4]diazepine-2(7H)-carboxamide | A |
| 130_E1 | (R*)-N-(3-bromo-4-fluorophenyl)-8-(((2,2-difluoroethyl)amino)methyl)-10-methyl-11-oxo-3,4,8,9,10,11-hexahydro-1H-pyrido[4',3':3,4]pyrazolo[1,5-a][1,4]diazepine-2(7H)-carboxamide | A |
| 130_E2 | (S*)-N-(3-bromo-4-fluorophenyl)-8-(((2,2-difluoroethyl)amino)methyl)-10-methyl-11-oxo-3,4,8,9,10,11-hexahydro-1H-pyrido[4',3':3,4]pyrazolo[1,5-a][1,4]diazepine-2(7H)-carboxamide | A |
| 131_E1 | (R*)-N-(2,4-difluoro-3-(trifluoromethyl)phenyl)-8-(((2,2-difluoroethyl)amino)methyl)-10-methyl-11-oxo-3,4,8,9,10,11-hexahydro-1H-pyrido[4',3':3,4]pyrazolo[1,5-a][1,4]diazepine-2(7H)-carboxamide | B |
| 131_E2 | (S*)-N-(2,4-difluoro-3-(trifluoromethyl)phenyl)-8-(((2,2-difluoroethyl)amino)methyl)-10-methyl-11-oxo-3,4,8,9,10,11-hexahydro-1H-pyrido[4',3':3,4]pyrazolo[1,5-a][1,4]diazepine-2(7H)-carboxamide | B |
| 132 | N-(3-chloro-4-fluorophenyl)-3-hydroxy-10'-methyl-11'-oxo-1',3',4',9',10',11'-hexahydro-2'H,7'H-spiro[cyclobutane-1,8'-pyrido[4',3':3,4]pyrazolo[1,5-a][1,4]diazepine]-2'-carboxamide | A |
| 133_D1 | (3R,8R*)-8-fluoro-N-(4-fluoro-3-(trifluoromethyl)phenyl)-8-(hydroxymethyl)-3,10-dimethyl-11-oxo-1,3,4,7,8,9,10,11-octahydro-2H-pyrido[4',3':3,4]pyrazolo[1,5-a][1,4]diazepine-2-carboxamide | A |
| 133_D2 | (3R,8S*)-8-fluoro-N-(4-fluoro-3-(trifluoromethyl)phenyl)-8-(hydroxymethyl)-3,10-dimethyl-11-oxo-1,3,4,7,8,9,10,11-octahydro-2H-pyrido[4',3':3,4]pyrazolo[1,5-a][1,4]diazepine-2-carboxamide | A |
| 134_D1 | (3R,8R)-N-(3-Cyano-4-fluorophenyl)-8-((2,2-difluoroethoxy)methyl)-3,10-dimethyl-11-oxo-1,3,4,7,8,9,10,11-octahydro-2H-pyrido[4',3':3,4]pyrazolo[1,5-a][1,4]diazepine-2-carboxamide | A |
| 134_D2 | (3R,8S)-N-(3-cyano-4-fluorophenyl)-8-((2,2-difluoroethoxy)methyl)-3,10-dimethyl-11-oxo-1,3,4,7,8,9,10,11-octahydro-2H-pyrido[4',3':3,4]pyrazolo[1,5-a][1,4]diazepine-2-carboxamide | A |
| 135_D1 | (3R,8R)-8-((2,2-difluoroethoxy)methyl)-N-(4-fluoro-3-(trifluoromethyl)phenyl)-3,10-dimethyl-11-oxo-1,3,4,7,8,9,10,11-octahydro-2H-pyrido[4',3':3,4]pyrazolo[1,5-a][1,4]diazepine-2-carboxamide | A |
| 135_D2 | (3R,8S)-8-((2,2-difluoroethoxy)methyl)-N-(4-fluoro-3-(trifluoromethyl)phenyl)-3,10-dimethyl-11-oxo-1,3,4,7,8,9,10,11-octahydro-2H-pyrido[4',3':3,4]pyrazolo[1,5-a][1,4]diazepine-2-carboxamide | A |
| 136 | (R)-N-(3-cyano-4-fluorophenyl)-8,8-difluoro-3,10-dimethyl-11-oxo-1,3,4,7,8,9,10,11-octahydro-2H-pyrido[4',3':3,4]pyrazolo[1,5-a][1,4]diazepine-2-carboxamide. | A |
| 137_D1 | (3R,8R*)-N-(3-cyano-4-fluorophenyl)-8-fluoro-3,10-dimethyl-11-oxo-1,3,4,7,8,9,10,11-octahydro-2H-pyrido[4',3':3,4]pyrazolo[1,5-a][1,4]diazepine-2-carboxamide. | A |
| 137_D2 | (3R,8S*)-N-(3-Cyano-4-fluorophenyl)-8-fluoro-3,10-dimethyl-11-oxo-1,3,4,7,8,9,10,11-octahydro-2H-pyrido[4',3':3,4]pyrazolo[1,5-a][1,4]diazepine-2-carboxamide | A |
| 138 | (3R,8R*)-8-fluoro-N-(4-fluoro-3-(trifluoromethyl)phenyl)-3,10-dimethyl-11-oxo-1,3,4,7,8,9,10,11-octahydro-2H-pyrido[4',3':3,4]pyrazolo[1,5-a][1,4]diazepine-2-carboxamide | A |
| 139 | (R)-N-(3-cyano-4-fluorophenyl)-3,8,8,10-tetramethyl-11-oxo-1,3,4,7,8,9,10,11-octahydro-2H-pyrido[4',3':3,4]pyrazolo[1,5-a][1,4]diazepine-2-carboxamide | A |
| 140 | (R)-N-(4-Fluoro-3-(trifluoromethyl)phenyl)-3,8,8,10-tetramethyl-11-oxo-1,3,4,7,8,9,10,11-octahydro-2H-pyrido[4',3':3,4]pyrazolo[1,5-a][1,4]diazepine-2-carboxamide | A |
| 141 | (R)-N-(3-Cyano-4-fluorophenyl)-3-hydroxy-3',10'-dimethyl-11'-oxo-1',3',4',9',10',11'-hexahydro-2'H,7'H-spiro[cyclobutane-1,8'-pyrido[4',3':3,4]pyrazolo[1,5-a][1,4]diazepine]-2'-carboxamide | A |
| 142 | (R)-N-(3-Cyano-4-fluorophenyl)-3-fluoro-3',10'-dimethyl-11'-oxo-1',3',4',9',10',11'-hexahydro-2'H,7'H-spiro[cyclobutane-1,8'-pyrido[4',3':3,4]pyrazolo[1,5-a][1,4]diazepine]-2'-carboxamide | A |
| 143 | (R)-N-(3-Cyano-4-fluorophenyl)-3,3-difluoro-3',10'-dimethyl-11'-oxo-1',3',4',9',10',11'-hexahydro-2'H,7'H-spiro[cyclobutane-1,8'-pyrido[4',3':3,4]pyrazolo[1,5-a][1,4]diazepine]-2'-carboxamide | A |
| 144_E1 | (S)-N-(3-Cyano-4-fluorophenyl)-8-fluoro-10-methyl-11-oxo-1,3,4,7,8,9,10,11-octahydro-2H-pyrido[4',3':3,4]pyrazolo[1,5-a][1,4]diazepine-2-carboxamide | N/A |
| 144_E2 | (R)-N-(3-Cyano-4-fluorophenyl)-8-fluoro-10-methyl-11-oxo-1,3,4,7,8,9,10,11-octahydro-2H-pyrido[4',3':3,4]pyrazolo[1,5-a][1,4]diazepine-2-carboxamide | N/A |
| 145_D1 | (R)-N-(3-Cyano-4-fluorophenyl)-8-(2,2-difluoroethoxy)-10-methyl-11-oxo-1,3,4,7,8,9,10,11-octahydro-2H-pyrido[4',3':3,4]pyrazolo[1,5-a][1,4]diazepine-2-carboxamide | N/A |
| 145_D2 | (S)-N-(3-Cyano-4-fluorophenyl)-8-(2,2-difluoroethoxy)-10-methyl-11-oxo-1,3,4,7,8,9,10,11-octahydro-2H-pyrido[4',3':3,4]pyrazolo[1,5-a][1,4]diazepine-2-carboxamide | N/A |
| 146 | (R)-N-(3-Cyano-4-fluorophenyl)-3-methyl-11-oxo-1,3,4,7,8,9,10,11-octahydro-2H-pyrido[4',3':3,4]pyrazolo[1,5-a][1,4]diazepine-2-carboxamide | N/A |
| 147 | (R)-N-(4-Fluoro-3-(trifluoromethyl)phenyl)-3-methyl-11-oxo-1,3,4,7,8,9,10,11-octahydro-2H-[4',3':3,4]pyrazolo[1,5-a][1,4]diazepine-2-carboxamide | N/A |
| 148 | (3R,8S)-N-(3-Cyano-4-fluorophenyl)-8-(hydroxymethyl)-3,9-dimethyl-10-oxo-3,4,7,8,9,10-hexahydropyrido[4',3':3,4]pyrazolo[1,5-a]pyrazine-2(1H)-carboxamide | N/A |
| 149 | (3R,8S)-N-(3-cyano-4-fluorophenyl)-8-(fluoromethyl)-3,9-dimethyl-10-oxo-3,4,7,8,9,10-hexahydropyrido[4',3':3,4]pyrazolo[1,5-a]pyrazine-2(1H)-carboxamide | A |
| 150 | (3R,8S)-N-(3-cyano-4-fluorophenyl)-8-((2,2-difluoroethoxy)methyl)-3,9-dimethyl-10-oxo-3,4,7,8,9,10-hexahydropyrido[4',3':3,4]pyrazolo[1,5-a]pyrazine-2(1H)-carboxamide | A |

Example 3: Crystalline Form of Intermediate 16 Analogue

The crystalline form of compound 151, which is the di p-nitro-benzoic acid analogue of Intermediate 16, is described herein.

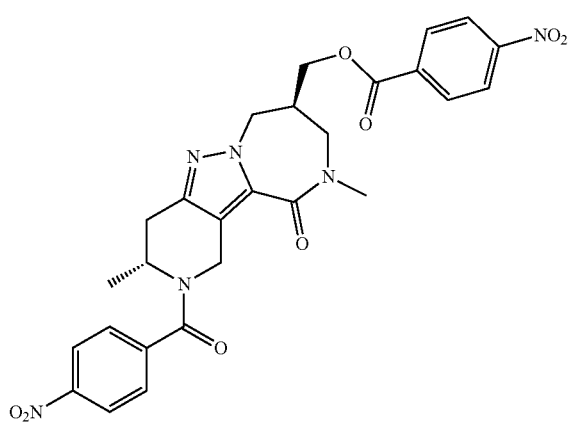 [SMILES: C[C@@H]1Cc2nn3c(c2CN1C(=O)c1ccc([N+](=O)[O-])cc1)C(=O)N(C)C[C@H](COC(=O)c1ccc([N+](=O)[O-])cc1)C3]

The X-ray crystal structure is shown in FIG. 1. Table 7 also shows crystal data and structure refinement for this intermediate.

TABLE 7

Crystal data and structure refinement.

| | |
|---|---|
| Empirical formula | C27 H26 N6 O8 |
| Formula weight | 562.54 |
| Temperature | 296(2) K |
| Wavelength | 1.54178 A |
| Crystal system, space group | Monoclinic, P 21 |
| Unit cell dimensions | a = 13.87660(10) A alpha = 90 deg. |
| | b = 6.09990(10) A beta = 95.24 deg. |
| | c = 15.60460(10) A gamma = 90 deg. |
| Volume | 1315.34(3) A^3 |
| Z, Calculated density | 2, 1.420 Mg/m^3 |
| Absorption coefficient | 0.899 mm^-1 |
| F(000) | 588 |
| Crystal size | 0.30 × 0.30 × 0.15 mm |
| Theta range for data collection | 2.84 to 67.00 deg. |
| Limiting indices | -16<=h<= 16, -6<=k<=6, -18<=l<=18 |
| Reflections collected/unique | 11901/4328 [R(int) = 0.0202] |
| Completeness to theta = 67.23 | 97.1% |
| Absorption correction | Semi-empirical from equivalents |
| Max. and min. transmission | 0.7532 and 0.6289 |
| Refinement method | Full-matrix least-squares on F^2 |
| Data/restraints/parameters | 4328/1/371 |
| Goodness-of-fit on F^2 | 1.060 |
| Final R indices [I > 2sigma(I)] | R1 = 0.0288, wR2 = 0.0778 |
| R indices (all data) | R1 = 0.0291, wR2 = 0.0781 |
| Absolute structure parameter | 0.07(15) |
| Largest diff. peak and hole | 0.162 and -0.124 e.A^-3 |

Table 8 also shows atomic coordinates ($\times 10^4$) and equivalent isotropic displacement parameters ($A^2 \times 10^3$) for the intermediate.

TABLE 8

Atomic coordinates and equivalent isotropic displacement parameters.

| | x | y | z | U(eq) |
|---|---|---|---|---|
| O(1) | 10223(1) | 8815(2) | 1656(1) | 59(1) |
| O(2) | 6267(1) | 12793(2) | 1058(1) | 48(1) |
| O(3) | 5071(1) | 15033(3) | 570(1) | 81(1) |

TABLE 8-continued

Atomic coordinates and equivalent isotropic displacement parameters.

| | x | y | z | U(eq) |
|---|---|---|---|---|
| O(4) | 4223(2) | 11263(7) | 4829(2) | 162(1) |
| O(5) | 3652(2) | 14510(6) | 4722(1) | 132(1) |
| O(6) | 9682(1) | 8853(2) | 4999(1) | 56(1) |
| O(7) | 7319(1) | 3348(3) | 8223(1) | 83(1) |
| O(8) | 7495(1) | 6700(3) | 8642(1) | 84(1) |
| N(1) | 7671(1) | 8706(2) | 1391(1) | 39(1) |
| N(2) | 6991(1) | 7802(2) | 1845(1) | 42(1) |
| N(3) | 8627(1) | 6844(2) | 4144(1) | 36(1) |
| N(4) | 9298(1) | 11581(3) | 1053(1) | 47(1) |
| N(5) | 4082(1) | 12982(6) | 4444(2) | 105(1) |
| N(6) | 7554(1) | 5251(3) | 8112(1) | 57(1) |
| C(1) | 7622(1) | 11769(3) | 313(1) | 42(1) |
| C(2) | 7454(1) | 9327(3) | 486(1) | 44(1) |
| C(3) | 7465(1) | 7305(2) | 2603(1) | 39(1) |
| C(4) | 7014(1) | 6415(3) | 3363(1) | 47(1) |
| C(5) | 7790(1) | 5336(3) | 3989(1) | 40(1) |
| C(6) | 9150(1) | 7438(3) | 3399(1) | 42(1) |
| C(7) | 8446(1) | 7817(3) | 2631(1) | 37(1) |
| C(8) | 8558(1) | 8748(3) | 1841(1) | 37(1) |
| C(9) | 9435(1) | 9715(3) | 1508(1) | 43(1) |
| C(10) | 8374(1) | 12757(3) | 981(1) | 45(1) |
| C(11) | 6694(1) | 13079(3) | 255(1) | 46(1) |
| C(12) | 5452(1) | 13897(3) | 1126(1) | 54(1) |
| C(13) | 5087(1) | 13564(3) | 1990(1) | 55(1) |
| C(14) | 4541(1) | 15226(4) | 2303(1) | 70(1) |
| C(15) | 4221(1) | 15041(5) | 3113(2) | 80(1) |
| C(16) | 4437(1) | 13182(5) | 3583(1) | 78(1) |
| C(17) | 4965(1) | 11492(5) | 3278(2) | 78(1) |
| C(18) | 5302(1) | 11713(4) | 2477(1) | 65(1) |
| C(19) | 9008(1) | 7555(2) | 4917(1) | 36(1) |
| C(20) | 8587(1) | 6829(3) | 5730(1) | 36(1) |
| C(21) | 8409(1) | 4676(3) | 5940(1) | 43(1) |
| C(22) | 8072(1) | 4170(3) | 6720(1) | 48(1) |
| C(23) | 7928(1) | 5821(3) | 7289(1) | 43(1) |
| C(24) | 8137(1) | 7966(3) | 7120(1) | 57(1) |
| C(25) | 8476(1) | 8447(3) | 6335(1) | 54(1) |
| C(26) | 10114(1) | 12629(4) | 698(1) | 67(1) |

As can be seen, the stereo configuration of the Intermediate 16 analogue is 4S, 9R. Accordingly, the stereo configuration of compounds derived from Intermediate 16 is known.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

The invention claimed is:

1. A compound of Formula IA:

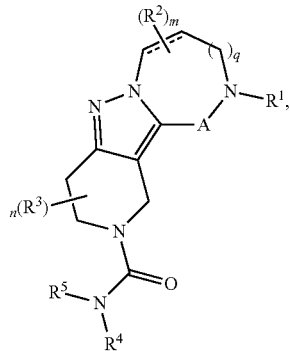

or a pharmaceutically acceptable salt thereof, wherein
A is $CH_2$ or C=O;
$R^1$ is H, $C_1$-$C_6$-alkyl, $C_1$-$C_6$-alkenyl, $C_1$-$C_6$-alkyl-OH, or $C_1$-$C_6$-haloalkyl;
$R^2$ is, at each occurrence, independently selected from OH, halo, $C_1$-$C_6$-alkyl, $C_1$-$C_6$-alkenyl, $C_0$-$C_6$-alkyl-$C_3$-$C_6$-cycloalkyl, $C_0$-$C_6$-alkyl-4-6 membered heterocyclyl, $C_0$-$C_6$-alkyl-$OR^6$, $C_0$-$C_6$-alkyl-$N(R^7)_2$, $C_0$-$C_6$-alkyl-$SR^8$, $C_0$-$C_6$-alkyl-$S(O)R^8$, $C_0$-$C_6$-alkyl-$S(O)_2R^8$, $C_0$-$C_6$-alkyl-$C(O)OR^9$, $C_0$-$C_6$-alkyl-$OC(O)R^9$, $C_0$-$C_6$-alkyl-$OC(O)OR^9$, $C_0$-$C_6$-alkyl-$OC(O)N(R^7)_2$, and $C_0$-$C_6$-alkyl-$C(O)N(R^7)_2$, and wherein alkyl, alkenyl, cycloalkyl, and heterocyclyl are optionally substituted with 1, 2, or 3 groups, each independently selected from OH and halo;
or two $R^2$ groups together form a $C_3$-$C_6$ spiro cycloalkyl, wherein the cyloalkyl is optionally substituted with 1, 2, or 3 groups, each individually selected from —OH and halo;
$R^3$ is, at each occurrence, independently selected from —OH, halo, $C_1$-$C_6$-alkyl, $C_1$-$C_6$-haloalkyl, —O—$C_1$-$C_6$-alkyl, and $C_1$-$C_6$-alkyl-OH;
$R^4$ is selected from $(CR^aR^b)_p$-6-membered heteroaryl, $(CR^aR^b)_p$—$C_6$-$C_{12}$-aryl, $(CR^aR^b)_p$—$C_3$-$C_7$-cycloalkyl, and $(CR^aR^b)_p$-4-6 membered heterocyclyl, and wherein heteroaryl, aryl, cycloalkyl, and heterocycloalkyl are optionally substituted with 1, 2, 3, or 4 groups, each independently selected from —OH, halo, —CN, —$SF_5$, $C_1$-$C_6$-haloalkyl, —O—$C_1$-$C_6$-alkyl, and $C_1$-$C_6$-alkyl-OH;
$R^5$ is selected from H, $C_1$-$C_6$-alkyl, and $C_1$-$C_6$-alkyl-OH;
$R^6$ is selected from H, $C_1$-$C_6$-alkyl, $C_1$-$C_6$-haloalkyl, $C_1$-$C_6$-alkenyl, and $C_0$-$C_6$-alkyl-$C_3$-$C_6$-cycloalkyl;
$R^7$ is, at each occurrence, independently selected from H, $C_1$-$C_6$-alkyl, $C_1$-$C_6$-haloalkyl, C(O) $C_1$-$C_6$-alkyl and $C_1$-$C_6$-alkyl-OH;
$R^8$ is selected from H and $C_1$-$C_6$-alkyl;
$R^9$ is selected from H and $C_1$-$C_6$-alkyl;
$R^a$ is, at each occurrence, independently selected from H, —OH, halo, $C_1$-$C_6$-alkyl, $C_1$-$C_6$-haloalkyl, —O—$C_1$-$C_6$-alkyl, and $C_1$-$C_6$-alkyl-OH;
$R^b$ is, at each occurrence, independently selected from H and $C_1$-$C_6$-alkyl;
m is 0, 1, 2, 3, or 4;
n is 0, 1, 2, 3, or 4;
p is 0, 1, 2, 3, or 4;
q is 0 or 1; and
a ---- line denotes an optionally double bond.

2. The compound of claim 1, wherein A is C=O.
3. The compound of claim 1, wherein q is 1.
4. The compound of claim 1, wherein $R^1$ is H, $C_1$-$C_6$-alkyl, or $C_1$-$C_6$-haloalkyl.
5. The compound of claim 1, wherein $R^1$ is —$CH_3$, or —$CH_2CHF_2$.
6. The compound of claim 1, having the structure of Formula II:

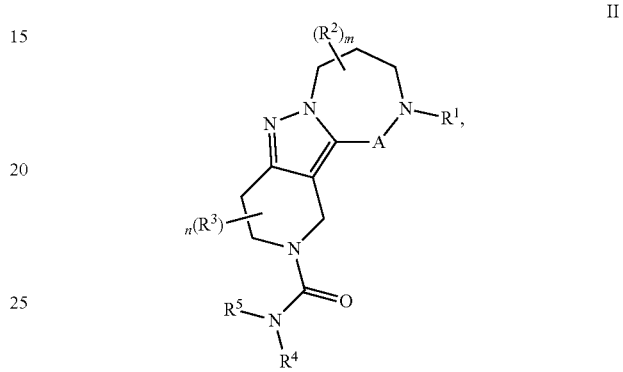

or a pharmaceutically acceptable salt thereof.
7. The compound of claim 1, having the structure of Formula III:

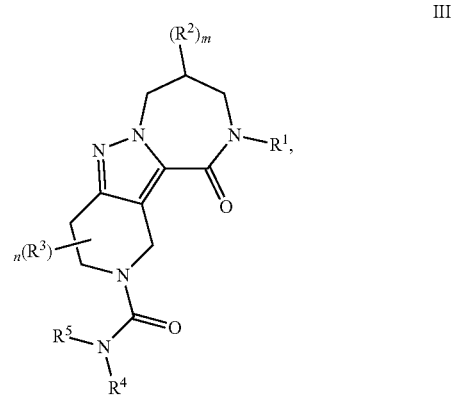

or a pharmaceutically acceptable salt thereof,
wherein m is 0, 1, or 2.
8. The compound of claim 1, wherein
m is 0, 1, or 2; and
$R^2$ is, at each occurrence, independently selected from —OH, halo, $C_1$-$C_6$-alkyl, $C_1$-$C_6$-alkenyl, $C_0$-$C_6$-alkyl-$OR^6$, $C_0$-$C_6$-alkyl-$N(R^7)_2$, $C_0$-$C_6$-alkyl-$C_3$-$C_6$-cycloalkyl, $C_0$-$C_6$-alkyl-4-6 membered heterocyclyl, $C_0$-$C_6$-alkyl-$SR^8$, $C_0$-$C_6$-alkyl-$S(O)R^8$, $C_0$-$C_6$-alkyl-$S(O)_2R^8$, $C_0$-$C_6$-alkyl-$C(O)OR^9$, and $C_0$-$C_6$-alkyl-$C(O)N(R^7)_2$, and wherein alkyl, cycloalkyl, and heterocyclyl are optionally substituted with 1 or 2 groups, each independently selected from —OH and halo.
9. The compound of claim 1, wherein
m is 1 or 2; and
$R^2$, is at each occurrence, independently selected from =$CH_2$, —$CH_2OH$, —OH, —F, —$CH_3$, —$CHF_2$, —OCH₃, —OCH₂CH₃, —OCH₂CHF₂, —NH₂, —N(CH₃)₂, morpholinyl, azetidinyl, pyrrolidinyl, —SCH₃, —S(O)CH₃, —S(O)₂CH₃, —CH₂C(O)OCH₃, —CH₂CH₂OH, —C(O)OH, —C(O)OCH₃, —C(O)OCH₂CH₃, —C(O)NHCH₃, —C(O)N(CH₃)₂, —C(OH)(CH₃)₂, —CH(OH)CH₃, —CH(OH)CH₂CH₃, and —CH(OH)-cyclopropyl, wherein morpholinyl, azetidinyl, and pyrrolidinyl are optionally substituted with 1 or 2 groups, each independently selected from —OH and halo.

10. The compound of claim 1, wherein
n is 0, 1, or 2; and
R³ is, at each occurrence, selected from —OH, halo, and C₁-C₆-alkyl.

11. The compound of claim 1, wherein
R⁴ is (CRᵃRᵇ)ₚ-6-membered heteroaryl or (CRᵃRᵇ)ₚ—C₆-aryl, wherein the heteroaryl contains one to four heteroatoms, and wherein heteroaryl and aryl are optionally substituted with 1, 2, 3, or 4 groups, each independently selected from —OH, halo, —CN, —SF₅, C₁-C₆-alkyl, C₁-C₆-haloalkyl, —O—C₁-C₆-alkyl, and C₁-C₆-alkyl-OH;
Rᵃ is H or C₁-C₆-alkyl;
Rᵇ is H or C₁-C₆-alkyl; and
p is 0 or 1.

12. The compound of claim 1, wherein R⁴ is 6-membered heteroaryl or C₆-aryl, any of which is optionally substituted with 1, 2, 3, or 4 groups, each independently selected from halo, —CN, C₁-C₆-alkyl, and C₁-C₆-haloalkyl.

13. The compound of claim 1, wherein R⁴ is phenyl or pyridinyl, any of which is optionally substituted with 1, 2, 3, or 4 groups, each independently selected from halo, —CN, C₁-C₆-alkyl, and C₁-C₆-haloalkyl.

14. The compound of claim 1, wherein R⁴ is selected from the group consisting of:

15. The compound of claim 1, wherein R⁵ is H or C₁-C₆-alkyl.

16. The compound of claim 1, wherein R⁵ is H.

17. The compound of claim 1, wherein
A is C=O;
R¹ is C₁-C₆-alkyl;
R² is, at each occurrence, independently selected from —OH, halo, C₁-C₆-alkyl, C₁-C₆-alkenyl, C₀-C₆-alkyl-C₃-C₆-cycloalkyl, C₀-C₆-alkyl-4-6 membered heterocyclyl, C₀-C₆-alkyl-OR⁶, C₀-C₆-alkyl-N(R⁷)₂, C₀-C₆-alkyl-SR⁸, C₀-C₆-alkyl-S(O)R⁸, C₀-C₆-alkyl-S(O)₂R⁸, C₀-C₆-alkyl-C(O)OR⁹, and C₀-C₆-alkyl-C(O)N(R⁷)₂, and wherein alkyl, cycloalkyl, and heterocyclyl are optionally substituted with 1, 2, or 3 groups, each independently selected from —OH and halo;
R⁴ is (CRᵃRᵇ)ₚ—C₆-C₁₂-aryl, wherein aryl is optionally substituted with 1, 2, 3, or 4 groups, each independently selected from halo, —CN, and C₁-C₆-alkyl;
R⁵ is H;
R⁶ is selected from H, C₁-C₆-alkyl, and C₁-C₆-haloalkyl;
R⁷ is, at each occurrence, independently selected from H, and C₁-C₆-alkyl;
R⁸ is C₁-C₆-alkyl;
R⁹ is selected from H and C₁-C₆-alkyl;
m is 0, 1, or 2;
n is 0;
p is 0; and
q is 1.

18. The compound of claim 1, having the structure of Formula IV:

IV wherein
m is 1 or 2; and
R², is at each occurrence, independently selected from =CH₂, —CH₂OH, —OH, —F, —CH₃, —CHF₂, —OCH₃, —OCH₂CH₃, —OCH₂CHF₂, —NH₂, —N(CH₃)₂, morpholinyl, azetidinyl, pyrrolidinyl, —SCH₃, —S(O)CH₃, —S(O)₂CH₃, —CH₂C(O)OCH₃, —CH₂CH₂OH, —C(O)OH, —C(O)OCH₃, —C(O)OCH₂CH₃, —C(O)NHCH₃, —C(O)N(CH₃)₂, —C(OH)(CH₃)₂, —CH(OH)CH₃, —CH(OH)CH₂CH₃, —CH(OH)-cyclopropyl, —CH₂N(H)(C (O)—CH$_3$), —CH$_2$N(H)CH$_2$CHF$_2$, —CH$_2$N(H)CH$_2$CF$_3$, —CH(OH)CH=CH$_2$ and spiro-cyclobutyl, which is substituted with —OH, wherein morpholinyl, azetidinyl, and pyrrolidinyl are optionally substituted with 1 or 2 groups, each independently selected from —OH and halo.

19. The compound of claim 1, wherein
m is 0, 1, or 2; and
R$^2$ is, at each occurrence, independently selected from —OH, halo, C$_1$-C$_6$-alkyl, C$_1$-C$_6$-alkenyl, C$_0$-C$_6$-alkyl-C$_3$-C$_6$-cycloalkyl, C$_0$-C$_6$-alkyl-4-6 membered heterocyclyl, C$_0$-C$_6$-alkyl-OR$^6$, C$_0$-C$_6$-alkyl-N(R$^7$)$_2$, C$_0$-C$_6$-alkyl-SR$^8$, C$_0$-C$_6$-alkyl-S(O)R$^8$, C$_0$-C$_6$-alkyl-S(O)$_2$R$^8$, C$_0$-C$_6$-alkyl-C(O)OR$^9$, C$_0$-C$_6$-alkyl-OC(O)R$^9$, C$_0$-C$_6$-alkyl-OC(O)OR$^9$, C$_0$-C$_6$-alkyl-OC(O)N(R$^7$)$_2$, and C$_0$-C$_6$-alkyl-C(O)N(R$^7$)$_2$, and wherein alkyl, alkenyl, cycloalkyl, and heterocyclyl are optionally substituted with 1, 2, or 3 groups, each independently selected from —OH and halo;
or two R$^2$ groups together form a C$_3$—O$_6$ spiro cycloalkyl, wherein the cyloalkyl is optionally substituted with 1, 2, or 3 groups, each individually selected from —OH and halo.

20. The compound of claim 1, wherein
m is 1 or 2; and
R$^2$, is at each occurrence, independently selected from —CH$_2$N(H)(C(O)—CH$_3$), —CH$_2$N(H)CH$_2$CHF$_2$, CH$_2$N(H)CH$_2$CF$_3$, CH(OH)CH=CH$_2$ and spiro-cyclobutyl, which is substituted with —OH.

21. The compound of claim 1, wherein
A is C=O;
R$^1$ is C$_1$-C$_6$-alkyl;
R$^2$ is, at each occurrence, independently selected from —OH, halo, C$_1$-C$_6$-alkyl, C$_1$-C$_6$-alkenyl, C$_0$-C$_6$-alkyl-C$_3$-C$_6$-cycloalkyl, C$_0$-C$_6$-alkyl-4-6 membered heterocyclyl, C$_0$-C$_6$-alkyl-OR$^6$, C$_0$-C$_6$-alkyl-N(R$^7$)$_2$, C$_0$-C$_6$-alkyl-SR$^8$, C$_0$-C$_6$-alkyl-S(O)R$^8$, C$_0$-C$_6$-alkyl-S(O)$_2$R$^8$, C$_0$-C$_6$-alkyl-C(O)OR$^9$, and C$_0$-C$_6$-alkyl-C(O)N(R$^7$)$_2$, wherein the heterocycloalkyl contains one to four heteroatoms, and wherein alkyl, alkenyl, cycloalkyl, and heterocyclyl are optionally substituted with 1, 2, or 3 groups, each independently selected from —OH and halo;
or two R$^2$ groups together form a C$_3$-C$_6$ spiro cycloalkyl, wherein the cyloalkyl is optionally substituted with 1, 2, or 3 groups, each individually selected from —OH and halo;
R$^4$ is (CR$^a$R$^b$)$_p$—C$_6$-C$_{12}$-aryl, wherein aryl is optionally substituted with 1, 2, 3, or 4 groups, each independently selected from halo, —CN, and C$_1$-C$_6$-alkyl;
R$^5$ is H;
R$^6$ is selected from H, C$_1$-C$_6$-alkyl, and C$_1$-C$_6$-haloalkyl;
R$^7$ is, at each occurrence, independently selected from H, C$_1$-C$_6$-haloalkyl, C(O) C$_1$-C$_6$-alkyl and C$_1$-C$_6$-alkyl-OH;
R$^8$ is C$_1$-C$_6$-alkyl;
R$^9$ is selected from H and C$_1$-C$_6$-alkyl;
m is 0, 1, or 2;
n is 0;
p is 0; and
q is 1.

22. A compound of Formula V:

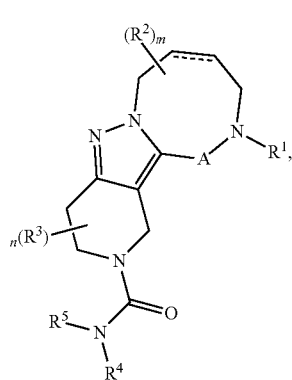

or a pharmaceutically acceptable salt thereof, wherein
A is CH$_2$ or C=O;
R$^1$ is H, C$_1$-C$_6$-alkyl, C$_1$-C$_6$-alkenyl, C$_1$-C$_6$-alkyl-OH, or C$_1$-C$_6$-haloalkyl;
R$^2$ is, at each occurrence, independently selected from —OH, halo, C$_1$-C$_6$-alkyl, C$_1$-C$_6$-alkenyl, C$_0$-C$_6$-alkyl-C$_3$-C$_6$-cycloalkyl, C$_0$-C$_6$-alkyl-4-6 membered heterocyclyl, C$_0$-C$_6$-alkyl-OR$^6$, C$_0$-C$_6$-alkyl-N(R$^7$)$_2$, C$_0$-C$_6$-alkyl-SR$^8$, C$_0$-C$_6$-alkyl-S(O)R$^8$, C$_0$-C$_6$-alkyl-S(O)$_2$R$^8$, C$_0$-C$_6$-alkyl-C(O)OR$^9$, C$_0$-C$_6$-alkyl-OC(O)R$^9$, C$_0$-C$_6$-alkyl-OC(O)OR$^9$, C$_0$-C$_6$-alkyl-OC(O)N(R$^7$)$_2$, or C$_0$-C$_6$-alkyl-C(O)N(R$^7$)$_2$, and wherein alkyl, alkenyl, cycloalkyl, and heterocyclyl are optionally substituted with 1, 2, or 3 groups, each independently selected from —OH and halo; or
two R$^2$ groups together form a C$_3$—O$_6$ spiro cycloalkyl, wherein the cyloalkyl is optionally substituted with 1, 2, or 3 groups, each individually selected from —OH and halo;
R$^3$ is, at each occurrence, independently selected from —OH, halo, C$_1$-C$_6$-alkyl, C$_1$-C$_6$-haloalkyl, —O—C$_1$-C$_6$-alkyl, and C$_1$-C$_6$-alkyl-OH;
R$^4$ is selected from (CR$^a$R$^b$)$_p$-6-membered heteroaryl, (CR$^a$R$^b$)$_p$—C$_6$-C$_{12}$-aryl, (CR$^a$R$^b$)$_p$—C$_3$-C$_7$-cycloalkyl, and (CR$^a$R$^b$)$_p$-4-6 membered heterocyclyl, and wherein heteroaryl, aryl, cycloalkyl, and heterocycloalkyl are optionally substituted with 1, 2, 3, or 4 groups, each independently selected from —OH, halo, —CN, —SF$_5$, C$_1$-C$_6$-alkyl, C$_1$-C$_6$-haloalkyl, —O—C$_1$-C$_6$-alkyl, and C$_1$-C$_6$-alkyl-OH;
R$^5$ is selected from H, C$_1$-C$_6$-alkyl, and C$_1$-C$_6$-alkyl-OH;
R$^6$ is selected from H, C$_1$-C$_6$-alkyl, C$_1$-C$_6$-haloalkyl, C$_1$-C$_6$-alkenyl, and C$_0$-C$_6$-alkyl-C$_3$-C$_6$-cycloalkyl;
R$^7$ is, at each occurrence, independently selected from H, C$_1$-C$_6$-alkyl, C$_1$-C$_6$-haloalkyl, C(O) C$_1$-C$_6$-alkyl and C$_1$-C$_6$-alkyl-OH;
R$^8$ is selected from H and C$_1$-C$_6$-alkyl;
R$^9$ is selected from H and C$_1$-C$_6$-alkyl;
R$^a$ is, at each occurrence, independently selected from H, —OH, halo, C$_1$-C$_6$-alkyl, C$_1$-C$_6$-haloalkyl, —O—C$_1$-C$_6$-alkyl, and C$_1$-C$_6$-alkyl-OH;
R$^b$ is, at each occurrence, independently selected from H and C$_1$-C$_6$-alkyl;
m is 0, 1, 2, 3, or 4;
n is 0, 1, 2, 3, or 4;
p is 0, 1, 2, 3, or 4; and
a ---- line denotes an optionally double bond.

23. The compound of claim 22, wherein A is C=O.

24. The compound of claim 22, wherein $R^1$ is H or $C_1$-$C_6$-alkyl.

25. The compound of claim 22, wherein m is 0.

26. The compound of claim 22, wherein $R^4$ is $(CR^aR^b)_p$-6-membered heteroaryl or $(CR^aR^b)_p$—$C_6$-aryl, and wherein heteroaryl and aryl are optionally substituted with 1, 2, 3, or 4 groups, each independently selected from —OH, halo, —CN, —SF$_5$, $C_1$-$C_6$-alkyl, $C_1$-$C_6$-haloalkyl, —O—$C_1$-$C_6$-alkyl, and $C_1$-$C_6$-alkyl-OH;

$R^a$ is H or $C_1$-$C_6$-alkyl;

$R^b$ is H or $C_1$-$C_6$-alkyl; and p is 0 or 1.

27. The compound of claim 22, wherein

A is C=O;

$R^1$ is —CH$_3$;

$R^4$ is $(CR^aR^b)_p$—$C_6$-$C_{12}$-aryl, wherein aryl is optionally substituted with 1, 2, 3, or 4 groups, each independently selected from halo, —CN, and $C_1$-$C_6$-alkyl;

$R^5$ is H;

m is 0;

n is 0; and p is O.

28. A pharmaceutical composition comprising a compound of claim 1, and a pharmaceutically acceptable carrier.

29. A method of treating an HBV infection in an individual in need thereof, comprising administering to the individual a therapeutically effective amount of a compound of claim 1.

30. A method of inhibiting or reducing the formation or presence of HBV DNA-containing particles or HBV RNA-containing particles in an individual in need thereof, comprising administering to the individual a therapeutically effective amount of a compound of claim 1.

31. The method of claim 29, further comprising administering to the individual at least one additional therapeutic agent selected from the group consisting of an HBV polymerase inhibitor, immunomodulatory agents, interferon, viral entry inhibitor, viral maturation inhibitor, capsid assembly modulator, reverse transcriptase inhibitor, cyclophilin/TNF inhibitor, TLR-agonist, HBV vaccine, and any combination thereof.

* * * * *

UNITED STATES PATENT AND TRADEMARK OFFICE
CERTIFICATE OF CORRECTION

PATENT NO. : 10,975,077 B2
APPLICATION NO. : 16/314001
DATED : April 13, 2021
INVENTOR(S) : Scott Kuduk Page 1 of 2

It is certified that error appears in the above-identified patent and that said Letters Patent is hereby corrected as shown below:

In the Claims

Claim 1, Column 373, Line 49, should read:
-- –SF5, C1-C6-alkyl, C1-C6-haloalkyl, –O-C1-C6-alkyl, and --

Claim 6, Column 374, Lines 15-27, should read:

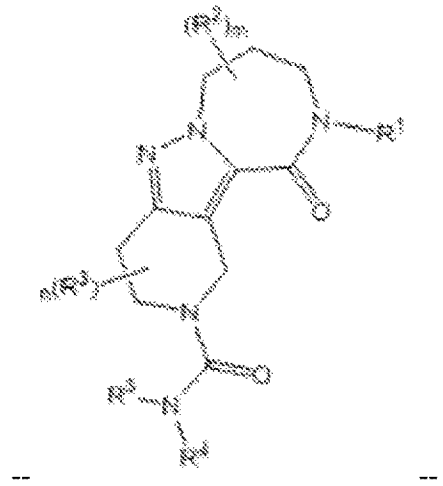

-- --

Claim 11, Column 375, Lines 18-19, should read:
-- C6-aryl and wherein heteroaryl and aryl are --

Claim 19, Column 377, Line 21, should read:
-- or two R2 groups together form a C3-C6 spiro cycloal- --

Claim 21, Column 377, Lines 41-43, should read:
-- C0-C6-alkyl-C(O)OR9, and C0-C6-alkyl-C(O)N(R7)2, and wherein alkyl, alkenyl, cycloalkyl, and --

Signed and Sealed this
Thirteenth Day of September, 2022

Katherine Kelly Vidal
*Director of the United States Patent and Trademark Office*

CERTIFICATE OF CORRECTION (continued)
U.S. Pat. No. 10,975,077 B2

Claim 21, Column 377, Line 58, should read:
-- C1-C6-alkyl, C1-C6-haloalkyl, C(O) C1-C6-alkyl and C1-C6-alkyl- --

Claim 22, Column 378, Line 36, should read:
-- two R2 groups together form a C3-C6 spiro cycloalkyl, --

Claim 27, Column 380, Line 4, should read:
-- p is 0. --